United States Patent
Kowalczyk et al.

(10) Patent No.: US 8,633,224 B2
(45) Date of Patent: *Jan. 21, 2014

(54) HEMIASTERLIN DERIVATIVES AND USES THEREOF IN THE TREATMENT OF CANCER

(75) Inventors: James J. Kowalczyk, Andover, MA (US); Galina Kuznetsov, Lexington, MA (US); Shawn Schiller, Haverhill, MA (US); Boris M. Seletsky, Andover, MA (US); Mark Spyvee, Hampstead, NH (US); Hu Yang, Andover, MA (US)

(73) Assignee: Eisai Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/365,728

(22) Filed: Feb. 3, 2012

(65) Prior Publication Data

US 2012/0309938 A1   Dec. 6, 2012

Related U.S. Application Data

(63) Continuation of application No. 12/394,882, filed on Feb. 27, 2009, now Pat. No. 8,129,407, which is a continuation of application No. 11/701,969, filed on Feb. 2, 2007, now Pat. No. 7,528,152, which is a continuation of application No. 10/508,607, filed as application No. PCT/US03/08888 on Mar. 21, 2003, now Pat. No. 7,192,972.

(60) Provisional application No. 60/366,592, filed on Mar. 22, 2002.

(51) Int. Cl.
*A61K 31/454* (2006.01)
*C07D 401/12* (2006.01)

(52) U.S. Cl.
USPC .......................................... 514/326; 546/208

(58) Field of Classification Search
USPC .......................................... 514/326; 546/208
See application file for complete search history.

(56) References Cited

U.S. PATENT DOCUMENTS

| | | | |
|---|---|---|---|
| 5,661,175 | A | 8/1997 | Kashman et al. |
| 5,798,355 | A | 8/1998 | Steiner et al. |
| 6,057,297 | A | 5/2000 | Politi et al. |
| 6,143,721 | A | 11/2000 | Janssen et al. |
| 6,153,590 | A | 11/2000 | Andersen et al. |
| 7,022,677 | B1 | 4/2006 | Ishiyama et al. |
| 7,064,211 | B2 | 6/2006 | Kowalczyk et al. |
| 7,192,972 | B2 | 3/2007 | Kowalczyk et al. |
| 7,528,152 | B2 | 5/2009 | Kowalczyk et al. |
| 7,585,976 | B2 | 9/2009 | Campagna et al. |
| 2006/0148014 | A1 | 7/2006 | Agoulnik |
| 2006/0281690 | A1 | 12/2006 | Campagna et al. |
| 2008/0051434 | A1 | 2/2008 | Kowalczyk et al. |
| 2008/0108820 | A1 | 5/2008 | Campagna et al. |

FOREIGN PATENT DOCUMENTS

| | | |
|---|---|---|
| DE | 4016994 | 11/1991 |
| DE | 10230874 | 1/2004 |
| JP | 04-235163 | 8/1992 |
| JP | 8-73444 | 3/1996 |
| WO | WO96/33211 | 10/1996 |
| WO | WO97/43305 | 11/1997 |
| WO | WO98/13375 | 4/1998 |
| WO | WO99/31122 | 6/1999 |
| WO | WO99/32509 | 7/1999 |
| WO | WO99/65299 | 12/1999 |
| WO | WO0048623 A1 | 8/2000 |
| WO | WO01/18032 | 3/2001 |
| WO | WO01/79167 | 10/2001 |
| WO | WO03/008378 | 1/2003 |
| WO | WO03/082268 | 10/2003 |
| WO | WO2004/047615 | 6/2004 |
| WO | WO2004/048527 | 6/2004 |

OTHER PUBLICATIONS

Hauske et al., J. Med. Chem. 1992, 35, 4284-4296.*
Kuznetsov, Galina et al., "In vitro and in vivo antitumor activities of novel hemiasterlin analog E7974," American Association for Cancer Research, 96th Annual Meeting, abstract No. 3432 (2005).
ATCC No. CCL-243. Nov. 11, 2008.
ATCC No. CRL-1593.2. Nov. 11, 2008.
ATCC No. CRL-1469. Nov. 11, 2008.
ATCC No. HTB-103. Nov. 11, 2008.
ATCC No. ATB-177. Nov. 11, 2008.
Bissoon-Haqqani et al., "Nuclear Expression of Thymidylate Synthase in Colorectal Cancer Cell Lines and Clinical Samples," Journal of Histochemistry & Cytochemistry, vol. 54(1):19-29 (2006).
Brantley, Eileen et al., "Anti-tumor drug candidate 2-(4-amino-3-methylphenyl)-5-fluorobenzothiazole induces single-strand breaks and DNA-protein cross-links in sensitive MCF-7 breast cancer cells," Cancer Chemother. Pharmacol., vol. 58:62-72 (2006).
Hernandez, Silvia et al., "cdc25 Cell Cycle-activating Phosphatases and c-myc Expression in Human Non-Hodgkin's Lymphomas," Cancer Research, vol. 58:1762-1767 (1998).
Hu, Limin et al., "Phosphatidylinostol 3-Kinase Angiogenesis and Vascular Permeability Associated with Ovarian Carcinoma," Clin. Cancer Res., vol. 11(22):8208-8212 (2005).
Kubota, Hisayo et al., "Increased expression of GRP94 protein is associated with decreased sensitivity to X-rays in cervical cancer cell lines," Int. J. Radiat. Biol., vol. 81(9):701-709 (2005).

(Continued)

*Primary Examiner* — Jason M Nolan
(74) *Attorney, Agent, or Firm* — Lathrop & Gage LLP; Brian C. Trinque

(57) ABSTRACT

The present invention provides compounds having formula (I):

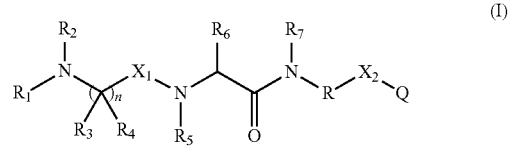

and additionally provides methods for the synthesis thereof and methods for the use thereof in the treatment of cancer, wherein $R_1$-$R_7$, $X_1$, $X_2$, R, Q, and n are as defined herein.

20 Claims, No Drawings

(56) References Cited

OTHER PUBLICATIONS

Mickey, Don D. et al., "Heterotransplantation of a Human Prostatic Adenocarcinoma Cell Line in Nude Mice," Cancer Research, vol. 37:4049-4058 (1977).

ATCC No. CCL-247 Nov. 11, 2008.

Plowman, Jacqueline et al., "Preclinical Antitumor Activity of Temozolomide in Mice: Efficacy against Human Brain Tumor Xenografts and Synergism with 1,3-Bis(2-chlorkoethyl)-1-nitrosourea," Cancer Research, vol. 54:3793-3799 (1994).

Stickle, Natalie H. et al., "Expression of p53 in renal carcinoma cells is independent of pVHL," Mutation Research, vol. 578:23-32 (2005).

Warters, Raymond et al., "Melanoma Cells Express Elevated Levels of Phosphorylated Histone H2AX Foci," J. Invest. Dermatol., vol. 124:807-817 (2005).

Andersen, Raymond J. et al., "Total Synthesis of (−)-Hemiasterlin, a Structurally Novel Tripeptide that Exhibits Potent Cytotoxic Activity," Tetrahedron Letters, vol. 38(3):317-320 (1997).

Bhatnagar, Pradip Kumar et al., CAplus AC 1999:811016, "Compositions and methods using glycinamide-containing peptide for expansion of hematopoietic cells," (2006).

Billson, Jeremy et al., "The Design and Synthesis of Inhibitors of the Cysteinyl Protease, DERPI," Bioorgiinic & Medicinal Chemistry Letters, vol. 8:993-998 (1998).

Dragovich, Peter S. et al., "Structure-Based Design, Synthesis, and Biological Evaluation of Irreversible Human Rhinovirus 3C Protease Inhibitors. 1. Michael Acceptor Structure-Activity Studies," J. Med. Chem., vol. 41:2806-2818 (1998).

Jones, Iwan G. et al., "The use of norbornene derivatives in the synthesis of conformationally constrained peptides and pseudo-peptides," Letters in Peptide Science, vol. 5:171-173 (1998).

Kovacs, Gabor L. et al., CAplus AC 1989:400176, "Antiamnesic effects of D-pipecolic acid and analogs of Pro-Leu-Gly-NH2 in rats," (1998).

Kovacs, Gabor L. et al., "Antiamnesic Effects of D-Pipecolic Acid and Analogues of Pro-Leu-Gly-HN.sub.2 in Rats," Pharmacology, Biochemistry & Behavior, vol. 31:833-837 (1989).

Martha, P.M. et al., "Prolonged Suppression of Circulating Estrogen Levels Without an Initial Hormonal Flare Using Abarelix-Depot, a Pure GnRH Antagonist in Women With Endometriosis," Fertility and Sterility, vol. 72(6):S210-S211, No. P-375 (1999).

Nieman, James A. et al., "Synthesis and Antimitotic/Cytotoxic Activity of Hemiasterlin Analogues," J. Nat. Prod., vol. 66:183-199 (2003).

Politi, Vincenzo, et al., CAplus AC 1997:244196, "Method for determining the therapeutic activity of metalloproteinase inhibitor compounds, new inhibitor compounds, and the therapeutic use thereof," (1997).

Sato, Yoshinari et al., CAplus AC 1996:353193, "Preparation of benzodiazepines as cholecystokinin B antagonists," (1996).

Szabo, Gyula et al., CAplus AC 1985:179250, "Effects of oxytocin fragment and its analogs on brain monoamine levels in rat brains," (1985).

Szabo, Gyula et al., "Effects of Ocytocin Fragment and its Analogs on Brain Monoamine Levels in Rat Brains," Neuropeptides and Psychosomatic Processes, Int. Conf. Integr Neurohumoral Mech., Meeting, pp. 195-200 (1983).

* cited by examiner

HEMIASTERLIN DERIVATIVES AND USES THEREOF IN THE TREATMENT OF CANCER

PRIORITY CLAIM

The present application is a continuation application of U.S. Ser. No. 12/394,882, filed Feb. 27, 2009, which is a continuation application of U.S. Ser. No. 11/701,969, filed on Feb. 2, 2007, which is a continuation application of U.S. Ser. No. 10/508,607, filed on Sep. 22, 2004, now U.S. Pat. No. 7,192,972, which claims the benefit under 35 USC §371 of International Application No. PCT/US03/08888, filed Mar. 21, 2003, which claims priority to U.S. Provisional Patent Application No. 60/366,592, filed Mar. 22, 2002. The entire contents of the aforementioned applications are hereby incorporated herein by reference.

BACKGROUND OF THE INVENTION

Hemiasterlin (I) was first isolated from the sponge *Hemiasterella minor* (class, Demospongiae; order, Hadromedidia; family, Henmiasterllidae) collected in Sodwana Bay, South Africa (see, Kashman et al. U.S. Pat. No. 5,661,175). It was reported that Hemiasterlin exhibited antitumor activity against several cell lines, including human lung carcinoma, human colon carcinoma and human melanoma.

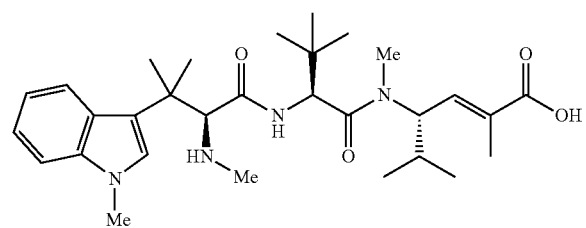

(I)

After the initial isolation and reporting of this compound, additional hemiasterlins were isolated, and several hemiasterlin derivatives were synthesized and their biological activity was also investigated. It was subsequently reported that Hemiasterlins and certain analogs thereof exhibit antimitotic activity and thus are useful for the treatment of certain cancers (see, U.S. Pat. No. 6,153,590 and PCT application WO 99/32509). However, only a rather limited number of Hemiasterlin analogs were prepared, half of which were the natural products themselves, isolated from *Cymbastela* sp., or were obtained by modifications to the natural products. Thus the number and types of derivatives that could be prepared and evaluated for biological activity were limited.

Clearly, there remains a need to develop synthetic methodologies to access and examine the therapeutic effect of a variety of novel derivatives of Hemiasterlin, particularly those that are inaccessible by making modifications to the natural product. It would also be of particular interest to develop novel compounds that exhibit a favorable therapeutic profile in vivo (e.g., are safe and effective, while retaining stability in biological media).

SUMMARY OF THE INVENTION

As discussed above, there remains a need to develop novel Hemiasterlin analogs to evaluate their potential as therapeutic agents for the treatment of cancer. The present invention provides novel compounds of general formula (I),

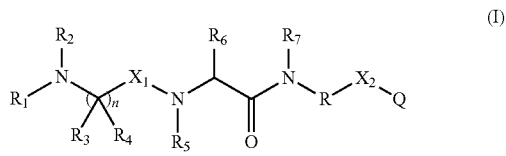

(I)

and additionally provides methods for the synthesis thereof and methods for the use thereof in the treatment of cancer, wherein $R_1$-$R_7$, $X_1$, $X_2$, R, Q, and n are as defined herein. The inventive compounds also find use in the prevention of restenosis of blood vessels subject to traumas such as angioplasty and stealing.

DETAILED DESCRIPTION OF CERTAIN PREFERRED EMBODIMENTS OF THE INVENTION

In recognition of the need to access and farther explore the biological activity of novel derivatives of Hemiasterlin, and this class of peptides in general, the present invention provides novel peptide compounds, as described in more detail herein, which demonstrate antitumor activity. Thus, the compounds of the invention, and pharmaceutical compositions thereof, are useful for the treatment of cancer. In certain embodiments, the compounds of the present invention can be used for the treatment of diseases and disorders including, hut not limited to prostate, breast, colon, bladder, cervical, skin, testicular, kidney, ovarian, stomach, brain, liver, pancreatic or esophageal cancer, lymphoma, leukemia and multiple myeloma. In certain other embodiments, the inventive compounds also find use in the prevention of restenosis of blood vessels subject to traumas such as angioplasty and stenting.

1) General Description of Compounds of the Invention

The compounds of the invention include compounds of the general formula (I) as further defined below:

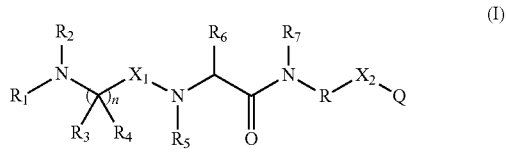

(I)

wherein n is 0, 1, 2, 3 or 4;

$X_1$ and $X_2$ are each independently $CR_AR_B$, C(=O), or —$SO_2$—; wherein each occurrence of $R_A$ and $R_B$ is independently hydrogen, or an aliphatic, alicyclic, heteroaliphatic, heteroalicyclic, aryl or heteroaryl moiety;

$R_1$ and $R_2$ are each independently hydrogen, —(C=O)$R_C$ or an aliphatic, alicyclic, heteroaliphatic, heteroalicyclic, aryl or heteroaryl moiety; wherein each occurrence of $R_C$ is independently hydrogen, OH, O$R_D$, or an aliphatic, alicyclic, heteroaliphatic, heteroalicyclic, aryl or heteroaryl moiety, wherein $R_D$ is an aliphatic, alicyclic, heteroaliphatic, heteroalicyclic, aryl or heteroaryl moiety;

each occurrence of $R_3$ and $R_4$ is independently hydrogen, or an aliphatic, alicyclic, heteroaliphatic, heteroalicyclic, aryl or heteroaryl moiety; or wherein any two $R_1$, $R_2$, $R_3$ and $R_4$ groups, taken together, may form an alicyclic, heteroalicyclic, alicyclicc(aryl), heteroalicyclic(aryl), alicyclic(heteroaryl) or heteroalicyclic(heteroaryl) moiety, or an aryl or heteroaryl moiety;

$R_5$, $R_6$ and $R_7$ are each independently hydrogen, —(C═O) $R_B$ or an aliphatic, alicyclic, heteroaliphatic, heteroalicyclic, aryl or heteroaryl moiety, wherein each occurrence of $R_E$ is independently hydrogen, OH, $OR_F$, or an aliphatic, alicyclic, heteroaliphatic, heteroalicyclic, aryl or heteroaryl moiety, or wherein any two $R_5$, $R_6$ and $R_7$ groups, taken together, form an alicyclic, heteroalicyclic, alicyclic(aryl), heteroalicyclic (aryl), alicyclic(heteroaryl) or heteroalcyclic(heteroaryl) moiety, or an aryl or heteroaryl moiety; wherein $R_F$ is an aliphatic, alicyclic, heteroaliphatic, heteroalicyclic, aryl or heteroaryl moiety; or $R_7$ may be absent when $NR_7$ is linked to R via double bond;

R is an aliphatic, alicyclic, heteroaliphatic, heteroalicyclic, aryl or heteroaryl moiety; and Q is $OR^{Q'}$, $SR^{Q'}$, $NR^{Q'}R^{Q''}$, $N_3$, ═N—OH, or an aliphatic, alicyclic, heteroaliphatic, heteroalicyclic, aryl or heteroaryl moiety, wherein $R^{Q'}$ and $R^{Q''}$ are each independently hydrogen, or an aliphatic, alicyclic, heteroaliphatic, heteroalicyclic, aryl or heteroaryl moiety, or $R^{Q'}$ and $R^{Q''}$, taken together with the nitrogen, atom to which they are attached, may form an alicyclic, heteroalicyclic, alicyclic(aryl), heteroalicyclic (aryl), alicyclic(heteroaryl) or heteroalicyclic(heteroaryl) moiety, or an aryl or heteroaryl moiety; and pharmaceutically acceptable derivatives thereof.

In certain embodiments, compounds of formula (I) and compounds described in classes and subclasses herein, are not naturally occurring Hemiasterlins.

In certain embodiments, compounds of formula (I) and compounds described in classes and subclasses herein, do not have the following structure:

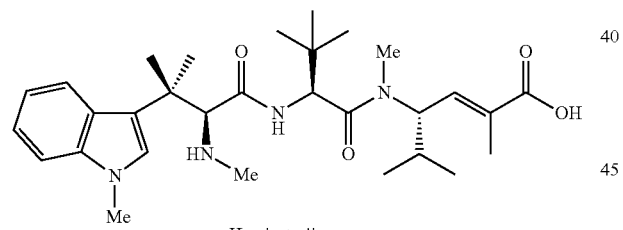

Hemiasterlin

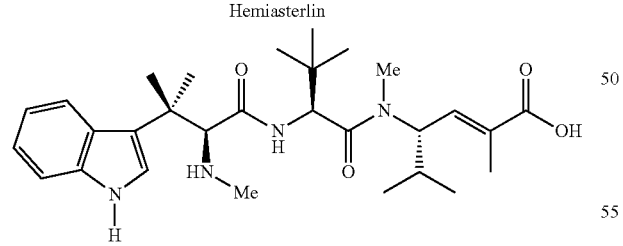

Hemiasterlin A

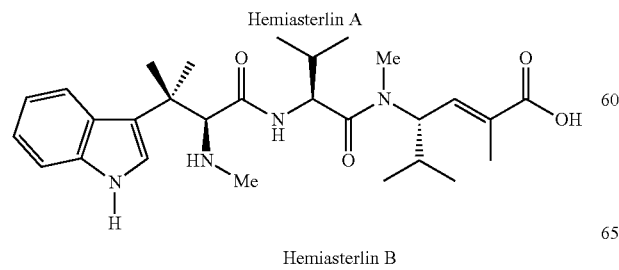

Hemiasterlin B

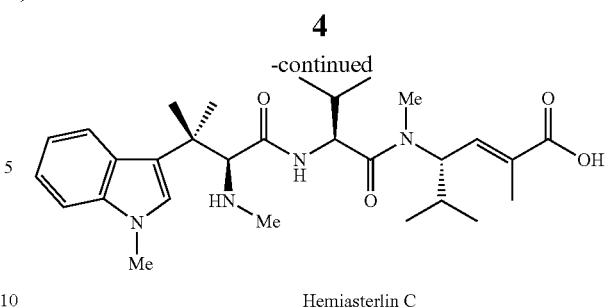

Hemiasterlin C

In certain embodiments of compounds described directly above and compounds as described in certain classes and subclasses herein, the compounds do not comprise more than four consecutive α-amino acid residues, and/or one or more of the following groups do not occur simultaneously as defined:

(a) n is 1;

$X_1$ and $X_2$ are each C(═O);

$R_1$ and $R_2$ are each independently hydrogen, aliphatic, alicyclic, heteroaliphatic, heteroalicyclic, Ar-aliphatic-, Ar-alicyclic-; and, where at least one of $R_1$ and $R_2$ is aliphatic, alicyclic, heteroaliphatic, heteroalicyclic, Ar-aliphatic-, Ar-alicyclic- and neither are Ar, Ar-aliphatic- or Ar-alicyclic-, $R_1$ and $R_2$, taken together, may form a three- to seven-membered ring; wherein Ar is defined as substituted or unsubstituted phenyl, naphtyl, anthracyl, phenanthryl, furyl, pyrrolyl, thiophenyl, benzofuryl, benzothiophenyl, quinolyl, isoquinolyl, imidazolyl, thiazolyl, oxazolyl or pyridyl;

$R_3$ is hydrogen;

$R_4$ is —$CR_{4a}R_{4b}R_{4c}$ wherein $R_{4a}$ and $R_{4b}$ are each independently hydrogen, aliphatic, alicyclic, heteroaliphatic, heteroalicyclic, Ar-aliphatic-. Ar-alicyclic-; and, where at least one of $R_{4a}$ and $R_{4b}$ is aliphatic, alicyclic, heteroaliphatic, heteroalicyclic, Ar-aliphatic-, Ar-alicyclic- and neither are Ar, Ar-aliphatic- or Ar-alicyclic-, $R_{4a}$ and $R_{4b}$, taken together, may form a three- to seven-membered ring; and $R_{4c}$ is hydrogen, aliphatic, alicyclic, heteroaliphatic, heteroalicyclic, Ar-aliphatic-, Ar-alicyclic- and Ar; wherein Ar is as defined directly above;

$R_5$, $R_6$ and $R_7$ are each independently hydrogen, aliphatic, alicyclic, heteroaliphatic, heteroalicyclic, Ar-aliphatic-, Ar-alicyclic- and Ar;

R is a moiety selected from the group consisting of: a linear, saturated or unsaturated, substituted or unsubstituted alkyl group containing one to six carbon atoms; and Q is —$OR_G$, —$SR_G$, —$NR_GR_H$, —$NHCH(R_K)CO_2H$, or —$NRCH(R_K)CO_2H$, wherein $R_G$ and $R_H$ are each independently hydrogen, aliphatic, alicyclic, heteroaliphatic or heteroalicyclic; $R_K$ is aliphatic, alicyclic, heteroaliphatic, heteroalicyclic, or a moiety having the structure —$(CH_2)_tNR_{K1}R_{K2}$, wherein t=1-4 and $R_{K1}$ and $R_{K2}$ are independently hydrogen, aliphatic, alicyclic, heteroaliphatic, heteroalicyclic or —C(NH)(NH$_2$);

(b) n is 1;

$X_1$ and $X_2$ are each C(═O);

$R_1$ is an optionally substituted methylene or —CH═ group bonded to the indole moiety thereby forming a tricyclic moiety;

R$_2$ is hydrogen, an optionally substituted alkyl or acyl group, or is absent when R$_1$ is —CH= as defined above;

R$_3$ is hydrogen or is absent when CR$_3$ and CR$_y$R$_z$, as defined herein, are linked by a double bond;

R$_4$ is a moiety having the structure:

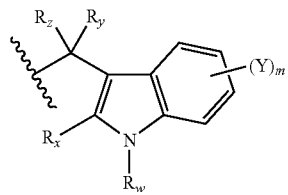

wherein R$_w$, R$_y$ and R$_z$ are each independently hydrogen, or optionally substituted alkyl or acyl, or R$_z$ is absent when CR$_3$ and CR$_y$R$_z$, as defined herein, are linked by a double bond; R$_x$ is hydrogen or an optional substituent, or is absent when R$_1$ is an optionally substituted methylene or —CH= group as defined above; Y is an optional substituent; and m is 0, 1, 2, 3 or 4;

R$_5$ is hydrogen, OH or an optionally substituted alkyl or acyl group;

R$_6$ is hydrogen, or an optionally substituted alkyl group;

R$_7$ is hydrogen or alkyl; and

—R—X$_2$-Q together represent an optionally substituted alkyl moiety;

(c) n is 1;

X$_1$ and X$_2$ are each C(=O);

R$_1$ is hydrogen, an optionally substituted alkyl or acyl group, or an optionally substituted methylene or —CH= group bonded to the indole moiety thereby forming a tricyclic moiety;

R$_2$ is hydrogen, an optionally substituted alkyl or acyl group, or is absent when R$_1$ is —CH= as defined above;

R$_3$ is hydrogen or is absent when CR$_3$ and CR$_y$R$_z$, as defined herein, are linked by a double bond;

R$_4$ is a moiety having the structure:
wherein R$_w$, R$_y$ and

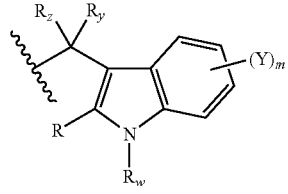

R$_z$ are each independently hydrogen, or optionally substituted alkyl or acyl, or R$_z$ is absent when CR$_3$ and CR$_y$R$_z$, as defined herein, are linked by a double bond; with the limitation that R$_y$ and R$_z$ are not simultaneously hydrogen; R$_x$ is hydrogen or an optional substituent, or is absent when R$_1$ is an optionally substituted methylene or —CH= group as defined above; Y is an optional substituent; and m is 0, 1, 2, 3 or 4;

R$_5$ is hydrogen, OH or an optionally substituted alkyl or acyl group;

R$_6$ is hydrogen or an optionally substituted alkyl group;

R$_7$ is hydrogen or alkyl; and

—R—X$_2$-Q together represent an optionally substituted alkyl moiety or -Q—C(O)X, wherein Q' is an optionally substituted —CH$_2$—, —CH$_2$CH$_2$—, —CH$_2$CH$_2$CH$_2$—, —CH$_2$CH=CH—, —CH$_2$C≡C— or phenylene moiety, wherein X is —OR', —SR' or —NR'R" and each occurrence of R' and R" is independently hydrogen or optionally substituted alkyl;

(d) n is 1;

X$_1$ is C=O;

R$_1$ is methyl;

R$_2$ and R$_3$, taken together, form a piperidine moiety;

R$_4$ and R$_5$ are each hydrogen,

R$_6$ is —CH(CH$_3$)CH$_2$CH$_3$;

R$_7$ is —CH$_2$OC(=O)CH$_2$CH(CH$_3$)$_2$—CH$_2$OC(=O)CH$_2$CH$_2$CH$_3$ or —CH$_2$OC(=O)CH$_2$CH$_3$; and —R—X$_2$-Q together represent the moiety having the structure:

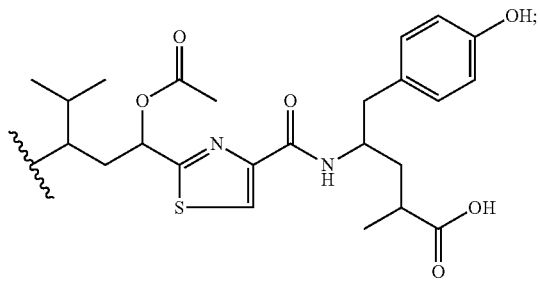 [SMILES: *C(CC(OC(C)=O)c1nc(C(=O)NC(Cc2ccc(O)cc2)CC(C)C(=O)O)cs1)C(C)C]

(e) n is 1;

X$_1$ is C=O;

R$_1$, R$_2$, and R$_7$ are each methyl;

R$_3$ and R$_5$ are each hydrogen;

R$_4$ and R$_6$ are each i-propyl; and

—R—X$_2$-Q together represent the moiety having the structure:

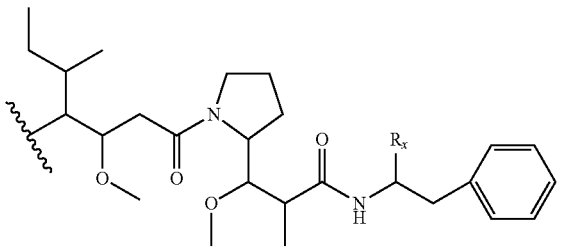

wherein R$_x$ is hydrogen or 2-thiazolyl; and/or (f) n is 1;

X$_1$ is C=O;

R$_1$ and R$_2$ are each independently hydrogen or C$_{1-4}$alkyl;

R$_3$ and R$_5$ are each hydrogen;

R$_4$ and R$_6$ are each i-propyl;

R$_7$ is methyl; and

—R—X$_2$-Q together represent a moiety having the structure:

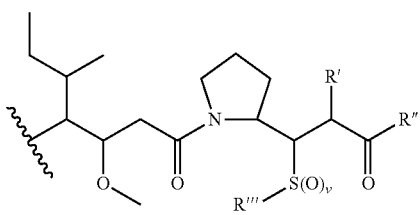

wherein v is 0, 1 or 2;

R' is hydrogen or $C_{1-4}$alkyl;

R" is $C_{1-6}$alkylamino; hydroxy; $C_{3-7}$cycloalkylamino optionally substituted by phenyl or benzyl; arylamino; $C_{1-4}$alkoxy; benzhydrazino; heterocyclyl optionally substituted with one to three substituents selected from the group consisting of benzyl, benzhydryl, alkyl, hydroxy, alkoxy, alkylcarbamoyloxy, amino, mono- or di-alkylamino, acylamino, alkoxycarbonylamino, phenyl or halogen; heterocyclylamino; heterocycloalkylamino with the heterocyclyc group optionally substituted with one to three substituents selected from the group consisting of benzyl, benzhydryl, alkyl, hydroxy, alkoxy, alkylcarbamoyloxy, amino, di-alkylamino, acylamino, alkoxycarbonylamino or halogen; aralkyloxy or aralkyl both optionally substituted with one to three substituents selected from the group consisting of halogen, alkoxyxarbonyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkoxycarbonylamino, heterocyclyl, 1,3-dioxolyl, 1,4-dioxolyl, amino, aminosulfonyl or benzyl; or aralkylamino having $C_{1-4}$alkylene and the aryl group optionally substituted with one to three substituents selected from the group consisting of halogen, alkoxyxarbonyl, sulfamoyl, alkylcarbonyloxy, carbamoyloxy, cyano, mono- or di-alkylamino, alkyl, alkoxy, phenyl, phenoxy, trifluoromethyl, trifluoromethoxy, alkylthio, hydroxy, alkoxycarbonylamino, heterocyclyl, 1,3-dioxolyl, 1,4-dioxolyl, amino or benzyl; and R''' is hydrogen, alkyl optionally substituted with one to three substituents selected from the group consisting of hydroxy, alkoxy, amino, mono- or di-alkylamino, carboxy, alkoxycarbonyl, carbamoyl, alkylcarbonyloxy, carbamoyloxy or halogen; alkenyl; alkynyl; $C_{3-7}$cycloalkyl; aryl optionally substituted with one to three substituents selected from the group consisting of halogen, alkoxyxarbonyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkoxycarbonylamino, heterocyclyl, 1,3-dioxolyl, 1,4-dioxolyl, amino or benzyl; aralkyl with the aryl group optionally substituted with one to three substituents selected from the group consisting of halogen, alkoxyxarbonyl, carbamoyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkoxycarbonylamino, heterocyclyl, 1,3-dioxolyl, 1,4-dioxolyl, amino or benzyl; or heterocyclylalkyl;

wherein the groups recited in paragraph (f) above are defined as follows;

alkyl refers to a straight-chain or branched-chain hydrocarbon group optionally substituted with hydroxy, alkoxy, amino, mono- or di-alkylamino, acetoxy, alkylcarbonyloxy, alkoxycarbonyl, carbamoyloxy, carbamoyl or halogen;

alkenyl refers to a hydrocarbon chain as defined for alkyl above having at least one double bond;

alkynyl refers to a hydrocarbon chain as defined for alkyl above having at least one triple bond;

$C_{3-7}$cycloalkyl refers to a saturated, cyclic hydrocarbon group with 3-7 carbon atoms optionally substituted with alkyl, phenyl, amino, hydroxy or halogen;

$C_{1-4}$alkylene refers to a biradical linear or branched hydrocarbon chain containing 1-4 carbon atoms;

Aralkyl, refers to an aryl group attached to an alkylene group;

Heterocyclyl refers to saturated, unsaturated or aromatic monovalent cyclic radical having one to three heteroatoms selected from O, N and S, or combination thereof, optionally substituted with one or more occurrences of benzyl, benzhydryl, alkyl, hydroxy, alkoxy, alkylcarbamoyloxy, amino, mono- or di-alkylamino, acylamino, alkoxycarbonylamino or halogen;

Amino refers to —$NH_2$ and includes amino groups which are further substituted by lower alkyl groups, or nitrogen protecting groups know in the art;

Cycloalkylamino refers to cycloalkyl groups as defined above attached to a structure via an amino radical;

Arylamino is defined as aryl-NH—;

Aralkylamino is defined as aralkyl-NH—;

Carbamoyl refers to the group —C(=O)—$NH_2$;

Carbamoyloxy refers to the group —O—C(=O)—NH—;

Alkylcarbamoyloxy refers to the group —O—C(=O)—NH-alkyl;

Alkylcarbonyloxy refers to the group —O—C(=O)-alkyl;

Aralkyloxy refers to the group —O-aralkyl; and

Alkylthio refers to the group Alkyl-S—.

In certain other embodiments of compounds described in (a) above and compounds as described in certain classes and subclasses herein, the following groups do not occur simultaneously as defined:

n is 1; $X_1$ and $X_2$ are each C(=O); $R_1$ and $R_2$ are each independently hydrogen, methyl, ethyl, propyl, n-butyl, acetyl; or $R_1$ and $R_2$, taken together, form a moiety selected from the group consisting of cyclopropyl, cyclobutyl, cyclopentyl, and cyclohexyl; $R_3$ is hydrogen; $R_4$ is —$CR_{4a}R_{4b}R_{4c}$ wherein $R_{4a}$ and $R_{4b}$ are each independently methyl, ethyl, n-propyl or n-butyl; or $R_{4a}$ and $R_{4b}$, taken together, form a moiety selected from the group consisting of β-cyclopropyl, β-cyclobutyl, β-cyclopentyl, and β-cyclcohexyl; and $R_{4c}$ is phenyl, naphtyl, anthracyl or pyrrolyl; $R_5$ and $R_7$ are each independently hydrogen or methyl; $R_6$ is a three to six carbon, branched alkyl group; and —R—$X_2$-Q together represent the moiety having the structure:

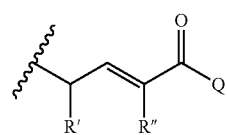

wherein R' is methyl, ethyl, n-propyl, isopropyl, tert-butyl, iso-butyl, or sec-butyl; R" is hydrogen, methyl, ethyl, propyl, iso-propyl, n-butyl, iso-butyl or sec-butyl; and Q is OH or $OR_G$ wherein $R_G$ is a linear or branched one to six carbon alkyl group.

In certain other embodiments of compounds described in (a) above and compounds as described in certain classes and subclasses herein, the following groups do not occur simultaneously as defined:

n is 1; $X_1$ and $X_2$ are each C(=O); $R_1$, $R_3$ and $R_5$ are each hydrogen; $R_2$ is methyl; $R_4$ is —$CR_{4a}R_{4b}R_{4c}$, $R_6$ is tert-butyl; and —R—$X_2$-Q together represent the moiety having the structure:

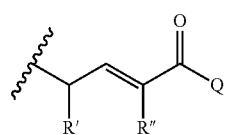

wherein R' is isopropyl; R" is methyl; and Q is OH; and
(a) $R_{4a}$ and $R_{4b}$ are each methyl; $R_{4c}$ is methyl or phenyl; and $R_7$ is hydrogen or methyl;
(b) $R_{4a}$ and $R_{4b}$ are each methyl; $R_{4c}$ is hydrogen; and $R_7$ is methyl; or
(c) $R_{4a}$ and $R_{4b}$ are each hydrogen; $R_{4c}$ is phenyl; and $R_7$ is methyl.

In certain other embodiments, compounds of formula (I) and compounds described in classes and subclasses herein, do not have the structure of any one or more of the compounds disclosed on page 8 line 28 through page 25 line 9, page 28 line 1 through page 32 line 9 and page 39 line 16 through, page 80 line 20 of WO 03/008378, which is incorporated herein by reference in its entirety.

In certain other embodiments, compounds of formula (I) and compounds described in classes and subclasses herein, do not have the structure of any one or more of the compounds disclosed on page 10 line 24 through page 17 line 18; page 17 line 26 through page 19 line 3, page 19 line 10 through page 20 line 3, page 20 line 17 through page 21 line 9, page 21 lines 14-29, page 22 lines 1-12, page 22 lines 16-18, page 22 lines 22-27, page 23 line 1 through page 24 line 21, page 24 line 26 through page 25 line 9, and page 28 line 1 through page 32 line 9 of WO 03/008378.

In certain other embodiments, compounds of formula (I) and compounds described in classes and subclasses herein, do not have the structure of any one or more of the compounds disclosed in Nieman J. et al., "Synthesis and Antitumotic/Cytotoxic Activity of Hemiasterlin Analogues", *Journal of Natural Products,* 2003, 66(2): 183-199, which is incorporated herein by reference in its entirety.

In certain embodiments, compounds of formula (I) and compounds described in classes and subclasses herein, do not have any one or more of the following structure:

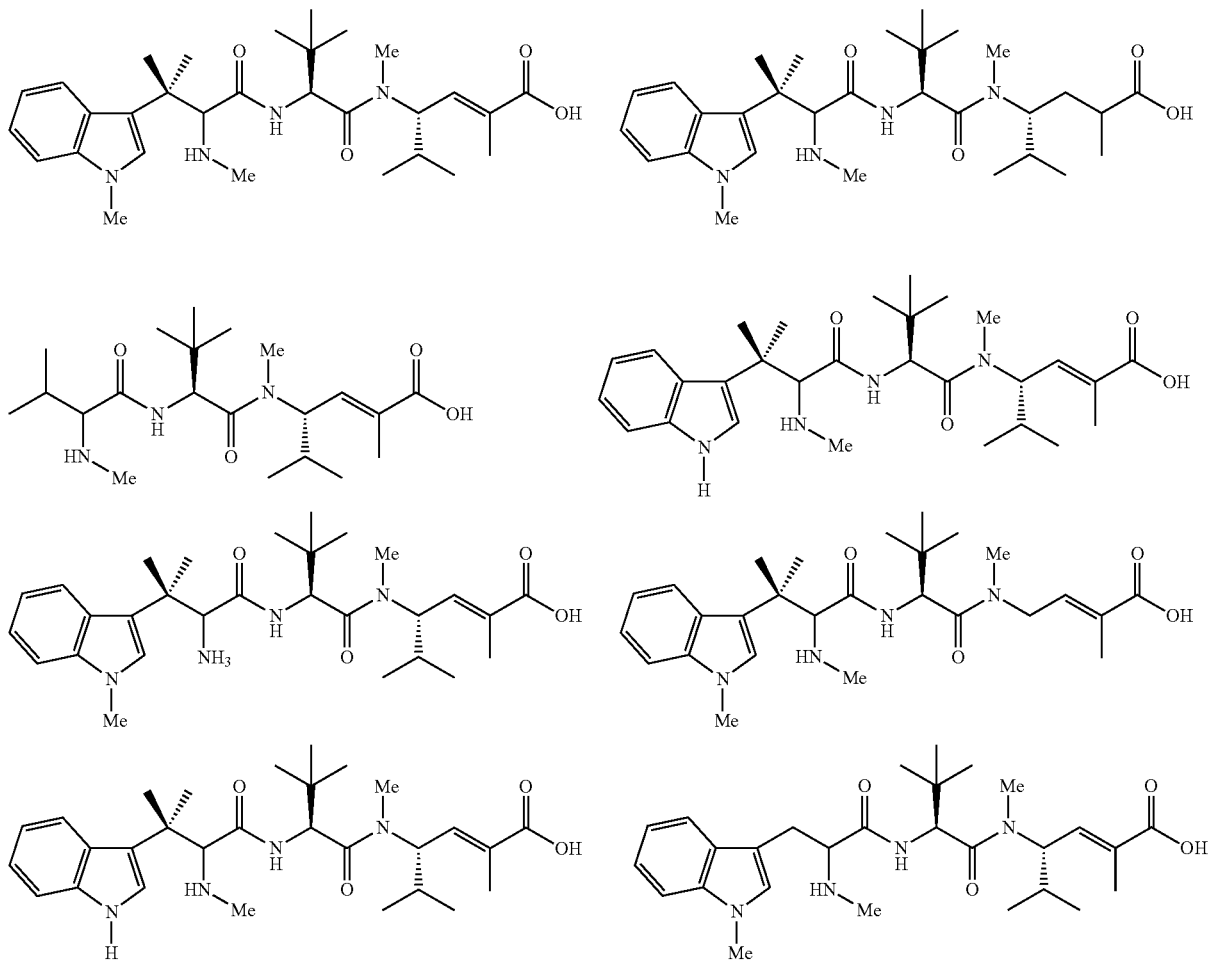

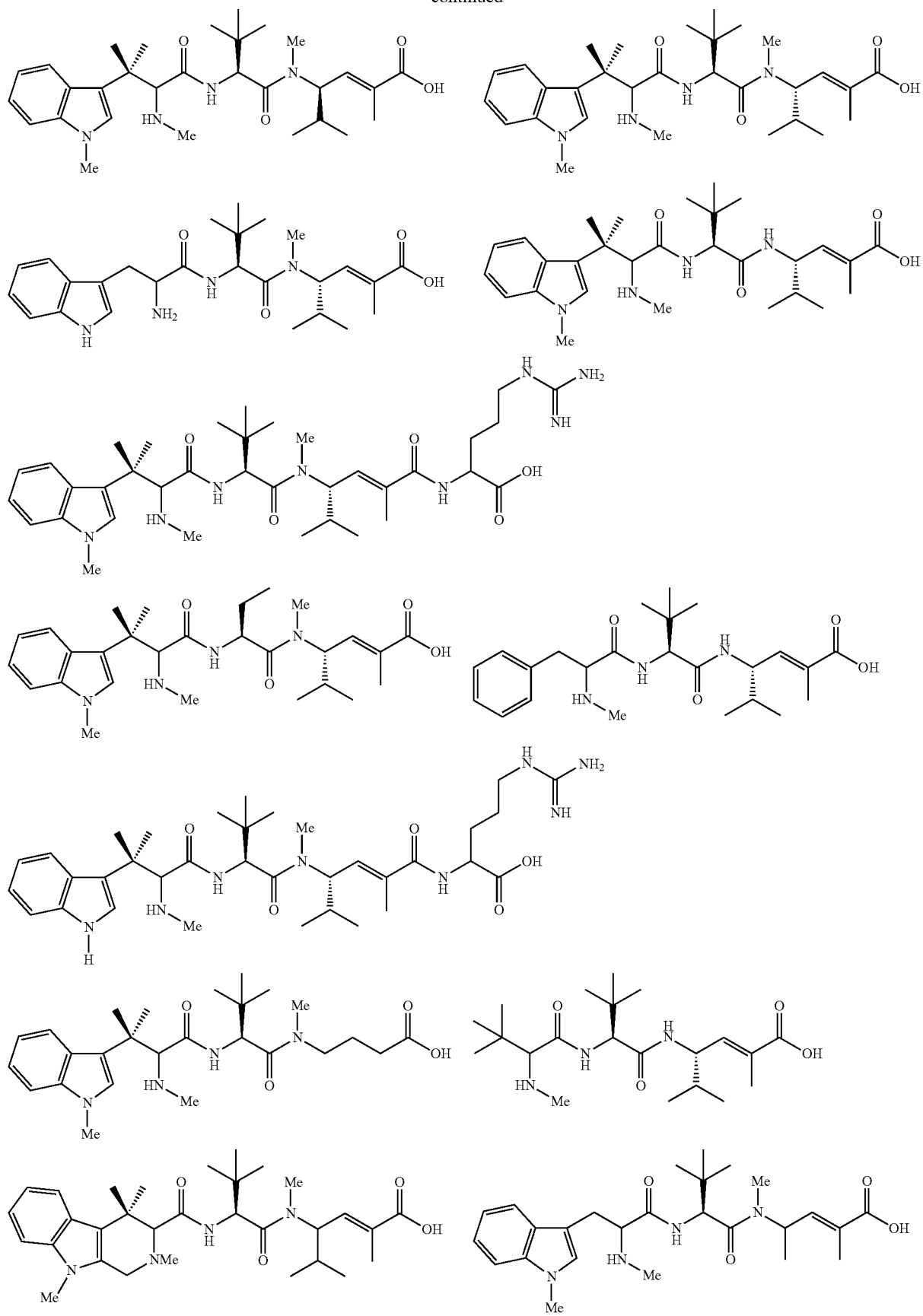

-continued

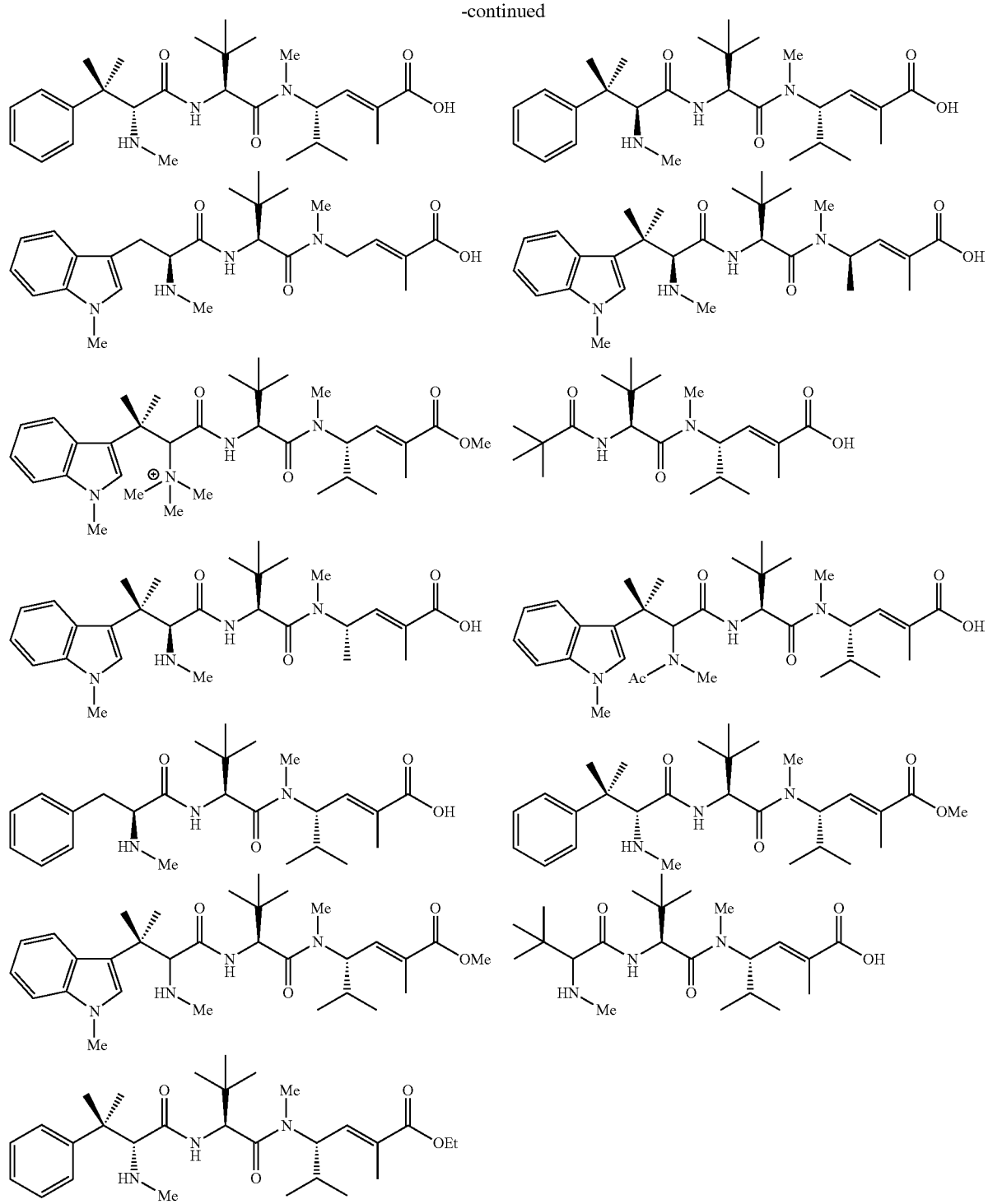

In certain other embodiments, compounds of formula (I) are defined as follows:

$X_1$ and $X_2$ are each independently $CHR_AR_B$, $SO_2$ or C=O; wherein $R_A$ and $R_B$ are each independently hydrogen or substituted or unsubstituted, linear or branched, cyclic or acyclic, or saturated or unsaturated lower alkyl;

$R_1$ and $R_2$ are each independently hydrogen, or a linear or branched, cyclic or acyclic, or saturated or unsaturated lower alkyl, lower heteroalkyl or acyl moiety, or an aryl or heteroaryl moiety; wherein the alkyl, heteroalkyl, and aryl moieties may be substituted or unsubstituted; or $R_1$ and $R_2$, taken together, may form a saturated or unsaturated, substituted or unsubstituted cyclic ring of 5 to 8 atoms;

each occurrence of $R_3$ and $R_4$ is independently hydrogen, or a linear or branched, cyclic or acyclic, or saturated or unsaturated lower alkyl, lower heteroalkyl, lower-alkyl(aryl), lower-heteroalkyl(aryl) moiety, or an aryl or heteroaryl moiety; wherein the alkyl, heteroalkyl, -alkyl(aryl), heteroalkyl (aryl), aryl and heteroaryl moieties may be substituted or unsubstituted; or $R_3$ and $R_4$, taken together, may form a saturated or unsaturated, substituted or unsubstituted cyclic ring of 3 to 8 atoms;

the carbon atom bearing $R_3$ and $R_4$ may be of S configuration;

n is 1;

$R_5$ is hydrogen or a protecting group; wherein the protecting group may be a nitrogen protecting group;

$R_6$ is hydrogen, or substituted or unsubstituted, linear or branched, cyclic or acyclic, or saturated or unsaturated lower alkyl or heteroalkyl; or a substituted or unsubstituted aryl or heteroaryl moiety;

the carbon atom bearing $R_6$ may be of S configuration;

$R_7$ is hydrogen, or substituted or unsubstituted, linear or branched, cyclic or acyclic, or saturated or unsaturated lower alkyl or heteroalkyl; or a substituted or unsubstituted aryl or heteroaryl moiety; or $R_7$ may be absent when $NR_7$ is linked to R via a double bond;

R is a substituted or unsubstituted, linear or branched, cyclic or acyclic, or saturated or unsaturated alkyl moiety; or a heteroaliphatic moiety containing 1-10 carbon atoms, 1 to 4 nitrogen atoms, 0 to 4 oxygen atoms and 0 to 4 sulfur atoms; whereby the heteroaliphatic moiety may be substituted or unsubstituted, linear or branched, cyclic or acyclic, or saturated or unsaturated;

wherein (i) the alkyl moiety may have the structure:

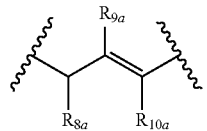

wherein $R_{8a}$, $R_{9a}$ and $R_{10a}$ are each independently absent, hydrogen, or substituted or unsubstituted, linear or branched, cyclic or acyclic, or saturated or unsaturated lower alkyl or heteroalkyl; or a substituted or unsubstituted aryl or heteroaryl moiety; wherein any two $R_7$, $R_{8a}$, $R_{9a}$ and $R_{10a}$ groups may form a substituted or unsubstituted, saturated or unsaturated cyclic alkyl, heteroalkyl, alky(aryl) or heteroalkyl (aryl) moiety or an aryl or heteroaryl moiety; and wherein the carbon atom bearing $R_{8a}$ may be of S configuration;

(ii) the heteroalkyl moiety may have the structure:

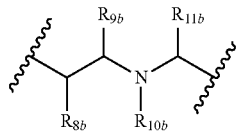

wherein $R_{8b}$, $R_{9b}$, $R_{10b}$ and $R_{11b}$ are each independently absent, hydrogen, or substituted or unsubstituted, linear or branched, cyclic or acyclic, or saturated or unsaturated lower alkyl, heteroalkyl or acyl; or a substituted or unsubstituted aryl or heteroaryl moiety; wherein any two $R_7$, $R_{8b}$, $R_{9b}$, $R_{10b}$ and $R_{11b}$ groups may form a substituted or unsubstituted, saturated or unsaturated cyclic alkyl, heteroalkyl, alky(aryl) or heteroalkyl(aryl) moiety, or a substituted or unsubstituted aryl or heteroaryl moiety; wherein $NR_7$ and $CR_{8b}$, $CR_{8b}$ and $CR_{9b}$, $CR_{9b}$ and $NR_{10b}$, and $NR_{10b}$ and $CR_{11b}$ are each independently linked by a single or double-bond as valency permits; and wherein the carbon atom bearing $R_{8b}$ may be of S configuration;

(iii) or the heteroalkyl moiety may have the structure:

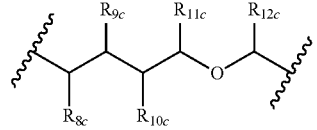

wherein $R_{8c}$, $R_{9c}$, $R_{10c}$, $R_{11c}$ and $R_{12c}$ are each independently absent, hydrogen, or substituted or unsubstituted, linear or branched, cyclic or acyclic, or saturated or unsaturated lower alkyl or heteroalkyl; or a substituted or unsubstituted aryl or heteroaryl moiety; wherein any two $R_7$, $R_{8c}$, $R_{9c}$, $R_{10c}$, $R_{11c}$ and $R_{12c}$ groups may form a substituted or unsubstituted, saturated or unsaturated cyclic alkyl, heteroalkyl, alky(aryl) or heteroalkyl(aryl) moiety, or a substituted or unsubstituted aryl or heteroaryl moiety; wherein $NR_7$ and $CR_{8c}$, $CR_{8c}$ and $CR_{9c}$, $CR_{9c}$ and $CR_{10c}$, $CR_{10c}$ and $CR_{11c}$ are each independently linked by a single or double bond as valency permits; and wherein the carbon atom bearing $R_{8c}$ may be of S configuration; and Q is $OR^{Q'}$, $SR^{Q'}$, $NR^{Q'}R^{Q''}$, wherein $R^{Q'}$ and $R^{Q''}$ are each independently hydrogen or a substituted or unsubstituted, linear or branched, cyclic or acyclic, or saturated or unsaturated lower alkyl or heteroalkyl moiety, or a substituted or unsubstituted aryl or heteroaryl moiety; or wherein $R^{Q'}$ and $R^{Q''}$, taken together, may form a substituted or unsubstituted, saturated or unsaturated cyclic alkyl or heteroalkyl moiety or a substituted or unsubstituted aryl or heteroaryl moiety, and pharmaceutically acceptable derivatives thereof.

In certain embodiments, the present invention defines certain classes of compounds which are of special interest. For example, one class of compounds of special interest includes those compounds having the structure of formula (I) in which R is —$CH(R_{8a})C(R_{9a})$=$C(R_{10a})$— and the compound has the structure (Ia):

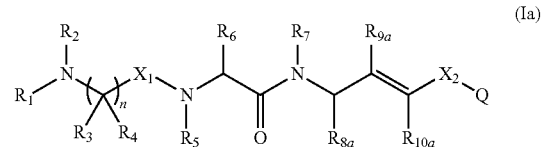

(Ia)

wherein $R_1$-$R_7$, $X_1$, $X_2$, Q and n are defined in classes and subclasses herein;

$R_{8a}$, $R_{9a}$ and $R_{10a}$ are each independently hydrogen, or an aliphatic, alicyclic, heteroaliphatic, heteroalicyclic, aryl or heteroaryl moiety; and wherein any two $R_7$, $R_{8a}$, $R_{9a}$ and $R_{10a}$ groups may form a substituted or unsubstituted, saturated or unsaturated alicyclic, heteroalicyclic, alicyclic(aryl), heteroalicyclic(aryl), alicyclic(heteroaryl) or heteroalicyclic (heteroaryl) moiety, or an aryl or heteroaryl moiety.

Another class of compounds of special interest, herein referred to as class (Ib), consists of compounds having the structure of formula (I) in which $X_2$ is C=O and R is a heteroaliphatic moiety containing 1-10 carbon atoms, 1 to 4 nitrogen atoms, 0 to 4 oxygen atoms and 0 to 4 sulfur atoms, whereby the heteroaliphatic moiety may be substituted or unsubstituted, linear or branched, cyclic or acyclic, or saturated or unsaturated.

Another class of compounds of special interest, consists of compounds having the structure of formula (I) in which $X_1$ is C=O; n is 1; $R_1$ and $R_4$, taken together, form a cyclic heterocyclic or heteroaryl moiety; $R_3$ is hydrogen or is absent when the carbon atom bearing $R_3$ is linked to N or E via a double bond; and the compound has the structure (Ic):

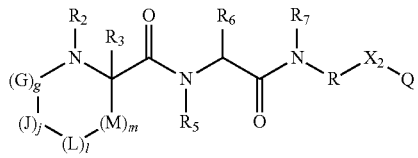
(Ic)

wherein $R_2$, $R_5$-$R_7$, $X_2$ and Q are defined in classes and subclasses herein;

each occurrence of G, J, L and M is independently $CHR^{iv}$, $CR^{iv}R^v$, O, S, $NR^{iv}R^v$, wherein each occurrence of $R^{iv}$ and $R^v$ is independently absent, hydrogen, —C(=O)$R^{vi}$, or an aliphatic, alicyclic, heteroaliphatic, heteroalicyclic, aryl or heteroaryl moiety; or wherein any two adjacent $R_2$, $R^{iv}$, $R^v$ or $R^{vi}$ groups, taken together, form a substituted or unsubstituted, saturated or unsaturated alicyclic or heteroalicyclic moiety containing 3-6 atoms or an aryl or heteroaryl moiety; wherein each occurrence of $R^{vi}$ is an aliphatic, alicyclic, heteroaliphatic, heteroalicyclic, aryl or heteroaryl moiety;

N and G, G and J, J and L, L and M, M and $CR_3$, and $CR_3$ and N are each independently linked by a single or double bond as valency permits; and g, j, l and m are each independently 0, 1, 2, 3, 4, 5 or 6, wherein the sum of g, j, l and m is 3-6.

Another class of compounds of special interest consists of compounds having the structure of formula (I) in which $X_1$ is C=O; n is 1; $R_3$ and $R_4$ are each independently an aliphatic, alicyclic, heteroaliphatic, heteroalicyclic, aryl or heteroaryl moiety, or, when taken together, form an alicyclic, heteroalicyclic, alicyclic(aryl), heteroalicyclic(aryl), alicyclic(heteroaryl) or heteroalicyclic(heteroaryl) moiety; and the compound has the structure (Id):

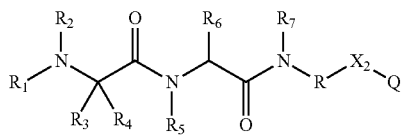
(Id)

wherein $R_1$, $R_2$, $R_5$-$R_7$, R, $X_2$ and Q are defined in classes and subclasses herein.

The following structures illustrate several exemplary types of compounds of class (Ia). Additional compounds are described in the Exemplification herein.

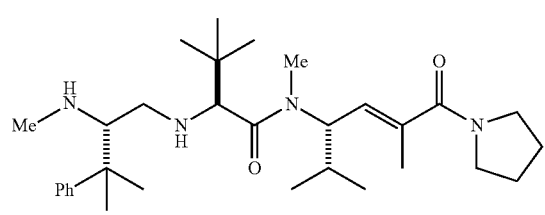

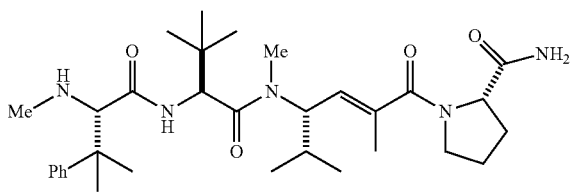

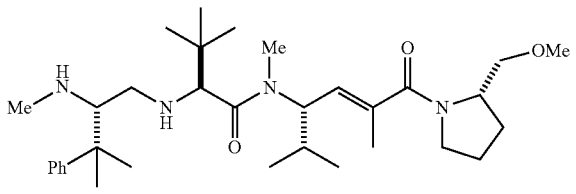

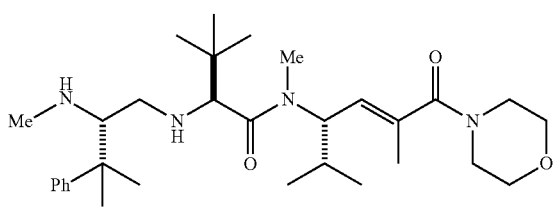

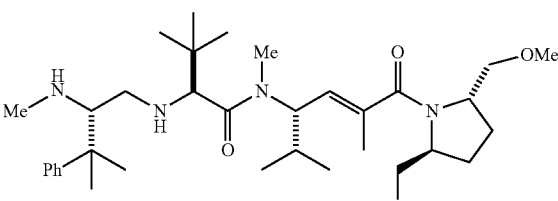

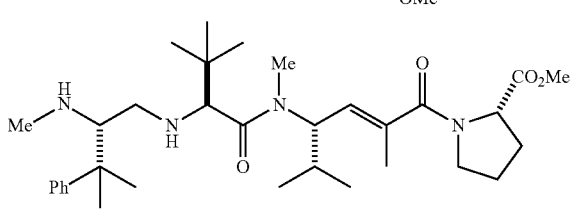

The following structures illustrate several exemplary types of compounds of class (Ib). Additional compounds are described in the Exemplification herein.

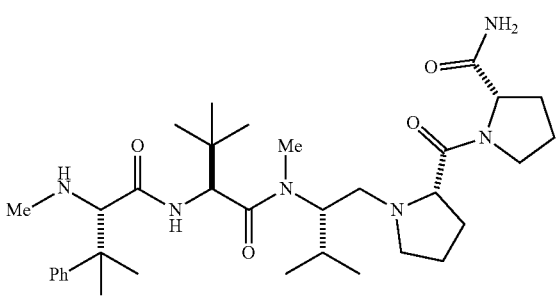

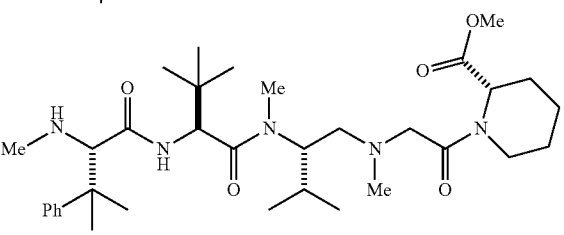

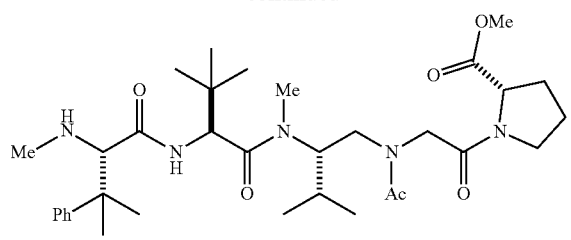
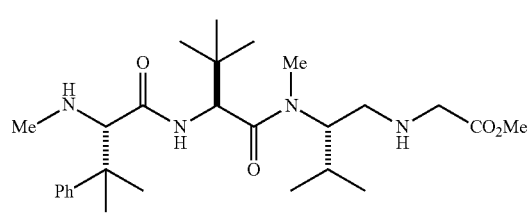
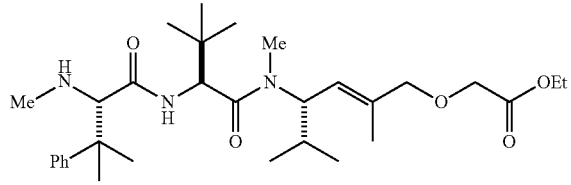
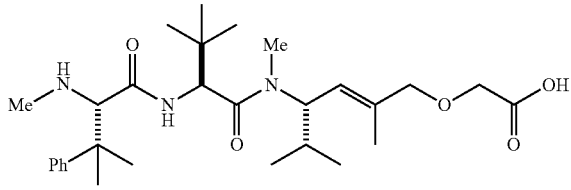
The following structures illustrate several exemplary types of compounds of class (Ic). Additional compounds are described in the Exemplification herein.
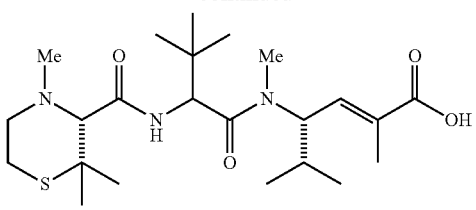
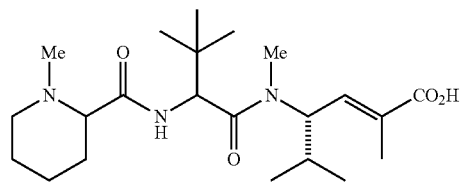
cis
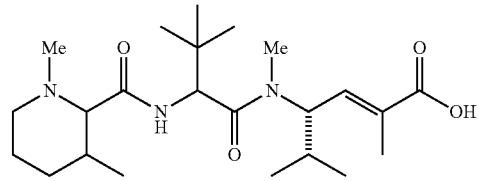
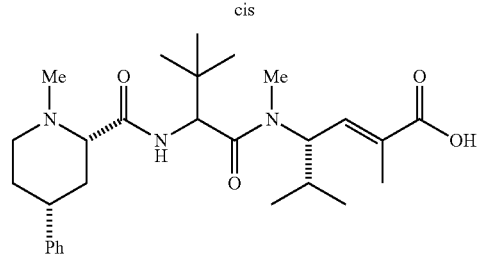
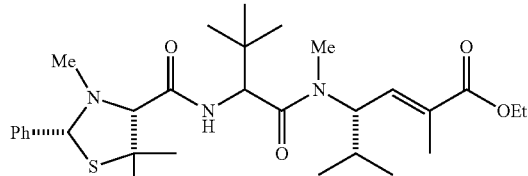
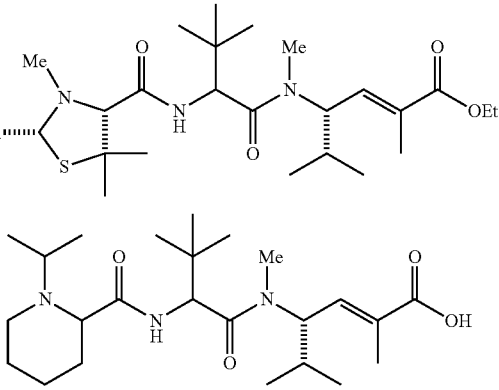
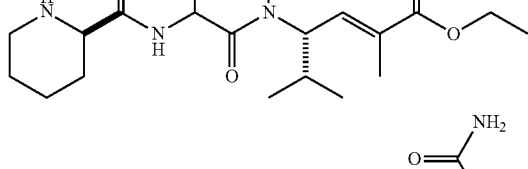
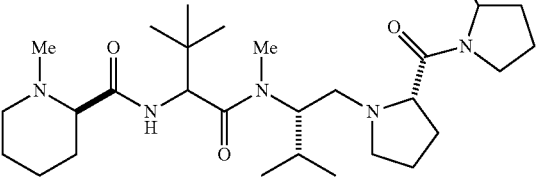
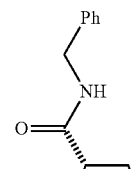
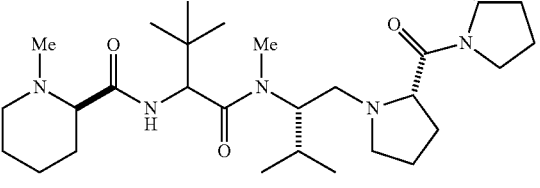
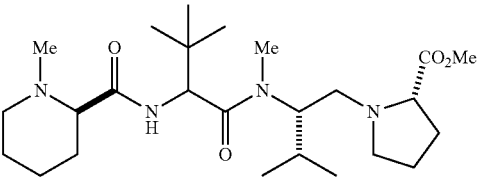
The following structures illustrate several exemplary types of compounds of class (Id). Additional compounds are described in fee Exemplification herein.

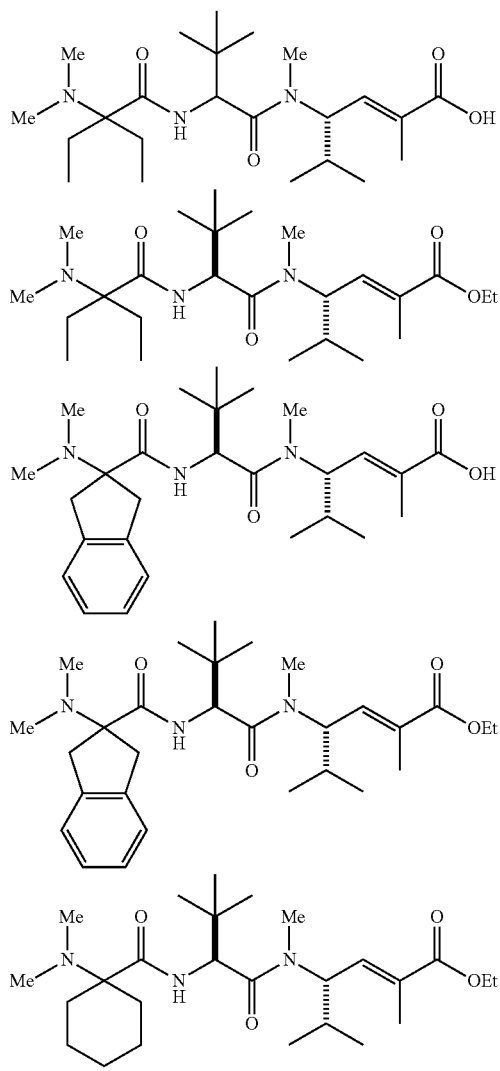

Other compounds of the invention will be readily apparent to the reader.

A number of important subclasses of each of the foregoing classes deserve separate mention; for example, one important subclass of class (Ia) includes those compounds having the structure of formula (Ia) in which $X_2$ is C=O; and the compound has the following structure:

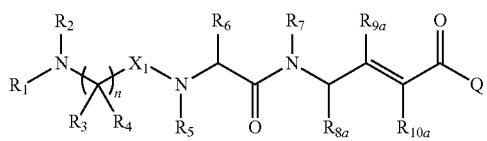

wherein $R_1$-$R_7$, n and Q are defined in classes and subclasses herein;

$R_{8a}$, $R_{9a}$ and $R_{10a}$ are each independently hydrogen, or an alkyl, heteroalkyl, aryl or heteroaryl moiety; and wherein any two $R_7$, $R_{8a}$, $R_{9a}$ and $R_{10a}$ groups may form a cyclic alkyl, heteroalkyl, -alkyl(aryl), -heteroalykl(aryl), -alkyl(heteroaryl) or -heteroalkyl(heteroaryl) moiety, or an aryl or heteroaryl moiety; and $X_1$ is $CR_AR_B$, $SO_2$ or C=O; wherein $R_A$ and $R_B$ are each independently hydrogen, alkyl, heteroalkyl, aryl or heteroaryl.

Another important subclass of class (Ia) includes those compounds having the structure of formula (Ia) in which $X_1$ is C=O; and the compound has the following structure:

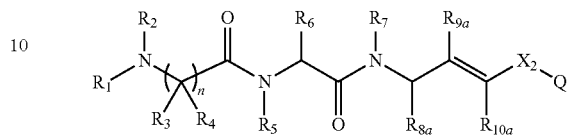

wherein $R_1$-$R_7$, n and Q are defined in classes and subclasses herein;

$R_{8a}$, $R_{9a}$ and $R_{10a}$ are each independently hydrogen, or an alkyl, heteroalkyl, aryl or heteroaryl moiety; and wherein any two $R_7$, $R_{8a}$, $R_{9a}$ and $R_{10a}$ groups may form a cyclic, alkyl, heteroalkyl, -alkyl(aryl), -heteroalykl(aryl), -alkyl(heteroaryl) or heteroalkyl(heteroaryl) moiety, or an aryl or heteroaryl moiety; and $X_2$ is $CR_AR_B$, $SO_2$ or C=O; wherein $R_A$ and $R_B$ are each independently hydrogen, alkyl, heteroalkyl, aryl or heteroaryl.

Another important subclass of class (Ia) Includes those compounds having the structure of formula (Ia) in which $X_1$ and $X_2$ are each C=O; n is 1; $R_3$ is hydrogen; $R_4$ is a moiety having the structure —$CR_{4a}R_{4b}R_{4c}$; and the compound has the following structure;

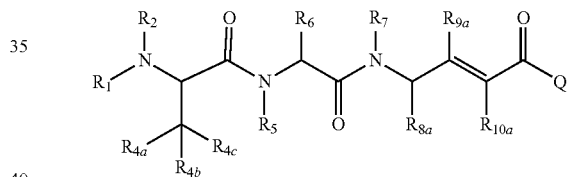

wherein $R_1$-$R_2$, $R_5$-$R_7$ and Q are defined, in classes and subclasses herein; and $R_{4a}$ and $R_{4b}$ are each independently hydrogen or lower alkyl or heteroalkyl, and $R_{4c}$ is aryl or heteroaryl; and $R_{8a}$, $R_{9a}$ and $R_{10a}$ are each independently hydrogen, or an alkyl, heteroalkyl, aryl or heteroaryl moiety; and wherein any two $R_7$, $R_{8a}$, $R_{9a}$ and $R_{10a}$ groups may form a cyclic alkyl, heteroalkyl, -alkyl(aryl), -heteroalykl(aryl), -alkyl(heteroaryl) or -heteroalkyl(heteroaryl) moiety, or an aryl or heteroaryl moiety.

Another important subclass of class (Ia) includes those compounds having the structure of formula (Ia) in which $X_1$ and $X_2$ are each C=O; Q is an optionally substituted nitrogen-containing cyclic moiety; and the compound has the following structure:

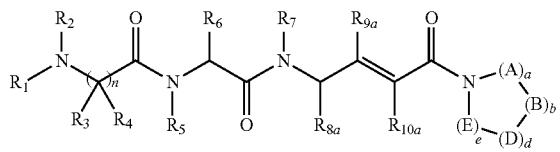

wherein $R_1$-$R_7$ and n are defined in classes and subclasses herein;

$R_{8a}$, $R_{9a}$ and $R_{10a}$ are each independently hydrogen, or an alkyl, heteroalkyl, aryl or heteroaryl moiety; and wherein any two $R_7$, $R_{8a}$, $R_{9a}$ and $R_{10a}$ groups may form a cyclic alkyl, heteroalkyl, -alkyl(aryl), -heteroalykl(aryl), -alkyl(heteroaryl) or -heteroalkyl(heteroaryl) moiety, or an aryl or heteroaryl moiety;

each occurrence of A, B, D or E is independently $CHR^i$, $CR^iR^{ii}$, O, S, $NR^iR^{ii}$, wherein each occurrence of $R^i$ and $R^{ii}$ is independently absent, hydrogen, —C(=O)$R^{iii}$, or an aliphatic, alicyclic, heteroaliphatic, heteroalicyclic, aryl or heteroaryl moiety; or wherein any two adjacent $R^i$, $R^{ii}$ or $R^{iii}$ groups, taken together, form a alicyclic or heteroalicyclic moiety containing 3-6 atoms or an aryl or heteroaryl moiety; wherein each occurrence of $R^{iii}$ is an aliphatic, alicyclic, heteroaliphatic, heteroalicyclic, aryl or heteroaryl moiety;

N and A, A and B, B and D, D and E, and E and N are each independently linked by a single or double bond as valency permits; and a, b, d and e are each independently 0, 1, 2, 3, 4, 5, 6 or 7, wherein the sum of a, b, d and e is 4-7.

Another important subclass of class (Ia) includes those compounds having the structure of formula (Ia) in which $X_1$ and $X_2$ are each C=O; Q is an optionally substituted nitrogen-containing cyclic moiety; n is 1; $R_3$ is hydrogen; $R_4$ is a moiety having the structure —$CR_{4a}R_{4b}R_{4c}$; and the compound has the following structure:

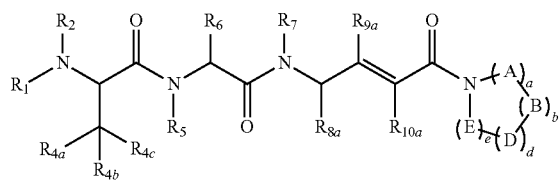

wherein $R_1$, $R_2$, $R_5$-$R_7$, A, B, D, E, a, b; d and e are defined in classes and subclasses herein;

$R_{4a}$ and $R_{4b}$ are each independently hydrogen or lower alkyl or heteroalkyl, and $R_{4c}$ is a substituted or unsubstitued aryl or heteroaryl group;

$R_{8a}$, $R_{9a}$ and $R_{10a}$ are each independently hydrogen, or an alkyl, heteroalkyl, aryl or heteroaryl moiety; and wherein any two $R_7$, $R_{8a}$, $R_{9a}$ and $R_{10a}$ groups may form a cyclic alkyl, heteroalkyl, -alkyl(aryl), heteroalykl(aryl), -alkyl(heteroaryl) or -heteroalkyl(heteroaryl) moiety, or an aryl or heteroaryl moiety.

A number of important subclasses of each of the foregoing subclasses of class (Ia) deserve separate mention; these subclasses include subclasses of the foregoing subclasses of class (Ia) in which:

i-a. $R_1$ and $R_2$ are independently hydrogen or substituted or unsubstituted, linear or branched, cyclic or acyclic, saturated or unsaturated lower alkyl, heteroalkyl, -alkyl(aryl) or acyl;

ii-a. $R_1$ is hydrogen and $R_2$ is substituted or unsubstituted, linear or branched, cyclic or acyclic, saturated or unsaturated lower alkyl, heteroalkyl, -alkyl(aryl) or acyl;

iii-a. $R_1$ is hydrogen and $R_2$ is substituted or unsubtituted, linear or branched, cyclic or acyclic, saturated or unsaturated lower alkyl;

iv-a. $R_1$ is hydrogen and $R_2$ is methyl, ethyl, propyl, butyl, pentyl, tert-butyl, i-propyl, —CH(CH$_3$)CH$_2$CH$_3$, —CH(CH$_3$)CH$_2$CH$_2$CH$_3$, —CH$_2$CH(CH$_3$)$_2$, —CH(CH$_3$)CH(CH$_3$)$_2$, —CH(CH$_3$)$_2$CH$_2$CH$_3$, —CH(CH$_3$)cyclobutyl, —CH(Et)$_2$, —CH(CH$_3$)$_2$C CH, cyclohexyl, cyclopentyl, cyclobutyl or cyclopropyl;

v-a. $R_1$ and $R_2$ are each hydrogen;

vi-a. The carbon atom bearing $R_3$ and $R_4$ is of S configuration;

vii-a. $R_3$ is hydrogen and $R_4$ is substituted or unsubstituted, linear or branched, cyclic or acyclic, or saturated or unsaturated lower alkyl, heteroalkyl or -alkyl(aryl) or substituted or unsubstituted aryl or heteroaryl;

viii-a. $R_3$ is hydrogen and $R_4$ is —$CR_{4a}R_{4b}R_{4c}$; wherein $R_{4a}$ and $R_{4b}$ are independently hydrogen, or a substituted or unsubtituted, linear or branched, cyclic or acyclic, saturated or unsaturated lower alkyl moiety and $R_{4c}$ is substituted or unsubstituted aryl or heteroaryl;

ix-a. $R_3$ is hydrogen and $R_4$ is —$CR_{4a}R_{4b}$Ph; wherein $R_{4a}$ and $R_{4b}$ are independently hydrogen, or a substituted or unsubstituted, linear or branched, cyclic or acyclic, saturated or unsaturated lower alkyl moiety;

x-a. $R_4$ is a substituted or unsubstituted 3-indole moiety;

xi-a. $R_3$ is hydrogen;

xii-a. $R_1$ and $R_4$, taken together, form a substituted or unsubstituted pyrrolidine group;

xiii-a. $R_1$ and $R_4$, taken together, form a substituted or unsubstituted piperidine group;

xiv-a. $R_1$ and $R_4$, taken together, form a substituted or unsubstituted thiazolidine group;

xv-a. $R_1$ and $R_4$, taken together, form a substituted or unsubstituted morpholine group;

xvi-a. $R_1$ and $R_4$, taken together, form a substituted or unsubstituted thiomorpholine group;

xvii-a. $R_1$ and $R_4$, taken together, form a substituted or unsubstituted indole group;

xviii-a. $R_1$ and $R_4$ are each independently substituted or unsubstituted, linear or blanched, cyclic or acyclic, or saturated or unsaturated lower alkyl heteroalkyl or -alkyl(aryl) or substituted or unsubstituted aryl or heteroaryl;

xix-a. $R_3$ and $R_4$ are, each independently substituted or unsubstituted, linear or branched, cyclic or acyclic, or saturated or unsaturated lower alkyl, -alkyl(aryl) or substituted or unsubstituted aryl;

xx-a. $R_3$ and $R_4$ are each, independently substituted or unsubstituted lower alkyl, aryl or heteroaryl;

xxi-a. $R_3$ and $R_4$ are each independently methyl, ethyl, propyl, butyl, pentyl, tert-butyl, i-propyl, —CH(CH$_3$)CH$_2$CH$_3$, —CH(CH$_3$)CH$_2$CH$_2$CH$_3$, —CH$_2$CH(CH)$_2$, —CH(CH$_3$)CH(CH$_3$)$_2$, —CH(CH$_3$)$_2$CH$_2$CH$_3$, —CH(CH$_3$)cyclobutyl, —CH(Et)$_2$, cyclohexyl, cyclopentyl, cyclobutyl, cyclopropyl, phenyl, —$C_{1-6}$alkyl$OR^a$, —$C_{1-6}$alkyl$SR^a$ or —$CR^aR^bR^c$; wherein $R^a$ and $R^b$ are independently hydrogen, substituted or unsubstituted, linear or branched, cyclic or acyclic, or saturated or unsaturated lower alkyl and $R^c$ is substituted or unsubstituted aryl or heteroaryl;

xxii-a. $R^3$ and $R^4$ are each, independently methyl, ethyl, propyl, butyl, pentyl, tert-butyl, i-propyl, —CH(CH$_3$)CH$_2$CH$_3$, —CH(CH$_3$)CH$_2$CH$_2$CH$_3$, —CH$_2$CH(CH$_3$)$_2$, —CH(CH$_3$)CH(CH$_3$)$_2$, —CH(CH$_3$)$_2$CH$_2$CH$_3$, —CH(CH$_3$)cyclobutyl, —CH(Et)$_2$, cyclohexyl, cyclopentyl, cyclobutyl, cyclopropyl, phenyl, —$C_{1-6}$alkyl$OR^a$, —$C_{1-6}$alkyl$SR^a$ or —$CR^bR^c$Ph; wherein $R^a$ is hydrogen, substituted or unsubstituted, linear or branched, cyclic or acyclic, or saturated or unsaturated lower alkyl and $R^b$ and $R^c$ are each independently substituted or unsubstituted linear or branched, cyclic or acyclic, or saturated or unsaturated lower alkyl;

xxiii-a. $R_3$ and $R_4$ are each ethyl;

xxiv-a. $R_3$ is phenyl and $R_4$ is lower alkyl;

xxv-a. $R_3$ is phenyl and $R_4$ is ethyl;

xxvi-a. $R_3$ and $R_4$, taken together, form a substituted or unsubstituted cycloalkyl group;
xxvii-a. $R_3$ and $R_4$, taken together, form a cyclohexyl group;
xxviii-a. $R_3$ and $R_4$, taken together, form a substituted or unsubstituted cycloalkyl(aryl) group;
xxix-a. $R_5$ is hydrogen;
xxx-a. $R_6$ is substituted or unsubstituted, linear or branched, cyclic or acyclic, saturated or unsaturated lower alkyl;
xxxi-a. $R_6$ is methyl, ethyl, propyl, butyl, pentyl, tert-butyl, i-propyl, —CH(CH$_3$)CH$_2$CH$_3$, —CH$_2$CH(CH$_3$)$_2$, cyclohexyl, cyclopentyl, cyclobutyl or cyclopropyl;
xxxii-a. $R_6$ is tert-butyl;
xxxiii-a. The $R_6$-bearing carbon atom is of S configuration;
xxxiv-a. $R_7$ is substituted or unsubstituted, linear or branched, cyclic or acyclic, saturated or unsaturated lower alkyl;
xxxv-a. $R_7$ is methyl;
xxxvi-a. R is —CH($R_{8a}$)C($R_{9a}$)..C($R_{10a}$)—; and
 a) $R_{8a}$ is substituted or unsubstituted, linear or branched, cyclic or acyclic, saturated or unsaturated lower alkyl;
 b) $R_{8a}$ is iso-propyl;
 c) The $R_{8a}$-bearing carbon atom is of S configuration;
 d) $R_{9a}$ is hydrogen or substituted or unsubstituted, linear or branched, cyclic or acyclic, saturated or unsaturated lower alkyl;
 e) $R_{9a}$ is hydrogen;
 f) $R_{10a}$ is hydrogen or substituted or unsubstituted, linear or branched, cyclic or acyclic, saturated or unsaturated lower alkyl;
 g) $R_{10a}$ is methyl;
xxxvii-a. n is 1;
xxxviii-a. $X_1$ is C=O;
xxxix-a. $X_1$ is CH$_2$;
xl-a. $X_1$ is SO$_2$;
xli-a. $X_2$ is C=O;
xlii-a. $X_2$ is CH$_2$;
xliii-a. $X_2$ is SO$_2$;
xliv-a. Q is OR$^{Q'}$, SR$^{Q'}$, NR$^{Q'}$R$^{Q''}$, N$_3$, =N—OH, or a moiety selected from the group consisting of:

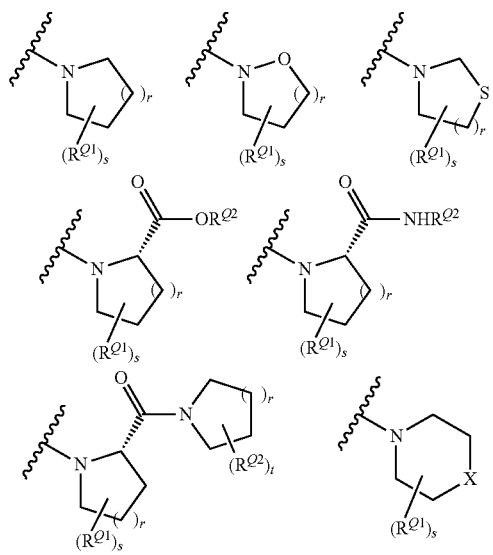

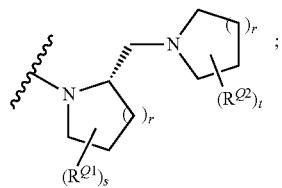

wherein each occurrence of r is 0, 1 or 2; s and t are independently an integer from 0-8; X is O, S, or NR$^K$; each occurrence of R$^{Q1}$ and R$^{Q2}$ is independently hydrogen, halogen, —CN, —S(O)$_h$R$^J$, —NO$_2$, —COR$^J$, —CO$_2$R$^J$, —NR$^J$COR$^J$, —NR$^J$CO$_2$R$^J$, —CONR$^J$R$^J$, —CO(NOR$^J$)R$^J$, aliphatic, alicyclic, heteroaliphatic, heteroalicyclic, aryl or heteroaryl moiety, or —Z$_1$R$^f$; wherein h is 1 or 2; and Z$_1$ is independently —O—, —S—, NR$^K$, —C(O)—, wherein each occurrence of R$^J$ and R$^K$ is independently hydrogen, COR$^L$, COOR$^L$, CONR$^L$R$^M$, —NR$^L$R$^M$, —S(O)$_2$R$^L$, or an aliphatic, alicyclic, heteroaliphatic, heteroalicyclic, aryl or heteroaryl moiety, and wherein each occurrence of R$^L$ and R$^M$ is independently hydrogen, or an aliphatic, alicyclic, heteroaliphatic, heteroalicyclic, aryl or heteroaryl moiety; and R$^{Q'}$ and R$^{Q''}$ are independently hydrogen, or a substituted or unsubstituted, linear or branched, cyclic or acyclic alkyl or heteroalkyl moiety, or a substituted or unsubstituted aryl or heteroaryl moiety; or R$^{Q'}$ and R$^{Q''}$, taken together with the nitrogen atom to which they are attached, form a substituted or unsubstituted heterocyclic, aryl or heteroaryl moiety; and
 xlv-a. Q is OR$^{Q'}$, SR$^{Q'}$, NR$^{Q'}$R$^{Q''}$, N$_3$, =N—OH, or a moiety selected from the group consisting of:

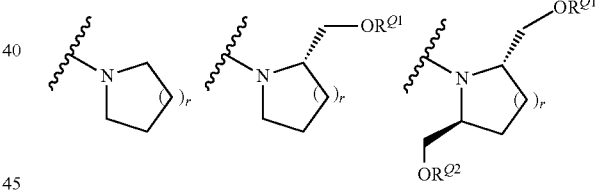

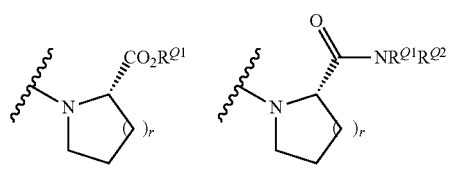

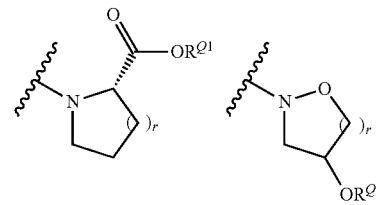

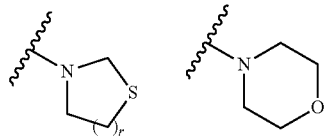

-continued

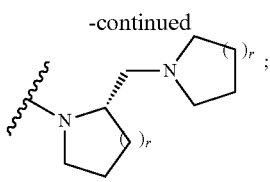

wherein each occurrence of r is 0, 1 or 2; s and t are independently an integer from 0-8; each occurrence of $R^{Q1}$ and $R^{Q2}$ is independently hydrogen, or a substituted or unsubstituted, linear or branched, cyclic or acyclic alkyl or heteroalkyl moiety, or a substituted or unsubstituted aryl or heteroaryl moiety; or $R^{Q1}$ and taken together with the nitrogen atom to which they are attached, form a substituted or unsubstituted heterocyclic moiety; and $R^{Q'}$ and $R^{Q''}$ are independently hydrogen, or a substituted or unsubstituted, linear or branched, cyclic or acyclic alkyl or heteroalkyl moiety, or a substituted or unsubstituted aryl or heteroaryl moiety; or $R^{Q'}$ and $R^{Q''}$, taken together with the nitrogen atom to which they are attached, form a substituted or unsubstituted heterocyclic, aryl or heteroaryl moiety; and/or xliv-a. Q is $OR^{Q'}$, $SR^{Q'}$, $NR^{Q'}R^{Q''}$, $N_3$, =N—OH, or a moiety selected from the group consisting of:

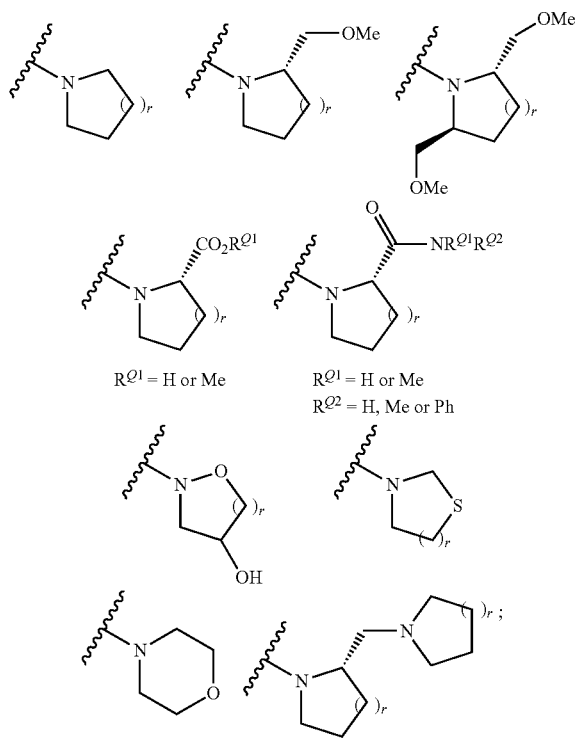

wherein each occurrence of r is 0, 1 or 2; and $R^{Q'}$ and $R^{Q''}$ are independently hydrogen, or a substituted or unsubstituted, linear or branched, cyclic or acyclic alkyl or heteroalkyl moiety, or a substituted or unsubstituted aryl or heteroaryl moiety; or $R^{Q'}$ and $R^{Q''}$, taken together with the nitrogen atom to which they are attached, form a substituted or unsubstituted heterocyclic, aryl or heteroaryl moiety.

An important subclass of class (Ib) includes those compounds having the structure of formula (Ib) in which R is —C($R_{8b}$)C($R_{9b}$)N($R_{10b}$)V($R_{11b}$)—; and the compound has the following structure;

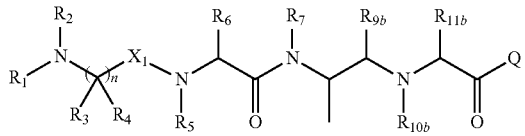

wherein $R_1R_7$, n, $X_1$ and Q are defined in classes and subclasses herein;

$R_{8b}$, $R_{9b}$, $R_{10b}$ and $R_{11b}$ are each independently absent, hydrogen, —(C=O)$R_L$ or an aliphatic, alicyclic, heteroaliphatic, heteroalicyclic, aryl or heteroaryl moiety, wherein each occurrence of $R_L$ is independently hydrogen, OH, $OR_M$, or an aliphatic, alicyclic, heteroaliphatic, heteroalicyclic, aryl or heteroaryl moiety, or wherein any two $R_{8b}$, $R_{9b}$, $R_{10b}$ and $R_{11b}$ groups, taken together, form a alicyclic or heteroalicyclic moiety, or an aryl or heteroaryl moiety; wherein $R_M$ is an aliphatic, alicyclic, heteroaliphatic, heteroalicyclic, aryl or heteroaryl moiety; and $NR_7$ and $CR_{8b}$, $CR_{8b}$ and $CR_{9b}$, $CR_{9b}$ and $NR_{10b}$, $NR_{10b}$ and $CR_{11b}$ are each independently linked by a single or double bond as valency permits.

Another important subclass of class (Ib) includes those compounds having the structure of formula (Ib) in which $X_1$ is C=O; R is —C($R_{8b}$)C($R_{9b}$)N($R_{10b}$)C($R_{11b}$)—; n is 1; $R_3$ is hydrogen; $R_4$ is a moiety having the structure —$CR_{4a}R_{4b}R_c$; and the compound has the following structure:

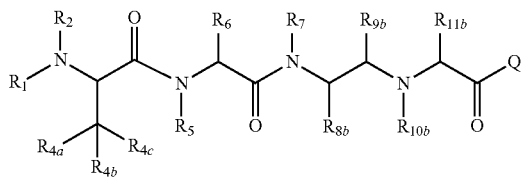

wherein $R_1$-$R_2$, $R_5$-$R_7$ and Q' are defined in classes and subclasses herein; and $R_{4a}$ and $R_{4b}$ are each independently hydrogen or lower alkyl and $R_{4c}$ is aryl or heteroaryl;

$R_{8a}$, $R_{9b}$, $R_{10b}$ and $R_{11b}$ are each independently absent, hydrogen, —(C=O)$R_L$ or an aliphatic, alicyclic, heteroaliphatic, heteroalicyclic, aryl or heteroaryl moiety, wherein each occurrence of $R_L$ is independently hydrogen, OH, $OR_M$, or an aliphatic, alicyclic, heteroaliphatic, heteroalicyclic, aryl or heteroaryl moiety, or wherein any two $R_{8b}$, $R_{9b}$, $R_{10b}$ and $R_{11b}$ groups, taken together, form a alicyclic or heteroalicyclic moiety, or an aryl or heteroaryl moiety; wherein $R_M$ is an aliphatic, alicyclic, heteroaliphatic, heteroalicyclic, aryl or heteroaryl moiety; and $NR_7$ and $CR_{8b}$, $CR_{8b}$ and $CR_{9b}$, $CR_{9b}$ and $NR_{10b}$, $NR_{10b}$ and $CR_{11b}$ are each independently linked by a single or double bond as valency permits.

Another important subclass of class (Ib) includes those compounds having the structure of formula (Ib) in which R is —C($R_{8b}$)C($R_{9b}$)N($R_{10b}$)C($R_{11b}$)—; $R_{10b}$ and $R_{11b}$, taken together, form a substituted or unsubstituted cyclic heteroalkyl or heteroaryl moiety; and the compound has the following structure:

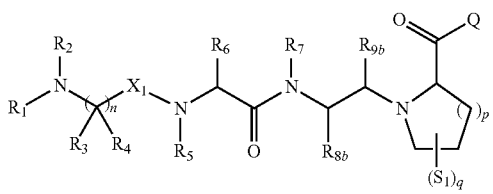

wherein $R_1$-$R_7$, n and Q are defined in classes and subclasses herein;

p is 1, 2, 3 or 4;

q is 0-12;

each occurrence of $S_1$ is independently an aliphatic, alicyclic, heteroaliphatic, heteroalicyclic, aryl or heteroaryl moiety, or any two adjacent $S_1$ moieties, taken together, may form an an alicyclic, heteroalicyclic, aryl or heteroaryl moiety;

$R_{8b}$ and $R_{9b}$ are each independently absent, hydrogen, —C(=O)$R_L$ or an aliphatic, alicyclic, heteroaliphatic, heteroalicyclic, aryl or heteroaryl moiety, wherein each occurrence of $R_L$ is independently hydrogen, OH, O$R_M$, or an aliphatic, alicyclic, heteroaliphatic, heteroalicyclic, aryl or heteroaryl moiety, or wherein $R_{8b}$ and $R_{9b}$, taken together, form a alicyclic or heteroalicyclic moiety, or an aryl or heteroaryl moiety; wherein $R_M$ is an aliphatic, alicyclic, heteroaliphatic, heteroalicyclic, aryl or heteroaryl moiety; and $NR_7$ and $CR_8$, and $CR_{8b}$ and $CR_{9b}$ are each independently linked by a single or double bond as valency permits.

Another important subclass of class (Ib) includes those compounds having the structure of formula (Ib) in which n is 1; R is —C($R_{8b}$)C($R_{9b}$)N($R_{10b}$)C($R_{11b}$)—; $R_{10b}$ and $R_{11b}$, taken together, form a substituted or unsubstituted cyclic heteroalkyl or heteroaryl moiety; $R_4$ is a moiety having the structure —C$R_{4a}R_{4b}R_{4c}$; and the compound has the following structure:

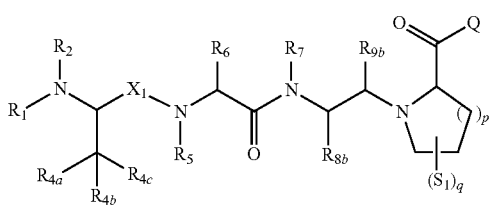

wherein $R_1$-$R_7$, $X_1$ and Q are defined in classes and subclasses herein;

p is 1, 2, 3 or 4;

is 0, 1, 2, 3, 4, 5 or 6;

each occurrence of $S_1$ is independently an aliphatic, alicyclic, heteroaliphatic, heteroalicyclic, aryl or heteroaryl moiety, or any two adjacent $S_1$ moieties, taken together, may form an an alicyclic, heteroalicyclic, aryl or heteroaryl moiety;

$R_{4a}$ and are each independently hydrogen or lower alkyl or heteroalkyl; and $R_{4c}$ is aryl or heteroaryl;

$R_{8b}$ and $R_{9b}$ are each independently hydrogen, —C(=O)$R_L$ or an aliphatic, alicyclic, heteroaliphatic, heteroalicyclic, aryl or heteroaryl moiety, wherein each occurrence of $R_L$ is independently hydrogen, OH, O$R_M$, or an aliphatic, alicyclic, heteroaliphatic, heteroalicyclic, aryl or heteroaryl moiety, or wherein $R_{8b}$ and $R_{9b}$, taken together, form a alicyclic or heteroalicyclic moiety, or an aryl or heteroaryl moiety; wherein $R_M$ is an aliphatic, alicyclic, heteroaliphatic, heteroalicyclic, aryl or heteroaryl moiety; and $NR_7$ and $CR_{8b}$, and $CR_{8b}$ and $CR_{9b}$ are each independently linked by a single or double bond as valency permits.

Another important subclass of class (Ib) includes those compounds having the structure of formula (Ib) in which R is —C($R_{8c}$)C($R_{9c}$)C($R_{10c}$)C($R_{11c}$)OC($R_{12c}$)—; and the compound has the following structure:

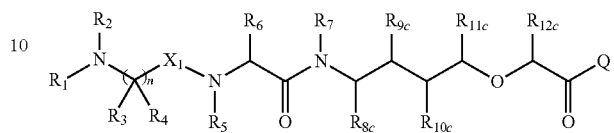

wherein $R_1$-$R_7$, n, $X_1$ and Q are defined in classes and subclasses herein;

$R_{8c}$, $R_{9c}$, $R_{10c}$, $R_{11c}$ and $R_{12c}$ and are each independently absent, hydrogen, —C(=O)$R_L$ or an aliphatic, alicyclic, heteroaliphatic, heteroalicyclic, aryl or heteroaryl moiety, wherein each occurrence of $R_L$ is independently hydrogen, OH, O$R_M$, or an aliphatic, alicyclic, heteroaliphatic, heteroalicyclic, aryl or heteroaryl moiety, or wherein any two $R_{8c}$, $R_{9c}$, $R_{10c}$, $R_{11c}$ and $R_{12c}$ groups, taken together, form a alicyclic or heteroalicyclic moiety, or an aryl or heteroaryl moiety; wherein $R_M$ is an aliphatic, alicyclic, heteroaliphatic, heteroalicyclic, aryl or heteroaryl moiety; and $NR_7$ and $CR_{8c}$, $CR_{8c}$ and $CR_{9c}$, $CR_{9c}$ and $CR_{10c}$, and $CR_{10c}$ and $CR_{11c}$ are each independently linked by a single, or double bond as valency permits.

Another important subclass of class (Ib) includes those compounds having the structure of formula (Ib) in which $X_1$ is C=O; n is 1; $R_3$ is hydrogen; $R_4$ is a moiety having the structure —C$R_{4a}R_{4b}R_{4c}$; R is —C($R_{8c}$)C($R_{9c}$)C($R_{10c}$)C($R_{11c}$)OC($R_{12c}$)—; and the compound has the following structure:

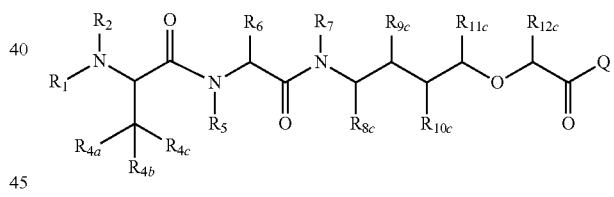

wherein $R_1$, $R_2$, $R_5$-$R_7$ and Q are defined in classes and subclasses herein;

$R_4$ and $R_{4b}$ are each independently hydrogen, or lower alkyl or heteroalkyl; and $R_{4c}$ is aryl or heteroaryl;

$R_{8c}$, $R_{9c}$, $R_{10c}$, $R_{11c}$ and $R_{12c}$ are each independently absent, hydrogen, —C(=O)$R_L$ or an aliphatic, alicyclic, heteroaliphatic, heteroalicyclic, aryl or heteroaryl moiety, wherein each occurrence of $R_L$ is independently hydrogen, OH, O$R_M$, or an aliphatic, alicyclic, heteroaliphatic, heteroalicyclic, aryl or heteroaryl moiety, or wherein any two $R_{8c}$, $R_{9c}$, $R_{10c}$, $R_{11c}$ and $R_{12c}$ groups, taken together, form a alicyclic or heteroalicyclic moiety, or an aryl or heteroaryl moiety; wherein $R_M$ is an aliphatic, alicyclic, heteroaliphatic, heteroalicyclic, aryl or heteroaryl moiety; and $NR_7$ and $CR_{8c}$, $CR_{8c}$ and $CR_{9c}$, $CR_{9c}$ and $CR_{10c}$, and $CR_{10c}$ and $CR_{11c}$ are each independently linked by a single or double bond as valency permits.

A number of important subclasses of each of the foregoing subclasses of class (Ib) deserve separate mention; these subclasses include subclasses of the foregoing subclasses of class (Ib) in which:

i-b. $R_1$ and $R_2$ are independently hydrogen or substituted or unsubstituted, linear or branched, cyclic or acyclic, or saturated or unsaturated lower alkyl, heteroalkyl, -alkyl(aryl) or acyl;

ii-b. $R_1$ is hydrogen and $R_2$ is substituted or unsubstituted, linear or branched, cyclic or acyclic, saturated or unsaturated lower alkyl, heteroalkyl, -alkyl(aryl) or acyl;

iii-b. $R_1$ is hydrogen and $R_2$ is substituted or unsubstituted, linear or branched, cyclic or acyclic, saturated or unsaturated lower alkyl;

iv-b. $R_1$ is hydrogen and $R_2$ is methyl, ethyl, propyl, butyl, pentyl, tert-butyl, i-propyl, —CH($CH_3$)$CH_2CH_3$, —CH($CH_3$)$CH_2CH_2CH_3$, —$CH_2$CH($CH_3$)$_2$, —CH($CH_3$)CH($CH_3$)$_2$, —CH($CH_3$)$_2CH_2CH_3$, —CH($CH_3$)cyclobutyl, —CH(Et)$_2$, —CH($CH_3$)$_2$C CH, cyclohexyl, cyclopentyl, cyclobutyl or cyclopropyl;

v-b. $R_1$ and $R_2$ are each hydrogen;

vi-b. The carbon atom bearing $R_3$ and $R_4$ is of S configuration;

vii-b. $R_3$ is hydrogen and $R_4$ is substituted or unsubstituted, linear or branched, cyclic or acyclic, or saturated or unsaturated lower alkyl, heteroalkyl or -alkyl(aryl) or substituted or unsubstituted aryl or heteroaryl;

viii-b. $R_3$ is hydrogen and $R_4$ is —$CR_{4a}R_{4b}R_{4c}$; wherein $R_{4a}$ and $R_{4b}$ are independently hydrogen, or a substituted or unsubstituted, linear or branched, cyclic or acyclic, saturated or unsaturated lower alkyl moiety and $R_{4c}$ is substituted or unsubstituted aryl or heteroaryl;

ix-b. $R_3$ is hydrogen and $R_4$ is —$CR_{4a}R_{4b}$Ph; wherein $R_{4a}$ and $R_{4b}$ are independently hydrogen, or a substituted or unsubstituted, linear or branched, cyclic or acyclic, saturated or unsaturated lower alkyl moiety;

x-b. $R_4$ is a substituted or unsubstituted 3-indole moiety;

xi-b. $R_3$ is hydrogen;

xii-b. $R_1$ and $R_4$, taken together, form a substituted or unsubstituted pyrrolidine group;

xiii-b. $R_1$ and $R_4$ taken together, form a substituted or unsubstituted piperidine group;

xiv-b. $R_1$ and $R_4$, taken together, form a substituted or unsubstituted thiazolidine group;

xv-b. $R_1$ and $R_4$, taken together, form a substituted or unsubstituted morpholine group;

xvi-b. $R_1$ and $R_4$, taken together, form a substituted or unsubstituted thiomorpholine group;

xvii-b. $R_1$ and $R_4$, taken together, form a substituted or unsubstituted indole group;

xviii-b. $R_3$ and $R_4$ are each independently substituted or unsubstituted, linear or branched, cyclic or acyclic, or saturated or unsaturated lower alkyl, heteroalkyl or -alkyl(aryl) or substituted or unsubstituted aryl or heteroaryl;

xix-b. $R_3$ and $R_4$ are each independently substituted or unsubstituted, linear or branched, cyclic or acyclic, or saturated or unsaturated lower alkyl, -alkyl(aryl) or substituted or unsubstituted aryl;

xx-b. $R_3$ and $R_4$ are each independently substituted or unsubstituted lower alkyl, aryl or heteroaryl;

xxi-b. $R_3$ and $R_4$ are each independently methyl, ethyl, propyl, butyl, pentyl, tert-butyl, i-propyl, —CH($CH_3$)$CH_2CH_3$, —CH($CH_3$)$CH_2CH_2CH_3$, —$CH_2$CH($CH_3$)$_2$, —CH($CH_3$)CH($CH_3$)$_2$, —CH($CH_3$)$_2CH_2CH_3$, —CH($CH_3$)cyclobutyl, —CH(Et)$_2$, cyclohexyl, cyclopentyl, cyclobutyl, cyclopropyl, phenyl, —$C_{1-6}$alkylO$R^a$, —$C_{1-6}$alkylS$R^a$ or —$CR^aR^bR^c$; wherein $R^a$ and $R^b$ are independently hydrogen, substituted or unsubstituted, linear or branched, cyclic or acyclic, or saturated or unsaturated lower alkyl and $R^c$ is substituted or unsubstituted aryl or heteroaryl;

xxii-b. $R_3$ and $R_4$ are each independently methyl ethyl, propyl, butyl, pentyl, tert-butyl, i-propyl, —CH($CH_3$)$CH_2CH_3$, —CH($CH_3$)$CH_2CH_2CH_3$, —$CH_2$CH($CH_3$)$_2$, —CH($CH_3$)CH($CH_3$)$_2$, —CH($CH_3$)$_2CH_2CH_3$, CH($CH_3$)cyclobutyl, —CH(Et)$_2$, cyclohexyl, cyclopentyl, cyclobutyl, cyclopropyl, phenyl, —$C_{1-6}$alkylO$R^a$, —$C_{1-6}$alkylS$R^a$ or —$CR^bR^c$Ph; wherein $R^a$ is hydrogen, substituted or unsubstituted, linear or branched, cyclic or acyclic, or saturated or unsaturated lower alkyl and $R^b$ And $R^c$ are each independently substituted or unsubstituted linear or branched, cyclic or acyclic, or saturated or unsaturated lower alkyl;

xxiii-b. $R_3$ and $R_4$ are each ethyl;

xxiv-b. $R_3$ is phenyl and $R_4$ is lower alkyl;

xxv-b. $R_3$ is phenyl and $R_4$ is ethyl;

xxvi-b. $R_3$ and $R_4$, taken together, form a substituted or unsubstituted cycloalkyl group;

xxvii-b. $R_3$ and $R_4$, taken together, form a cyclohexyl group;

xxviii-b. $R_3$ and $R_4$, taken together, form a substituted or unsubstituted cycloalkyl(aryl) group;

xxix-b. $R_5$ is hydrogen;

xxx-b. $R_6$ is substituted or unsubstituted, linear or branched, cyclic or acyclic, or saturated or unsaturated lower alkyl;

xxxi-b. $R_6$ is methyl, ethyl, propyl, butyl, pentyl, tert-butyl, i-propyl, —CH($CH_3$)$CH_2CH_3$, —$CH_2$CH($CH_3$)$_2$, cyclohexyl, cyclopentyl, cyclobutyl or cyclopropyl;

xxxii-b. $R_6$ is tert-butyl;

xxxiii-b. The $R_6$-bearing carbon atom is of S configuration;

xxxiv-b. $R_7$ is substituted or unsubstituted, linear or branched, cyclic or acyclic, or saturated or unsaturated lower alkyl;

xxxv-b. $R_7$ is methyl;

xxxvi-b. R is —$C(R_{8b})C(R_{9b})N(R_{10b})CR_{11b}$— and
a) $R_{8b}$ is substituted or unsubstituted, linear or branched, cyclic or acyclic, or saturated or unsaturated lower alkyl;
b) $R_{8b}$ is iso-propyl;
c) The $R_{8b}$-bearing carbon atom is of S configuration;
d) $R_{9b}$ is hydrogen or substituted or unsubstituted, linear or branched, cyclic or acyclic, or saturated or unsaturated lower alkyl;
e) $R_{10b}$ is hydrogen, substituted or unsubstituted, linear or branched, cyclic or acyclic, or saturated or unsaturated lower alkyl or acyl;
f) $R_{10b}$ is hydrogen, methyl or acetyl;
g) $R_{10b}$ and $R_{11b}$, taken, together, form a substituted or unsubstituted pyrrolidine ring; or
h) $R_{9b}$ and $R_{11b}$, taken together, form a substituted or unsubstituted thiazole ring;

xxxvii-b. R is —$C(R_{8c})C(R_{9c})C(R_{10c})CR_{11c}OCR_{12c}$— and
a) $R_{8c}$ is substituted or unsubstituted, linear or branched, cyclic or acyclic, or saturated or unsaturated lower alkyl;
b) $R_{8c}$ is iso-propyl;
c) The $R_{8c}$-bearing carbon atom is of S configuration;
d) $R_{9c}$ and $R_{10c}$ are each independently hydrogen or substituted or unsubstituted, linear or branched, cyclic or acyclic, or saturated or unsaturated lower alkyl;
e) $CR_{9c}$ and $CR_{10c}$ are linked via a double bond;

f) CR$_{9c}$ and CR$_{10c}$ are linked via a double bond and R$_{9c}$ is hydrogen; or g) CR$_{9c}$ and CR$_{10c}$ are linked via a double bond and R$_{10c}$ is methyl;

xxxviii-b. n is 1;

xxxix-b. X$_1$ is C=O;

xl-b. X$_1$ is CH$_2$;

xli-b. X$_1$ is SO$_2$;

xlii-b. Q is OR$^{Q'}$, SR$^{Q'}$, NR$^{Q'}$R$^{Q''}$, N$_3$, =N—OH, or a moiety selected from the group consisting of:

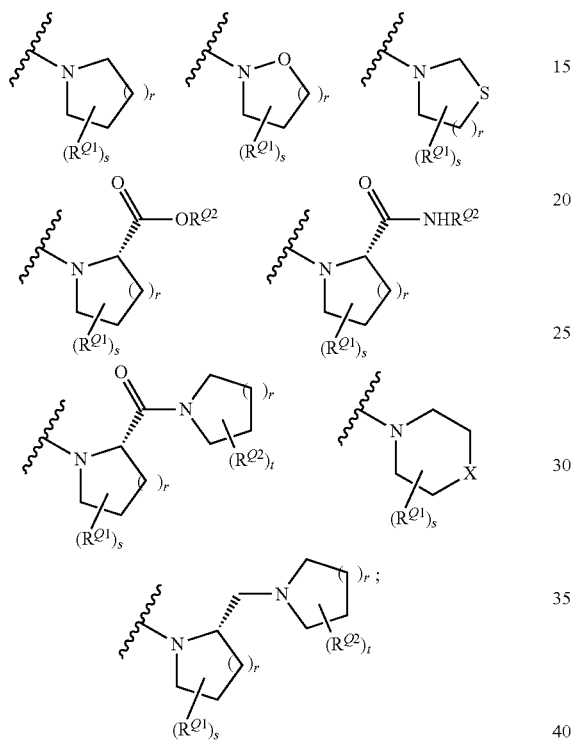

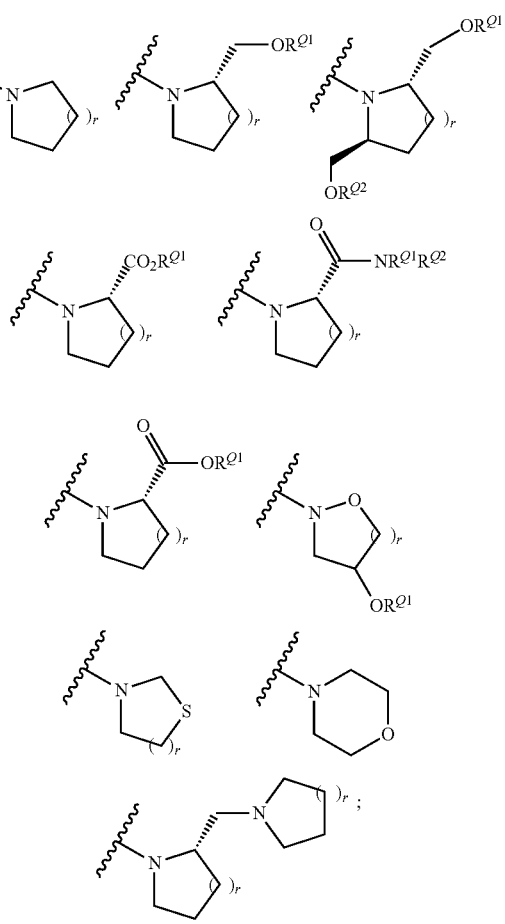

wherein each occurrence of r is 0, 1 or 2; s and t are independently an integer from 0-8; X is O, S, or NR$^K$; each occurrence of R$^{Q1}$ and R$^{Q2}$ is independently hydrogen, halogen, —CN, —S(O)$_h$R$^J$, —NO$_2$, —COR$^J$, —CO$_2$R$^J$, —NR$^J$COR$^J$, NR$^J$CO$^J$R$^J$, —CONR$^J$R$^J$, —CO(NOR$^J$)R$^J$, aliphatic, alicyclic, heteroaliphatic, heteroalicyclic, aryl or heteroaryl moiety, or —Z$_1$R$^J$; wherein h is 1 or 2; and Z$_1$ is independently —O—, —S—, NR$^K$, —C(O)—, wherein each occurrence of R$^J$ and R$^K$ is independently hydrogen, COR$^L$, COOR$^L$, CONR$^L$R$^M$, —NR-$^L$R$^M$, —S(O)$_2$R$^L$; or an aliphatic, alicyclic, heteroaliphatic, heteroalicyclic, aryl or heteroaryl moiety, and wherein each occurrence of R$^L$ and R$^M$ is independently hydrogen, or an aliphatic, alicyclic, heteroaliphatic, heteroalicyclic, aryl or heteroaryl moiety; and R$^{Q'}$ and R$^{Q''}$ are independently hydrogen, or a substituted or unsubstituted, linear or branched, cyclic or acyclic alkyl or heteroalkyl moiety, or a substituted or unsubstituted aryl or heteroaryl moiety; or R$^{Q'}$ and R$^{Q''}$, taken together with the nitrogen atom to which they are attached, form a substituted or unsubstituted heterocyclic, aryl or heteroaryl moiety;

xliii-b. Q is OR$^{Q'}$, SR$^{Q'}$, NR$^{Q'}$R$^{Q''}$, N$_3$, =N—OH, or a moiety selected from the group consisting of:

wherein each occurrence of r is 0, 1 or 2; s and t are independently an integer from 0-8; each occurrence of R$^{Q1}$ and R$^{Q2}$ is independently hydrogen, or a substituted or unsubstituted, linear or branched, cyclic or acyclic alkyl or heteroalkyl moiety, or a substituted or unsubstituted aryl or heteroaryl moiety; or R$^{Q1}$ and R$^{Q2}$, taken together with the nitrogen atom to which they are attached, form a substituted or unsubstituted heterocyclic moiety; and R$^{Q'}$ and R$^{Q''}$ are independently hydrogen, or a substituted or unsubstituted, linear or branched, cyclic or acyclic alkyl or heteroalkyl moiety, or a substituted or unsubstituted aryl or heteroaryl moiety; or R$^{Q'}$ and R$^{Q''}$, taken together with the nitrogen atom to which they are attached, form a substituted or unsubstituted heterocyclic, aryl or heteroaryl moiety; and/or xliv-b. Q is OR$^{Q'}$, SR$^{Q'}$, NR$^{Q'}$R$^{Q''}$, N$_3$, =N—OH, or a moiety selected from the group consisting of:

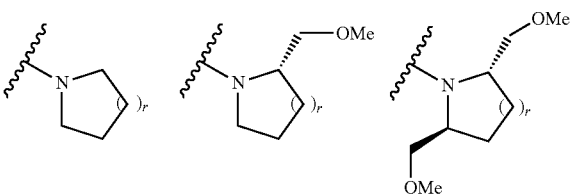

-continued

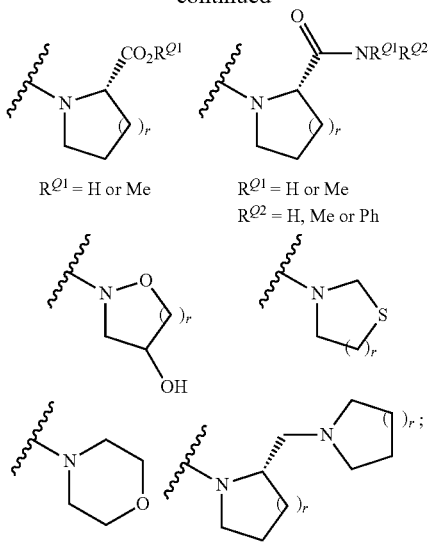

wherein each occurrence of r is 0, 1 or 2; and $R^{Q'}$ and $R^{Q''}$ are independently hydrogen, or a substituted or unsubstituted, linear or branched, cyclic or acyclic alkyl or heteroalkyl moiety, or a substituted or unsubstituted aryl or heteroaryl moiety; or $R^{Q'}$ and $R^{Q''}$ taken together with the nitrogen atom to which they are attached, form a substituted or unsubstituted heterocyclic, aryl or heteroaryl moiety.

An important subclass of class (Ic) includes those compounds having the structure of formula (Ic) in which $X_2$ is C=O; R is —CH($R_{8a}$)C($R_{9a}$)=C($R_{10a}$)—; j is 0; l and m are each 1; $R_3$ is hydrogen; G is $CR_{G1}$; M is $CR_{M1}R_{M2}$, and the compound has the structure:

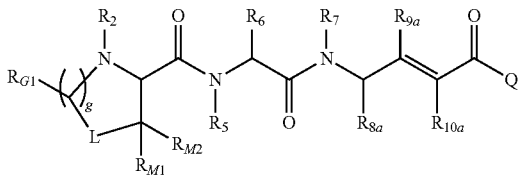

wherein $R_2$, $R_5$-$R_7$ and Q are defined in classes and subclasses herein;
g is 1, 2, 3 or 4;
$R_{8a}$, $R_{9a}$ and $R_{10a}$ are each independently hydrogen, or an alkyl, heteroalkyl, aryl or heteroaryl moiety; and wherein any two $R_7$, $R_{8a}$, $R_{9a}$ and $R_{10a}$ groups may form a cyclic alkyl, heteroalkyl, -alkyl(aryl), -heteroalykl(aryl), -alkyl(heteroaryl) or -heteroalkyl(heteroaryl) moiety, or an aryl, or heteroaryl moiety;
L is $CR_{L1}R_{L2}$, S, O or $NR_{L3}$, wherein each occurrence of $R_{L1}$, $R_{L2}$ and $R_{L3}$ is independently hydrogen or an aliphatic, alicyclic, heteroaliphatic, heteroalicyclic, aryl or heteroaryl moiety;
each occurrence of $R_{G1}$, $R_{M1}$ and $R_{M2}$ is each independently hydrogen or an aliphatic, alicyclic, heteroaliphatic, heteroalicyclic, aryl or heteroaryl moiety;
wherein any two adjacent $R_{L1}$, $R_{L2}$, $R_{L3}$, $R_{G1}$, $R_{M1}$ or $R_{M2}$ groups, taken together, form a substituted or unsubstituted alicyclic or heteroalicyclic moiety containing 3-6 atoms or an aryl or heteroaryl moiety.

Another important subclass of class (Ic) includes those compounds having the structure of formula (Ic) in which $X_2$ is C=O; G, J and M are each $CH_2$; j, l and m are each 1; R is —CH($R_{8a}$)C($R_{9a}$)=C($R_{10a}$)—; $R_3$ is hydrogen; and the compound has the structure:

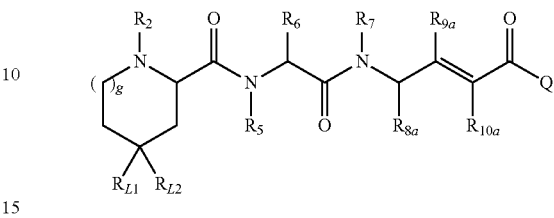

wherein $R_2$, $R_5$-$R_7$ and Q are defined in classes and subclasses herein;
g is 0, 1, 2 or 3;
$R_{8a}$, $R_{9a}$ and $R_{10a}$ are each independently hydrogen, or an alkyl, heteroalkyl, aryl or heteroaryl moiety; and wherein any two $R_7$, $R_{8a}$, $R_{9a}$ and $R_{10a}$ groups may form a cyclic alkyl, heteroalkyl, -alkyl(aryl), -heteroalykl(aryl), -alkyl(heteroaryl) or -heteroalkyl(heteroaryl) moiety, or an aryl or heteroaryl moiety;
$R_{L1}$ and $R_{L2}$ are independently hydrogen or an aliphatic, alicyclic, heteroaliphatic, heteroalicyclic, aryl or heteroaryl moiety.

Another important subclass of class (Ic) includes those compounds having the structure of formula (Ic) in which $X_2$ is C=O; R is —C($R_{8b}$)C($R_{9b}$)N($R_{10b}$)C($R_{11b}$)—; j is 0; l and m are each 1; $R_3$ is hydrogen; G is $CHR_{G1}$, M is $CR_{M1}R_{M2}$, and the compound has the structure:

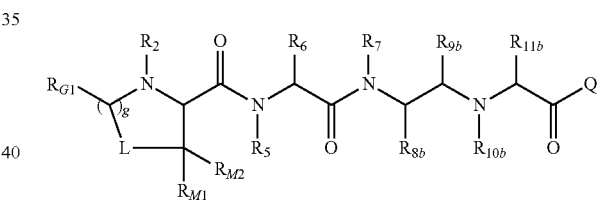

wherein $R_2$, $R_5$-$R_7$ and Q are defined in classes and subclasses herein;
g is 1, 2 or 3;
L is $CR_{L1}R_{L2}$, S, O or $NR_{L3}$, wherein each occurrence of $R_{L1}$, $R_{L2}$ and $R_{L3}$ is independently hydrogen or an aliphatic, alicyclic, heteroaliphatic, heteroalicyclic, aryl or heteroaryl moiety;
each occurrence of $R_{G1}$, $R_{M1}$ and $R_{M2}$ is independently hydrogen or an aliphatic, alicyclic, heteroaliphatic, heteroalicyclic, aryl or heteroaryl moiety;
any two adjacent $R_{L1}$, $R_{L2}$, $R_{L3}$, $R_{G1}$, $R_{M1}$ or $R_{M2}$ groups taken together, may form a substituted or unsubstituted alicyclic or heteroalicyclic moiety containing 3-6 atoms or an aryl or heteroaryl moiety;
$R_{8b}$, $R_{9b}$, $R_{10b}$ and $R_{11b}$ are each independently absent, hydrogen, —(C=O)$R_L$ or an aliphatic, alicyclic, heteroaliphatic, heteroalicyclic, aryl or heteroaryl moiety, wherein each occurrence of $R_L$ is independently hydrogen, OH, $OR_M$, or an aliphatic, alicyclic, heteroaliphatic, heteroalicyclic, aryl or heteroaryl moiety, or wherein any two adjacent $R_{8b}$, $R_{9b}$, $R_{10b}$ and $R_{11b}$ groups, taken together, form a alicyclic or heteroalicyclic moiety, or an aryl or heteroaryl moiety; wherein $R_M$ is an aliphatic, alicyclic, heteroaliphatic, heteroalicyclic, aryl or heteroaryl moiety; and NR$_7$ and CR$_{8b}$, CR$_{8b}$ and CR$_{9b}$, CR$_{9b}$ and NR$_{10b}$, NR$_{10b}$ and CR$_{11b}$ are each independently linked by a single or double bond as valency permits.

Another important subclass of class (Ic) includes those compounds having the structure of formula (Ic) in which X$_2$ is C=O; R is —C(R$_{8b}$)C(R$_{9b}$)N(R$_{10b}$)C(R$_{11b}$)—; j is 0; l and m are each 1; R$_3$ is hydrogen; G is CHR$_{G1}$, M is CR$_{M1}$R$_{M2}$; R$_{10b}$ and R$_{11b}$, taken together, form a cyclic heteroalkyl group; and the compound has the structure:

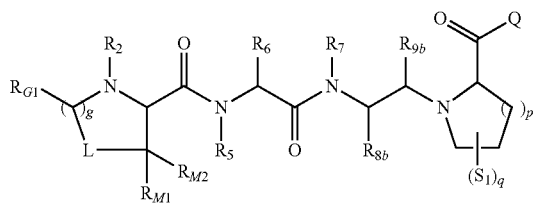

wherein R$_2$, R$_5$-R$_7$ and Q are defined in classes and subclasses herein;

p is 1, 2, 3 or 4;

q is 0-12;

each occurrence of S$_1$ is independently an aliphatic, alicyclic, heteroaliphatic, heteroalicyclic, aryl or heteroaryl moiety, or any two adjacent S$_1$ moieties, taken together, may form an alicyclic, heteroalicyclic, aryl or heteroaryl moiety;

R$_{8b}$ and R$_{9b}$ are each independently absent, hydrogen, —(C=O)R$_L$ or an aliphatic, alicyclic, heteroaliphatic, heteroalicyclic, aryl or heteroaryl moiety, wherein each occurrence of R$_L$ is independently hydrogen, OH, OR$_M$, or an aliphatic, alicyclic, heteroaliphatic, heteroalicyclic, aryl or heteroaryl moiety, or wherein R$_{8b}$ and R$_{9b}$, taken together, form a alicyclic or heteroalicyclic moiety, or an aryl or heteroaryl moiety; wherein R$_M$ is an aliphatic, alicyclic, heteroaliphatic, heteroalicyclic, aryl or heteroaryl moiety; and NR$_7$ and CR$_{8b}$, and CR$_{8b}$ and CR$_{9b}$ are each independently linked by a single or double bond as valency permits.

Another important subclass of class (Ic) includes those compounds having the structure of formula (Ic) in which X$_2$ is C=O; G, J and M are each CH$_2$; j, l and m are each 1; R is —C(R$_{8b}$)C(R$_{9b}$)N(R$_{10b}$)C(R$_{11b}$)—; R$_3$ is hydrogen; and the compound has the structure:

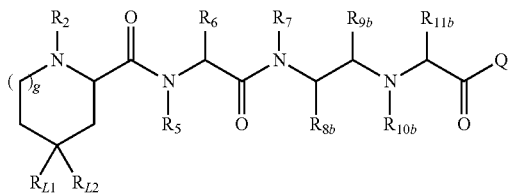

wherein R$_2$, R$_5$-R$_7$ and Q are defined in classes and subclasses herein;

g is 0, 1, 2 or 3;

R$_{L1}$ and R$_{L2}$ are independently hydrogen or an aliphatic, alicyclic, heteroaliphatic, heteroalicyclic, aryl or heteroaryl moiety;

R$_{8b}$, R$_{9b}$, R$_{10b}$ and R$_{11b}$ are each independently absent, hydrogen, —(C=O)R$_L$ or an aliphatic, alicyclic, heteroaliphatic, heteroalicyclic, aryl or heteroaryl moiety, wherein each occurrence of R$_L$ is independently hydrogen, OH, OR$_M$, or an aliphatic, alicyclic, heteroaliphatic, heteroalicyclic, aryl or heteroaryl moiety, or wherein any two adjacent R$_{8b}$, R$_{9b}$, R$_{10b}$ and R$_{11b}$ groups, takes together, form a alicyclic or heteroalicyclic moiety, or an aryl or heteroaryl moiety; wherein R$_M$ is an aliphatic, alicyclic, heteroaliphatic, heteroalicyclic, aryl or heteroaryl moiety; and NR$_7$ and CR$_{8b}$, CR$_{8b}$ and CR$_{9b}$, CR$_{9b}$ and NR$_{10b}$, NR$_{10b}$ and CR$_{11b}$ are each independently linked by a single or double bond as valency permits.

Another important subclass of class (Ic) includes those compounds having the structure of formula (Ic) in which X$_2$ is C=O; G, J and M are each CH$_2$; j, l and m are each 1; R is —C(R$_{8b}$)C(R$_{9b}$)N(R$_{10b}$)C(R$_{11b}$)—; R$_3$ is hydrogen; R$_{10b}$ and R$_{11b}$, taken together, form a cyclic heteroalkyl group; and the compound has the structure:

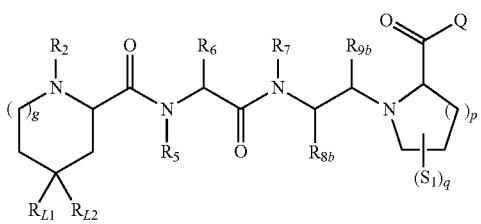

wherein R$_2$, R$_5$-R$_7$ and Q are defined in classes and subclasses herein;

p is 1, 2, 3 or 4;

q is 0-12;

g is 0, 1, 2 or 3;

R$_{L1}$ and R$_{L2}$ are independently hydrogen or an aliphatic, alicyclic, heteroaliphatic, heteroalicyclic, aryl or heteroaryl moiety;

each occurrence of S$_1$ is independently an aliphatic, alicyclic, heteroaliphatic, heteroalicyclic, aryl or heteroaryl moiety, or any two adjacent S$_1$ moieties, taken together, may form an an alicyclic, heteroalicyclic, aryl or heteroaryl moiety;

R$_{8b}$ and R$_{9b}$ are each independently hydrogen, —(C=O)R$_L$ or an aliphatic, alicyclic, heteroaliphatic, heteroalicyclic, aryl or heteroaryl moiety, wherein each occurrence of R$_L$ is independently hydrogen, OH, OR$_M$, or an aliphatic, alicyclic, heteroaliphatic, heteroalicyclic, aryl or heteroaryl moiety, or wherein R$_{8b}$ and R$_{9b}$, taken together, form a alicyclic or heteroalicyclic moiety, or an aryl or heteroaryl moiety; wherein R$_M$ is an aliphatic, alicyclic, heteroaliphatic, heteroalicyclic, aryl or heteroaryl moiety; and NR$_7$ and CR$_{8b}$, and CR$_{8b}$ and CR$_{9b}$ are each independently linked by a single or double-bond as valency permits.

Another important subclass of class (Ic) includes those compounds having the structure of formula (Ic) in which X$_2$ is C=O; R is —C(R$_{8c}$)C(R$_{9c}$)C(R$_{10c}$)C(R$_{11c}$)OC(R$_{12c}$)—; j is 0; l and m are each 1; R$_3$ is hydrogen; G is CHR$_{G1}$, M is CR$_{M1}$R$_{M2}$; and the compound has the following structure:

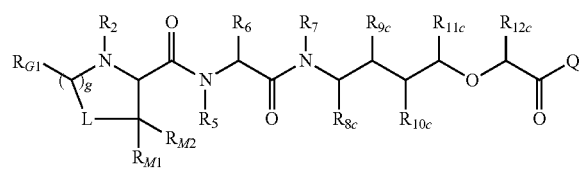

wherein R$_1$, R$_2$, R$_5$-R$_7$ and Q are defined in classes and subclasses herein;

g is 1, 2 or 3;

L is $CR_{L1}R_{L2}$, S, O or $NR_{L3}$, wherein each occurrence of $R_{L1}$, $R_{L2}$ and $R_{L3}$ is independently hydrogen or an aliphatic, alicyclic, heteroaliphatic, heteroalicyclic, aryl or heteroaryl moiety;

each occurrence of $R_{G1}$, $R_{M1}$ and $R_{M2}$ is independently hydrogen or an aliphatic, alicyclic, heteroaliphatic, heteroalicyclic, aryl or heteroaryl moiety;

any two adjacent $R_{L1}$, $R_{L2}$, $R_{L3}$, $R_{G1}$, $R_{M1}$ or $R_{M2}$ groups, taken, together, may form a substituted or unsubstituted alicyclic or heteroalicyclic moiety containing 3-6 atoms or an aryl or heteroaryl moiety;

$R_{8c}$, $R_{9c}$, $R_{10c}$, $R_{11c}$ and $R_{12c}$ are each independently absent, hydrogen, —(C=O)$R_L$ or an aliphatic, alicyclic, heteroaliphatic, heteroalicyclic, aryl or heteroaryl moiety, wherein each occurrence of $R_L$ is independently hydrogen, OH, $OR_M$, or an aliphatic, alicyclic, heteroaliphatic, heteroalicyclic, aryl or heteroaryl moiety, or wherein any two $R_{8c}$, $R_{9c}$, $R_{10c}$, $R_{11c}$ and $R_{12c}$ groups, taken together, form a alicyclic or heteroalicyclic moiety, or an aryl or heteroaryl moiety; wherein $R_M$ is an aliphatic, alicyclic, heteroaliphatic, heteroalicyclic, aryl or heteroaryl moiety; and $NR_7$ and $CR_{8c}$, $CR_{8c}$ and $CR_{9c}$, $CR_{9c}$ and $CR_{10c}$, and $CR_{10c}$ and $CR_{11c}$ are each independently linked by a single or double bond as valency permits.

Another important subclass of class (Ic) includes those compounds having the structure of formula (Ic) in which $X_2$ is C=O; R is —C($R_{8c}$)C($R_{9c}$)C($R_{10c}$)C($R_{11c}$)OC($R_{12c}$)—; G, J and M are each $CH_2$; j, l and m are each 1; $R_3$ is hydrogen; and the compound has the following structure:

wherein $R_1$, $R_2$, $R_5$-$R_7$ and Q are defined in classes and subclasses herein;

g is 0, 1, 2 or 3;

$R_{L1}$ and $R_{L2}$ are independently hydrogen or an aliphatic, alicyclic, heteroaliphatic, heteroalicyclic, aryl or heteroaryl moiety;

$R_{8c}$, $R_{9c}$, $R_{10c}$, $R_{11c}$ and $R_{12c}$ are each independently absent, hydrogen, —(C=O)$R_L$ or an aliphatic, alicyclic, heteroaliphatic, heteroalicyclic, aryl or heteroaryl moiety, wherein each occurrence of $R_L$ is independently hydrogen, OH, $OR_M$, or an aliphatic, alicyclic, heteroaliphatic, heteroalicyclic, aryl or heteroaryl moiety, or wherein any two $R_{8c}$, $R_{9c}$, $R_{10c}$, $R_{11c}$ and $R_{12c}$ groups, taken together, form a alicyclic or heteroalicyclic moiety, or an aryl or heteroaryl moiety; wherein $R_M$ is an aliphatic, alicyclic, heteroaliphatic, heteroalicyclic, aryl or heteroaryl moiety; and $NR_7$ and $CR_{8c}$, $CR_{8c}$ and $CR_{9c}$, $CR_{9c}$ and $CR_{10c}$, and $CR_{10c}$ and $CR_{11c}$ are each independently linked by a single or double bond as valency permits.

A number of important subclasses of each of the foregoing subclasses of class (Ic) deserve separate mention; these subclasses include subclasses of the foregoing subclasses of class (Ic) in which:

i-c. $R_2$ is hydrogen, or a substituted or unsubstituted, linear or branched, cyclic or acyclic, or saturated or unsaturated lower alkyl, heteroalkyl, -alkyl(aryl) or acyl moiety;

ii-c. $R_2$ is substituted, or unsubstituted, linear or branched, cyclic or acyclic, saturated or unsaturated lower alkyl, heteroalkyl, -alkyl(aryl) or acyl;

iii-e. $R_2$ is substituted or unsubstituted, linear or branched, cyclic or acyclic, saturated or unsaturated lower alkyl;

iv-c. $R_2$ is methyl, ethyl, propyl, butyl, pentyl, tert-butyl, -propyl, —CH(CH$_3$)CH$_2$CH$_3$, —CH(CH$_3$)CH$_2$CH$_2$CH$_3$, —CH$_2$CH(CH$_3$)$_2$, —CH(CH$_3$)CH(CH$_3$)$_2$, —CH(CH$_3$)$_2$CH$_2$CH$_3$, —CH(CH$_3$)cyclobutyl, —CH(Et)$_2$, —CH(CH$_3$)$_2$C CH, cyclohexyl, cyclopentyl, cyclobutyl or cyclopropyl;

v-c. $R_2$ is hydrogen;

vi-c. $R_2$ is hydrogen, methyl or benzyl:

vii-c. $R_2$ is methyl;

viii-c. $R_2$ is acyl, wherein the acyl group is a nitrogen protecting group;

ix-c. $R_3$ is hydrogen;

x-c. $R_1$ and $R_4$, taken together, form a substituted or unsubstituted pyrrolidine group:

xi-c. $R_1$ and $R_4$, taken together, form a substituted or unsubstituted piperidine group;

xii-c. $R_1$ and $R_4$, taken together, form a substituted or unsubstituted thiazolidine group;

xiii-c. $R_1$ and $R_4$, taken together, form a substituted or unsubstituted morpholine group;

xiv-c. $R_1$ and $R_4$, taken together, form a substituted or unsubstituted thiomorpholine group;

xv-c. $R_1$ and $R_4$, taken together, form a substituted or unsubstituted indole group;

xvi-c. $R_5$ is hydrogen;

xvii-c. $R_6$ is substituted or unsubstituted, linear or branched, cyclic or acyclic, or saturated or unsaturated lower alkyl;

xviii-c. $R_6$ is methyl, ethyl, propyl, butyl, pentyl, tert-butyl, -propyl, —CH(CH$_3$)CH$_2$CH$_3$, —CH$_2$CH(CH$_3$)$_2$, cyclohexyl, cyclopentyl, cyclobutyl or cyclopropyl;

xix-c. $R_6$ is tert-butyl;

xx-c. The $R_6$-bearing carbon atom is of S configuration;

xxi-c. $R_7$ is substituted or unsubstituted, linear or branched, cyclic or acyclic, or saturated or unsaturated lower alkyl;

xxii-c. $R_7$ is methyl;

xxiii-c. R is —CH($R_{8a}$)C($R_{9a}$)=C($R_{10a}$)—; and
  a) $R_{8a}$ is substituted or unsubstituted, linear or branched, cyclic or acyclic, or saturated or unsaturated lower alkyl;
  b) $R_{8a}$ is iso-propyl;
  c) The $R_{8a}$-bearing carbon atom is of S configuration;
  d) $R_{9a}$ is hydrogen or substituted or unsubstituted, linear or branched, cyclic or acyclic, or saturated or unsaturated lower alkyl;
  e) $R_{9a}$ is hydrogen;
  f) $R_{10a}$ is hydrogen or substituted or unsubstituted, linear or branched, cyclic or acyclic, or saturated or unsaturated lower alkyl; or
  g) $R_{10a}$ is methyl;

xxiv-c. R is —C($R_{8b}$)C($R_{9b}$)N($R_{10b}$)$CR_{11b}$— and
  a) $R_{8b}$ is substituted or unsubstituted, linear or branched, cyclic or acyclic, or saturated or unsaturated lower alkyl;
  b) $R_{8b}$ is iso-propyl;
  c) The $R_{8b}$-bearing carbon atom is of S configuration;
  d) $R_{9b}$ is hydrogen or substituted or unsubstituted, linear or branched, cyclic or acyclic, or saturated or unsaturated lower alkyl;
  e) $R_{10b}$ is hydrogen, or a substituted or unsubstituted, linear or branched, cyclic or acyclic, or saturated or unsaturated lower alkyl or acyl moiety;
  f) $R_{10b}$ is hydrogen, methyl or acetyl;

g) $R_{10b}$ and $R_{11b}$, taken together, form a substituted or unsubstituted pyrrolidine ring; or h) $R_{9b}$ and $R_{11b}$, taken together, form a substituted or unsubstituted thiazole ring;

xxxv-d. R is $-C(R_{8c})C(R_{9c})C(R_{10c})CR_{11c}OCR_{12c}-$ and a) $R_{8c}$ is substituted or unsubstituted, linear or branched, cyclic or acyclic, or saturated or unsaturated lower alkyl;

b) $R_{8c}$ is iso-propyl;

c) The $R_{8c}$-bearing carbon atom is of S configuration;

d) $R_{9c}$ and $R_{10c}$ are each independently hydrogen or substituted or unsubstituted, linear or branched, cyclic or acyclic, or saturated or unsaturated lower alkyl;

e) $CR_{9c}$ and $CR_{10c}$ are linked via a double bond;

f) $CR_{9c}$ and $CR_{10c}$ linked via a double bond and $R_{9c}$ is hydrogen; or g) $CR_{9c}$ and $CR_{10c}$ are linked via a double bond and $R_{10c}$ is methyl;

xxv-c. $-C(R_3)(R_4)N(R_1)(R_2)$ together represent, the moiety having the structure:

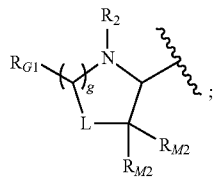

and a) $R_2$ is hydrogen, or a substituted or unsubstituted, linear or branched, cyclic or acyclic, or saturated or unsaturated lower-alkyl, heteroalkyl, -alkyl(aryl) or acyl moiety;

b) $R_2$ is methyl, ethyl or propyl;

c) $R_{G1}$ is hydrogen, substituted or unsubstituted, linear or branched, cyclic or acyclic, or saturated or unsaturated lower alkyl or substituted or unsubstituted phenyl;

d) $R_{G1}$ is hydrogen, methyl or phenyl;

e) $R_{G1}$ and the substituents on L, taken together, form a substituted or unsubstituted phenyl group;

f) $R_{M1}$ and $R_{M2}$ are each independently hydrogen, hydroxyl, a substituted or unsubstituted, linear or branched, cyclic or acyclic, or saturated or unsaturated lower alkyl moiety; a substituted or unsubstituted phenyl moiety, or $R_{M2}$ is absent when $R_{M1}$ and the substitutents on L, taken together, form a substituted or unsubstituted aryl or heteroaryl moiety;

g) g is 1 or 2; or h) L is $CH_2$, S or O;

xxvi-c. $-C(R_3)(R_4)N(R_1)(R_2)$ together represent the moiety having the structure:

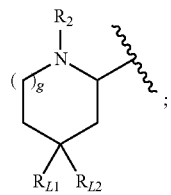

and a) $R_2$ is hydrogen, or a substituted or unsubstituted, linear or branched, cyclic or acyclic, or saturated or unsaturated lower alkyl, heteroalkyl, -alkyl(aryl) or acyl moiety;

b) $R_2$ is methyl, c) $R_{L1}$ and $R_{L2}$ are each independently hydrogen, substituted or unsubstituted, linear or branched, cyclic or acyclic, or saturated or unsaturated lower alkyl or substituted or unsubstituted phenyl;

d) $R_{L1}$ and $R_{L2}$ are each hydrogen;

e) $R_{L1}$ and $R_{L2}$ are each substituted or unsubstituted, linear or branched, cyclic or acyclic, or saturated or unsaturated lower alkyl; or f) g is 1 or 2;

xxvii-c. $X_2$ is C=O;

xxviii-c. $X_2$ is $CH_2$;

xxix-c. $X_2$ is $SO_2$;

xxx-c. Q is $OR^{Q'}$, $SR^{Q'}$, $NR^{Q'}R^{Q''}$, $N_3$, =N—OH, or a moiety selected from the group consisting of:

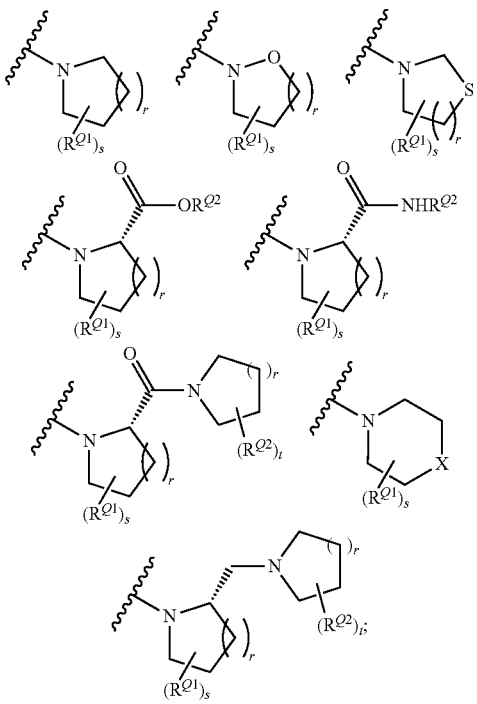

wherein each occurrence of r is 0, 1 or 2; s and t are independently an integer from 0-8; X is O, S, or $NR^K$; each occurrence of $R^{Q1}$ and $R^{Q2}$ is independently hydrogen, halogen, —CN, $-S(O)_hR^J$, $-NO_2$, $-COR^J$, $-CO_2R^J$, $-NR^JCOR^J$, $-NR^JCO_2R^J$, $-CONR^JR^J$, $-CO(NOR^J)R^J$, aliphatic, alicyclic, heteroaliphatic, heteroalicyclic, aryl or heteroaryl moiety, or $-Z_1R^J$; wherein h is 1 or 2; and $Z_1$ is independently —O—, —S—, $NR^K$, —C(O)—, wherein each occurrence of $R^J$ and $R^K$ is independently hydrogen, $COR^L$, $COOR^L$, $CONR^LR^M$, $-NR^LR^M$, $-S(O)_2R^L$, or an aliphatic, alicyclic, heteroaliphatic, heteroalicyclic, aryl or heteroaryl moiety, and wherein each occurrence of $R^L$ and $R^M$ is independently hydrogen, or an aliphatic, alicyclic, heteroaliphatic, heteroalicyclic, aryl or heteroaryl moiety; and $R^{Q'}$ and $R^{Q''}$ are independently hydrogen, or a substituted or unsubstituted, linear or branched, cyclic or acyclic alkyl or heteroalkyl moiety, or a substituted or unsubstituted aryl or heteroaryl moiety; or $R^{Q'}$ and $R^{Q''}$, taken together with the nitrogen atom to which they are attached, form a substituted or unsubstituted heterocyclic, aryl or heteroaryl moiety;

xxxi-c. Q is $OR^{Q'}$, $SR^{Q'}$, $NR^{Q'}R^{Q''}$, $N_3$, $=N-OH$, or a moiety selected from the group consisting of:

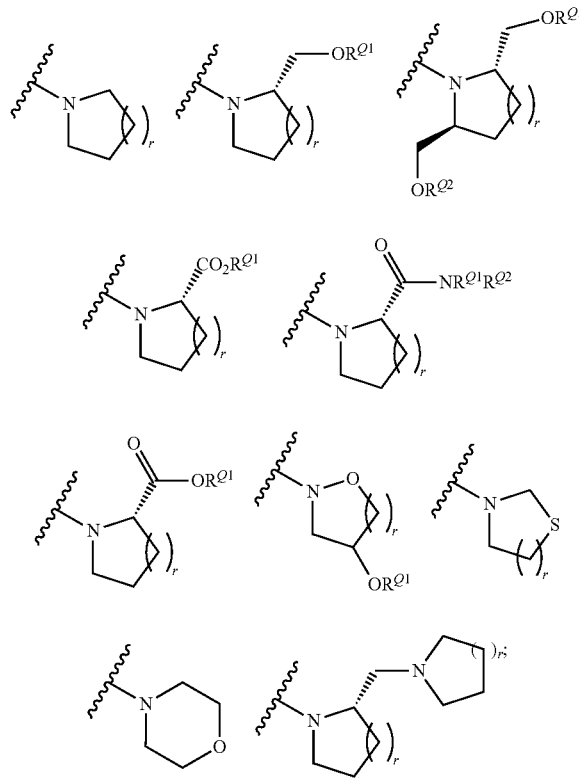

wherein each occurrence of r is 0, 1 or 2; s and l are independently an integer from 0-8; each occurrence of $R^{Q1}$ and $R^{Q2}$ is independently hydrogen, or a substituted or unsubstituted, linear or branched, cyclic, or acyclic alkyl or heteroalkyl moiety, or a substituted or unsubstituted aryl or heteroaryl moiety; or $R^{Q1}$ and $R^{Q2}$, taken together with the nitrogen atom to which they are attached, form a substituted or unsubstituted heterocyclic moiety; and $R^{Q'}$ and $R^{Q''}$ are independently hydrogen, or a substituted or unsubstituted, linear or branched, cyclic or acyclic alkyl or heteroalkyl moiety, or a substituted or unsubstituted aryl or heteroaryl moiety; or $R^{Q'}$ and $R^{Q''}$, taken together with the nitrogen atom to which they axe attached, form a substituted or unsubstituted heterocyclic, aryl or heteroaryl moiety; and/or xxxii-c. Q is $OR^{Q'}$, $SR^{Q'}$, $NR^{Q'}R^{Q''}$, $N_3$, $=N-OH$, or a moiety selected from the group consisting of:

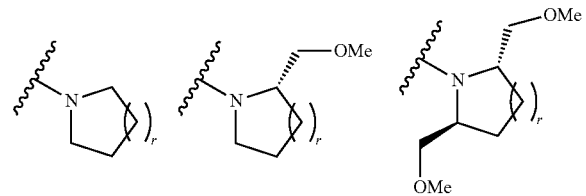

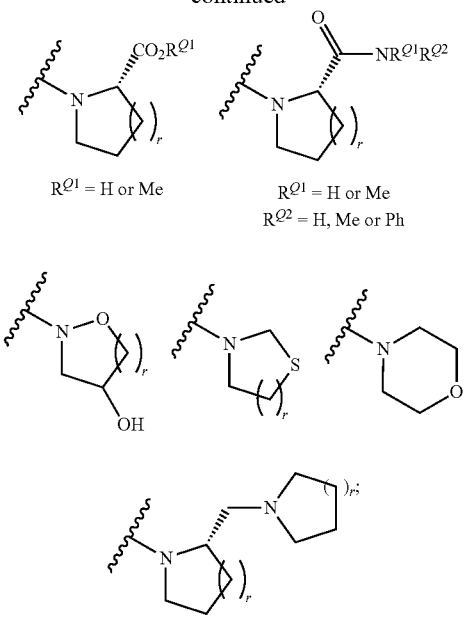

$R^{Q1}$ = H or Me $R^{Q1}$ = H or Me
$R^{Q2}$ = H, Me or Ph wherein each occurrence of r is 0, 1 or 2; and $R^{Q'}$ and $R^{Q''}$ are independently hydrogen, or a substituted or unsubstituted, linear or branched, cyclic or acyclic alkyl or heteroalkyl moiety, or a substituted or unsubstituted aryl or heteroaryl moiety; or $R^{Q'}$ and $R^{Q''}$, taken together with the nitrogen atom to which they are attached, form a substituted or unsubstituted heterocyclic, aryl or heteroaryl moiety.

An important subclass of class (Id) includes those compounds having the structure of formula (Id) in which R is $-CH(R_{8a})C(R_{9a})=C(R_{10a})-$; $X_2$ is C=O; and the compound has the following structure:

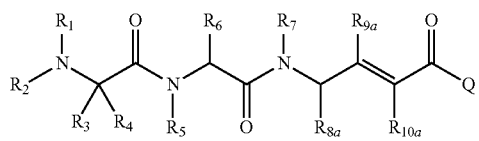

wherein $R_3$ and $R_4$ are each independently an aliphatic, alicyclic, heteroaliphatic, heteroalicyclic, aryl or heteroaryl moiety, or, when taken together, form an alicyclic, heteroalicyclic, alicyclic(aryl), heteroalicyclic(aryl), alicyclic(heteroaryl) or heteroalicyclic(heteroaryl) moiety; $R_1$, $R_2$, $R_5$-$R_7$ and Q are defined in classes and subclasses herein; and $R_{8a}$, $R_{9a}$ and $R_{10a}$ are each independently hydrogen, or an aliphatic, alicyclic, heteroaliphatic, heteroalicyclic, aryl or heteroaryl moiety; and wherein any two $R_7$, $R_{8a}$, $R_{9a}$ and $R_{10a}$ groups may form an alicyclic, heteroalicyclic, alicyclicc (aryl), heteroalicyclic(aryl), alicyclic(heteroaryl) or heteroalicyclic(heteroaryl) moiety, or an aryl or heteroaryl moiety.

Another important subclass of class (Id) includes those compounds having the structure of formula (Id) in which R is $-C(R_{8b})C(R_{9b})N(R_{10b})C(R_{11b})-$; $X_2$ is C=O; and the compound has the following structure:

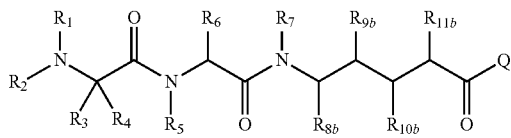

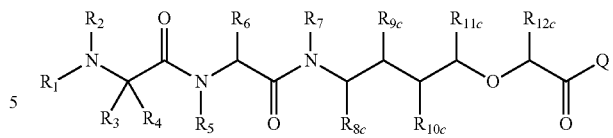

wherein R₃ and R₄ are each independently an aliphatic, alicyclic, heteroaliphatic, heteroalicyclic, aryl or heteroaryl moiety, or, when taken together, form an alicyclic, heteroalicyclic, alicyclic(aryl), heteroalicyclic(aryl), alicyclic(heteroaryl) or heteroalicyclic(heteroaryl) moiety; $R_1$, $R_2$, $R_5$-$R_7$ and Q are defined in classes and subclasses herein;

$R_{8b}$, $R_{9b}$, $R_{10b}$ and $R_{11b}$ are each independently absent, hydrogen, —(C═O)$R_L$ or an aliphatic, alicyclic, heteroaliphatic, heteroalicyclic, aryl or heteroaryl moiety, wherein each occurrence of $R_L$ is independently hydrogen, OH, OR$_M$, or an aliphatic, alicyclic, heteroaliphatic, heteroalicyclic, aryl or heteroaryl moiety, or wherein any two $R_{8b}$, $R_{9b}$, $R_{10b}$ and $R_{11b}$ groups, taken together, form a alicyclic or heteroalicyclic moiety, or an aryl or heteroaryl moiety; wherein $R_M$ is an aliphatic, alicyclic, heteroaliphatic, heteroalicyclic, aryl or heteroaryl moiety; and $NR_7$ and $CR_{8b}$, $CR_{8b}$ and $CR_{9b}$, $CR_{9b}$ and $NR_{10b}$, $NR_{10b}$ and $CR_{11b}$ are independently linked by a single or double bond as valency permits.

Another important subclass of class (Id) includes those compounds having the structure of formula (Id) in which R is —C($R_{8b}$)C($R_{9b}$)N($R_{10b}$)C($R_{11b}$)—; $X_2$ is C═O; $R_{10b}$ and $R_{11b}$, taken together, form a cyclic heteroalkyl group; and the compound has the following structure:

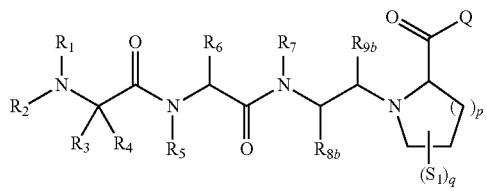

wherein R₃ and R₄ are each independently an aliphatic, alicyclic, heteroaliphatic, heteroalicyclic, aryl or heteroaryl moiety, or, when taken together, form an alicyclic, heteroalicyclic, alicyclic(aryl), heteroalicyclic(aryl), alicyclic(heteroaryl) or heteroalicyclic(heteroaryl) moiety; $R_1$, $R_2$, $R_5$-$R_7$ and Q are defined in classes and subclasses herein;

p is 1, 2, 3 or 4;

q is 0-12;

each occurrence of $S_1$ is independently an aliphatic, alicyclic, heteroaliphatic, heteroalicyclic, aryl or heteroaryl moiety, or any two adjacent $S_1$ moieties, taken together, may form an an alicyclic, heteroalicyclic, aryl or heteroaryl moiety;

$R_{8b}$ and $R_{9b}$ are each independently hydrogen, —(C═O)$R_L$ or an aliphatic, alicyclic, heteroaliphatic, heteroalicyclic, aryl or heteroaryl moiety, wherein each occurrence of $R_L$ is independently hydrogen, OH, OR$_M$, or an aliphatic, alicyclic, heteroaliphatic, heteroalicyclic, aryl or heteroaryl moiety, or wherein $R_{8b}$ and $R_{9b}$, taken together, form a alicyclic or heteroalicyclic moiety, or an aryl or heteroaryl moiety; wherein $R_M$ is an aliphatic, alicyclic, heteroaliphatic, heteroalicyclic, aryl or heteroaryl moiety; and $NR_7$ and $CR_8$, and $CR_{8b}$ and $CR_{9b}$ are independently linked by a single or double bond as valency permits.

Another important subclass of class (Id) includes those compounds having the structure of formula (Id) in which $X_2$ is C═O; R is —C($R_{8c}$)C($R_{9c}$)C($R_{10c}$)C($R_{11c}$)OC($R_{12c}$)—; and the compound has the following structure:

wherein R₃ and R₄ are each independently an aliphatic, alicyclic, heteroaliphatic, heteroalicyclic, aryl or heteroaryl moiety, or, when taken together, form an alicyclic, heteroalicyclic, alicyclic(aryl), heteroalicyclic(aryl), alicyclic(heteroaryl) or heteroalicyclic(heteroaryl) moiety; $R_1$, $R_2$, $R_5$-$R_7$ and Q are defined in classes and subclasses herein;

$R_{8c}$, $R_{9c}$, $R_{10c}$, $R_{11c}$ and $R_{12c}$ are each independently absent, hydrogen, —(C═O)$R_L$ or an aliphatic, alicyclic, heteroaliphatic, heteroalicyclic, aryl or heteroaryl moiety, wherein each occurrence of $R_L$ is independently hydrogen, OH, OR$_M$, or an aliphatic, alicyclic, heteroaliphatic, heteroalicyclic, aryl or heteroaryl moiety, or wherein any two $R_{8c}$, $R_{9c}$, $R_{10c}$, $R_{11c}$ and $R_{12c}$ groups, taken together, form a alicyclic or heteroalicyclic moiety, or an aryl or heteroaryl moiety; wherein $R_M$ is an aliphatic, alicyclic, heteroaliphatic, heteroalicyclic, aryl or heteroaryl moiety; and $NR_7$ and $CR_{8c}$, $CR_{8c}$ and $CR_{9c}$, $CR_{9c}$ and $CR_{10c}$, and $CR_{10c}$ and $CR_{11c}$ are each independently linked by a single or double bond as valency permits.

A number of important subclasses of each of the foregoing subclasses of class (Id) deserve separate mention; these subclasses include subclasses of the foregoing subclasses of class (Id) in which:

i-d. $R_1$ and $R_2$ are independently hydrogen or substituted or unsubstituted, linear or branched, cyclic or acyclic, or saturated or unsaturated lower alkyl, heteroalkyl, -alkyl(aryl) or acyl;

ii-d. $R_1$ is hydrogen and $R_2$ is substituted or unsubstituted, linear or branched, cyclic or acyclic, saturated or unsaturated lower alkyl, heteroalkyl, -alkyl(aryl) or acyl;

iii-d. $R_1$ is hydrogen and $R_2$ is substituted or unsubstituted, linear or branched, cyclic or acyclic, saturated or unsaturated lower alkyl;

iv-d. $R_1$ is hydrogen and $R_2$ is methyl, ethyl, propyl, butyl, pentyl, tert-butyl, i-propyl, —CH(CH₃)CH₂CH₃, —CH(CH₃)CH₂CH₂CH₃, —CH₂CH(CH₃)₂, —CH(CH₃)CH(CH₃)₂, —CH(CH₃)₂CH₂CH₃, —CH(CH₃)cyclobutyl, —CH(Et)₂, —CH(CH₃)₂C CH, cyclohexyl, cyclopentyl, cyclobutyl or cyclopropyl;

v-d. $R_1$ and $R_2$ are each, hydrogen;

vi-d. $R_1$ and $R_2$ are independently hydrogen or methyl;

vii-d. $R_1$ and $R_2$ are each methyl:

viii-d. $R_3$ and $R_4$ are each independently substituted or unsubstituted, linear or branched, cyclic or acyclic, or saturated or unsaturated lower alkyl, heteroalkyl or -alkyl(aryl) or substituted or unsubstituted aryl or heteroaryl;

ix-d. $R_3$ and $R_4$ are each independently substituted or unsubstituted, linear or branched, cyclic or acyclic, or saturated or unsaturated lower alkyl, -alkyl(aryl) or substituted or unsubstituted aryl;

x-d. $R_3$ and $R_4$ are each independently substituted or unsubstituted lower alkyl, aryl or heteroaryl;

xi-d. $R_3$ and $R_4$ are each independently methyl, ethyl, propyl, butyl, pentyl, tert-butyl, iso-propyl, —CH(CH₃)CH₂CH₃, —CH(CH₃)CH₂CH₂CH₃, —CH₂CH(CH₃)₂, —CH(CH₃)CH(CH₃)₂, —CH(CH₃)₂CH₂CH₃, —CH(CH₃)cyclobutyl, —CH(Et)₂, cyclohexyl, cyclopentyl, cyclobutyl, cyclopropyl phenyl, —C₁₋₆alkylOR$^a$, —C₁₋₆ alkylSR$^a$ or —CR$^a$R$^b$R$^c$; wherein R$^a$ and R$^b$ are independently hydrogen, substituted or unsubstituted, linear or branched, cyclic or acyclic, or saturated or unsaturated lower alkyl and $R^c$ is substituted or unsubstituted aryl or heteroaryl;

xii-d. $R_3$ and $R_4$ are each independently methyl, ethyl, propyl, butyl, pentyl, tert-butyl, iso-propyl, —CH(CH$_3$)CH$_2$CH$_3$, —CH(CH$_3$)CH$_2$CH$_2$CH$_3$, —CH$_2$CH(CH$_3$)$_2$, —CH(CH$_3$)CH(CH$_3$)$_2$, —CH(CH$_3$)$_2$CH$_2$CH$_3$, —CH(CH$_3$)cyclobutyl, —CH(Et)$_2$, cyclohexyl, cyclopentyl, cyclobutyl, cyclopropyl, phenyl, —C$_{1-6}$alkylOR$^a$, —C$_{1-6}$alkylSR$^a$ or —CR$^b$R$^c$Ph; wherein R$^a$ is hydrogen, substituted or unsubstituted, linear or branched, cyclic or acyclic, or saturated or unsaturated lower alkyl and R$^b$ and R$^c$ are each independently substituted or unsubstituted linear or branched, cyclic or acyclic, or saturated or unsaturated lower alkyl;

xiii-d. $R_3$ and $R_4$ are each ethyl;

xiv-d. $R_3$ is phenyl and $R_4$ is lower alkyl;

xv-d. $R_3$ is phenyl and $R_4$ is ethyl;

xvi-d. $R_3$ and $R_4$, taken together, form a substituted or unsubstituted cycloalkyl group;

xvii-d. $R_3$ and $R_4$, taken together, form a cyclohexyl group;

xviii-d. $R_3$ and $R_4$, taken together, form a substituted or unsubstituted cycloalkyl(aryl) group;

xix-d. $R_5$ is hydrogen;

xx-d. $R_6$ is substituted or unsubstituted, linear or branched, cyclic or acyclic, or saturated or unsaturated lower alkyl;

xxi-d. $R_6$ is methyl, ethyl, propyl, butyl, pentyl, tert-butyl, iso-propyl, —CH(CH$_3$)CH$_2$CH$_3$, —CH$_2$CH(CH$_3$)$_2$, cyclohexyl, cyclopentyl, cyclobutyl or cyclopropyl;

xxii-d. $R_6$ is tert-butyl;

xxiii-d. The $R_6$-bearing carbon atom is of S configuration;

xxiv-d. $R_7$ is substituted or unsubstituted, linear or branched, cyclic or acyclic, or saturated or unsaturated lower alkyl;

xxv-d. $R_7$ is methyl;

xxvi-d. R is —CH(R$_{8a}$)C(R$_{9a}$)=C(R$_{10a}$)—; and
  i) $R_{8a}$ is substituted or unsubstituted, linear or branched, cyclic or acyclic, or saturated or unsaturated lower alkyl;
  j) $R_{8a}$ is iso-propyl;
  k) The $R_{8a}$-bearing carbon atom is of S configuration;
  l) $R_{9a}$ is hydrogen or substituted or unsubstituted, linear or branched, cyclic or acyclic, or saturated or unsaturated lower alkyl;
  m) $R_{9a}$ is hydrogen;
  n) $R_{10a}$ is hydrogen or substituted or unsubstituted, linear or branched, cyclic or acyclic, or saturated or unsaturated lower alkyl; or
  o) $R_{10a}$ is methyl;

xxvii-d. R is —C(R$_{8b}$)C(R$_{9b}$)N(R$_{10b}$)CR$_{11b}$— and
  p) $R_{8b}$ is substituted or unsubstituted, linear or branched, cyclic or acyclic, or saturated or unsaturated lower alkyl;
  q) $R_{8b}$ is iso-propyl;
  r) The $R_{8b}$-bearing carbon atom is of S configuration;
  s) $R_{9b}$ is hydrogen or substituted or unsubstituted, linear or branched, cyclic or acyclic, or saturated or unsaturated lower alkyl;
  t) $R_{10b}$ is hydrogen, or a substituted or unsubstituted, linear or branched, cyclic or acyclic, or saturated or unsaturated lower alkyl or acyl moiety;
  u) $R_{10b}$ is hydrogen, methyl or acetyl;
  v) $R_{10b}$ and $R_{11b}$, taken together, form a substituted or unsubstituted pyrrolidine ring; or
  w) $R_{9b}$ and $R_{11b}$, taken together, form a substituted or unsubstituted thiazole ring;

xxviii-d. R is —C(R$_{8c}$)C(R$_{9c}$)C(R$_{10c}$)CR$_{11c}$OCR$_{12c}$— and
  h) $R_{8c}$ is substituted or unsubstituted, linear or branched, cyclic or acyclic, or saturated or unsaturated lower alkyl;
  i) $R_{8c}$ is iso-propyl;
  j) The $R_{8c}$-bearing carbon atom is of S configuration;
  k) $R_{9c}$ and $R_{10c}$ are each independently hydrogen or substituted or unsubstituted, linear or branched, cyclic or acyclic, or saturated or unsaturated lower alkyl;
  l) $CR_{9c}$ and $CR_{10c}$ are linked via a double bond;
  m) $CR_{9c}$ and $CR_{10c}$ are linked via a double bond and is hydrogen; or
  n) $CR_{9c}$ and $CR_{10c}$ are linked via a double bond and $R_{10c}$ is methyl;

xxix-d. $X_2$ is C=O;

xxx-d. $X_2$ is CH$_2$;

xxxi-d. $X_2$ is SO$_2$;

xxxii-d. Q is OR$^{Q'}$, SR$^{Q'}$, NR$^{Q'}$R$^{Q''}$, N$_3$, =N—OH, or a moiety selected from the group consisting of:

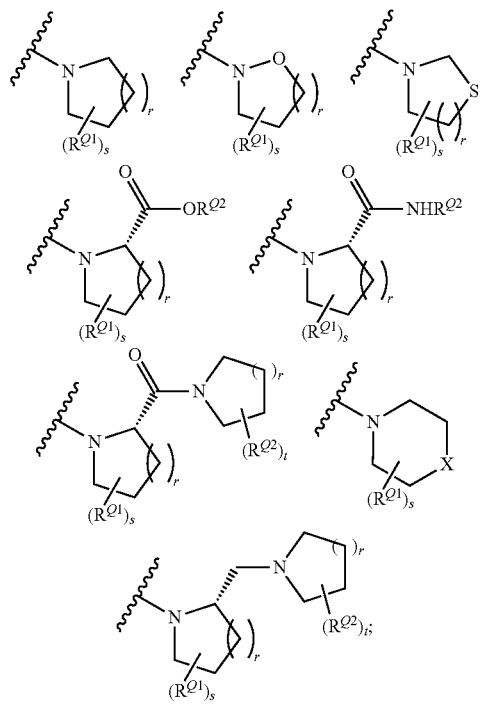

wherein each occurrence of r is 0, 1 or 2; s and t are independently an integer from 0-8; X is O, S, or NR$^K$; each occurrence of R$^{Q1}$ and R$^{Q2}$ is independently hydrogen, halogen, —CN, —S(O)$_h$R$^J$, —NO$_2$, —COR$^J$, —CO$_2$R$^J$, —NR$^J$COR$^J$, —NR$^J$CO$_2$R$^J$, —CONR$^J$R$^J$, —CO(NOR$^J$)R$^J$, aliphatic, alicyclic, heteroaliphatic, heteroalicyclic, aryl or heteroaryl moiety, or —Z$_1$R$^J$; wherein h is 1 or 2; and Z$_1$ is independently —O—, —S—, NR$^K$, —C(O)—, wherein each occurrence of R$^J$ and R$^K$ is independently hydrogen, COR$^L$, COOR$^L$, CONR$^L$R$^M$, —NR$^L$R$^M$, —S(O)$_2$R$^L$, or an aliphatic, alicyclic, heteroaliphatic, heteroalicyclic, aryl or heteroaryl moiety, and wherein each occurrence of R$^L$ and R$^M$ is independently hydrogen, or an aliphatic, alicyclic, heteroaliphatic, heteroalicyclic, aryl or heteroaryl moiety; and R$^{Q'}$ and R$^{Q''}$ are independently hydrogen, or a substituted or unsubstituted, linear or branched, cyclic or acyclic alkyl or heteroalkyl moiety, or a substituted or unsubstituted aryl or heteroaryl moiety; or R$^{Q'}$ and R$^{Q''}$, taken together with the nitrogen atom to which they are attached, form a substituted or unsubstituted heterocyclic, aryl or heteroaryl moiety;

xxxiii-d. Q is OR$^{Q'}$, SR$^{Q'}$, NR$^{Q'}$R$^{Q''}$, N$_3$, =N—OH, or a moiety selected from the group consisting of:

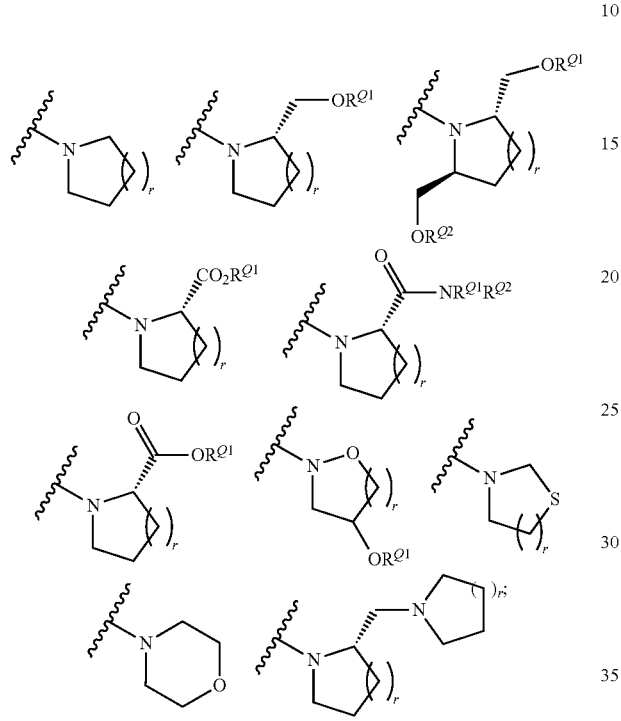

wherein each occurrence of r is 0, 1 or 2; s and t are independently an integer from 0-8; each occurrence of R$^{Q1}$ and R$^{Q2}$ is independently hydrogen, or a substituted or unsubstituted, linear or branched, cyclic or acyclic alkyl or heteroalkyl moiety, or a substituted or unsubstituted aryl or heteroaryl moiety; or R$^{Q1}$ and R$^{Q2}$, taken together with the nitrogen atom to which they are attached, form a substituted or unsubstituted heterocyclic moiety; and R$^{Q'}$ and R$^{Q''}$ are independently hydrogen, or a substituted or unsubstituted, linear or branched, cyclic or acyclic alkyl or heteroalkyl moiety, or a substituted or unsubstituted aryl or heteroaryl moiety; or R$^{Q'}$ and R$^{Q''}$, taken together with the nitrogen atom to which they are attached, form a substituted or unsubstituted heterocyclic, aryl or heteroaryl moiety; and/or xxxiv-d. Q is OR$^{Q'}$, SR$^{Q'}$, NR$^{Q'}$R$^{Q''}$, N$_3$, =N—OH, =N—OH, or a moiety selected from the group consisting of:

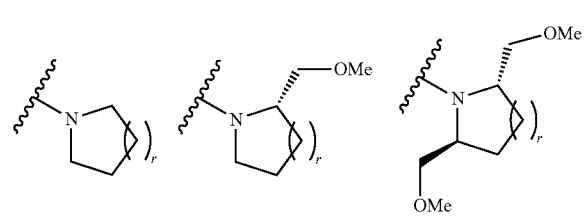

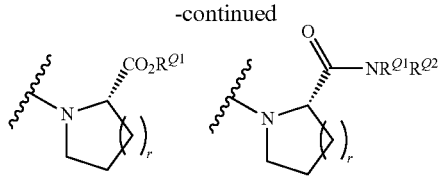

R$^{Q1}$ = H or Me

R$^{Q1}$ = H or Me
R$^{Q2}$ = H, Me or Ph

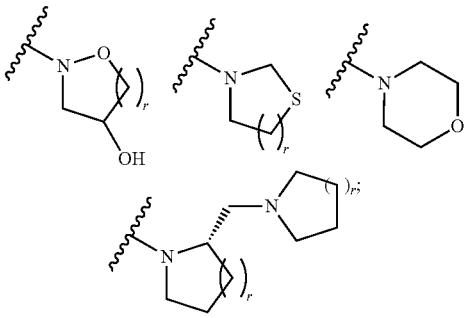

wherein each occurrence of r is 0, 1 or 2; and R$^{Q'}$ and R$^{Q''}$ are independently hydrogen, or a substituted or unsubstituted, linear or branched, cyclic or acyclic alkyl or heteroalkyl moiety, or a substituted or unsubstituted aryl or heteroaryl moiety; or R$^{Q'}$ and R$^{Q''}$, taken together with the nitrogen atom to which they are attached, form a substituted or unsubstituted heterocyclic, aryl or heteroaryl moiety.

As the reader will appreciate, compounds of particular interest include, among others, those which share the attributes of one or more of the foregoing subclasses. Some of those subclasses are illustrated by tire following sorts of compounds:

I) Compounds of the formula (and pharmaceutically acceptable derivatives thereof):

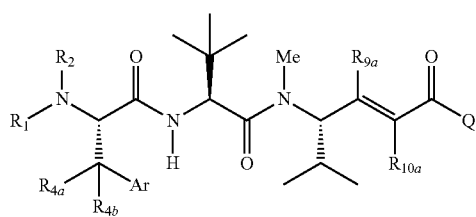

wherein R$_1$-R$_2$, R$_{4a}$, R$_{4b}$, R$_{9a}$-R$_{10b}$ and Q are as defined above and in subclasses herein; and Ar is a substituted or unsubstitued aryl or heteroaryl moiety.

II) Compounds of the formula (and pharmaceutically acceptable derivatives thereof):

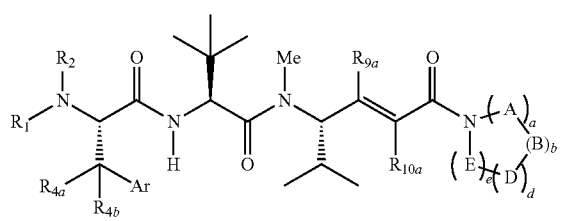

wherein A, B, D, E, a, b, d, e, $R_1$-$R_2$, $R_{4a}$, $R_{4b}$, and $R_{9a}$-$R_{10b}$ are as defined above and in subclasses herein; and Ar is a substituted or unsubstitued aryl or heteroaryl moiety.

It will also be appreciated that for each of the subgroups I-II described, above, a variety of other subclasses are of special interest, including, but not limited to those classes i-a. through xliv-a. described above and classes, subclasses and species of compounds described above and in the examples herein.

III) Compounds of the formula (and pharmaceutically acceptable derivatives thereof);

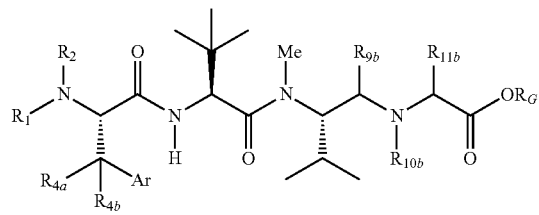

wherein $R_1$-$R_2$, $R_{4a}$, $R_{4b}$, $R_{9b}$-$R_{11b}$ and $R_G$ are as defined above and in subclasses herein; and Ar is a substituted or unsubstituted aryl or heteroaryl moiety.

IV) Compounds of the formula (and pharmaceutically acceptable derivatives thereof):

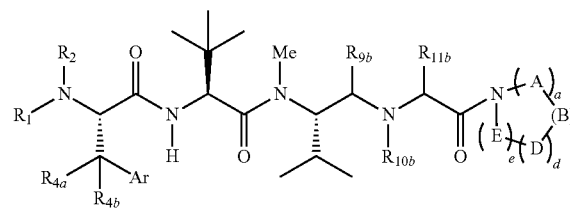

wherein A, B, D, E, a, b, d, e, $R_1$-$R_2$, $R_{4a}$, $R_{4b}$, and $R_{9b}$-$R_{11b}$ are as defined above and in subclasses herein; and Ar is a substituted or unsubstituted aryl or heteroaryl moiety.

V) Compounds of the formula (and pharmaceutically acceptable derivatives thereof):

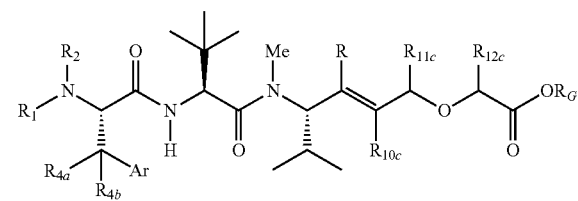

wherein $R_1$-$R_2$, $R_{4a}$, $R_{4b}$, $R_{9c}$-$R_{12c}$ and $R_G$ are as defined above and in subclasses herein; and Ar is a substituted or unsubstitued aryl or heteroaryl moiety.

It will also be appreciated that for each of the subgroups III-V described above, a variety of other subclasses are of special interest, including, but not limited to those classes i-b. through xiii-b. described above and classes, subclasses and species of compounds described above and in the examples herein.

VI) Compounds of the formula (and pharmaceutically acceptable derivatives thereof):

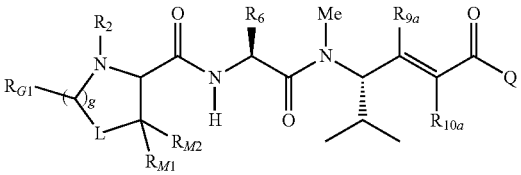

wherein L, $R_{9a}$-$R_{10a}$, $R_{G1}$, $R_{M1}$ and $R_{M2}$ are as defined above and in subclasses herein; g is 1 or 2; Q is $OR^{Q'}$, wherein $R^{Q'}$ is hydrogen or lower alkyl; and $R_2$ and $R_6$ are independently substituted or unsubstituted linear or branched lower alkyl.

VII) Compounds of the formula (and pharmaceutically acceptable derivatives thereof):

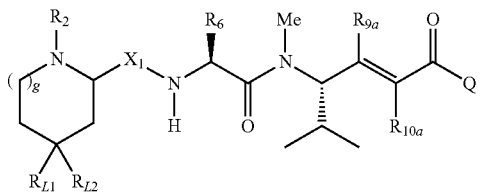

wherein g, $R_{9a}$-$R_{10a}$, $R_{L1}$ and $R_{L2}$ are as defined above and in subclasses herein; $X_1$ is $CH_2$ or C=O; $R_2$ and $R_6$ are independently substituted or unsubstituted linear or branched lower alkyl; and Q is $OR^{Q'}$ or $NR^{Q'}R^{Q''}$ wherein $R^{Q'}$ is hydrogen or lower alkyl, or $R^{Q'}$ and $R^{Q''}$, taken together with the nitrogen atom to which they are attached, form a substituted or unsubstituted heterocyclic moiety, whereby each of the foregoing alkyl moieties may be substituted or unsubstituted, linear or branched, cyclic or acyclic.

VIII) Compounds of the formula (and pharmaceutically acceptable derivatives thereof):

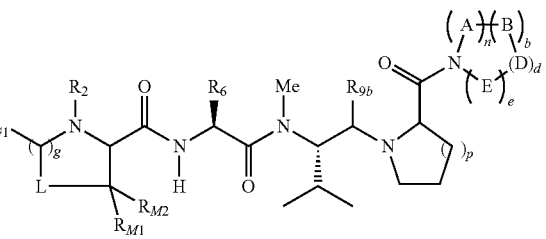

wherein A, B, D, E, L, a, b, d, e, p, $R_{9b}$, $R_{G1}$, $R_{M1}$ and $R_{M2}$ are as defined above and in subclasses herein; g is 1 or 2; and $R_2$ and $R_6$ are independently substituted or unsubstituted linear or branched lower alkyl.

IX) Compounds of the formula (and pharmaceutically acceptable derivatives thereof):

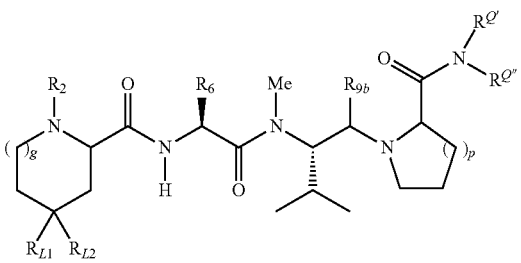

wherein p, $R_{9b}$, $R_{L1}$, $R_{L2}$, $R^{Q'}$ and $R^{Q'}$ are as defined above and in subclasses herein; and $R_2$ and $R_6$ are independently substituted or unsubstituted linear or branched lower alkyl.

It will also be appreciated that for each of the subgroups VI-IX described above, a variety of other subclasses are of special interest, including, but not limited to those classes i-c. through xxxii-c. described above and classes, subclasses and species of compounds described above and in the examples herein. In certain embodiments, for compounds of subgroups VI-IX above, $R_2$ is methyl, iso-propyl, sec-butyl or —CH(CH$_3$)CH(CH$_3$)$_2$. In certain embodiments, for compounds of subgroups VI-IX above, $R_6$ is tert-butyl or iso-propyl. In certain embodiments, for compounds of subgroups VI-IX above, $R_2$ is methyl, iso-propyl, sec-butyl or —CH(CH$_3$)CH(CH$_3$)$_2$, and $R_6$ is tert-butyl or iso-propyl. In certain exemplary embodiments, for compounds of subgroups VI-IX above, $R_2$ is methyl and $R_6$ is tert-butyl. In certain exemplary embodiments, for compounds of subgroups VI-IX above, $R_2$ is iso-propyl and $R_6$ is tert-butyl. In certain exemplary embodiments, for compounds of subgroups VI-IX above, $R_2$ is sec-butyl and $R_6$ is tert-butyl or iso-propyl. In certain exemplary embodiments, for compounds of subgroups VI-IX above, $R_2$ is —CH(CH$_2$)CH(CH$_3$)$_2$, and $R_6$ is tert-butyl.

X) Compounds of the formula (and pharmaceutically acceptable derivatives thereof):

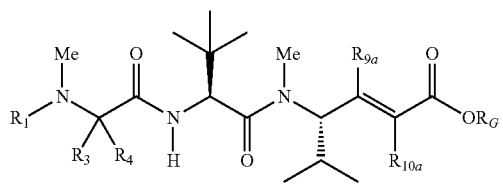

wherein $R_1$, $R_{9a}$, $R_{10a}$ and $R_G$ are as defined above and in subclasses herein; and $R_3$ and $R_4$ are each independently an alkyl, heteroalkyl, heteroalkyl(aryl) or alkyl(aryl) moiety, or $R_3$ and $R_4$, taken together, form a cyclic alkyl or heteroalkyl moiety.

It will also be appreciated that for subgroup X described above, a variety of other subclasses are of special interest, including, but not limited to those classes i-d. through xxxii-d. described above and classes, subclasses and species of compounds described above and in the examples herein.

Some of the foregoing compounds can comprise one or more asymmetric centers, and thus can exist in various isomeric forms, e.g., stereoisomers and/or diastereomers. It is to be understood that the invention encompasses every possible isomer such as geometric isomer, optical isomer, stereoisomer and tautomer based on asymmetric carbon, which can occur in the structures of the inventive compounds, and mixtures of such isomers, and is not limited to the specific stereochemistry shown for the compounds disclosed in the present specification. It will be further appreciated that the absolute stereochemistry of some of the compounds recited in the Exemplification herein has not been determined, and that when a stereochemistry was assigned for those compounds it is meant to be tentative and to indicate that a set of diastereomers exists for those compounds and/or that a diastereomer was isolated in pure form. Thus, inventive compounds and pharmaceutical compositions thereof may be in the form of an individual enaotiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. The invention also encompasses tautomers of specific compounds as described above. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (I) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

2) Compounds and Definitions

As discussed above, this invention provides novel compounds with a range of biological properties. Compounds of this invention have biological activities relevant for the treatment of diseases or other disorders such as proliferative diseases, including, but not limited to cancer. In certain other embodiments, the inventive compounds also find use in the prevention of restenosis of blood vessels subject to traumas such as angioplasty and stenting.

Compounds of this invention include those specifically set forth above and described herein, and are illustrated in pail by the various classes, subgenera and species disclosed elsewhere herein.

Additionally, the present invention provides pharmaceutically acceptable derivatives of the inventive compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Numerous suitable prodrug moieties, and information concerning their selection, synthesis and use are well known in the art. Examples of prodrug moieties of interest include, among others, prodrug moieties that can be attached to primary or secondary amine-containing functionalities. Examples of such prodrug moieties include the following:

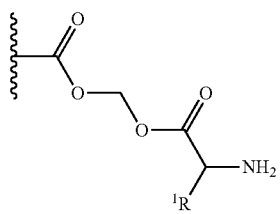

$R^1$ = all natural,
unnatural amino acids

For the synthesis of the prodrug groups, see Borchardl, R. T. et. al.,
*J. Org. Chem.* 1997, 43, 3641-3652

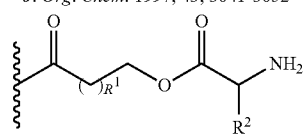

$R^1$ = C1-C4alkyl, cycloalkyl, oxyalkyl,
aminoalkyl, etc.

$R^2$ = all natural, unnatural amino acids

For the synthesis of the prodrug groups, see
Zhou, X—X et. al., PCT WO 99/51613.

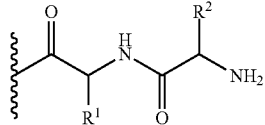

$R^1$, $R^2$ = all natural, unnatural amino acids

For the synthesis of the prodrug groups, see Ezra, A. et. al.,
*J. Med. Chem.* 2000, 43, 3641-3652

Other examples of prodrug moieties of interest include prodrug moieties that can be attached to hydroxyl-containing functionalities. Such prodrug moieties a well-known in the art, and will be readily identified by a person skilled in the relevant art. The present invention encompasses any prodrug form of the compounds described herein.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", as used herein, it is meant that a particular functional moiety, e.g., O, S, or N, Is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably non-toxic reagents that do not attack the other functional groups; the protecting group forms an easily separable derivative (more preferably without fee generation of new stereogenic centers); and die protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups cars be readily identified, using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the terra "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of cancer. The term "stable", as used herein, preferably refers to compounds which possess stability sufficient to allow manufacture and which maintain the integrity of the compound for a sufficient period of time to be detected and preferably for a sufficient period of time to be useful fox the purposes detailed herein.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited, to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl-n, cyclohexyl, —$CH_2$-cyclohexyl, cyclohexenylethyl, cyclohexanylethyl, norborbyl moieties and the like, which again, may bear one or more substituents.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms, in certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —$NHR'$ wherein $R'$ is alkyl, as defined herein. The term "aminoalkyl" refers to a group having the structure $NH_2R'$—, wherein $R'$ is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHI_2$; —$CH_2OH$; —$CH_2CH_2OH$; —$CH_2NH_2$; —$CH_2SO_2CH_3$; —$C(O)R_x$; —$CO_2(R_x)$; —$CON(R_x)$; —$OC(O)R_x$; —$OCO_2R_x$; —$OCON(R_x)_2$; —$N(R_x)_2$; —$S(O)_2R_x$, —$NR_x(CO)R_x$ wherein each occurrence of $R_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, aryl, heteroaryl, alkylaryl, or alkylheteroaryl, substituents described above and herein, may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. It will also be appreciated that aryl and heteroaryl moieties, as defined herein may be attached via an aliphatic, alicyclic, heteroaliphatic, heteroalicyclic, alkyl or heteroalkyl moiety and thus also include -(aliphatic)aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and -(heteroalkyl)heteroaryl moieties. Thus, as used herein, the phrases "aryl or heteroaryl" and "aryl, heteroaryl, -(aliphalic)aryl, -(heteroaliphatic)aryl, -(alphalic)heteroaryl, -(heteroaliphatic)heteroaryl, -(alkyl)aryl, -(heteroalkyl)aryl, -(heteroalkyl)aryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound, in certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated, that aryl and heteroaryl groups (including bycyclic aryl groups) can be unsubstituted or substituted, wherein substitution includes replacement of one, two or three of the hydrogen atoms thereon independently with any one or more of the following moieties including, but not limited to: aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, aryl, heteroaryl, alkylaryl, or alkylheteroaryl, substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyelopentyl, cyclohexyl, cycloheptyl and the like, which, as in the case of other aliphatic, heteroaliphatic or hetercyclic moieties, may optionally be substituted with substituents including, but not limited to -aliphatic; -alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, aryl, heteroaryl, alkylaryl, or alkylheteroaryl, substituents described above and herein may be substituted or unsubstituted, branched or inbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have have substituted with an heteroatom. Thus, a heteroaliphatic group refers to an aliphatic chain which contains one or more oxygen sulfur, nitrogen, phosphorus or silicon atoms, e.g., in place of carbon atoms. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$); —OC(O)R$_x$; —OCO$_2$R$_x$; —OCON(R$_x$)$_2$; N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroalicyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like, The term "heterocycloalkyl" or "heterocycle", as used herein, refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazodinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, aryl, heteroaryl, alkylaryl, or alkylheteroaryl, substituents described above and herein may be substituted or unsubstituted, branched or unbranched, cyclic or acyclic, and wherein any of the aryl or heteroaryl substitutents described above and herein may be substituted or unsubstituted. Additional examples or generally applicable substituents are illustrated by the specific embodiments shown in the Examples, which are described herein.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heteroalicyclic", "heterocycloalkyl", "heterocycle", and the like encompass substituted and unsubstituted, and saturated and unsaturated groups. In addition, the terms "alphatic(aryl)", "heteroaliphatic(aryl)", "aliphatic(heteroaryl)", "heteroaliphatic(heteroaryl)", "alicyclic(aryl)", "heteroalicyclic (aryl)", "alicyclic(heteroaryl)", "heteroalicyclic (heteroaryl)", "alkyl(aryl)", "heteroalkyl(aryl)", "alkyl(heteroaryl)", "heteroalkyl(heteroaryl)", and the like encompass substituted and unsubstituted, and saturated and unsaturated (i.e., non-aromatic portion of the moiety) groups. Additionally, the terms "cycloalkyl", "cycloalkenyl", "cycloalkynyl", "heterocycloalkyl", "heterocycloalkenyl", "heterocycloalkynyl", "aryl", "heteroaryl" and the like encompass both substituted and unsubstituted groups, unless otherwise indicated.

3) Synthetic Methodology

According to the present invention, any available techniques can be used, to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

In one aspect, the present invention provides novel peptides having formula (I) as described above and in certain classes and subclasses herein. Examples of synthetic methods for preparing exemplary types of compounds of the invention are provided below, as detailed in Schemes 1-12, and in the Exemplification herein. It will be appreciated that the methods as described herein can be applied to each of the compounds as disclosed herein and equivalents thereof. Additionally, the reagents and starting materials are well known to those skilled in the art. Although the following schemes describe certain exemplary compounds, it will be appreciated that the use of alternate starting materials will yield other analogs of the invention. For example, compounds are described below where X$_1$ and X$_2$ are each C=O, R$_5$ is hydrogen, R$_6$ is tert-butyl and R$_7$ is methyl; however, it will be appreciated that alternate starting materials and/or intermediates can be utilized to generate compounds where, for example, X$_1$ and X$_7$ may be independently C=O, CH$_2$, SO$_2$, and R$_5$-R$_7$ may represent moieties other than those depicted herein, such as alkyl, heteroalkyl, aryl, heteroaryl, etc. It will also be appreciated that any available techniques known in the art can be used to make the inventive compounds or compositions including them. A person of ordinary skill in the art will recognize that suitable synthetic methods are not limited to those depicted in Schemes 1-12 below, and that any suitable synthetic methods known in the art can be used to prepare the inventive compounds.

In certain embodiments, the inventive compounds, have the general structure (I') as shown in Scheme 1, where R, R' and Q are aliphatic, heteroaliphatic, aryl or heteroaryl moieties. In preferred embodiments, R, R' and Q are moieties such as those described in classes and subclasses herein. Examples of preferred structures for R, R' and Q are depicted in Scheme I.

Scheme 1

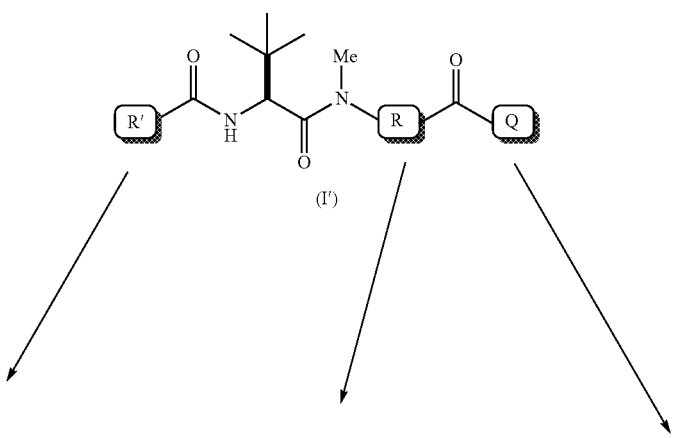

(I')

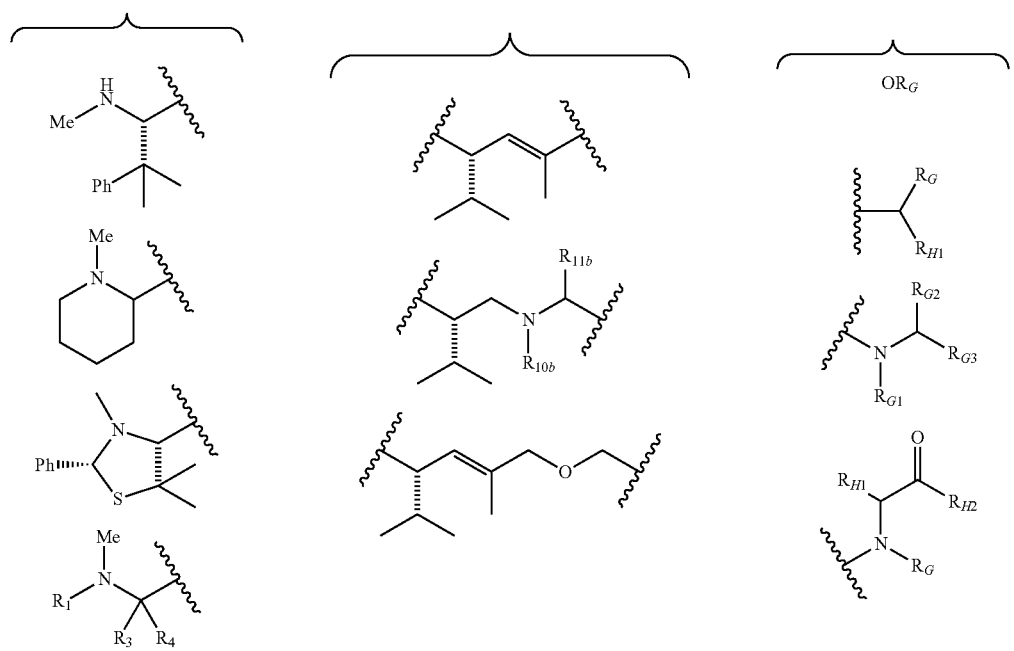

Examples of compounds of this sort include, but are not limited to, compounds wherein:
$R_1$ = H or Me
$R_3$ = Me, Et, or forms a 5-6 membered ring with $R_4$
$R_4$ = Me, Et, or forms a 5-6 membered ring with $R_3$
$R_{10b}$ = H, Me, Ac or forms a 5-6 membered ring with $R_{11b}$
$R_{11b}$ = H, or forms a 5-6 membered ring with $R_{10b}$
$R_G$ = H, Me, Et or forms a 5-6 membered ring with $R_{H1}$
$R_{H1}$ = H, Me, Et or forms a 5-6 membered ring with $R_G$
$R_{H2}$ = H, $CO_2H$, $CO_2Me$, $CONH_2$, CONHMe, $CONHMe_2$, CONHBn, $CH_2OMe$
$R_{G1}$ = H, Me, or forms a 5-6 membered ring with $R_{G2}$
$R_{G2}$ = H, or forms a 5-6 membered ring with $R_{G1}$
$R_{G3}$ = H, $CO_2H$, $CO_2Me$, $CONH_2$, CONHMe, $CONHMe_2$, CONHBn, $CH_2OMe$ In certain embodiments, the inventive compounds belong to class (Ia) and subclasses thereof, as described herein. Scheme 2 depicts the synthesis of exemplary compounds of this class (compounds of general structure 11). As shown in Scheme 2, the dipeptide core can be constructed, for example, from N-Boc-N-methyl-valinal (2) and N-Boc-tert-leucine (4). The N-terminal moiety of the compounds of the invention (R' in Scheme 1) may be provided by (S)—N-Boc-neo-phenylalanine (6). As depicted in Scheme 2, a variety of synthetic methods allow access to a variety of analogs, for example, carboxylic esters of general structure 7, carboxylic acid 8 or amides of general structure 11. The reader will appreciate that other synthetic methods known in the art can be used to prepare other derivatives.

Scheme 2

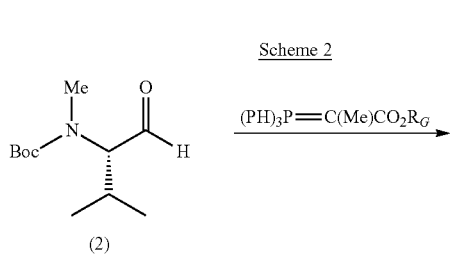

-continued

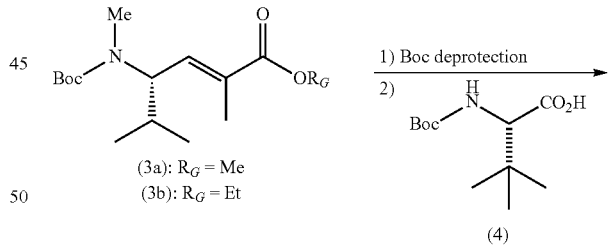

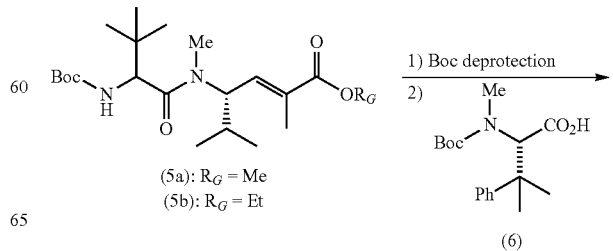

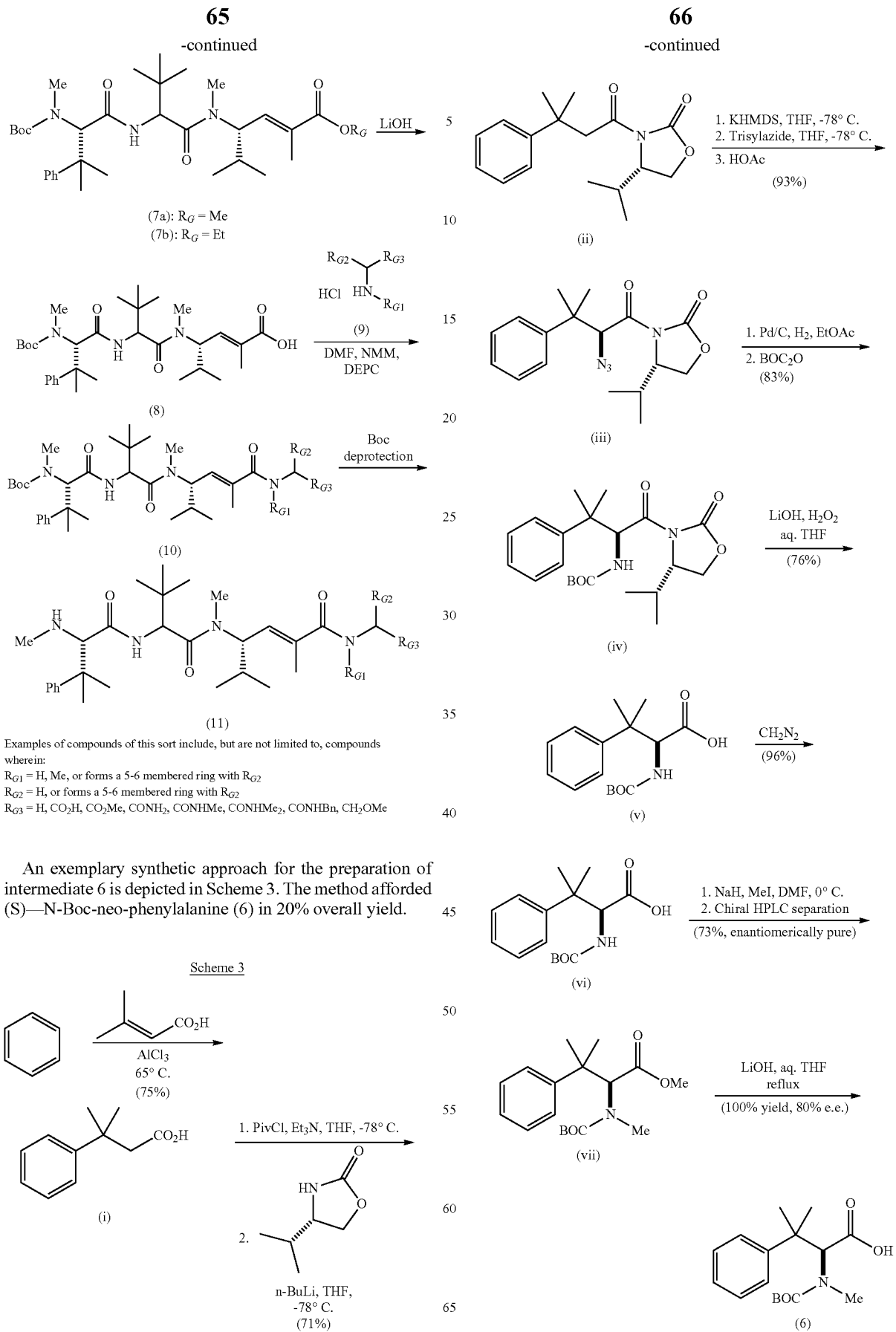

In certain other embodiments, the inventive compounds belong to class (Ib) and subclasses thereof, as described herein. Schemes 4-6 depict the synthesis of exemplary types of compounds of this class (for example, Amine Esters, Amine Acids, Amine Amides and N-Acetyl Amine Amides of general structure 18, 20, 23, respectively as seen in Schemes 4; See also Amine Esters, Amine Acids, Amine Amides and N-Acetyl Amine Amides of general structure 25, 26 and 27, respectively in Scheme 5). In certain embodiments, R may be a nitrogen-containing heteroalkyl moiety (see Schemes 4 and 5) or an unsaturated oxygen-containing heteroalkyl moiety (see Scheme 6), Although Schemes 4-6 depict compounds comprising an N-terminal moiety derived from (S)—N-Boc-neo-phenylalanine (6), a person of ordinary skill in the art would appreciate that a wide variety of organic moieties other than those described in Schemes 4-6 may be used to construct the compounds of the Invention. Similarly, Schemes 4-6 recite compounds where the C-terminal moiety may be carboxylic esters, carboxylic acids or amides. It is to be understood that the scope of the invention is not limited to these compounds, hut rather encompasses derivatives and analogs of these compounds, or compounds obtained from different starting materials.

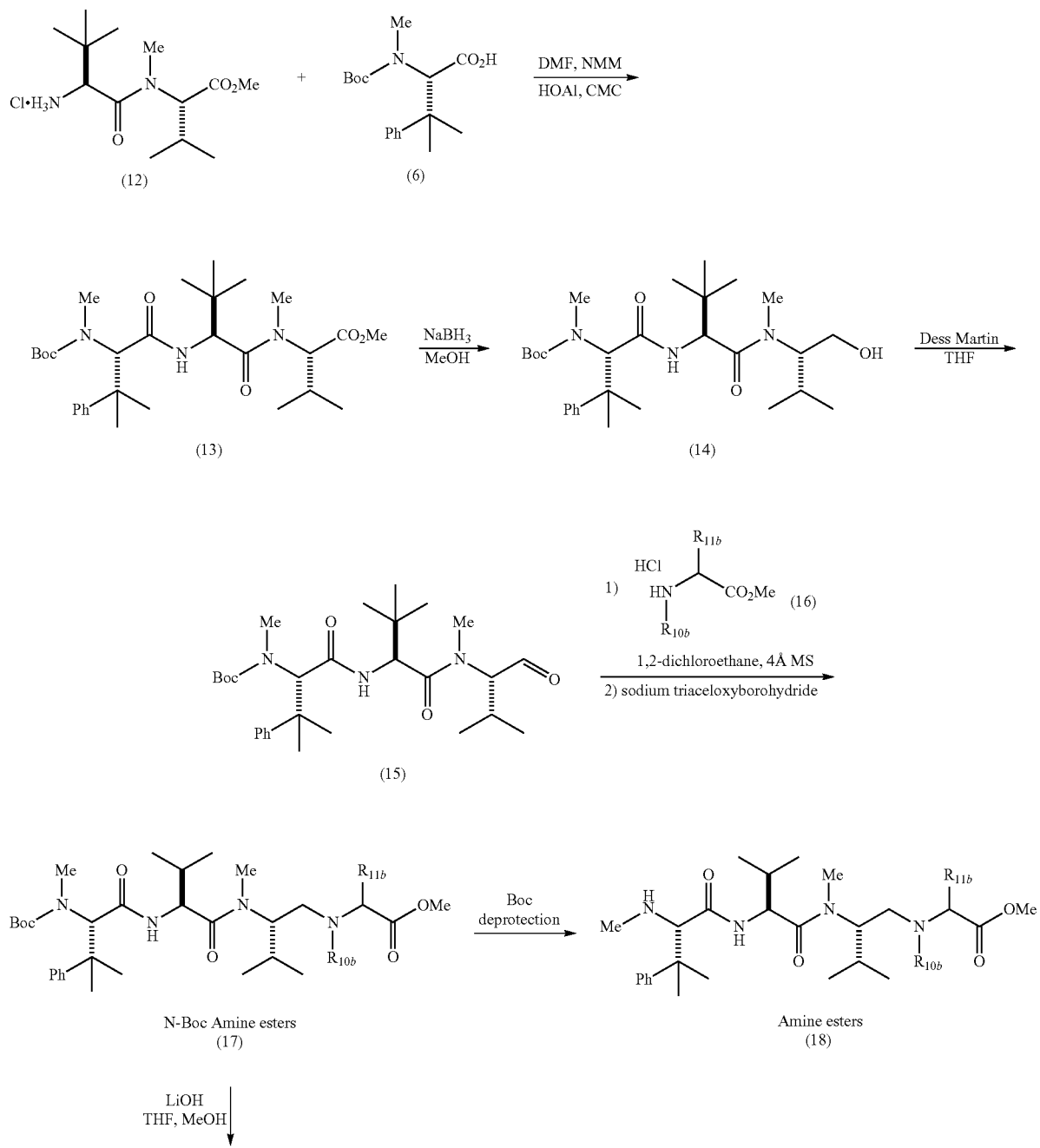

-continued
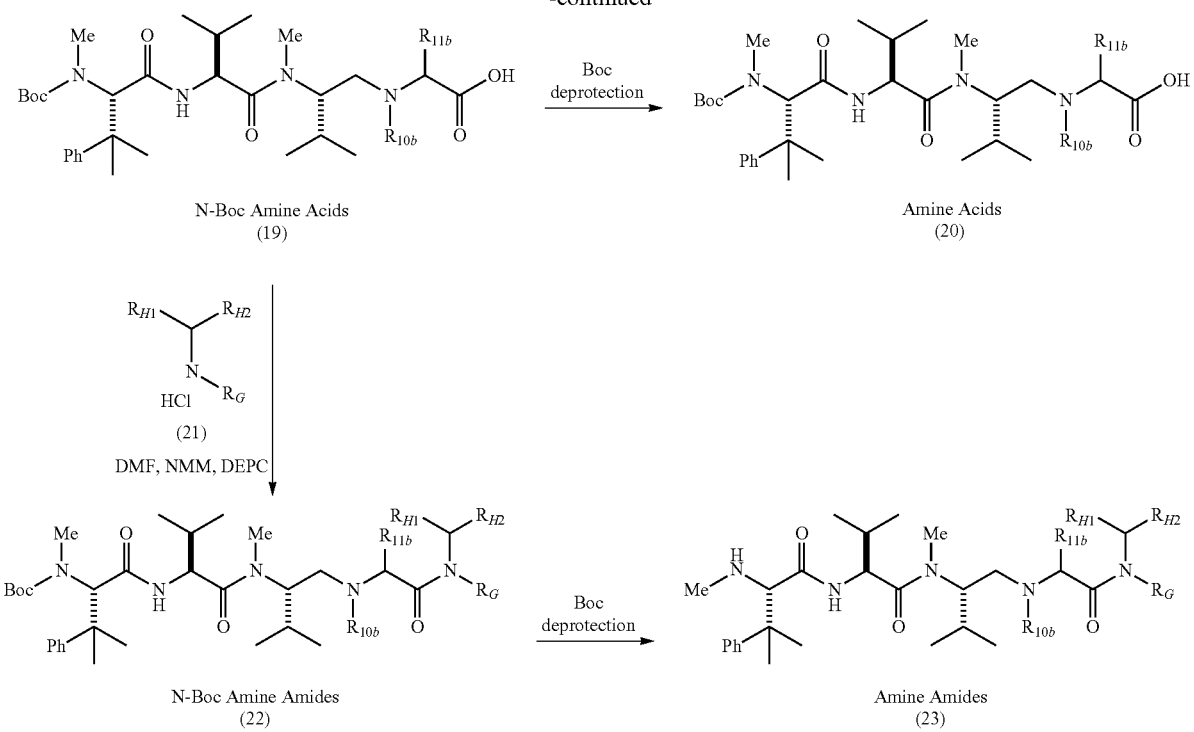
Examples of compounds of this sort include, but are not limited to, compounds wherein:
$R_{10b}$ = H, Me, or forms a 5-6 membered ring with $R_{11b}$
$R_{11b}$ = H, or forms a 5-6 membered ring with $R_{10b}$
$R_G$ = H, Me, or forms a 5-6 membered ring with $R_{H1}$
$R_{H1}$ = H, or forms a 5-6 membered ring with $R_G$
$R_{H2}$ = H, $CO_2H$, $CO_2Me$, $CONH_2$, $CONHMe$, $CONHMe_2$, $CONHBn$, $CH_2OMe$
Scheme 5
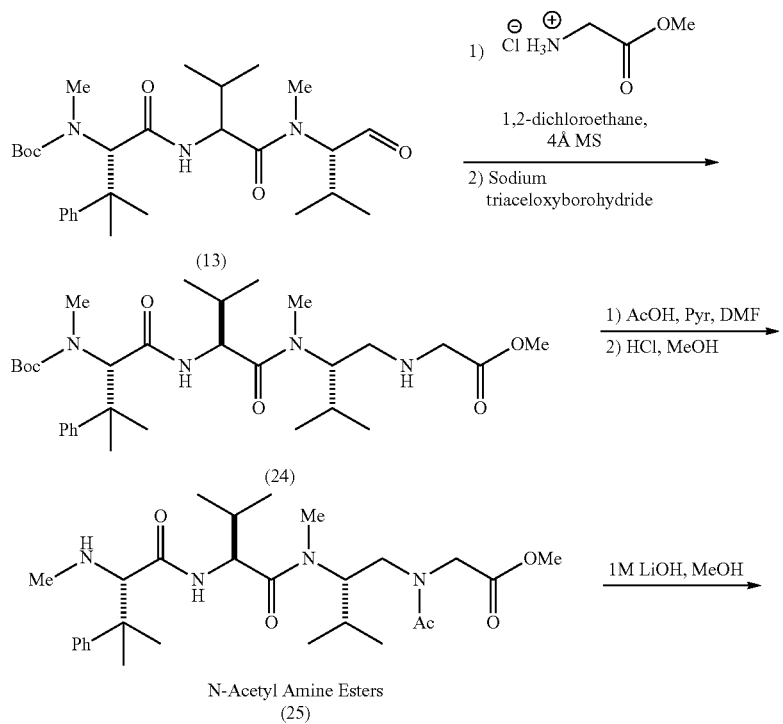

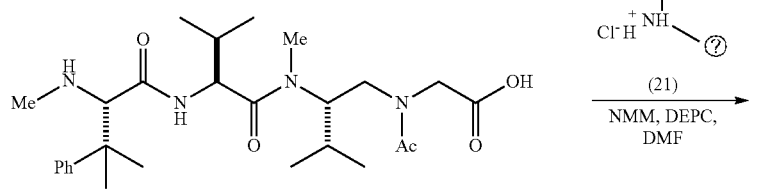
N-Acetyl Amine Acids
(26)
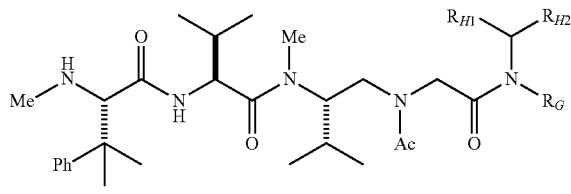
N-Acetyl Amine Amides
(27)
Examples of compounds of this sort include, but are not limited to, compounds wherein:
$R_G$ = forms a 5 or 6 membered ring with $R_{H1}$
$R_{H1}$ = forms a 5 or 6 membered ring with $R_G$
$R_{H2}$ = $CO_2Me$, $CONH_2$
Scheme 6
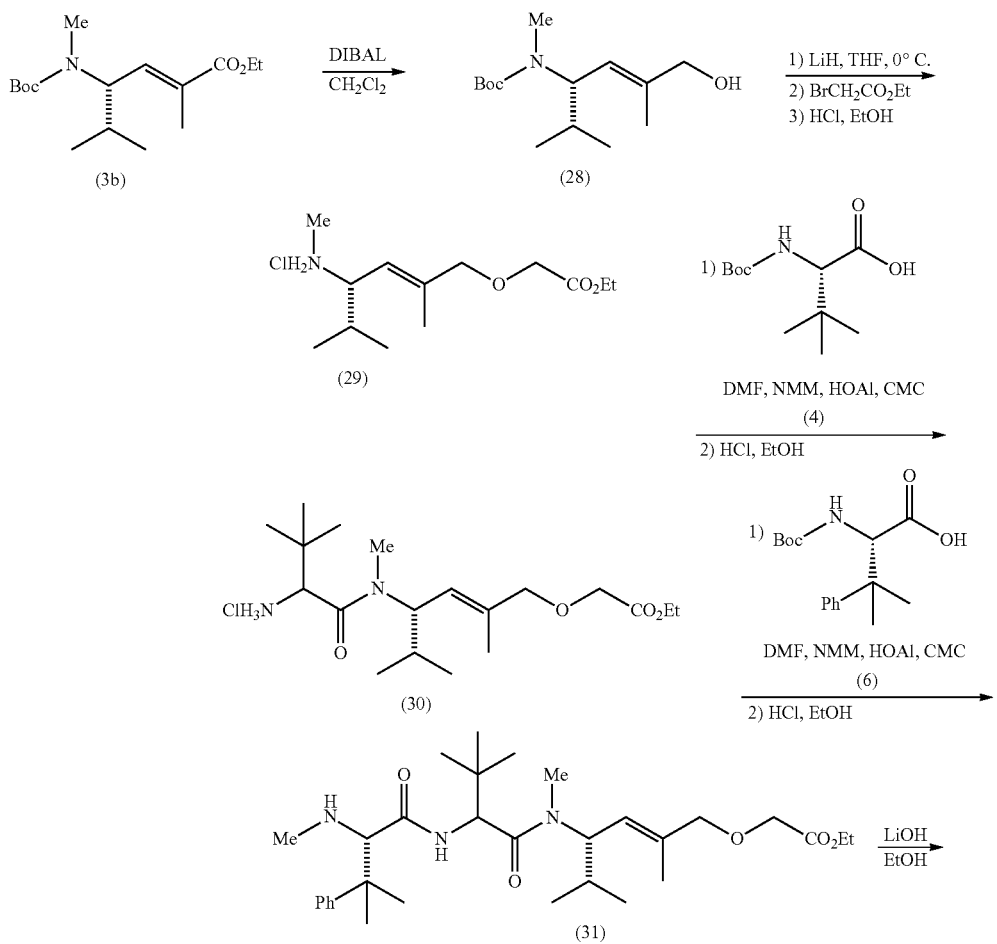

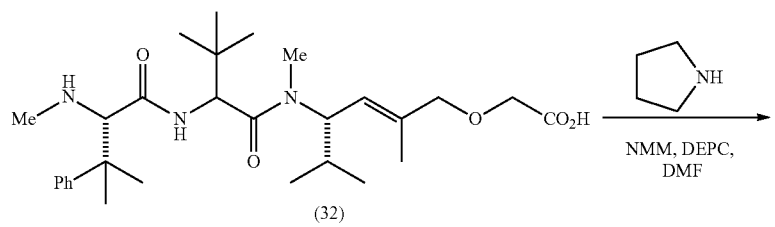

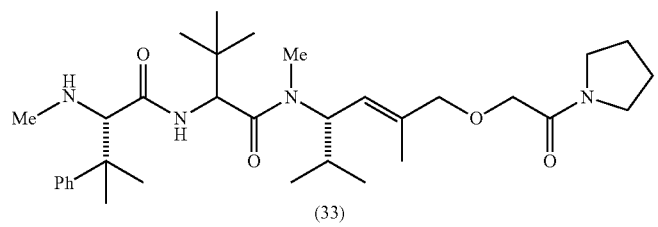

In certain other embodiments, the inventive compounds belong to class (Ic) and subclasses thereof, as described herein. Schemes 7-10 depict the synthesis of exemplary types of compounds of this class (for example Amine Esters, Amine Acids and Amine Amides of general structure 42, 43 and 45, respectively, as seen in Scheme 7). In certain embodiments, the compounds of the invention comprise a nitrogen-containing heterocyclic N-terminal moiety. For example, the heterocyclic moiety may be a piperidine ring (Schemes 7, 8 and 9) or a thiazolidine ring (Scheme 10). Examples of other suitable moieties are described in the Exemplification herein, or will be apparent to the person of ordinary skill in the art. As discussed above, R may be a nitrogen-containing heteroalkyl moiety (Scheme 7) or an unsaturated alkyl moiety (Schemes 8, 9 and 10).

Scheme 7

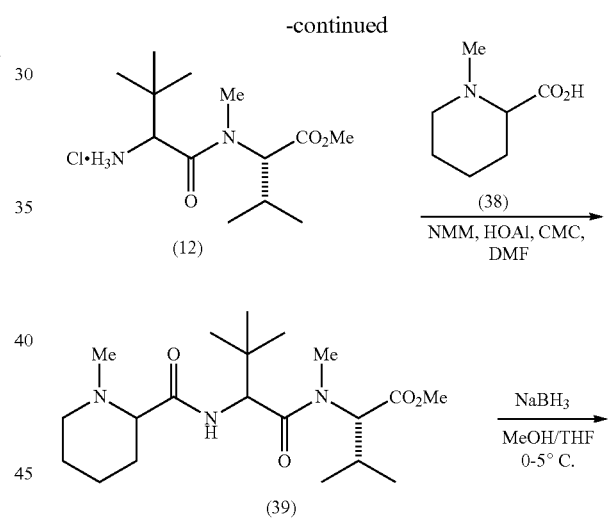

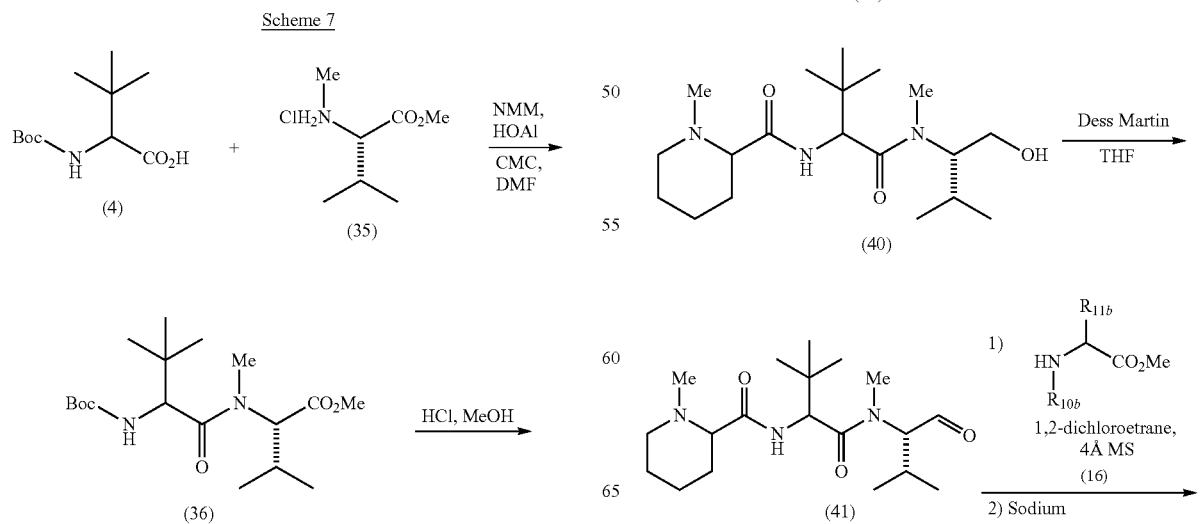

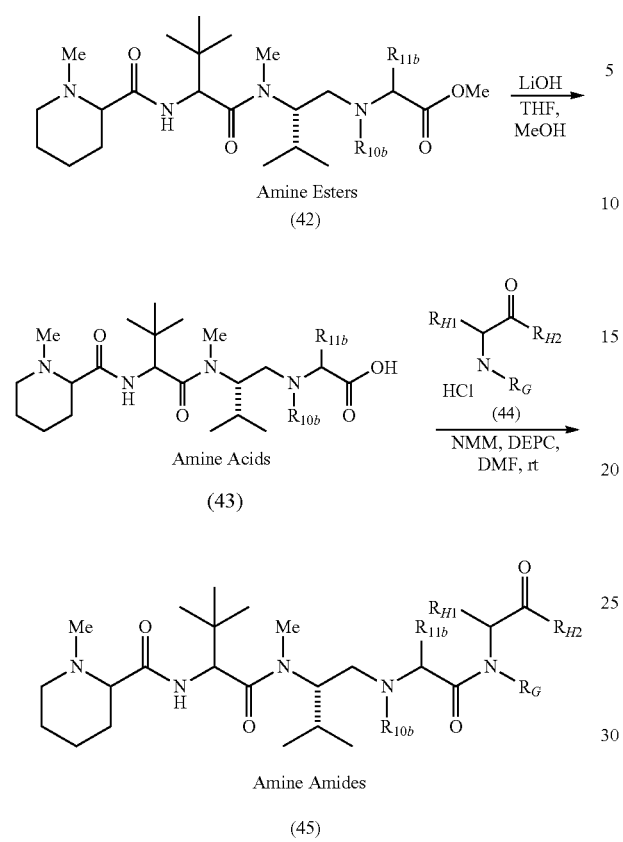

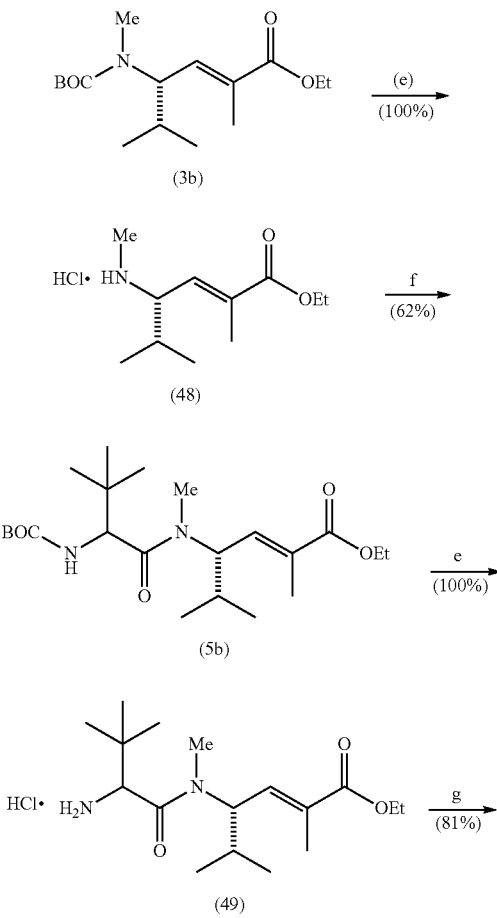

Examples of compounds of this sort include, but are not limited to, compounds wherein:
$R_{10b}$ = H, Me, or forms a 5-6 membered ring with $R_{11b}$
$R_{11b}$ = H, or forms a 5-6 membered ring with $R_{10b}$
$R_G$ = H, Me, OMe, or forms a 5-6 membered ring with $R_{H1}$
$R_{H1}$ = H, i-Pr, or forms a 5-6 membered ring with $R_G$
$R_{H2}$ = OH, OMe, OBn, O———iPr, O-cyclo-Bu, O-cyclo-Pent, O-cyclo-Hex, $NH_2$, NHBn, NH(2-Naphth)

Scheme 8

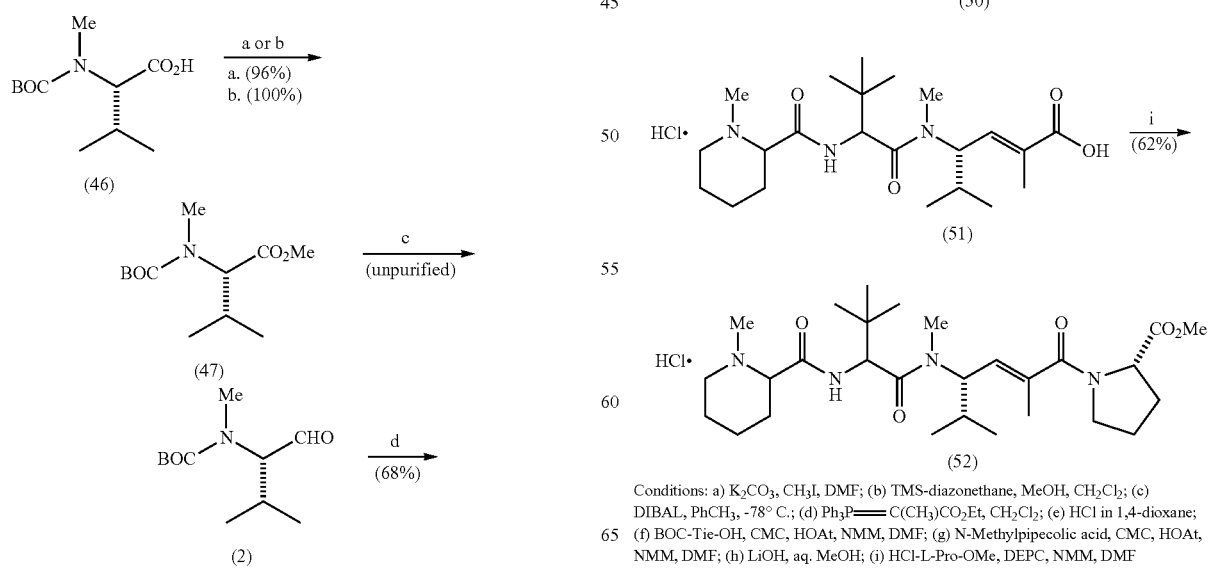

Conditions: a) $K_2CO_3$, $CH_3I$, DMF; (b) TMS-diazonethane, MeOH, $CH_2Cl_2$; (c) DIBAL, $PhCH_3$, -78° C.; (d) $Ph_3P$=$C(CH_3)CO_2Et$, $CH_2Cl_2$; (e) HCl in 1,4-dioxane; (f) BOC-Tie-OH, CMC, HOAt, NMM, DMF; (g) N-Methylpipecolic acid, CMC, HOAt, NMM, DMF; (h) LiOH, aq. MeOH; (i) HCl-L-Pro-OMe, DEPC, NMM, DMF

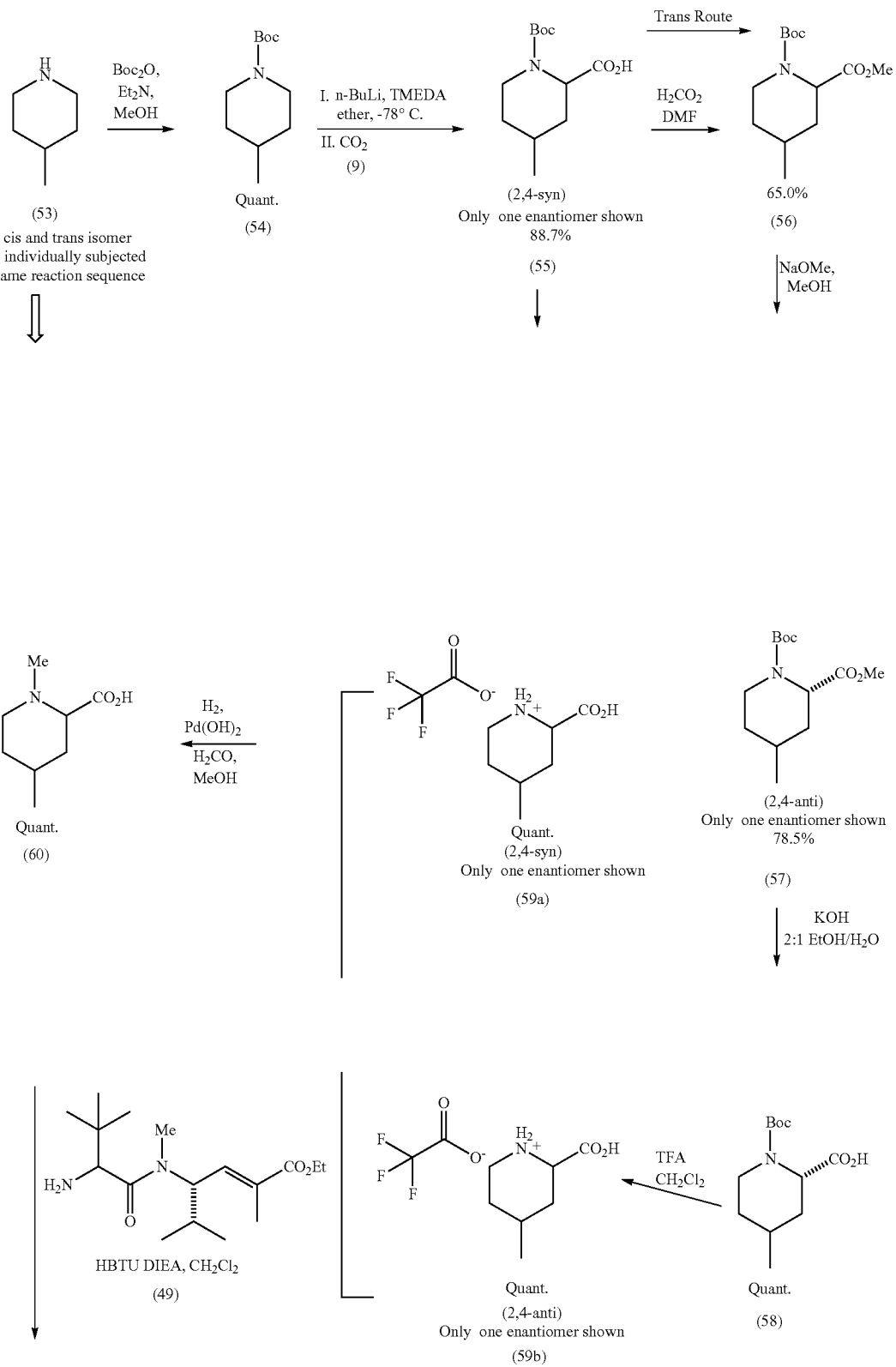

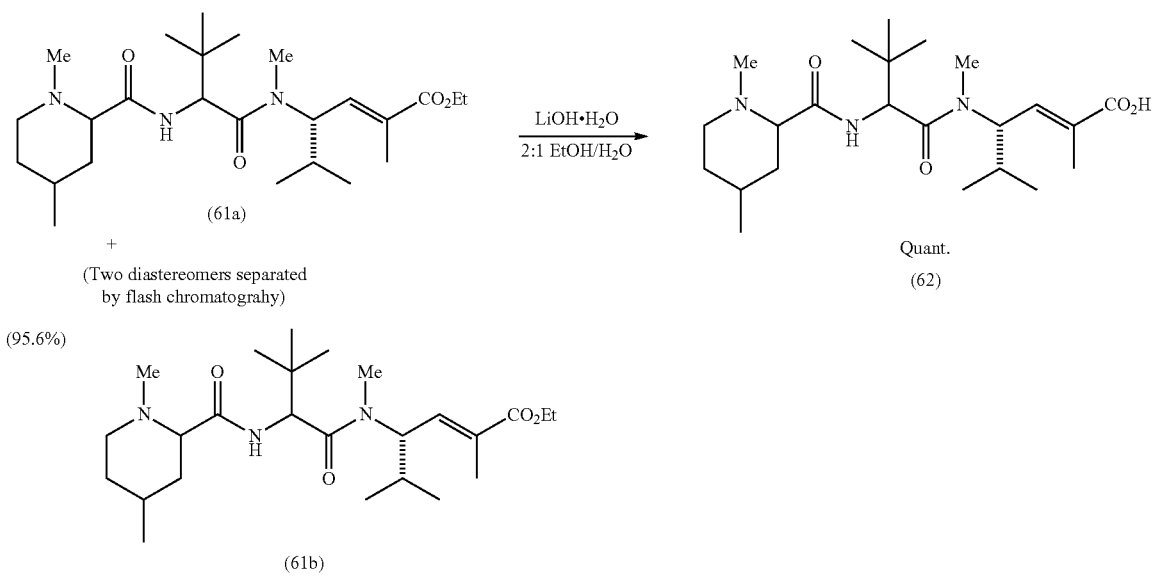
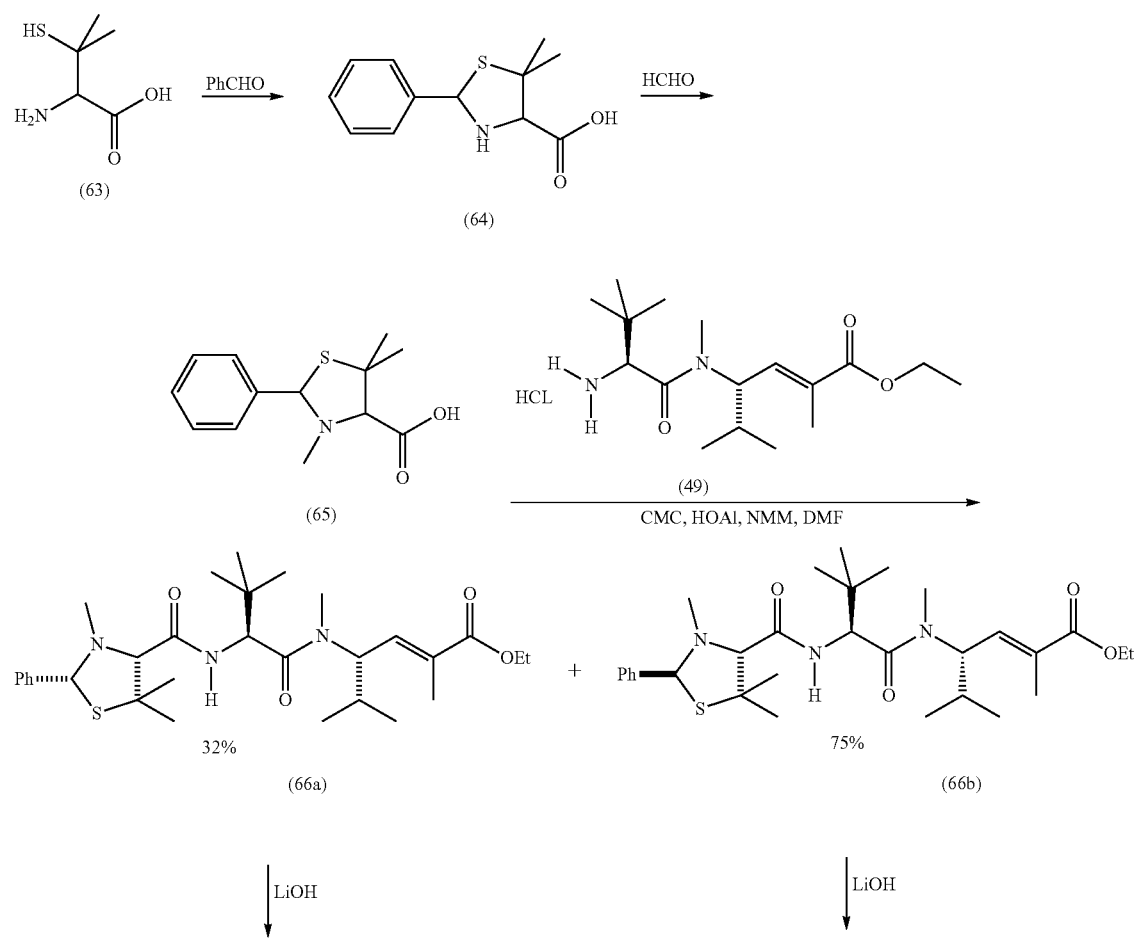
Scheme 10

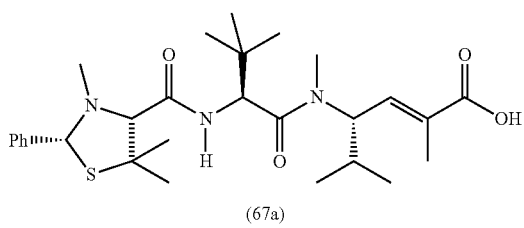

(67a)

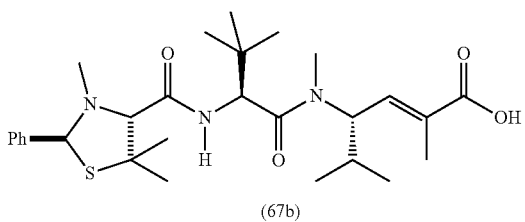

(67b)

In certain other embodiments, the inventive compounds belong to class (Id) and subclasses thereof, as described herein. One skilled in the art would appreciate that the exemplary heterocyclic starting materials described in Schemes 7-10, that are used in the preparation of compounds of class (Ic) (namely compounds 38, 60 or 65) could be substituted for acyclic α-amino acid moieties to access compounds of class (Id), as illustrated in Scheme 11 below:

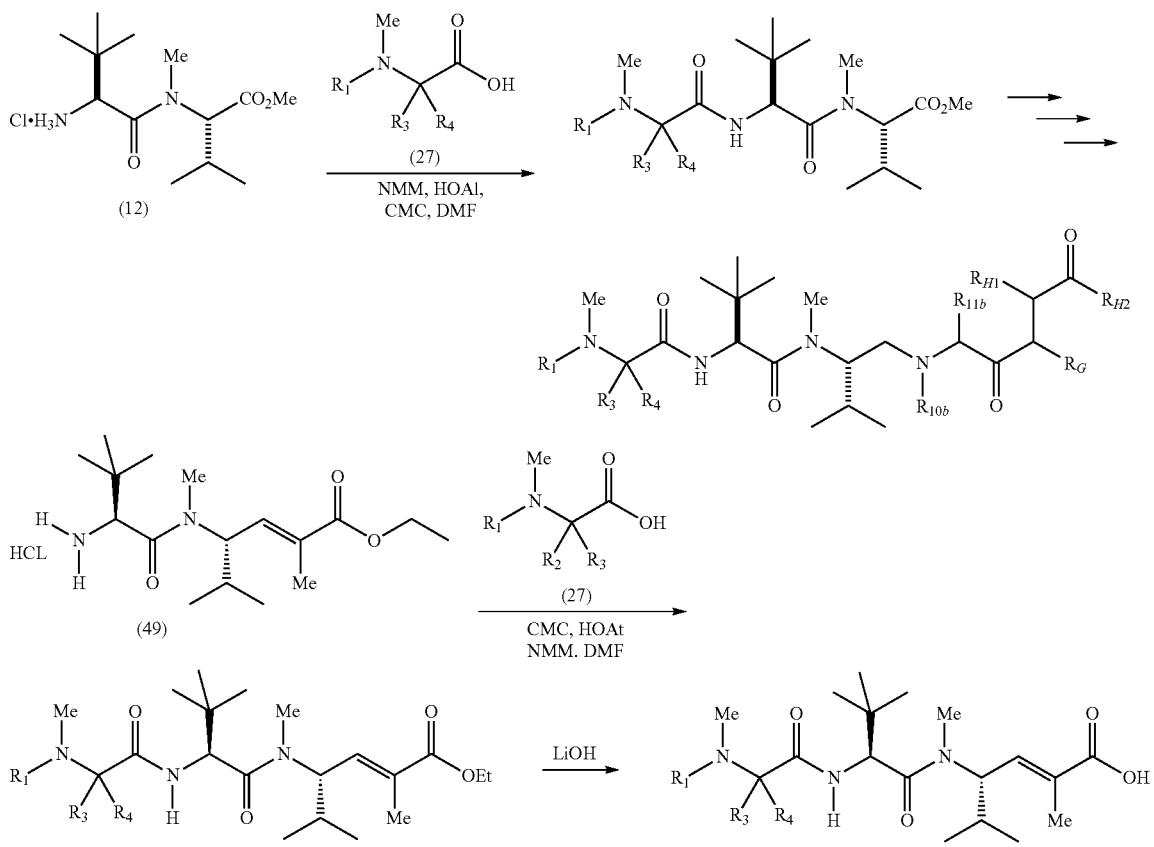

Scheme 11

Examples of compounds of this sort include, but are not limited to, compounds wherein:
$R_1$ = H or Me
$R_3$ = Me, Et, or forms a 5-6 membered ring with $R_4$
$R_4$ = Me, Et, or forms a 5-6 membered ring with $R_3$
$R_{10b}$ = H, Me, or forms a 5-6 membered ring with $R_{11b}$
$R_{11b}$ = H, or forms a 5-6 membered ring with $R_{10b}$
$R_G$ = H, Me, or forms a 5-6 membered ring with $R_{H1}$
$R_{H1}$ = H, or forms a 5-6 membered ring with $R_G$
$R_{H2}$ = H, $CO_2H$, $CO_2Me$, $CONH_2$, $CONHMe$, $CONHMe_2$, $CONHBn$, $CH_2OMe$ For example, reaction of diethylglycine (72) with amine HCl salt 49 gives the N-terminal gem-diethyl ethyl ester 73, or the corresponding carboxylic acid 74, after hydrolysis under suitable conditions (Scheme 12).

Scheme 12

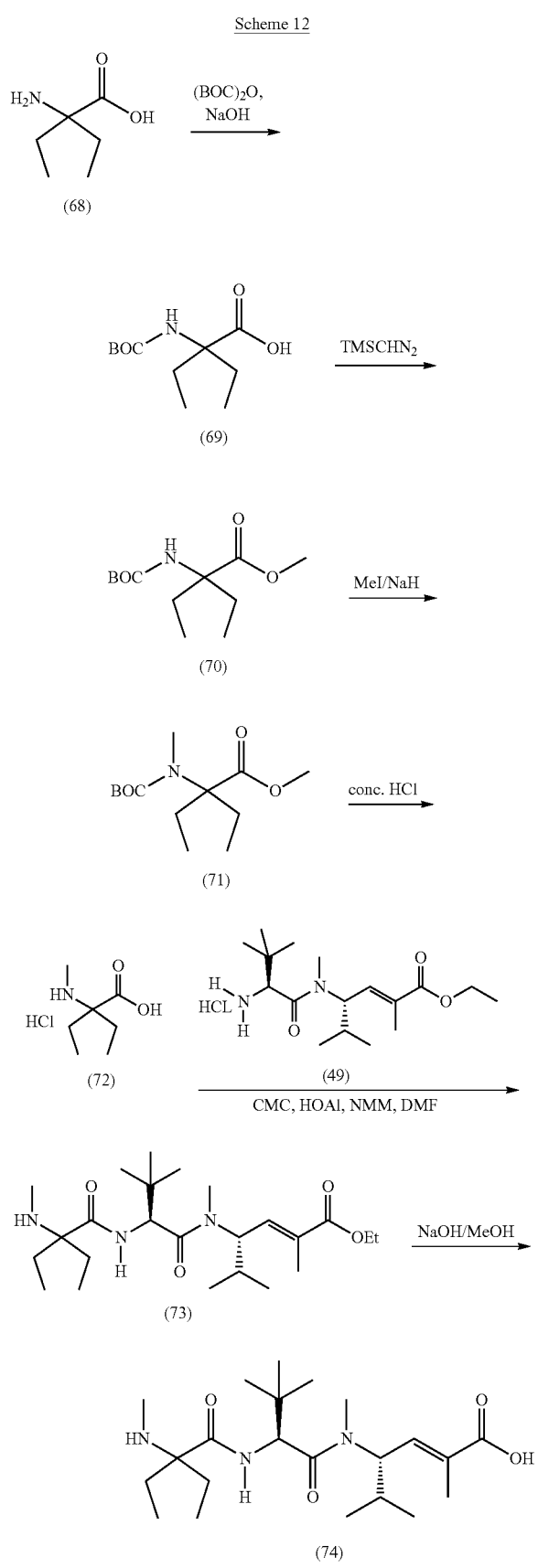

It will be appreciated that each of the reactions described in Schemes 2-12 above can be carried out using reagents and conditions as described for the synthesis of various types of exemplary compounds described above, or they may be modified using other available reagents or starting materials. For example, a variety of amide formation conditions, esterification, hydrolysis and aromatic nucleus functionalization conditions are well-known in the art and can be utilized in the method of the invention. See, generally, March, Advanced Organic Chemistry, $5^{th}$ ed., John Wiley & Sons, 2001; and "Comprehensive Organic Transformations, a guide to functional group preparations", Richard C. Larock, VCH publishers, 1999; the entire contents of which are incorporated herein by reference.

As mentioned above, it will be appreciated that the invention is not limited in scope to the compounds recited herein. Synthetic strategies or starting materials other than those described herein, may be used to prepare compounds of general structure (I). It will also be appreciated that each of the components/starting materials used in the synthesis of the compounds of the invention can be diversified either before synthesis or alternatively after the construction of the peptide construct. As used herein, the term "diversifying" or "diversify" means reacting an inventive compound, as defined herein, at one or more reactive sites to modify a functional moiety or to add a functional moiety. For example, where an aromatic sing is present in the compound, the aromatic ring can be diversified (prior to or after reaction) to either add functionality (e.g., where hydrogen is present, a halogen or other functionality can be added) or to modify functionality (e.g., where a hydroxyl group is present on the aromatic ring, the aromatic ring can be diversified by reacting with a reagent to protect the hydroxyl group, or to convert it into an aliphatic or heteroaliphatic moiety). Described generally below are a variety of schemes to assist the reader in the synthesis of a variety of analogues, either by diversification of the intermediate components or by diversification of the peptide construct.

In certain embodiments, the preparation of chemically diverse derivatives may be achieved by diversifying the C-terminal moiety of the compounds. For example, where the C-terminal moiety is a carboxylic acid, examples of chemical transformations suitable to achieve such derivatization include, but are not limited to, reduction to the corresponding aldehyde or alcohol, amidation, Wittig reaction, decarboxylation, esterification, addition of nucleophiles, conversion to ketones, imines, hydrazines, azides, etc. . . . Examples of such transformations are depicted in Schemes 12 and 13. One skilled in the art will recognize that possible chemical, transformations suitable to achieve diversification of the compounds of the invention are not limited to those depicted in Schemes 1-13. Rather, any suitable synthetic methods known in fee art can be used to achieve desired chemical transformations.

Scheme 12
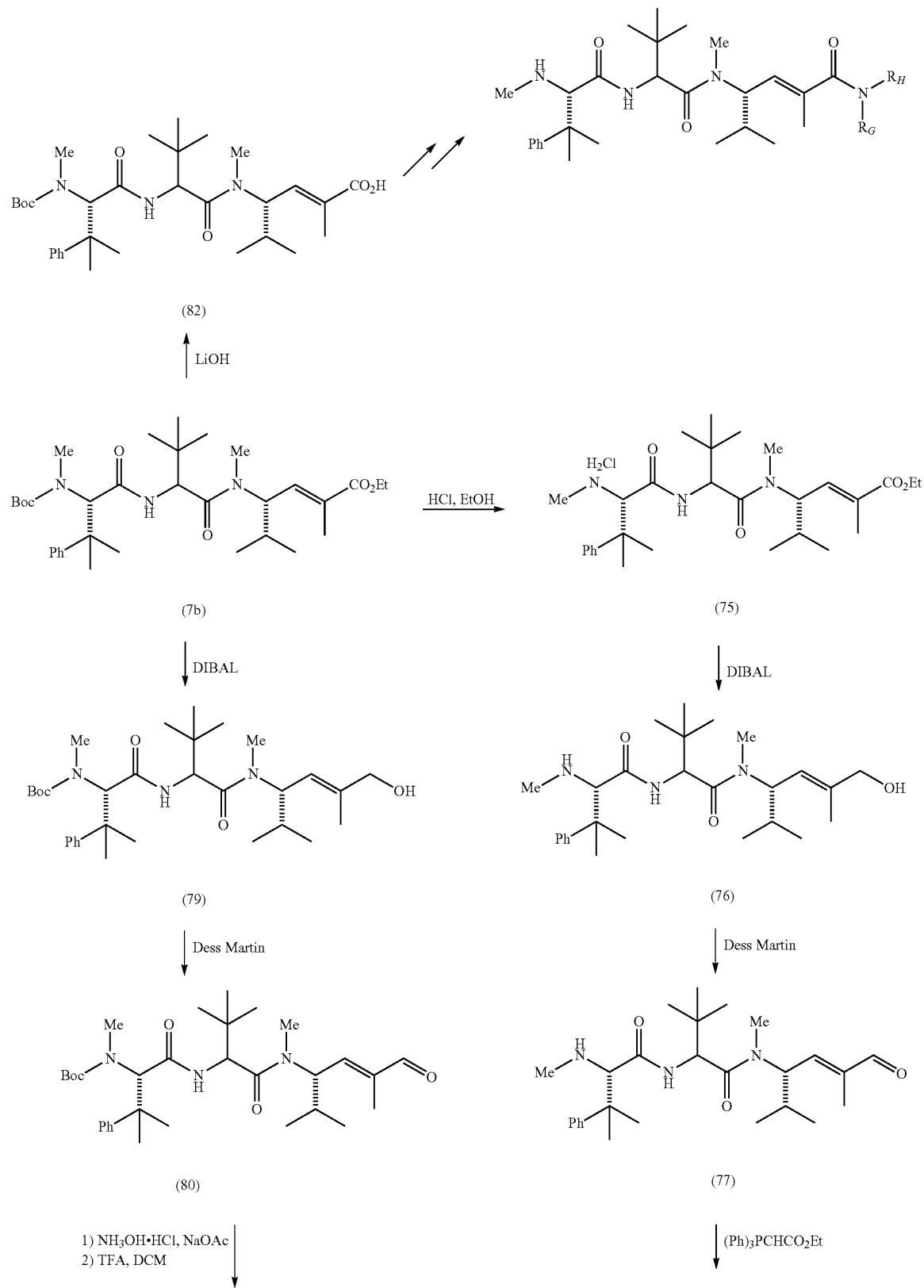

-continued
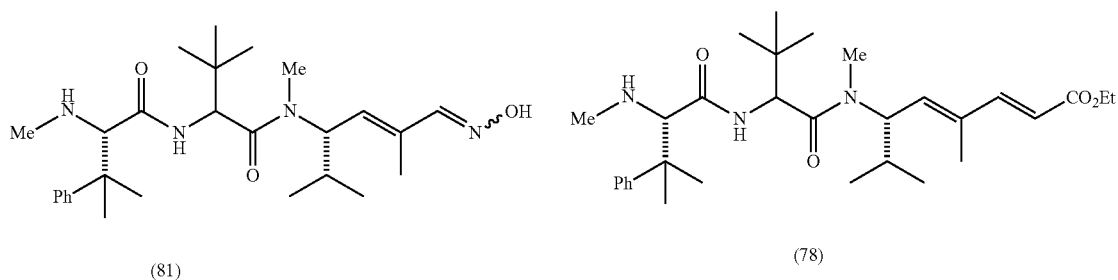 [SMILES: CN[C@H](C(=O)NC(C(=O)N(C)[C@H](/C=C(\C)C=NO)C(C)C)C(C)(C)C)C(C)(C)c1ccccc1 ; CCOC(=O)/C=C/C(C)=C/[C@H](C(C)C)N(C)C(=O)C(NC(=O)[C@@H](NC)C(C)(C)c1ccccc1)C(C)(C)C]
Scheme 13
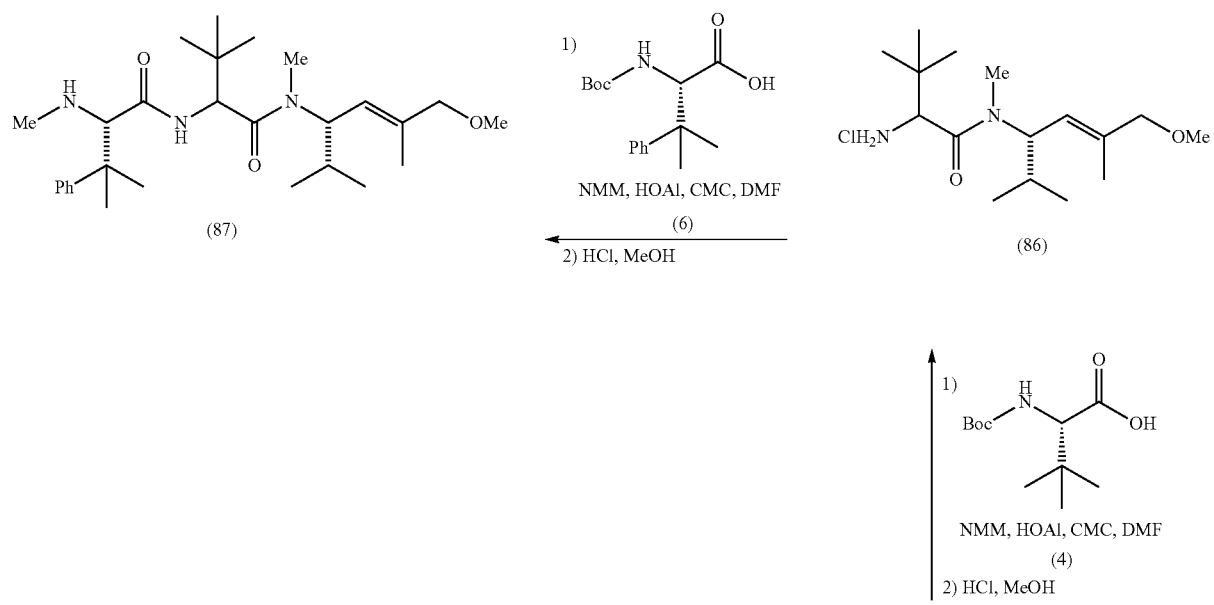
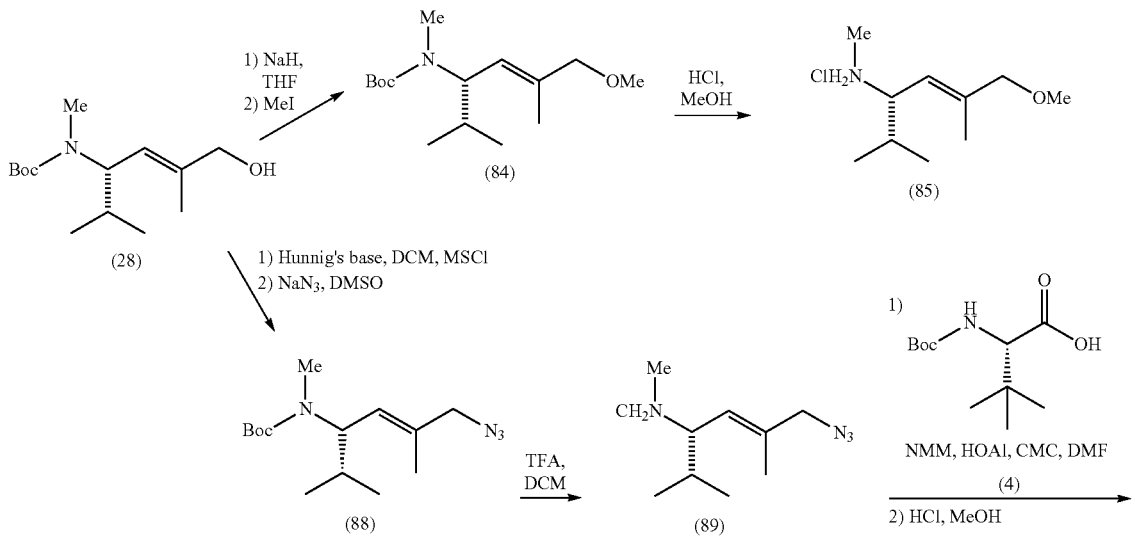

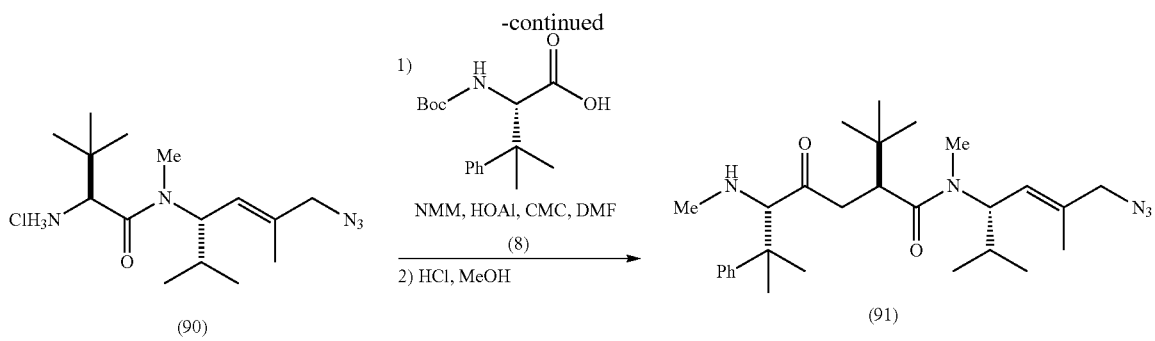

4) Research Uses, Formulation and Administration

According to the present invention, the inventive compounds may be assayed in any of the available assays known in the art for identifying compounds having a pre-determined biological activity. For example, the assay may be cellular or non-cellular, in vivo or in vitro, high- or low-throughput format, etc. In certain exemplary embodiments, the inventive compounds are tested in assays to identify those compounds having cytotoxic or growth inhibitory effect in vitro, or cause tumor regression and/or inhibition of tumor growth in vivo.

Compounds of this invention which are of particular interest include those which:
- exhibit cytotoxic and/or growth inhibitory effect on cancer cell lines maintained in vitro or in animal studies using a scientifically acceptable cancer cell xenograft model;
- preferably cause tumor regression in vivo;
- exhibit low sensitivity to MDR;
- exhibit low cytotoxicity to non-dividing normal cells; and/or
- exhibit a favorable therapeutic profile (e.g., safety, efficacy, and stability).

As detailed in the exemplification herein, in assays to determine the ability of compounds to inhibit the growth of tumor cell lines in vitro, certain inventive compounds exhibited $IC_{50}$ so values 10 µM. In other embodiments, compounds of the invention exhibit $IC_{50}$ values 5 µM. In other embodiments, compounds of the invention exhibit $IC_{50}$ values 1 µM. In other embodiments, compounds of the invention exhibit $IC_{50}$ values 750 nM. In other embodiments, compounds of the invention exhibit $IC_{50}$ values 500 nM. In other embodiments, compounds of the invention exhibit $IC_{50}$ values 250 nM. In other embodiments, compounds of the invention exhibit $IC_{50}$ values 100 nM. In other embodiments, compounds of the invention exhibit $IC_{50}$ values 50 nM. In other embodiments, compounds of the invention exhibit $IC_{50}$ values 25 nM. In other embodiments, compounds of the invention exhibit $IC_{50}$ values 10 nM. In other embodiments, compounds of the invention exhibit $IC_{50}$ values 7.5 nM. In other embodiments, compounds of the invention exhibit $IC_{30}$ values 5 nM. In other embodiments, compounds of the invention exhibit $IC_{50}$ values 2.5 nM. In other embodiments, compounds of the Invention exhibit $IC_{50}$ values 1 nM. In other embodiments, compounds of the invention exhibit $IC_{50}$ values 0.75 nM. In other embodiments, compounds of the invention exhibit $IC_{50}$ values 0.5 nM. In other embodiments, compounds of the invention exhibit $IC_{50}$ values 0.25 nM. In other embodiments, compounds of the invention exhibit $IC_{50}$ values 0.1 nM. In certain embodiments, compounds of the invention exhibit growth inhibition IC50 values in cultured human cancer cells in the range of 0.1 nM-10 nM.

In certain other embodiments, compounds of the invention exhibit low sensitivity to MDR. In certain exemplary embodiments, compounds of the invention have a ratio [cell growth inhibition in MDR-positive cells]/[cell growth inhibition in MDR-negative cells] (i.e., resistance ratio) 10. In certain exemplary embodiments, compounds of the invention have a resistance ratio 9. In certain exemplary embodiments, compounds of the invention have a resistance ratio 8. In certain exemplary embodiments, compounds of the invention have a resistance ratio 7. In certain exemplary embodiments, compounds of the invention have a resistance ratio 6. In certain exemplary embodiments, compounds of the invention have a resistance ratio 5. Its certain exemplary embodiments, compounds of the invention have a resistance ratio 4.

In certain other embodiments, compounds of the invention exhibit low cytotoxicity to non-dividing normal cells. In certain exemplary embodiments, inventive compounds exhibit little or no cytotoxicity in nets-dividing normal cells at concentrations 1000 fold the concentration at which they inhibit cancer cell growth. In certain exemplary embodiments, Inventive compounds exhibit little or no cytotoxicity in non-dividing normal cells at concentrations in the range of up to 1-10 µM.

In certain embodiments, inventive compounds exhibit stability in mouse serum.

In certain embodiments, inventive compounds exhibit a low mitotic block reversibility ratio. In certain embodiments, inventive compounds exhibit mitotic block reversibility ratios of 1 to about 30. In certain embodiments, inventive compounds exhibit mitotic block reversibility ratios of 1 to about 25. In certain embodiments, inventive compounds exhibit mitotic block reversibility ratios of 1 to about 20. In certain embodiments, inventive compounds exhibit mitotic block reversibility ratios of 1 to about 15. In certain embodiments, inventive compounds exhibit mitotic block reversibility ratios of 1 to about 10. In certain embodiments, inventive compounds exhibit mitotic block reversibility ratios of 1 to about 5, In certain embodiments, inventive compounds exhibit mitotic block reversibility ratios of 1 to about 3.

In certain embodiments, compounds of the invention cause tumor regression in vivo. In certain exemplary embodiments, compounds of the invention cause tumor regression in vivo in suitable mouse tumor xenograph models. In certain exemplary embodiments, compounds of the invention cause reduction of tumor size to below 70% of the size at the start of compound administration in a suitable cancer cell xenograft model In certain exemplary embodiments, compounds of the invention cause reduction of tumor size to below 65% of the size at the start of compound administration in a suitable cancer cell xenograft model In certain exemplary embodiments, compounds of the invention cause reduction of tumor size to below 60% of the size at the start of compound administration in a suitable cancer cell xenograft model. In certain exemplary embodiments, compounds of the invention cause reduction of tumor size to below 55% of the size at the start of compound administration in a suitable cancer cell xenograft model. In certain exemplary embodiments, compounds of the invention cause reduction of tumor size to below 50% of the size at the start of compound administration in a suitable cancer ceil xenograft model. In certain exemplary embodiments, compounds of the invention cause tumor regression in certain multidrug resistant xenograph models.

In certain exemplary embodiments, compounds of the invention, cause inhibition of tumor growth in vivo. In certain exemplary embodiments, compounds of the invention cause significant inhibition of tumor growth in suitable cancer cell xenograft models. In certain exemplary embodiments, compounds of the invention cause significant inhibition of tumor growth in suitable multidrug resistant cancer cell xenograft models. In certain exemplary embodiments, compounds of the invention cause inhibition of tumor growth in treated animals by >50% compared to that of control animals (i.e., "treated" tumor size <50% "control" turner size; or T/C value<50%) in suitable cancer cell xenograft models. In certain embodiments, compounds of the invention have T/C values<70%. In certain embodiments, compounds of the invention have T/C values<65%. In certain embodiments, compounds of the invention have T/C values<60%. In certain embodiments, compounds of the invention have T/C values<55%.

In certain embodiments, compounds of the invention inhibit the growth of human cancer cells in vitro, exhibit low sensitivity to MDR (e.g., low resistance ratio), exhibit low cytotoxicity to non-dividing normal cells, exhibit stability in mouse serum, have a low mitotic block reversibility ratio, cause tumor regression, in vivo, and/or cause inhibition of tumor growth in vivo.

In certain embodiments, compounds of the invention inhibit the growth of human cancer cells in vitro, exhibit low sensitivity to MDR (e.g., low resistance ratio), exhibit low cytotoxicity to non-dividing normal cells, exhibit stability in mouse serum, have a low mitotic block reversibility ratio, cause rumor regression in vivo, and cause inhibition of tumor growth in vivo.

In certain embodiments, compounds of the invention have any one or more of the following properties:
(i) exhibit growth inhibition $IC_{50}$ values in cultured human cancer cells in the range of 0.1 nM-10 nM;
(ii) have a resistance ratio preferably 10, preferably 9, preferably 8, preferably 7, preferably 6, preferably 5, more preferably 4;
(iii) exhibit little or no cytotoxicity in non-dividing normal cells at concentrations in the range of up to 1-10 µM;
(iv) exhibit stability in mouse serum;
(v) exhibit mitotic block reversibility ratios of 1 to about 30, preferably of 1 to about 25, preferably of 1 to about 20, preferably of 1 to about 15, preferably of 1 to about 10, preferably of 1 to about 5, most preferably of about 1 to about 3;
(vi) cause reduction of tumor size to below 70%, preferably below 65%, preferably below 60%, preferably below 55%, most preferably below 50%, of the size at the start of compound administration in suitable cancer cell xenograft models; and/or
(vii) cause significant inhibition of tumor growth in suitable cancer cell xenograft model (e.g., T/C value preferably <70%, preferably <65%, preferably <60%, preferably <55%, most preferably <50%).

In certain embodiments, compounds of the invention have the following properties:
(i) exhibit growth inhibition $IC_{50}$ values in cultured human cancer cells in the range of 0.1 nM-10 nM;
(ii) have a resistance ratio preferably 10, preferably 9, preferably 8, preferably 7, preferably 6, preferably 5, more preferably 4;
(iii) exhibit little or no cytotoxicity in non-dividing normal cells at concentrations in fee range of up to 1-10 µM;
(iv) exhibit stability in mouse serum:
(v) exhibit mitotic block reversibility ratios of 1 to about 30, preferably of 1 to about 25, preferably of 1 to about 20, preferably of 1 to about 15, preferably of 1 to about 10, preferably of 1 to about 5, most preferably of about 1 to about 3;
(vi) cause reduction of tumor size to below 70%, preferably below 65%, preferably below 60%, preferably below 55%, most preferably below 50%, of the size al the start of compound administration in suitable cancer cell xenograft models; and
(vii) cause significant inhibition of tumor growth in suitable cancer cell xenograft model (e.g., T/C value preferably <70%, preferably <65%, preferably <60%, preferably <55%, most preferably <50%).

Examples of compounds exhibiting desired properties include ER-805913, ER-805736, ER-807102, ER-807328, ER-806925, ER-807850, ER-807904, ER-807974, ER-808368, ER-808662, ER-808824, and salts thereof (See Table below).

As discussed above, compounds of the invention exhibit activity for the inhibition of tumor cell growth. As such, the inventive compounds as useful for the treatment of a variety of disorders, including, but not limited to, glioblastoma, retinoblastoma, breast cancer, cervical cancer, colon and rectal cancer, leukemia, lung cancer (including, but not limited to small cell lung cancer), melanoma, multiple myeloma, non-Hodgkin's lymphoma, ovarian cancer, pancreatic cancer, prostate cancer and gastric cancer, to name a few. In certain embodiments, the inventive compounds are useful for the treatment of solid and non-solid tumors. In still other embodiments of interest, the inventive compounds are particularly useful for the treatment of breast cancer, prostate cancer, colon cancer, lung cancer, leukemia and lymphoma.

In certain embodiment, the method involves the administration of a therapeutically effective amount of the compound or a pharmaceutically acceptable derivative thereof to a subject (including, but not limited to a human or animal) in need of it. In certain embodiments, the inventive compounds as useful for the treatment of cancer (including, but not limited to, glioblastoma, retinoblastoma, breast cancer, cervical cancer, colon and rectal cancer, leukemia, lymphoma, lung cancer (including, but not limited to small cell lung cancer), melanoma and/or skin cancer, multiple myeloma, non-Hodgkin's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer).

Pharmaceutical Compositions

As discussed above this invention provides novel compounds that have biological properties useful for the treatment of cancer. In certain embodiments, certain of the compounds as described herein act as inhibitors of tumor growth and thus are useful. In the treatment of cancer and in the inhibition of tumor growth and in the killing of cancer cells. In certain embodiments, the inventive compounds are useful for the treatment of solid tumors or non-solid tumors. In still other embodiments of interest, the inventive compounds are useful for the treatment of glioblastoma, retinoblastoma, breast cancer, cervical cancer, colon and rectal cancer, leukemia, lymphoma, lung cancer (including, but not limited to small cell lung cancer), melanoma, multiple myeloma, non-Hodgkin's lymphoma, ovarian cancer, pancreatic cancer, prostate cancer and gastric cancer, to name a few. The inventive compounds also find use in the prevention of restenosis of blood vessels subject to traumas such as angioplasty and stenting.

Accordingly, in another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, the compounds are capable of inhibiting the growth of or killing cancer cells. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be a cytotoxic agent or anticancer agent approved for the treatment of cancer, as discussed in more detail herein, or it may be any one of a number of agents undergoing approval in the Food and Drug Administration that ultimately obtain approval for the treatment of an immune disorder or cancer. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals with little or no undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, el al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salt thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used is the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, trifluoroacetate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moeity advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine, talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agent, preservatives and antioxidants can also be present in the composition, according to the judgment of the formulator.

Uses and Formulations of Compounds of the Invention

As described in more detail herein, in general, the present invention provides compounds useful for the treatment of cancer and proliferative disorders.

As discussed above, certain of the compounds as described herein act as inhibitors of tumor growth and thus are useful in the treatment of cancer and in the inhibition of tumor growth and in the killing of cancer cells. The invention further provides a method for inhibiting tumor growth and/or tumor metastasis. The method involves the administration of a therapeutically effective amount of the compound or a pharmaceutically acceptable derivative thereof to a subject (including, but not limited to a human or animal) in need of it. In certain embodiments, the inventive compounds are useful for the treatment of solid tumors or non-solid tumors. In still other embodiments of interest, the inventive compounds are useful for the treatment of glioblastoma, retinoblastoma, breast cancer, cervical cancer, colon and rectal cancer, leukemia, lymphoma, lung cancer (including, but not limited to small cell lung cancer), melanoma, multiple myeloma, non-Hodgkin's lymphoma, ovarian cancer, pancreatic cancer, prostate cancer and gastric cancer, to name a few.

As described in more detail herein, in general, the present invention provides compounds useful for the treatment of cancer, particularly solid and non-solid tumors. Specifically, certain compounds of the invention have been shown to inhibit the growth of certain tumor cell lines in vitro, as described in more detail herein, and are useful for the treatment of cancer, including solid and non-solid tumors.

As discussed above, the inventive compounds also find use in the prevention of restenosis of blood vessels subject to traumas such as angioplasty and stenting. For example, it is contemplated that the compounds of the invention will be useful as a coating for implanted medical devices, such as tubings, shunts, catheters, artificial implants, pins, electrical implants such as pacemakers, and especially for arterial or venous stents, including balloon-expandable stents. In certain embodiments inventive compounds may be bound to an implantable medical device, or alternatively, may be passively adsorbed to the surface of the implantable device. In certain other embodiments, the inventive compounds may be formulated to be contained within, or, adapted to release by a surgical or medical device or implant, such as, for example, stents, sutures, indwelling catheters, prosthesis, and the like.

In certain exemplary embodiments, the inventive compounds may be used as coating for stents. A stent is typically an open tubular structure that has a pattern (or patterns) of apertures extending from tire outer surface of the stent to the lumen. It is commonplace to make stents of biocompatible metallic materials, with the patterns cut on the surface with a laser machine. The stent can be electro-polished to minimize surface irregularities since these irregularities can trigger an adverse biological response. However, stents may still stimulate foreign body reactions that result in thrombosis or restenosis. To avoid these complications, a variety of stent coatings and compositions have been proposed in the prior art literature both to reduce the incidence of these complications or other complications and restore tissue function by itself or by delivering therapeutic compound to the lumen. For example, drugs having antiproliferative and anti-inflammatory activities have been evaluated as stent coatings, and have shown promise in preventing retenosis (See, for example. Presbitero P. et al., "Drug eluting stents do they make the difference?", *Minerva Cardioangiol,* 2002, 50(5):431-442; Ruygrok P. N. et al., "Rapamycin in cardiovascular medicine" *Intern. Med. J.,* 2003, 33(3): 103-109; and Marx S. O. et al., "Bench to bedside: the development of rapamycin and its application to stent restenosis", *Circulation,* 2001, 104(8): 852-855, each of these references is incorporated herein by reference in its entirety). Accordingly, without wishing to be bound to any particular theory, Applicant proposes that the inventive compounds, having antiproliferative effects, can be used as stent coatings and/or in stent drug delivery devices, inter alia for the prevention of restenosis. A variety of compositions and methods related to stent coating and/or local stent drug delivery for preventing restenosis are known in the art (see, for example, U.S. Pat. Nos. 6,517,889; 6,273,913; 6,258,121; 6,251,136; 6,248,127; 6,231,600; 6,203,551; 6,153,252; 6,071,305; 5,891,507; 5,837,313 and published U.S. patent application No.: US2001/0027340, each of which is incorporated herein by reference in its entirety). For example, stents may be coated with polymer-drug conjugates by dipping the stent in polymer-drug solution or spraying the stent with such a solution. In certain embodiment, suitable materials for the implantable device include biocompatible and nontoxic materials, and may be chosen from the metals such as nickel-titanium alloys, steel, or biocompatible polymers, hydrogels, polyurethanes, polyethylenes, ethylenevinyl acetate copolymers, etc. In certain embodiments, the inventive compound, is coated onto a stent for insertion into an artery or vein following balloon angioplasty.

The invention may be described therefore, in certain broad aspects as a method of inhibiting arterial restenosis or arterial occlusion following vascular trauma comprising administering to a subject in need thereof, a composition comprising an inventive compound conjugated to a suitable polymer or polymeric material. In the practice of the method, the subject may be a coronary bypass, vascular surgery, organ transplant or coronary or any other arterial angioplasty patient, for example, and the composition may be administered directly, intravenously, or even coated on a stent to be implanted at the sight of vascular trauma.

In another aspect, the invention encompasses implants and surgical or medical devices, including stents and grafts, coated with or otherwise constructed to contain and/or release any of the inventive compounds disclosed herein. In certain embodiments, the compounds have antiproliferative activity. In certain other embodiments, the compounds inhibit smooth muscle cell proliferation. Representative examples of the inventive implants and surgical or medical devices include cardiovascular devices (e.g., implantable venous catheters, venous ports, tunneled venous catheters, chronic infusion lines or ports, including hepatic artery infusion catheters, pacemaker wires, implantable defibrillators); neurologic/neurosurgical devices (e.g., ventricular peritoneal shunts, ventricular atrial shunts, nerve stimulator devices, dural patches and implants to prevent epidural fibrosis post-laminectomy, devices for continuous subarachnoid infusions);

gastrointestinal devices (e.g., chronic indwelling catheters, feeding tubes, portosystemic shunts, shunts for ascites, peritoneal implants for drug delivery, peritoneal dialysis catheters, implantable meshes for hernias, suspensions or solid implants to prevent surgical adhesions, including meshes); genitourinary devices (e.g., uterine implants, including intrauterine devices (IUDs) and devices to prevent endometrial hyperplasia, fallopian tubal implants, including reversible sterilization devices, fallopian tubal stents, artificial sphincters and periurethral implants for incontinence, ureteric stents, chronic indwelling catheters, bladder augmentations, or wraps or splints for vasovasostomy); phthalmologic implants (e.g., multino implants and other implants for neovascular glaucoma, drug eluting contact lenses for pterygiums, splints for failed dacrocystalrhinostomy, drug eluting contact lenses for corneal neovascularity, implants for diabetic retinopathy, drug eluting contact lenses for high risk corneal transplants); otolaryngology devices (e.g., ossicular implants, Eustachian tube splints or stents for glue ear or chronic otitis as an alternative to transtempanic drains); plastic surgery implants (e.g., prevention of fibrous contracture in response to gel- or saline-containing breast implants in the subpectoral or subglandular approaches or post-mastectomy, or chin implants), and orthopedic implants (e.g., cemented orthopedic prostheses).

Implants and other surgical or medical devices may be coated with (or otherwise adapted to release) compositions of the present invention in a variety of manners, including for example: (a) by directly affixing to the implant or device an inventive compound or composition (e.g., by either spraying the implant or device with a polymer/drug film, or by dipping the implant or device into a polymer/drug solution, or by other covalent or noncovalent means); (b) by coating the implant or device with a substance such as a hydrogel which will in turn absorb the inventive compound or composition; (c) by interweaving inventive compound- or composition-coated thread (or the polymer itself formed into a thread) into the implant or device; (d) by inserting the implant or device into a sleeve or mesh which is comprised of or coated with an inventive compound or composition; (e) constructing the implant or device itself with an inventive compound or composition; or (f) by otherwise adapting the implant or device to release the inventive compound. In certain embodiments, the composition should firmly adhere to the implant or device during storage and at the time of insertion. The inventive compound or composition should also preferably not degrade during storage, prior to insertion, or when warmed to body temperature after insertion inside the body (if this is required). In addition, it should preferably coat the implant or device smoothly and evenly, with a uniform distribution of inventive compound, while not changing the stent contour. Within preferred embodiments of the invention, the inventive implant or device should provide a uniform, predictable, prolonged release of the inventive compound or composition into the tissue surrounding the implant or device once it has been deployed. For vascular stents, in addition to the above properties, the composition should not render the stent thrombogenic (causing blood clots to form), or cause significant turbulence in blood flow (more than the stent itself would be expected to cause if it was uncoated).

In the case of stents, a wide variety of stents may be developed to contain and/or release the inventive compounds or compositions provided herein, including esophageal stents, gastrointestinal stents, vascular stents, biliary stents, colonic stents, pancreatic stents, ureteric and urethral stents, lacrimal stents, Eustachian tube stents, fallopian tube stents and tracheal/bronchial stents (See, for example, U.S. Pat. No. 6,515, 016, the entire contents of which are incorporated herein by reference). Stents may be readily obtained from commercial sources, or constructed in accordance with well-known techniques. Representative examples of stents include those described in U.S. Pat. No. 4,768,523, entitled "Hydrogel Adhesive"; U.S. Pat. No. 4,776,337, entitled "Expandable Intraluminal Graft, and Method and Apparatus for Implanting and Expandable Intraluminal Graft"; U.S. Pat. No. 5,041,126 entitled "Endovascular Stent and Delivery System"; U.S. Pat. No. 5,052,998 entitled "Indwelling Stent and Method of Use"; U.S. Pat. No. 5,064,435 entitled "Self-Expanding Prosthesis Having Stable Axial Length"; U.S. Pat. No. 5,089,606, entitled "Water-insoluble Polysaccharide Hydrogel Foam for Medical Applications"; U.S. Pat. No. 5,147,370, entitled "Nitinol Stent for Hollow Body Conduits"; U.S. Pat. No. 5,176,626, entitled "Indwelling Stent"; U.S. Pat. No. 5,213, 580, entitled "Biodegradable Polymeric Endoluminal Sealing Process"; and U.S. Pat. No. 5,328,471, entitled "Method and Apparatus for Treatment of Focal Disease in Hollow Tubular Organs and Other Tissue Lumens."

As discussed above, the stent coated with (or otherwise adapted to release) compositions of the present invention may be used to eliminate a vascular obstruction and prevent restenosis and/or reduce the rate of restenosis. Within other aspects of the present invention, stents coated with (or otherwise adapted to release) compositions of the present invention are provided for expanding the lumen of a body passageway. Specifically, a stent having a generally tubular structure, and a surface coated with (or otherwise adapted to release) an inventive compound or composition may be inserted into the passageway, such that the passageway is expanded. In certain embodiments, the stent coated with (or otherwise adapted to release) compositions of the present invention may be used to eliminate a biliary, gastrointestinal, esophageal tracheal/bronchial, urethral or vascular obstruction.

In another aspect of the invention, methods for the treatment of cancer are provided comprising administering a therapeutically effective amount of a compound of formula (I), as described herein, to a subject in need thereof. In certain embodiments, the inventive compounds are useful for the treatment of solid and non-solid tumors. It will be appreciated that the compounds and compositions, according to the method of the present invention, may be administered using any amount and any route of administration effective for the treatment of cancer. Thus, the expression "effective amount" as used herein, refers to a sufficient amount of agent to kill or inhibit the growth of tumor cells, or refers to a sufficient amount to reduce the growth of tumor cells. The exact amount required will vary from subject to subject, depending on the species, age, and general condition of the subject, the severity of the infection, the particular anticancer agent, its mode of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety).

In certain other embodiments, methods are provided for using the inventive implants and other surgical or medical devices coated with (or otherwise adapted to release) compounds and compositions of the present invention. In certain embodiments, methods are provided for preventing restenosis, comprising inserting a stent into an obstructed blood vessel, the stent having a generally tubular structure, the surface of the structure being coated with (or otherwise adapted to release) an inventive compound or composition, such that the obstruction is eliminated and the inventive compound or composition is delivered in amounts effective to prevent restenosis and/or reduce the rate of restenosis. In other embodiments, methods are provided for preventing restenosis, comprising inserting a stent into an obstructed blood vessel, the stent having a generally tubular structure, the surface of the structure being coated with (or otherwise adapted to release) an inventive compound or composition, such that the obstruction is eliminated and the inventive compound or composition is delivered in amounts effective to inhibit smooth muscle cell proliferation.

Within other aspects of the present invention, methods are provided for expanding the lumen of a body passageway, comprising inserting a stent into the passageway, the stent having a generally tubular structure, the surface of the structure being coated with (or otherwise adapted to release) an inventive compound or composition, such that the passageway is expanded. In certain embodiments, the lumen of a body passageway is expanded in order to eliminate a biliary, gastrointestinal, esophageal, tracheal/bronchial, urethral and/or vascular obstruction.

In certain embodiments, methods are provided for eliminating biliary obstructions, comprising inserting a biliary stent into a biliary passageway, the stent having a generally tubular structure, the surface of the structure being coated with (or otherwise adapted to release) an inventive compound or composition, such that the biliary obstruction is eliminated. Briefly, tumor overgrowth of the common bile duct results in progressive cholestatic jaundice which is incompatible with life. Generally, the biliary system which drains bile from the liver into the duodenum is most often obstructed by (1) a tumor composed of bile duct cells (cholangiocarcinoma), (2) a tumor which invades the bile duct (e.g., pancreatic carcinoma), or (3) a tumor which exerts extrinsic pressure and compresses the bile duct (e.g., enlarged lymph nodes). Both primary biliary tumors, as well as other tumors which cause compression of the biliary tree may be treated utilizing stents implants and other surgical or medical devices may be coated with (or otherwise adapted to release) compositions of the present invention. One example of primary biliary rumors are adenocarcinomas (which are also called Klatskin tumors when found at the bifurcation of the common hepatic duct). These tumors are also referred to as biliary carcinomas, choledocholangiocarcinomas, or adenocarcinomas of the biliary system. Benign tumors which affect the bile duct (e.g., adenoma of the biliary system), and, in rare cases, squamous cell carcinomas of the bile duct and adenocarcinomas of the gallbladder, may also cause compression of the biliary tree and therefore, result in biliary obstruction. Compression of the biliary tree is most commonly due to tumors of the liver and pancreas which compress and therefore obstruct the ducts. Most of the tumors from the pancreas arise from cells of the pancreatic ducts. This is a highly fatal form of cancer (5% of all cancer deaths; 26,000 new cases per year in the U.S.) with an average of 6 months survival and a 1 year survival rate of only 10%. When these tumors are located in the head of the pancreas they frequently cause biliary obstruction, and this detracts significantly from the quality of life of the patient. While all types of pancreatic tumors are generally referred to as "carcinoma of the pancreas" there are histologic subtypes including: adenocarcinoma, adenosquamous carcinoma, cystadenocarcinoma, and acinar cell carcinoma. Hepatic tumors, as discussed above, may also cause compression of the biliary tree, and therefore cause obstruction of the biliary ducts.

In certain embodiments, a biliary stent is first inserted into a biliary passageway in one of several ways: from the top end by inserting a needle through the abdominal wall and through the liver (a percutaneous transhepatic cholangiogram or "PTC"); from the bottom end by cannulating the bile duct through an endoscope inserted through the mouth, stomach, and duodenum (an endoscopic retrograde cholangiogram or "ERCP"); or by direct incision during a surgical procedure. In certain embodiments, a preinsertion examination, PTC, ERCP, or direct visualization at the time of surgery is performed to determine the appropriate position for stent insertion. A guidewire is then advanced through the lesion, and over this a delivery catheter is passed to allow the stent to be inserted in its collapsed form. If the diagnostic exam was a PTC, the guidewire and delivery catheter is inserted via the abdominal wall, while if the original exam was an ERCP the stent may be placed via the mouth. The stent is then positioned under radiologic, endoscopic, or direct visual control taking particular care to place it precisely across the narrowing in the bile duct. The delivery catheter is then removed leaving the stent standing as a scaffolding which holds the bile duct open. A further cholangiogram may be performed to document that the stent is appropriately positioned.

In certain embodiments, methods are provided for eliminating esophageal obstructions, comprising inserting an esophageal stent into an esophagus, the stent having a generally tubular structure, the surface of the structure being coated with (or otherwise adapted to release) an inventive compound or composition, such that the esophageal obstruction is eliminated. Briefly, the esophagus is the hallow tube which transports food and liquids from the mouth to the stomach. Cancer of the esophagus or invasion by cancer arising in adjacent organs (e.g., cancer of the stomach or lung) results in the inability to swallow food or saliva. In certain embodiments, a preinsertion examination, usually a barium swallow or endoscopy is performed in order to determine the appropriate position for stent insertion. A catheter or endoscope may then be positioned through the mouth, and a guidewire is advanced through the blockage. A stent delivery catheter is passed over the guidewire under radiologic or endoscopic control, and a stent is placed precisely across the narrowing in the esophagus. A post-insertion examination, usually a barium swallow x-ray, may be utilized to confirm appropriate positioning.

In certain embodiments, methods are provided for eliminating colonic obstructions, comprising inserting a colonic stent into a colon, the stent having a generally tubular structure, the surface of the structure being coated with (or otherwise adapted to release) an inventive compound or composition, such that the colonic obstruction is eliminated. Briefly, the colon is the hollow tube which transports digested food and waste materials from the small intestines to the anus. Cancer of the rectum and/or colon or invasion by cancer arising in adjacent organs (e.g., cancer of the uterus, ovary, bladder) results in the inability to eliminate feces from the bowel. In certain embodiments, a preinsertion examination, usually a barium enema or colonoscopy is performed in order to determine the appropriate position for stent insertion. A catheter or endoscope may then be positioned through, the anus, and a guidewire is advanced through the blockage. A stent delivery catheter is passed over the guidewire under radiologic or endoscopic control, and a stent is placed precisely across the narrowing in the colon or rectum. A post-insertion examination, usually a barium enema x-ray, may be utilized to confirm appropriate positioning.

In certain embodiments, methods are provided for eliminating tracheal/bronchial obstructions, comprising inserting a tracheal/bronchial stent into a trachea or bronchi, the stent having a generally tubular structure, the surface of the structure being coated with (or otherwise adapted to release) an inventive compound or composition, such that the tracheal/bronchial obstruction is eliminated. Briefly, the trachea and bronchi are tubes which carry air from the mouth and nose to the lungs. Blockage of the trachea by cancer, invasion by cancer arising in adjacent organs (e.g., cancer of the lung), or collapse of the trachea or bronchi due to chondromalacia (weakening of the cartilage rings) results in inability to breathe. In certain embodiments, preinsertion examination, usually as endoscopy, is performed in order to determine the appropriate position for stent insertion. A catheter or endoscope is then positioned through the mouth, and a guidewire advanced through the blockage. A delivery catheter is then passed over the guidewire in order to allow a collapsed stent to be inserted. The stent is placed under radiologic or endoscopic control in order to place it precisely across the narrowing. The delivery catheter may then be removed leaving the stent standing as a scaffold on its own. A post-insertion examination, usually a bronchoscopy may be utilized to confirm appropriate positioning.

In certain embodiments, methods are provided for eliminating urethral obstructions, comprising inserting a urethral stent into a urethra, the stent having a generally tubular structure, the surface of the structure being coated with (or otherwise adapted to release) an inventive compound or composition, such that the urethral obstruction is eliminated. Briefly, the urethra is the tube which drains the bladder through the penis. Extrinsic narrowing of the urethra as it passes through the prostate, due to hypertrophy of the prostate, occurs in virtually every man over the age of 60 and causes progressive difficulty with urination. In certain embodiments, a preinsertion examination, usually an endoscopy or urethrogram is first performed in order to determine the appropriate position for stent insertion, which is above the external urinary sphincter at the lower end, and close to flush with the bladder neck at the upper end. An endoscope or catheter is then positioned through the penile opening and a guidewire advanced into the bladder. A delivery catheter is then passed over the guidewire in order to allow stent insertion. The delivery catheter is then removed, and the stent expanded into place. A post-insertion examination, usually endoscopy or retrograde urethrogram, may be utilized to confirm appropriate position.

In certain embodiments, methods are provided for eliminating vascular obstructions, comprising inserting a vascular stent into a blood vessel, the stent having a generally tubular structure, the surface of the structure being coated with (or otherwise adapted to release) an inventive compound or composition, such that the vascular obstruction is eliminated. Briefly, stents may be placed in a wide array of blood vessels, both arteries and veins, to prevent recurrent stenosis at the site of failed angioplasties, to treat narrowings that would likely fail if treated with angioplasty, and to treat post-surgical narrowings (e.g., dialysis graft stenosis). Suitable sites include, but are not limited to, the iliac, renal, and coronary arteries, the superior vena cava, and in dialysis grafts. In certain embodiments, angiography is first performed in order to localize the site for placement of the stent. This is typically accomplished by injecting radiopaque contrast through a catheter inserted into an artery or vein as an x-ray is taken. A catheter may men be inserted either percutaneously or by surgery into the femoral artery, brachial artery, femoral vein, or brachial vein, and advanced into the appropriate blood vessel by steering it through the vascular system under fluoroscopic guidance. A stent may then be positioned across the vascular stenosis. A post-insertion angiogram may also be utilized in order to confirm appropriate positioning.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drag from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soil and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and macrocrystalline cellulose. In the case of capsules, tablets and pills, the dosage forms may also comprise buffering agents. They may optionally contain opacifying agents and can also be of a composition that they release the active ingredients(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects). For example, other therapies or anticancer agents that may be used in combination with the inventive anticancer agents of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to same a few), hyperthermia and cryotherapy, agents to attenuate any adverse effects (e.g., antiemetics), and other approved chemotherapeutic drugs, including, but not limited to, alkylating drags (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin); enzymes (Asparaginase), and hormones (Tamoxifen, Leuprolide, Flutamide, and Megestrol), to name a few. For a more comprehensive discussion of updated cancer therapies see, The Merck Manual, Seventeenth Ed. 1999, the entire contents of which are hereby incorporated by reference. See also the National Cancer Institute (NCI) website (www.nci.nih.gov) and the Food and Drug Administration (FDA) website for a list of the PDA approved oncology drugs (www.fda.gov/cder/cancer/druglistframe—See Appendix A).

In certain embodiments, the pharmaceutical compositions of the present invention further comprise one or more additional therapeutically active ingredients (e.g., chemotherapeutic and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

TREATMENT KITS

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The practitioner has a well-established literature of peptide chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in tins document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed are considered to fall within the scope of the present invention as described herein and as hereinafter claimed.

According to the present invention, any available techniques can be used to make or prepare tire inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used, in preparing these compounds are either available from commercial suppliers such as Aldrich Chemical Company (Milwaukee, Wis.), Bachem (Torrance, Calif.), Sigma (St. Louis, Mo.), or are prepared by methods well known to a person, of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation crystallization chromatography, and the like. They may be characterized using conventional methods, including physical constants and spectral data.

Certain exemplary compounds of the invention are listed below and are referred to by compound number as indicated.

| Compound | Structure |
|---|---|
| ER-803840 (HEMIASTERLIN) | 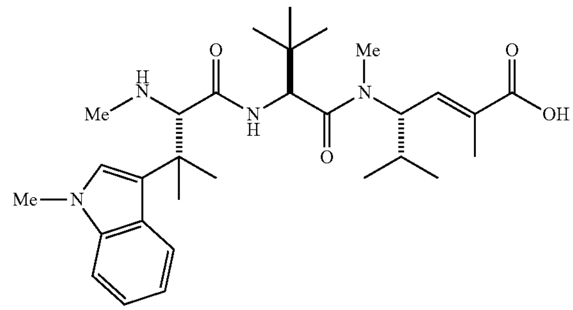 [SMILES: CN[C@H](C(=O)N[C@H](C(=O)N(C)[C@H](/C=C(\C)C(=O)O)C(C)C)C(C)(C)C)C(C)(C)c1cn(C)c2ccccc12] |
| ER-803887 | 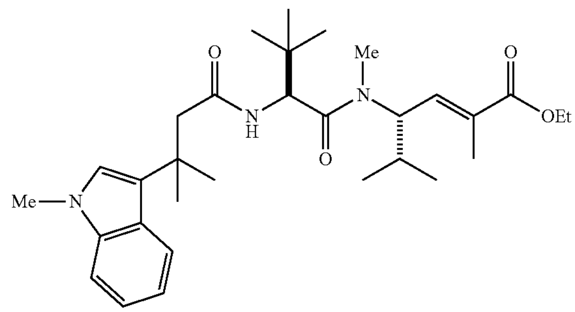 [SMILES: CCOC(=O)/C(C)=C/[C@H](C(C)C)N(C)C(=O)[C@@H](NC(=O)CC(C)(C)c1cn(C)c2ccccc12)C(C)(C)C] |
| ER-803888 | 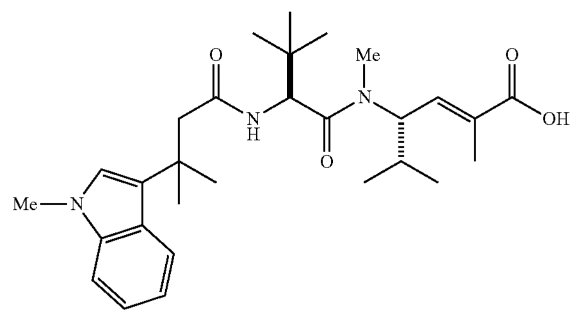 [SMILES: C/C(=C\[C@H](C(C)C)N(C)C(=O)[C@@H](NC(=O)CC(C)(C)c1cn(C)c2ccccc12)C(C)(C)C)C(=O)O] |
| ER-803889 | 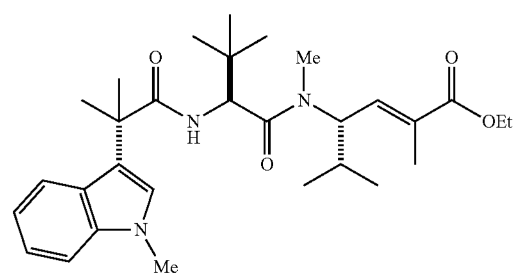 |
| ER-803890 | 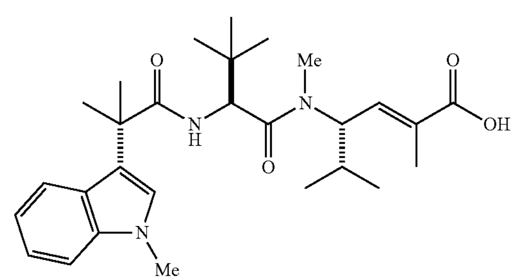 |

-continued

| Compound | Structure |
|---|---|
| ER-803921 | 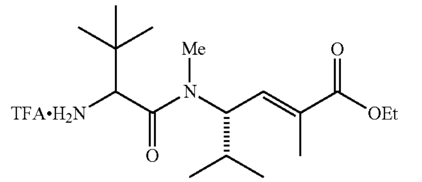 |
| ER-803995 | 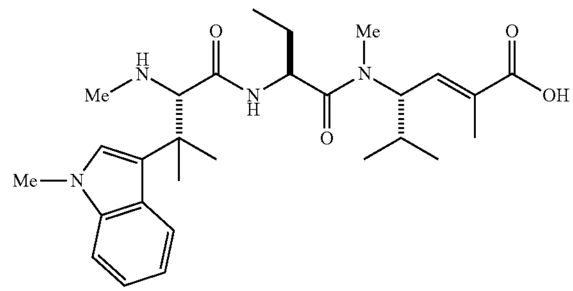 [SMILES: CC[C@H](NC(=O)[C@@H](NC)C(C)(C)c1cn(C)c2ccccc12)C(=O)N(C)[C@H](/C=C(\C)C(=O)O)C(C)C] |
| ER-803996 | 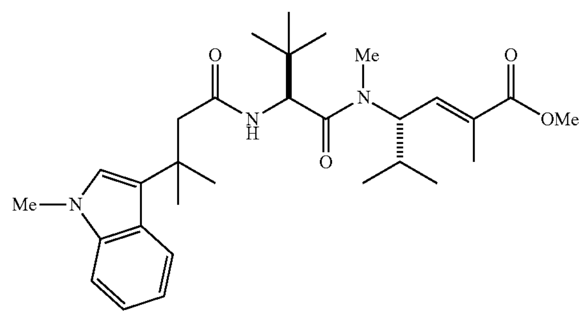 [SMILES: COC(=O)/C(C)=C/[C@H](C(C)C)N(C)C(=O)[C@@H](NC(=O)CC(C)(C)c1cn(C)c2ccccc12)C(C)(C)C] |
| ER-803997 Higher Rf diastereomer | 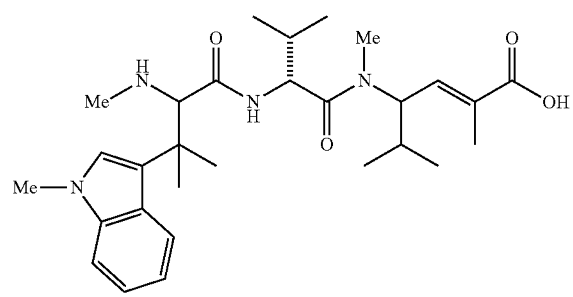 [SMILES: CNC(C(=O)N[C@@H](C(=O)N(C)C(/C=C(\C)C(=O)O)C(C)C)C(C)C)C(C)(C)c1cn(C)c2ccccc12] |
| ER-803998 Lower Rf diastereomer | 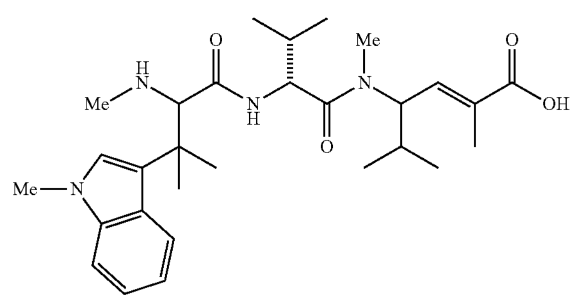 [SMILES: CNC(C(=O)N[C@@H](C(=O)N(C)C(/C=C(\C)C(=O)O)C(C)C)C(C)C)C(C)(C)c1cn(C)c2ccccc12] |

-continued

| Compound | Structure |
|---|---|
| ER-803999 | 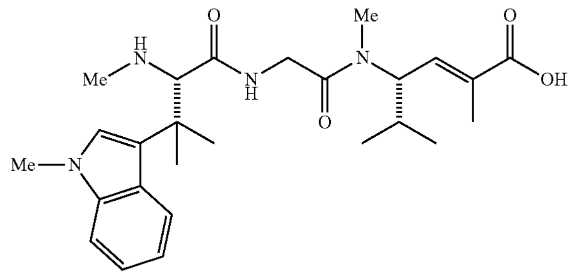 [SMILES: CN[C@H](C(=O)NCC(=O)N(C)[C@H](/C=C(\C)C(=O)O)C(C)C)C(C)(C)c1cn(C)c2ccccc12] |
| ER-804000 | 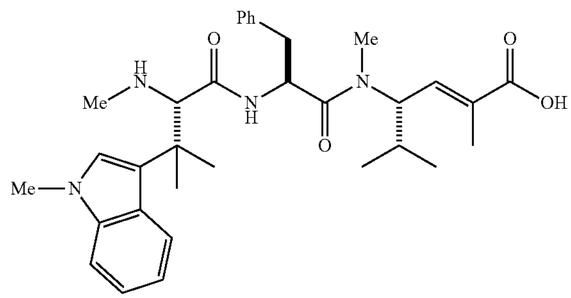 [SMILES: CN[C@H](C(=O)N[C@@H](Cc1ccccc1)C(=O)N(C)[C@H](/C=C(\C)C(=O)O)C(C)C)C(C)(C)c1cn(C)c2ccccc12] |
| ER-804001 | 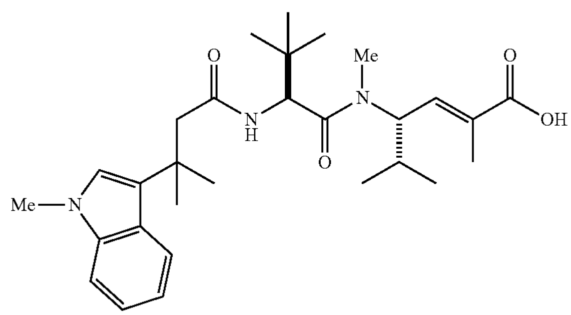 [SMILES: C/C(=C\[C@H](C(C)C)N(C)C(=O)[C@@H](NC(=O)CC(C)(C)c1cn(C)c2ccccc12)C(C)(C)C)C(=O)O] |
| ER-804002 | 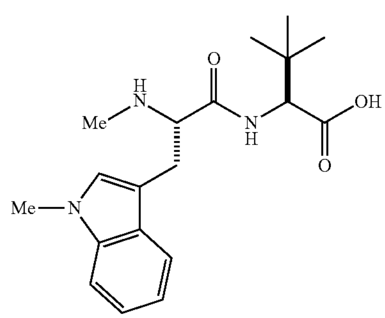 [SMILES: CN[C@@H](Cc1cn(C)c2ccccc12)C(=O)N[C@H](C(=O)O)C(C)(C)C] |
| ER-804332 | 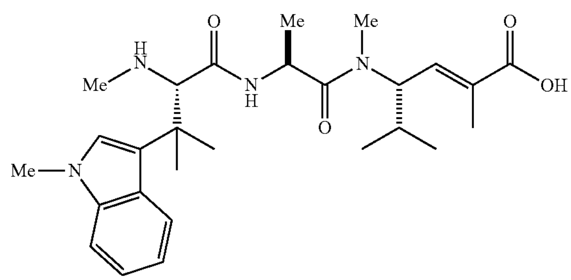 |

-continued

| Compound | Structure |
|---|---|
| ER-804333 | 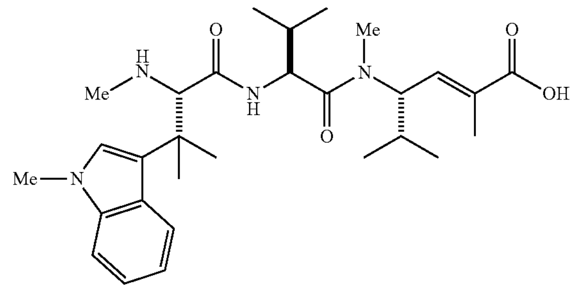 [SMILES: CN[C@H](C(=O)N[C@H](C(=O)N(C)[C@H](/C=C(\C)C(=O)O)C(C)C)C(C)C)C(C)(C)c1cn(C)c2ccccc12] |
| ER-804334 | 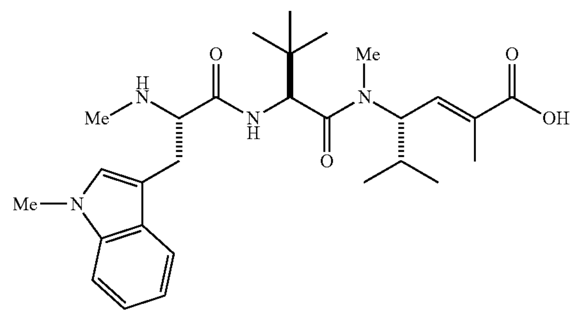 |
| ER-804635 | 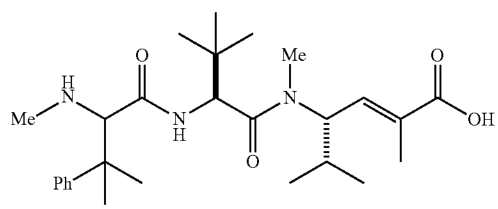 [SMILES: CNC(C(=O)N[C@H](C(=O)N(C)[C@H](/C=C(\C)C(=O)O)C(C)C)C(C)(C)C)C(C)(C)c1ccccc1] |
| ER-804636 | 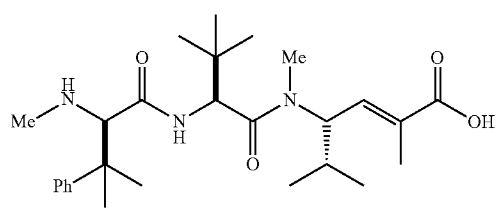 |
| ER-804762 | 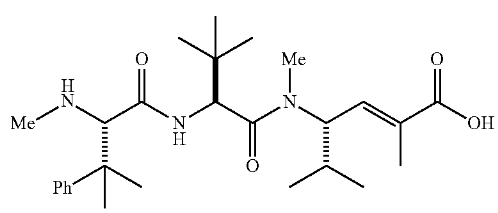 [SMILES: CN[C@H](C(=O)N[C@H](C(=O)N(C)[C@H](/C=C(\C)C(=O)O)C(C)C)C(C)(C)C)C(C)(C)c1ccccc1] |
| ER-805206 | 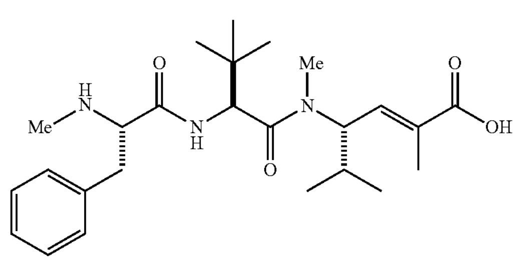 |

-continued

| Compound | Structure |
|---|---|
| ER-805230 | 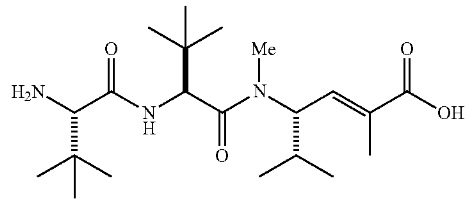 [SMILES: C/C(=C\[C@H](C(C)C)N(C)C(=O)[C@@H](NC(=O)[C@@H](N)C(C)(C)C)C(C)(C)C)C(=O)O] |
| ER-805231 | 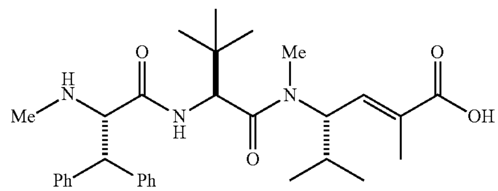 [SMILES: CN[C@H](C(=O)N[C@H](C(=O)N(C)[C@H](/C=C(\C)C(=O)O)C(C)C)C(C)(C)C)C(c1ccccc1)c1ccccc1] |
| ER-805257 | 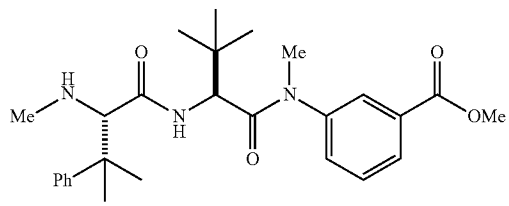 [SMILES: CN[C@H](C(=O)N[C@H](C(=O)N(C)c1cccc(C(=O)OC)c1)C(C)(C)C)C(C)(C)c1ccccc1] |
| ER-805258 | 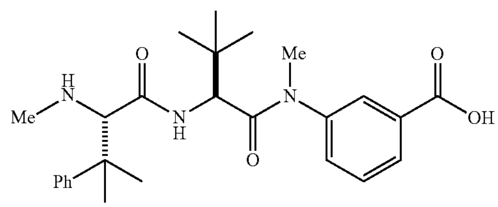 [SMILES: CN[C@H](C(=O)N[C@H](C(=O)N(C)c1cccc(C(=O)O)c1)C(C)(C)C)C(C)(C)c1ccccc1] |
| ER-805268 | 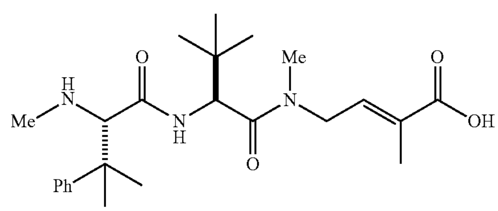 [SMILES: CN[C@H](C(=O)N[C@H](C(=O)N(C)C/C=C(\C)C(=O)O)C(C)(C)C)C(C)(C)c1ccccc1] |
| ER-805316 | 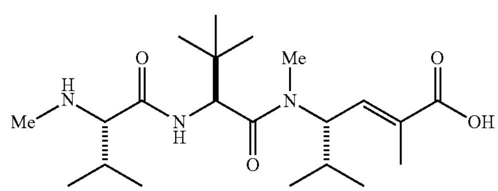 [SMILES: CN[C@H](C(=O)N[C@H](C(=O)N(C)[C@H](/C=C(\C)C(=O)O)C(C)C)C(C)(C)C)C(C)C] |
| ER-805324 | 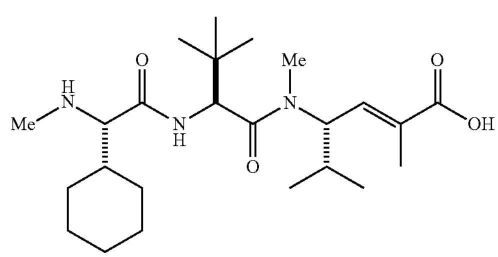 [SMILES: CN[C@H](C(=O)N[C@H](C(=O)N(C)[C@H](/C=C(\C)C(=O)O)C(C)C)C(C)(C)C)C1CCCCC1] |

| Compound | Structure |
|---|---|
| ER-805532 | 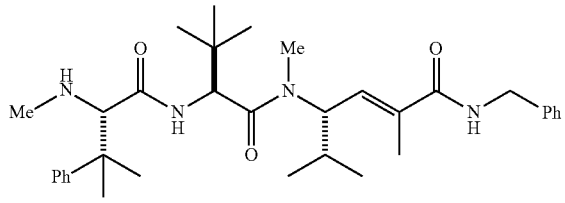 [SMILES: CN[C@H](C(=O)N[C@H](C(=O)N(C)[C@H](/C=C(\C)C(=O)NCc1ccccc1)C(C)C)C(C)(C)C)C(C)(C)c1ccccc1] |
| ER-805590 | 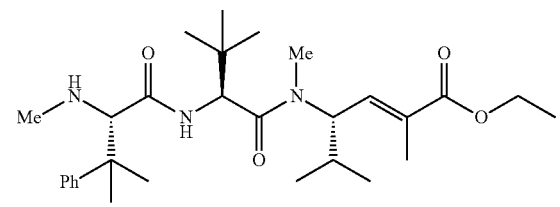 [SMILES: CCOC(=O)/C(C)=C/[C@H](C(C)C)N(C)C(=O)[C@@H](NC(=O)[C@@H](NC)C(C)(C)c1ccccc1)C(C)(C)C] |
| ER-805594 | 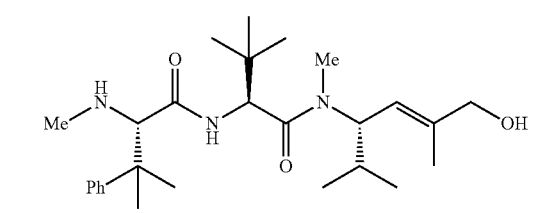 [SMILES: CN[C@H](C(=O)N[C@H](C(=O)N(C)[C@H](/C=C(\C)CO)C(C)C)C(C)(C)C)C(C)(C)c1ccccc1] |
| ER-805599 | 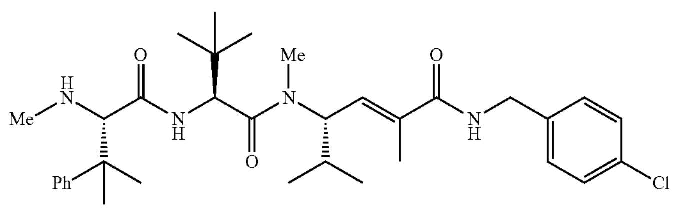 [SMILES: CN[C@H](C(=O)N[C@H](C(=O)N(C)[C@H](/C=C(\C)C(=O)NCc1ccc(Cl)cc1)C(C)C)C(C)(C)C)C(C)(C)c1ccccc1] |
| ER-805697 | 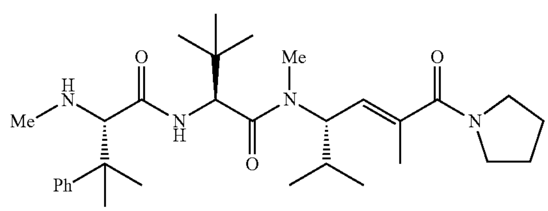 [SMILES: CN[C@H](C(=O)N[C@H](C(=O)N(C)[C@H](/C=C(\C)C(=O)N1CCCC1)C(C)C)C(C)(C)C)C(C)(C)c1ccccc1] |
| ER-805701 | 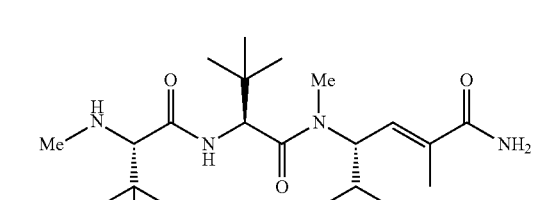 |
| ER-805711 | 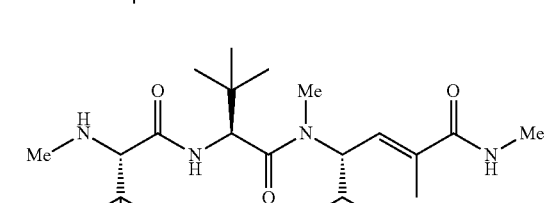 |

-continued
| Compound | Structure |
|---|---|
| ER-805713 | 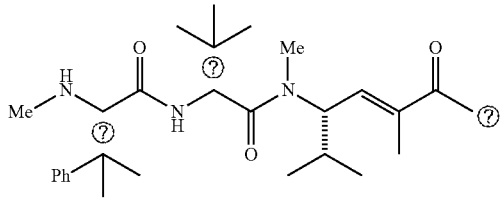 |
| ER-805734 | 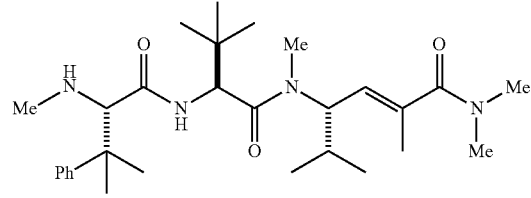 [SMILES: CN[C@H](C(=O)N[C@H](C(=O)N(C)[C@H](/C=C(\C)C(=O)N(C)C)C(C)C)C(C)(C)C)C(C)(C)c1ccccc1] |
| ER-805735 | 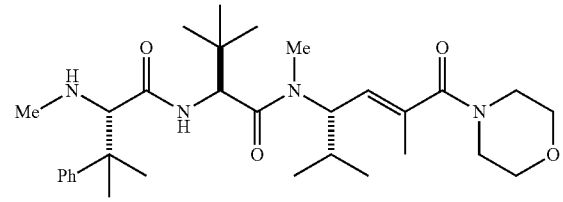 [SMILES: CN[C@H](C(=O)N[C@H](C(=O)N(C)[C@H](/C=C(\C)C(=O)N1CCOCC1)C(C)C)C(C)(C)C)C(C)(C)c1ccccc1] |
| ER-805736 | 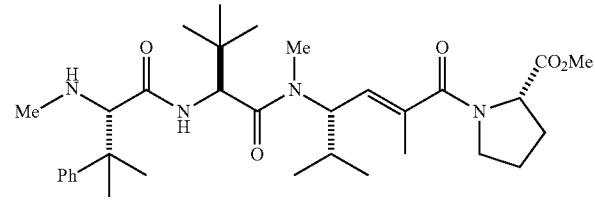 [SMILES: CN[C@H](C(=O)N[C@H](C(=O)N(C)[C@H](/C=C(\C)C(=O)N1CCC[C@H]1C(=O)OC)C(C)C)C(C)(C)C)C(C)(C)c1ccccc1] |
| ER-805738 | 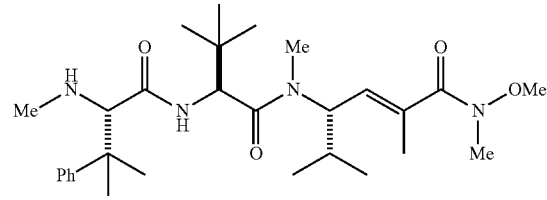 [SMILES: CN[C@H](C(=O)N[C@H](C(=O)N(C)[C@H](/C=C(\C)C(=O)N(C)OC)C(C)C)C(C)(C)C)C(C)(C)c1ccccc1] |
| ER-805847 | 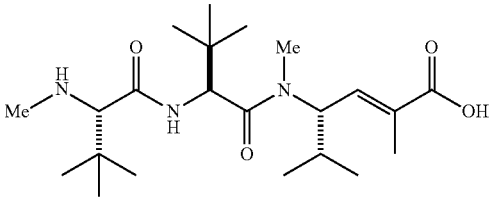 [SMILES: CN[C@H](C(=O)N[C@H](C(=O)N(C)[C@H](/C=C(\C)C(=O)O)C(C)C)C(C)(C)C)C(C)(C)C] |
| ER-805865 | 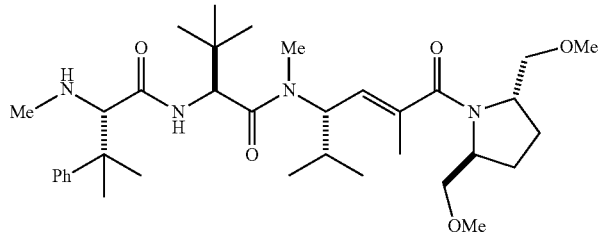 [SMILES: CN[C@H](C(=O)N[C@H](C(=O)N(C)[C@H](/C=C(\C)C(=O)N1[C@H](COC)CC[C@H]1COC)C(C)C)C(C)(C)C)C(C)(C)c1ccccc1] |

-continued

| Compound | Structure |
| --- | --- |
| ER-805876 | 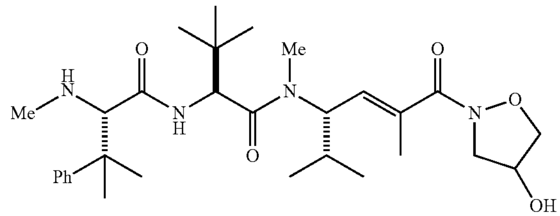 [SMILES: CN[C@H](C(=O)N[C@H](C(=O)N(C)[C@H](/C=C(\C)C(=O)N1CC(O)CO1)C(C)C)C(C)(C)C)C(C)(C)c1ccccc1] |
| ER-805913 | 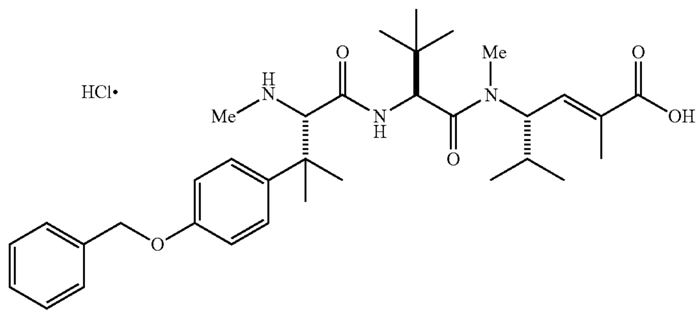 [SMILES: CN[C@H](C(=O)N[C@H](C(=O)N(C)[C@H](/C=C(\C)C(=O)O)C(C)C)C(C)(C)C)C(C)(C)c1ccc(OCc2ccccc2)cc1] |
| ER-805914 | 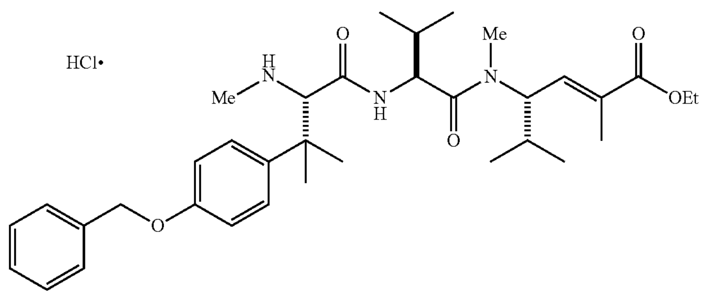 [SMILES: CCOC(=O)/C(C)=C/[C@H](C(C)C)N(C)C(=O)[C@@H](NC(=O)[C@@H](NC)C(C)(C)c1ccc(OCc2ccccc2)cc1)C(C)C] |
| ER-805925 | 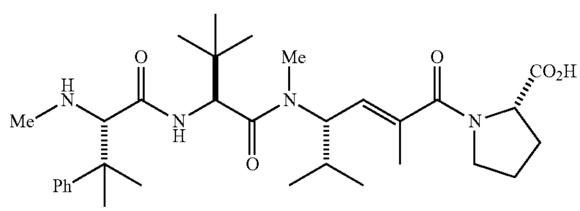 [SMILES: CN[C@H](C(=O)N[C@H](C(=O)N(C)[C@H](/C=C(\C)C(=O)N1CCC[C@H]1C(=O)O)C(C)C)C(C)(C)C)C(C)(C)c1ccccc1] |
| ER-805938 | 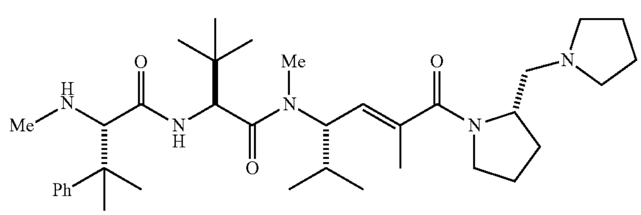 [SMILES: CN[C@H](C(=O)N[C@H](C(=O)N(C)[C@H](/C=C(\C)C(=O)N1CCC[C@H]1CN1CCCC1)C(C)C)C(C)(C)C)C(C)(C)c1ccccc1] |
| ER-805968 | 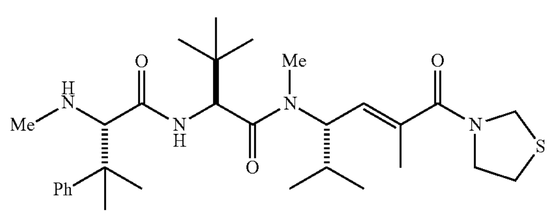 [SMILES: CN[C@H](C(=O)N[C@H](C(=O)N(C)[C@H](/C=C(\C)C(=O)N1CCSC1)C(C)C)C(C)(C)C)C(C)(C)c1ccccc1] |

-continued
| Compound | Structure |
|---|---|
| ER-805974 | 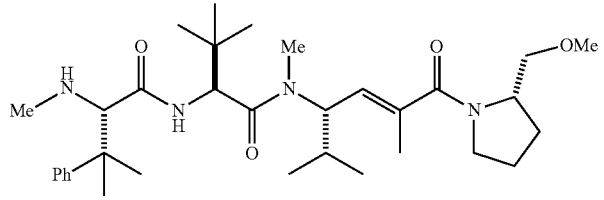 [SMILES: CN[C@H](C(=O)N[C@H](C(=O)N(C)[C@H](/C=C(\C)C(=O)N1CCC[C@H]1COC)C(C)C)C(C)(C)C)C(C)(C)c1ccccc1] |
| ER-806004 | 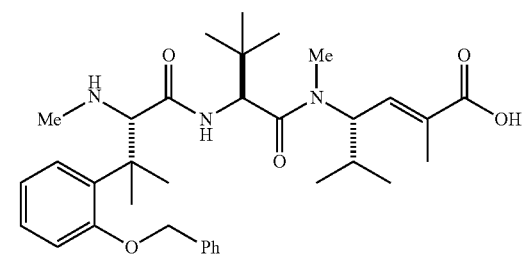 [SMILES: CN[C@H](C(=O)N[C@H](C(=O)N(C)[C@H](/C=C(\C)C(=O)O)C(C)C)C(C)(C)C)C(C)(C)c1ccccc1OCc1ccccc1] |
| ER-806005 | 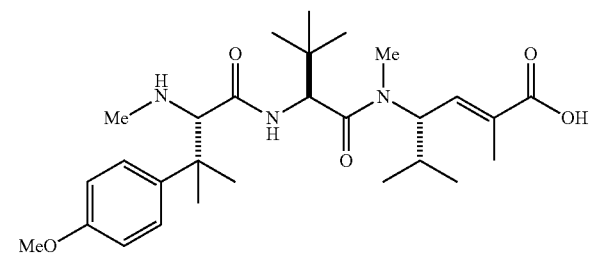 [SMILES: CN[C@H](C(=O)N[C@H](C(=O)N(C)[C@H](/C=C(\C)C(=O)O)C(C)C)C(C)(C)C)C(C)(C)c1ccc(OC)cc1] |
| ER-806021 | 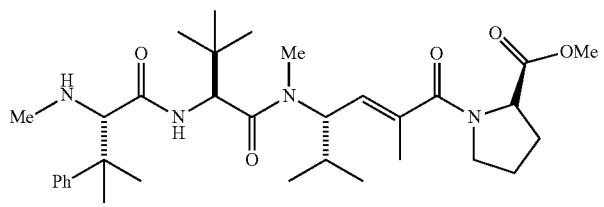 |
| ER-806022 | 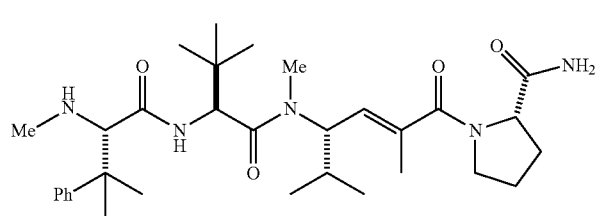 [SMILES: CN[C@H](C(=O)N[C@H](C(=O)N(C)[C@H](/C=C(\C)C(=O)N1CCC[C@H]1C(N)=O)C(C)C)C(C)(C)C)C(C)(C)c1ccccc1] |
| ER-806023 | 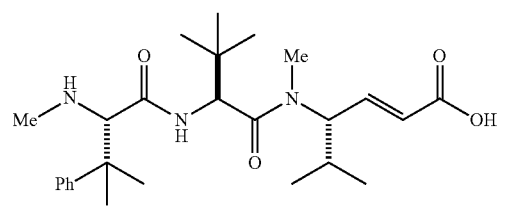 [SMILES: CN[C@H](C(=O)N[C@H](C(=O)N(C)[C@H](/C=C/C(=O)O)C(C)C)C(C)(C)C)C(C)(C)c1ccccc1] |
| ER-806031 | 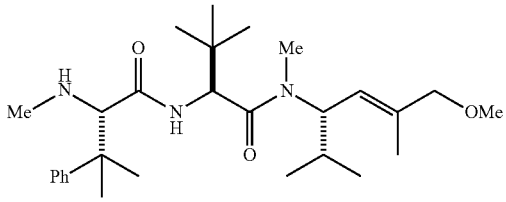 [SMILES: CN[C@H](C(=O)N[C@H](C(=O)N(C)[C@H](/C=C(\C)COC)C(C)C)C(C)(C)C)C(C)(C)c1ccccc1] |

-continued
| Compound | Structure |
|---|---|
| ER-806032 | 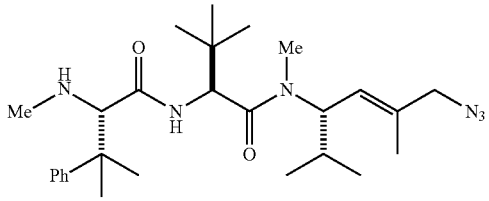 [SMILES: CN[C@H](C(=O)N[C@H](C(=O)N(C)[C@H](/C=C(\C)CN=[N+]=[N-])C(C)C)C(C)(C)C)C(C)(C)c1ccccc1] |
| ER-806073 | 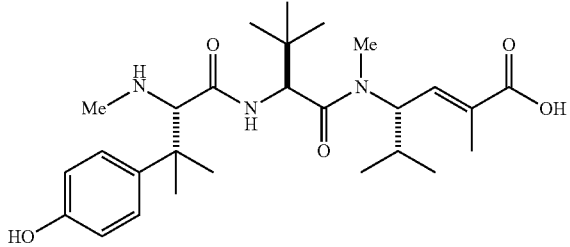 [SMILES: CN[C@H](C(=O)N[C@H](C(=O)N(C)[C@H](/C=C(\C)C(=O)O)C(C)C)C(C)(C)C)C(C)(C)c1ccc(O)cc1] |
| ER-806085 | 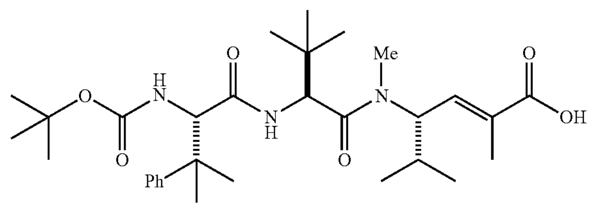 [SMILES: C/C(=C\[C@H](C(C)C)N(C)C(=O)[C@@H](NC(=O)[C@@H](NC(=O)OC(C)(C)C)C(C)(C)c1ccccc1)C(C)(C)C)C(=O)O] |
| ER-806086 | 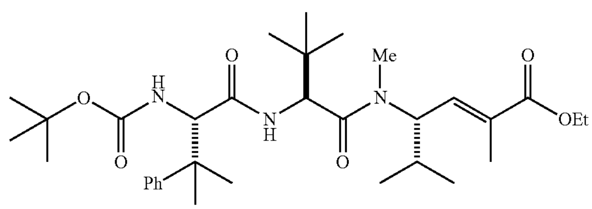 [SMILES: CCOC(=O)/C(C)=C/[C@H](C(C)C)N(C)C(=O)[C@@H](NC(=O)[C@@H](NC(=O)OC(C)(C)C)C(C)(C)c1ccccc1)C(C)(C)C] |
| ER-806105 | 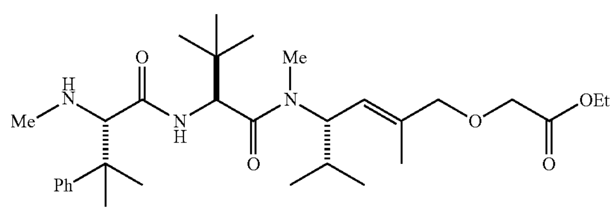 [SMILES: CCOC(=O)COC/C(C)=C/[C@H](C(C)C)N(C)C(=O)[C@@H](NC(=O)[C@@H](NC)C(C)(C)c1ccccc1)C(C)(C)C] |
| ER-806110 | 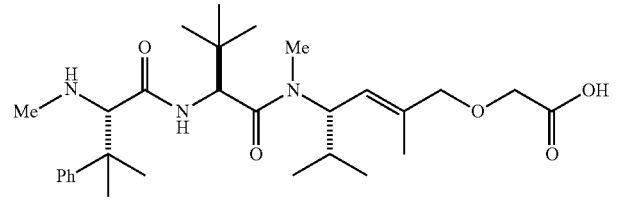 [SMILES: CN[C@H](C(=O)N[C@H](C(=O)N(C)[C@H](/C=C(\C)COCC(=O)O)C(C)C)C(C)(C)C)C(C)(C)c1ccccc1] |
| ER-806119 | 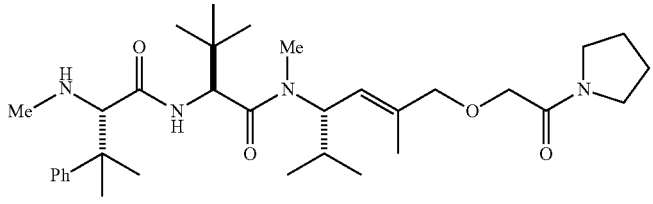 [SMILES: CN[C@H](C(=O)N[C@H](C(=O)N(C)[C@H](/C=C(\C)COCC(=O)N1CCCC1)C(C)C)C(C)(C)C)C(C)(C)c1ccccc1] |

-continued

| Compound | Structure |
|---|---|
| ER-806135 | 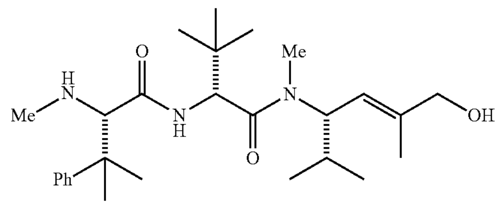 [SMILES: CN[C@H](C(=O)N[C@@H](C(=O)N(C)[C@H](/C=C(\C)CO)C(C)C)C(C)(C)C)C(C)(C)c1ccccc1] |
| ER-806147 | 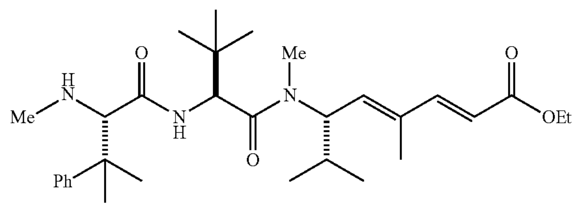 [SMILES: CCOC(=O)/C=C/C(C)=C/[C@H](C(C)C)N(C)C(=O)[C@@H](NC(=O)[C@@H](NC)C(C)(C)c1ccccc1)C(C)(C)C] |
| ER-806180 | 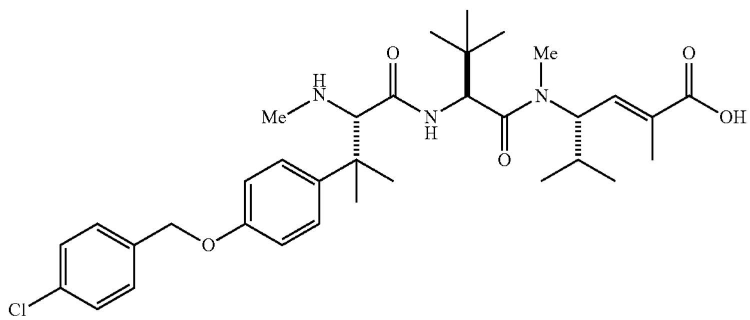 |
| ER-806223 | 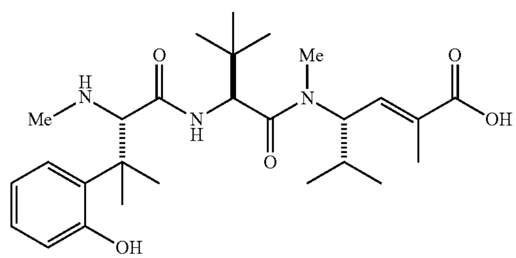 [SMILES: CN[C@H](C(=O)N[C@H](C(=O)N(C)[C@H](/C=C(\C)C(=O)O)C(C)C)C(C)(C)C)C(C)(C)c1ccccc1O] |
| ER-806318 | 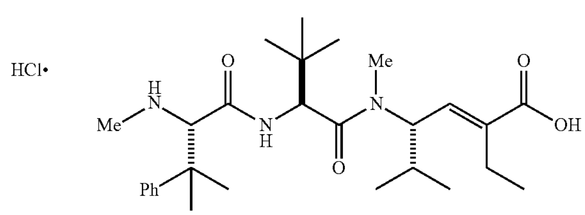 |
| ER-806356 | 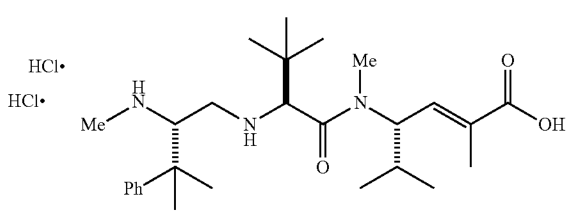 [SMILES: CN[C@H](CN[C@H](C(=O)N(C)[C@H](/C=C(\C)C(=O)O)C(C)C)C(C)(C)C)C(C)(C)c1ccccc1] |

| Compound | Structure |
|---|---|
| ER-806371 | 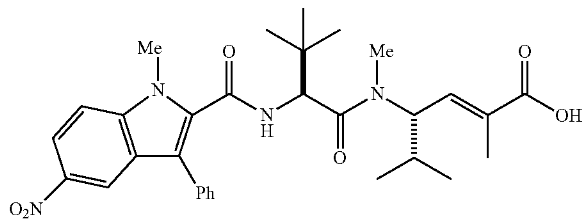 [SMILES: C/C(=C\[C@H](C(C)C)N(C)C(=O)[C@@H](NC(=O)c1c(-c2ccccc2)c2cc([N+](=O)[O-])ccc2n1C)C(C)(C)C)C(=O)O] |
| ER-806395 | 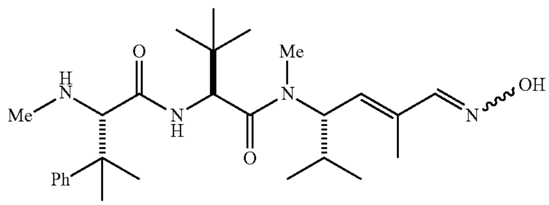 [SMILES: CN[C@H](C(=O)N[C@H](C(=O)N(C)[C@H](/C=C(\C)C=NO)C(C)C)C(C)(C)C)C(C)(C)c1ccccc1] |
| ER-806396 | 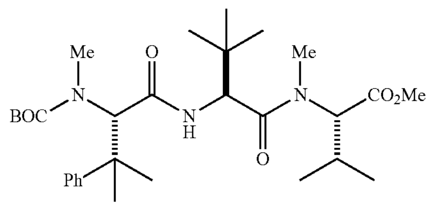 [SMILES: COC(=O)[C@H](C(C)C)N(C)C(=O)[C@@H](NC(=O)[C@@H](N(C)C(=O)OC(C)(C)C)C(C)(C)c1ccccc1)C(C)(C)C] |
| ER-806397 | 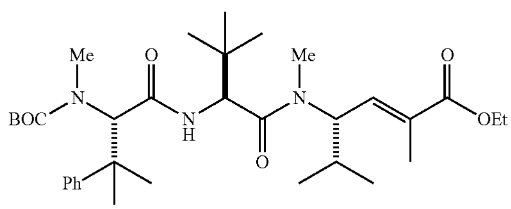 [SMILES: CCOC(=O)/C(C)=C/[C@H](C(C)C)N(C)C(=O)[C@@H](NC(=O)[C@@H](N(C)C(=O)OC(C)(C)C)C(C)(C)c1ccccc1)C(C)(C)C] |
| ER-806398 | 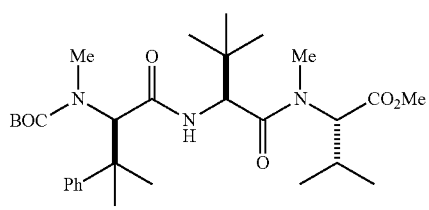 |
| ER-806399 | 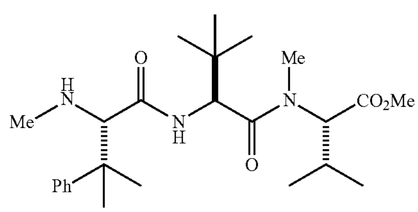 [SMILES: CN[C@H](C(=O)N[C@H](C(=O)N(C)[C@H](C(=O)OC)C(C)C)C(C)(C)C)C(C)(C)c1ccccc1] |
| ER-806400 | 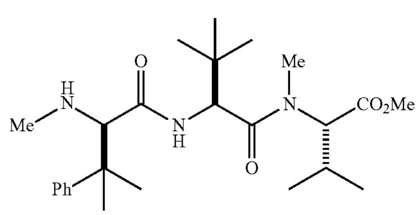 |

| Compound | Structure |
| --- | --- |
| ER-806409 | 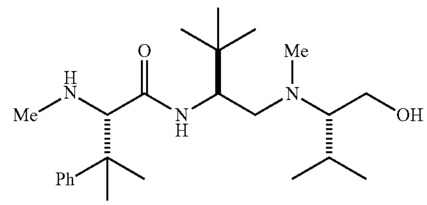 [SMILES: CN[C@H](C(=O)N[C@H](CN(C)[C@H](CO)C(C)C)C(C)(C)C)C(C)(C)c1ccccc1] |
| ER-806418 | 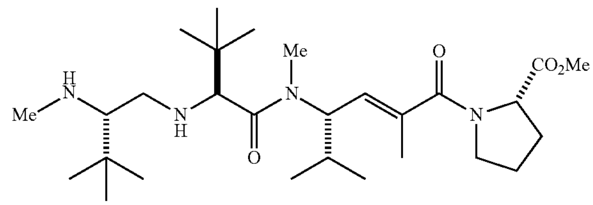 [SMILES: CN[C@H](CN[C@H](C(=O)N(C)[C@H](/C=C(\C)C(=O)N1CCC[C@H]1C(=O)OC)C(C)C)C(C)(C)C)C(C)(C)C] |
| ER-806713 | 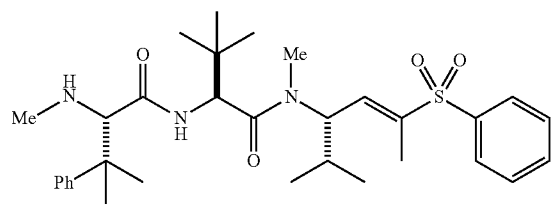 [SMILES: CN[C@H](C(=O)N[C@H](C(=O)N(C)[C@H](/C=C(\C)S(=O)(=O)c1ccccc1)C(C)C)C(C)(C)C)C(C)(C)c1ccccc1] |
| ER-806717 | 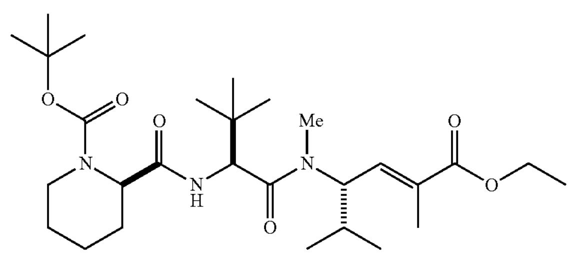 [SMILES: CCOC(=O)/C(C)=C/[C@H](C(C)C)N(C)C(=O)[C@@H](NC(=O)[C@H]1CCCCN1C(=O)OC(C)(C)C)C(C)(C)C] |
| ER-806718 | 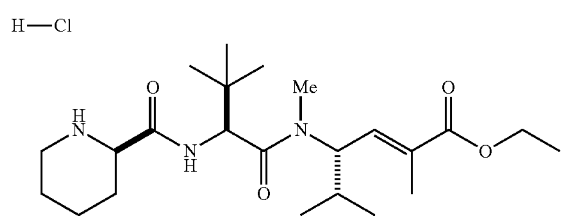 [SMILES: Cl ; CCOC(=O)/C(C)=C/[C@H](C(C)C)N(C)C(=O)[C@@H](NC(=O)[C@H]1CCCCN1)C(C)(C)C] |
| ER-806735 | 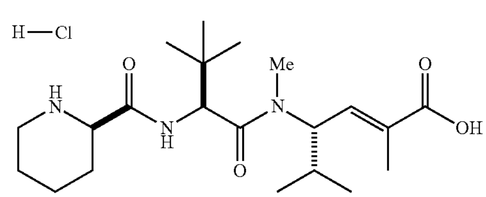 [SMILES: Cl ; C/C(=C\[C@H](C(C)C)N(C)C(=O)[C@@H](NC(=O)[C@H]1CCCCN1)C(C)(C)C)C(=O)O] |
| ER-806748 | 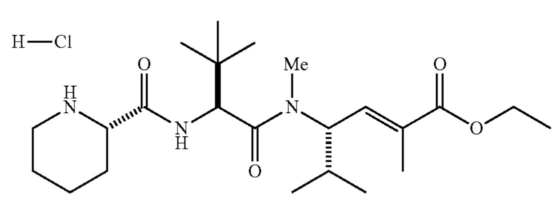 |

-continued
| Compound | Structure |
|---|---|
| ER-806749 | 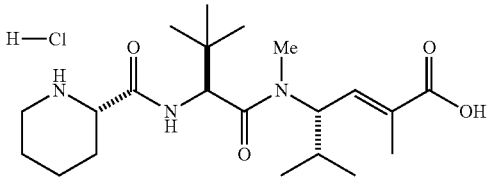 |
| ER-806791 | 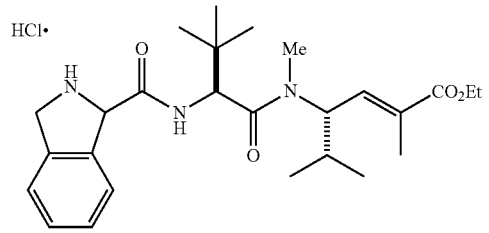 [SMILES: CCOC(=O)/C(C)=C/[C@H](C(C)C)N(C)C(=O)[C@@H](NC(=O)C1NCc2ccccc21)C(C)(C)C] |
| ER-806792 | 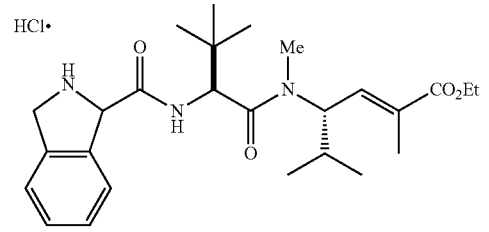 [SMILES: CCOC(=O)/C(C)=C/[C@H](C(C)C)N(C)C(=O)[C@@H](NC(=O)C1NCc2ccccc21)C(C)(C)C] |
| ER-806793 | 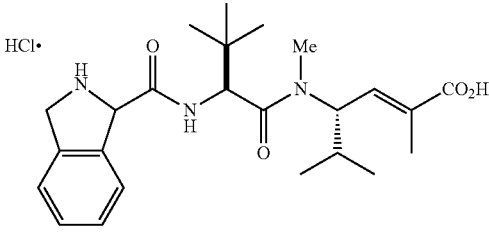 [SMILES: C/C(=C\[C@H](C(C)C)N(C)C(=O)[C@@H](NC(=O)C1NCc2ccccc21)C(C)(C)C)C(=O)O] |
| ER-806794 | 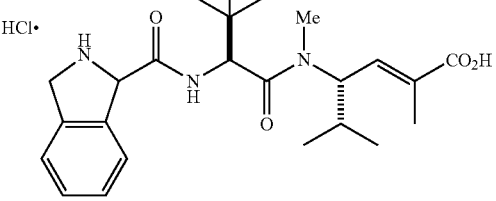 |
| ER-806822 | 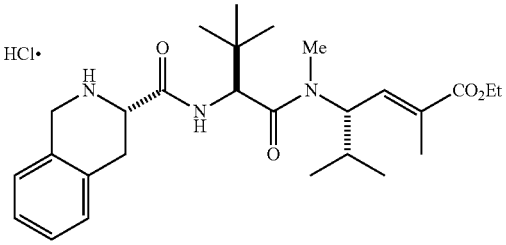 [SMILES: CCOC(=O)/C(C)=C/[C@H](C(C)C)N(C)C(=O)[C@@H](NC(=O)[C@@H]1Cc2ccccc2CN1)C(C)(C)C] |

| Compound | Structure |
|---|---|
| ER-806823 | 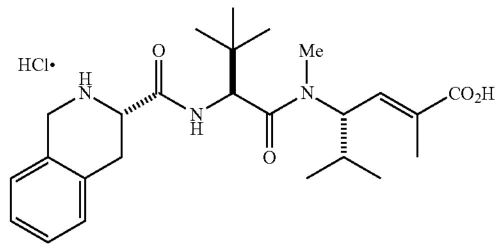 [SMILES: C/C(=C\[C@H](C(C)C)N(C)C(=O)[C@@H](NC(=O)[C@@H]1Cc2ccccc2CN1)C(C)(C)C)C(=O)O] |
| ER-806824 | 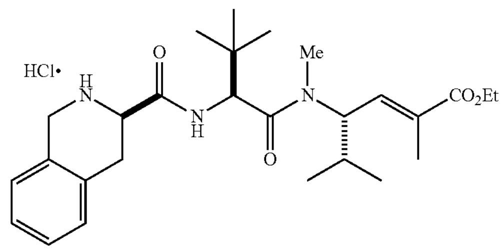 [SMILES: CCOC(=O)/C(C)=C/[C@H](C(C)C)N(C)C(=O)[C@@H](NC(=O)[C@H]1Cc2ccccc2CN1)C(C)(C)C] |
| ER-806825 | 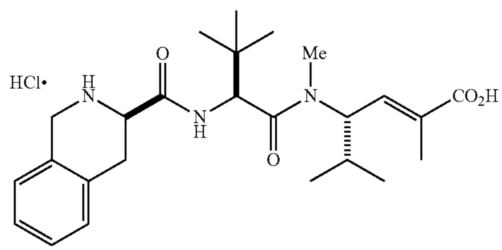 [SMILES: C/C(=C\[C@H](C(C)C)N(C)C(=O)[C@@H](NC(=O)[C@H]1Cc2ccccc2CN1)C(C)(C)C)C(=O)O] |
| ER-806830 | 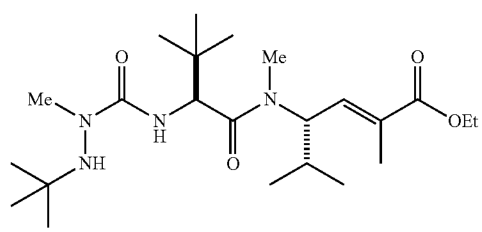 [SMILES: CCOC(=O)/C(C)=C/[C@H](C(C)C)N(C)C(=O)[C@@H](NC(=O)N(C)NC(C)(C)C)C(C)(C)C] |
| ER-806831 | 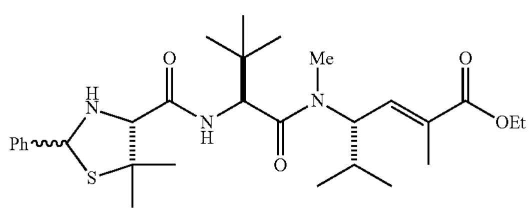 |
| ER-806853 | 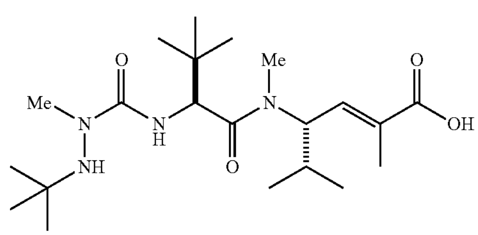 [SMILES: C/C(=C\[C@H](C(C)C)N(C)C(=O)[C@@H](NC(=O)N(C)NC(C)(C)C)C(C)(C)C)C(=O)O] |

-continued

| Compound | Structure |
|---|---|
| ER-806854 | 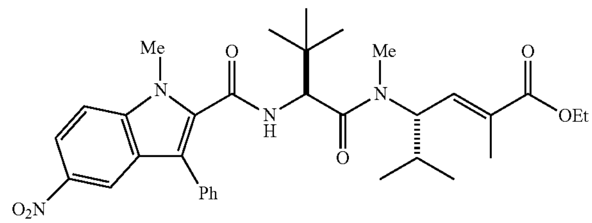 [SMILES: CCOC(=O)/C(C)=C/[C@H](C(C)C)N(C)C(=O)[C@@H](NC(=O)c1c(-c2ccccc2)c2cc([N+](=O)[O-])ccc2n1C)C(C)(C)C] |
| ER-806861 | 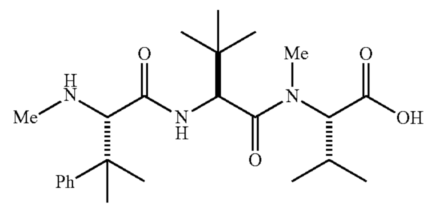 [SMILES: CN[C@H](C(=O)N[C@H](C(=O)N(C)[C@H](C(=O)O)C(C)C)C(C)(C)C)C(C)(C)c1ccccc1] |
| ER-806862 | 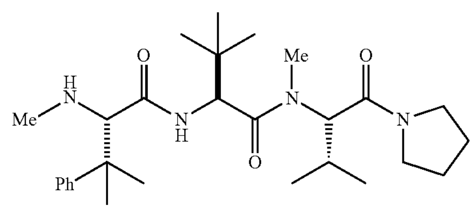 |
| ER-806863 | 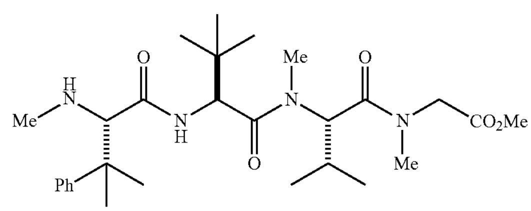 [SMILES: CN[C@H](C(=O)N[C@H](C(=O)N(C)[C@H](C(=O)N(C)CC(=O)OC)C(C)C)C(C)(C)C)C(C)(C)c1ccccc1] |
| ER-806864 | 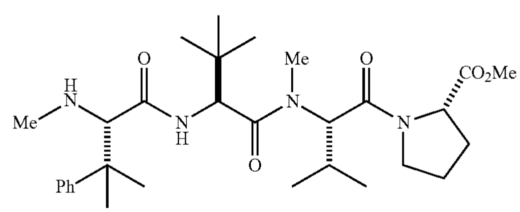 [SMILES: CN[C@H](C(=O)N[C@H](C(=O)N(C)[C@H](C(=O)N1CCC[C@H]1C(=O)OC)C(C)C)C(C)(C)C)C(C)(C)c1ccccc1] |
| ER-806865 | 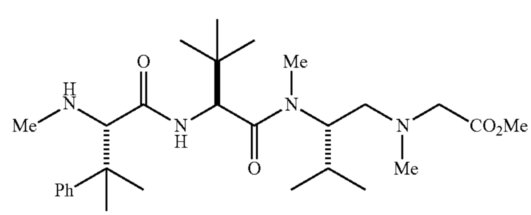 [SMILES: CN[C@H](C(=O)N[C@H](C(=O)N(C)[C@H](CN(C)CC(=O)OC)C(C)C)C(C)(C)C)C(C)(C)c1ccccc1] |
| ER-806866 | 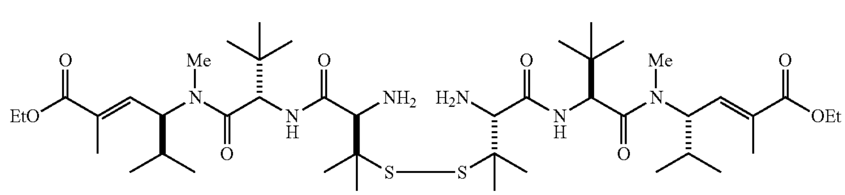 |

-continued

| Compound | Structure |
|---|---|
| ER-806867 | 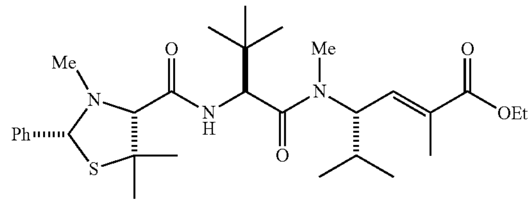 |
| ER-806868 | 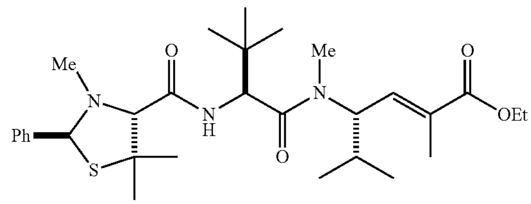 |
| ER-806869 | 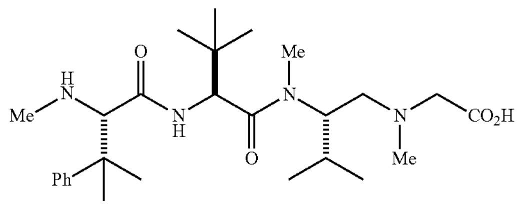 [SMILES: CN[C@H](C(=O)N[C@H](C(=O)N(C)[C@H](CN(C)CC(=O)O)C(C)C)C(C)(C)C)C(C)(C)c1ccccc1] |
| ER-806870 | 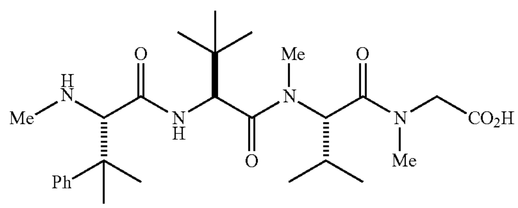 [SMILES: CN[C@H](C(=O)N[C@H](C(=O)N(C)[C@H](C(=O)N(C)CC(=O)O)C(C)C)C(C)(C)C)C(C)(C)c1ccccc1] |
| ER-806871 | 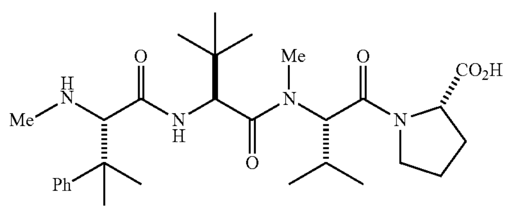 [SMILES: CN[C@H](C(=O)N[C@H](C(=O)N(C)[C@H](C(=O)N1CCC[C@H]1C(=O)O)C(C)C)C(C)(C)C)C(C)(C)c1ccccc1] |
| ER-806879 | 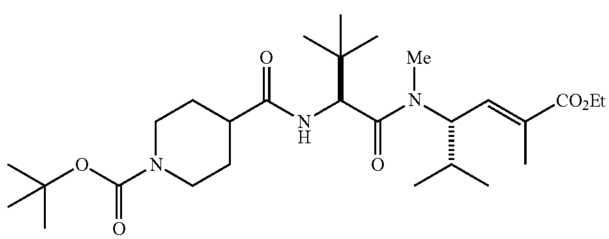 [SMILES: CCOC(=O)/C(C)=C/[C@H](C(C)C)N(C)C(=O)[C@@H](NC(=O)C1CCN(C(=O)OC(C)(C)C)CC1)C(C)(C)C] |
| ER-806880 | 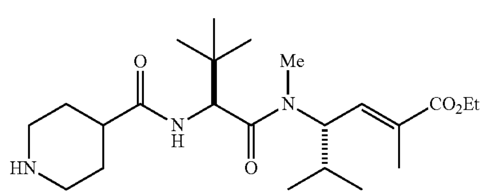 |

-continued

| Compound | Structure |
|---|---|
| ER-806881 | 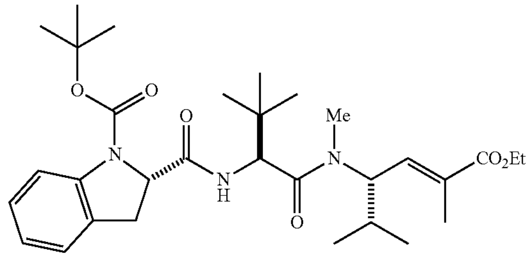 |
| ER-806882 | 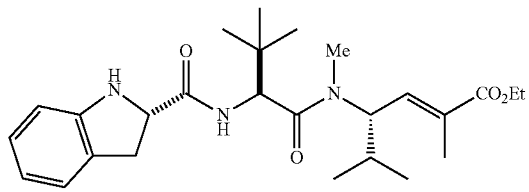 [SMILES: CCOC(=O)/C(C)=C/[C@H](C(C)C)N(C)C(=O)[C@@H](NC(=O)[C@@H]1Cc2ccccc2N1)C(C)(C)C] |
| ER-806920 | 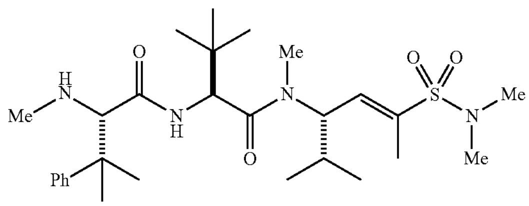 [SMILES: CN[C@H](C(=O)N[C@H](C(=O)N(C)[C@H](/C=C(\C)S(=O)(=O)N(C)C)C(C)C)C(C)(C)C)C(C)(C)c1ccccc1] |
| ER-806921 | 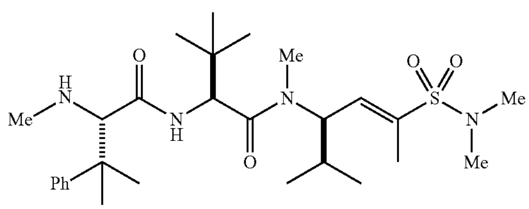 |
| ER-806922 | 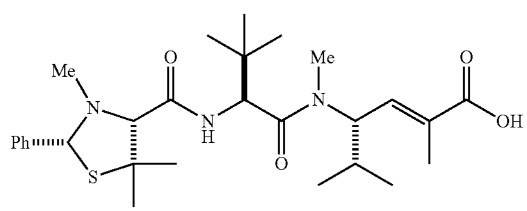 |
| ER-806923 | 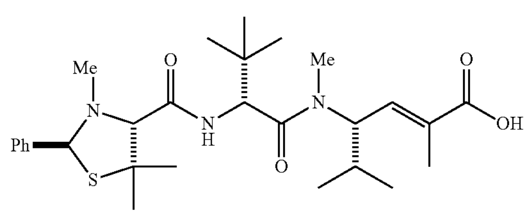 |
| ER-806924 | 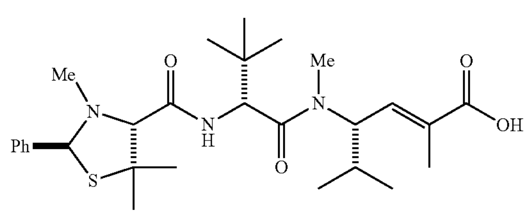 |

-continued

| Compound | Structure |
|---|---|
| ER-806925 | 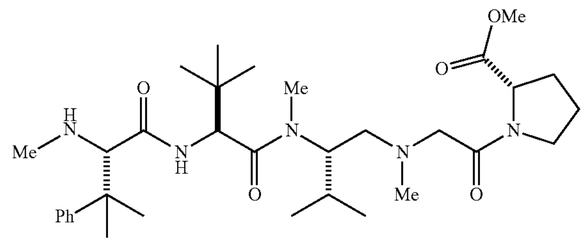 [SMILES: CN[C@H](C(=O)N[C@H](C(=O)N(C)[C@H](CN(C)CC(=O)N1CCC[C@H]1C(=O)OC)C(C)C)C(C)(C)C)C(C)(C)c1ccccc1] |
| ER-807000 | 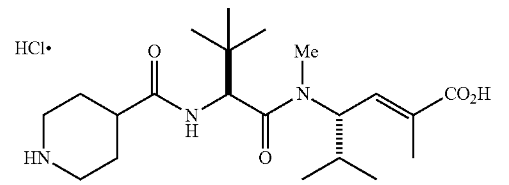 [SMILES: C/C(=C\[C@H](C(C)C)N(C)C(=O)[C@@H](NC(=O)C1CCNCC1)C(C)(C)C)C(=O)O] |
| ER-807001 | 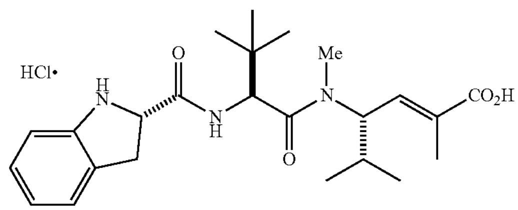 [SMILES: C/C(=C\[C@H](C(C)C)N(C)C(=O)[C@@H](NC(=O)[C@@H]1Cc2ccccc2N1)C(C)(C)C)C(=O)O] |
| ER-807002 | 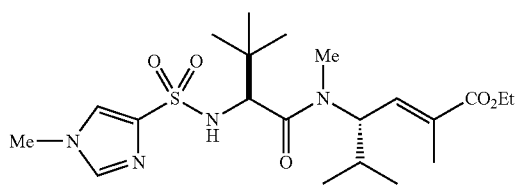 [SMILES: CCOC(=O)/C(C)=C/[C@H](C(C)C)N(C)C(=O)[C@@H](NS(=O)(=O)c1cn(C)cn1)C(C)(C)C] |
| ER-807077 single diastereomer | 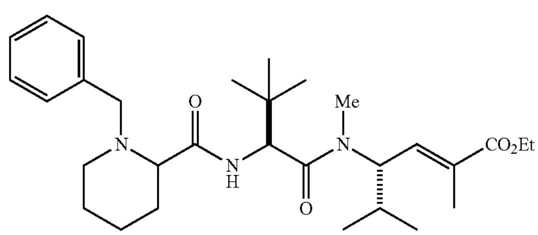 [SMILES: CCOC(=O)/C(C)=C/[C@H](C(C)C)N(C)C(=O)[C@@H](NC(=O)C1CCCCN1Cc1ccccc1)C(C)(C)C] |
| ER-807078 single diastereomer | 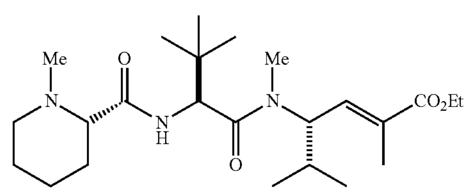 |
| ER-807079 | 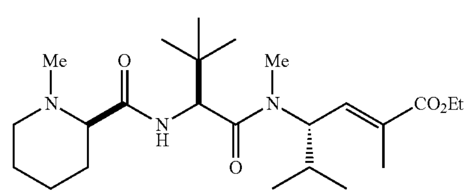 [SMILES: CCOC(=O)/C(C)=C/[C@H](C(C)C)N(C)C(=O)[C@@H](NC(=O)[C@H]1CCCCN1C)C(C)(C)C] |

-continued

| Compound | Structure |
|---|---|
| ER-807080 | 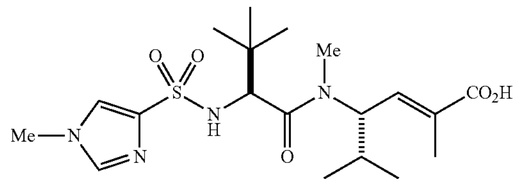 [SMILES: C/C(=C\[C@H](C(C)C)N(C)C(=O)[C@@H](NS(=O)(=O)c1cn(C)cn1)C(C)(C)C)C(=O)O] |
| ER-807081 single diastereomer | 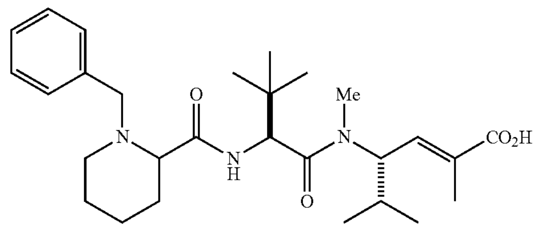 |
| ER-807096 | 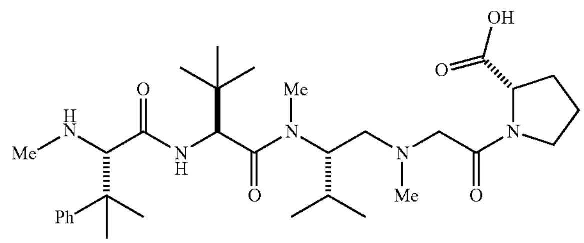 |
| ER-807101 | 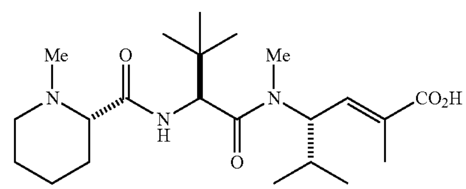 [SMILES: C/C(=C\[C@H](C(C)C)N(C)C(=O)[C@@H](NC(=O)[C@@H]1CCCCN1C)C(C)(C)C)C(=O)O] |
| ER-807102 | 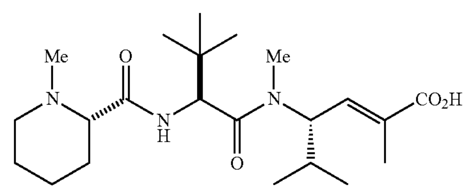 |
| ER-807133 | 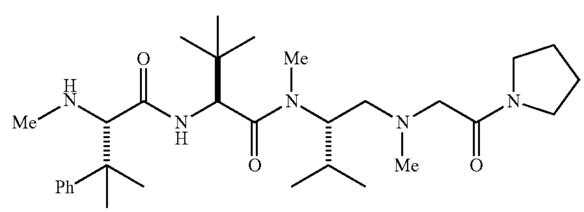 [SMILES: CN[C@H](C(=O)N[C@H](C(=O)N(C)[C@H](CN(C)CC(=O)N1CCCC1)C(C)C)C(C)(C)C)C(C)(C)c1ccccc1] |
| ER-807134 | 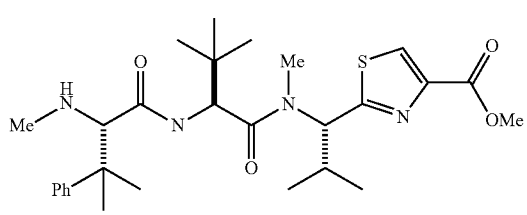 [SMILES: CN[C@H](C(=O)N[C@H](C(=O)N(C)[C@H](c1nc(C(=O)OC)cs1)C(C)C)C(C)(C)C)C(C)(C)c1ccccc1] |

-continued
| Compound | Structure |
|---|---|
| ER-807135 | 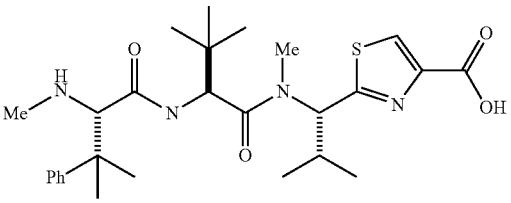 [SMILES: CN[C@H](C(=O)N[C@H](C(=O)N(C)[C@H](c1nc(C(=O)O)cs1)C(C)C)C(C)(C)C)C(C)(C)c1ccccc1] |
| ER-807145 | 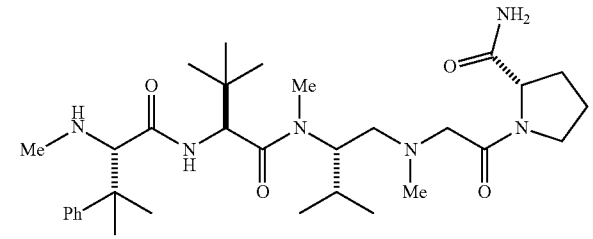 |
| ER-807146 | 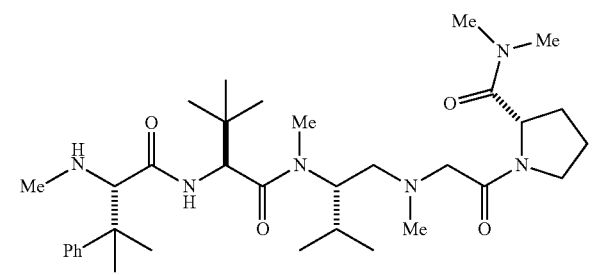 [SMILES: CN[C@H](C(=O)N[C@H](C(=O)N(C)[C@H](CN(C)CC(=O)N1CCC[C@H]1C(=O)N(C)C)C(C)C)C(C)(C)C)C(C)(C)c1ccccc1] |
| ER-807147 | 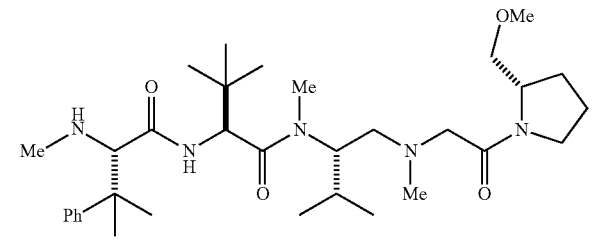 [SMILES: CN[C@H](C(=O)N[C@H](C(=O)N(C)[C@H](CN(C)CC(=O)N1CCC[C@H]1COC)C(C)C)C(C)(C)C)C(C)(C)c1ccccc1] |
| ER-807148 | 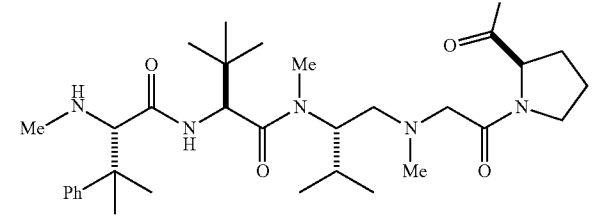 |
| ER-807160 | 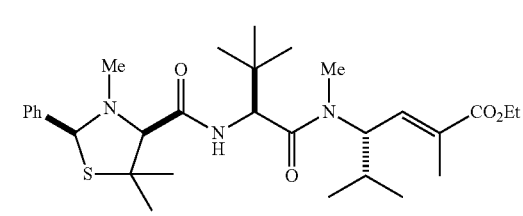 |

-continued

| Compound | Structure |
|---|---|
| ER-807161 | 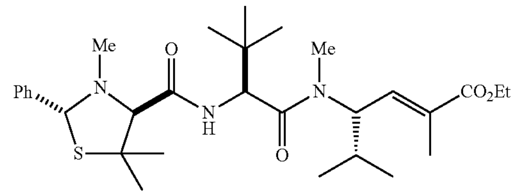 |
| ER-807180 | 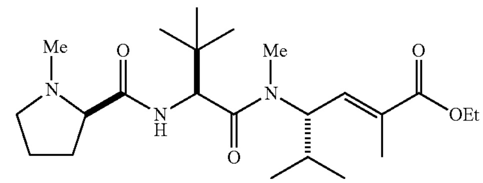 [SMILES: CCOC(=O)/C(C)=C/[C@H](C(C)C)N(C)C(=O)[C@@H](NC(=O)[C@H]1CCCN1C)C(C)(C)C] |
| ER-807192 | 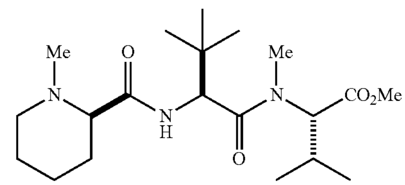 [SMILES: COC(=O)[C@H](C(C)C)N(C)C(=O)[C@@H](NC(=O)[C@H]1CCCCN1C)C(C)(C)C] |
| ER-807193 | 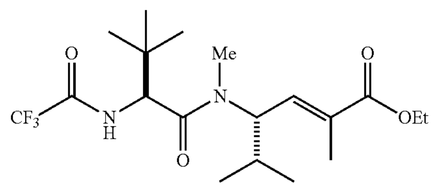 [SMILES: CCOC(=O)/C(C)=C/[C@H](C(C)C)N(C)C(=O)[C@@H](NC(=O)C(F)(F)F)C(C)(C)C] |
| ER-807194 | 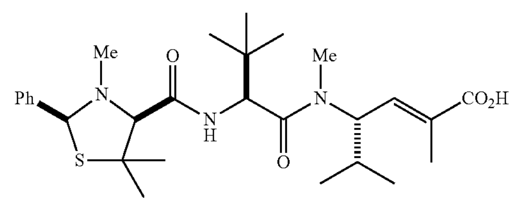 [SMILES: C/C(=C\[C@H](C(C)C)N(C)C(=O)[C@@H](NC(=O)[C@@H]1N(C)CSC1(C)C)C(C)(C)C)C(=O)O ; "Ph"] |
| ER-807195 | 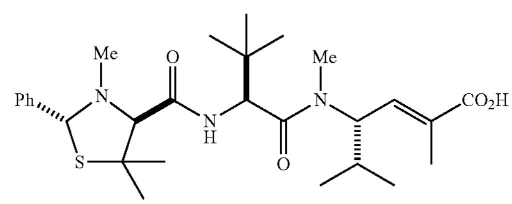 [SMILES: C/C(=C\[C@H](C(C)C)N(C)C(=O)[C@@H](NC(=O)[C@@H]1N(C)[C@@H](c2ccccc2)SC1(C)C)C(C)(C)C)C(=O)O] |
| ER-807209 | 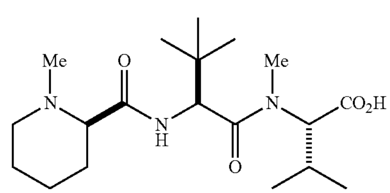 [SMILES: CC(C)[C@@H](C(=O)O)N(C)C(=O)[C@@H](NC(=O)[C@H]1CCCCN1C)C(C)(C)C] |
| ER-807210 | 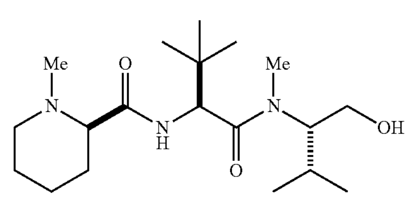 [SMILES: CC(C)[C@@H](CO)N(C)C(=O)[C@@H](NC(=O)[C@H]1CCCCN1C)C(C)(C)C] |

-continued

| Compound | Structure |
|---|---|
| ER-807212 | 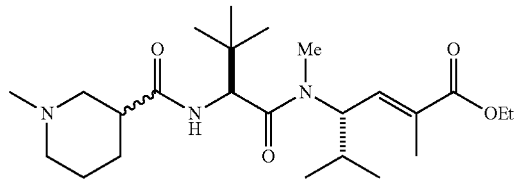 [SMILES: CCOC(=O)/C(C)=C/[C@H](C(C)C)N(C)C(=O)[C@@H](NC(=O)C1CCCN(C)C1)C(C)(C)C] |
| ER-807213 | 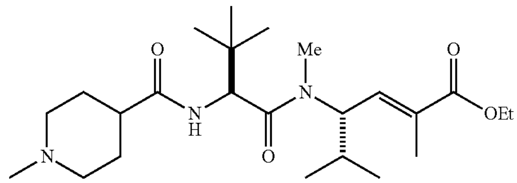 [SMILES: CCOC(=O)/C(C)=C/[C@H](C(C)C)N(C)C(=O)[C@@H](NC(=O)C1CCN(C)CC1)C(C)(C)C] |
| ER-807214 | 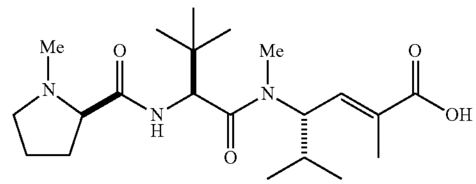 [SMILES: C/C(=C\[C@H](C(C)C)N(C)C(=O)[C@@H](NC(=O)[C@H]1CCCN1C)C(C)(C)C)C(=O)O] |
| ER-807215 | 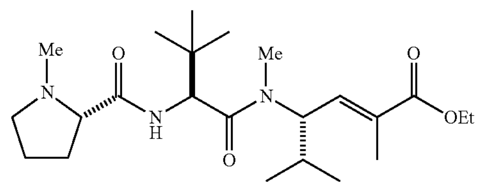 [SMILES: CCOC(=O)/C(C)=C/[C@H](C(C)C)N(C)C(=O)[C@@H](NC(=O)[C@@H]1CCCN1C)C(C)(C)C] |
| ER-807217 | 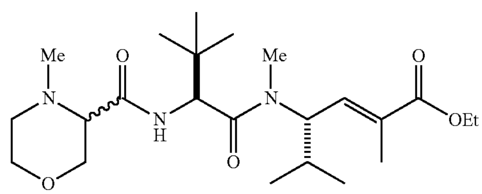 [SMILES: CCOC(=O)/C(C)=C/[C@H](C(C)C)N(C)C(=O)[C@@H](NC(=O)C1COCCN1C)C(C)(C)C] |
| ER-807218 | 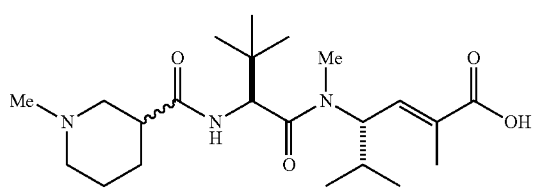 [SMILES: C/C(=C\[C@H](C(C)C)N(C)C(=O)[C@@H](NC(=O)C1CCCN(C)C1)C(C)(C)C)C(=O)O] |
| ER-807219 | 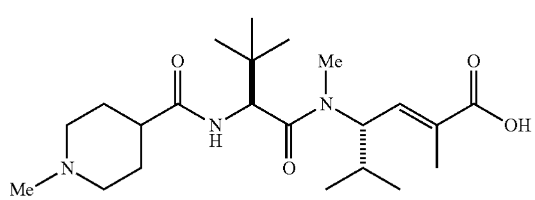 [SMILES: C/C(=C\[C@H](C(C)C)N(C)C(=O)[C@@H](NC(=O)C1CCN(C)CC1)C(C)(C)C)C(=O)O] |
| ER-807222 | 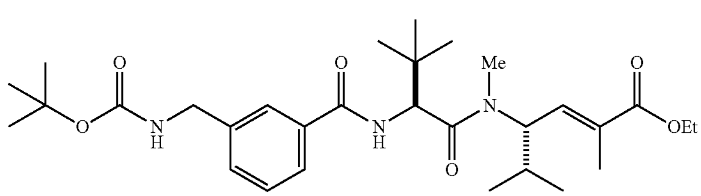 [SMILES: CCOC(=O)/C(C)=C/[C@H](C(C)C)N(C)C(=O)[C@@H](NC(=O)c1cccc(CNC(=O)OC(C)(C)C)c1)C(C)(C)C] |

| Compound | Structure |
|---|---|
| ER-807226 | 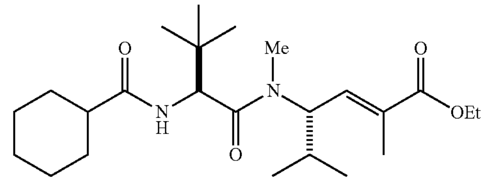 |
| ER-807228 | 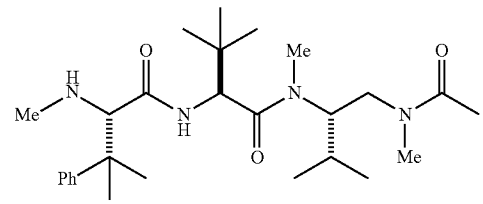 [SMILES: CN[C@H](C(=O)N[C@H](C(=O)N(C)[C@H](CN(C)C(C)=O)C(C)C)C(C)(C)C)C(C)(C)c1ccccc1] |
| ER-807229 | 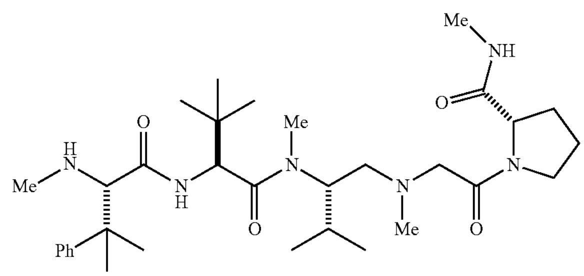 [SMILES: CNC(=O)[C@@H]1CCCN1C(=O)CN(C)C[C@H](C(C)C)N(C)C(=O)[C@@H](NC(=O)[C@@H](NC)C(C)(C)c1ccccc1)C(C)(C)C] |
| ER-807230 | 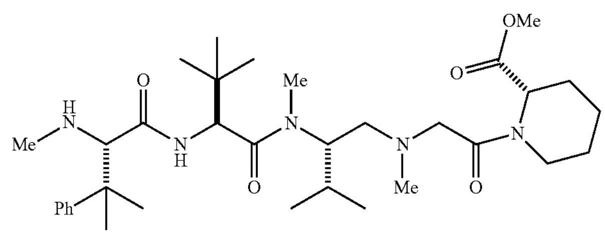 |
| ER-807231 | 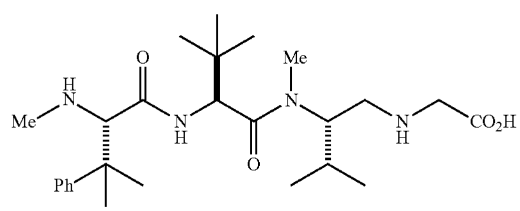 [SMILES: CN[C@H](C(=O)N[C@H](C(=O)N(C)[C@H](CNCC(=O)O)C(C)C)C(C)(C)C)C(C)(C)c1ccccc1] |
| ER-807232 | 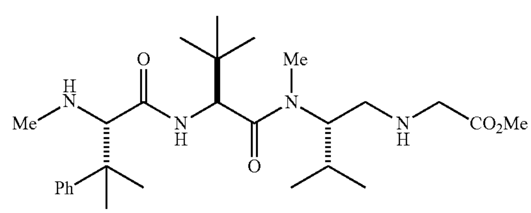 [SMILES: CN[C@H](C(=O)N[C@H](C(=O)N(C)[C@H](CNCC(=O)OC)C(C)C)C(C)(C)C)C(C)(C)c1ccccc1] |
| ER-807237 | 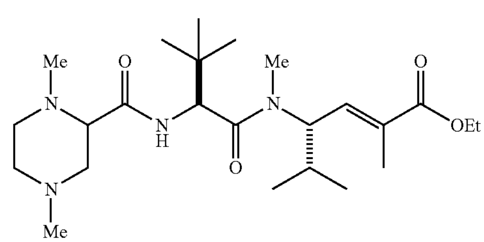 [SMILES: CCOC(=O)/C(C)=C/[C@H](C(C)C)N(C)C(=O)[C@@H](NC(=O)C1CN(C)CCN1C)C(C)(C)C] |

| Compound | Structure |
|---|---|
| ER-807238 | 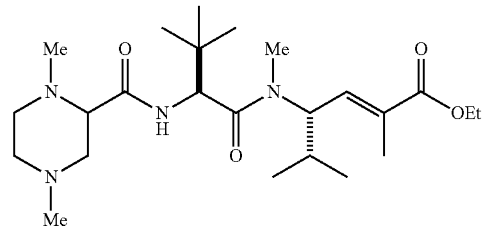 [SMILES: CCOC(=O)/C(C)=C/[C@H](C(C)C)N(C)C(=O)[C@@H](NC(=O)C1CN(C)CCN1C)C(C)(C)C] |
| ER-807246 | 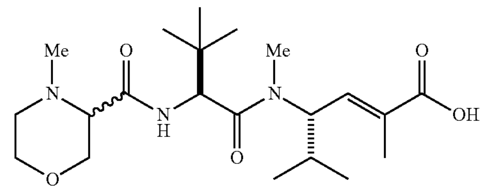 [SMILES: C/C(=C\[C@H](C(C)C)N(C)C(=O)[C@@H](NC(=O)C1COCCN1C)C(C)(C)C)C(=O)O] |
| ER-807247 | 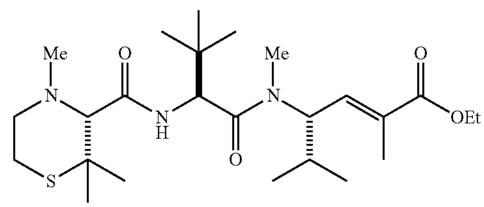 |
| ER-807248 | 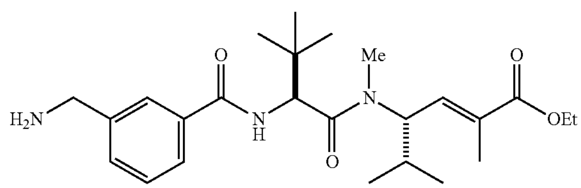 [SMILES: CCOC(=O)/C(C)=C/[C@H](C(C)C)N(C)C(=O)[C@@H](NC(=O)c1cccc(CN)c1)C(C)(C)C] |
| ER-807249 | 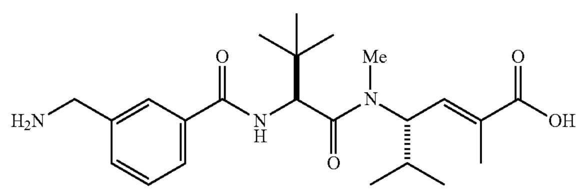 |
| ER-807303 | 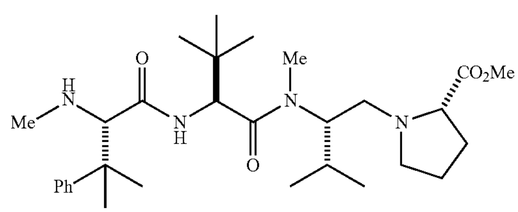 [SMILES: CN[C@H](C(=O)N[C@H](C(=O)N(C)[C@H](CN1CCC[C@H]1C(=O)OC)C(C)C)C(C)(C)C)C(C)(C)c1ccccc1] |
| ER-807324 | 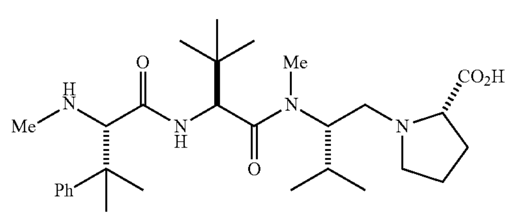 [SMILES: CN[C@H](C(=O)N[C@H](C(=O)N(C)[C@H](CN1CCC[C@H]1C(=O)O)C(C)C)C(C)(C)C)C(C)(C)c1ccccc1] |

| Compound | Structure |
|---|---|
| ER-807328 | 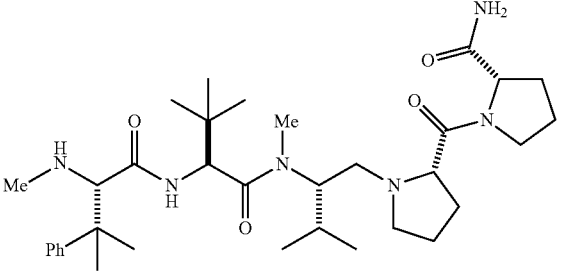 [SMILES: CN[C@H](C(=O)N[C@H](C(=O)N(C)[C@H](CN1CCC[C@H]1C(=O)N1CCC[C@H]1C(N)=O)C(C)C)C(C)(C)C)C(C)(C)c1ccccc1] |
| ER-807329 | 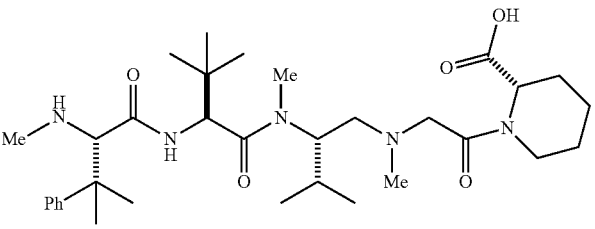 [SMILES: CN[C@H](C(=O)N[C@H](C(=O)N(C)[C@H](CN(C)CC(=O)N1CCCC[C@H]1C(=O)O)C(C)C)C(C)(C)C)C(C)(C)c1ccccc1] |
| ER-807332 | 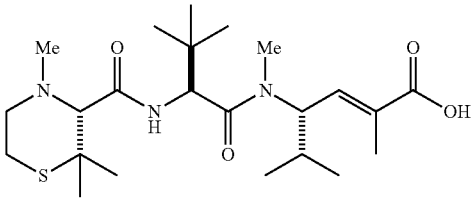 |
| ER-807334 | 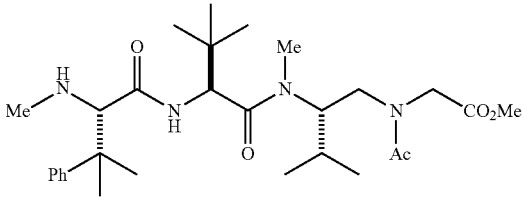 [SMILES: CN[C@H](C(=O)N[C@H](C(=O)N(C)[C@H](CN(CC(=O)OC)C(C)=O)C(C)C)C(C)(C)C)C(C)(C)c1ccccc1] |
| ER-807339 | 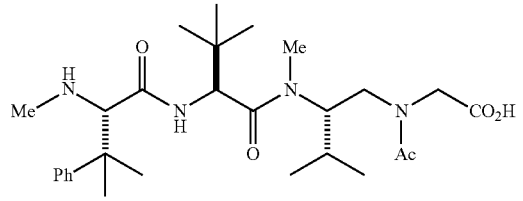 |
| ER-807341 | 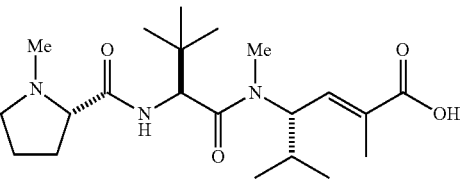 [SMILES: C/C(=C\[C@H](C(C)C)N(C)C(=O)[C@@H](NC(=O)[C@@H]1CCCN1C)C(C)(C)C)C(=O)O] |
| ER-807342 | 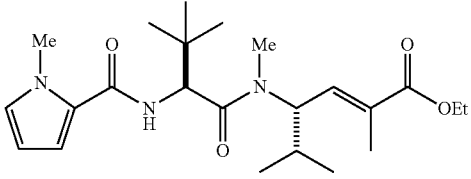 [SMILES: CCOC(=O)/C(C)=C/[C@H](C(C)C)N(C)C(=O)[C@@H](NC(=O)c1cccn1C)C(C)(C)C] |

-continued
| Compound | Structure |
|---|---|
| ER-807343 | 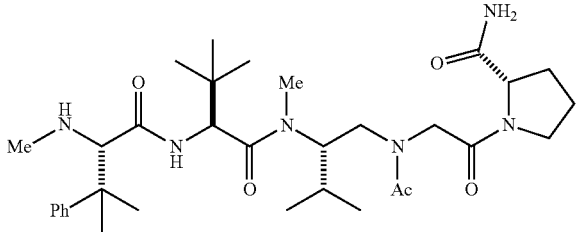 |
| ER-807344 | 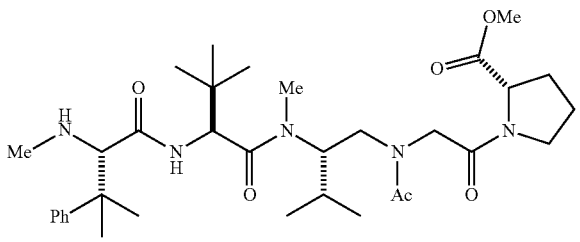 [SMILES: CN[C@H](C(=O)N[C@H](C(=O)N(C)[C@H](CN(CC(=O)N1CCC[C@H]1C(N)=O)C(C)=O)C(C)C)C(C)(C)C)C(C)(C)c1ccccc1] |
| ER-807345 | 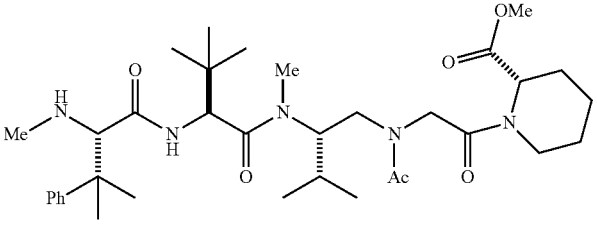 |
| ER-807346 | 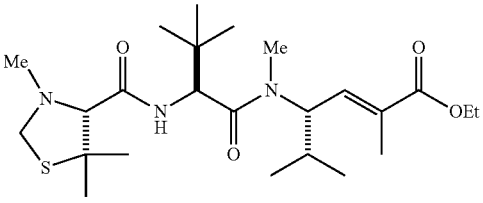 |
| ER-807347 | 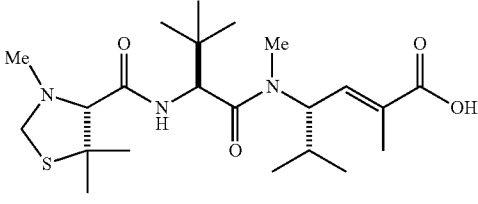 |
| ER-807352 | 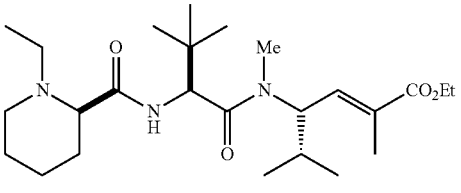 |
| ER-807353 | 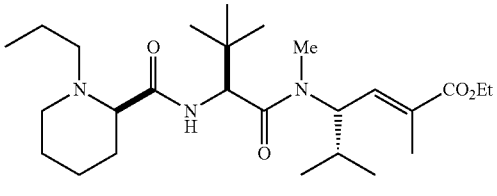 |

-continued

| Compound | Structure |
|---|---|
| ER-807354 | 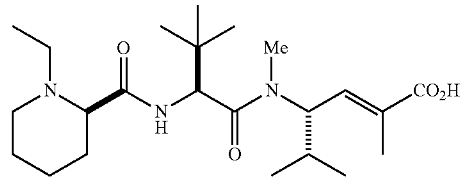 [SMILES: CCN1CCCC[C@@H]1C(=O)N[C@H](C(=O)N(C)[C@H](/C=C(\C)C(=O)O)C(C)C)C(C)(C)C] |
| ER-807355 | 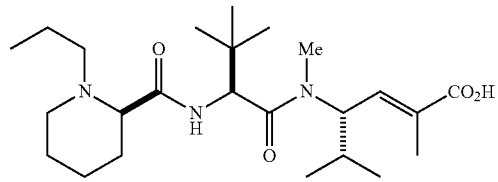 [SMILES: CCCN1CCCC[C@@H]1C(=O)N[C@H](C(=O)N(C)[C@H](/C=C(\C)C(=O)O)C(C)C)C(C)(C)C] |
| ER-807360 | 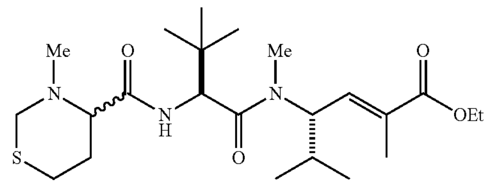 [SMILES: CCOC(=O)/C(C)=C/[C@H](C(C)C)N(C)C(=O)[C@@H](NC(=O)C1CCSCN1C)C(C)(C)C] |
| ER-807361 | 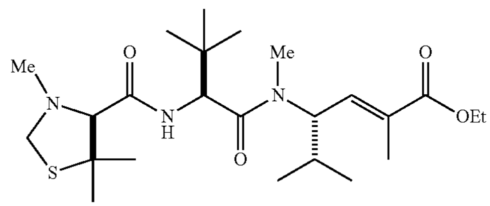 |
| R-807362 | 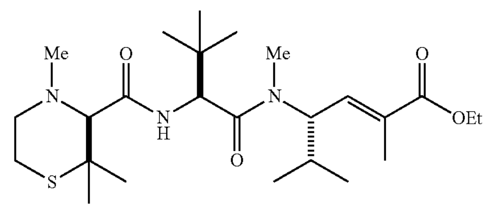 |
| ER-807364 | 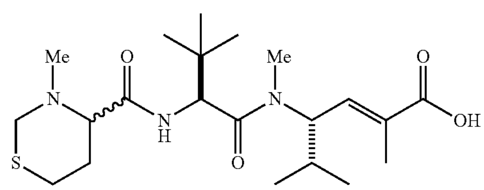 [SMILES: C/C(=C\[C@H](C(C)C)N(C)C(=O)[C@@H](NC(=O)C1CCSCN1C)C(C)(C)C)C(=O)O] |
| ER-807365 | 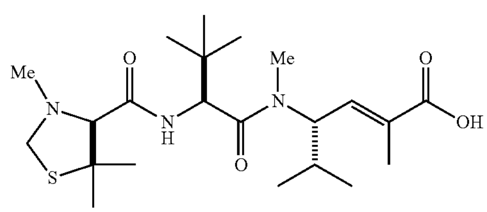 |
| ER-807366 | 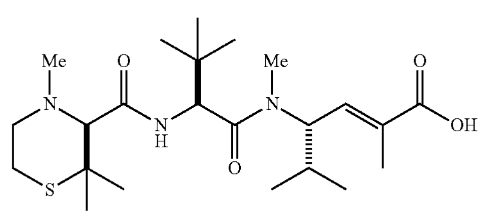 |

-continued

| Compound | Structure |
|---|---|
| ER-807370 | 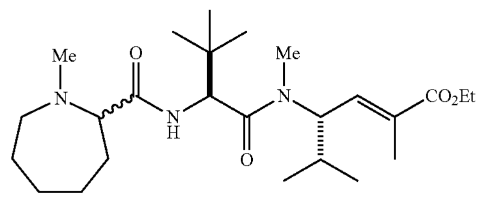 |
| ER-807371 | 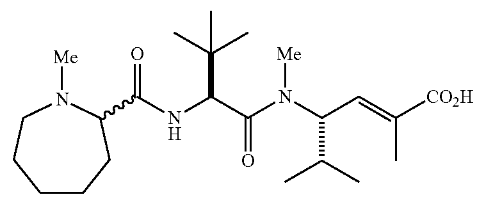 |
| ER-807374 | 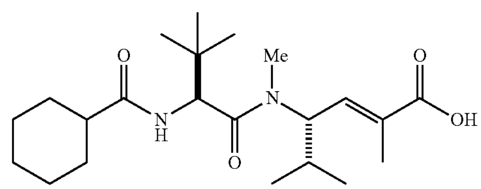 [SMILES: C/C(=C\[C@H](C(C)C)N(C)C(=O)[C@@H](NC(=O)C1CCCCC1)C(C)(C)C)C(=O)O] |
| ER-807375 | 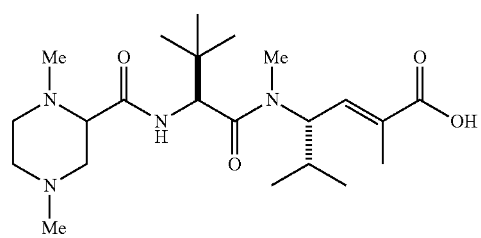 [SMILES: C/C(=C\[C@H](C(C)C)N(C)C(=O)[C@@H](NC(=O)C1CN(C)CCN1C)C(C)(C)C)C(=O)O] |
| ER-807393 | 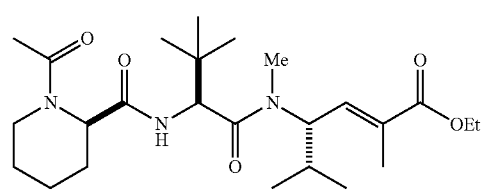 [SMILES: CCOC(=O)/C(C)=C/[C@H](C(C)C)N(C)C(=O)[C@@H](NC(=O)[C@H]1CCCCN1C(C)=O)C(C)(C)C] |
| ER-807413 | 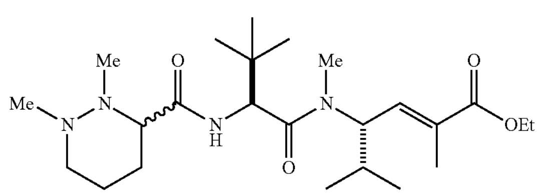 [SMILES: CCOC(=O)/C(C)=C/[C@H](C(C)C)N(C)C(=O)[C@@H](NC(=O)C1CCCN(C)N1C)C(C)(C)C] |
| ER-807414 | 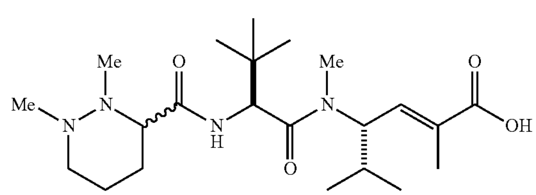 |

| Compound | Structure |
|---|---|
| ER-807417 | 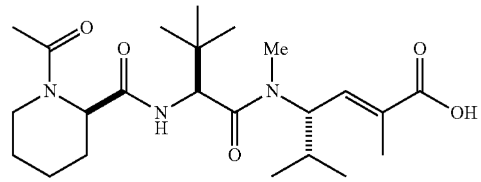 [SMILES: CC(=O)N1CCCC[C@@H]1C(=O)N[C@H](C(=O)N(C)[C@H](/C=C(\C)C(=O)O)C(C)C)C(C)(C)C] |
| ER-807418 | cis |
| ER-807419 | cis |
| ER-807420 | 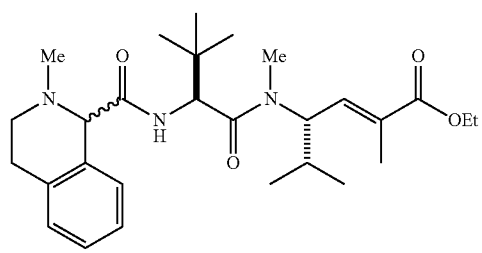 [SMILES: CCOC(=O)/C(C)=C/[C@H](C(C)C)N(C)C(=O)[C@@H](NC(=O)C1c2ccccc2CCN1C)C(C)(C)C] |
| ER-807421 | 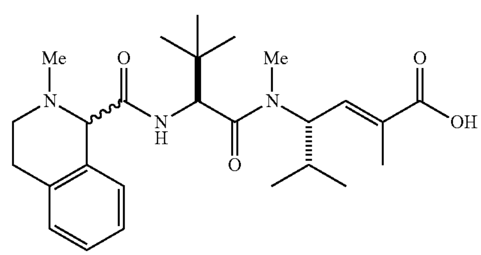 |
| ER-807431 | 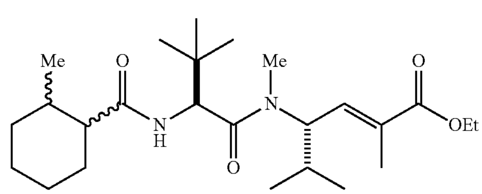 [SMILES: CCOC(=O)/C(C)=C/[C@H](C(C)C)N(C)C(=O)[C@@H](NC(=O)C1CCCCC1)C(C)(C)C ; "Me"] |
| ER-807461 | 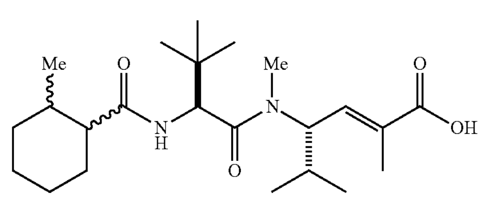 [SMILES: C/C(=C\[C@H](C(C)C)N(C)C(=O)[C@@H](NC(=O)C1CCCCC1)C(C)(C)C)C(=O)O ; "Me"] |

| Compound | Structure |
|---|---|
| ER-807470 single diastereomer | (structure shown) cis |
| ER-807471 single diastereomer | (structure shown) cis |
| ER-807480 single diastereomer | (structure shown) |
| ER-807481 single diastereomer | (structure shown) |
| ER-807482 single diastereomer | (structure shown) cis |
| ER-807483 single diastereomer | (structure shown) cis |
| ER-807484 | (structure shown) |

| Compound | Structure |
|---|---|
| ER-807487 | (structure) |
| ER-807494 | (structure) |
| ER-807495 | (structure) 1:1 mixture of diastereomers |
| ER-807499 | (structure) |
| ER-807500 | (structure) |
| ER-807501 | (structure) |
| ER-807502 | (structure) |

| Compound | Structure |
| --- | --- |
| ER-807503 | 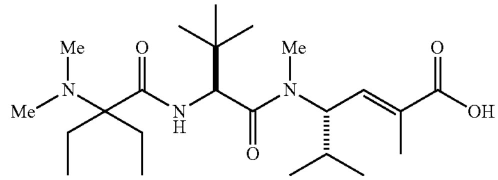 [SMILES: CCC(CC)(C(=O)N[C@H](C(=O)N(C)[C@H](/C=C(\C)C(=O)O)C(C)C)C(C)(C)C)N(C)C] |
| ER-807504 | 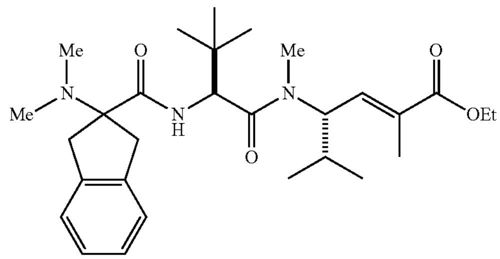 [SMILES: CCOC(=O)/C(C)=C/[C@H](C(C)C)N(C)C(=O)[C@@H](NC(=O)C1(N(C)C)Cc2ccccc2C1)C(C)(C)C] |
| ER-807529 | 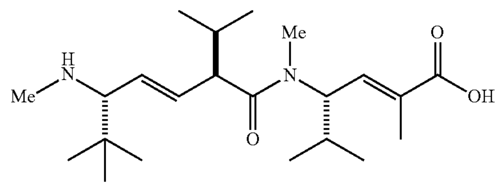 [SMILES: CN[C@H](/C=C/[C@H](C(=O)N(C)[C@H](/C=C(\C)C(=O)O)C(C)C)C(C)C)C(C)(C)C] |
| ER-807530 | 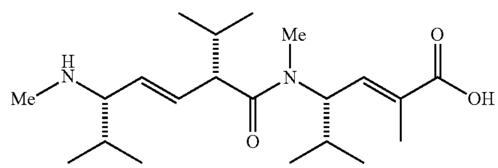 [SMILES: CN[C@H](/C=C/[C@@H](C(=O)N(C)[C@H](/C=C(\C)C(=O)O)C(C)C)C(C)C)C(C)C] |
| ER-807533 | 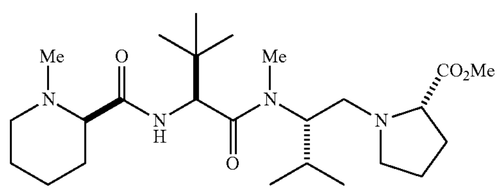 |
| ER-807534 | 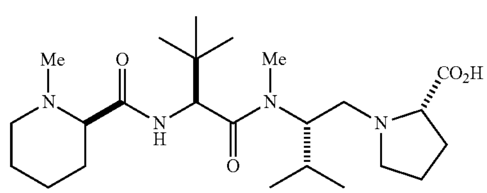 |
| ER-807535 | 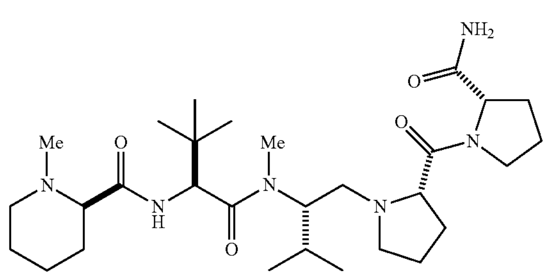 |

-continued

| Compound | Structure |
|---|---|
| ER-807540 | 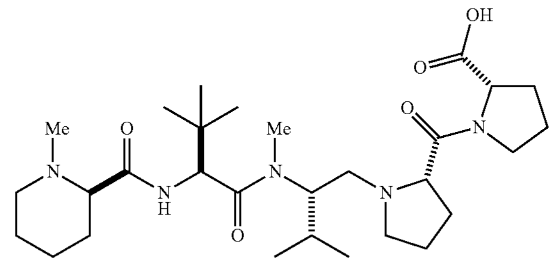 [SMILES: CC(C)[C@@H](CN1CCC[C@H]1C(=O)N1CCC[C@H]1C(=O)O)N(C)C(=O)[C@@H](NC(=O)[C@H]1CCCCN1C)C(C)(C)C] |
| ER-807541 | 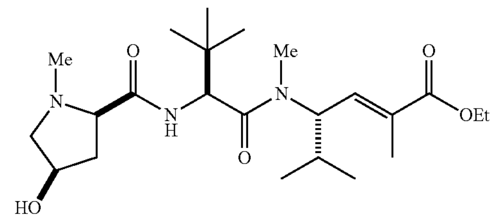 [SMILES: CCOC(=O)/C(C)=C/[C@H](C(C)C)N(C)C(=O)[C@@H](NC(=O)[C@H]1C[C@@H](O)CN1C)C(C)(C)C] |
| ER-807542 | 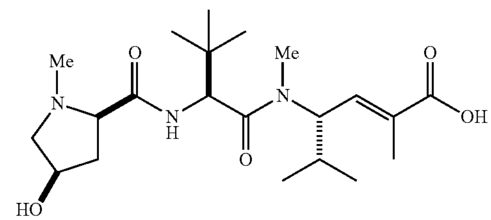 |
| ER-807575 | 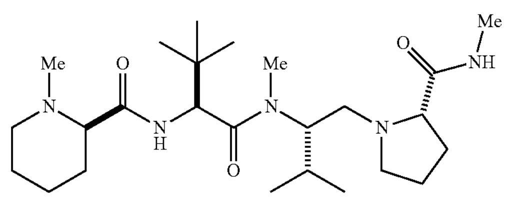 [SMILES: CNC(=O)[C@@H]1CCCN1C[C@H](C(C)C)N(C)C(=O)[C@@H](NC(=O)[C@H]1CCCCN1C)C(C)(C)C] |
| ER-807576 | 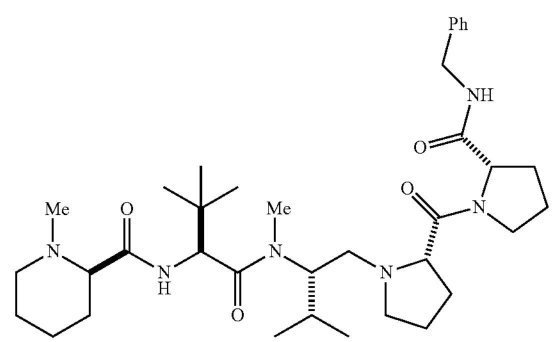 [SMILES: CC(C)[C@@H](CN1CCC[C@H]1C(=O)N1CCC[C@H]1C(=O)NCc1ccccc1)N(C)C(=O)[C@@H](NC(=O)[C@H]1CCCCN1C)C(C)(C)C] |
| ER-807577 | 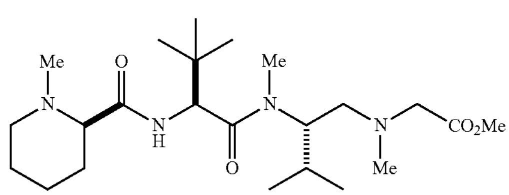 [SMILES: COC(=O)CN(C)C[C@H](C(C)C)N(C)C(=O)[C@@H](NC(=O)[C@H]1CCCCN1C)C(C)(C)C] |

-continued

| Compound | Structure |
|---|---|
| ER-807602 | 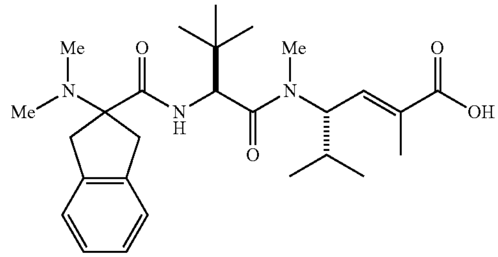 [SMILES: C/C(=C\[C@H](C(C)C)N(C)C(=O)[C@@H](NC(=O)C1(N(C)C)Cc2ccccc2C1)C(C)(C)C)C(=O)O] |
| ER-807603 | 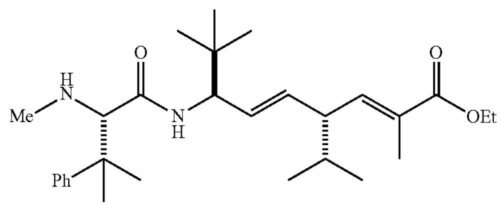 [SMILES: CCOC(=O)/C(C)=C/[C@@H](/C=C/[C@@H](NC(=O)[C@@H](NC)C(C)(C)c1ccccc1)C(C)(C)C)C(C)C] |
| ER-807619 | 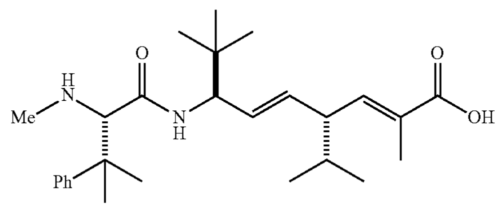 [SMILES: CN[C@H](C(=O)N[C@H](/C=C/[C@H](/C=C(\C)C(=O)O)C(C)C)C(C)(C)C)C(C)(C)c1ccccc1] |
| ER-807620 | 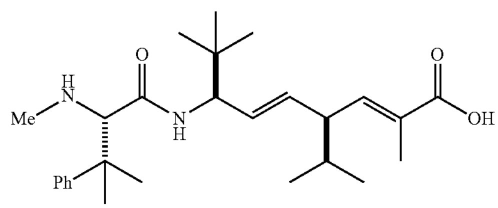 |
| ER-807621 | 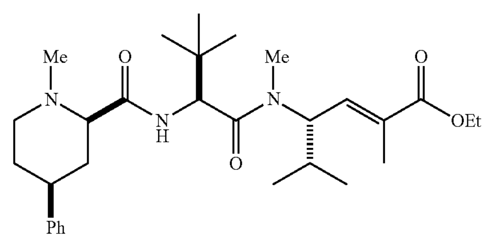 [SMILES: CCOC(=O)/C(C)=C/[C@H](C(C)C)N(C)C(=O)[C@@H](NC(=O)[C@H]1CCCCN1C)C(C)(C)C ; "Ph"] |
| ER-807622 | 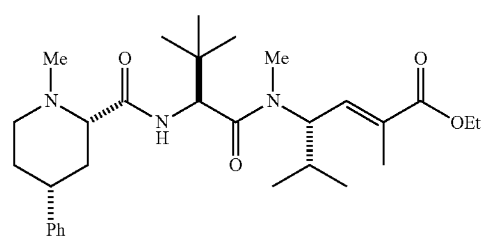 [SMILES: CCOC(=O)/C(C)=C/[C@H](C(C)C)N(C)C(=O)[C@@H](NC(=O)[C@@H]1CCCCN1C)C(C)(C)C ; "Ph"] |
| ER-807625 | 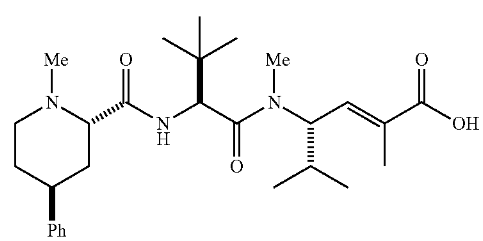 [SMILES: C/C(=C\[C@H](C(C)C)N(C)C(=O)[C@@H](NC(=O)[C@@H]1CCCCN1C)C(C)(C)C)C(=O)O ; "Ph"] |

-continued

| Compound | Structure |
|---|---|
| ER-807626 | 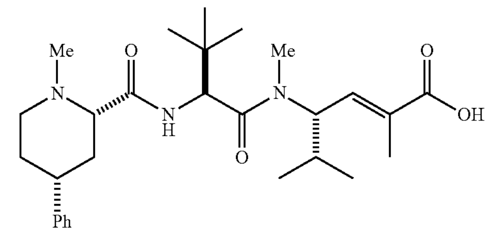 |
| ER-807739 | 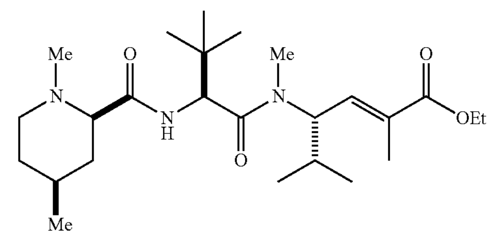 |
| ER-807740 | 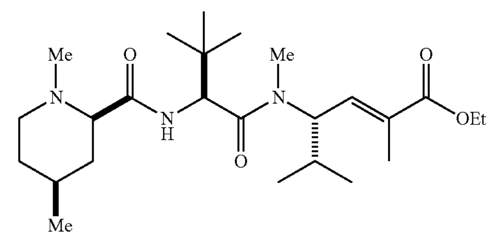 |
| ER-807742 | 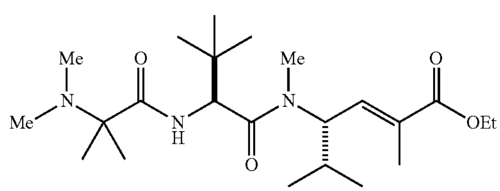 [SMILES: CCOC(=O)/C(C)=C/[C@H](C(C)C)N(C)C(=O)[C@@H](NC(=O)C(C)(C)N(C)C)C(C)(C)C] |
| ER-807743 | 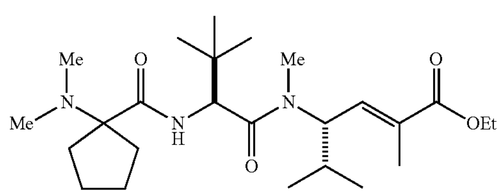 [SMILES: CCOC(=O)/C(C)=C/[C@H](C(C)C)N(C)C(=O)[C@@H](NC(=O)C1(N(C)C)CCCC1)C(C)(C)C] |
| ER-807744 | 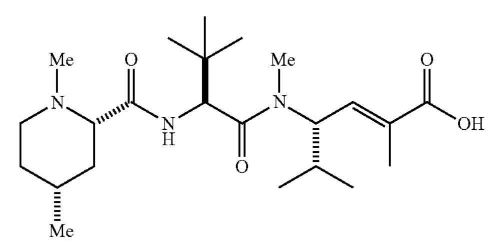 |
| ER-807745 | 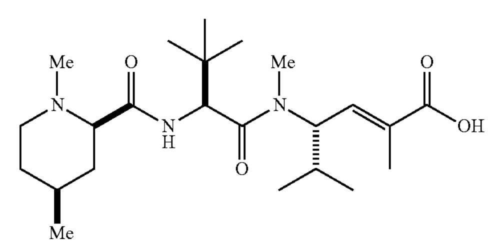 [SMILES: C/C(=C\[C@H](C(C)C)N(C)C(=O)[C@@H](NC(=O)[C@H]1CCCCN1C)C(C)(C)C)C(=O)O ; "Me"] |

-continued

| Compound | Structure |
|---|---|
| ER-807760 | 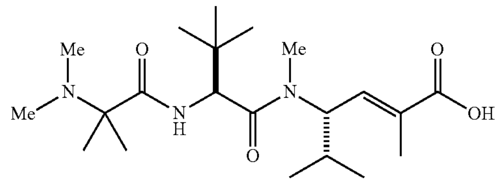 [SMILES: C/C(=C\[C@H](C(C)C)N(C)C(=O)[C@@H](NC(=O)C(C)(C)N(C)C)C(C)(C)C)C(=O)O] |
| ER-807761 | 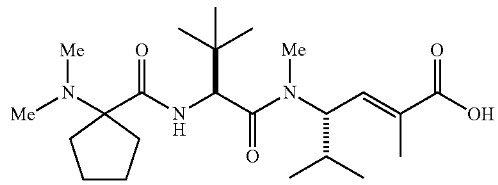 [SMILES: C/C(=C\[C@H](C(C)C)N(C)C(=O)[C@@H](NC(=O)C1(N(C)C)CCCC1)C(C)(C)C)C(=O)O] |
| ER-807796 Trans-substituents on the piperidine ring, but absolute stereochemistry is unknown. Single diastereomer. | |
| ER-807797 Trans-substituents on the piperidine ring, but absolute stereochemistry is unknown. Single diastereomer. | |
| ER-807798 | 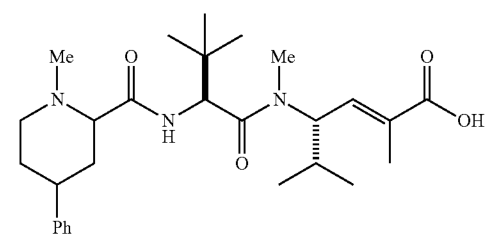 [SMILES: C/C(=C\[C@H](C(C)C)N(C)C(=O)[C@@H](NC(=O)C1CCCCN1C)C(C)(C)C)C(=O)O ; "Ph"] |
| ER-807799 Mixtrue of two diastereomers | |
| ER-807800 | 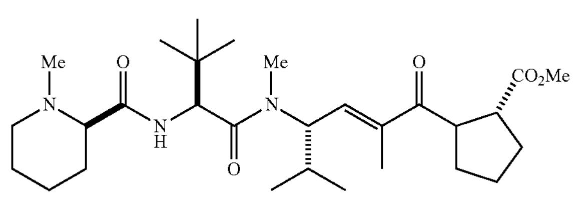 [SMILES: COC(=O)[C@@H]1CCCC1C(=O)/C(C)=C/[C@H](C(C)C)N(C)C(=O)[C@@H](NC(=O)[C@H]1CCCCN1C)C(C)(C)C] |

-continued

| Compound | Structure |
|---|---|
| ER-807801 | 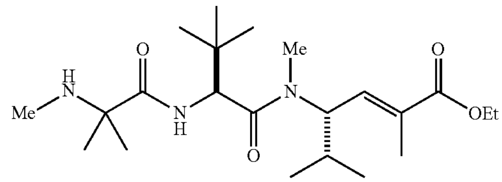 [SMILES: CCOC(=O)/C(C)=C/[C@H](C(C)C)N(C)C(=O)[C@@H](NC(=O)C(C)(C)NC)C(C)(C)C] |
| ER-807802 | 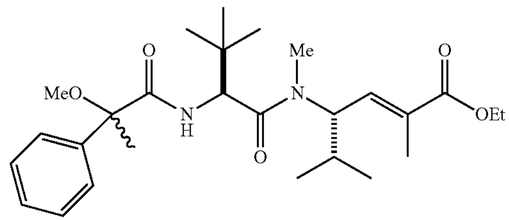 [SMILES: CCOC(=O)/C(C)=C/[C@H](C(C)C)N(C)C(=O)[C@@H](NC(=O)C(C)(OC)c1ccccc1)C(C)(C)C] |
| ER-807803 | 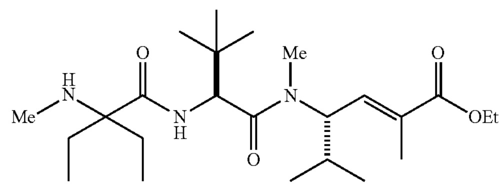 [SMILES: CCOC(=O)/C(C)=C/[C@H](C(C)C)N(C)C(=O)[C@@H](NC(=O)C(CC)(CC)NC)C(C)(C)C] |
| ER-807804 | 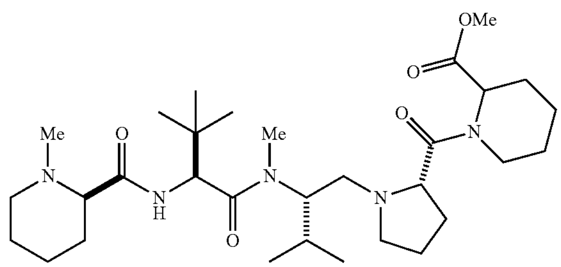 [SMILES: COC(=O)C1CCCCN1C(=O)[C@@H]1CCCN1C[C@H](C(C)C)N(C)C(=O)[C@@H](NC(=O)[C@H]1CCCCN1C)C(C)(C)C] |
| ER-807805 | 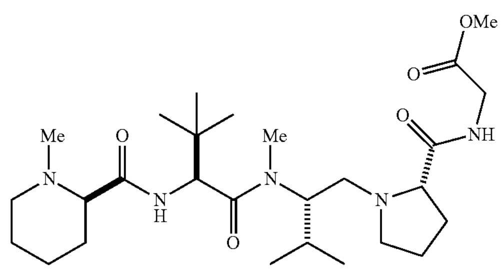 [SMILES: COC(=O)CNC(=O)[C@@H]1CCCN1C[C@H](C(C)C)N(C)C(=O)[C@@H](NC(=O)[C@H]1CCCCN1C)C(C)(C)C] |
| ER-807806 | 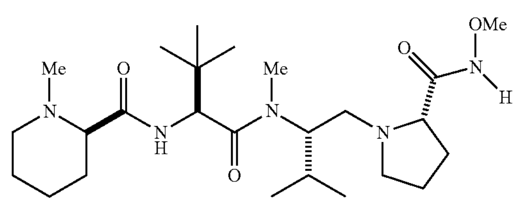 [SMILES: CONC(=O)[C@@H]1CCCN1C[C@H](C(C)C)N(C)C(=O)[C@@H](NC(=O)[C@H]1CCCCN1C)C(C)(C)C] |
| ER-807807 | 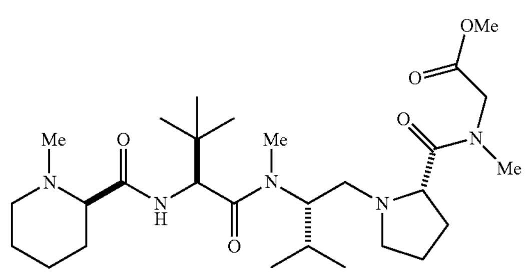 [SMILES: COC(=O)CN(C)C(=O)[C@@H]1CCCN1C[C@H](C(C)C)N(C)C(=O)[C@@H](NC(=O)[C@H]1CCCCN1C)C(C)(C)C] |

| Compound | Structure |
|---|---|
| ER-807808 | 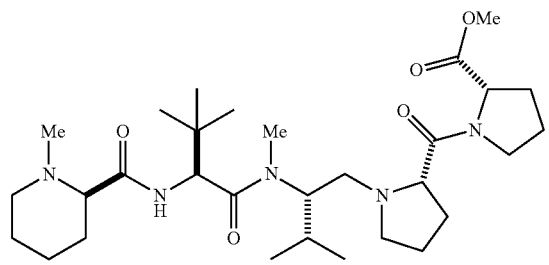 [SMILES: COC(=O)[C@@H]1CCCN1C(=O)[C@@H]1CCCN1C[C@H](C(C)C)N(C)C(=O)[C@@H](NC(=O)[C@H]1CCCCN1C)C(C)(C)C] |
| ER-807809 | 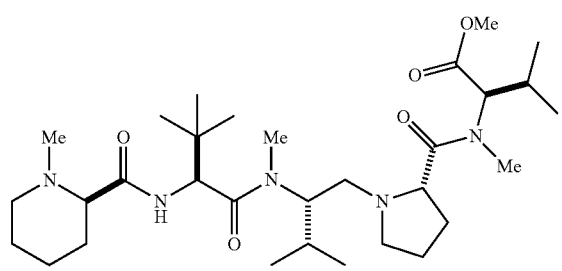 [SMILES: COC(=O)[C@@H](C(C)C)N(C)C(=O)[C@@H]1CCCN1C[C@H](C(C)C)N(C)C(=O)[C@@H](NC(=O)[C@H]1CCCCN1C)C(C)(C)C] |
| ER-807810 | 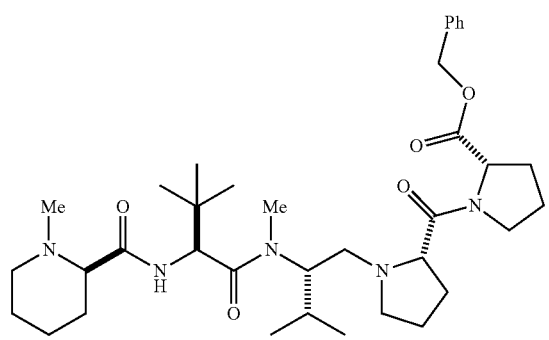 |
| ER-807811 | 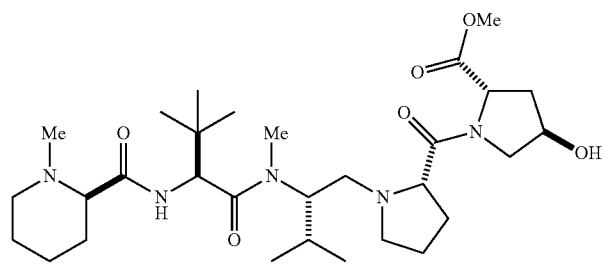 |
| ER-8087812 | 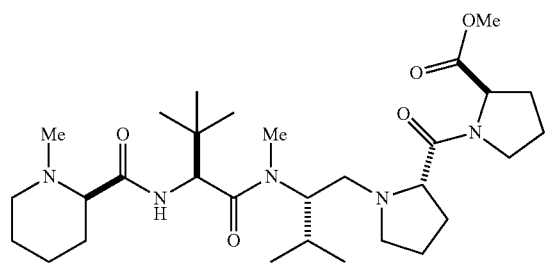 [SMILES: COC(=O)[C@H]1CCCN1C(=O)[C@@H]1CCCN1C[C@H](C(C)C)N(C)C(=O)[C@@H](NC(=O)[C@H]1CCCCN1C)C(C)(C)C] |

-continued

| Compound | Structure |
| --- | --- |
| ER-807820 single diastereomer | 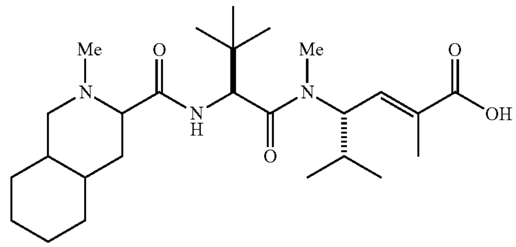 [SMILES: C/C(=C\[C@H](C(C)C)N(C)C(=O)[C@@H](NC(=O)C1CC2CCCCC2CN1C)C(C)(C)C)C(=O)O] |
| ER-807821 single diastereomer | 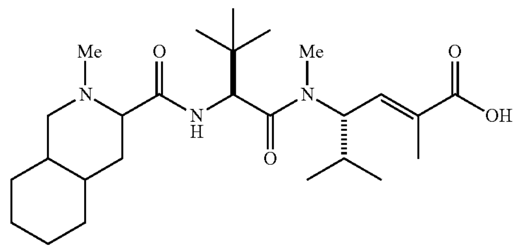 [SMILES: C/C(=C\[C@H](C(C)C)N(C)C(=O)[C@@H](NC(=O)C1CC2CCCCC2CN1C)C(C)(C)C)C(=O)O] |
| ER-807829 | 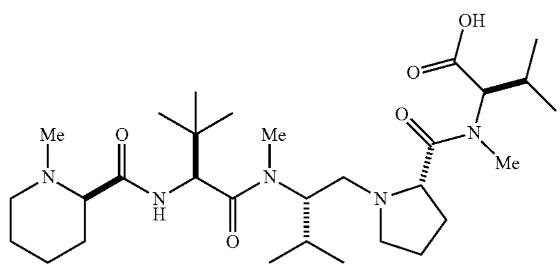 [SMILES: CC(C)[C@@H](CN1CCC[C@H]1C(=O)N(C)[C@@H](C(=O)O)C(C)C)N(C)C(=O)[C@@H](NC(=O)[C@H]1CCCCN1C)C(C)(C)C] |
| ER-807830 | 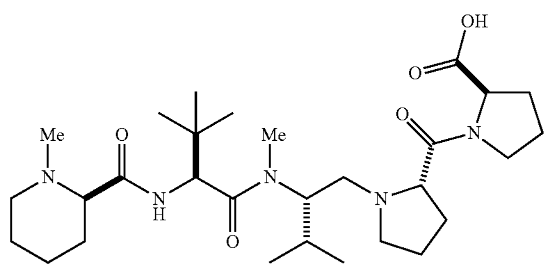 |
| ER-807831 | 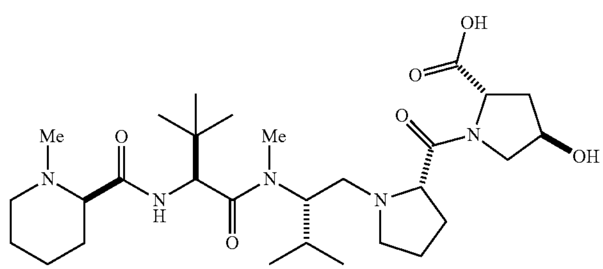 [SMILES: CC(C)[C@@H](CN1CCC[C@H]1C(=O)N1C[C@H](O)C[C@H]1C(=O)O)N(C)C(=O)[C@@H](NC(=O)[C@H]1CCCCN1C)C(C)(C)C] |
| ER-807832 | 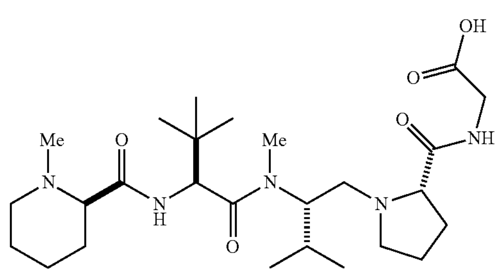 [SMILES: CC(C)[C@@H](CN1CCC[C@H]1C(=O)NCC(=O)O)N(C)C(=O)[C@@H](NC(=O)[C@H]1CCCCN1C)C(C)(C)C] |

| Compound | Structure |
| --- | --- |
| ER-807833 | 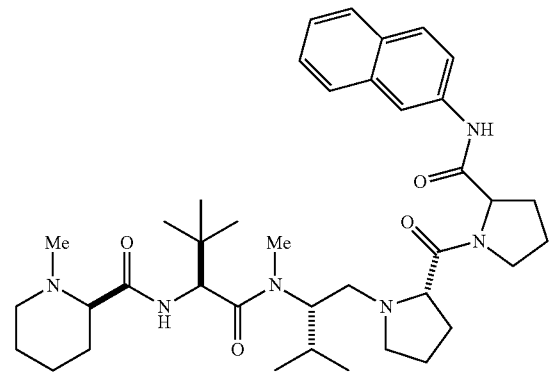 [SMILES: CC(C)[C@@H](CN1CCC[C@H]1C(=O)N1CCCC1C(=O)Nc1ccc2ccccc2c1)N(C)C(=O)[C@@H](NC(=O)[C@H]1CCCCN1C)C(C)(C)C] |
| ER-807839 | 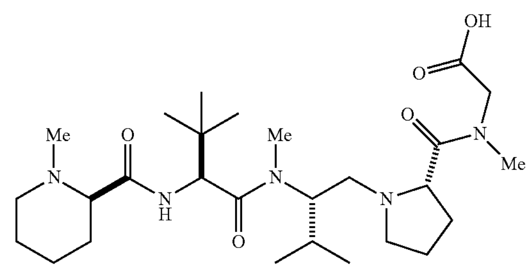 [SMILES: CC(C)[C@@H](CN1CCC[C@H]1C(=O)N(C)CC(=O)O)N(C)C(=O)[C@@H](NC(=O)[C@H]1CCCCN1C)C(C)(C)C] |
| ER-807840 | 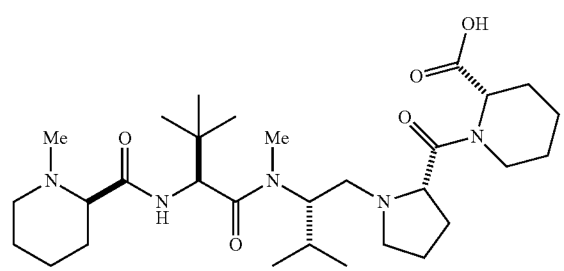 [SMILES: CC(C)[C@@H](CN1CCC[C@H]1C(=O)N1CCCC[C@H]1C(=O)O)N(C)C(=O)[C@@H](NC(=O)[C@H]1CCCCN1C)C(C)(C)C] |
| ER-807842 | 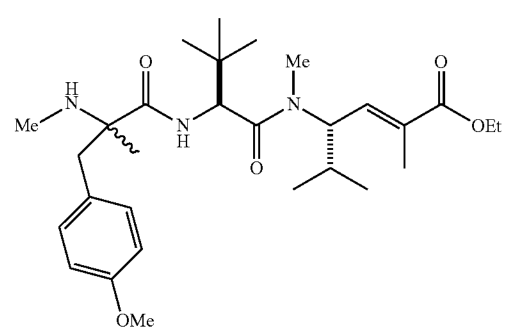 [SMILES: CCOC(=O)/C(C)=C/[C@H](C(C)C)N(C)C(=O)[C@@H](NC(=O)C(C)(Cc1ccc(OC)cc1)NC)C(C)(C)C] |
| ER-807844 | 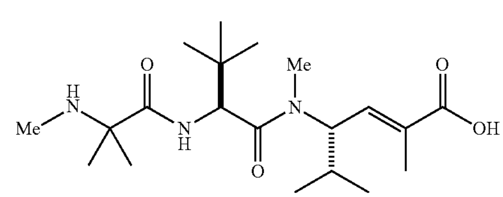 [SMILES: CNC(C)(C)C(=O)N[C@H](C(=O)N(C)[C@H](/C=C(\C)C(=O)O)C(C)C)C(C)(C)C] |

-continued

| Compound | Structure |
|---|---|
| ER-807846 | 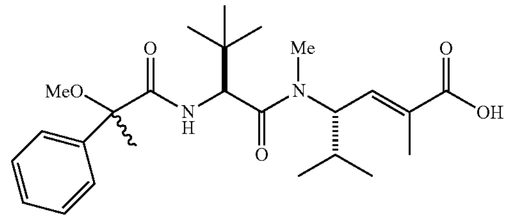 [SMILES: COC(C)(C(=O)N[C@H](C(=O)N(C)[C@H](/C=C(\C)C(=O)O)C(C)C)C(C)(C)C)c1ccccc1] |
| ER-807850 | 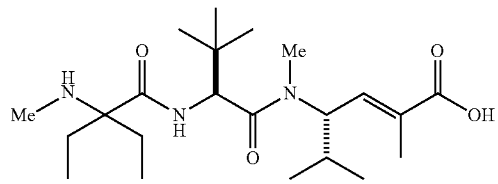 [SMILES: CCC(CC)(NC)C(=O)N[C@H](C(=O)N(C)[C@H](/C=C(\C)C(=O)O)C(C)C)C(C)(C)C] |
| ER-807860 | 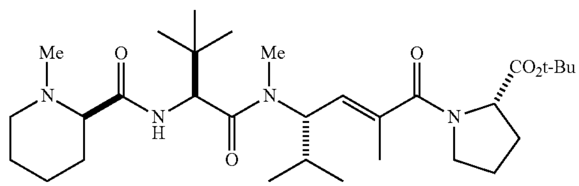 [SMILES: C/C(=C\[C@H](C(C)C)N(C)C(=O)[C@@H](NC(=O)[C@H]1CCCCN1C)C(C)(C)C)C(=O)N1CCC[C@H]1C(=O)OC(C)(C)C] |
| ER-807861 | 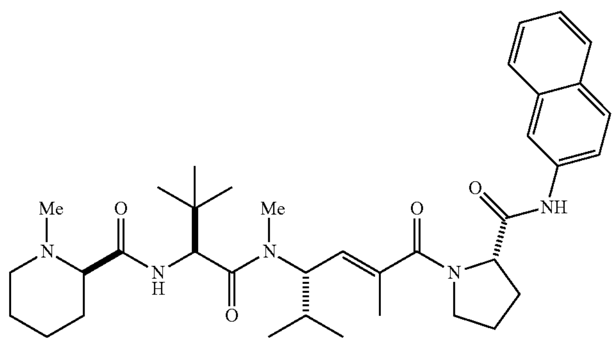 |
| ER-807863 Cis-substituents on the piperidine ring, but absolute stereochemistry is unknown. Single diastereomer. | |
| ER-807864 Cis-substituents on the piperidine ring, but absolute stereochemistry is unknown. Single diastereomer. | |
| ER-807874 | 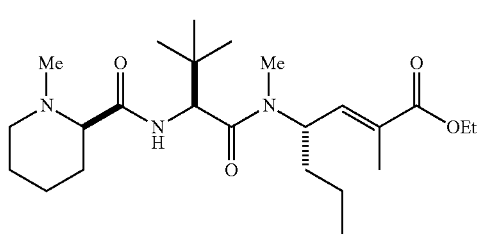 [SMILES: CCC[C@@H](/C=C(\C)C(=O)OCC)N(C)C(=O)[C@@H](NC(=O)[C@H]1CCCCN1C)C(C)(C)C] |

-continued

| Compound | Structure |
|---|---|
| ER-807875 | 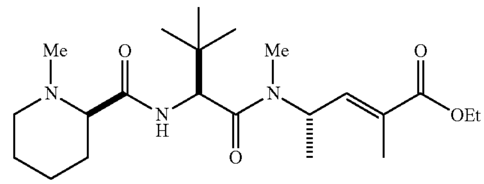 [SMILES: CCOC(=O)/C(C)=C/[C@H](C)N(C)C(=O)[C@@H](NC(=O)[C@H]1CCCCN1C)C(C)(C)C] |
| ER-807877<br>Cis-substituents on the piperidine ring. Two diastereomers (4:1). | |
| ER-807880 | 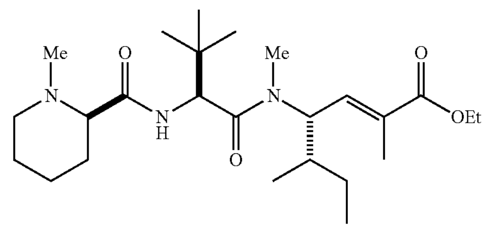 [SMILES: CCOC(=O)/C(C)=C/[C@H](C(C)CC)N(C)C(=O)[C@@H](NC(=O)[C@H]1CCCCN1C)C(C)(C)C] |
| ER-807881 | 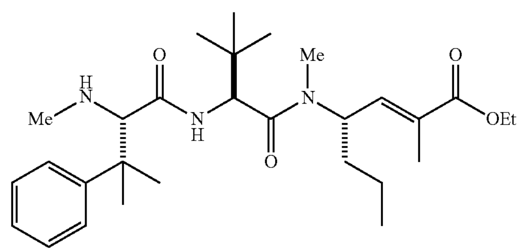 [SMILES: CCC[C@@H](/C=C(\C)C(=O)OCC)N(C)C(=O)[C@@H](NC(=O)[C@@H](NC)C(C)(C)c1ccccc1)C(C)(C)C] |
| ER-807882 | 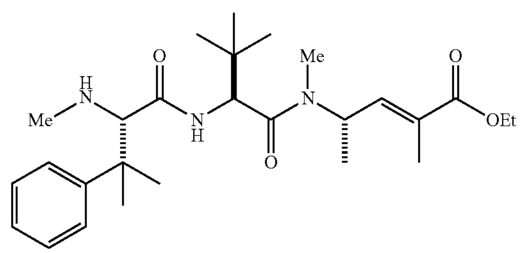 [SMILES: CCOC(=O)/C(C)=C/[C@H](C)N(C)C(=O)[C@@H](NC(=O)[C@@H](NC)C(C)(C)c1ccccc1)C(C)(C)C] |
| ER-807883 | 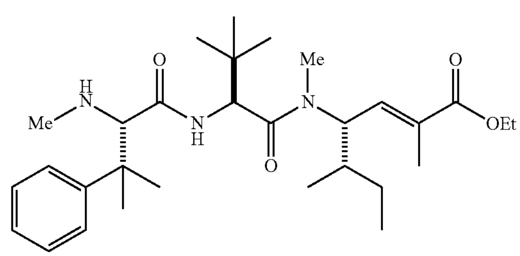 [SMILES: CCOC(=O)/C(C)=C/[C@H](C(C)CC)N(C)C(=O)[C@@H](NC(=O)[C@@H](NC)C(C)(C)c1ccccc1)C(C)(C)C] |
| ER-807884 | 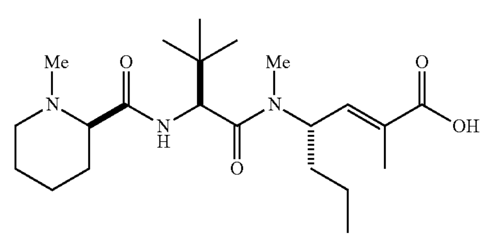 [SMILES: CCC[C@@H](/C=C(\C)C(=O)O)N(C)C(=O)[C@@H](NC(=O)[C@H]1CCCCN1C)C(C)(C)C] |

-continued

| Compound | Structure |
|---|---|
| ER-807885 | 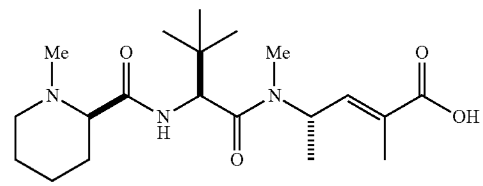 [SMILES: C/C(=C\[C@H](C)N(C)C(=O)[C@@H](NC(=O)[C@H]1CCCCN1C)C(C)(C)C)C(=O)O] |
| ER-807886 | 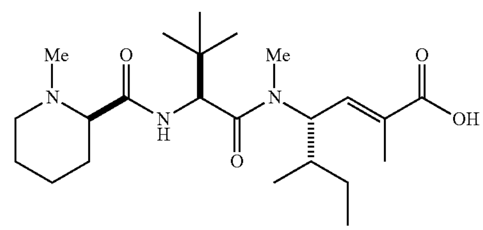 [SMILES: CCC(C)[C@@H](/C=C(\C)C(=O)O)N(C)C(=O)[C@@H](NC(=O)[C@H]1CCCCN1C)C(C)(C)C] |
| ER-807888 | 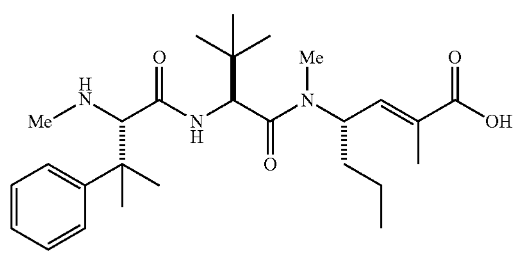 [SMILES: CCC[C@@H](/C=C(\C)C(=O)O)N(C)C(=O)[C@@H](NC(=O)[C@@H](NC)C(C)(C)c1ccccc1)C(C)(C)C] |
| ER-807889 | 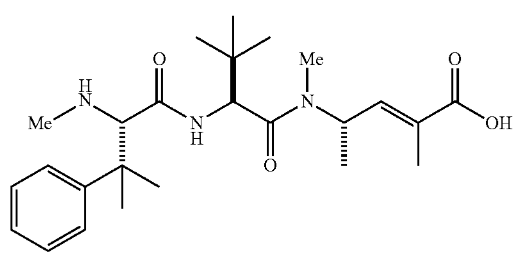 [SMILES: CN[C@H](C(=O)N[C@H](C(=O)N(C)[C@@H](C)/C=C(\C)C(=O)O)C(C)(C)C)C(C)(C)c1ccccc1] |
| ER-807890 | 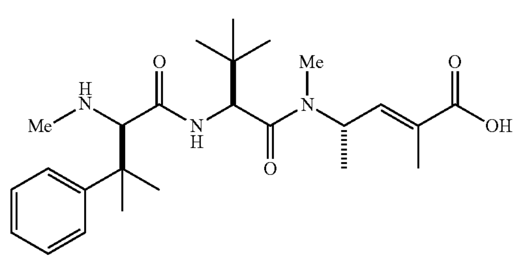 |
| ER-807891 | 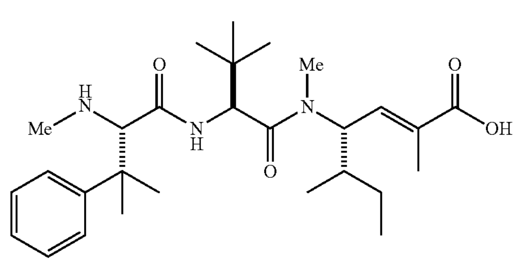 [SMILES: CCC(C)[C@@H](/C=C(\C)C(=O)O)N(C)C(=O)[C@@H](NC(=O)[C@@H](NC)C(C)(C)c1ccccc1)C(C)(C)C] |

-continued

| Compound | Structure |
|---|---|
| ER-807899 | 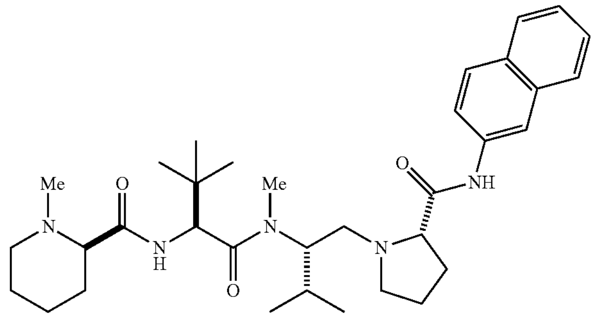 [SMILES: CC(C)[C@@H](CN1CCC[C@H]1C(=O)Nc1ccc2ccccc2c1)N(C)C(=O)[C@@H](NC(=O)[C@H]1CCCCN1C)C(C)(C)C] |
| ER-807900 | 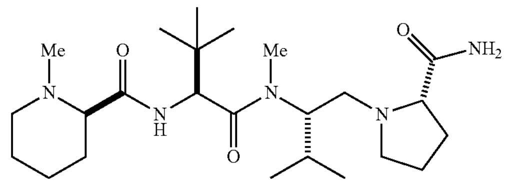 [SMILES: CC(C)[C@@H](CN1CCC[C@H]1C(N)=O)N(C)C(=O)[C@@H](NC(=O)[C@H]1CCCCN1C)C(C)(C)C] |
| ER-807902 | 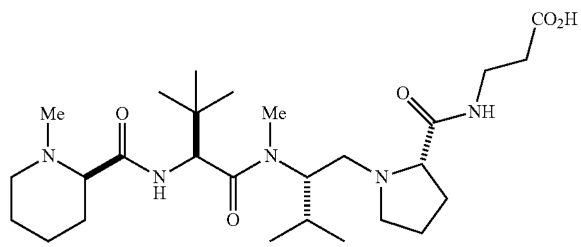 [SMILES: CC(C)[C@@H](CN1CCC[C@H]1C(=O)NCCC(=O)O)N(C)C(=O)[C@@H](NC(=O)[C@H]1CCCCN1C)C(C)(C)C] |
| ER-807904 | 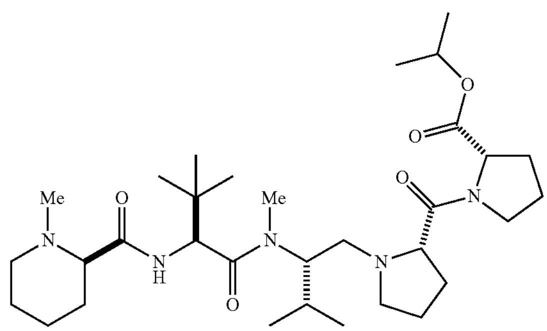 [SMILES: CC(C)OC(=O)[C@@H]1CCCN1C(=O)[C@@H]1CCCN1C[C@H](C(C)C)N(C)C(=O)[C@@H](NC(=O)[C@H]1CCCCN1C)C(C)(C)C] |
| ER-807905 | 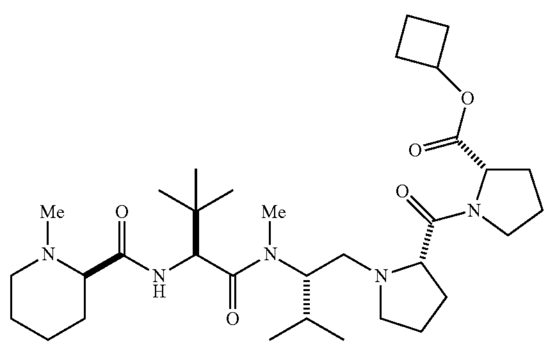 [SMILES: CC(C)[C@@H](CN1CCC[C@H]1C(=O)N1CCC[C@H]1C(=O)OC1CCC1)N(C)C(=O)[C@@H](NC(=O)[C@H]1CCCCN1C)C(C)(C)C] |

| Compound | Structure |
|---|---|
| ER-807906 | 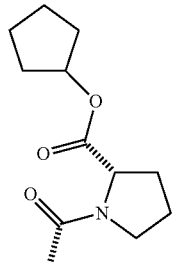 |
| ER-807907 | 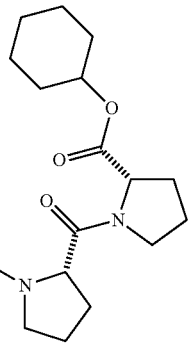 |
| ER-807908 | 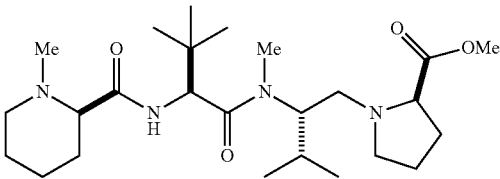 [SMILES: COC(=O)[C@H]1CCCN1C[C@H](C(C)C)N(C)C(=O)[C@@H](NC(=O)[C@H]1CCCCN1C)C(C)(C)C] |
| ER-807909 | 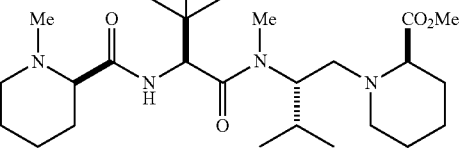 |
| ER-807911 | 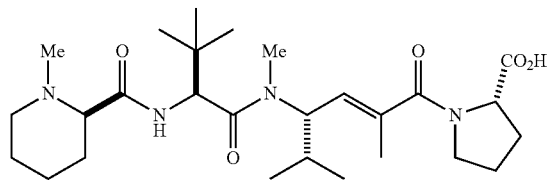 [SMILES: C/C(=C\[C@H](C(C)C)N(C)C(=O)[C@@H](NC(=O)[C@H]1CCCCN1C)C(C)(C)C)C(=O)N1CCC[C@H]1C(=O)O] |
| ER-807944 | 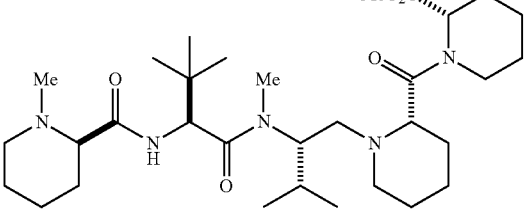 |

-continued

| Compound | Structure |
|---|---|
| ER-807945 | 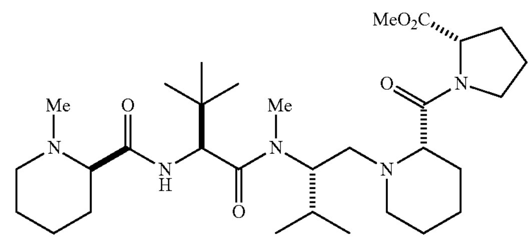 [SMILES: CC(C)[C@@H](CN1CCCC[C@H]1C(=O)N1CCCC1)N(C)C(=O)[C@@H](NC(=O)[C@H]1CCCCN1C)C(C)(C)C ; "MeO2C"] |
| ER-807947 | 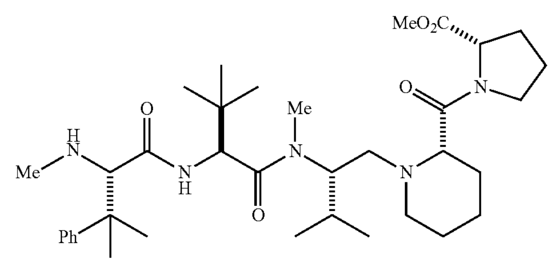 [SMILES: CN[C@H](C(=O)N[C@H](C(=O)N(C)[C@H](CN1CCCC[C@H]1C(=O)N1CCCC1)C(C)C)C(C)(C)C)C(C)(C)c1ccccc1 ; "MeO2C"] |
| ER-807948 | 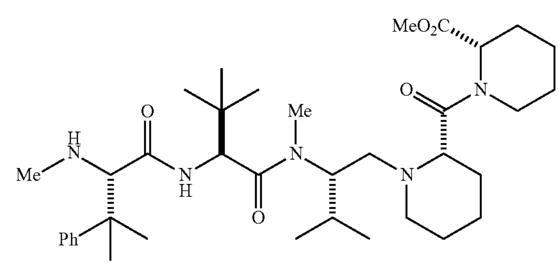 [SMILES: CN[C@H](C(=O)N[C@H](C(=O)N(C)[C@H](CN1CCCC[C@H]1C(=O)N1CCCCC1)C(C)C)C(C)(C)C)C(C)(C)c1ccccc1 ; "MeO2C"] |
| ER-807949 | 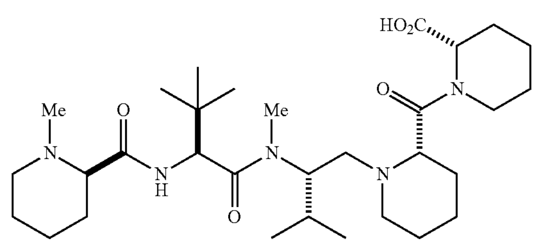 [SMILES: CC(C)[C@@H](CN1CCCC[C@H]1C(=O)N1CCCCC1)N(C)C(=O)[C@@H](NC(=O)[C@H]1CCCCN1C)C(C)(C)C ; "HO2C"] |
| ER-807950 | 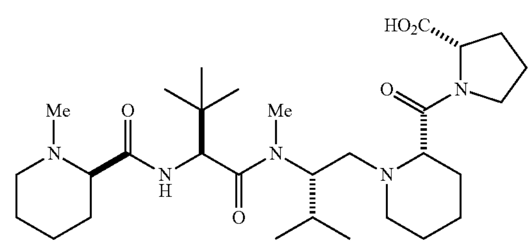 |
| ER-807951 | 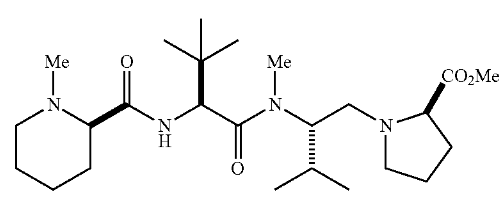 |

-continued

| Compound | Structure |
|---|---|
| ER-807953 | 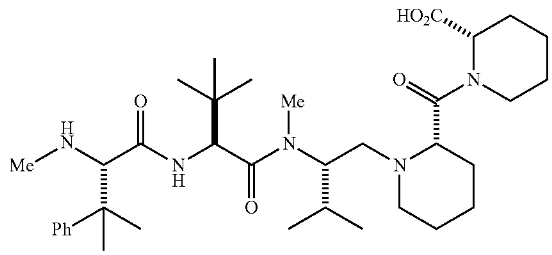 [SMILES: CN[C@H](C(=O)N[C@H](C(=O)N(C)[C@H](CN1CCCC[C@H]1C(=O)N1CCCCC1)C(C)C)C(C)(C)C)C(C)(C)c1ccccc1 ; "HO2C"] |
| ER-807954 | 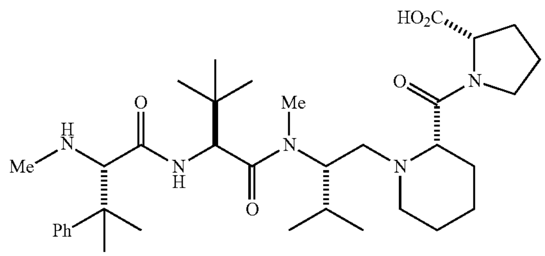 [SMILES: CN[C@H](C(=O)N[C@H](C(=O)N(C)[C@H](CN1CCCC[C@H]1C(=O)N1CCCC1)C(C)C)C(C)(C)C)C(C)(C)c1ccccc1 ; "HO2C"] |
| ER-807959 Cis-substituents on the piperidine ring, but absolute stereochemistry is unknown. Single diastereomer. | |
| ER-807960 Cis-substituents on the piperidine ring, but absolute stereochemistry is unknown. Single diastereomer. | |
| ER-807961 | 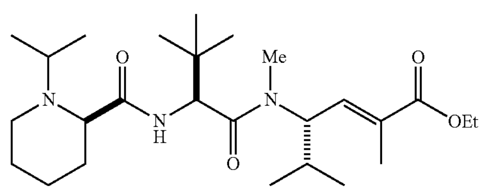 [SMILES: CCOC(=O)/C(C)=C/[C@H](C(C)C)N(C)C(=O)[C@@H](NC(=O)[C@H]1CCCCN1C(C)C)C(C)(C)C] |
| ER-807963 | 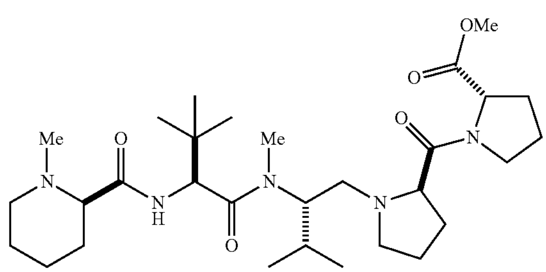 [SMILES: COC(=O)[C@@H]1CCCN1C(=O)[C@H]1CCCN1C[C@H](C(C)C)N(C)C(=O)[C@@H](NC(=O)[C@H]1CCCCN1C)C(C)(C)C] |
| ER-807973 | 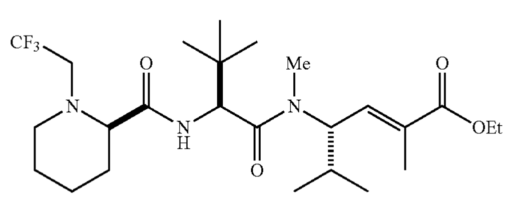 [SMILES: CCOC(=O)/C(C)=C/[C@H](C(C)C)N(C)C(=O)[C@@H](NC(=O)[C@H]1CCCCN1CC(F)(F)F)C(C)(C)C] |

-continued

| Compound | Structure |
|---|---|
| ER-807974 | 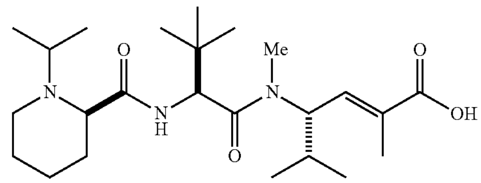 [SMILES: C/C(=C\[C@H](C(C)C)N(C)C(=O)[C@@H](NC(=O)[C@H]1CCCCN1C(C)C)C(C)(C)C)C(=O)O] |
| ER-807975 | 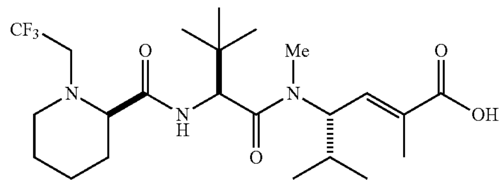 [SMILES: C/C(=C\[C@H](C(C)C)N(C)C(=O)[C@@H](NC(=O)[C@H]1CCCCN1CC(F)(F)F)C(C)(C)C)C(=O)O] |
| ER-807981 | 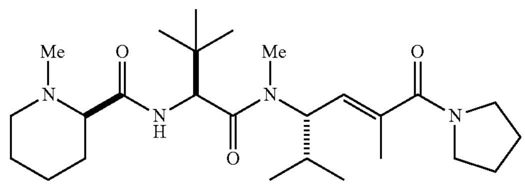 [SMILES: C/C(=C\[C@H](C(C)C)N(C)C(=O)[C@@H](NC(=O)[C@H]1CCCCN1C)C(C)(C)C)C(=O)N1CCCC1] |
| ER-807982 | 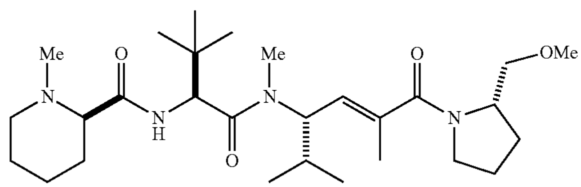 [SMILES: COC[C@@H]1CCCN1C(=O)/C(C)=C/[C@H](C(C)C)N(C)C(=O)[C@@H](NC(=O)[C@H]1CCCCN1C)C(C)(C)C] |
| ER-807983 | 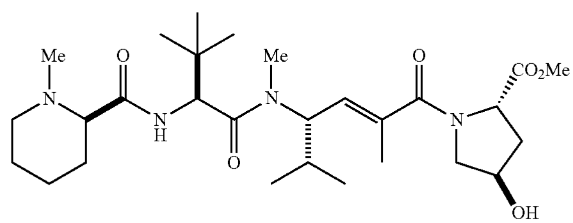 [SMILES: COC(=O)[C@@H]1C[C@@H](O)CN1C(=O)/C(C)=C/[C@H](C(C)C)N(C)C(=O)[C@@H](NC(=O)[C@H]1CCCCN1C)C(C)(C)C] |
| ER-807986 | 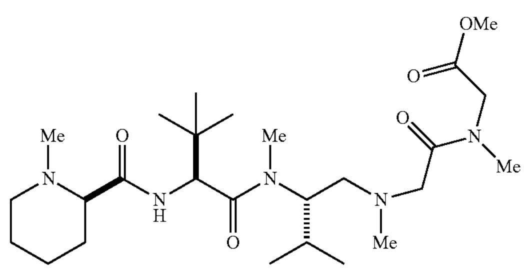 [SMILES: COC(=O)CN(C)C(=O)CN(C)C[C@H](C(C)C)N(C)C(=O)[C@@H](NC(=O)[C@H]1CCCCN1C)C(C)(C)C] |
| ER-807987 | 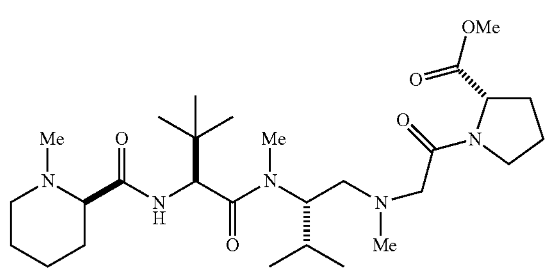 [SMILES: COC(=O)[C@@H]1CCCN1C(=O)CN(C)C[C@H](C(C)C)N(C)C(=O)[C@@H](NC(=O)[C@H]1CCCCN1C)C(C)(C)C] |

| Compound | Structure |
|---|---|
| ER-807988 | 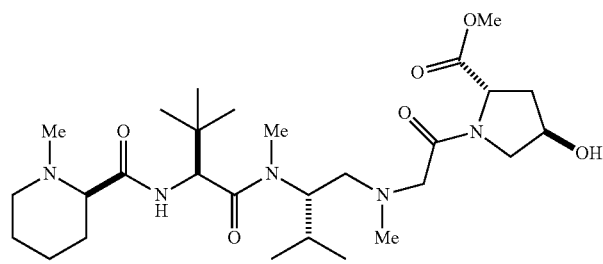 [SMILES: COC(=O)[C@@H]1C[C@@H](O)CN1C(=O)CN(C)C[C@H](C(C)C)N(C)C(=O)[C@@H](NC(=O)[C@H]1CCCCN1C)C(C)(C)C] |
| ER-807989 | 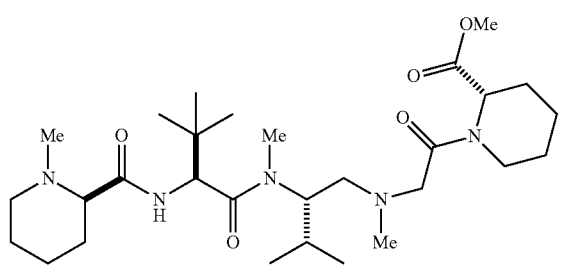 [SMILES: COC(=O)[C@@H]1CCCCN1C(=O)CN(C)C[C@H](C(C)C)N(C)C(=O)[C@@H](NC(=O)[C@H]1CCCCN1C)C(C)(C)C] |
| ER-807990 | 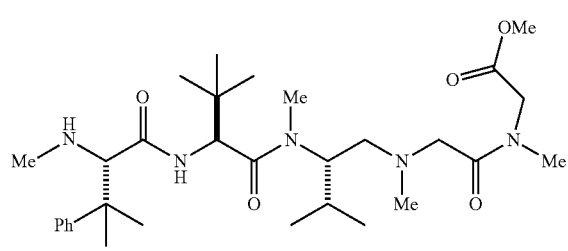 |
| ER-807991 | 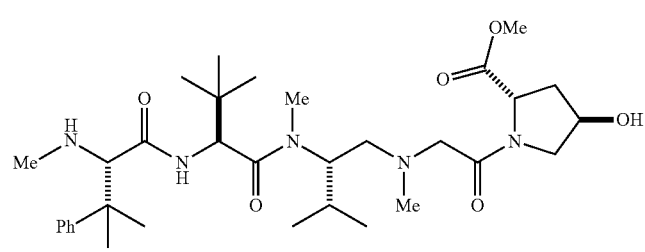 [SMILES: CN[C@H](C(=O)N[C@H](C(=O)N(C)[C@H](CN(C)CC(=O)N1C[C@H](O)C[C@H]1C(=O)OC)C(C)C)C(C)(C)C)C(C)(C)c1ccccc1] |
| ER-807992 | 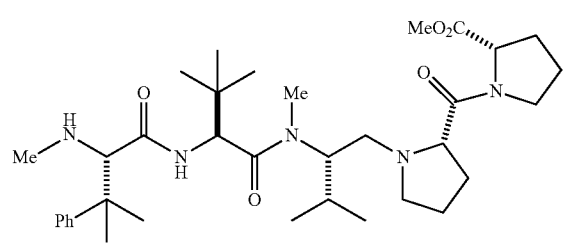 |
| ER-807994 | 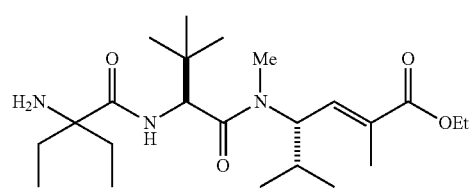 [SMILES: CCOC(=O)/C(C)=C/[C@H](C(C)C)N(C)C(=O)[C@@H](NC(=O)C(N)(CC)CC)C(C)(C)C] |

| Compound | Structure |
|---|---|
| ER-807995 | 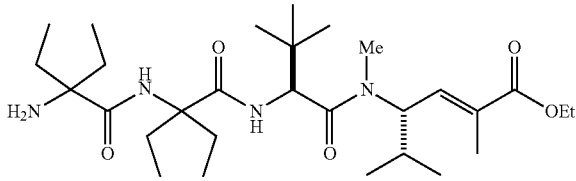 [SMILES: CCOC(=O)/C(C)=C/[C@H](C(C)C)N(C)C(=O)[C@@H](NC(=O)C(CC)(CC)NC(=O)C(N)(CC)CC)C(C)(C)C] |
| ER-807996 | 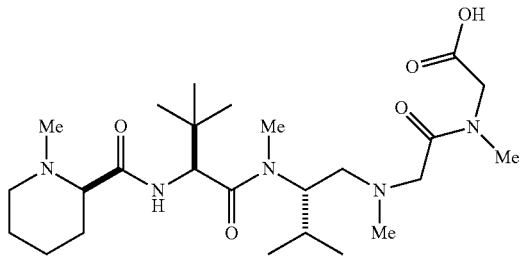 [SMILES: CC(C)[C@@H](CN(C)CC(=O)N(C)CC(=O)O)N(C)C(=O)[C@@H](NC(=O)[C@H]1CCCCN1C)C(C)(C)C] |
| ER-807997 | 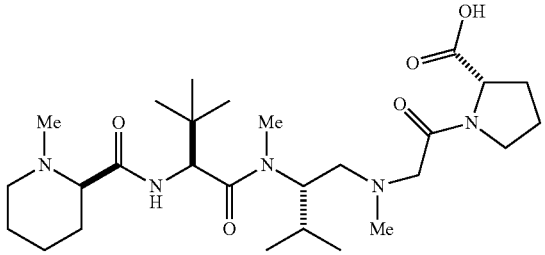 [SMILES: CC(C)[C@@H](CN(C)CC(=O)N1CCC[C@H]1C(=O)O)N(C)C(=O)[C@@H](NC(=O)[C@H]1CCCCN1C)C(C)(C)C] |
| ER-807998 | 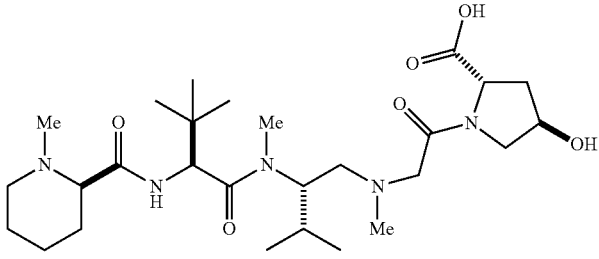 [SMILES: CC(C)[C@@H](CN(C)CC(=O)N1C[C@H](O)C[C@H]1C(=O)O)N(C)C(=O)[C@@H](NC(=O)[C@H]1CCCCN1C)C(C)(C)C] |
| ER-807999 | 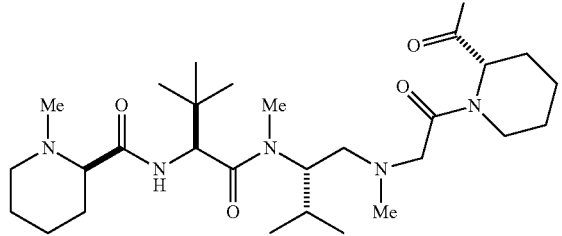 |
| ER-808000 | 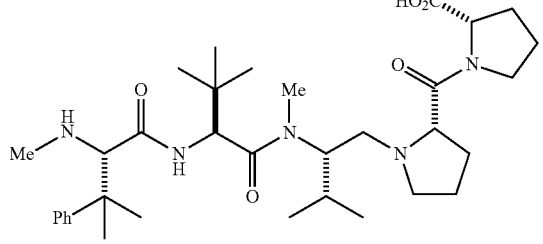 |

-continued
| Compound | Structure |
|---|---|
| ER-808001 | 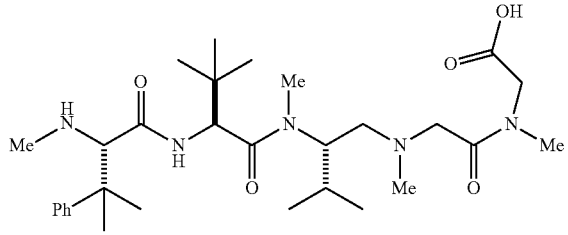 [SMILES: CN[C@H](C(=O)N[C@H](C(=O)N(C)[C@H](CN(C)CC(=O)N(C)CC(=O)O)C(C)C)C(C)(C)C)C(C)(C)c1ccccc1] |
| ER-808002 | 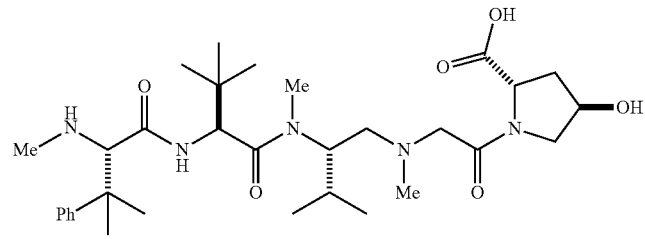 [SMILES: CN[C@H](C(=O)N[C@H](C(=O)N(C)[C@H](CN(C)CC(=O)N1C[C@H](O)C[C@H]1C(=O)O)C(C)C)C(C)(C)C)C(C)(C)c1ccccc1] |
| ER-808007 | 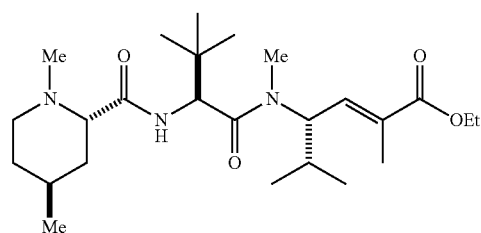 |
| ER-808008 | 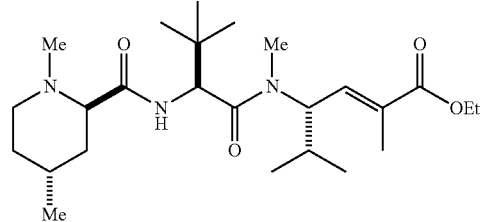 [SMILES: CCOC(=O)/C(C)=C/[C@H](C(C)C)N(C)C(=O)[C@@H](NC(=O)[C@H]1C[C@H](C)CCN1C)C(C)(C)C] |
| ER-808010 | 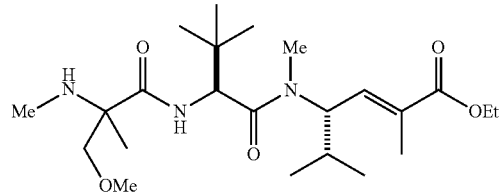 [SMILES: CCOC(=O)/C(C)=C/[C@H](C(C)C)N(C)C(=O)[C@@H](NC(=O)C(C)(COC)NC)C(C)(C)C] |
| ER-808011 | 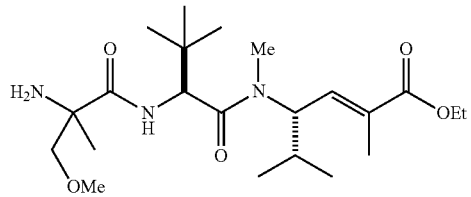 [SMILES: CCOC(=O)/C(C)=C/[C@H](C(C)C)N(C)C(=O)[C@@H](NC(=O)C(C)(N)COC)C(C)(C)C] |
| ER-808012 | 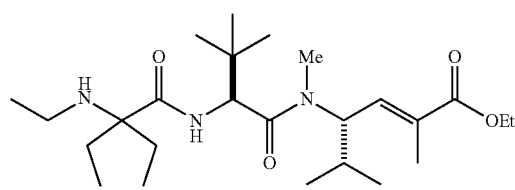 [SMILES: CCNC(CC)(CC)C(=O)N[C@H](C(=O)N(C)[C@H](/C=C(\C)C(=O)OCC)C(C)C)C(C)(C)C] |

-continued
| Compound | Structure |
|---|---|
| ER-808013 | 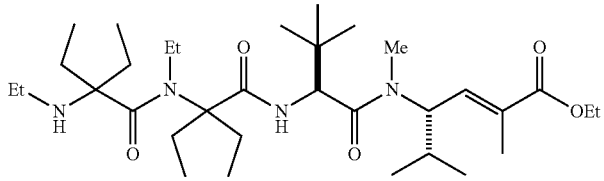 [SMILES: CCNC(CC)(CC)C(=O)N(CC)C(CC)(CC)C(=O)N[C@H](C(=O)N(C)[C@H](/C=C(\C)C(=O)OCC)C(C)C)C(C)(C)C] |
| ER-808029 | 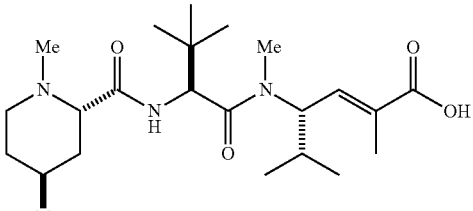 |
| ER-808030 | 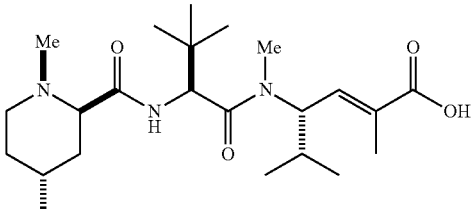 |
| ER-808031 | 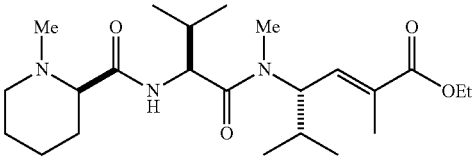 [SMILES: CCOC(=O)/C(C)=C/[C@H](C(C)C)N(C)C(=O)[C@@H](NC(=O)[C@H]1CCCCN1C)C(C)C] |
| ER-808032 | 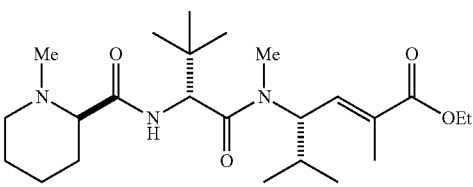 [SMILES: CCOC(=O)/C(C)=C/[C@H](C(C)C)N(C)C(=O)[C@H](NC(=O)[C@H]1CCCCN1C)C(C)(C)C] |
| ER-808033 | 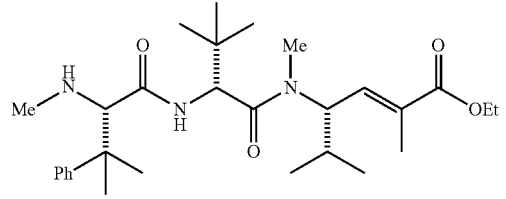 [SMILES: CCOC(=O)/C(C)=C/[C@H](C(C)C)N(C)C(=O)[C@H](NC(=O)[C@@H](NC)C(C)(C)c1ccccc1)C(C)(C)C] |
| ER-808034 | 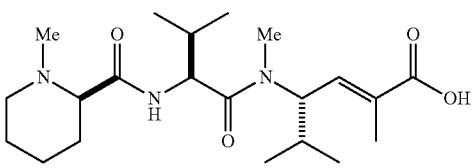 [SMILES: C/C(=C\[C@H](C(C)C)N(C)C(=O)[C@@H](NC(=O)[C@H]1CCCCN1C)C(C)C)C(=O)O] |
| ER-808035 | 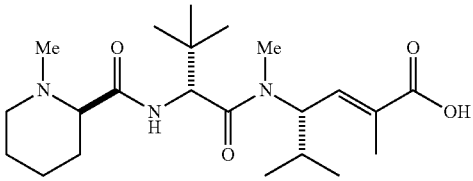 [SMILES: C/C(=C\[C@H](C(C)C)N(C)C(=O)[C@H](NC(=O)[C@H]1CCCCN1C)C(C)(C)C)C(=O)O] |

| Compound | Structure |
|---|---|
| ER-808037 | 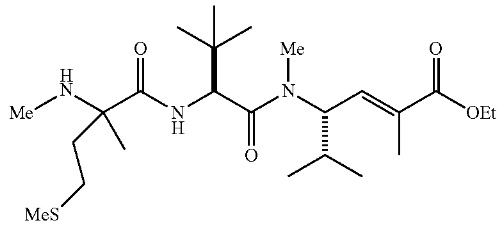 [SMILES: CCOC(=O)/C(C)=C/[C@H](C(C)C)N(C)C(=O)[C@@H](NC(=O)C(C)(CCSC)NC)C(C)(C)C] |
| ER-808038 | 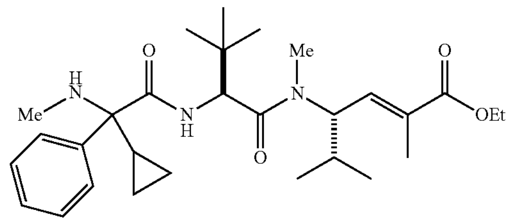 [SMILES: CCOC(=O)/C(C)=C/[C@H](C(C)C)N(C)C(=O)[C@@H](NC(=O)C(NC)(c1ccccc1)C1CC1)C(C)(C)C] |
| ER-808057 | 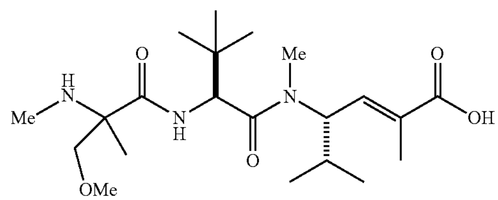 |
| ER-808058 | 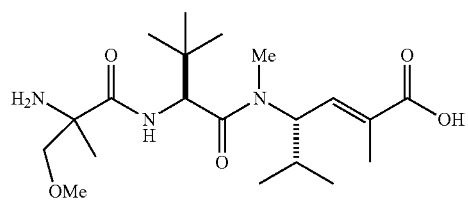 [SMILES: COCC(C)(N)C(=O)N[C@H](C(=O)N(C)[C@H](/C=C(\C)C(=O)O)C(C)C)C(C)(C)C] |
| ER-808059 | 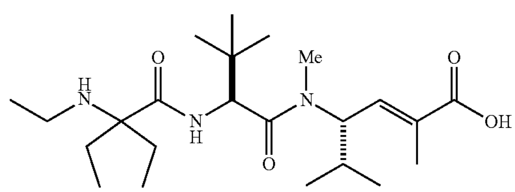 [SMILES: CCNC(CC)(CC)C(=O)N[C@H](C(=O)N(C)[C@H](/C=C(\C)C(=O)O)C(C)C)C(C)(C)C] |
| ER-808060 | 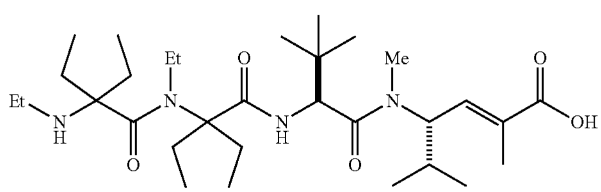 |
| ER-808061 | 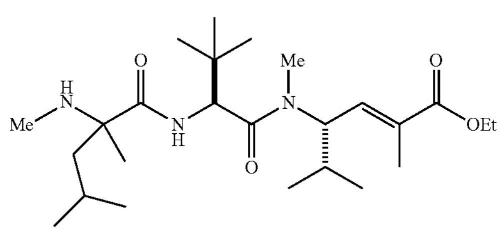 [SMILES: CCOC(=O)/C(C)=C/[C@H](C(C)C)N(C)C(=O)[C@@H](NC(=O)C(C)(CC(C)C)NC)C(C)(C)C] |

-continued

| Compound | Structure |
|---|---|
| ER-808062 | |
| ER-808063 | |
| ER-808065 Trans-substituents on the piperidine ring, but absolute sterochemistry is unknown. Single diastereomer. | |
| ER-808066 Trans-substituents on the piperidine ring, but absolute stereochemistry is unknown. Single diastereomer | |
| ER-808067 Trans-substituents on the piperidine ring, but absolute stereochemistry is unknown. Single diastereomer | |
| ER-808068 Trans-substituents on the piperidine ring, but absolute stereochemistry is unknown. Single diastereomer | |
| ER-808071 Trans-substituents on the piperidine ring, but absolute sterochemistry is unknown. Single diastereomer | |
| ER-808072 Trans-substituents on the piperidine ring, but absolute stereochemistry is unknown. Single diastereomer | |

| Compound | Structure |
|---|---|
| ER-808073<br>Trans-substituents on the piperidine ring, but absolute stereochemistry is unknown.<br>Single diastereomer | 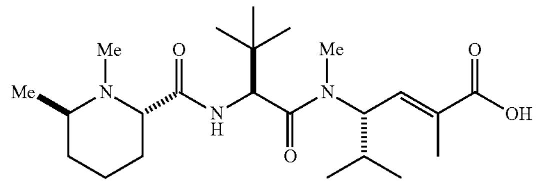 [SMILES: C/C(=C\[C@H](C(C)C)N(C)C(=O)[C@@H](NC(=O)[C@@H]1CCCCN1C)C(C)(C)C)C(=O)O ; "Me"] |
| ER-808074<br>Trans-substituents on the piperidine ring, but absolute stereochemistry is unknown.<br>Single diastereomer | 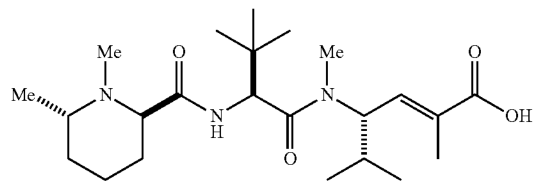 [SMILES: C/C(=C\[C@H](C(C)C)N(C)C(=O)[C@@H](NC(=O)[C@H]1CCC[C@H](C)N1C)C(C)(C)C)C(=O)O] |
| ER-808075 | 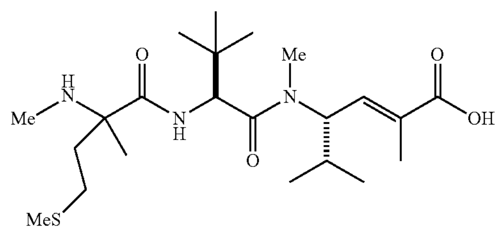 [SMILES: CNC(C)(CCSC)C(=O)N[C@H](C(=O)N(C)[C@H](/C=C(\C)C(=O)O)C(C)C)C(C)(C)C] |
| ER-808076 | 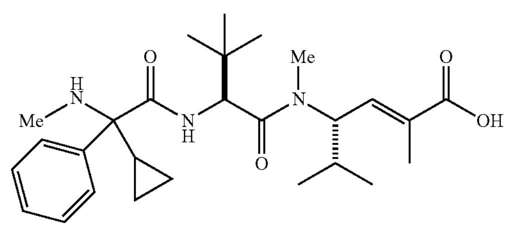 [SMILES: CNC(C(=O)N[C@H](C(=O)N(C)[C@H](/C=C(\C)C(=O)O)C(C)C)C(C)(C)C)(c1ccccc1)C1CC1] |
| ER-808077 | 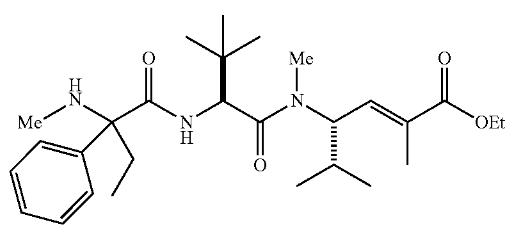 [SMILES: CCOC(=O)/C(C)=C/[C@H](C(C)C)N(C)C(=O)[C@@H](NC(=O)C(CC)(NC)c1ccccc1)C(C)(C)C] |
| ER-808108 | 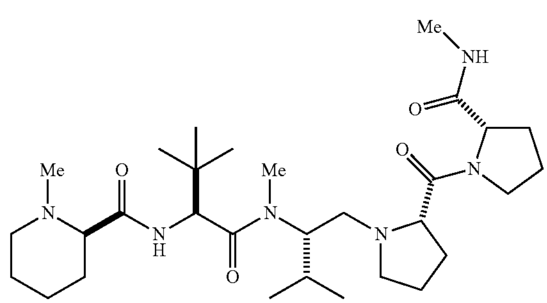 [SMILES: CNC(=O)[C@@H]1CCCN1C(=O)[C@@H]1CCCN1C[C@H](C(C)C)N(C)C(=O)[C@@H](NC(=O)[C@H]1CCCCN1C)C(C)(C)C] |

-continued

| Compound | Structure |
|---|---|
| ER-808109 | 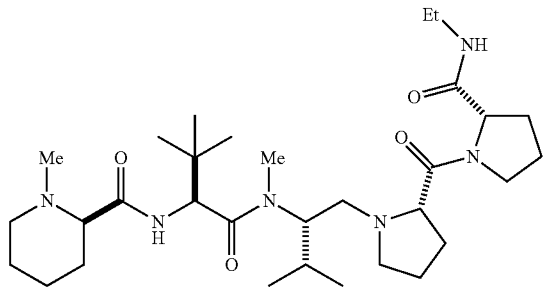 [SMILES: CCNC(=O)[C@@H]1CCCN1C(=O)[C@@H]1CCCN1C[C@H](C(C)C)N(C)C(=O)[C@@H](NC(=O)[C@H]1CCCCN1C)C(C)(C)C] |
| ER-808110 | 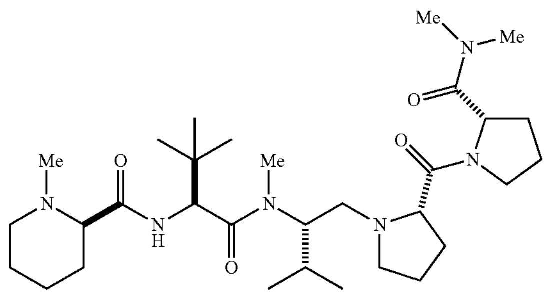 [SMILES: CCN(CC)C(=O)[C@@H]1CCCN1C(=O)[C@@H]1CCCN1C[C@H](C(C)C)N(C)C(=O)[C@@H](NC(=O)[C@H]1CCCCN1C)C(C)(C)C] |
| ER-808111 | 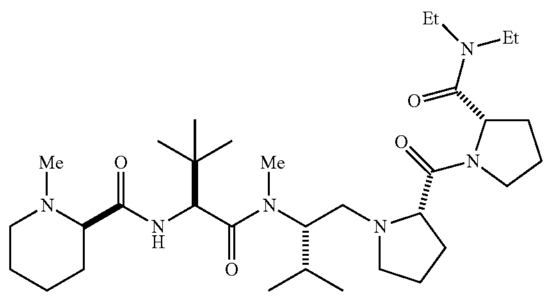 |
| ER-808112 | 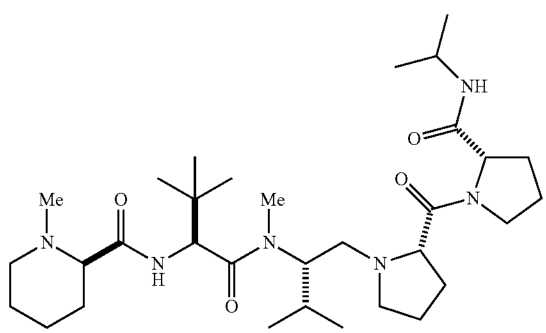 [SMILES: CC(C)NC(=O)[C@@H]1CCCN1C(=O)[C@@H]1CCCN1C[C@H](C(C)C)N(C)C(=O)[C@@H](NC(=O)[C@H]1CCCCN1C)C(C)(C)C] |
| ER-808113 | 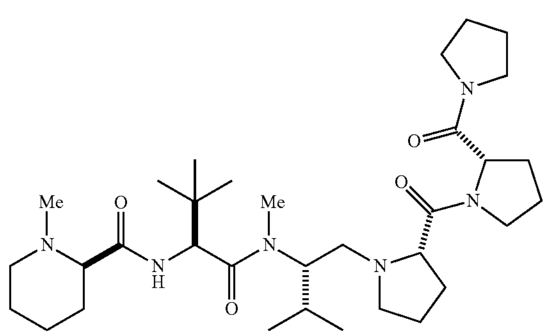 [SMILES: CC(C)[C@@H](CN1CCC[C@H]1C(=O)N1CCC[C@H]1C(=O)N1CCCC1)N(C)C(=O)[C@@H](NC(=O)[C@H]1CCCCN1C)C(C)(C)C] |

-continued

| Compound | Structure |
| --- | --- |
| ER-808114 | 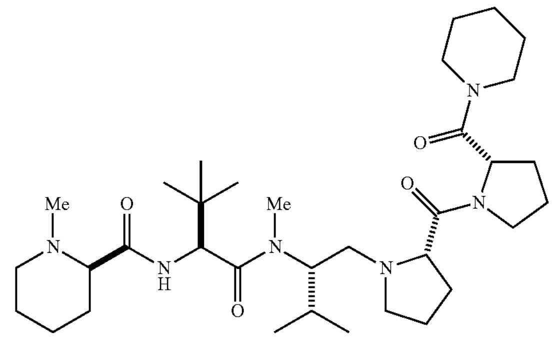 [SMILES: CC(C)[C@@H](CN1CCC[C@H]1C(=O)N1CCC[C@H]1C(=O)N1CCCCC1)N(C)C(=O)[C@@H](NC(=O)[C@H]1CCCCN1C)C(C)(C)C] |
| ER-808115 | 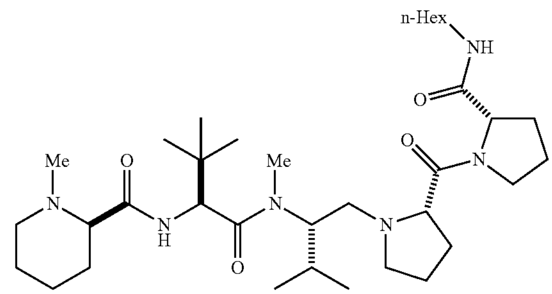 |
| ER-808116 | 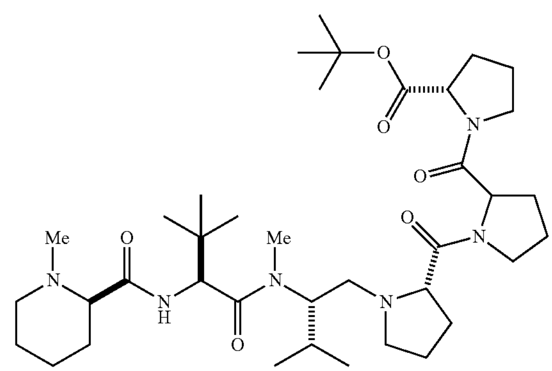 [SMILES: CC(C)[C@@H](CN1CCC[C@H]1C(=O)N1CCCC1C(=O)N1CCC[C@H]1C(=O)OC(C)(C)C)N(C)C(=O)[C@@H](NC(=O)[C@H]1CCCCN1C)C(C)(C)C] |
| ER-808117 | 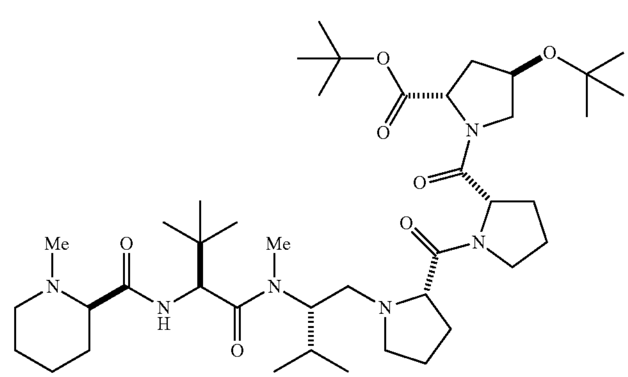 [SMILES: CC(C)[C@@H](CN1CCC[C@H]1C(=O)N1CCC[C@H]1C(=O)N1C[C@H](OC(C)(C)C)C[C@H]1C(=O)OC(C)(C)C)N(C)C(=O)[C@@H](NC(=O)[C@H]1CCCCN1C)C(C)(C)C] |

-continued

| Compound | Structure |
|---|---|
| ER-808118 | 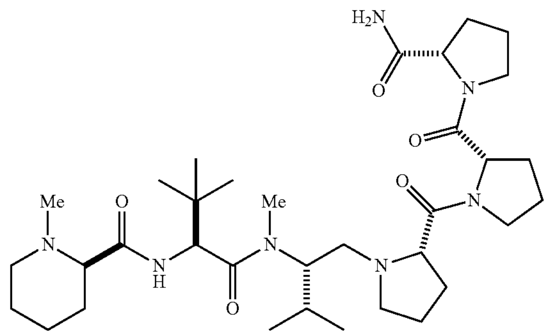 |
| ER-808119 | 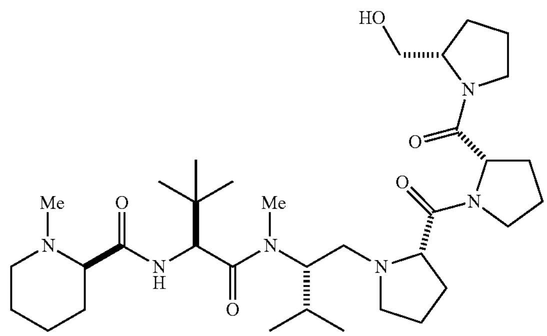 |
| ER-808120 | 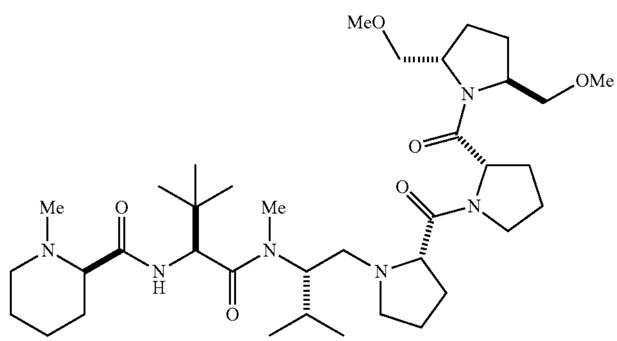 |
| ER-808121 | 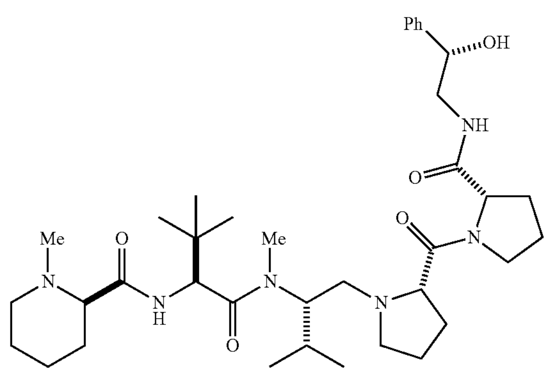 |

-continued
| Compound | Structure |
|---|---|
| ER-808122 | 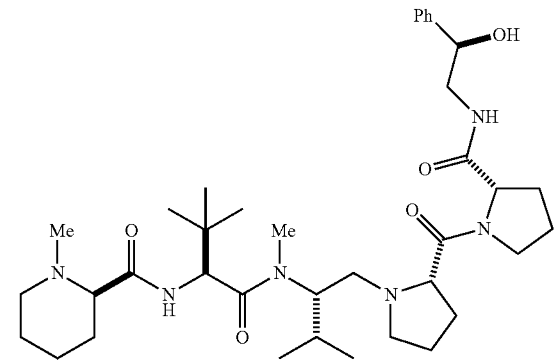 |
| ER-808123 | 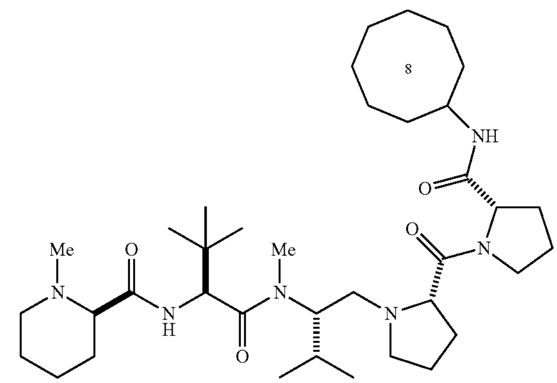 [SMILES: CC(C)[C@@H](CN1CCC[C@H]1C(=O)N1CCC[C@H]1C(=O)NC1CCCCCCC1)N(C)C(=O)[C@@H](NC(=O)[C@H]1CCCCN1C)C(C)(C)C] |
| ER-808124 | 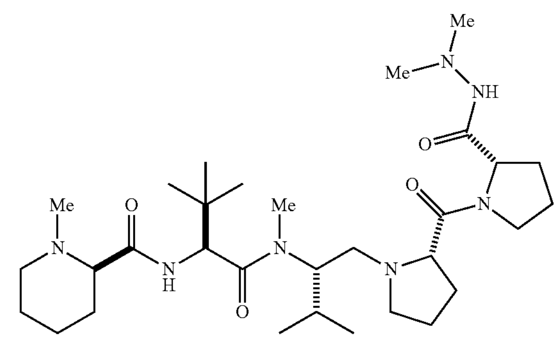 [SMILES: CC(C)[C@@H](CN1CCC[C@H]1C(=O)N1CCC[C@H]1C(=O)NN(C)C)N(C)C(=O)[C@@H](NC(=O)[C@H]1CCCCN1C)C(C)(C)C] |
| ER-808125 | 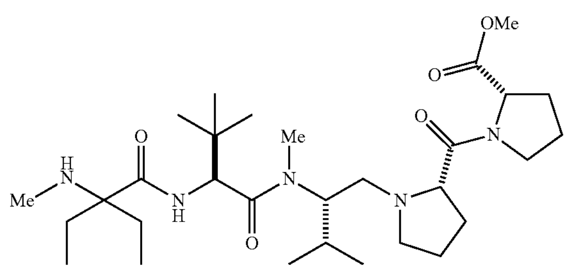 [SMILES: CCC(CC)(NC)C(=O)N[C@H](C(=O)N(C)[C@H](CN1CCC[C@H]1C(=O)N1CCC[C@H]1C(=O)OC)C(C)C)C(C)(C)C] |
| ER-808126 Absolute sterochemistry is unknown. Single diastereomer | 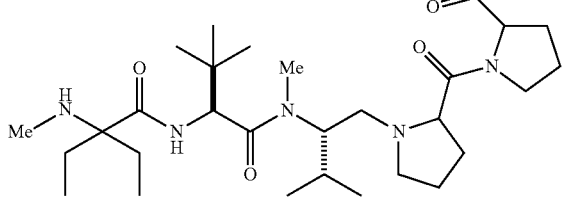 |

-continued
| Compound | Structure |
|---|---|
| ER-808131 | 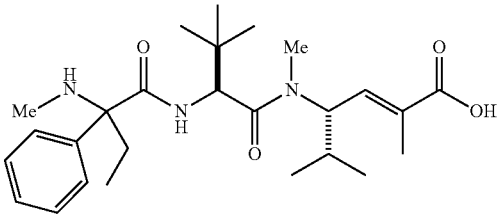 [SMILES: CCC(NC)(C(=O)N[C@H](C(=O)N(C)[C@H](/C=C(\C)C(=O)O)C(C)C)C(C)(C)C)c1ccccc1] |
| ER-808139 | 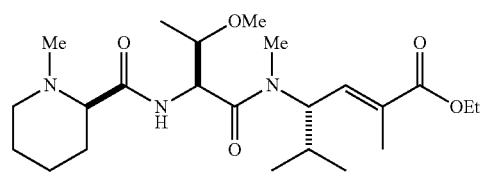 |
| ER-808140 | 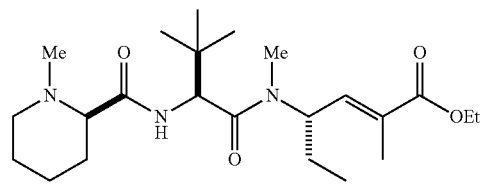 [SMILES: CCOC(=O)/C(C)=C/[C@H](CC)N(C)C(=O)[C@@H](NC(=O)[C@H]1CCCCN1C)C(C)(C)C] |
| ER-808141 | 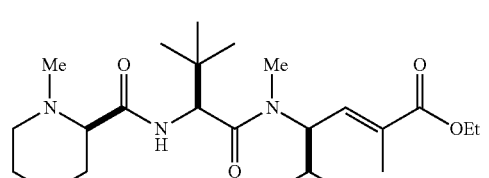 |
| ER-808142 | 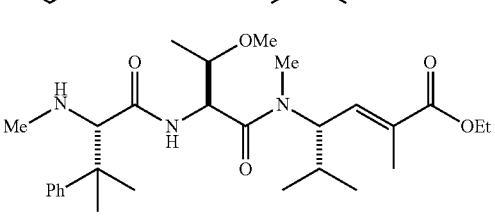 |
| ER-808143 | 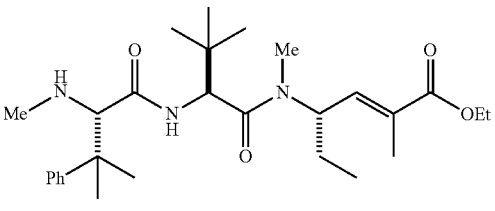 [SMILES: CCOC(=O)/C(C)=C/[C@H](CC)N(C)C(=O)[C@@H](NC(=O)[C@@H](NC)C(C)(C)c1ccccc1)C(C)(C)C] |
| ER-808144 | 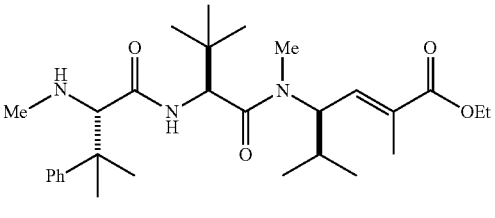 [SMILES: CCOC(=O)/C(C)=C/[C@@H](C(C)C)N(C)C(=O)[C@@H](NC(=O)[C@@H](NC)C(C)(C)c1ccccc1)C(C)(C)C] |
| ER-808145 | 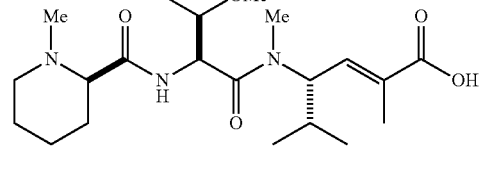 |

-continued

| Compound | Structure |
| --- | --- |
| ER-808146 | 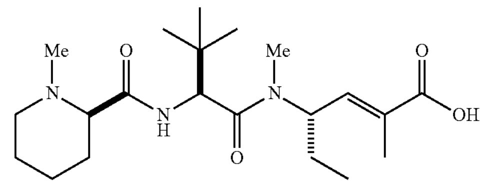 [SMILES: CC[C@@H](/C=C(\C)C(=O)O)N(C)C(=O)[C@@H](NC(=O)[C@H]1CCCCN1C)C(C)(C)C] |
| ER-808147 | 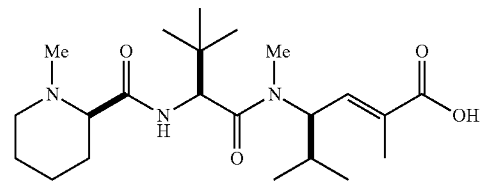 [SMILES: C/C(=C\[C@@H](C(C)C)N(C)C(=O)[C@@H](NC(=O)[C@H]1CCCCN1C)C(C)(C)C)C(=O)O] |
| ER-808148 | 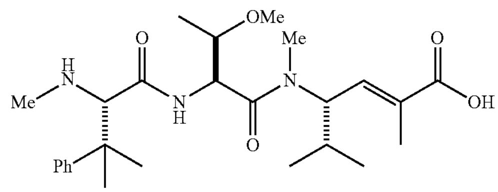 |
| ER-808149 | 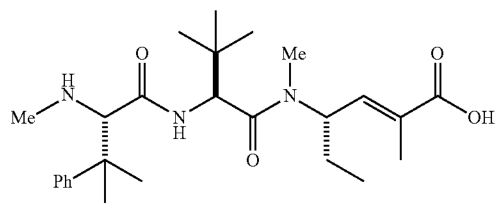 [SMILES: CC[C@@H](/C=C(\C)C(=O)O)N(C)C(=O)[C@@H](NC(=O)[C@@H](NC)C(C)(C)c1ccccc1)C(C)(C)C] |
| ER-808150 | 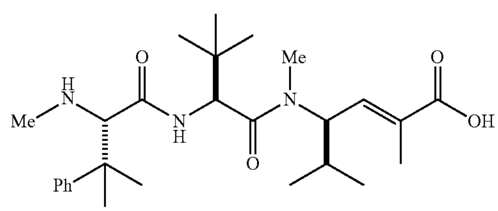 [SMILES: CN[C@H](C(=O)N[C@H](C(=O)N(C)[C@@H](/C=C(\C)C(=O)O)C(C)C)C(C)(C)C)C(C)(C)c1ccccc1] |
| ER-808161 | 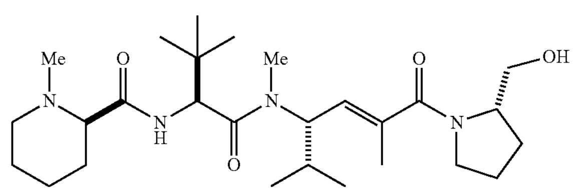 [SMILES: C/C(=C\[C@H](C(C)C)N(C)C(=O)[C@@H](NC(=O)[C@H]1CCCCN1C)C(C)(C)C)C(=O)N1CCC[C@H]1CO] |
| ER-808166 | 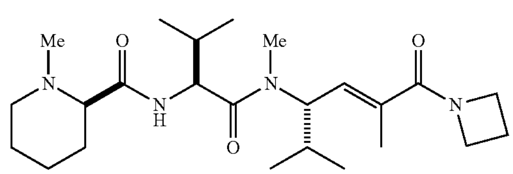 [SMILES: C/C(=C\[C@H](C(C)C)N(C)C(=O)[C@@H](NC(=O)[C@H]1CCCCN1C)C(C)C)C(=O)N1CCC1] |
| ER-808167 | 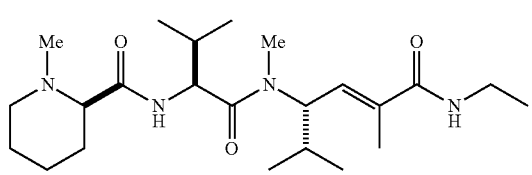 [SMILES: CCNC(=O)/C(C)=C/[C@H](C(C)C)N(C)C(=O)[C@@H](NC(=O)[C@H]1CCCCN1C)C(C)C] |

| Compound | Structure |
|---|---|
| ER-808168 | 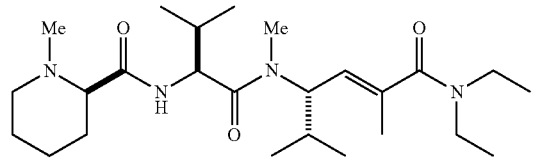 [SMILES: CCN(CC)C(=O)/C(C)=C/[C@H](C(C)C)N(C)C(=O)[C@@H](NC(=O)[C@H]1CCCCN1C)C(C)C] |
| ER-808169 | 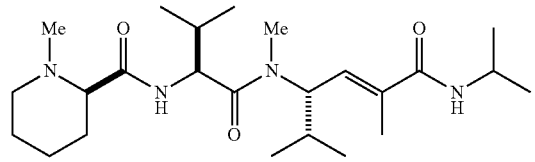 [SMILES: C/C(=C\[C@H](C(C)C)N(C)C(=O)[C@@H](NC(=O)[C@H]1CCCCN1C)C(C)C)C(=O)NC(C)C] |
| ER-808170 | 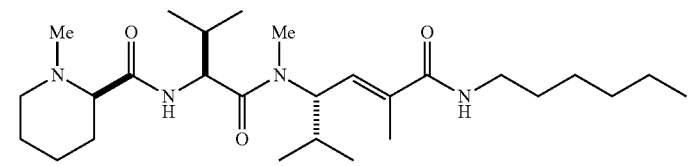 |
| ER-808171 | 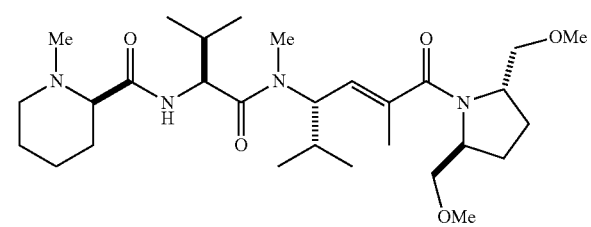 [SMILES: COC[C@@H]1CC[C@@H](COC)N1C(=O)/C(C)=C/[C@H](C(C)C)N(C)C(=O)[C@@H](NC(=O)[C@H]1CCCCN1C)C(C)C] |
| ER-808172 | 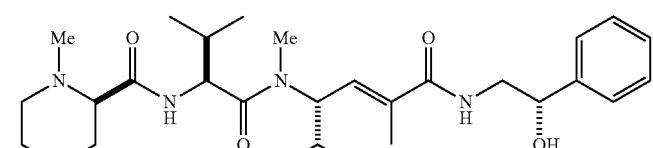 |
| ER-808173 | 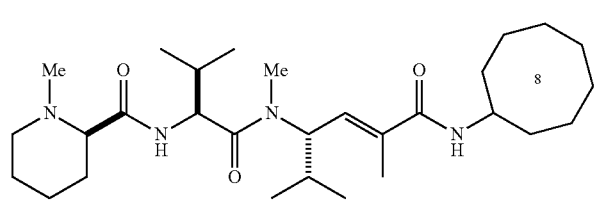 [SMILES: C/C(=C\[C@H](C(C)C)N(C)C(=O)[C@@H](NC(=O)[C@H]1CCCCN1C)C(C)C)C(=O)NC1CCCCCCC1] |
| ER-808174 | 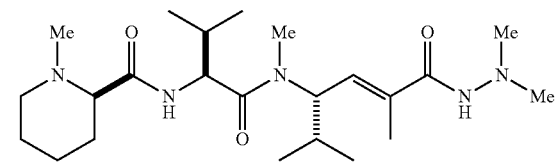 [SMILES: C/C(=C\[C@H](C(C)C)N(C)C(=O)[C@@H](NC(=O)[C@H]1CCCCN1C)C(C)C)C(=O)NN(C)C] |
| ER-808175 | 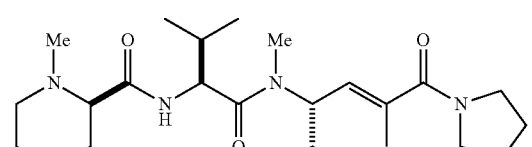 |

-continued

| Compound | Structure |
|---|---|
| ER-808176 | 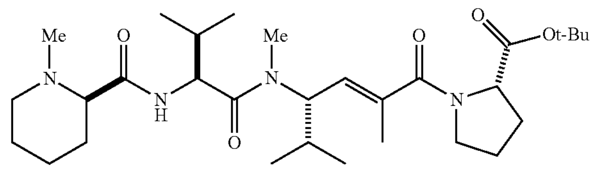 [SMILES: C/C(=C\[C@H](C(C)C)N(C)C(=O)[C@@H](NC(=O)[C@H]1CCCCN1C)C(C)C)C(=O)N1CCC[C@H]1C(=O)OC(C)(C)C] |
| ER-808177 | 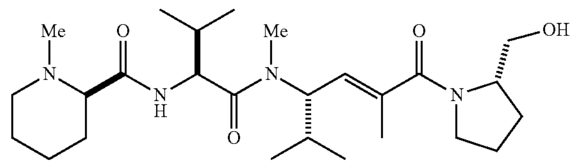 [SMILES: C/C(=C\[C@H](C(C)C)N(C)C(=O)[C@@H](NC(=O)[C@H]1CCCCN1C)C(C)C)C(=O)N1CCC[C@H]1CO] |
| ER-808178 | 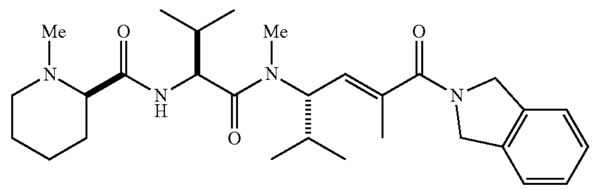 [SMILES: C/C(=C\[C@H](C(C)C)N(C)C(=O)[C@@H](NC(=O)[C@H]1CCCCN1C)C(C)C)C(=O)N1Cc2ccccc2C1] |
| ER-808179 | 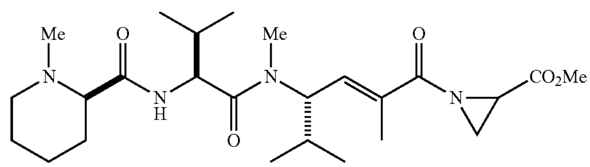 [SMILES: COC(=O)C1CN1C(=O)/C(C)=C/[C@H](C(C)C)N(C)C(=O)[C@@H](NC(=O)[C@H]1CCCCN1C)C(C)C] |
| ER-808180 | 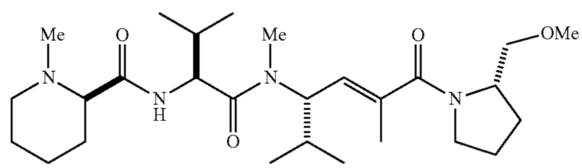 [SMILES: COC[C@@H]1CCCN1C(=O)/C(C)=C/[C@H](C(C)C)N(C)C(=O)[C@@H](NC(=O)[C@H]1CCCCN1C)C(C)C] |
| ER-808181 | 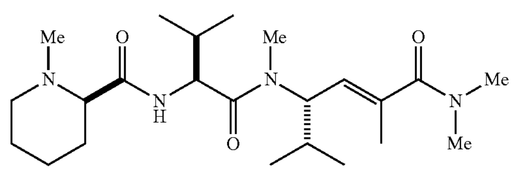 [SMILES: C/C(=C\[C@H](C(C)C)N(C)C(=O)[C@@H](NC(=O)[C@H]1CCCCN1C)C(C)C)C(=O)N(C)C] |
| ER-808182 | 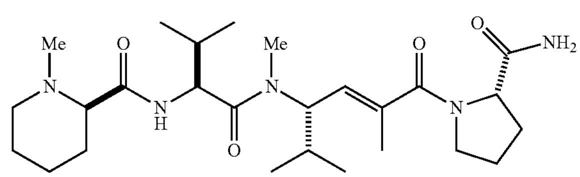 [SMILES: C/C(=C\[C@H](C(C)C)N(C)C(=O)[C@@H](NC(=O)[C@H]1CCCCN1C)C(C)C)C(=O)N1CCC[C@H]1C(N)=O] |
| ER-808183 | 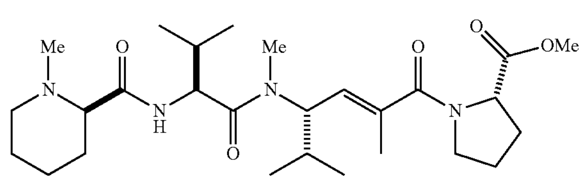 [SMILES: COC(=O)[C@@H]1CCCN1C(=O)/C(C)=C/[C@H](C(C)C)N(C)C(=O)[C@@H](NC(=O)[C@H]1CCCCN1C)C(C)C] |

| Compound | Structure |
|---|---|
| ER-808189 | 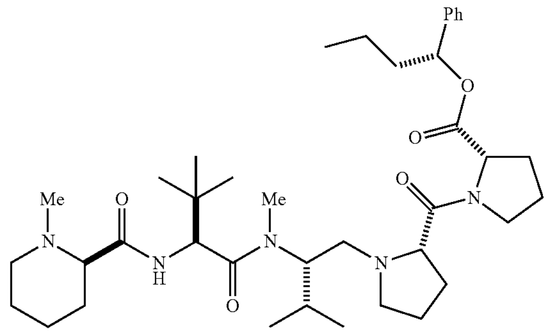 |
| ER-808190 | 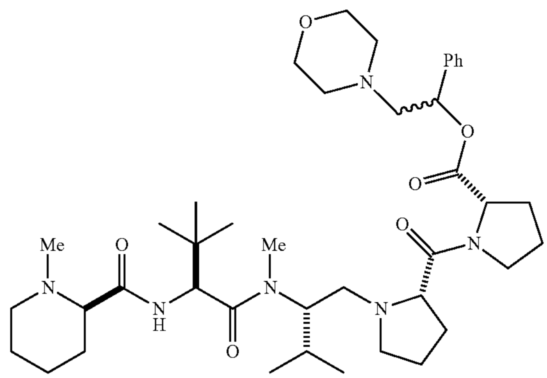 [SMILES: CC(C)[C@@H](CN1CCC[C@H]1C(=O)N1CCC[C@H]1C(=O)OC(CN1CCOCC1)c1ccccc1)N(C)C(=O)[C@@H](NC(=O)[C@H]1CCCCN1C)C(C)(C)C] |
| ER-808191 | 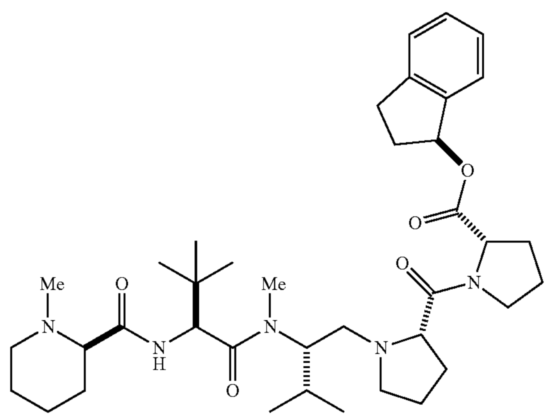 |
| ER-808192 | 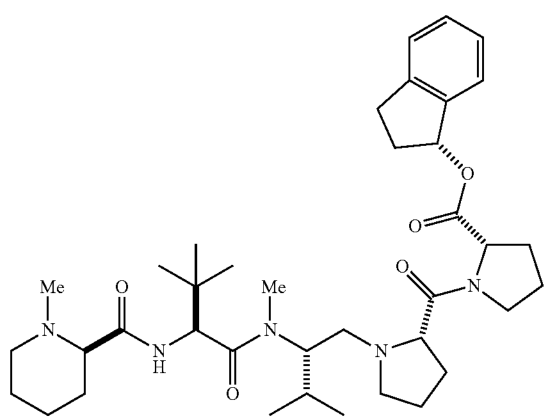 |

-continued
| Compound | Structure |
|---|---|
| ER-808193 | 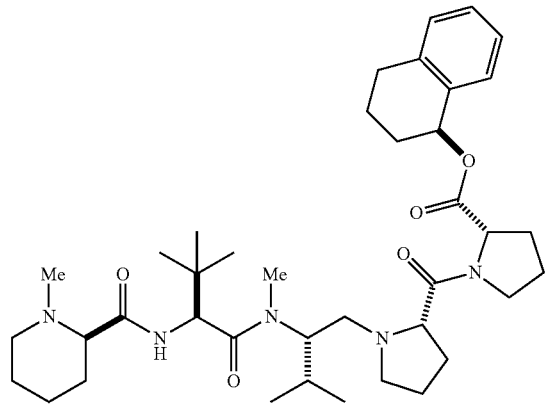 |
| ER-808194 | 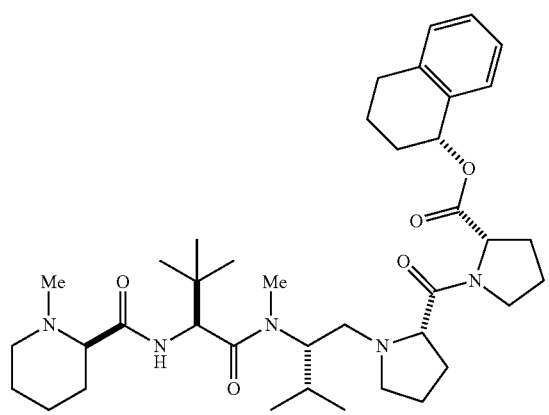 |
| ER-808195 | 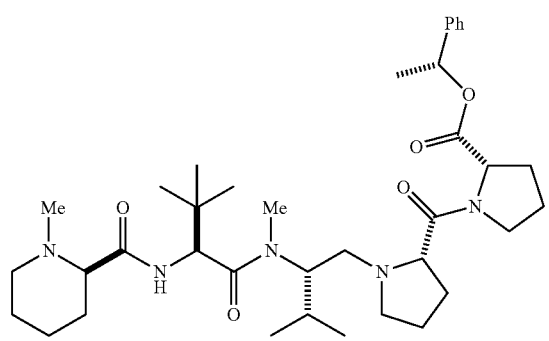 |
| ER-808196 | 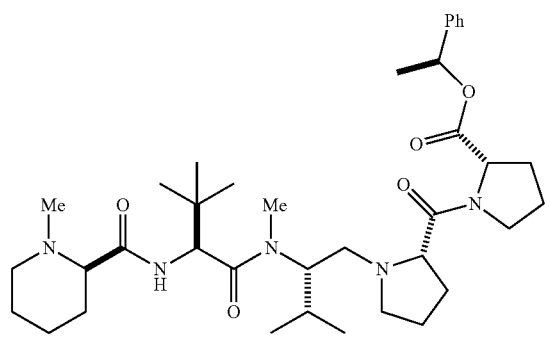 [SMILES: CC(C)[C@@H](CN1CCC[C@H]1C(=O)N1CCC[C@H]1C(=O)O[C@@H](C)c1ccccc1)N(C)C(=O)[C@@H](NC(=O)[C@H]1CCCCN1C)C(C)(C)C] |

-continued

| Compound | Structure |
| --- | --- |
| ER-808197 | 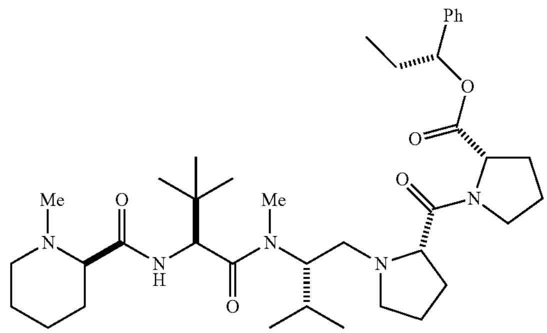 [SMILES: CC[C@@H](OC(=O)[C@@H]1CCCN1C(=O)[C@@H]1CCCN1C[C@H](C(C)C)N(C)C(=O)[C@@H](NC(=O)[C@H]1CCCCN1C)C(C)(C)C)c1ccccc1] |
| ER-808198 | 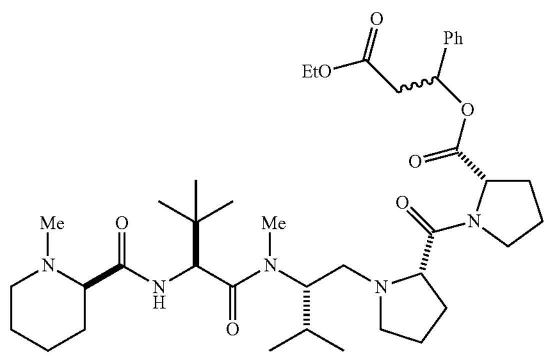 |
| ER-808199 | 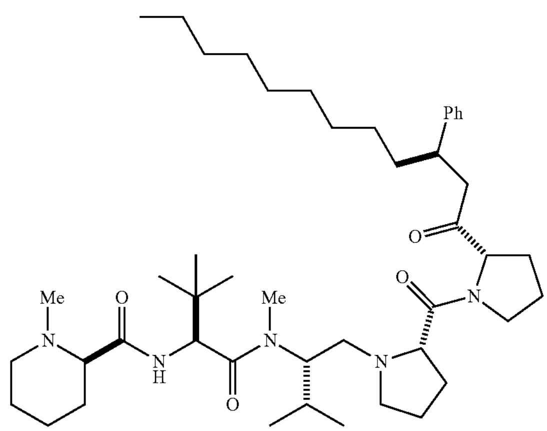 |
| ER-808200 | 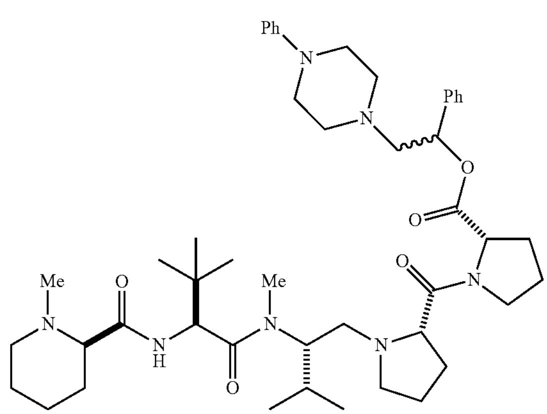 [SMILES: CC(C)[C@@H](CN1CCC[C@H]1C(=O)N1CCC[C@H]1C(=O)OC(CN1CCN(c2ccccc2)CC1)c1ccccc1)N(C)C(=O)[C@@H](NC(=O)[C@H]1CCCCN1C)C(C)(C)C] |

-continued

| Compound | Structure |
|---|---|
| ER-808201 | 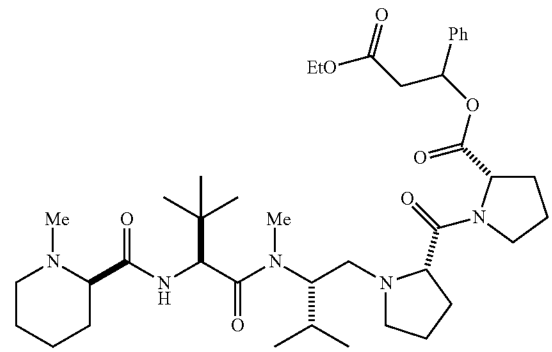 |
| ER-808202 | 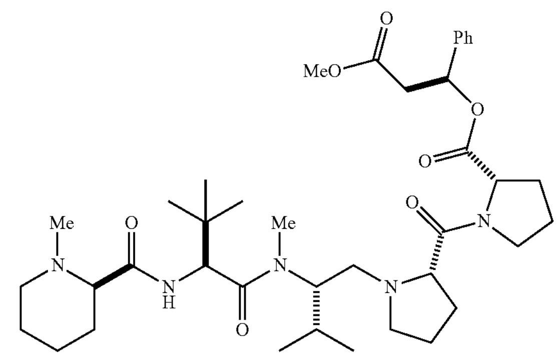 |
| ER-808203 | 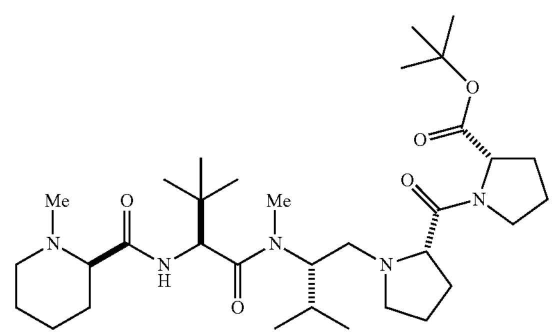 [SMILES: CC(C)[C@@H](CN1CCC[C@H]1C(=O)N1CCC[C@H]1C(=O)OC(C)(C)C)N(C)C(=O)[C@@H](NC(=O)[C@H]1CCCCN1C)C(C)(C)C] |
| ER-808204 Cis-substituents on the piperidine ring, but absolute stereochemistry is unknown. Single diastereomer | |
| ER-808205 Cis-substituents on the piperidine ring, but absolute stereochemistry is unknown. Single diastereomer | |

-continued

| Compound | Structure |
|---|---|
| ER-808206 | 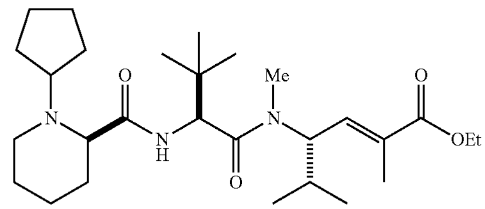 [SMILES: CCOC(=O)/C(C)=C/[C@H](C(C)C)N(C)C(=O)[C@@H](NC(=O)[C@H]1CCCCN1C1CCCC1)C(C)(C)C] |
| ER-808207 | 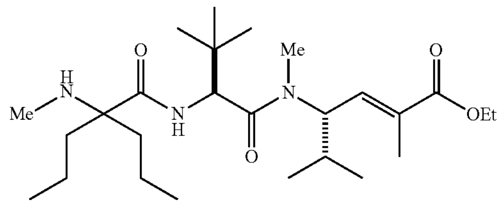 [SMILES: CCCC(CCC)(NC)C(=O)N[C@H](C(=O)N(C)[C@H](/C=C(\C)C(=O)OCC)C(C)C)C(C)(C)C] |
| ER-808208 | 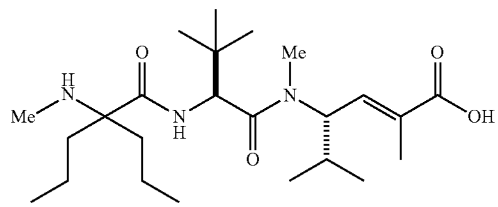 [SMILES: CCCC(CCC)(NC)C(=O)N[C@H](C(=O)N(C)[C@H](/C=C(\C)C(=O)O)C(C)C)C(C)(C)C] |
| ER-808209 | 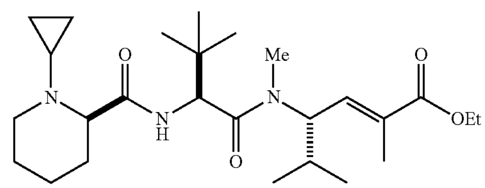 [SMILES: CCOC(=O)/C(C)=C/[C@H](C(C)C)N(C)C(=O)[C@@H](NC(=O)[C@H]1CCCCN1C1CC1)C(C)(C)C] |
| ER-808210 | 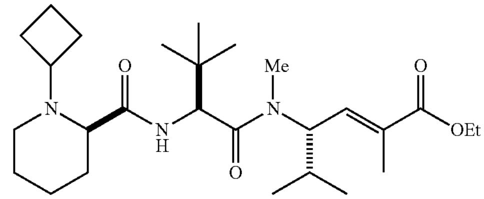 [SMILES: CCOC(=O)/C(C)=C/[C@H](C(C)C)N(C)C(=O)[C@@H](NC(=O)[C@H]1CCCCN1C1CCC1)C(C)(C)C] |
| ER-808211 | 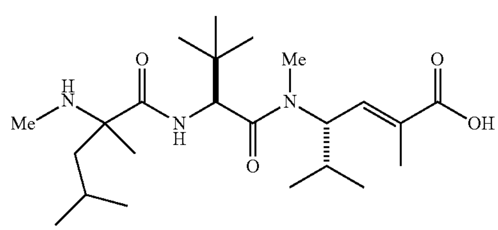 [SMILES: CNC(C)(CC(C)C)C(=O)N[C@H](C(=O)N(C)[C@H](/C=C(\C)C(=O)O)C(C)C)C(C)(C)C] |
| ER-808212 | 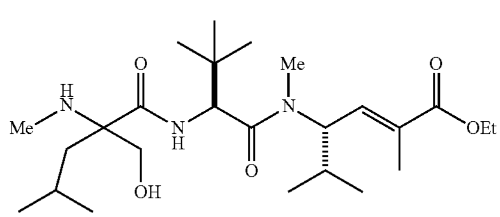 [SMILES: CCOC(=O)/C(C)=C/[C@H](C(C)C)N(C)C(=O)[C@@H](NC(=O)C(CO)(CC(C)C)NC)C(C)(C)C] |

-continued

| Compound | Structure |
| --- | --- |
| ER-808213 | 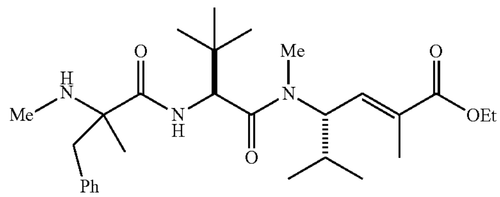 [SMILES: CCOC(=O)/C(C)=C/[C@H](C(C)C)N(C)C(=O)[C@@H](NC(=O)C(C)(Cc1ccccc1)NC)C(C)(C)C] |
| ER-808214 | 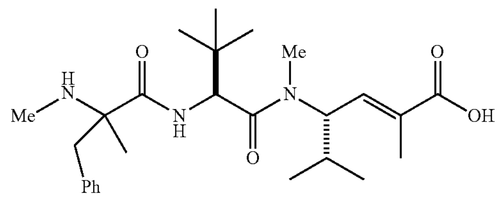 [SMILES: CNC(C)(Cc1ccccc1)C(=O)N[C@H](C(=O)N(C)[C@H](/C=C(\C)C(=O)O)C(C)C)C(C)(C)C] |
| ER-808215 | 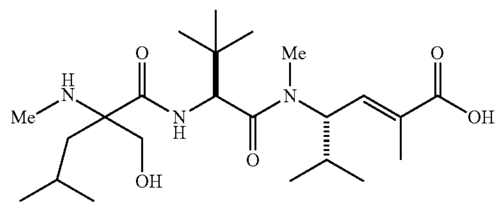 [SMILES: CNC(CO)(CC(C)C)C(=O)N[C@H](C(=O)N(C)[C@H](/C=C(\C)C(=O)O)C(C)C)C(C)(C)C] |
| ER-808216 | 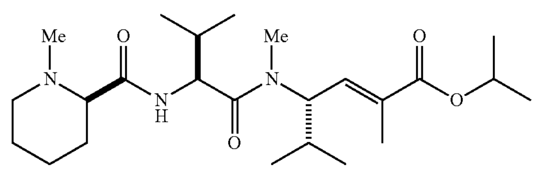 [SMILES: C/C(=C\[C@H](C(C)C)N(C)C(=O)[C@@H](NC(=O)[C@H]1CCCCN1C)C(C)C)C(=O)OC(C)C] |
| ER-808217 | 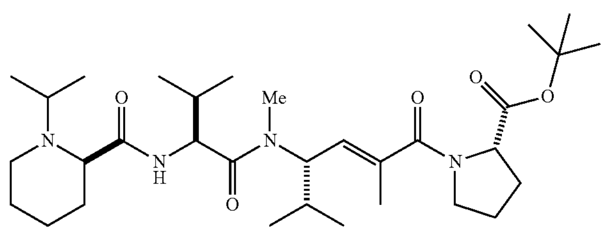 |
| ER-808218 | 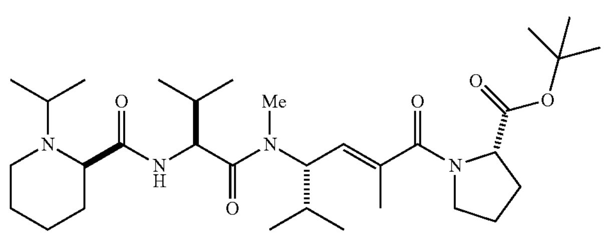 [SMILES: C/C(=C\[C@H](C(C)C)N(C)C(=O)[C@@H](NC(=O)[C@H]1CCCCN1C(C)C)C(C)C)C(=O)N1CCC[C@H]1C(=O)OC(C)(C)C] |
| ER-808219 | 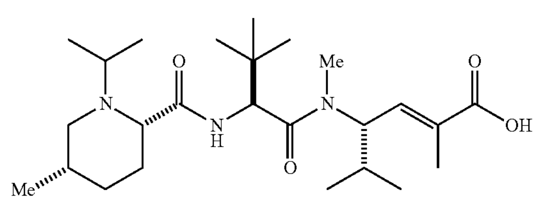 [SMILES: C/C(=C\[C@H](C(C)C)N(C)C(=O)[C@@H](NC(=O)[C@@H]1CC[C@H](C)CN1C(C)C)C(C)(C)C)C(=O)O] |

-continued
| Compound | Structure |
|---|---|
| ER-808220 | 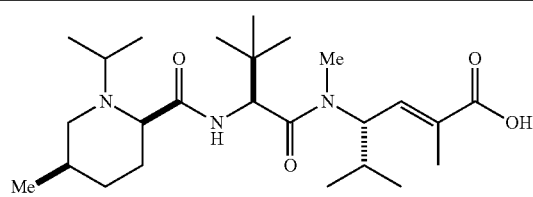 |
| ER-808221 | 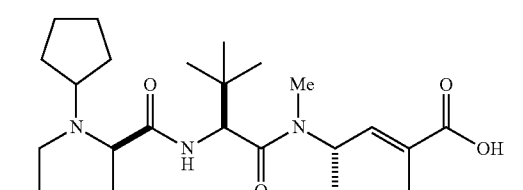 |
| ER-808222 | 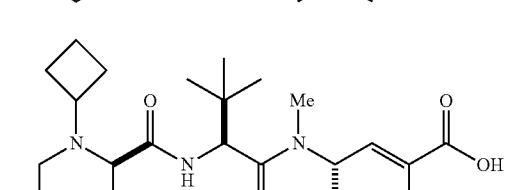 |
| ER-808223 | 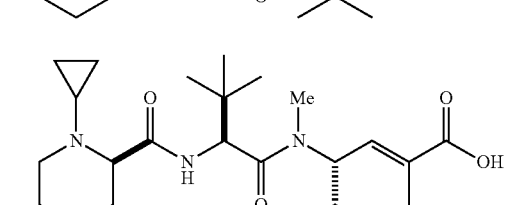 |
| ER-808224 | 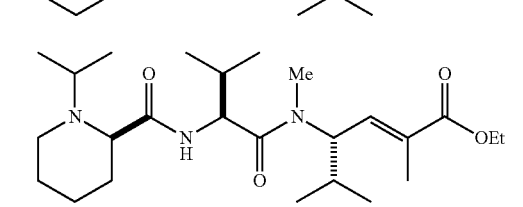 |
| ER-808225 | 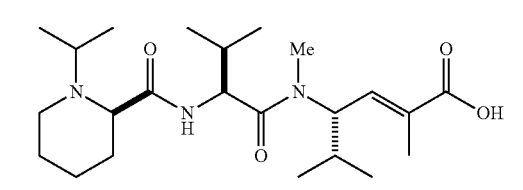 [SMILES: C/C(=C\[C@H](C(C)C)N(C)C(=O)[C@@H](NC(=O)[C@H]1CCCCN1C(C)C)C(C)C)C(=O)O] |
| ER-808226 | 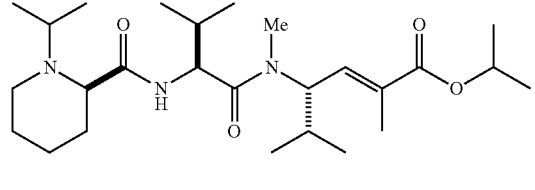 [SMILES: C/C(=C\[C@H](C(C)C)N(C)C(=O)[C@@H](NC(=O)[C@H]1CCCCN1C(C)C)C(C)C)C(=O)OC(C)C] |
| ER-808248 | 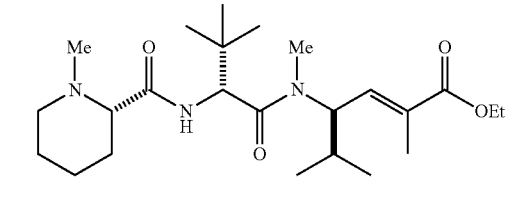 |

-continued

| Compound | Structure |
|---|---|
| ER-808249 | 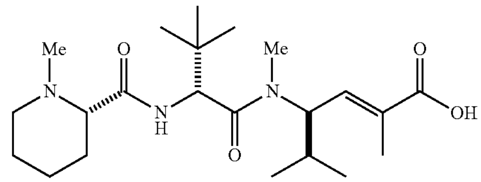 |
| ER-808251 | 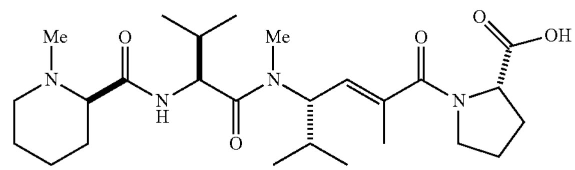 [SMILES: C/C(=C\[C@H](C(C)C)N(C)C(=O)[C@@H](NC(=O)[C@H]1CCCCN1C)C(C)C)C(=O)N1CCC[C@H]1C(=O)O] |
| ER-808253 | 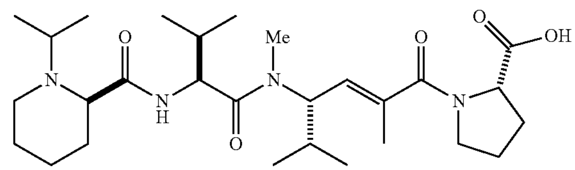 [SMILES: C/C(=C\[C@H](C(C)C)N(C)C(=O)[C@@H](NC(=O)[C@H]1CCCCN1C(C)C)C(C)C)C(=O)N1CCC[C@H]1C(=O)O] |
| ER-808292 | 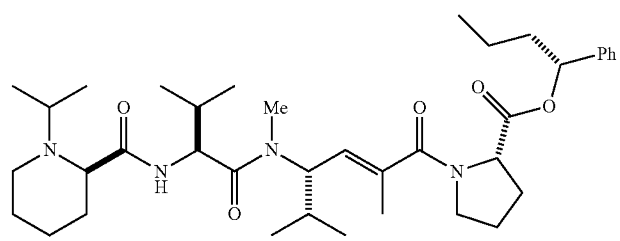 [SMILES: CCC[C@@H](OC(=O)[C@@H]1CCCN1C(=O)/C(C)=C/[C@H](C(C)C)N(C)C(=O)[C@@H](NC(=O)[C@H]1CCCCN1C(C)C)C(C)C)c1ccccc1] |
| ER-808293 | 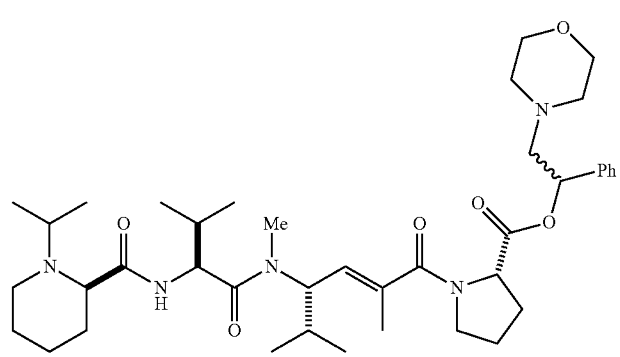 [SMILES: C/C(=C\[C@H](C(C)C)N(C)C(=O)[C@@H](NC(=O)[C@H]1CCCCN1C(C)C)C(C)C)C(=O)N1CCC[C@H]1C(=O)OC(CN1CCOCC1)c1ccccc1] |
| ER-808294 | 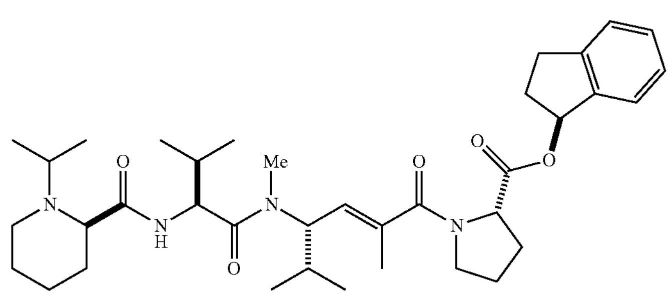 |

-continued
| Compound | Structure |
|---|---|
| ER-808295 | 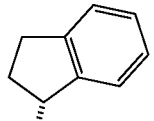 |
| ER-808296 | 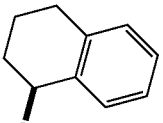 |
| ER-808297 | 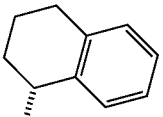 |
| ER-808298 | 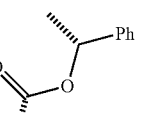 |
| ER-808299 | 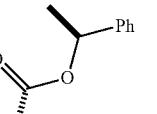 |
| ER-808300 | 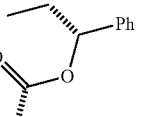 |

-continued

| Compound | Structure |
|---|---|
| ER-808301- | 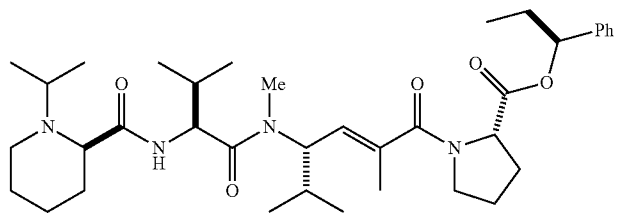 |
| ER-808302 | 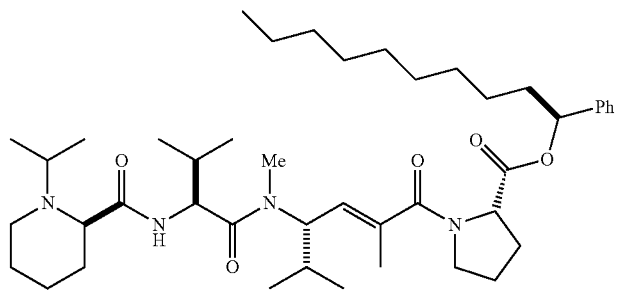 |
| ER-808303 | 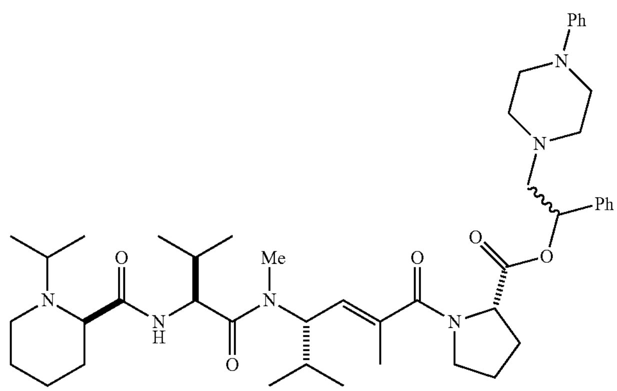 [SMILES: C/C(=C\[C@H](C(C)C)N(C)C(=O)[C@@H](NC(=O)[C@H]1CCCCN1C(C)C)C(C)C)C(=O)N1CCC[C@H]1C(=O)OC(CN1CCN(c2ccccc2)CC1)c1ccccc1] |
| ER-808304 | 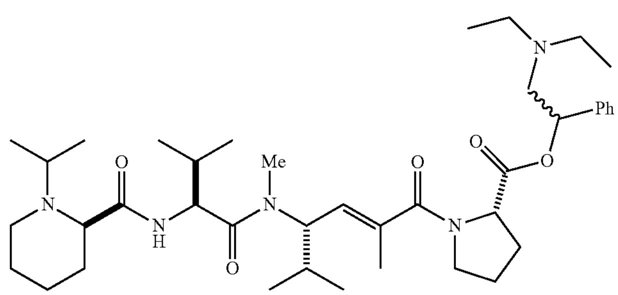 [SMILES: CCN(CC)CC(OC(=O)[C@@H]1CCCN1C(=O)/C(C)=C/[C@H](C(C)C)N(C)C(=O)[C@@H](NC(=O)[C@H]1CCCCN1C(C)C)C(C)C)c1ccccc1] |
| ER-808305 | 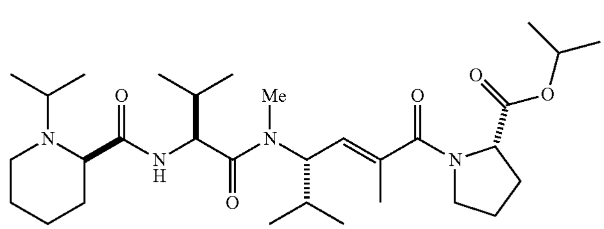 [SMILES: C/C(=C\[C@H](C(C)C)N(C)C(=O)[C@@H](NC(=O)[C@H]1CCCCN1C(C)C)C(C)C)C(=O)N1CCC[C@H]1C(=O)OC(C)C] |

-continued
| Compound | Structure |
|---|---|
| ER-808306 | 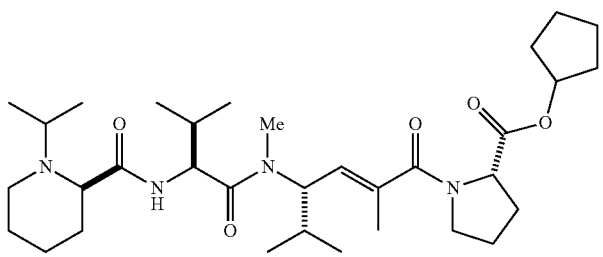 [SMILES: C/C(=C\[C@H](C(C)C)N(C)C(=O)[C@@H](NC(=O)[C@H]1CCCCN1C(C)C)C(C)C)C(=O)N1CCC[C@H]1C(=O)OC1CCCC1] |
| ER-808307 | 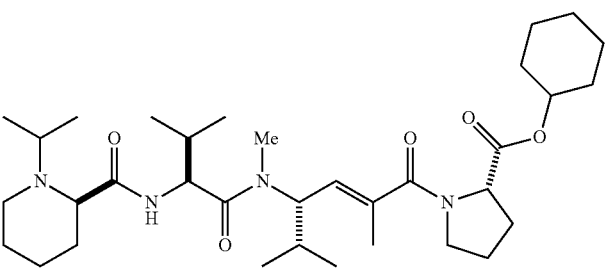 |
| ER-808308 | 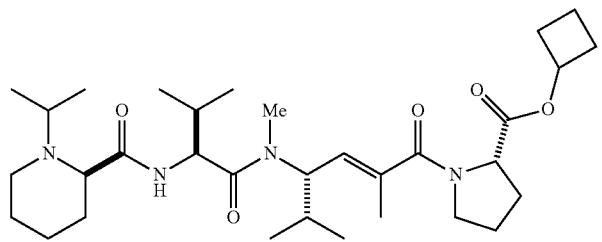 |
| ER-808309 | 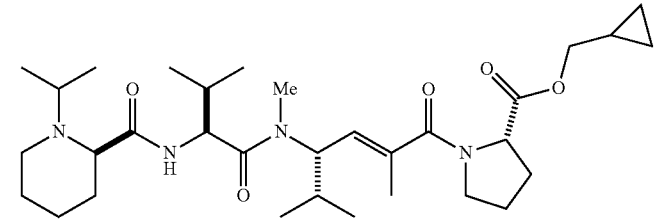 [SMILES: C/C(=C\[C@H](C(C)C)N(C)C(=O)[C@@H](NC(=O)[C@H]1CCCCN1C(C)C)C(C)C)C(=O)N1CCC[C@H]1C(=O)OCC1CC1] |
| ER-808323 | 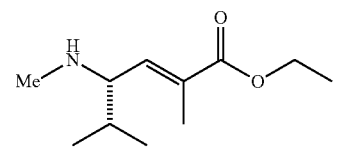 |
| ER-808324 | 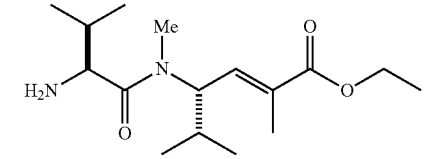 |
| ER-808325 | 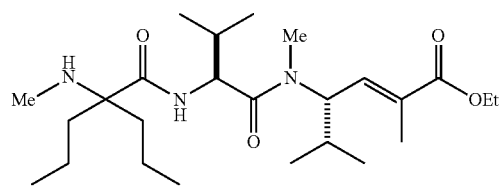 [SMILES: CCCC(CCC)(NC)C(=O)N[C@H](C(=O)N(C)[C@H](/C=C(\C)C(=O)OCC)C(C)C)C(C)C] |

| Compound | Structure |
|---|---|
| ER-808326 | 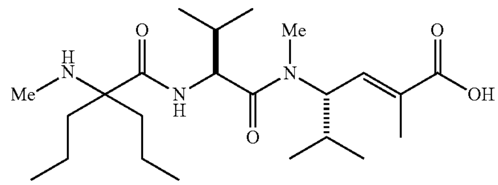 [SMILES: CCCC(CCC)(NC)C(=O)N[C@H](C(=O)N(C)[C@H](/C=C(\C)C(=O)O)C(C)C)C(C)C] |
| ER-808328 | 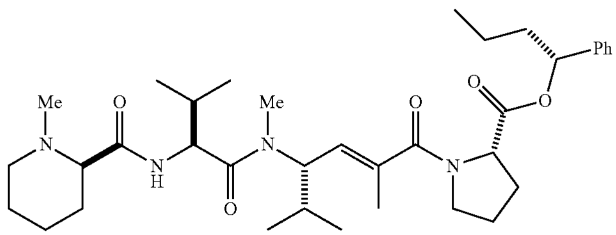 |
| ER-808329 | 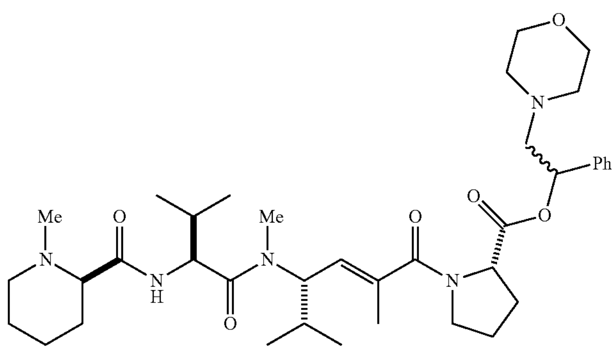 [SMILES: C/C(=C\[C@H](C(C)C)N(C)C(=O)[C@@H](NC(=O)[C@H]1CCCCN1C)C(C)C)C(=O)N1CCC[C@H]1C(=O)OC(CN1CCOCC1)c1ccccc1] |
| ER-808330 | 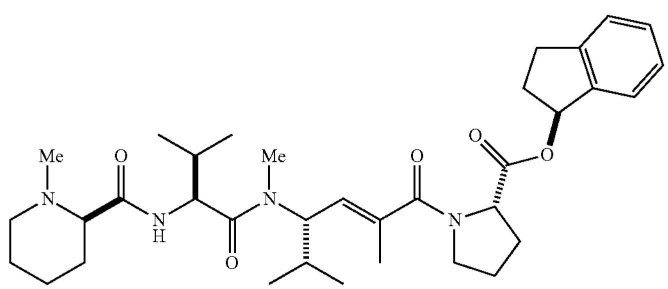 |
| ER-808331 | 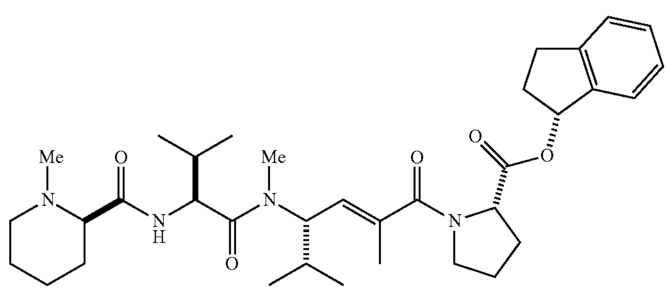 |

-continued

| Compound | Structure |
|---|---|
| ER-808332 | 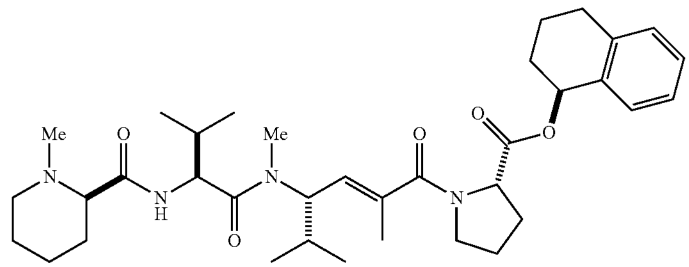 |
| ER-808333 | 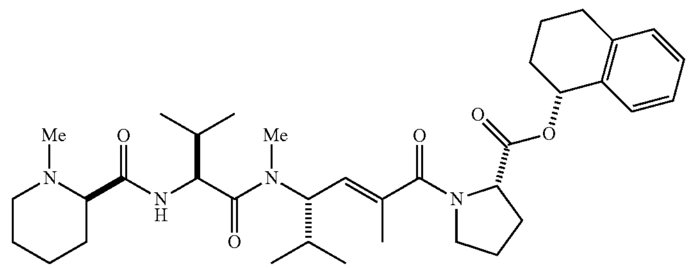 |
| ER-808334 | 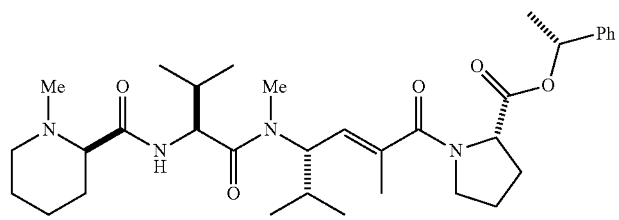 [SMILES: C/C(=C\[C@H](C(C)C)N(C)C(=O)[C@@H](NC(=O)[C@H]1CCCCN1C)C(C)C)C(=O)N1CCC[C@H]1C(=O)O[C@H](C)c1ccccc1] |
| ER-808335 | 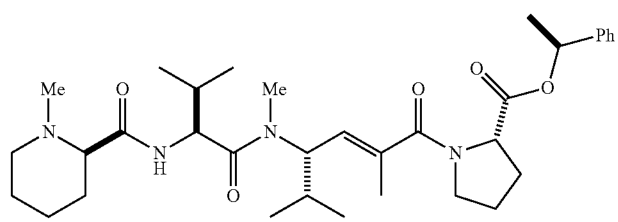 [SMILES: C/C(=C\[C@H](C(C)C)N(C)C(=O)[C@@H](NC(=O)[C@H]1CCCCN1C)C(C)C)C(=O)N1CCC[C@H]1C(=O)O[C@@H](C)c1ccccc1] |
| ER-808336 | 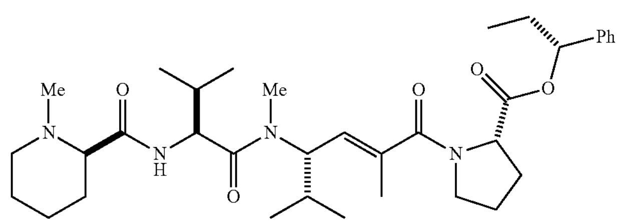 |
| ER-808337 | 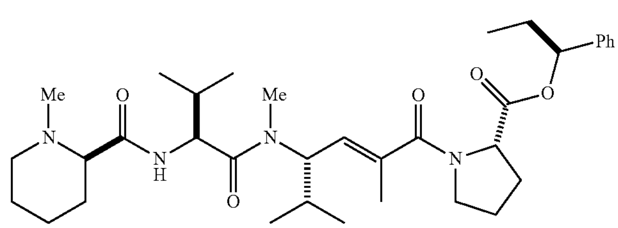 |

-continued

| Compound | Structure |
|---|---|
| ER-808338 | 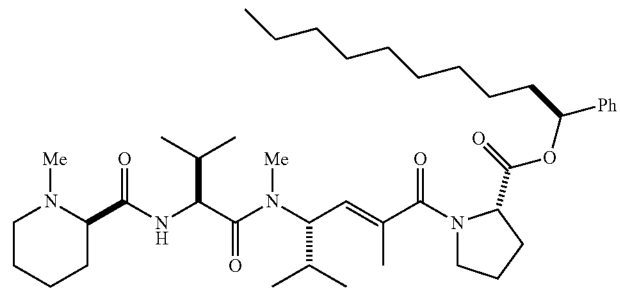 [SMILES: CCCCCCCCC[C@H](OC(=O)[C@@H]1CCCN1C(=O)/C(C)=C/[C@H](C(C)C)N(C)C(=O)[C@@H](NC(=O)[C@H]1CCCCN1C)C(C)C)c1ccccc1] |
| ER-808339 | 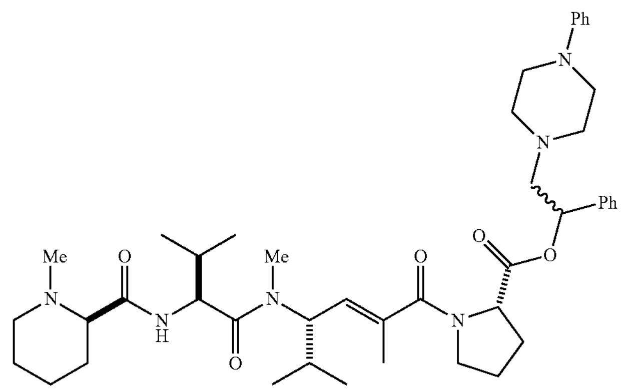 |
| ER-808340 | 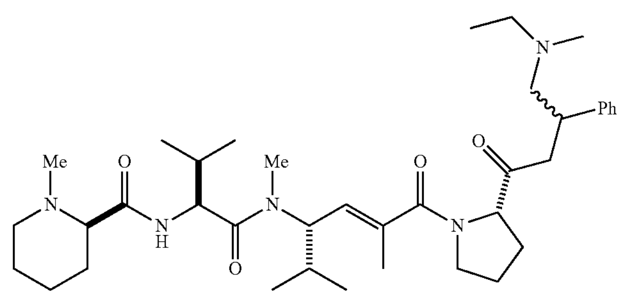 [SMILES: CCN(C)CC(CC(=O)[C@@H]1CCCN1C(=O)/C(C)=C/[C@H](C(C)C)N(C)C(=O)[C@@H](NC(=O)[C@H]1CCCCN1C)C(C)C)c1ccccc1] |
| ER-808341 | 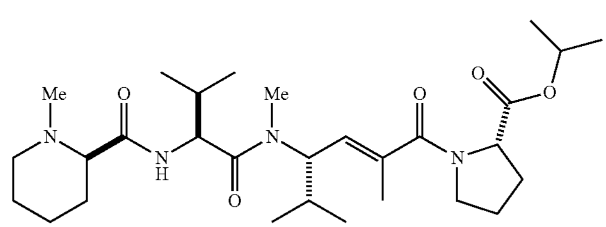 |
| ER-808342 | 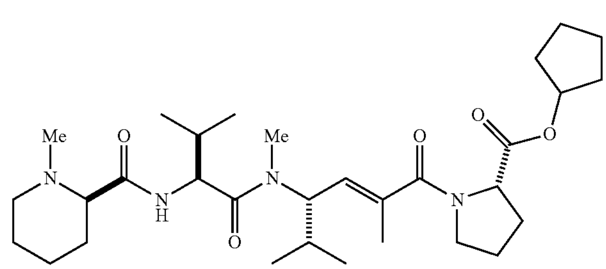 [SMILES: C/C(=C\[C@H](C(C)C)N(C)C(=O)[C@@H](NC(=O)[C@H]1CCCCN1C)C(C)C)C(=O)N1CCC[C@H]1C(=O)OC1CCCC1] |

| Compound | Structure |
|---|---|
| ER-808343 | 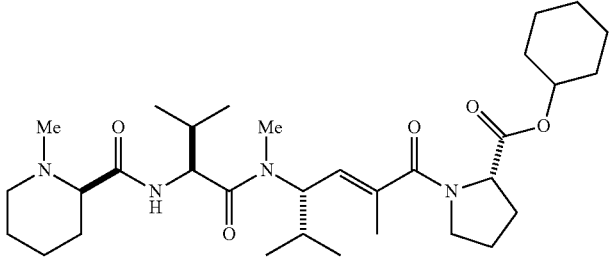 |
| ER-808344 | 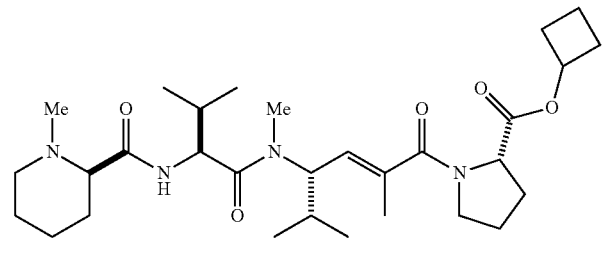 [SMILES: C/C(=C\[C@H](C(C)C)N(C)C(=O)[C@@H](NC(=O)[C@H]1CCCCN1C)C(C)C)C(=O)N1CCC[C@H]1C(=O)OC1CCC1] |
| ER-808345 | 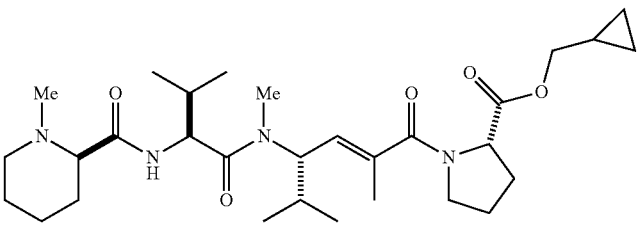 [SMILES: C/C(=C\[C@H](C(C)C)N(C)C(=O)[C@@H](NC(=O)[C@H]1CCCCN1C)C(C)C)C(=O)N1CCC[C@H]1C(=O)OCC1CC1] |
| ER-808357<br>single diastereomer | 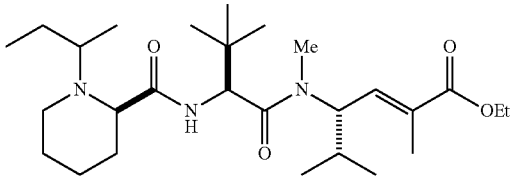 [SMILES: CCOC(=O)/C(C)=C/[C@H](C(C)C)N(C)C(=O)[C@@H](NC(=O)[C@H]1CCCCN1C(C)CC)C(C)(C)C] |
| ER-808358<br>single diastereomer | 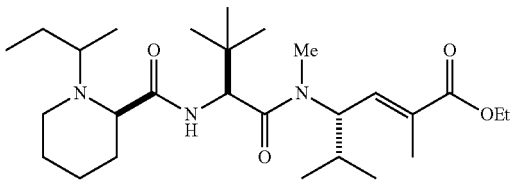 [SMILES: CCOC(=O)/C(C)=C/[C@H](C(C)C)N(C)C(=O)[C@@H](NC(=O)[C@H]1CCCCN1C(C)CC)C(C)(C)C] |
| ER-808359<br>single diastereomer | 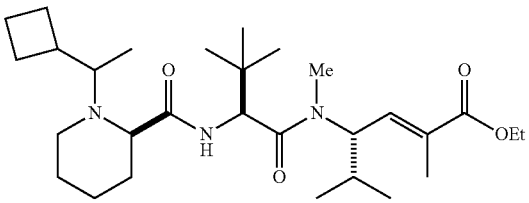 [SMILES: CCOC(=O)/C(C)=C/[C@H](C(C)C)N(C)C(=O)[C@@H](NC(=O)[C@H]1CCCCN1C(C)C1CCC1)C(C)(C)C] |
| ER-808366<br>single diastereomer | 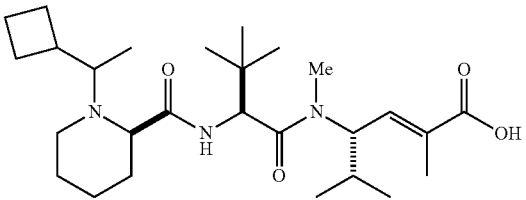 [SMILES: C/C(=C\[C@H](C(C)C)N(C)C(=O)[C@@H](NC(=O)[C@H]1CCCCN1C(C)C1CCC1)C(C)(C)C)C(=O)O] |

| Compound | Structure |
|---|---|
| ER-808367 | 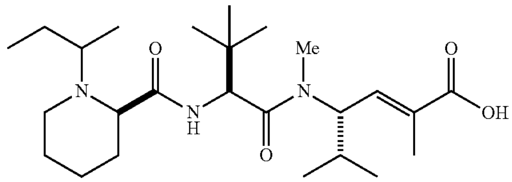 [SMILES: CCC(C)N1CCCC[C@@H]1C(=O)N[C@H](C(=O)N(C)[C@H](/C=C(\C)C(=O)O)C(C)C)C(C)(C)C] |
| ER-808368 | 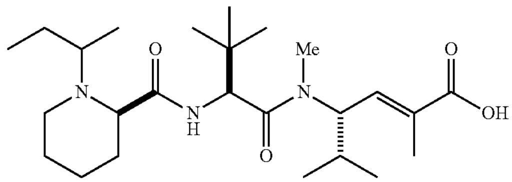 [SMILES: CCC(C)N1CCCC[C@@H]1C(=O)N[C@H](C(=O)N(C)[C@H](/C=C(\C)C(=O)O)C(C)C)C(C)(C)C] |
| ER-808383 | 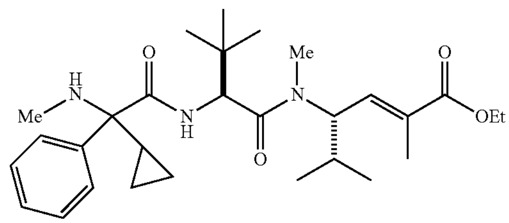 [SMILES: CCOC(=O)/C(C)=C/[C@H](C(C)C)N(C)C(=O)[C@@H](NC(=O)C(NC)(c1ccccc1)C1CC1)C(C)(C)C] |
| ER-808384 | 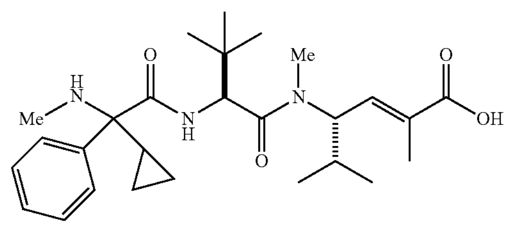 [SMILES: CNC(C(=O)N[C@H](C(=O)N(C)[C@H](/C=C(\C)C(=O)O)C(C)C)C(C)(C)C)(c1ccccc1)C1CC1] |
| ER-808389 | 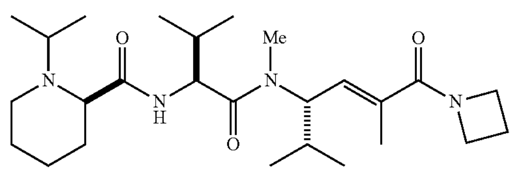 [SMILES: C/C(=C\[C@H](C(C)C)N(C)C(=O)[C@@H](NC(=O)[C@H]1CCCCN1C(C)C)C(C)C)C(=O)N1CCC1] |
| ER-808390 | 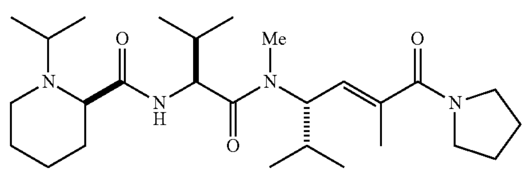 [SMILES: C/C(=C\[C@H](C(C)C)N(C)C(=O)[C@@H](NC(=O)[C@H]1CCCCN1C(C)C)C(C)C)C(=O)N1CCCC1] |
| ER-808391 | 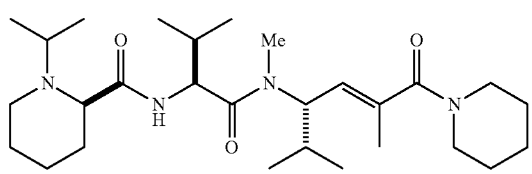 [SMILES: C/C(=C\[C@H](C(C)C)N(C)C(=O)[C@@H](NC(=O)[C@H]1CCCCN1C(C)C)C(C)C)C(=O)N1CCCCC1] |
| ER-808392 | 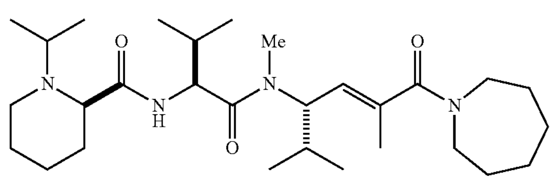 [SMILES: C/C(=C\[C@H](C(C)C)N(C)C(=O)[C@@H](NC(=O)[C@H]1CCCCN1C(C)C)C(C)C)C(=O)N1CCCCCC1] |

-continued
| Compound | Structure |
|---|---|
| ER-808393 | 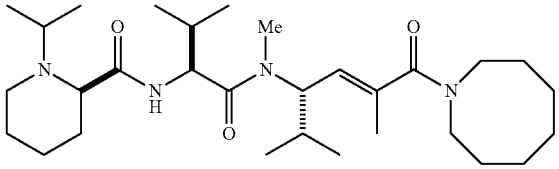 [SMILES: C/C(=C\[C@H](C(C)C)N(C)C(=O)[C@@H](NC(=O)[C@H]1CCCCN1C(C)C)C(C)C)C(=O)N1CCCCCCC1] |
| ER-808394 | 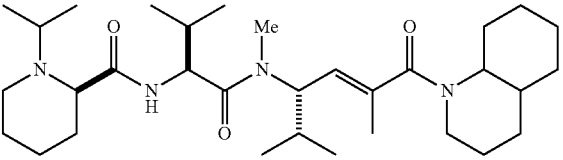 [SMILES: C/C(=C\[C@H](C(C)C)N(C)C(=O)[C@@H](NC(=O)[C@H]1CCCCN1C(C)C)C(C)C)C(=O)N1CCCC2CCCCC21] |
| ER-808395 | 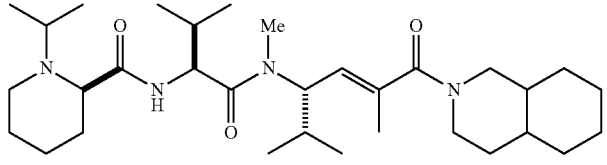 [SMILES: C/C(=C\[C@H](C(C)C)N(C)C(=O)[C@@H](NC(=O)[C@H]1CCCCN1C(C)C)C(C)C)C(=O)N1CCC2CCCCC2C1] |
| ER-808396 | 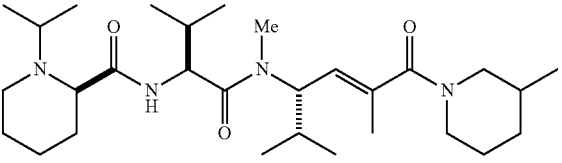 [SMILES: C/C(=C\[C@H](C(C)C)N(C)C(=O)[C@@H](NC(=O)[C@H]1CCCCN1C(C)C)C(C)C)C(=O)N1CCCC(C)C1] |
| ER-808397 | 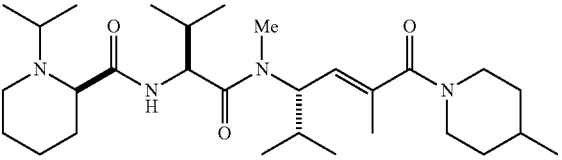 |
| ER-808398 | 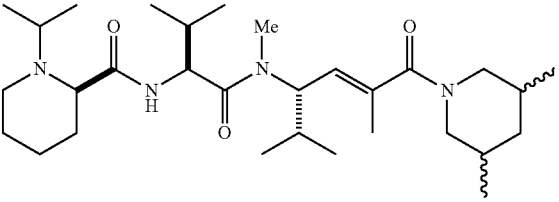 |
| ER-808399 | 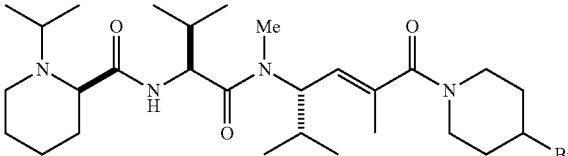 |
| ER-808400 | 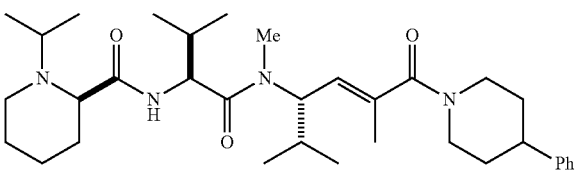 |

| Compound | Structure |
|---|---|
| ER-808401 | 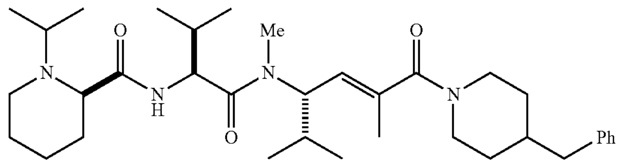 [SMILES: C/C(=C\[C@H](C(C)C)N(C)C(=O)[C@@H](NC(=O)[C@H]1CCCCN1C(C)C)C(C)C)C(=O)N1CCC(Cc2ccccc2)CC1] |
| ER-808402 | 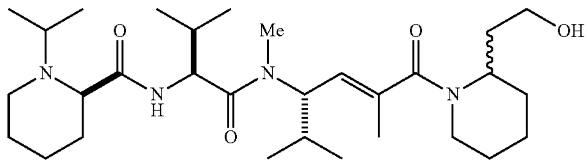 [SMILES: C/C(=C\[C@H](C(C)C)N(C)C(=O)[C@@H](NC(=O)[C@H]1CCCCN1C(C)C)C(C)C)C(=O)N1CCCCC1CCO] |
| ER-808403 | 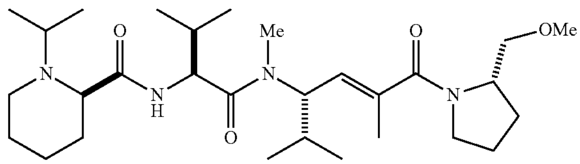 [SMILES: COC[C@@H]1CCCN1C(=O)/C(C)=C/[C@H](C(C)C)N(C)C(=O)[C@@H](NC(=O)[C@H]1CCCCN1C(C)C)C(C)C] |
| ER-808404 | 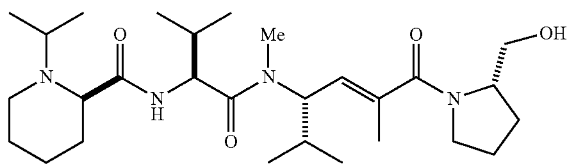 [SMILES: C/C(=C\[C@H](C(C)C)N(C)C(=O)[C@@H](NC(=O)[C@H]1CCCCN1C(C)C)C(C)C)C(=O)N1CCC[C@H]1CO] |
| ER-808433 | 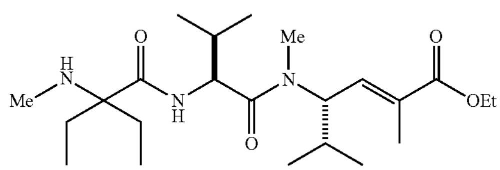 [SMILES: CCOC(=O)/C(C)=C/[C@H](C(C)C)N(C)C(=O)[C@@H](NC(=O)C(CC)(CC)NC)C(C)C] |
| ER-808434 | 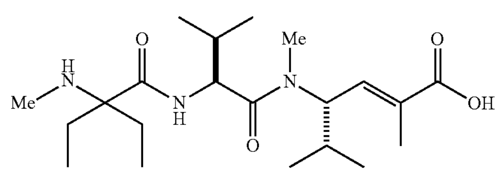 [SMILES: CCC(CC)(NC)C(=O)N[C@H](C(=O)N(C)[C@H](/C=C(\C)C(=O)O)C(C)C)C(C)C] |
| ER-808435 | 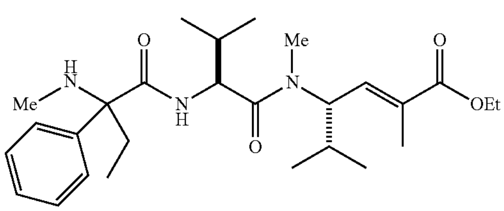 [SMILES: CCOC(=O)/C(C)=C/[C@H](C(C)C)N(C)C(=O)[C@@H](NC(=O)C(CC)(NC)c1ccccc1)C(C)C] |
| ER-808436 | 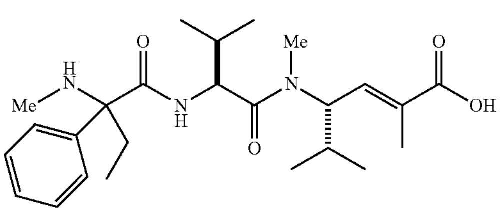 [SMILES: CCC(NC)(C(=O)N[C@H](C(=O)N(C)[C@H](/C=C(\C)C(=O)O)C(C)C)C(C)C)c1ccccc1] |

-continued

| Compound | Structure |
|---|---|
| ER-808437 | (structure) |
| ER-808447<br>Cis-substituents on the piperidine ring, but absolute stereochemistry is unknown.<br>Single diastereomer | (structure) |
| ER-808448<br>Cis-substituents on the piperidine ring, but absolute stereochemistry is unknown.<br>Single diastereomer | (structure) |
| ER-808449<br>Cis-substituents on the piperidine ring, but absolute stereochemistry is unknown.<br>Single diastereomer | (structure) |
| ER-808450<br>Cis-substituents on the piperidine ring, but absolute stereochemistry is unknown.<br>Single diastereomer | (structure) |
| ER-808451<br>Cis-substituents on the piperidine ring, but absolute stereochemistry is unknown.<br>Single diastereomer | (structure) |
| ER-808452<br>Cis-substituents on the piperidine ring, but absolute stereochemistry is unknown.<br>Single diastereomer | (structure) |
| ER-808453<br>Cis-substituents on the piperidine ring, but absolute sterochemistry is unknown.<br>Single diastereomer | (structure) |

-continued

| Compound | Structure |
|---|---|
| ER-808454 Cis-substituents on the piperidine ring, but absolute stereochemisty is unknown. Single diastereomer | |
| ER-808475 Single diastereomer | |
| ER-808476 Single diastereomer | |
| ER-808477 Single diastereomer | |
| ER-808478 Single diastereomer | |
| ER-808479 | |
| ER-808480 | |
| ER-808481 | |

-continued

| Compound | Structure |
|---|---|
| ER-808482 | 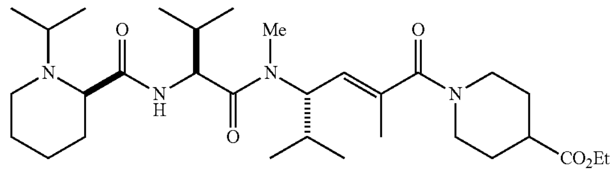 [SMILES: CCOC(=O)C1CCN(C(=O)/C(C)=C/[C@H](C(C)C)N(C)C(=O)[C@@H](NC(=O)[C@H]2CCCCN2C(C)C)C(C)C)CC1] |
| ER-808483 | 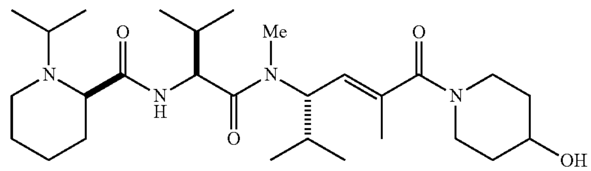 [SMILES: C/C(=C\[C@H](C(C)C)N(C)C(=O)[C@@H](NC(=O)[C@H]1CCCCN1C(C)C)C(C)C)C(=O)N1CCC(O)CC1] |
| ER-808484 | 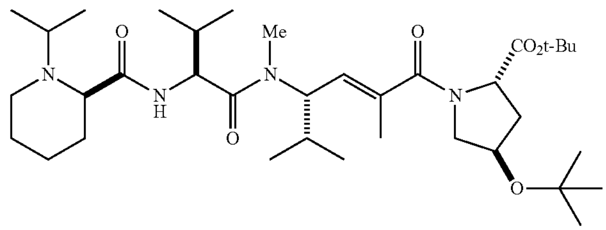 [SMILES: C/C(=C\[C@H](C(C)C)N(C)C(=O)[C@@H](NC(=O)[C@H]1CCCCN1C(C)C)C(C)C)C(=O)N1C[C@H](OC(C)(C)C)C[C@H]1C(=O)OC(C)(C)C] |
| ER-808485 | 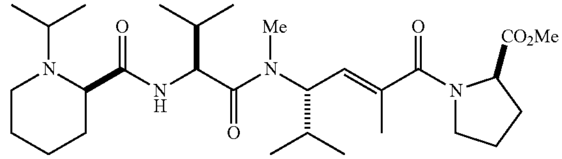 [SMILES: COC(=O)[C@H]1CCCN1C(=O)/C(C)=C/[C@H](C(C)C)N(C)C(=O)[C@@H](NC(=O)[C@H]1CCCCN1C(C)C)C(C)C] |
| ER-808486 | 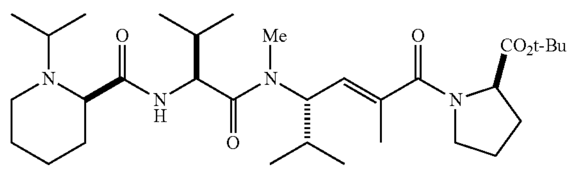 [SMILES: C/C(=C\[C@H](C(C)C)N(C)C(=O)[C@@H](NC(=O)[C@H]1CCCCN1C(C)C)C(C)C)C(=O)N1CCC[C@@H]1C(=O)OC(C)(C)C] |
| ER-808487 | 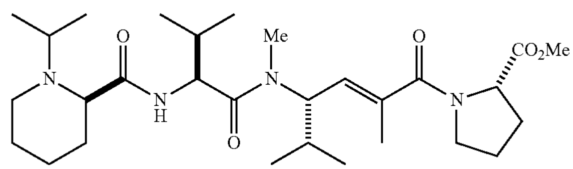 [SMILES: COC(=O)[C@@H]1CCCN1C(=O)/C(C)=C/[C@H](C(C)C)N(C)C(=O)[C@@H](NC(=O)[C@H]1CCCCN1C(C)C)C(C)C] |
| ER-808488 | 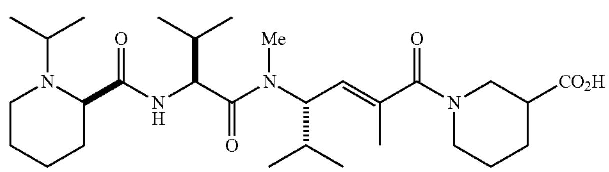 |
| ER-808489 | 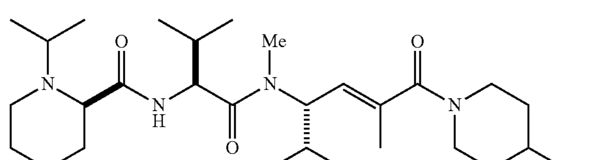 |

| Compound | Structure |
|---|---|
| ER-808490 | 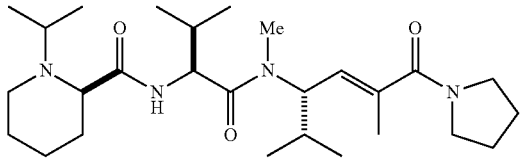 [SMILES: C/C(=C\[C@H](C(C)C)N(C)C(=O)[C@@H](NC(=O)[C@H]1CCCCN1C(C)C)C(C)C)C(=O)N1CCCC1] |
| ER-808491<br>Single diastereomer | 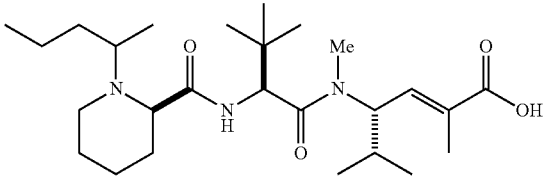 [SMILES: CCCC(C)N1CCCC[C@@H]1C(=O)N[C@H](C(=O)N(C)[C@H](/C=C(\C)C(=O)O)C(C)C)C(C)(C)C] |
| ER-808492<br>Single diastereomer | 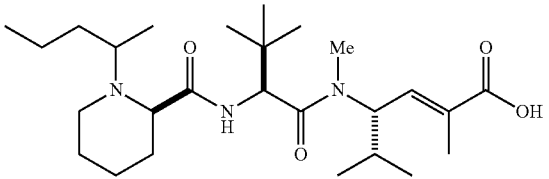 [SMILES: CCCC(C)N1CCCC[C@@H]1C(=O)N[C@H](C(=O)N(C)[C@H](/C=C(\C)C(=O)O)C(C)C)C(C)(C)C] |
| ER-808493<br>Single diastereomer | 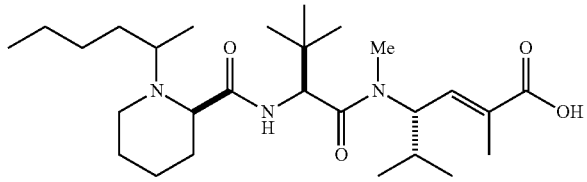 [SMILES: CCCCC(C)N1CCCC[C@@H]1C(=O)N[C@H](C(=O)N(C)[C@H](/C=C(\C)C(=O)O)C(C)C)C(C)(C)C] |
| ER-808494<br>Single diastereomer | 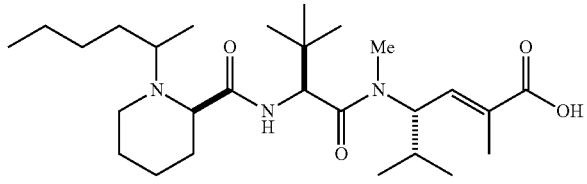 [SMILES: CCCCC(C)N1CCCC[C@@H]1C(=O)N[C@H](C(=O)N(C)[C@H](/C=C(\C)C(=O)O)C(C)C)C(C)(C)C] |
| ER-808495 | 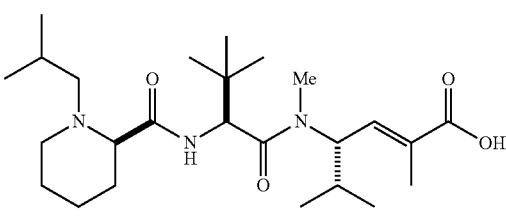 [SMILES: C/C(=C\[C@H](C(C)C)N(C)C(=O)[C@@H](NC(=O)[C@H]1CCCCN1CC(C)C)C(C)(C)C)C(=O)O] |
| ER-808552 | 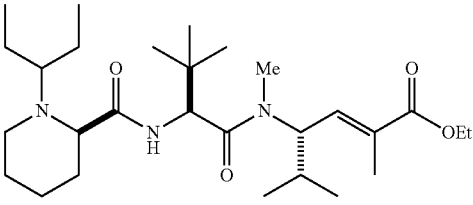 [SMILES: CCOC(=O)/C(C)=C/[C@H](C(C)C)N(C)C(=O)[C@@H](NC(=O)[C@H]1CCCCN1C(CC)CC)C(C)(C)C] |
| ER-808553 | 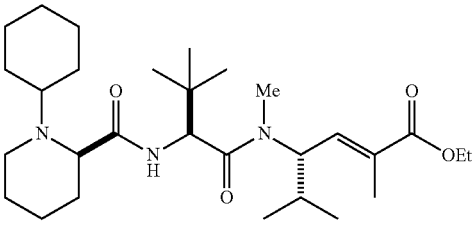 [SMILES: CCOC(=O)/C(C)=C/[C@H](C(C)C)N(C)C(=O)[C@@H](NC(=O)[C@H]1CCCCN1C1CCCCC1)C(C)(C)C] |

-continued

| Compound | Structure |
|---|---|
| ER-808563 | 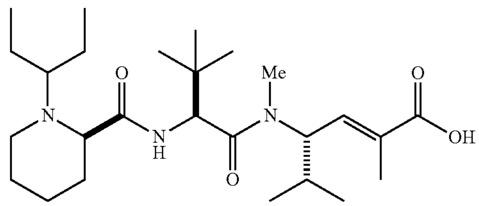 [SMILES: CCC(CC)N1CCCC[C@@H]1C(=O)N[C@H](C(=O)N(C)[C@H](/C=C(\C)C(=O)O)C(C)C)C(C)(C)C] |
| ER-808564 | 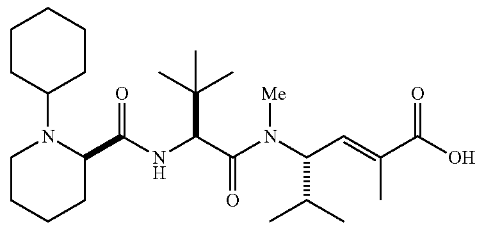 [SMILES: C/C(=C\[C@H](C(C)C)N(C)C(=O)[C@@H](NC(=O)[C@H]1CCCCN1C1CCCCC1)C(C)(C)C)C(=O)O] |
| ER-808565 | 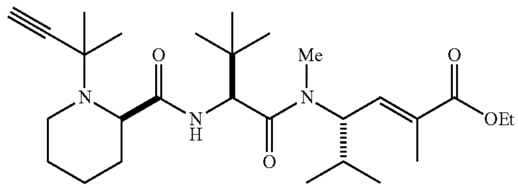 [SMILES: C#CC(C)(C)N1CCCC[C@@H]1C(=O)N[C@H](C(=O)N(C)[C@H](/C=C(\C)C(=O)OCC)C(C)C)C(C)(C)C] |
| ER-808566 | 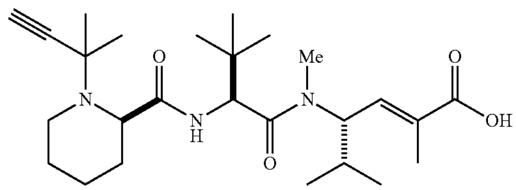 |
| ER-808567 | 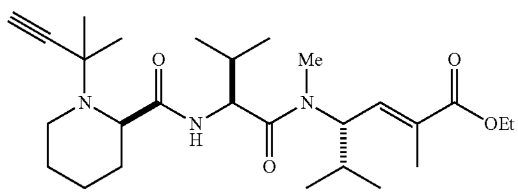 [SMILES: C#CC(C)(C)N1CCCC[C@@H]1C(=O)N[C@H](C(=O)N(C)[C@H](/C=C(\C)C(=O)OCC)C(C)C)C(C)C] |
| ER-808568 | 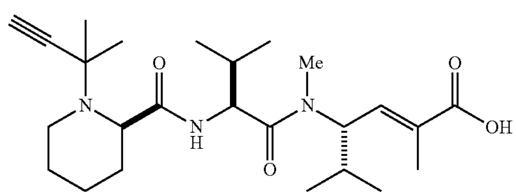 [SMILES: C#CC(C)(C)N1CCCC[C@@H]1C(=O)N[C@H](C(=O)N(C)[C@H](/C=C(\C)C(=O)O)C(C)C)C(C)C] |
| ER-808609 | 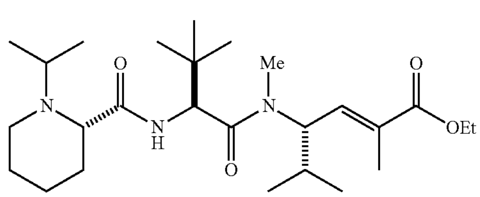 [SMILES: CCOC(=O)/C(C)=C/[C@H](C(C)C)N(C)C(=O)[C@@H](NC(=O)[C@@H]1CCCCN1C(C)C)C(C)(C)C] |

| Compound | Structure |
|---|---|
| ER-808610 | 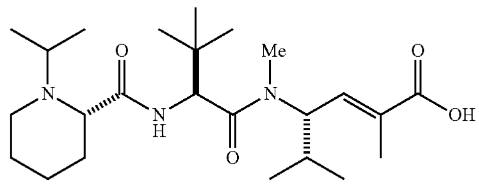 [SMILES: C/C(=C\[C@H](C(C)C)N(C)C(=O)[C@@H](NC(=O)[C@@H]1CCCCN1C(C)C)C(C)(C)C)C(=O)O] |
| ER-808656
Single diastereomer | |
| ER-808662
Single diastereomer | |
| ER-808674 | |
| ER-808676 | |
| ER-808677 | |
| ER-808678 | |

-continued
| Compound | Structure |
|---|---|
| ER-808679 | 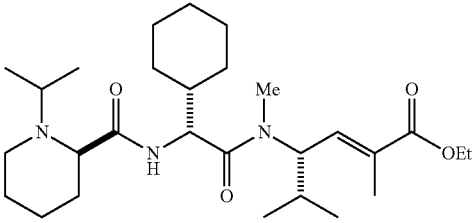 [SMILES: CCOC(=O)/C(C)=C/[C@H](C(C)C)N(C)C(=O)[C@H](NC(=O)[C@H]1CCCCN1C(C)C)C1CCCCC1] |
| ER-808680 | 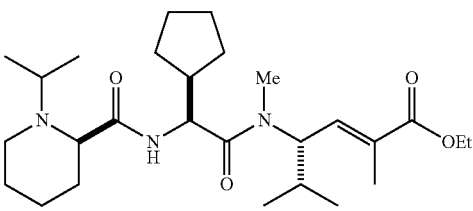 [SMILES: CCOC(=O)/C(C)=C/[C@H](C(C)C)N(C)C(=O)[C@@H](NC(=O)[C@H]1CCCCN1C(C)C)C1CCCC1] |
| ER-808681 | 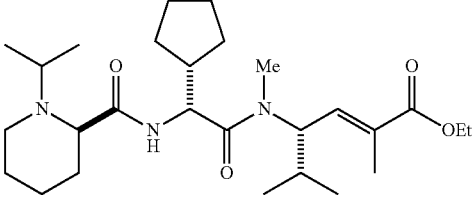 [SMILES: CCOC(=O)/C(C)=C/[C@H](C(C)C)N(C)C(=O)[C@H](NC(=O)[C@H]1CCCCN1C(C)C)C1CCCC1] |
| ER-808682 | 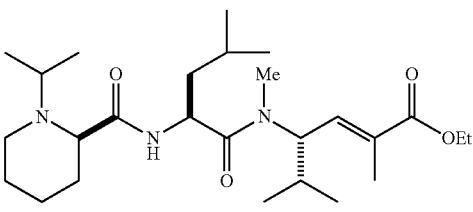 [SMILES: CCOC(=O)/C(C)=C/[C@H](C(C)C)N(C)C(=O)[C@H](CC(C)C)NC(=O)[C@H]1CCCCN1C(C)C] |
| ER-808683 | 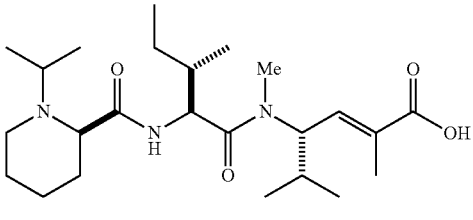 [SMILES: CC[C@H](C)[C@H](NC(=O)[C@H]1CCCCN1C(C)C)C(=O)N(C)[C@H](/C=C(\C)C(=O)O)C(C)C] |
| ER-808684 | 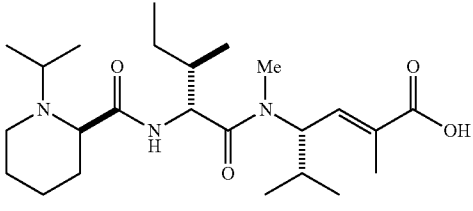 [SMILES: CC[C@@H](C)[C@@H](NC(=O)[C@H]1CCCCN1C(C)C)C(=O)N(C)[C@H](/C=C(\C)C(=O)O)C(C)C] |
| ER-808685 | 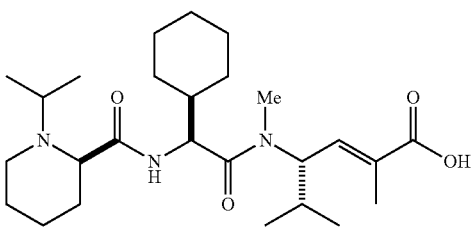 [SMILES: C/C(=C\[C@H](C(C)C)N(C)C(=O)[C@@H](NC(=O)[C@H]1CCCCN1C(C)C)C1CCCCC1)C(=O)O] |

-continued

| Compound | Structure |
|---|---|
| ER-808686 | 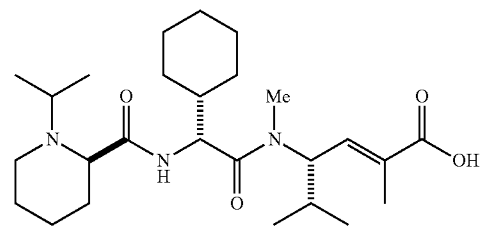 [SMILES: C/C(=C\[C@H](C(C)C)N(C)C(=O)[C@H](NC(=O)[C@H]1CCCCN1C(C)C)C1CCCCC1)C(=O)O] |
| ER-808687 | 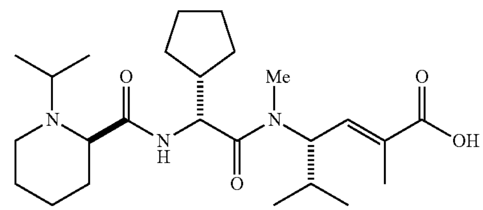 |
| ER-808688 | 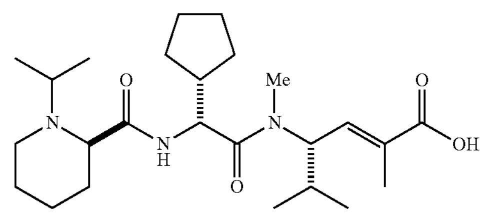 [SMILES: C/C(=C\[C@H](C(C)C)N(C)C(=O)[C@H](NC(=O)[C@H]1CCCCN1C(C)C)C1CCCC1)C(=O)O] |
| ER-808689 | 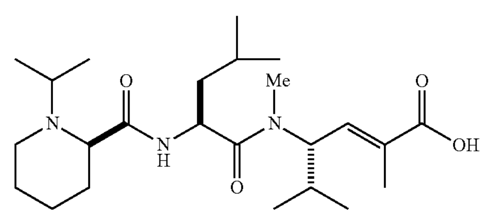 [SMILES: C/C(=C\[C@H](C(C)C)N(C)C(=O)[C@H](CC(C)C)NC(=O)[C@H]1CCCCN1C(C)C)C(=O)O] |
| ER-808690 | 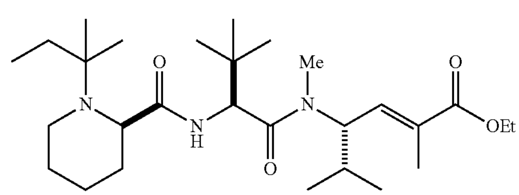 [SMILES: CCOC(=O)/C(C)=C/[C@H](C(C)C)N(C)C(=O)[C@@H](NC(=O)[C@H]1CCCCN1C(C)(C)CC)C(C)(C)C] |
| ER-808693 | 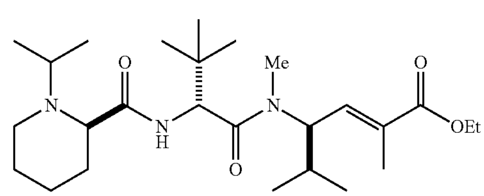 |
| ER-808694 | 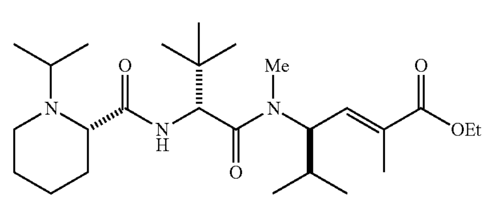 |

-continued

| Compound | Structure |
|---|---|
| ER-808695 | 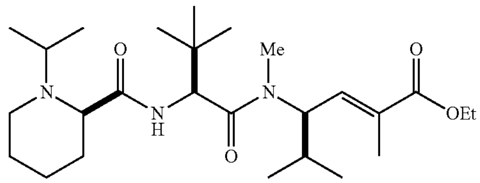 [SMILES: CCOC(=O)/C(C)=C/[C@@H](C(C)C)N(C)C(=O)[C@@H](NC(=O)[C@H]1CCCCN1C(C)C)C(C)(C)C] |
| ER-808696 | 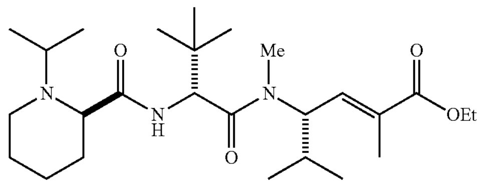 [SMILES: CCOC(=O)/C(C)=C/[C@H](C(C)C)N(C)C(=O)[C@H](NC(=O)[C@H]1CCCCN1C(C)C)C(C)(C)C] |
| ER-808697 | 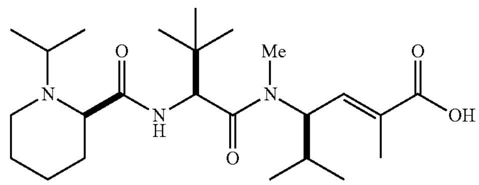 |
| ER-808698 | 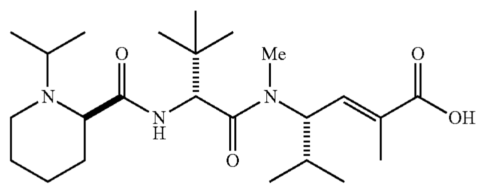 [SMILES: C/C(=C\[C@H](C(C)C)N(C)C(=O)[C@H](NC(=O)[C@H]1CCCCN1C(C)C)C(C)(C)C)C(=O)O] |
| ER-808699 | 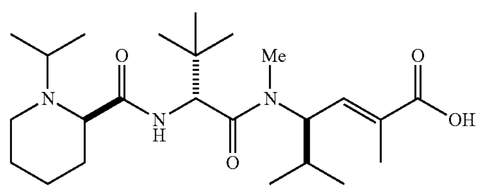 [SMILES: C/C(=C\[C@@H](C(C)C)N(C)C(=O)[C@H](NC(=O)[C@H]1CCCCN1C(C)C)C(C)(C)C)C(=O)O] |
| ER-808700 | 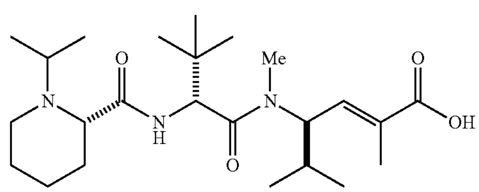 |
| ER-808706 Single diastereomer | 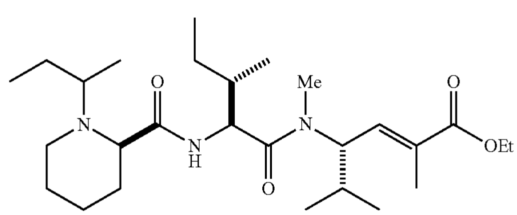 [SMILES: CCOC(=O)/C(C)=C/[C@H](C(C)C)N(C)C(=O)[C@@H](NC(=O)[C@H]1CCCCN1C(C)CC)[C@@H](C)CC] |
| ER-808707 Single diastereomer | 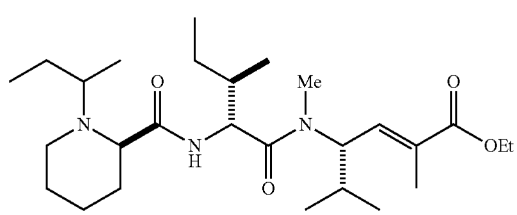 [SMILES: CCOC(=O)/C(C)=C/[C@H](C(C)C)N(C)C(=O)[C@H](NC(=O)[C@H]1CCCCN1C(C)CC)[C@H](C)CC] |

-continued

| Compound | Structure |
|---|---|
| ER-808708<br>Single diastereomer | 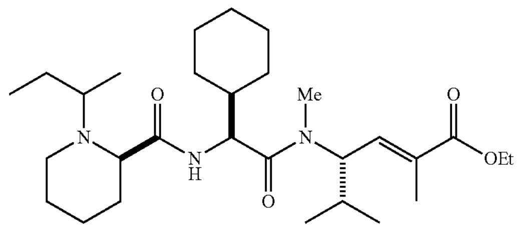 [SMILES: CCOC(=O)/C(C)=C/[C@H](C(C)C)N(C)C(=O)[C@@H](NC(=O)[C@H]1CCCCN1C(C)CC)C1CCCCC1] |
| ER-80870<br>Single diastereomer | 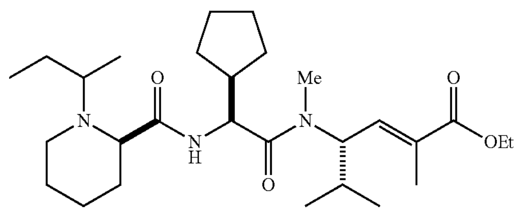 [SMILES: CCOC(=O)/C(C)=C/[C@H](C(C)C)N(C)C(=O)[C@@H](NC(=O)[C@H]1CCCCN1C(C)CC)C1CCCC1] |
| ER-808710<br>Single diastereomer | 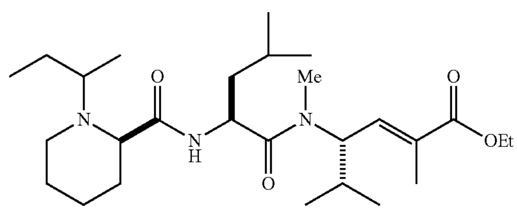 [SMILES: CCOC(=O)/C(C)=C/[C@H](C(C)C)N(C)C(=O)[C@H](CC(C)C)NC(=O)[C@H]1CCCCN1C(C)CC] |
| ER-808731 | 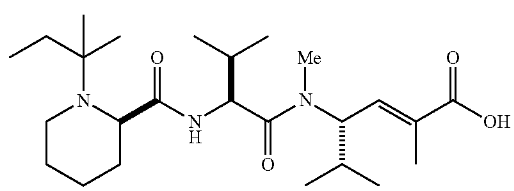 [SMILES: CCC(C)(C)N1CCCC[C@@H]1C(=O)N[C@H](C(=O)N(C)[C@H](/C=C(\C)C(=O)O)C(C)C)C(C)C] |
| ER-808732 | 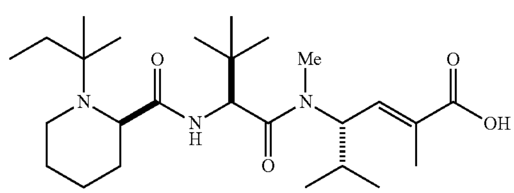 [SMILES: CCC(C)(C)N1CCCC[C@@H]1C(=O)N[C@H](C(=O)N(C)[C@H](/C=C(\C)C(=O)O)C(C)C)C(C)(C)C] |
| ER-808774<br>Single diastereomer | 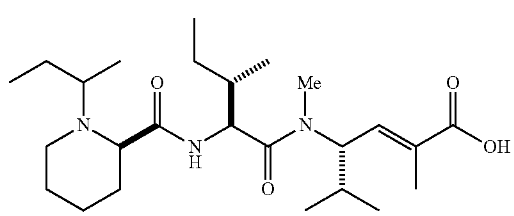 [SMILES: CCC(C)N1CCCC[C@@H]1C(=O)N[C@H](C(=O)N(C)[C@H](/C=C(\C)C(=O)O)C(C)C)[C@@H](C)CC] |
| ER-808775<br>Single diastereomer | 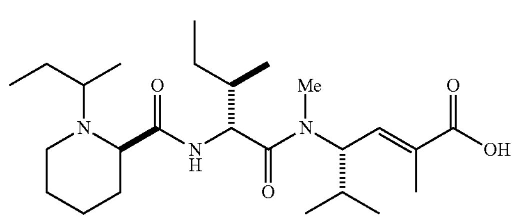 [SMILES: CCC(C)N1CCCC[C@@H]1C(=O)N[C@@H](C(=O)N(C)[C@H](/C=C(\C)C(=O)O)C(C)C)[C@H](C)CC] |

-continued

| Compound | Structure |
|---|---|
| ER-808777<br>Single diastereomer | 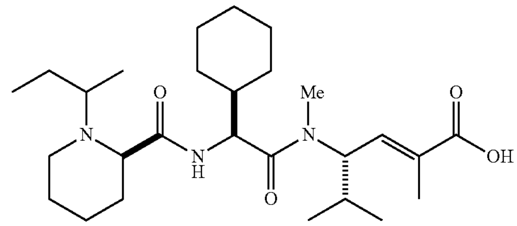 |
| ER-808779<br>Single diastereomer | 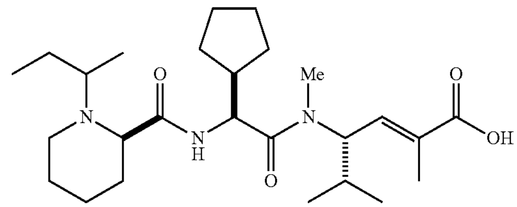 [SMILES: CCC(C)N1CCCC[C@@H]1C(=O)N[C@H](C(=O)N(C)[C@H](/C=C(\C)C(=O)O)C(C)C)C1CCCC1] |
| ER-808780<br>Single diastereomer | 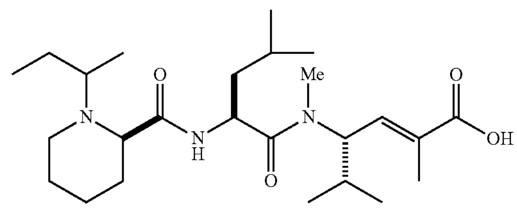 [SMILES: CCC(C)N1CCCC[C@@H]1C(=O)N[C@@H](CC(C)C)C(=O)N(C)[C@H](/C=C(\C)C(=O)O)C(C)C] |
| ER-808815<br>Single diastereomer | 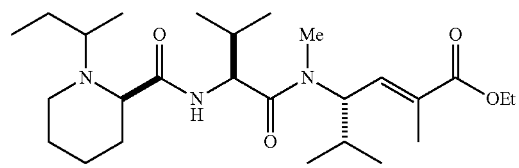 [SMILES: CCOC(=O)/C(C)=C/[C@H](C(C)C)N(C)C(=O)[C@@H](NC(=O)[C@H]1CCCCN1C(C)CC)C(C)C] |
| ER-808816<br>Single diastereomer | 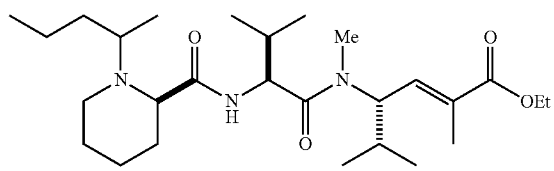 [SMILES: CCCC(C)N1CCCC[C@@H]1C(=O)N[C@H](C(=O)N(C)[C@H](/C=C(\C)C(=O)OCC)C(C)C)C(C)C] |
| ER-808817<br>Single diastereomer | 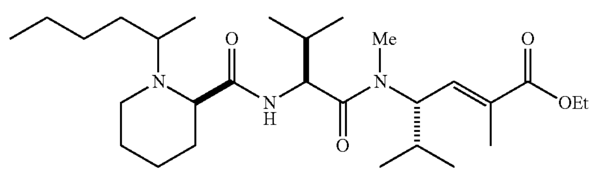 [SMILES: CCCCC(C)N1CCCC[C@@H]1C(=O)N[C@H](C(=O)N(C)[C@H](/C=C(\C)C(=O)OCC)C(C)C)C(C)C] |
| ER-808818<br>Cis-substituents on the piperidine ring, but absolute stereochemistry is unknown.<br>Single diastereomer | 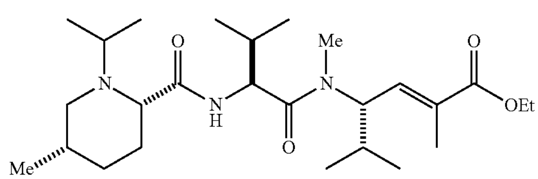 [SMILES: CCOC(=O)/C(C)=C/[C@H](C(C)C)N(C)C(=O)[C@@H](NC(=O)[C@@H]1CC[C@H](C)CN1C(C)C)C(C)C] |
| ER-808819<br>Cis-substituents on the piperidine ring, but absolute stereochemistry is unknown.<br>Single diastereomer | 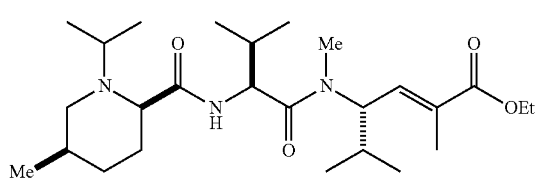 [SMILES: CCOC(=O)/C(C)=C/[C@H](C(C)C)N(C)C(=O)[C@@H](NC(=O)[C@H]1CCCCN1C(C)C)C(C)C ; "Me"] |

-continued

| Compound | Structure |
|---|---|
| ER-808820<br>Cis-substituents on the piperidine ring, but absolute stereochemistry is unknown.<br>Single diastereomer | 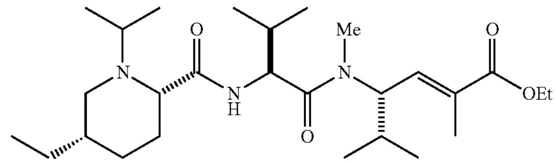 [SMILES: CCOC(=O)/C(C)=C/[C@H](C(C)C)N(C)C(=O)[C@@H](NC(=O)[C@@H]1CC[C@H](CC)CN1C(C)C)C(C)C] |
| ER-808821<br>Cis-substituents on the piperidine ring, but absolute stereochemistry is unknown.<br>Single diastereomer | 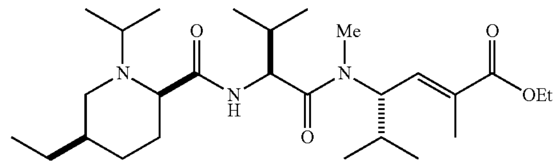 |
| ER-808822<br>Cis-substituents on the piperidine ring, but absolute stereochemistry is unknown.<br>Single diastereomer | 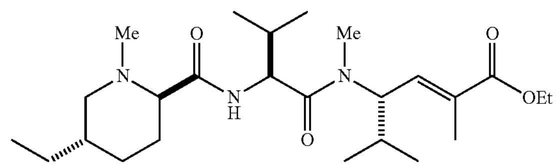 [SMILES: CCOC(=O)/C(C)=C/[C@H](C(C)C)N(C)C(=O)[C@@H](NC(=O)[C@H]1CC[C@H](CC)CN1C)C(C)C] |
| ER-808823<br>Cis-substituents on the piperidine ring, but absolute stereochemisty is unknown.<br>Single diastereomer | 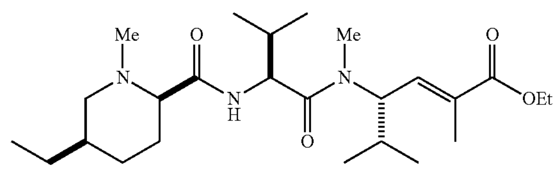 |
| ER-808824 | 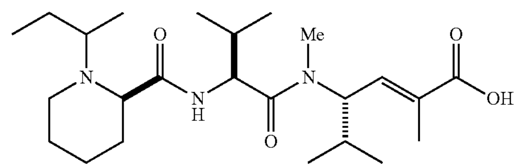 [SMILES: CCC(C)N1CCCC[C@@H]1C(=O)N[C@H](C(=O)N(C)[C@H](/C=C(\C)C(=O)O)C(C)C)C(C)C] |
| ER-808825 | 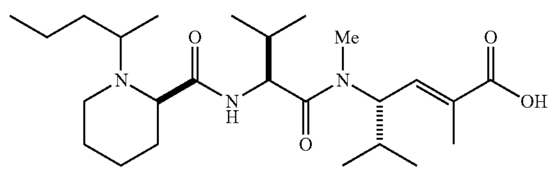 [SMILES: CCCC(C)N1CCCC[C@@H]1C(=O)N[C@H](C(=O)N(C)[C@H](/C=C(\C)C(=O)O)C(C)C)C(C)C] |
| ER-808826<br>Single diastereomer | 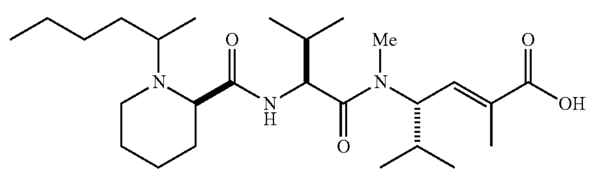 [SMILES: CCCCC(C)N1CCCC[C@@H]1C(=O)N[C@H](C(=O)N(C)[C@H](/C=C(\C)C(=O)O)C(C)C)C(C)C] |
| ER-808827<br>Cis-substituents on the piperidine ring, but absolute stereochemistry is unknown.<br>Single diastereomer | 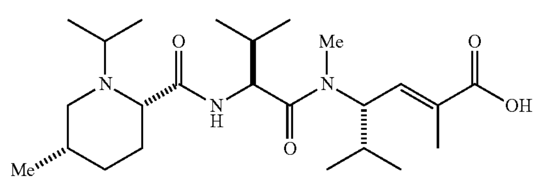 [SMILES: C/C(=C\[C@H](C(C)C)N(C)C(=O)[C@@H](NC(=O)[C@@H]1CC[C@H](C)CN1C(C)C)C(C)C)C(=O)O] |
| ER-808828<br>Cis-substituents on the piperidine ring, but absolute stereochemistry is unknown.<br>Single diastereomer | 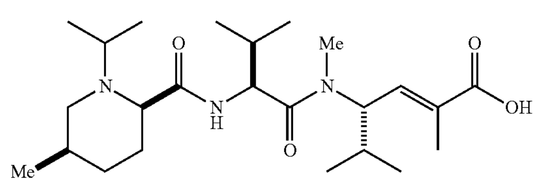 [SMILES: C/C(=C\[C@H](C(C)C)N(C)C(=O)[C@@H](NC(=O)[C@H]1CCCCN1C(C)C)C(C)C)C(=O)O ; "Me"] |

-continued

| Compound | Structure |
|---|---|
| ER-808829<br>Cis-substituents on the piperidine ring, but absolute stereochemistry is unknown.<br>Single diastereomer | 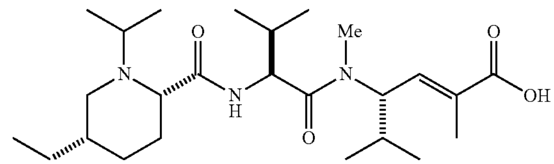 [SMILES: CC[C@H]1CC[C@@H](C(=O)N[C@H](C(=O)N(C)[C@H](/C=C(\C)C(=O)O)C(C)C)C(C)C)N(C(C)C)C1] |
| ER-808830<br>Cis-substituents on the piperidine ring, but absolute stereochemistry is unknown.<br>Single diastereomer | 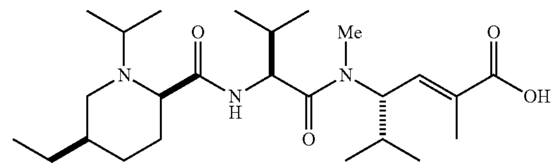 |
| ER-808831<br>Cis-substituents on the piperidine ring, but absolute stereochemistry is unknown.<br>Single diastereomer | 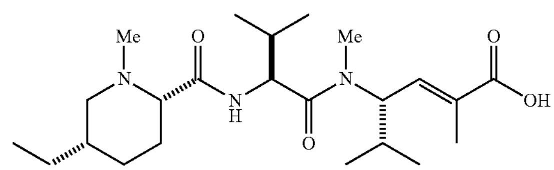 [SMILES: CC[C@H]1CC[C@@H](C(=O)N[C@H](C(=O)N(C)[C@H](/C=C(\C)C(=O)O)C(C)C)C(C)C)N(C)C1] |
| ER-808832<br>Cis-substituents on the piperidine ring, but absolute stereochemistry is unknown.<br>Single diastereomer | 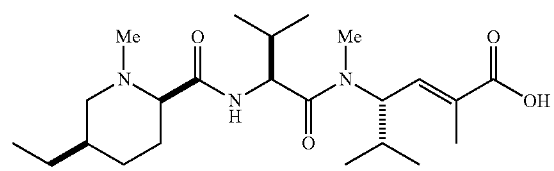 |
| ER-808861 | 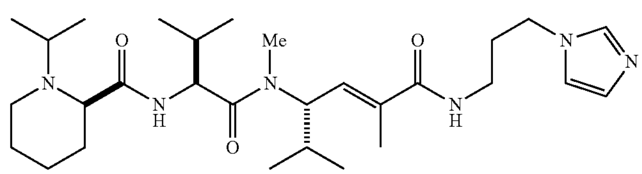 [SMILES: C/C(=C\[C@H](C(C)C)N(C)C(=O)[C@@H](NC(=O)[C@H]1CCCCN1C(C)C)C(C)C)C(=O)NCCCn1ccnc1] |
| ER-808862 | 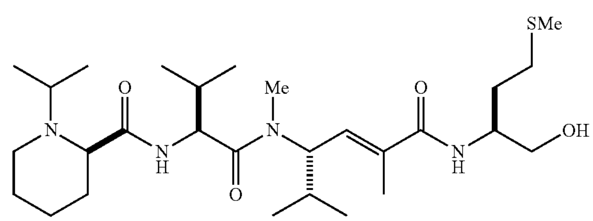 [SMILES: CSCC[C@@H](CO)NC(=O)/C(C)=C/[C@H](C(C)C)N(C)C(=O)[C@@H](NC(=O)[C@H]1CCCCN1C(C)C)C(C)C] |
| ER-808863 | 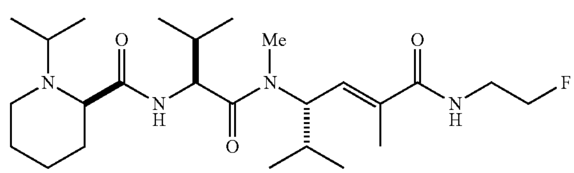 [SMILES: C/C(=C\[C@H](C(C)C)N(C)C(=O)[C@@H](NC(=O)[C@H]1CCCCN1C(C)C)C(C)C)C(=O)NCCF] |
| ER-808864 | 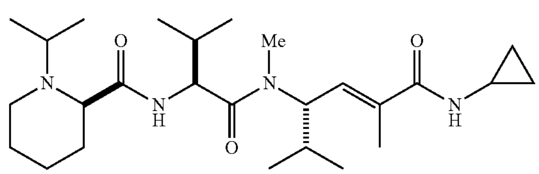 [SMILES: C/C(=C\[C@H](C(C)C)N(C)C(=O)[C@@H](NC(=O)[C@H]1CCCCN1C(C)C)C(C)C)C(=O)NC1CC1] |
| ER-808865 | 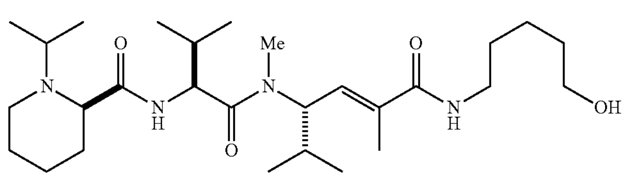 [SMILES: C/C(=C\[C@H](C(C)C)N(C)C(=O)[C@@H](NC(=O)[C@H]1CCCCN1C(C)C)C(C)C)C(=O)NCCCCCO] |

| Compound | Structure |
|---|---|
| ER-808866 | 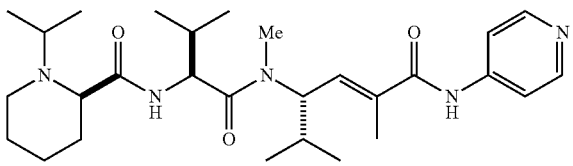 [SMILES: C/C(=C\[C@H](C(C)C)N(C)C(=O)[C@@H](NC(=O)[C@H]1CCCCN1C(C)C)C(C)C)C(=O)Nc1ccncc1] |
| ER-808867 | 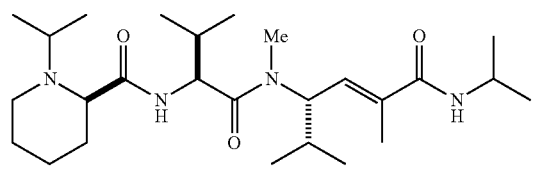 [SMILES: C/C(=C\[C@H](C(C)C)N(C)C(=O)[C@@H](NC(=O)[C@H]1CCCCN1C(C)C)C(C)C)C(=O)NC(C)C] |
| ER-808868 | 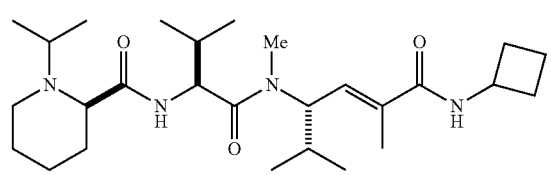 [SMILES: C/C(=C\[C@H](C(C)C)N(C)C(=O)[C@@H](NC(=O)[C@H]1CCCCN1C(C)C)C(C)C)C(=O)NC1CCC1] |
| ER-808869 | 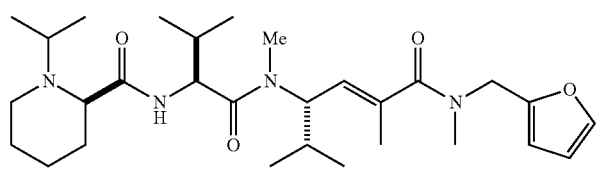 [SMILES: C/C(=C\[C@H](C(C)C)N(C)C(=O)[C@@H](NC(=O)[C@H]1CCCCN1C(C)C)C(C)C)C(=O)N(C)Cc1ccco1] |
| ER-808870 | 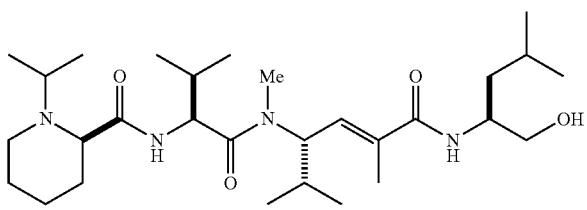 [SMILES: C/C(=C\[C@H](C(C)C)N(C)C(=O)[C@@H](NC(=O)[C@H]1CCCCN1C(C)C)C(C)C)C(=O)N[C@H](CO)CC(C)C] |
| ER-808871 | 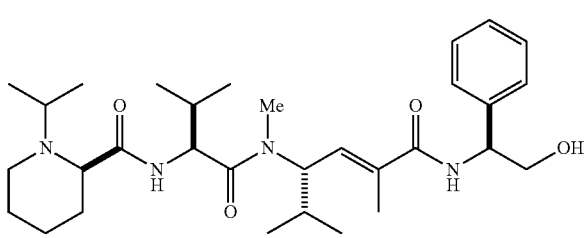 [SMILES: C/C(=C\[C@H](C(C)C)N(C)C(=O)[C@@H](NC(=O)[C@H]1CCCCN1C(C)C)C(C)C)C(=O)N[C@H](CO)c1ccccc1] |
| ER-808872 | 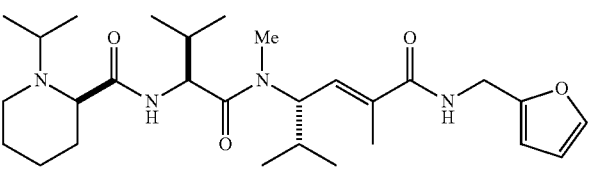 |
| ER-808873 | 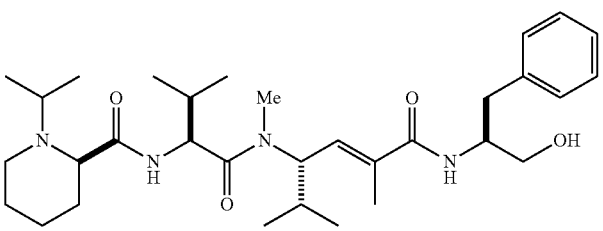 |

-continued

| Compound | Structure |
|---|---|
| ER-808874 | 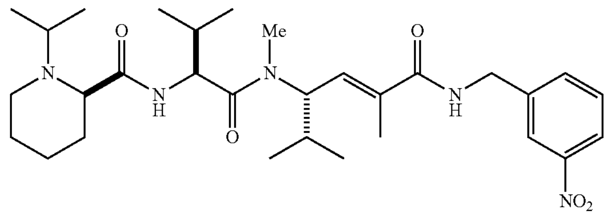 [SMILES: C/C(=C\[C@H](C(C)C)N(C)C(=O)[C@@H](NC(=O)[C@H]1CCCCN1C(C)C)C(C)C)C(=O)NCc1cccc([N+](=O)[O-])c1] |
| ER-808875 | 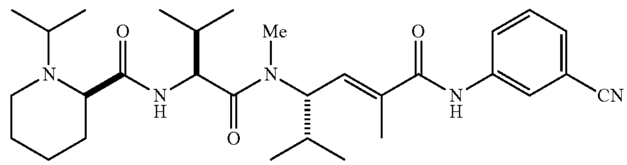 [SMILES: C/C(=C\[C@H](C(C)C)N(C)C(=O)[C@@H](NC(=O)[C@H]1CCCCN1C(C)C)C(C)C)C(=O)Nc1cccc(C#N)c1] |
| ER-808876 | 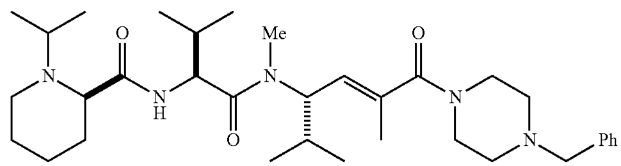 [SMILES: C/C(=C\[C@H](C(C)C)N(C)C(=O)[C@@H](NC(=O)[C@H]1CCCCN1C(C)C)C(C)C)C(=O)N1CCN(Cc2ccccc2)CC1] |
| ER-808877 | 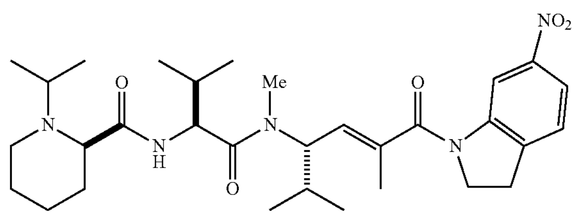 [SMILES: C/C(=C\[C@H](C(C)C)N(C)C(=O)[C@@H](NC(=O)[C@H]1CCCCN1C(C)C)C(C)C)C(=O)N1CCc2ccc([N+](=O)[O-])cc21] |
| ER-808878 | 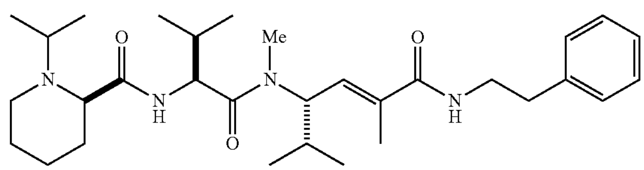 |
| ER-808879 | 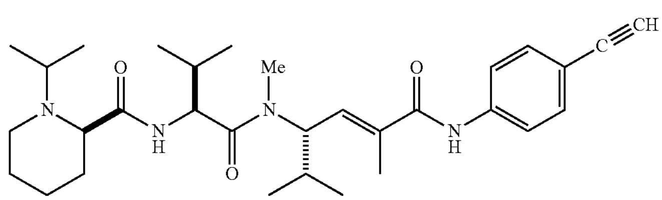 [SMILES: C#Cc1ccc(NC(=O)/C(C)=C/[C@H](C(C)C)N(C)C(=O)[C@@H](NC(=O)[C@H]2CCCCN2C(C)C)C(C)C)cc1] |
| ER-808880 | 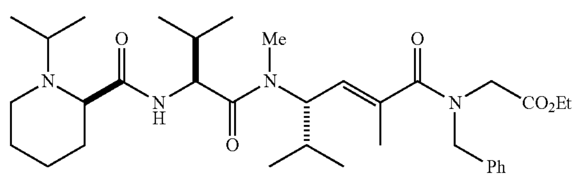 [SMILES: CCOC(=O)CN(Cc1ccccc1)C(=O)/C(C)=C/[C@H](C(C)C)N(C)C(=O)[C@@H](NC(=O)[C@H]1CCCCN1C(C)C)C(C)C] |
| ER-808881 | 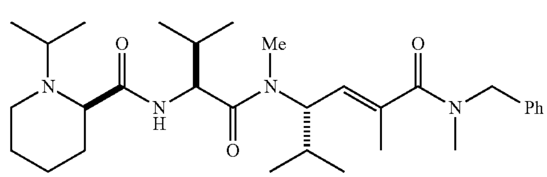 |

-continued

| Compound | Structure |
|---|---|
| ER-808882 | 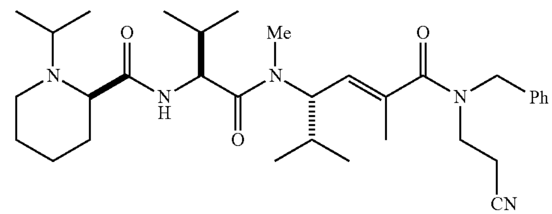 |
| ER-808883 | 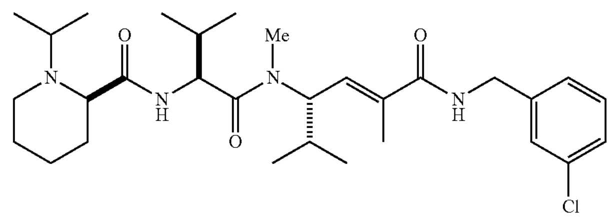 |
| ER-808884 | 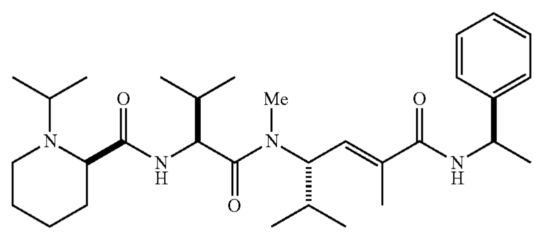 [SMILES: C/C(=C\[C@H](C(C)C)N(C)C(=O)[C@@H](NC(=O)[C@H]1CCCCN1C(C)C)C(C)C)C(=O)N[C@H](C)c1ccccc1] |
| ER-808885 | 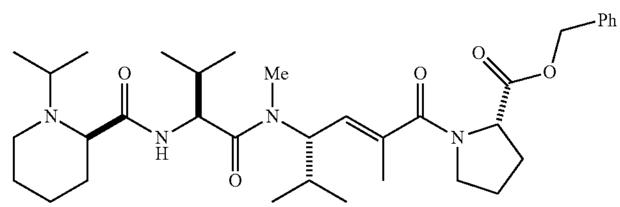 |
| ER-808886 | 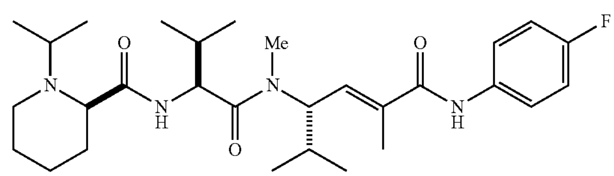 |
| ER-808887 | 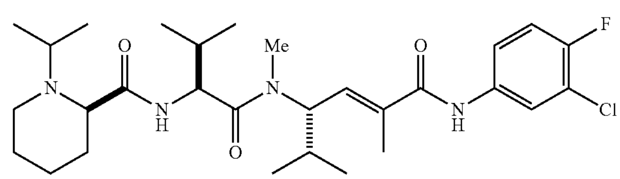 |
| ER-808888 | 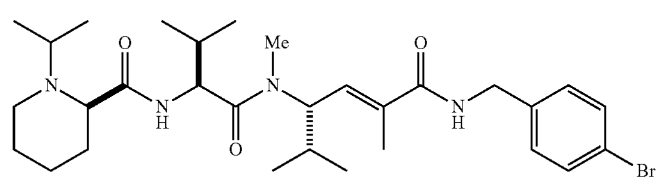 [SMILES: C/C(=C\[C@H](C(C)C)N(C)C(=O)[C@@H](NC(=O)[C@H]1CCCCN1C(C)C)C(C)C)C(=O)NCc1ccc(Br)cc1] |

-continued

| Compound | Structure |
|---|---|
| ER-808889 | 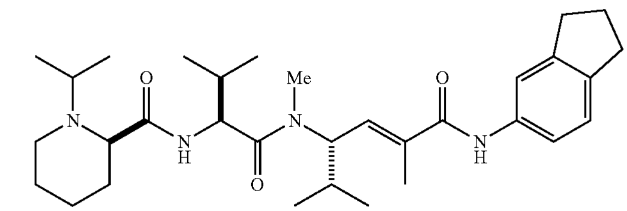 |
| ER-808890 | 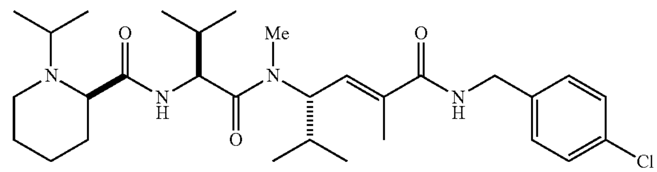 |
| ER-808891 | 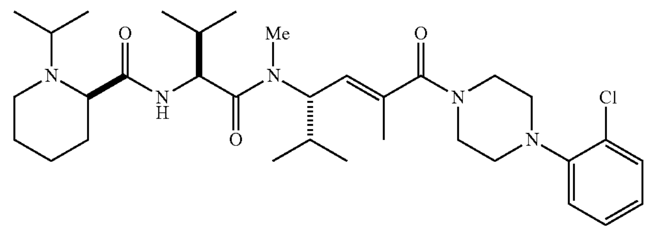 |
| ER-808892 | 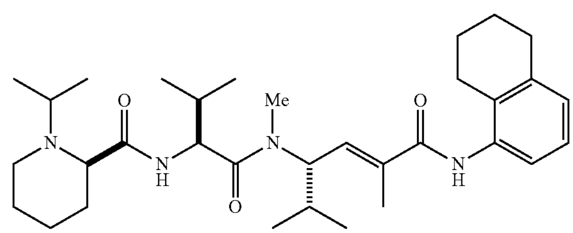 [SMILES: C/C(=C\[C@H](C(C)C)N(C)C(=O)[C@@H](NC(=O)[C@H]1CCCCN1C(C)C)C(C)C)C(=O)Nc1cccc2c1CCCC2] |
| ER-808893 | 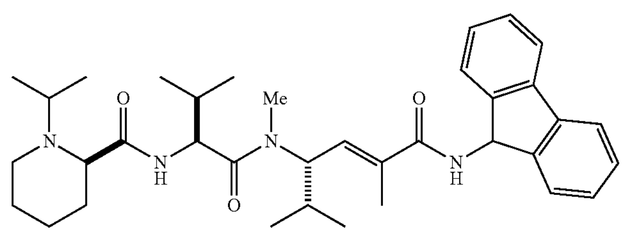 [SMILES: C/C(=C\[C@H](C(C)C)N(C)C(=O)[C@@H](NC(=O)[C@H]1CCCCN1C(C)C)C(C)C)C(=O)NC1c2ccccc2-c2ccccc21] |
| ER-808894 | 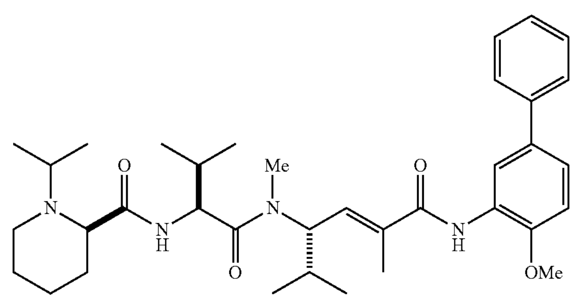 |
| ER-808895 | 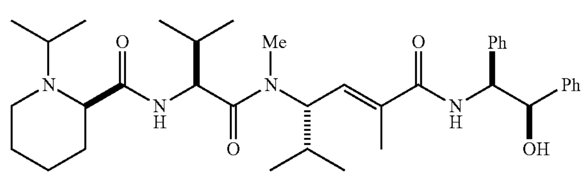 [SMILES: C/C(=C\[C@H](C(C)C)N(C)C(=O)[C@@H](NC(=O)[C@H]1CCCCN1C(C)C)C(C)C)C(=O)NC[C@H](O)c1ccccc1 ; "Ph"] |

-continued

| Compound | Structure |
|---|---|
| ER-808896 | 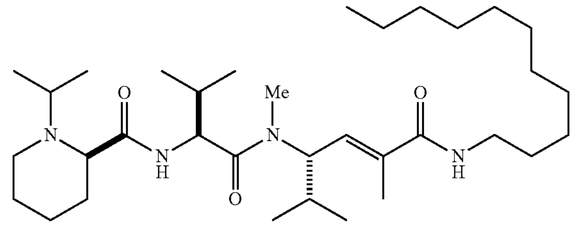 [SMILES: CCCCCCCCCCCNC(=O)/C(C)=C/[C@H](C(C)C)N(C)C(=O)[C@@H](NC(=O)[C@H]1CCCCN1C(C)C)C(C)C] |
| ER-808897 | 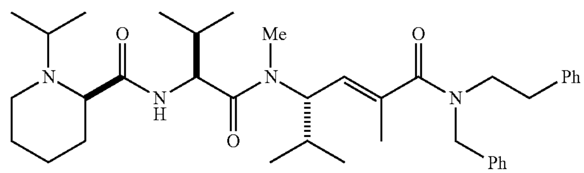 [SMILES: C/C(=C\[C@H](C(C)C)N(C)C(=O)[C@@H](NC(=O)[C@H]1CCCCN1C(C)C)C(C)C)C(=O)N(CCc1ccccc1)Cc1ccccc1] |
| ER-808898 | 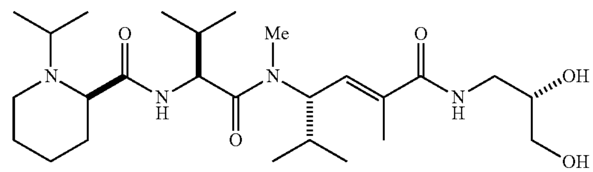 |
| ER-808899 | 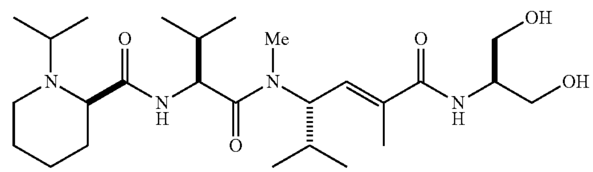 |
| ER-808900 | 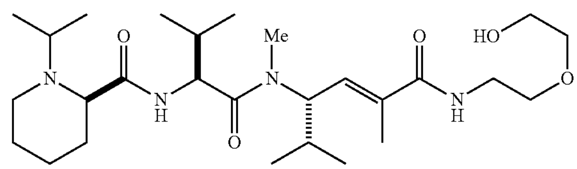 [SMILES: C/C(=C\[C@H](C(C)C)N(C)C(=O)[C@@H](NC(=O)[C@H]1CCCCN1C(C)C)C(C)C)C(=O)NCCOCCO] |
| ER-808901 | 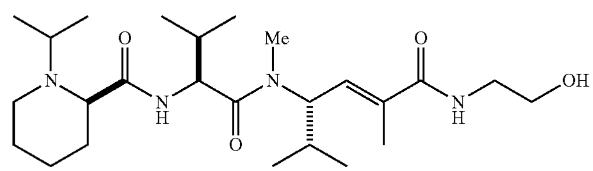 [SMILES: C/C(=C\[C@H](C(C)C)N(C)C(=O)[C@@H](NC(=O)[C@H]1CCCCN1C(C)C)C(C)C)C(=O)NCCO] |
| ER-808902 | 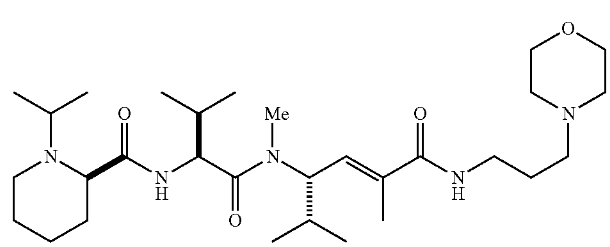 [SMILES: C/C(=C\[C@H](C(C)C)N(C)C(=O)[C@@H](NC(=O)[C@H]1CCCCN1C(C)C)C(C)C)C(=O)NCCCN1CCOCC1] |
| ER-808903 | 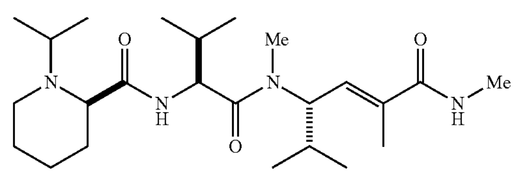 [SMILES: CNC(=O)/C(C)=C/[C@H](C(C)C)N(C)C(=O)[C@@H](NC(=O)[C@H]1CCCCN1C(C)C)C(C)C] |

| Compound | Structure |
|---|---|
| ER-808904 | 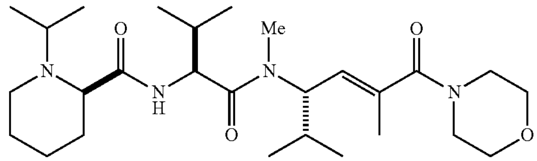 [SMILES: C/C(=C\[C@H](C(C)C)N(C)C(=O)[C@@H](NC(=O)[C@H]1CCCCN1C(C)C)C(C)C)C(=O)N1CCOCC1] |
| ER-808905 | 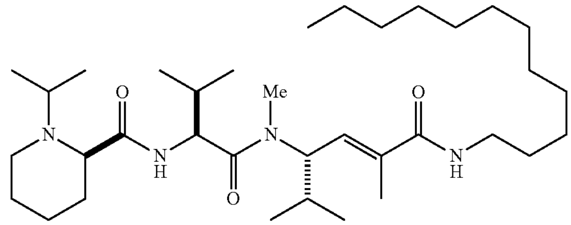 [SMILES: CCCCCCCCCCCCNC(=O)/C(C)=C/[C@H](C(C)C)N(C)C(=O)[C@@H](NC(=O)[C@H]1CCCCN1C(C)C)C(C)C] |
| ER-808906 | 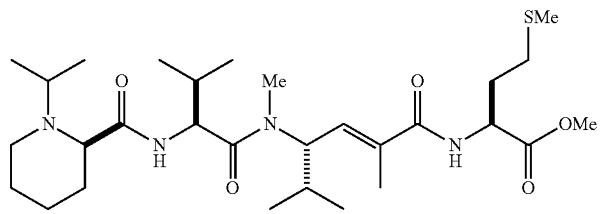 [SMILES: COC(=O)[C@H](CCSC)NC(=O)/C(C)=C/[C@H](C(C)C)N(C)C(=O)[C@@H](NC(=O)[C@H]1CCCCN1C(C)C)C(C)C] |
| ER-808907 | 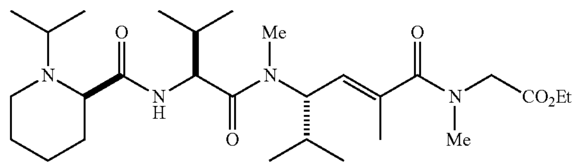 |
| ER-808908 | 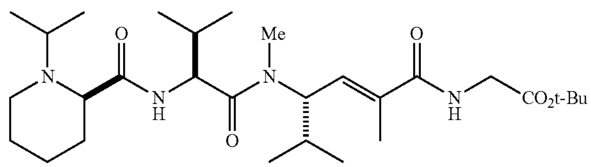 [SMILES: C/C(=C\[C@H](C(C)C)N(C)C(=O)[C@@H](NC(=O)[C@H]1CCCCN1C(C)C)C(C)C)C(=O)NCC(=O)OC(C)(C)C] |
| ER-808909 | 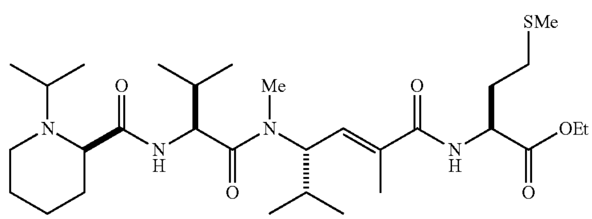 [SMILES: CCOC(=O)[C@H](CCSC)NC(=O)/C(C)=C/[C@H](C(C)C)N(C)C(=O)[C@@H](NC(=O)[C@H]1CCCCN1C(C)C)C(C)C] |
| ER-808910 | 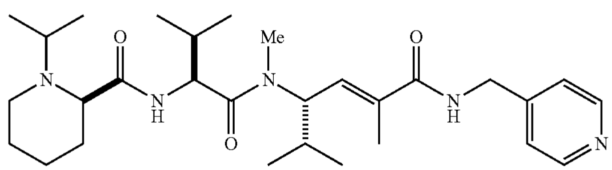 |
| ER-808911 | 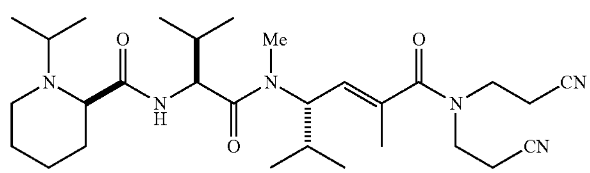 |

| Compound | Structure |
|---|---|
| ER-808912 | 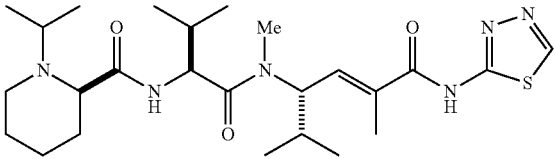 [SMILES: C/C(=C\[C@H](C(C)C)N(C)C(=O)[C@@H](NC(=O)[C@H]1CCCCN1C(C)C)C(C)C)C(=O)Nc1nncs1] |
| ER-808913 | 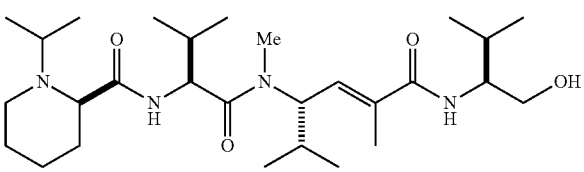 [SMILES: C/C(=C\[C@H](C(C)C)N(C)C(=O)[C@@H](NC(=O)[C@H]1CCCCN1C(C)C)C(C)C)C(=O)N[C@H](CO)C(C)C] |
| ER-808914 | 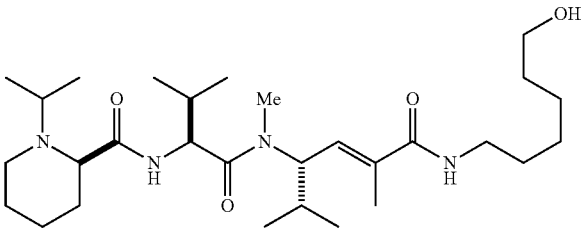 [SMILES: C/C(=C\[C@H](C(C)C)N(C)C(=O)[C@@H](NC(=O)[C@H]1CCCCN1C(C)C)C(C)C)C(=O)NCCCCCCO] |
| ER-808915 | 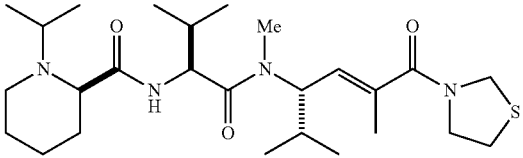 |
| ER-808916 | 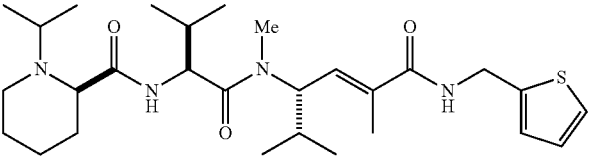 |
| ER-808917 | 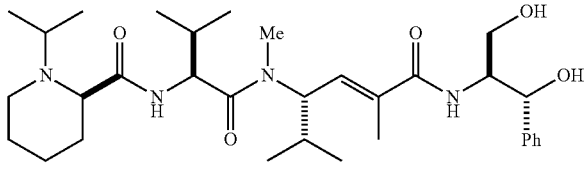 |
| ER-808918 | 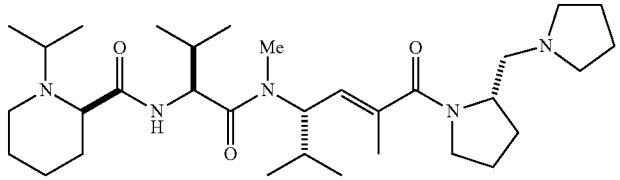 [SMILES: C/C(=C\[C@H](C(C)C)N(C)C(=O)[C@@H](NC(=O)[C@H]1CCCCN1C(C)C)C(C)C)C(=O)N1CCC[C@H]1CN1CCCC1] |
| ER-808919 | 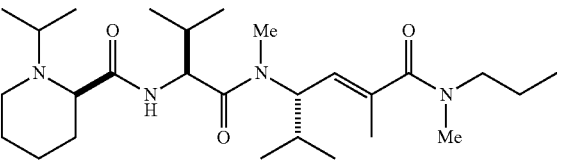 [SMILES: CCCN(C)C(=O)/C(C)=C/[C@H](C(C)C)N(C)C(=O)[C@@H](NC(=O)[C@H]1CCCCN1C(C)C)C(C)C] |

-continued

| Compound | Structure |
|---|---|
| ER-808920 | 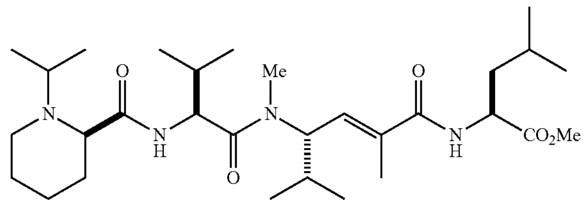 [SMILES: COC(=O)[C@H](CC(C)C)NC(=O)/C(C)=C/[C@H](C(C)C)N(C)C(=O)[C@@H](NC(=O)[C@H]1CCCCN1C(C)C)C(C)C] |
| ER-808921 | 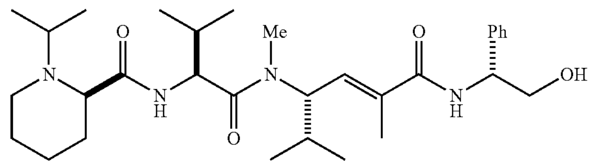 [SMILES: C/C(=C\[C@H](C(C)C)N(C)C(=O)[C@@H](NC(=O)[C@H]1CCCCN1C(C)C)C(C)C)C(=O)N[C@@H](CO)c1ccccc1] |
| ER-808922 | 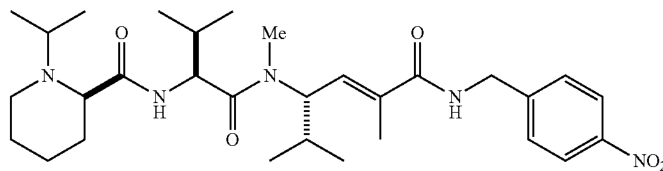 |
| ER-808923 | 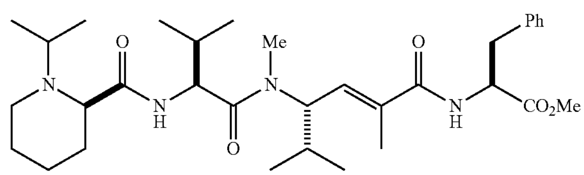 |
| ER-808987 | 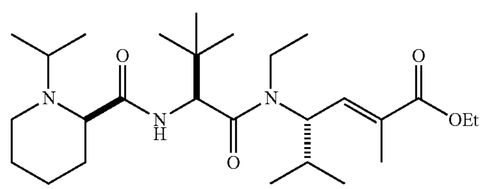 [SMILES: CCOC(=O)/C(C)=C/[C@H](C(C)C)N(CC)C(=O)[C@@H](NC(=O)[C@H]1CCCCN1C(C)C)C(C)(C)C] |
| ER-808988 | 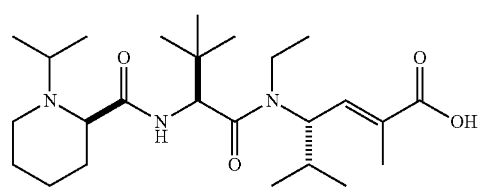 [SMILES: CCN(C(=O)[C@@H](NC(=O)[C@H]1CCCCN1C(C)C)C(C)(C)C)[C@H](/C=C(\C)C(=O)O)C(C)C] |
| ER-808990 | 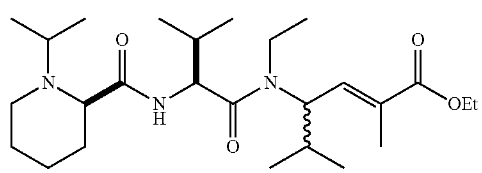 [SMILES: CCOC(=O)/C(C)=C/C(C(C)C)N(CC)C(=O)[C@@H](NC(=O)[C@H]1CCCCN1C(C)C)C(C)C] |
| ER-809040 Single diastereomer | |

| Compound | Structure |
|---|---|
| ER-809041 | 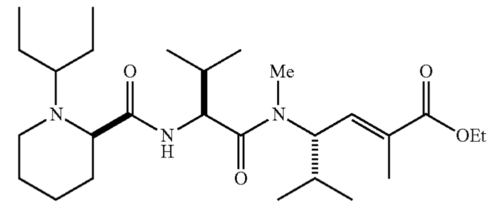 [SMILES: CCOC(=O)/C(C)=C/[C@H](C(C)C)N(C)C(=O)[C@@H](NC(=O)[C@H]1CCCCN1C(CC)CC)C(C)C] |
| ER-809043 | 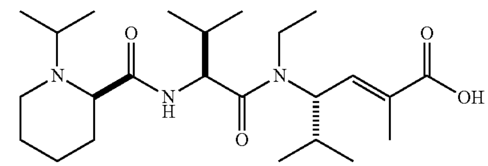 |
| ER-809044 | 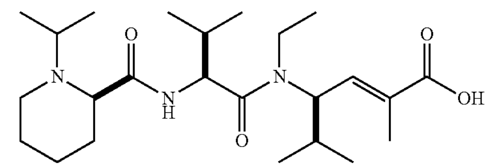 |
| ER-809045<br>Single diastereomer | |
| ER-809046 | 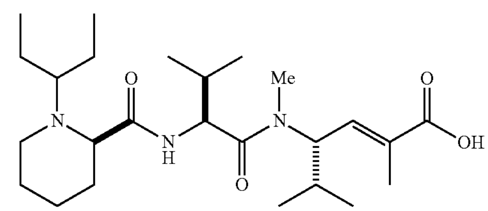 [SMILES: CCC(CC)N1CCCC[C@@H]1C(=O)N[C@H](C(=O)N(C)[C@H](/C=C(\C)C(=O)O)C(C)C)C(C)C] |
| ER-809054 | 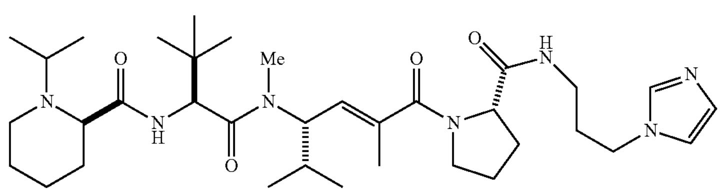 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NCCCn1ccnc1] |
| ER-809055 | 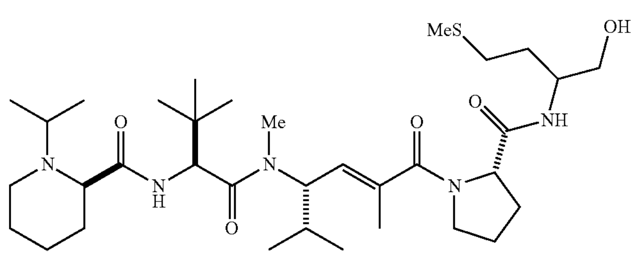 [SMILES: CSCCC(CO)NC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |

| Compound | Structure |
|---|---|
| ER-809056 | 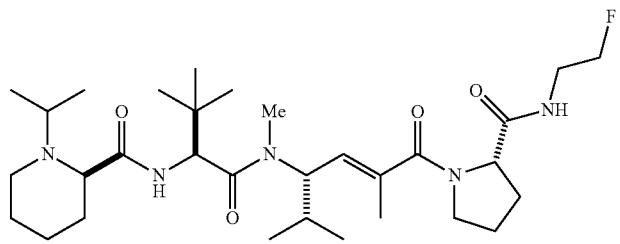 |
| ER-809057 | 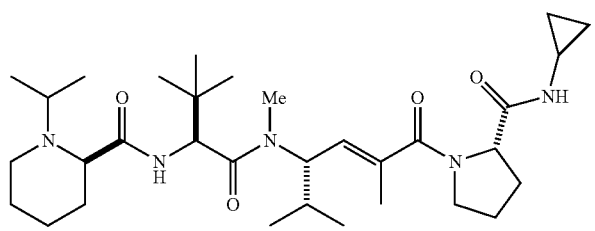 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NC1CC1] |
| ER-809058 | 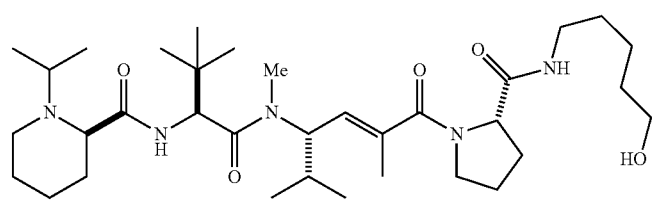 |
| ER-809059 | 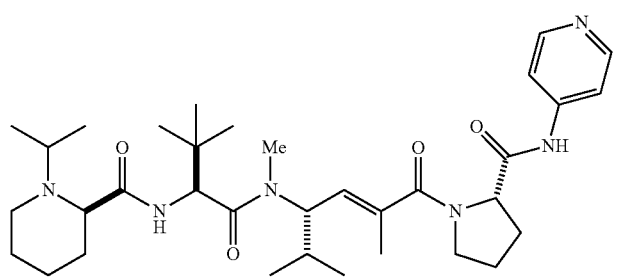 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)Nc1ccncc1] |
| ER-809060 | 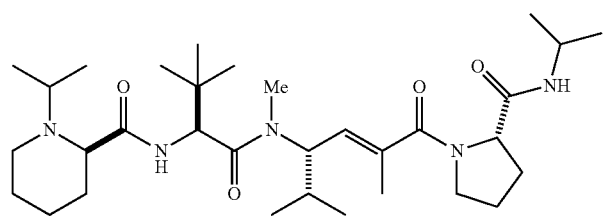 |
| ER-809061 | 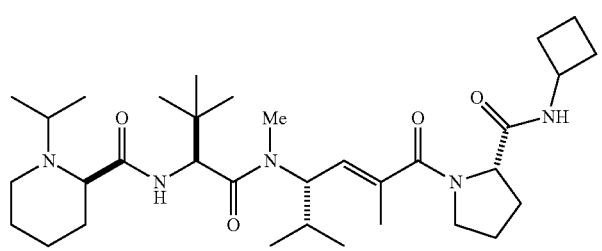 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NC1CCC1] |

-continued
| Compound | Structure |
|---|---|
| ER-809062 | 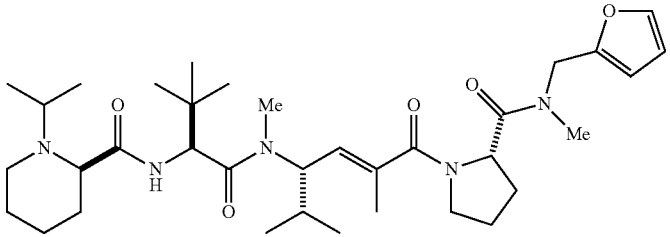 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)N(C)Cc1ccco1] |
| ER-809063 | 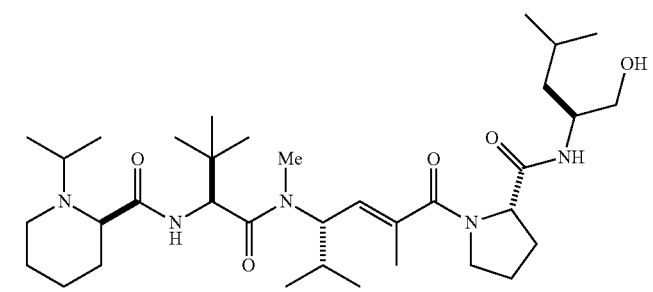 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)N[C@H](CO)CC(C)C] |
| ER-809064 | 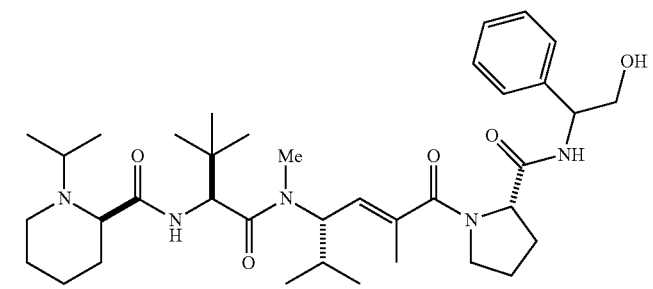 |
| ER-809065 | 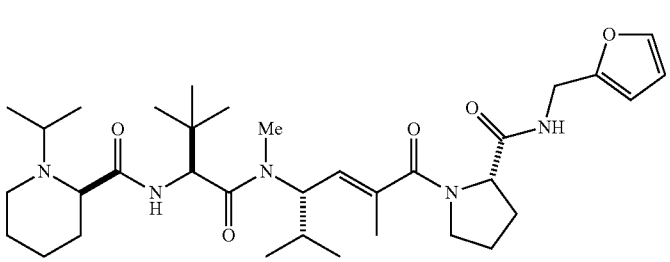 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NCc1ccco1] |
| ER-809066 | 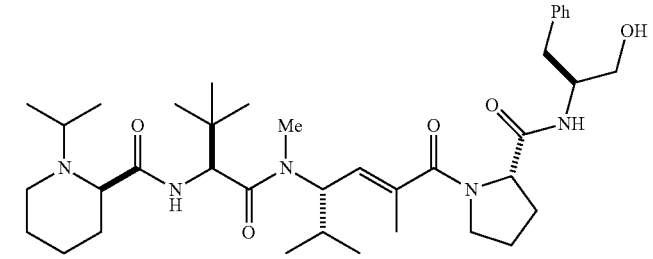 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)N[C@H](CO)Cc1ccccc1] |

-continued

| Compound | Structure |
|---|---|
| ER-809067 | 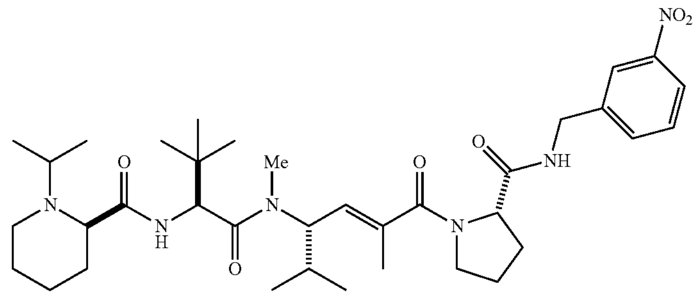 |
| ER-809068 | 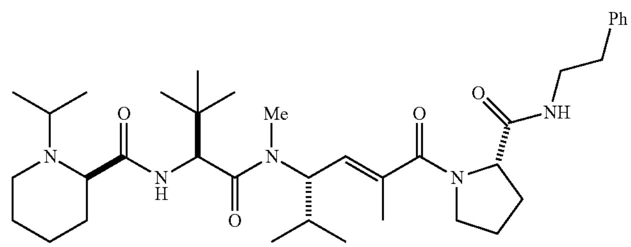 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NCCc1ccccc1] |
| ER-809069 | 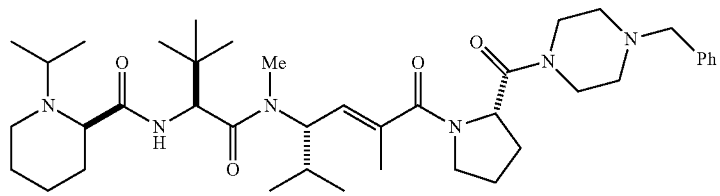 |
| ER-809070 | 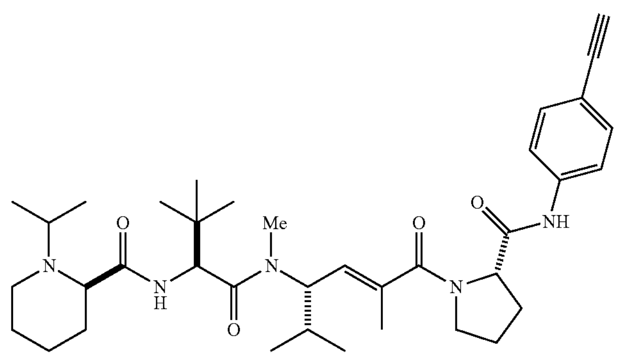 |
| ER-809071 | 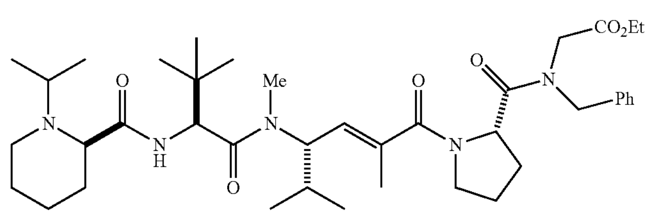 |
| ER-809072 | 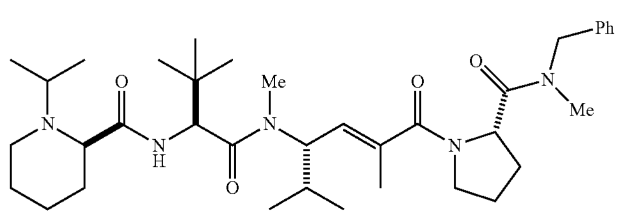 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)N(C)Cc1ccccc1] |

-continued

| Compound | Structure |
|---|---|
| ER-809073 | 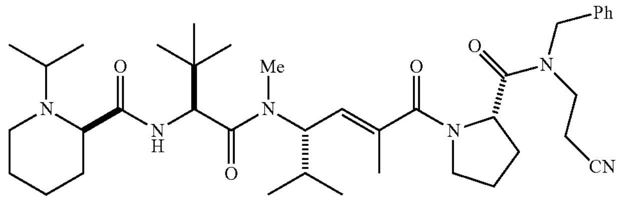 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)N(CCC#N)Cc1ccccc1] |
| ER-809074 | 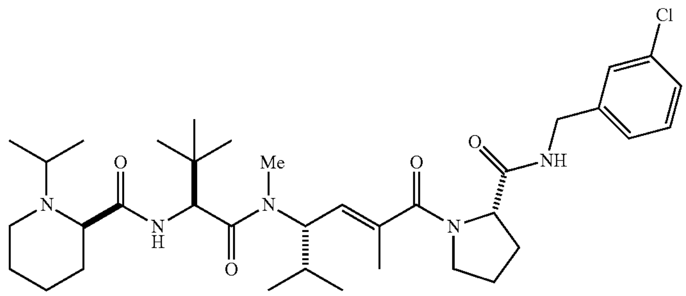 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NCc1cccc(Cl)c1] |
| ER-809075 | 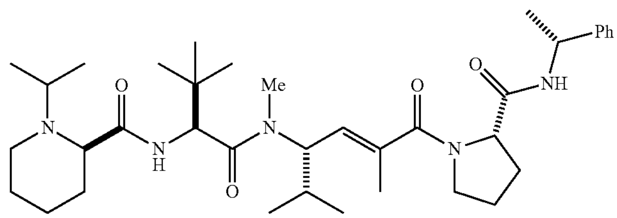 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)N[C@H](C)c1ccccc1] |
| ER-809076 | 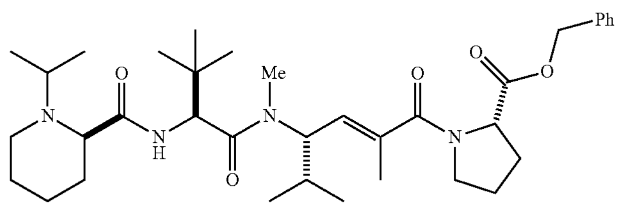 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)OCc1ccccc1] |
| ER-809077 | 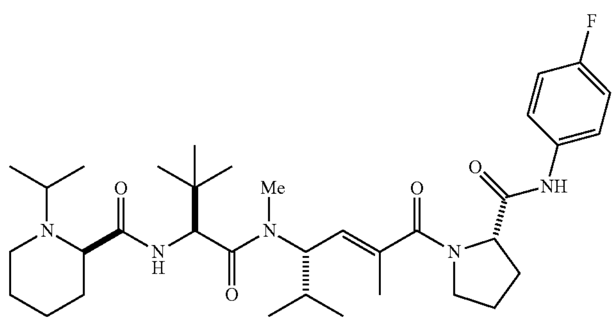 |
| ER-809078 | 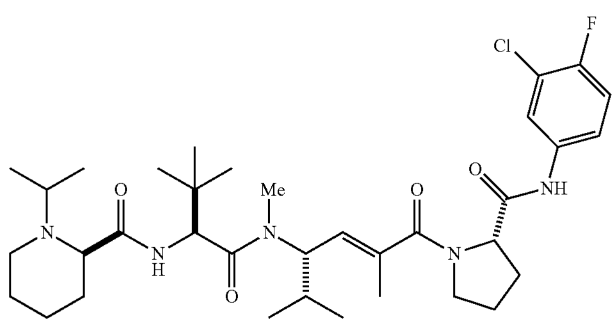 |

-continued
| Compound | Structure |
|---|---|
| ER-809079 | 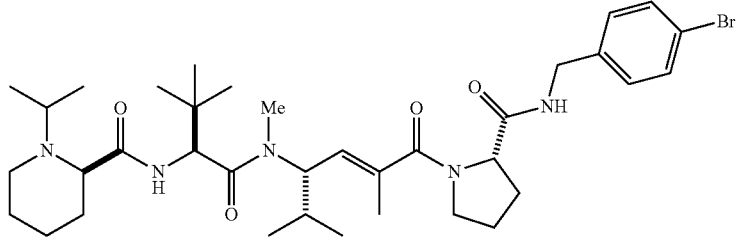 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NCc1ccc(Br)cc1] |
| ER-809080 | 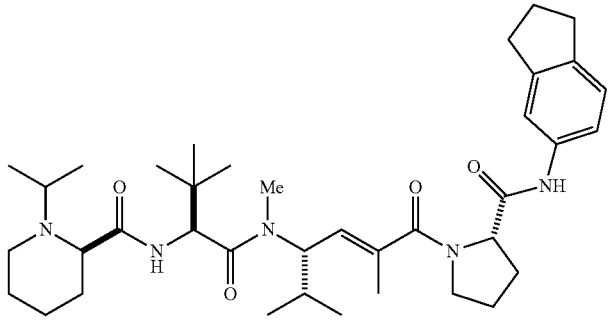 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)Nc1ccc2c(c1)CCC2] |
| ER-809081 | 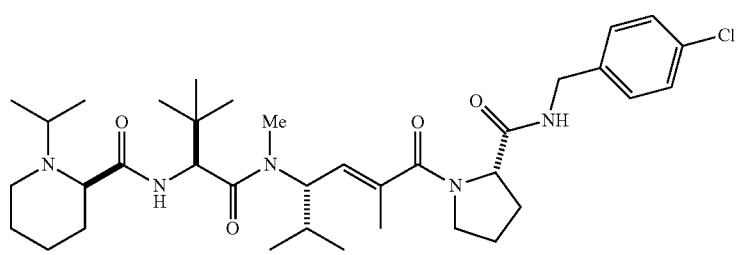 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NCc1ccc(Cl)cc1] |
| ER-809082 | 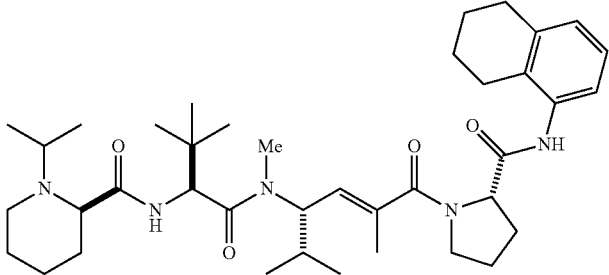 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)Nc1cccc2c1CCCC2] |
| ER-809083 | 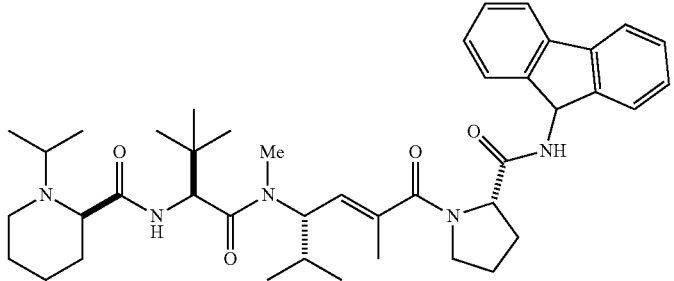 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NC1c2ccccc2-c2ccccc21] |

-continued
| Compound | Structure |
|---|---|
| ER-809084 | 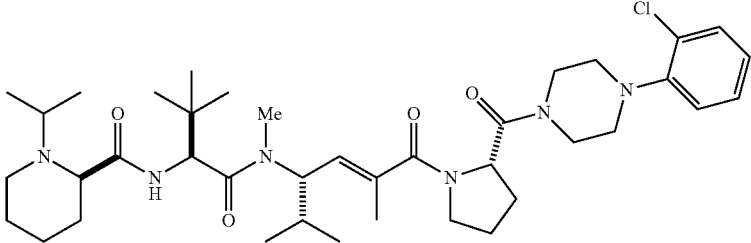 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)N1CCN(c2ccccc2Cl)CC1] |
| ER-809085 | 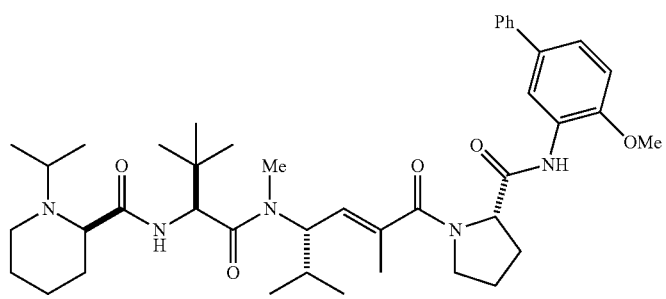 [SMILES: COc1ccc(-c2ccccc2)cc1NC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809086 | 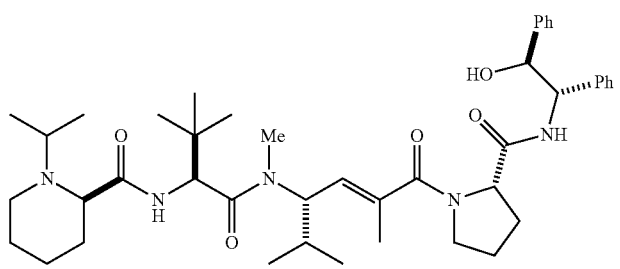 |
| ER-809087 | 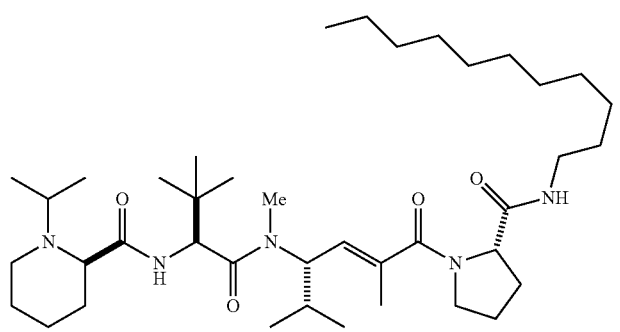 |
| ER-809088 | 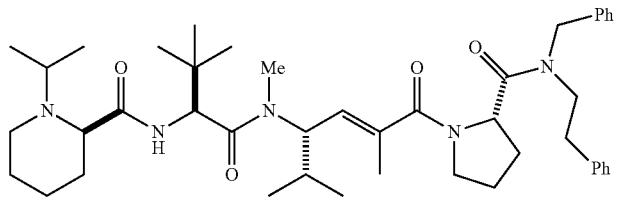 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)N(CCc1ccccc1)Cc1ccccc1] |

-continued

| Compound | Structure |
|---|---|
| ER-809089 | 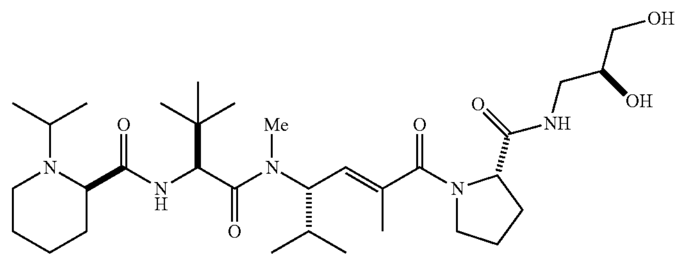 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NC[C@H](O)CO] |
| ER-809090 | 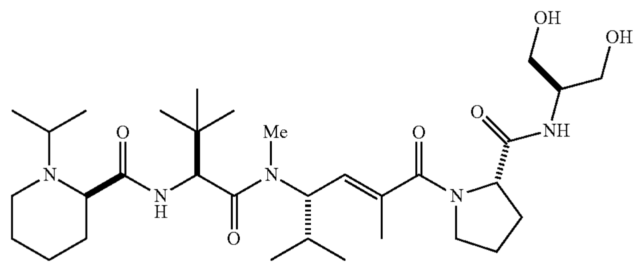 |
| ER-809091 | 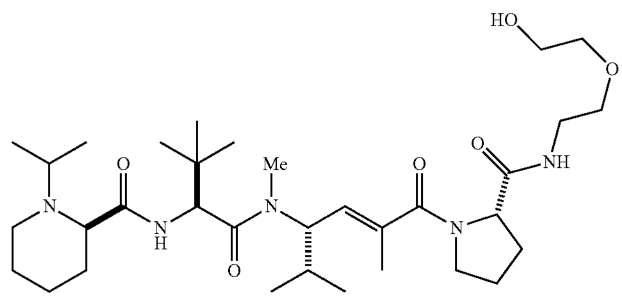 |
| ER-809092 | 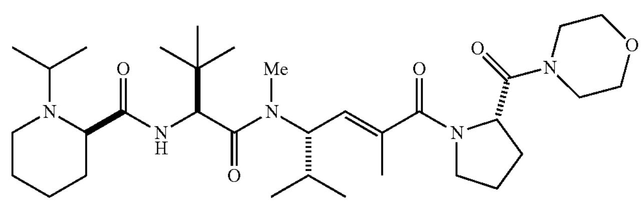 |
| ER-809093 | 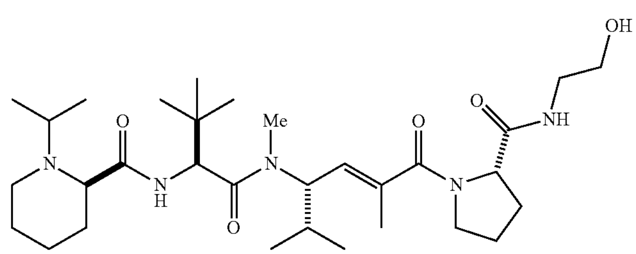 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NCCO] |
| ER-809094 | 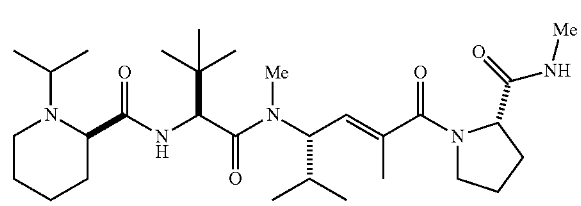 [SMILES: CNC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |

-continued

| Compound | Structure |
|---|---|
| ER-809095 | 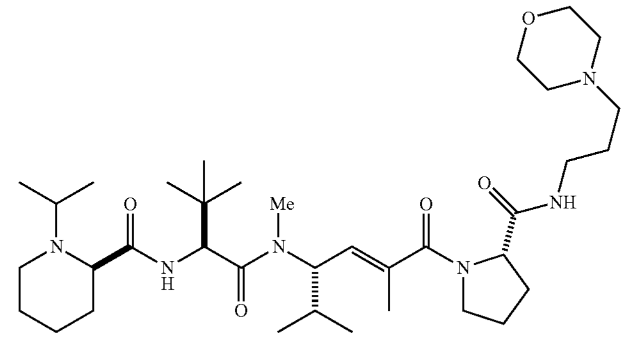 |
| ER-809096 | 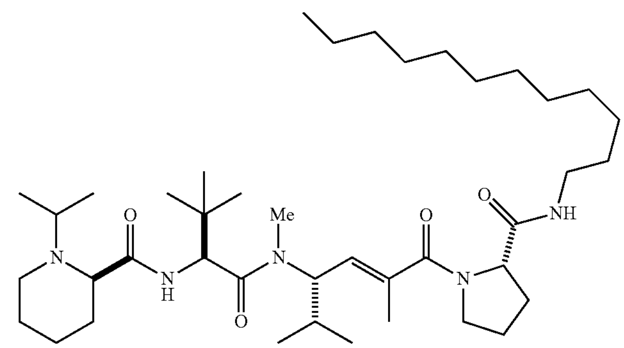 |
| ER-809097 | 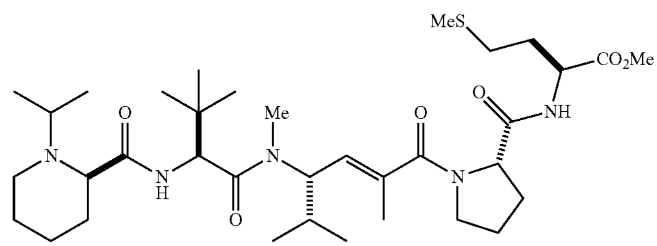 [SMILES: COC(=O)[C@H](CCSC)NC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809098 | 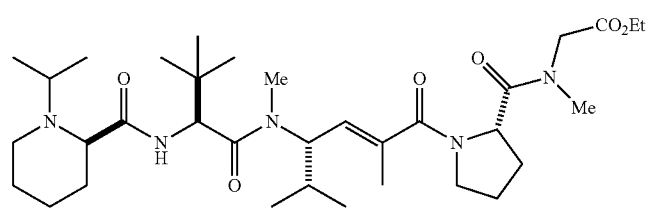 |
| ER-809099 | 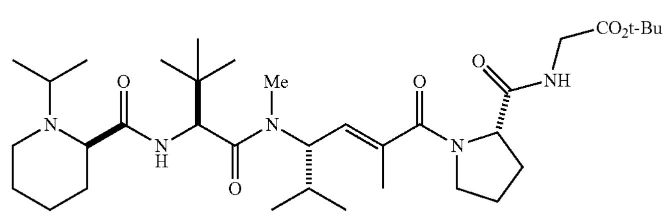 |
| ER-809100 | 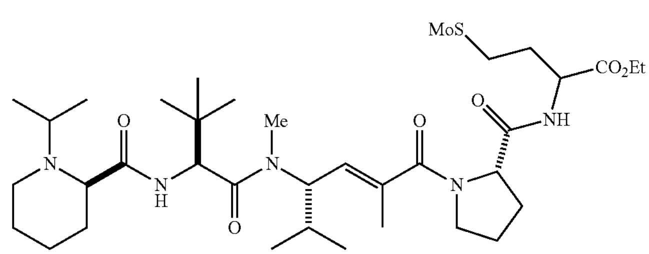 |

-continued

| Compound | Structure |
|---|---|
| ER-809101 | 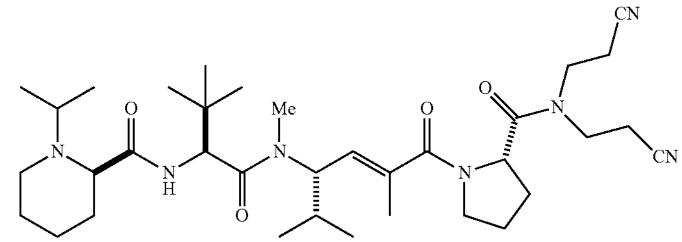 |
| ER-809102 | 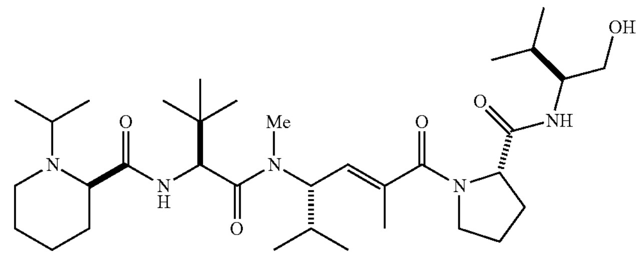 |
| ER-809103 | 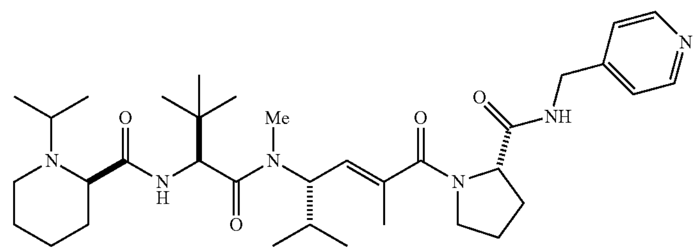 |
| ER-809104 | 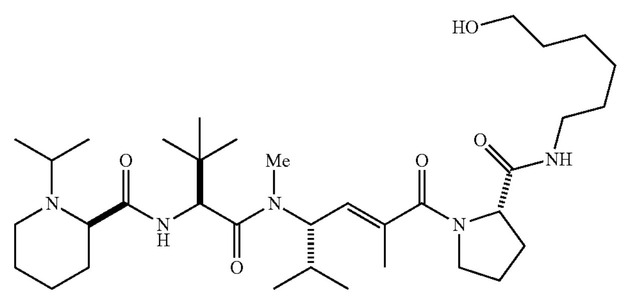 |
| ER-809105 | 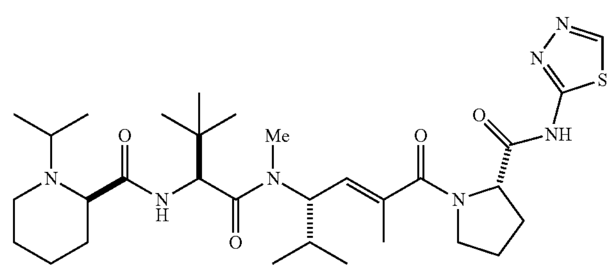 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)Nc1nncs1] |
| ER-809106 | 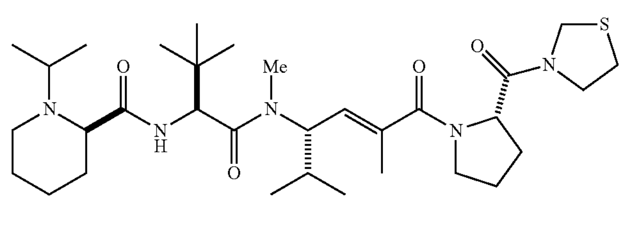 |

-continued

| Compound | Structure |
|---|---|
| ER-809107 | 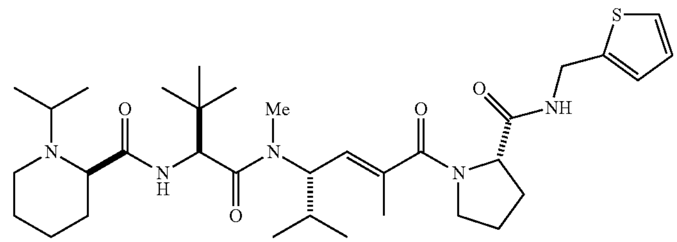 |
| ER-809108 | 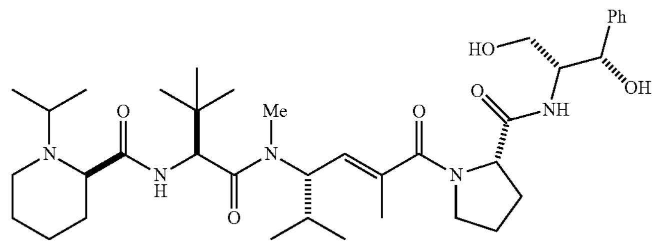 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)N[C@H](CO)[C@@H](O)c1ccccc1] |
| ER-809109 | 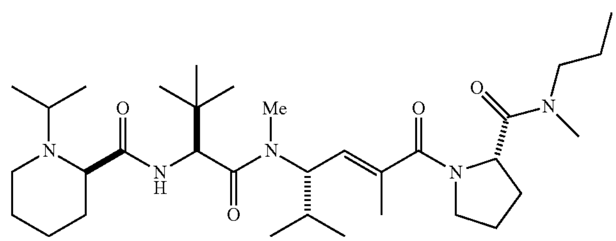 |
| ER-809110 | 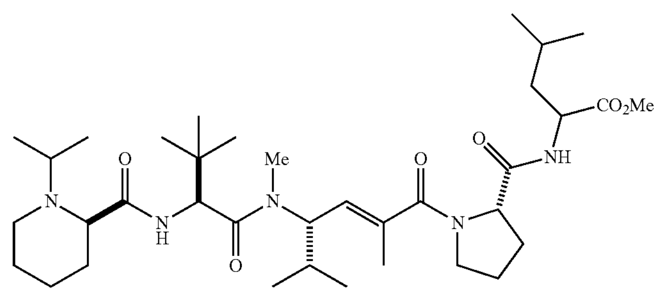 |
| ER-809111 | 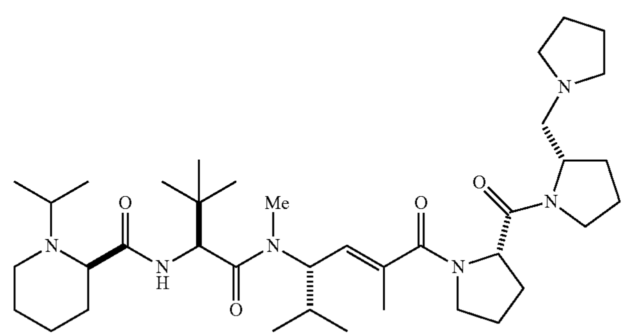 |
| ER-809112 | 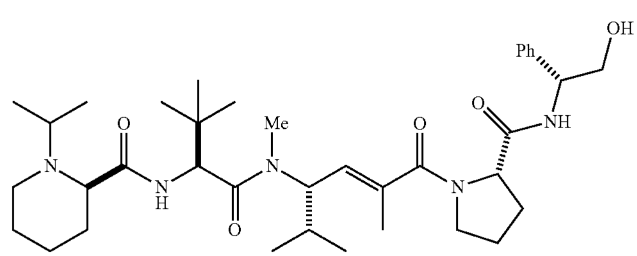 |

| Compound | Structure |
|---|---|
| ER-809113 | 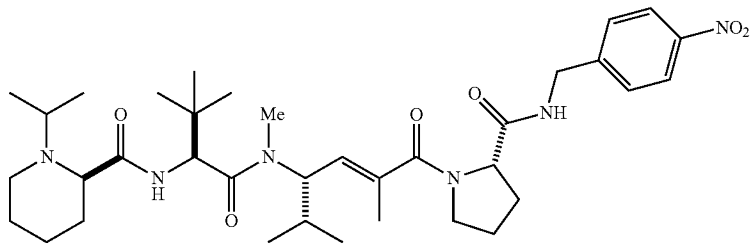 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NCc1ccc([N+](=O)[O-])cc1] |
| ER-809114 | 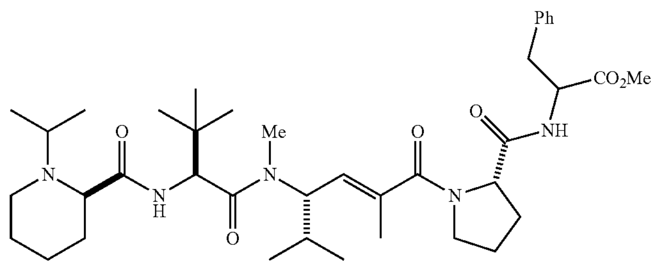 [SMILES: COC(=O)C(Cc1ccccc1)NC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809115 | 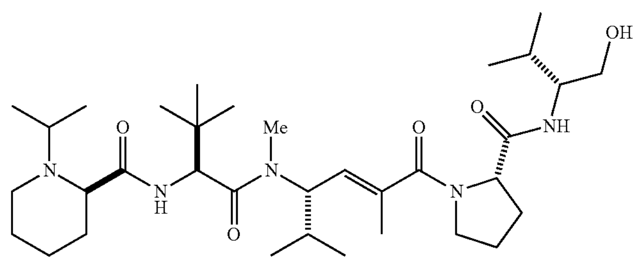 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)N[C@@H](CO)C(C)C] |
| ER-809116 | 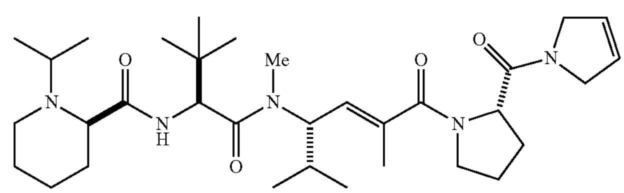 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)N1CC=CC1] |
| ER-809117 | 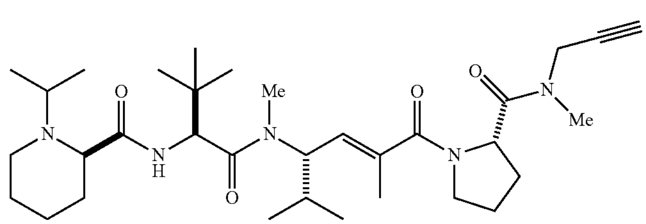 |
| ER-809118 | 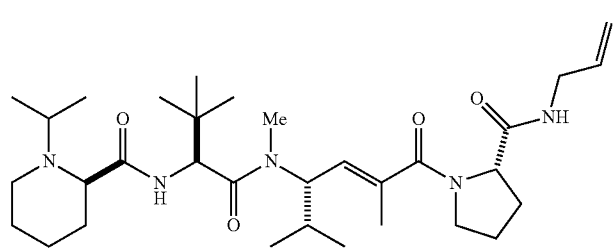 |

-continued

| Compound | Structure |
|---|---|
| ER-809119 | 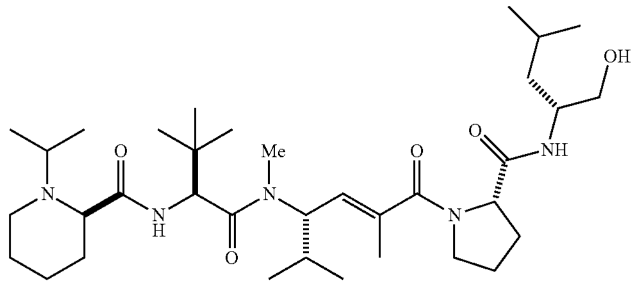 |
| ER-809120 | 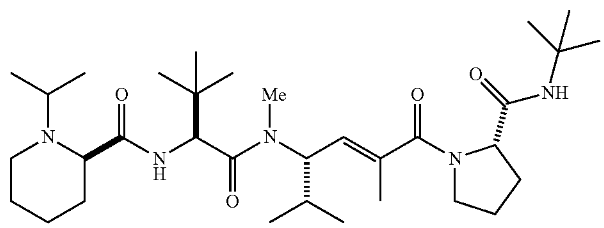 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NC(C)(C)C] |
| ER-809121 | 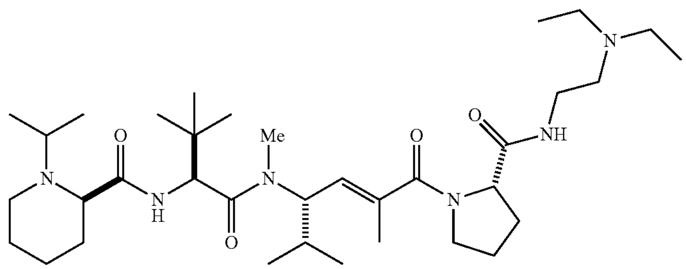 |
| ER-809122 | 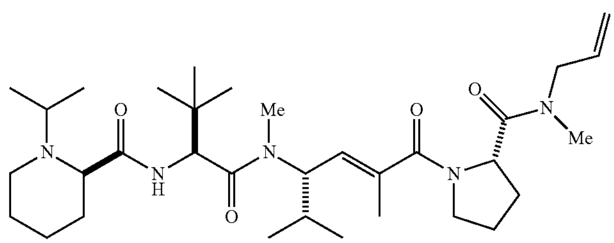 [SMILES: C=CCN(C)C(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809123 | 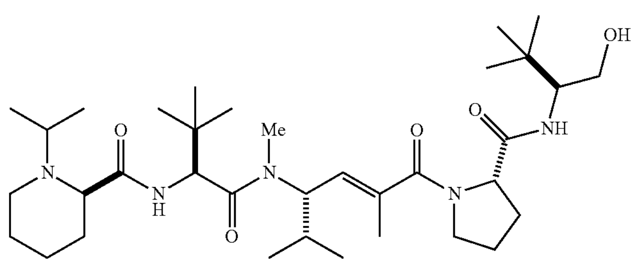 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)N[C@H](CO)C(C)(C)C] |
| ER-809124 | 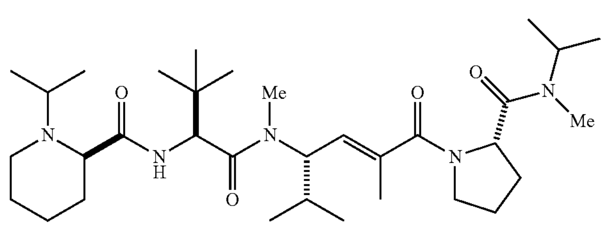 |

| Compound | Structure |
|---|---|
| ER-809125 | 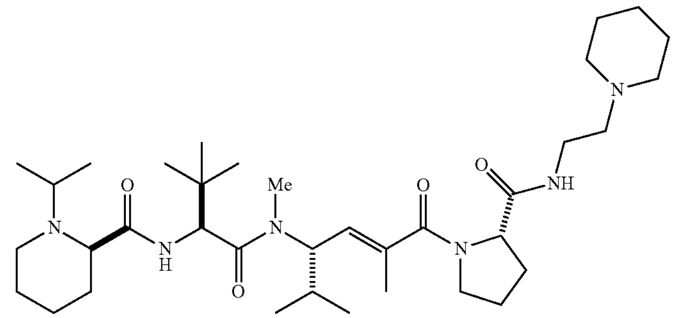 |
| ER-809126 | 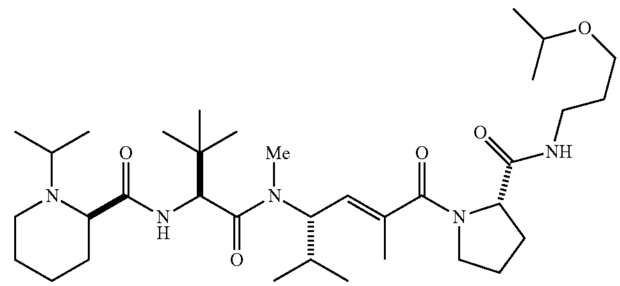 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NCCCOC(C)C] |
| ER-809127 | 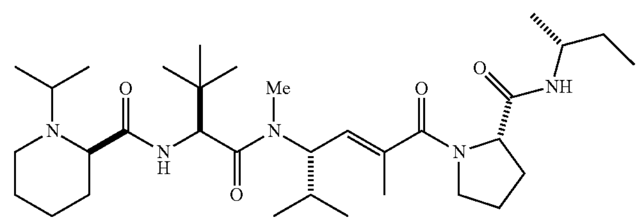 [SMILES: CC[C@@H](C)NC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809128 | 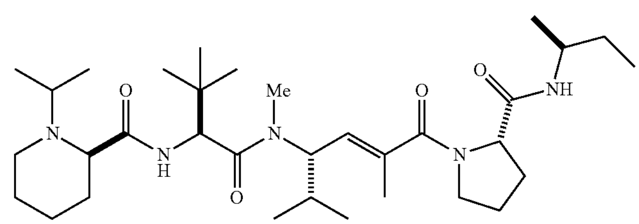 [SMILES: CC[C@H](C)NC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809129 | 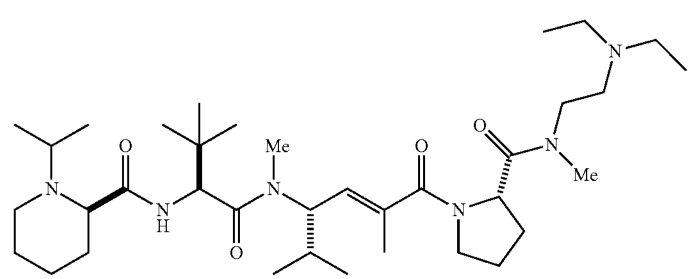 [SMILES: CCN(CC)CCN(C)C(=O)[C@@H]1CCCN1C(=O)/C(C)=C/[C@H](C(C)C)N(C)C(=O)[C@@H](NC(=O)[C@H]1CCCCN1C(C)C)C(C)(C)C] |

-continued
| Compound | Structure |
|---|---|
| ER-809130 | 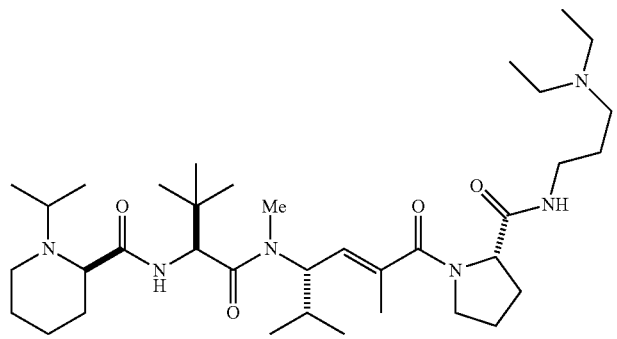 [SMILES: CCN(CC)CCCNC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809131 | 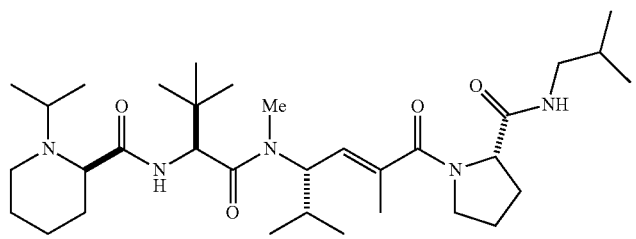 |
| ER-809132 | 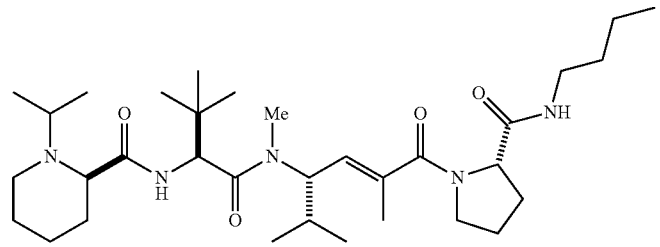 |
| ER-809133 | 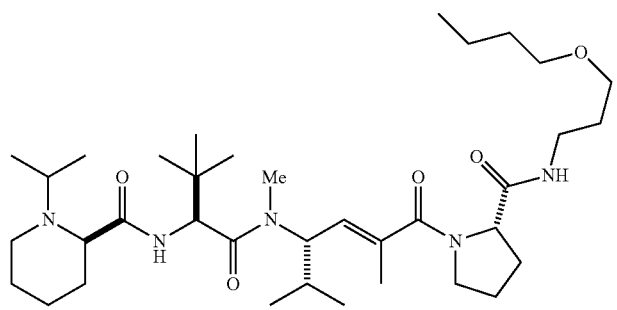 |
| ER-809134 | 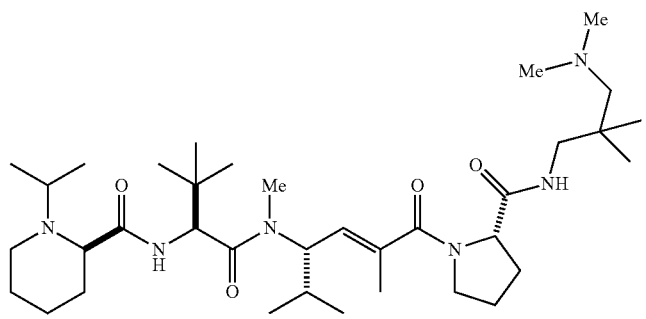 |

-continued

| Compound | Structure |
| --- | --- |
| ER-809135 | 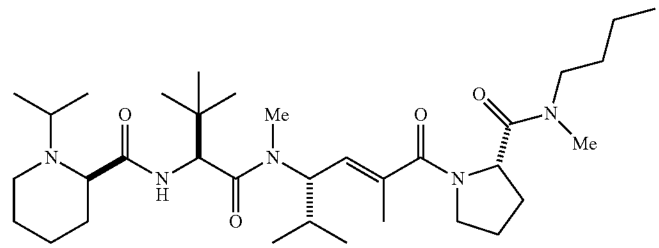 |
| ER-809136 | 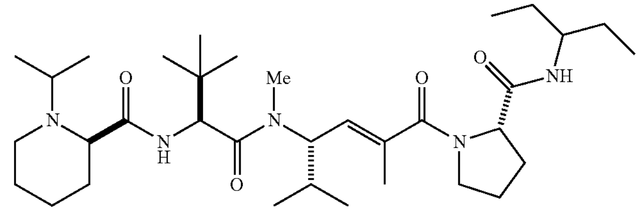 [SMILES: CCC(CC)NC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809137 | 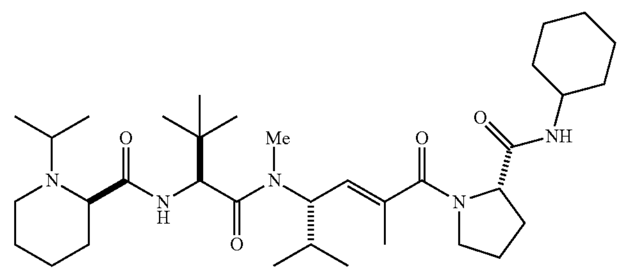 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NC1CCCCC1] |
| ER-809138 | 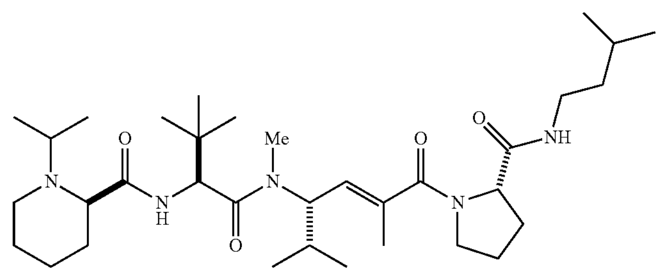 |
| ER-809139 | 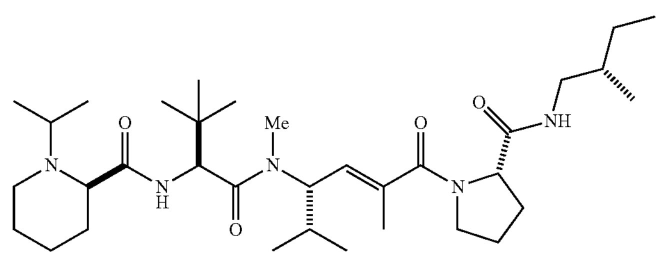 [SMILES: CC[C@H](C)CNC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809140 | 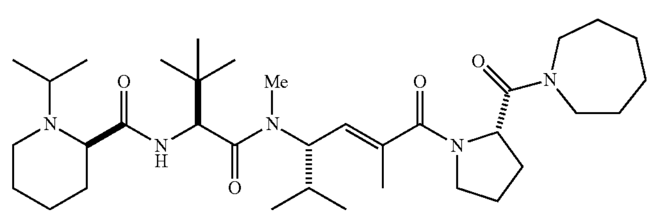 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)N1CCCCCC1] |

-continued

| Compound | Structure |
| --- | --- |
| ER-809141 | 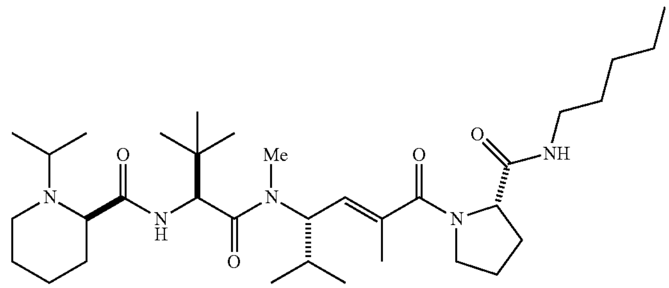 [SMILES: CCCCCNC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809142 | 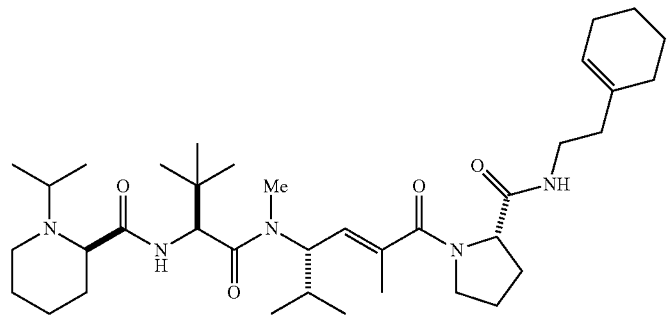 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NCCC1=CCCCC1] |
| ER-809143 | 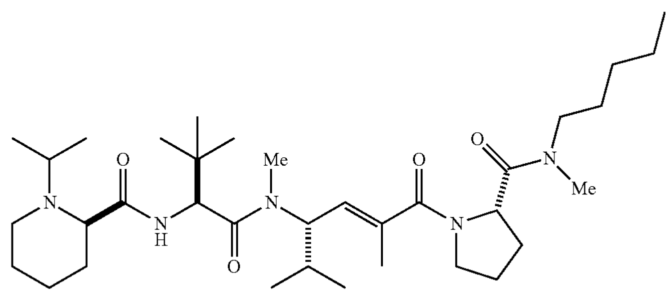 [SMILES: CCCCCN(C)C(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809144 | 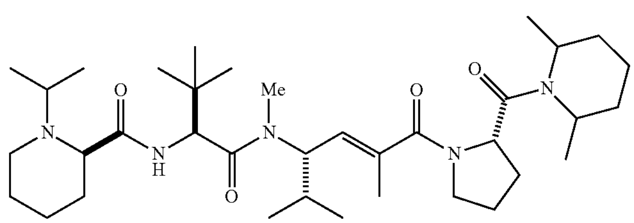 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)N1C(C)CCCC1C] |
| ER-809145 | 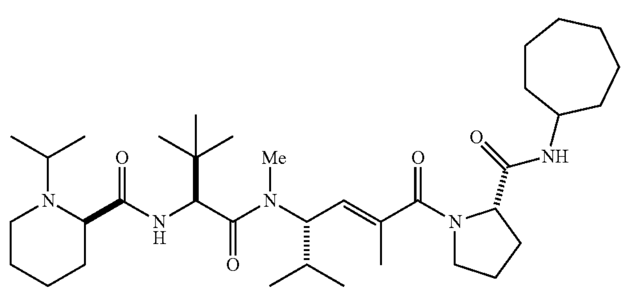 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NC1CCCCCC1] |

-continued
| Compound | Structure |
|---|---|
| ER-809146 | 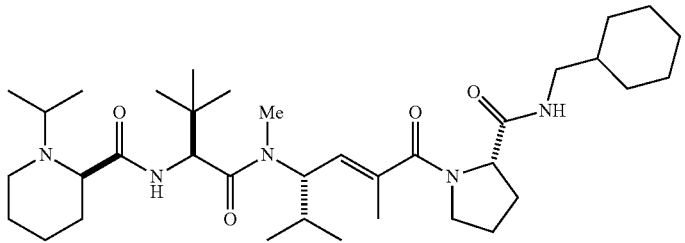 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NCC1CCCCC1] |
| ER-809147 | 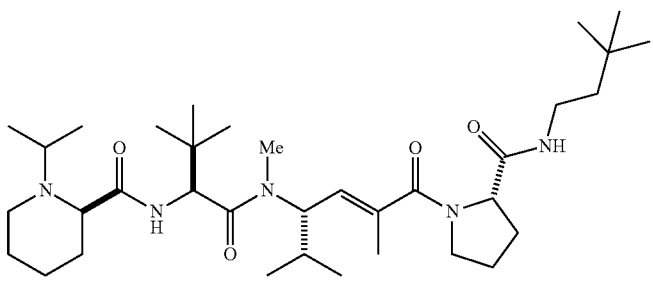 |
| ER-809148 | 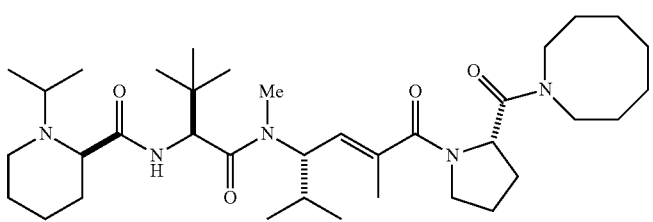 |
| ER-809149 | 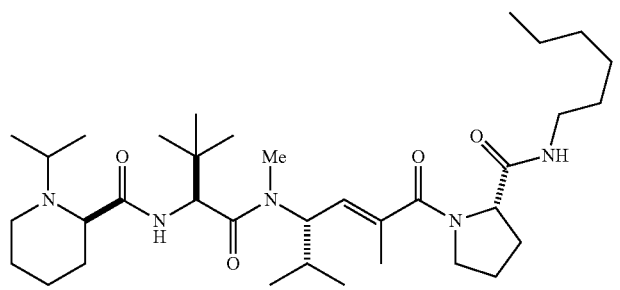 [SMILES: CCCCCCNC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809150 | 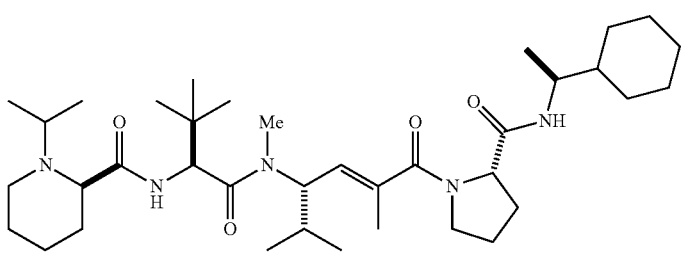 |
| ER-809151 | 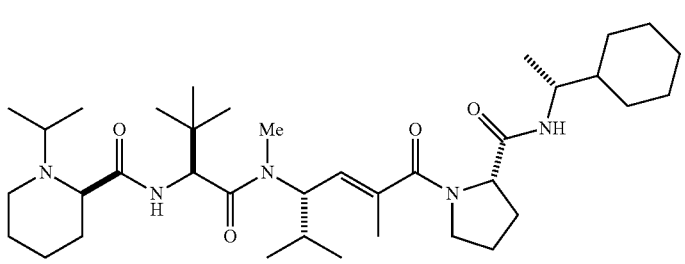 |

| Compound | Structure |
|---|---|
| ER-809152 | 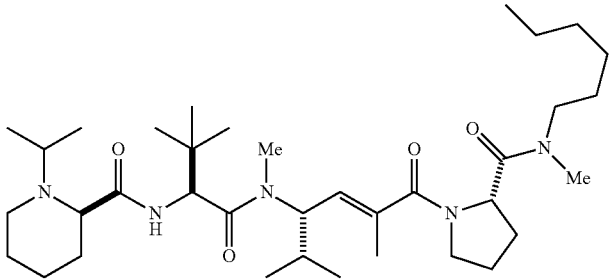 [SMILES: CCCCCCN(C)C(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809153 | 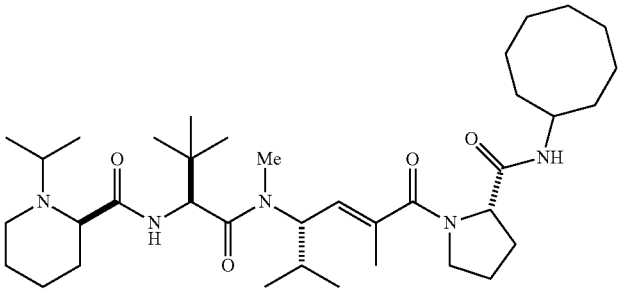 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)NC1CCCCCCC1] |
| ER-809154 | 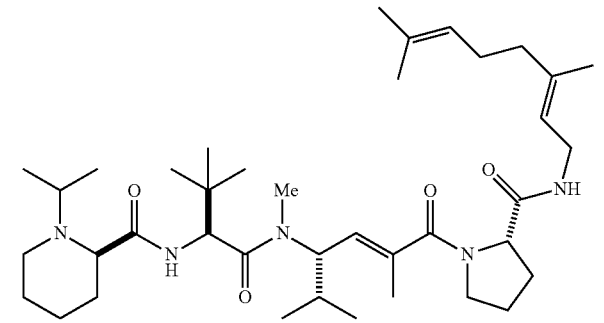 [SMILES: CC(C)=CCC/C(C)=C/CNC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809155 | 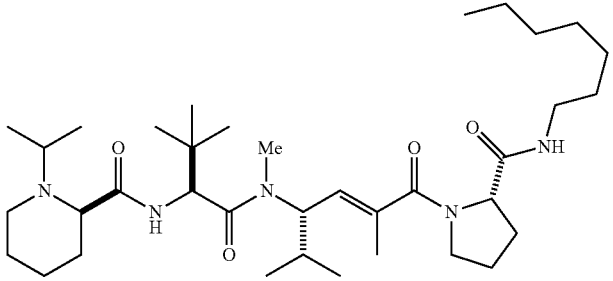 [SMILES: CCCCCCCNC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809156 | 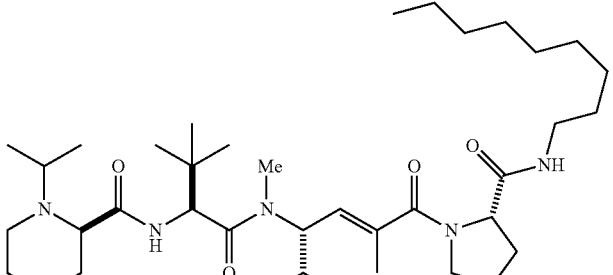 |

-continued

| Compound | Structure |
|---|---|
| ER-809157 | 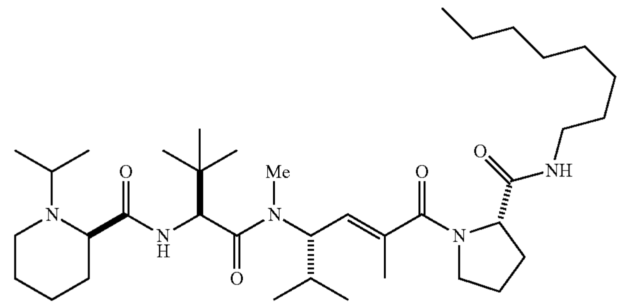 [SMILES: CCCCCCCCNC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809158 | 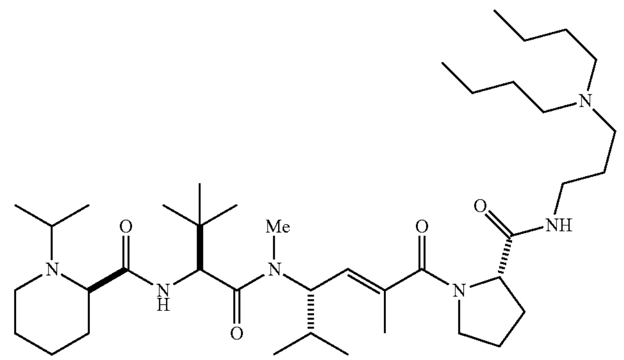 |
| ER-809159 | 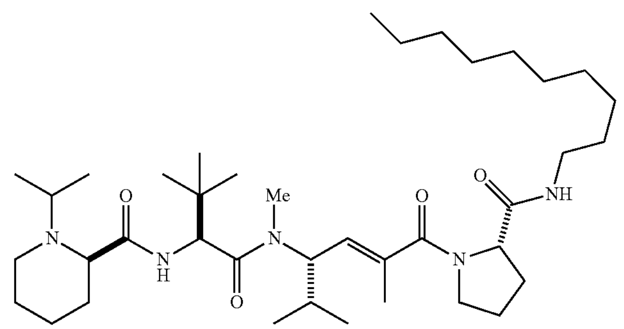 [SMILES: CCCCCCCCCCNC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809160 | 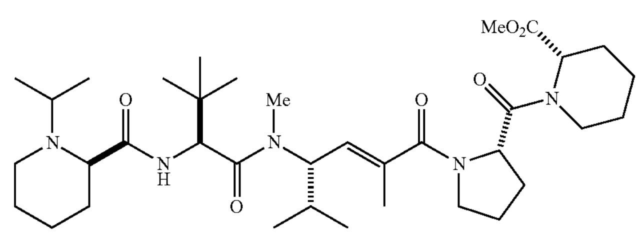 [SMILES: COC(=O)[C@@H]1CCCCN1C(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| ER-809161 | 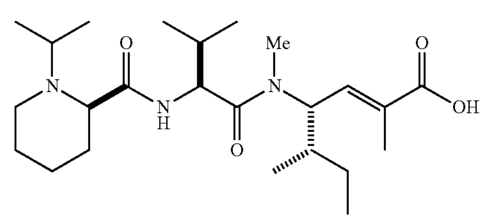 [SMILES: CC[C@H](C)[C@@H](/C=C(\C)C(=O)O)N(C)C(=O)[C@@H](NC(=O)[C@H]1CCCCN1C(C)C)C(C)C] |

-continued

| Compound | Structure |
|---|---|
| ER-809162 | 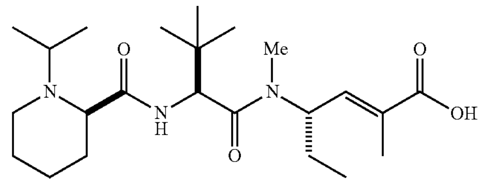 [SMILES: CC[C@@H](/C=C(\C)C(=O)O)N(C)C(=O)[C@@H](NC(=O)[C@H]1CCCCN1C(C)C)C(C)(C)C] |
| ER-809163 | 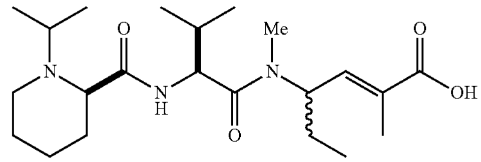 [SMILES: CCC(/C=C(\C)C(=O)O)N(C)C(=O)[C@@H](NC(=O)[C@H]1CCCCN1C(C)C)C(C)C] |
| ER-809164 | 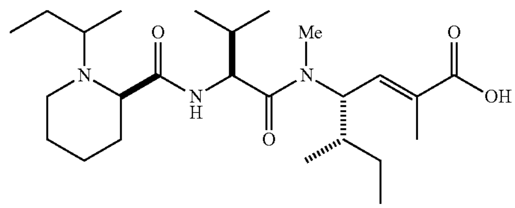 [SMILES: CCC(C)N1CCCC[C@@H]1C(=O)N[C@H](C(=O)N(C)[C@H](/C=C(\C)C(=O)O)[C@@H](C)CC)C(C)C] |
| ER-809165 | 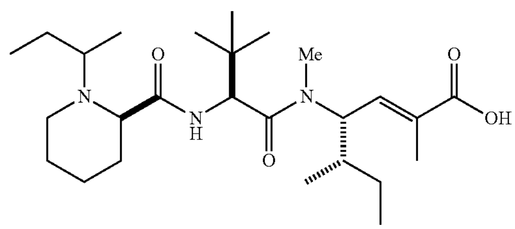 [SMILES: CCC(C)N1CCCC[C@@H]1C(=O)N[C@H](C(=O)N(C)[C@H](/C=C(\C)C(=O)O)[C@@H](C)CC)C(C)(C)C] |
| ER-809166 | 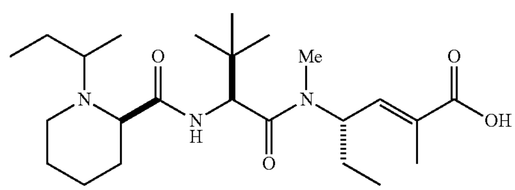 [SMILES: CCC(C)N1CCCC[C@@H]1C(=O)N[C@H](C(=O)N(C)[C@H](/C=C(\C)C(=O)O)CC)C(C)(C)C] |
| ER-809167 | 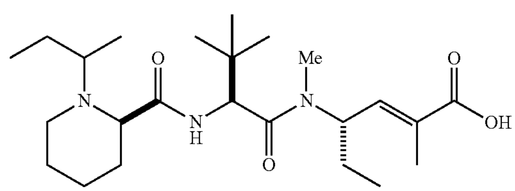 [SMILES: CCC(C)N1CCCC[C@@H]1C(=O)N[C@H](C(=O)N(C)[C@H](/C=C(\C)C(=O)O)CC)C(C)(C)C] |
| ER-809240 | 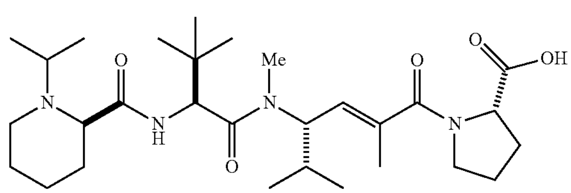 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)O] |
| ER-809241 | 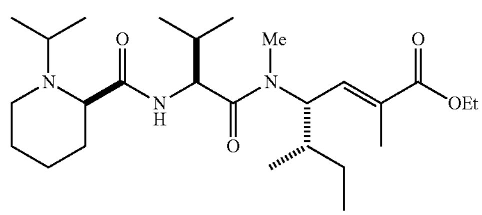 [SMILES: CCOC(=O)/C(C)=C/[C@H]([C@@H](C)CC)N(C)C(=O)[C@@H](NC(=O)[C@H]1CCCCN1C(C)C)C(C)C] |

-continued

| Compound | Structure |
|---|---|
| ER-8089242 | 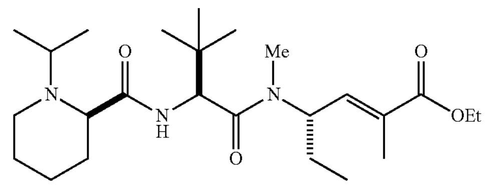 [SMILES: CCOC(=O)/C(C)=C/[C@H](CC)N(C)C(=O)[C@@H](NC(=O)[C@H]1CCCCN1C(C)C)C(C)(C)C] |
| ER-809243 | 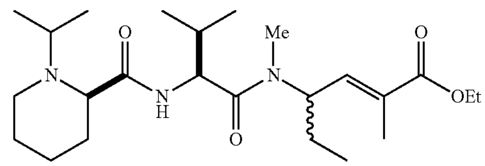 [SMILES: CCOC(=O)/C(C)=C/C(CC)N(C)C(=O)[C@@H](NC(=O)[C@H]1CCCCN1C(C)C)C(C)C] |
| ER-809244 | 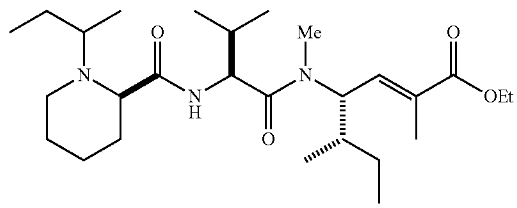 [SMILES: CCOC(=O)/C(C)=C/[C@H]([C@@H](C)CC)N(C)C(=O)[C@@H](NC(=O)[C@H]1CCCCN1C(C)CC)C(C)C] |
| ER-809245 | 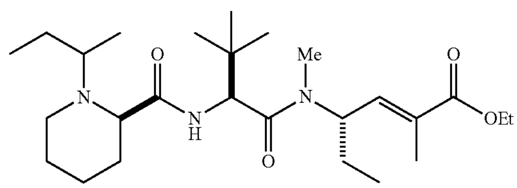 [SMILES: CCOC(=O)/C(C)=C/[C@H](CC)N(C)C(=O)[C@@H](NC(=O)[C@H]1CCCCN1C(C)CC)C(C)(C)C] |
| ER-809246 | 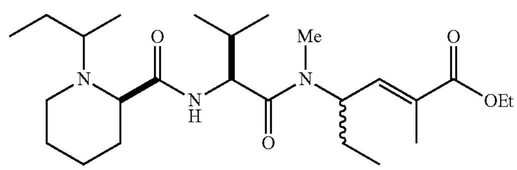 [SMILES: CCOC(=O)/C(C)=C/C(CC)N(C)C(=O)[C@@H](NC(=O)[C@H]1CCCCN1C(C)CC)C(C)C] |
| ER-809247 | 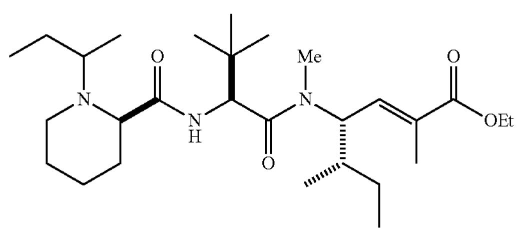 [SMILES: CCOC(=O)/C(C)=C/[C@H]([C@@H](C)CC)N(C)C(=O)[C@@H](NC(=O)[C@H]1CCCCN1C(C)CC)C(C)(C)C] |
| ER-809268 | 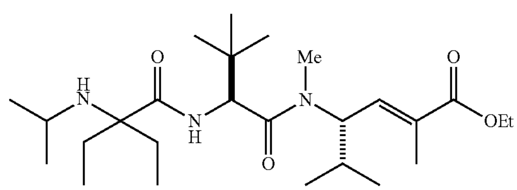 |
| ER-809269 | 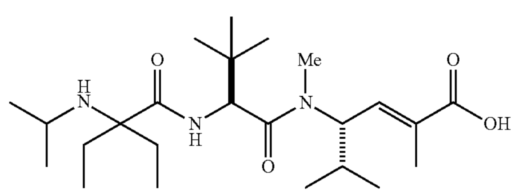 [SMILES: CCC(CC)(NC(C)C)C(=O)N[C@H](C(=O)N(C)[C@H](/C=C(\C)C(=O)O)C(C)C)C(C)(C)C] |

-continued

| Compound | Structure |
|---|---|
| ER-809282 | 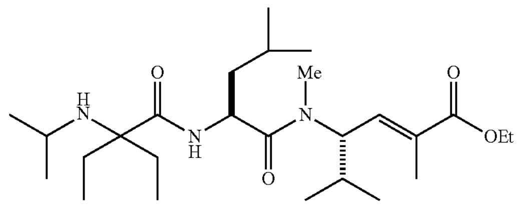 |
| ER-809283 | 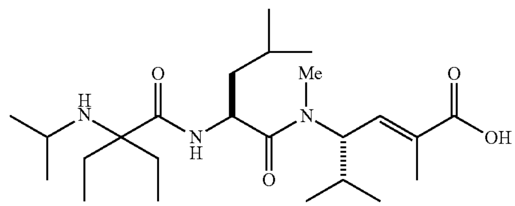 [SMILES: CCC(CC)(NC(C)C)C(=O)N[C@@H](CC(C)C)C(=O)N(C)[C@H](/C=C(\C)C(=O)O)C(C)C] |
| ER-809284 | 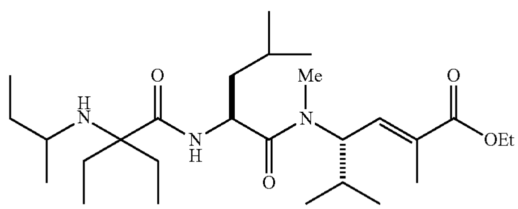 [SMILES: CCOC(=O)/C(C)=C/[C@H](C(C)C)N(C)C(=O)[C@H](CC(C)C)NC(=O)C(CC)(CC)NC(C)CC] |
| ER-809285 | 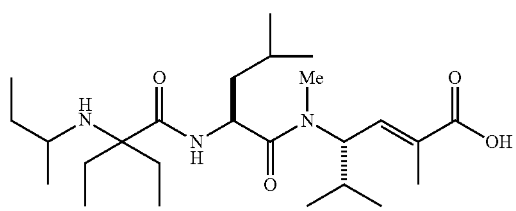 [SMILES: CCC(C)NC(CC)(CC)C(=O)N[C@@H](CC(C)C)C(=O)N(C)[C@H](/C=C(\C)C(=O)O)C(C)C] |
| ER-809300 | 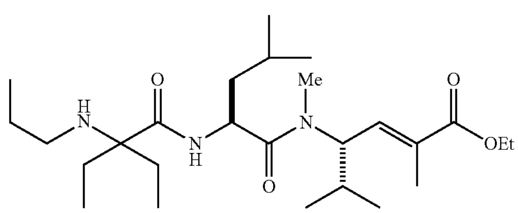 [SMILES: CCCNC(CC)(CC)C(=O)N[C@@H](CC(C)C)C(=O)N(C)[C@H](/C=C(\C)C(=O)OCC)C(C)C] |
| ER-809301 | 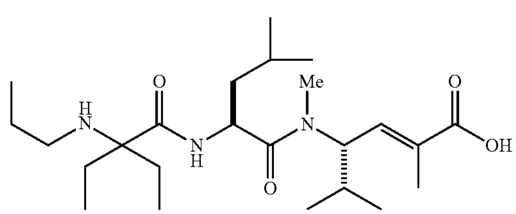 [SMILES: CCCNC(CC)(CC)C(=O)N[C@@H](CC(C)C)C(=O)N(C)[C@H](/C=C(\C)C(=O)O)C(C)C] |
| ER-809302 | 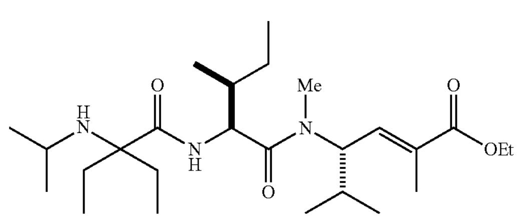 [SMILES: CCOC(=O)/C(C)=C/[C@H](C(C)C)N(C)C(=O)[C@@H](NC(=O)C(CC)(CC)NC(C)C)[C@@H](C)CC] |

-continued

| Compound | Structure |
|---|---|
| ER-809303 | 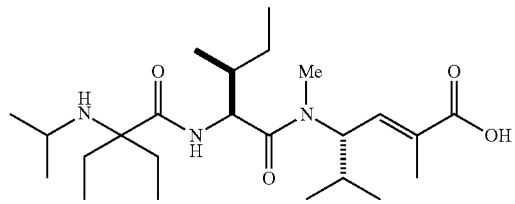 [SMILES: CC[C@H](C)[C@H](NC(=O)C(CC)(CC)NC(C)C)C(=O)N(C)[C@H](/C=C(\C)C(=O)O)C(C)C] |
| ER-809304 | 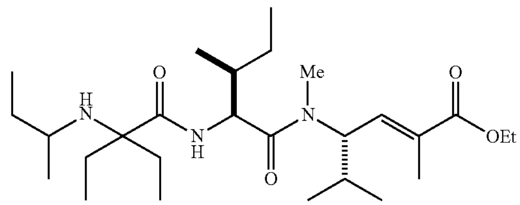 [SMILES: CCOC(=O)/C(C)=C/[C@H](C(C)C)N(C)C(=O)[C@@H](NC(=O)C(CC)(CC)NC(C)CC)[C@@H](C)CC] |
| ER-809305 | 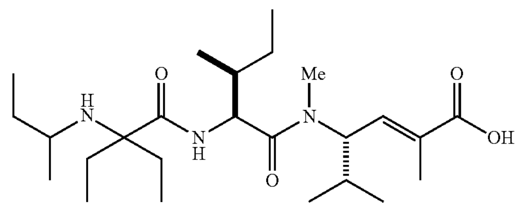 [SMILES: CCC(C)NC(CC)(CC)C(=O)N[C@H](C(=O)N(C)[C@H](/C=C(\C)C(=O)O)C(C)C)[C@@H](C)CC] |
| ER-809306 | 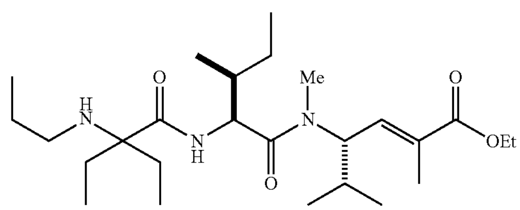 [SMILES: CCCNC(CC)(CC)C(=O)N[C@H](C(=O)N(C)[C@H](/C=C(\C)C(=O)OCC)C(C)C)[C@@H](C)CC] |
| ER-809308 | 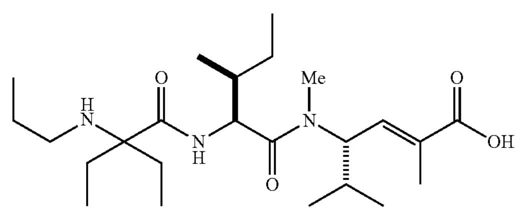 [SMILES: CCCNC(CC)(CC)C(=O)N[C@H](C(=O)N(C)[C@H](/C=C(\C)C(=O)O)C(C)C)[C@@H](C)CC] |
| ER-809309 | 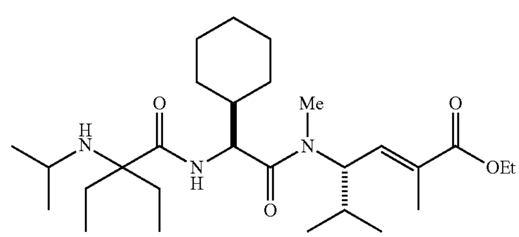 [SMILES: CCOC(=O)/C(C)=C/[C@H](C(C)C)N(C)C(=O)[C@@H](NC(=O)C(CC)(CC)NC(C)C)C1CCCCC1] |
| ER-809310 | 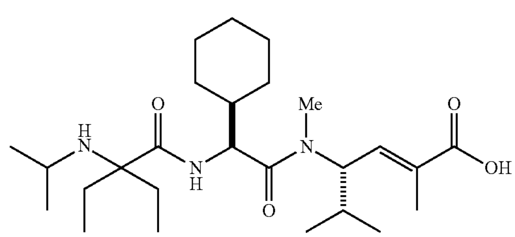 [SMILES: CCC(CC)(NC(C)C)C(=O)N[C@H](C(=O)N(C)[C@H](/C=C(\C)C(=O)O)C(C)C)C1CCCCC1] |

-continued

| Compound | Structure |
|---|---|
| ER-809311 | 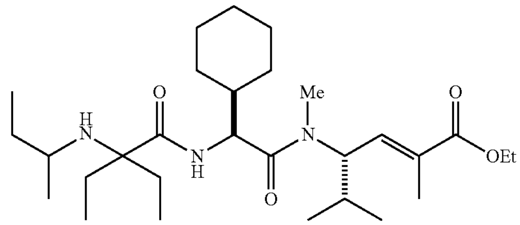 [SMILES: CCOC(=O)/C(C)=C/[C@H](C(C)C)N(C)C(=O)[C@@H](NC(=O)C(CC)(CC)NC(C)CC)C1CCCCC1] |
| ER-809312 | 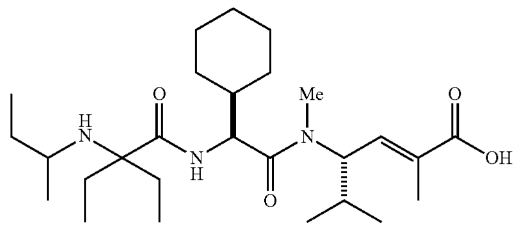 [SMILES: CCC(C)NC(CC)(CC)C(=O)N[C@H](C(=O)N(C)[C@H](/C=C(\C)C(=O)O)C(C)C)C1CCCCC1] |
| ER-809313 | 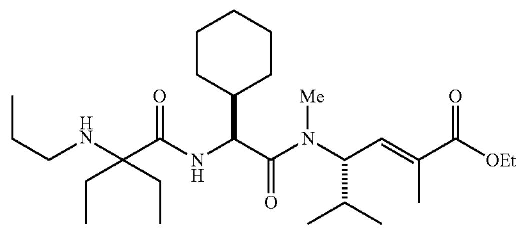 [SMILES: CCCNC(CC)(CC)C(=O)N[C@H](C(=O)N(C)[C@H](/C=C(\C)C(=O)OCC)C(C)C)C1CCCCC1] |
| ER-809314 | 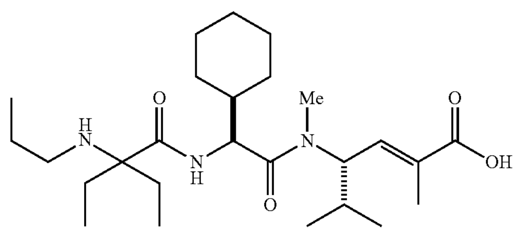 [SMILES: CCCNC(CC)(CC)C(=O)N[C@H](C(=O)N(C)[C@H](/C=C(\C)C(=O)O)C(C)C)C1CCCCC1] |
| ER-809315 | 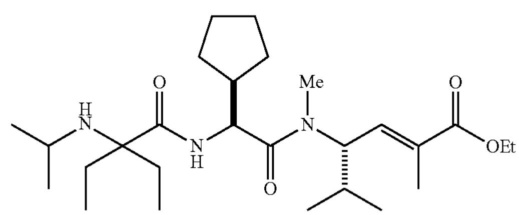 [SMILES: CCOC(=O)/C(C)=C/[C@H](C(C)C)N(C)C(=O)[C@@H](NC(=O)C(CC)(CC)NC(C)C)C1CCCC1] |
| ER-809316 | 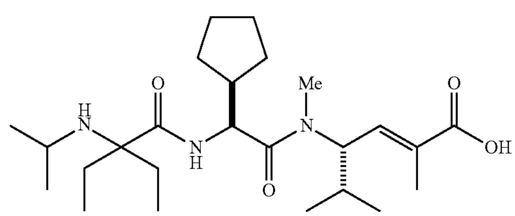 [SMILES: CCC(CC)(NC(C)C)C(=O)N[C@H](C(=O)N(C)[C@H](/C=C(\C)C(=O)O)C(C)C)C1CCCC1] |
| ER-809317 | 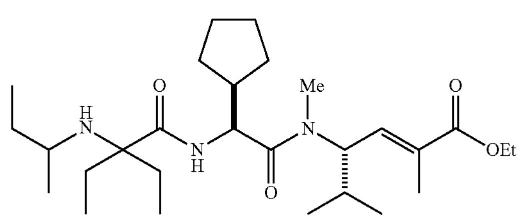 [SMILES: CCOC(=O)/C(C)=C/[C@H](C(C)C)N(C)C(=O)[C@@H](NC(=O)C(CC)(CC)NC(C)CC)C1CCCC1] |

| Compound | Structure |
|---|---|
| ER-809318 | 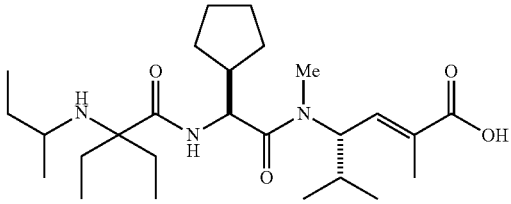 [SMILES: CCC(C)NC(CC)(CC)C(=O)N[C@H](C(=O)N(C)[C@H](/C=C(\C)C(=O)O)C(C)C)C1CCCC1] |
| ER-809319 | 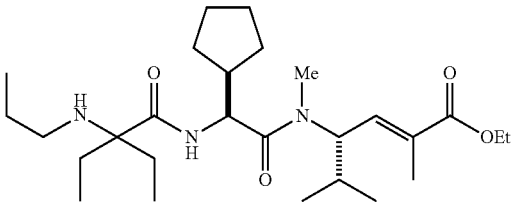 [SMILES: CCCNC(CC)(CC)C(=O)N[C@H](C(=O)N(C)[C@H](/C=C(\C)C(=O)OCC)C(C)C)C1CCCC1] |
| ER-809320 | 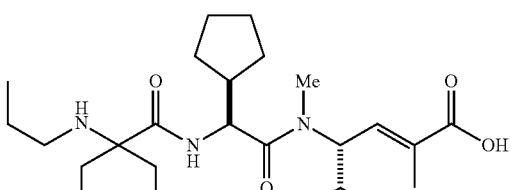 |
| ER-809321 | 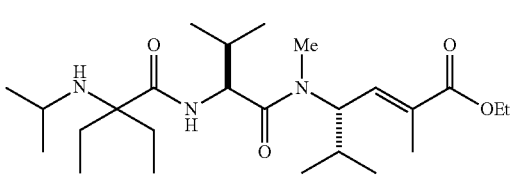 [SMILES: CCOC(=O)/C(C)=C/[C@H](C(C)C)N(C)C(=O)[C@@H](NC(=O)C(CC)(CC)NC(C)C)C(C)C] |
| ER-809322 | 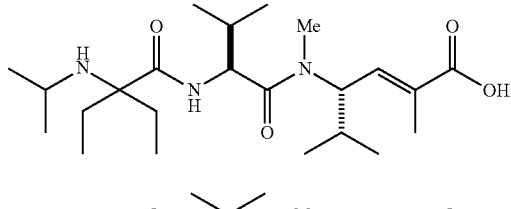 |
| ER-809323 | 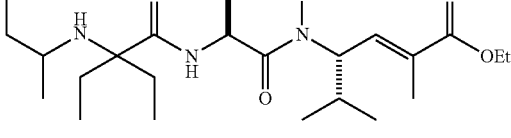 |
| ER-809324 | 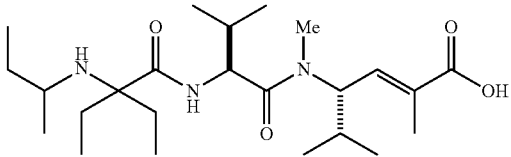 [SMILES: CCC(C)NC(CC)(CC)C(=O)N[C@H](C(=O)N(C)[C@H](/C=C(\C)C(=O)O)C(C)C)C(C)C] |
| ER-809325 | 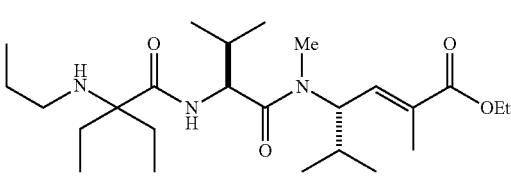 [SMILES: CCCNC(CC)(CC)C(=O)N[C@H](C(=O)N(C)[C@H](/C=C(\C)C(=O)OCC)C(C)C)C(C)C] |

| Compound | Structure |
|---|---|
| ER-809326 | 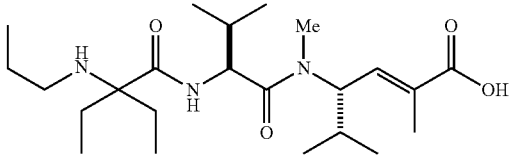 [SMILES: CCCNC(CC)(CC)C(=O)N[C@H](C(=O)N(C)[C@H](/C=C(\C)C(=O)O)C(C)C)C(C)C] |
| ER-809638 | 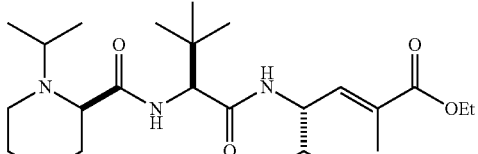 |
| ER-809640 | 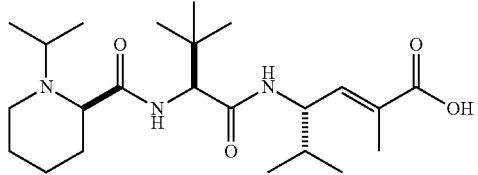 [SMILES: C/C(=C\[C@@H](NC(=O)[C@@H](NC(=O)[C@H]1CCCCN1C(C)C)C(C)(C)C)C(C)C)C(=O)O] |
| ER-809641<br>Single diastereomer | 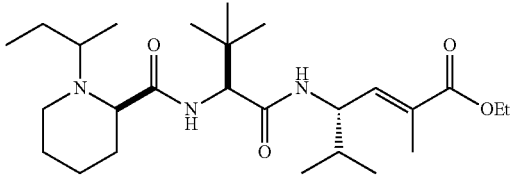 [SMILES: CCOC(=O)/C(C)=C/[C@@H](NC(=O)[C@@H](NC(=O)[C@H]1CCCCN1C(C)CC)C(C)(C)C)C(C)C] |
| ER-809642<br>Single diastereomer | 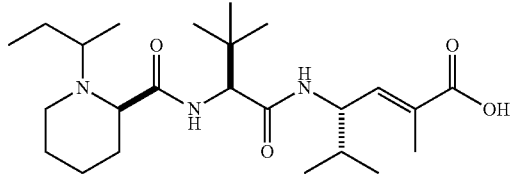 [SMILES: CCC(C)N1CCCC[C@@H]1C(=O)N[C@H](C(=O)N[C@H](/C=C(\C)C(=O)O)C(C)C)C(C)(C)C] |
| ER-809643<br>Single diastereomer | 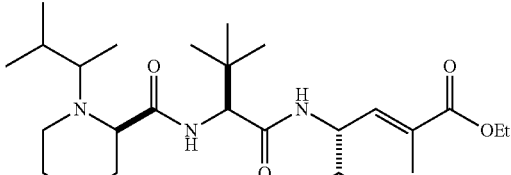 |
| ER-809644<br>Single diastereomer | 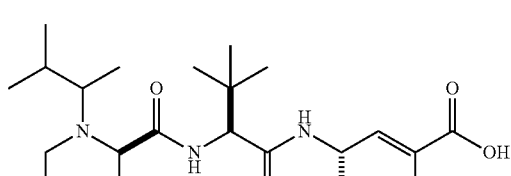 |
| ER-809645 | 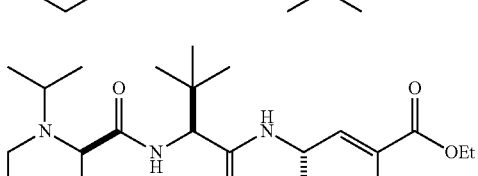 |

-continued
| Compound | Structure |
|---|---|
| ER-809646 | 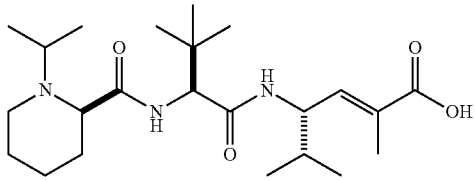 [SMILES: C/C(=C\[C@@H](NC(=O)[C@@H](NC(=O)[C@H]1CCCCN1C(C)C)C(C)(C)C)C(C)C)C(=O)O] |
| ER-809647
Single diastereomer | 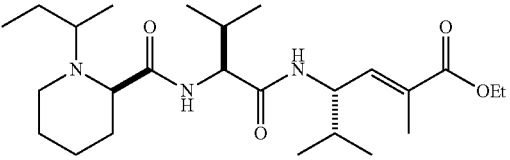 [SMILES: CCOC(=O)/C(C)=C/[C@@H](NC(=O)[C@@H](NC(=O)[C@H]1CCCCN1C(C)CC)C(C)C)C(C)C] |
| ER-809648
Single diastereomer | 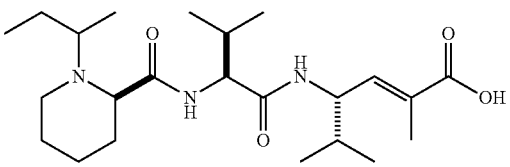 [SMILES: CCC(C)N1CCCC[C@@H]1C(=O)N[C@H](C(=O)N[C@H](/C=C(\C)C(=O)O)C(C)C)C(C)C] |
| ER-809649
Single diastereomer | 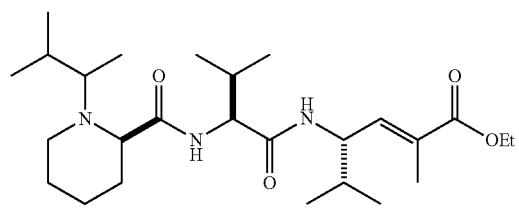 |
| ER-809650
Single diastereomer | 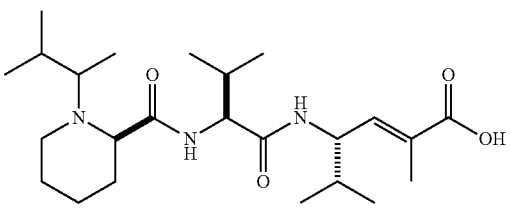 |
| | 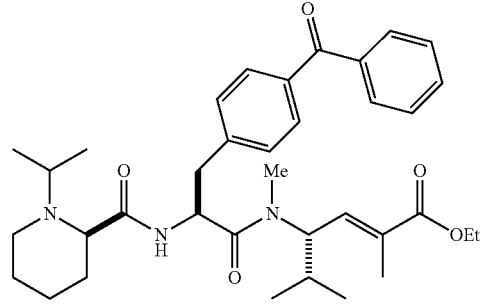 [SMILES: CCOC(=O)/C(C)=C/[C@H](C(C)C)N(C)C(=O)[C@H](Cc1ccc(C(=O)c2ccccc2)cc1)NC(=O)[C@H]1CCCCN1C(C)C] |
| | 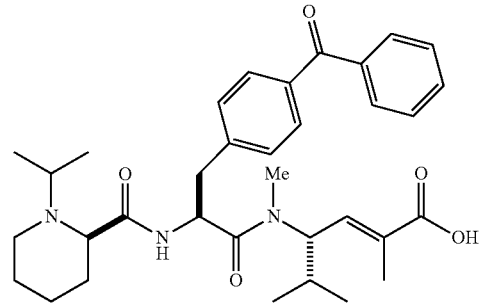 [SMILES: C/C(=C\[C@H](C(C)C)N(C)C(=O)[C@H](Cc1ccc(C(=O)c2ccccc2)cc1)NC(=O)[C@H]1CCCCN1C(C)C)C(=O)O] |

-continued
| Compound | Structure |
|---|---|
| | 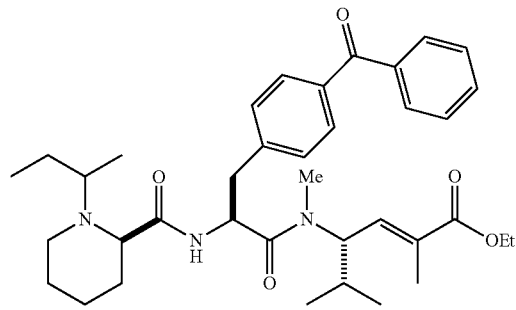 [SMILES: CCOC(=O)/C(C)=C/[C@H](C(C)C)N(C)C(=O)[C@H](Cc1ccc(C(=O)c2ccccc2)cc1)NC(=O)[C@H]1CCCCN1C(C)CC] |
| | 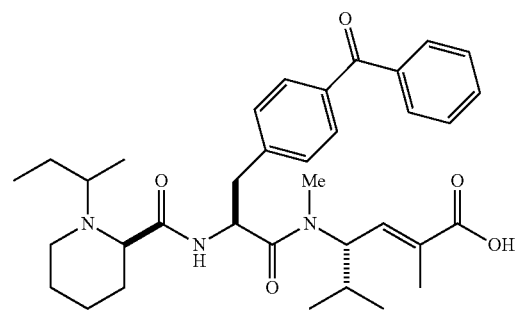 [SMILES: CCC(C)N1CCCC[C@@H]1C(=O)N[C@@H](Cc1ccc(C(=O)c2ccccc2)cc1)C(=O)N(C)[C@H](/C=C(\C)C(=O)O)C(C)C] |
| | 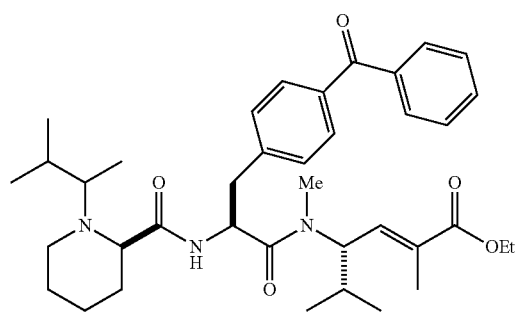 [SMILES: CCOC(=O)/C(C)=C/[C@H](C(C)C)N(C)C(=O)[C@H](Cc1ccc(C(=O)c2ccccc2)cc1)NC(=O)[C@H]1CCCCN1C(C)C(C)C] |
| | 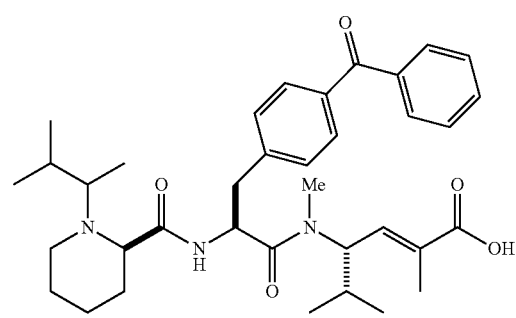 [SMILES: C/C(=C\[C@H](C(C)C)N(C)C(=O)[C@H](Cc1ccc(C(=O)c2ccccc2)cc1)NC(=O)[C@H]1CCCCN1C(C)C(C)C)C(=O)O] |
| | 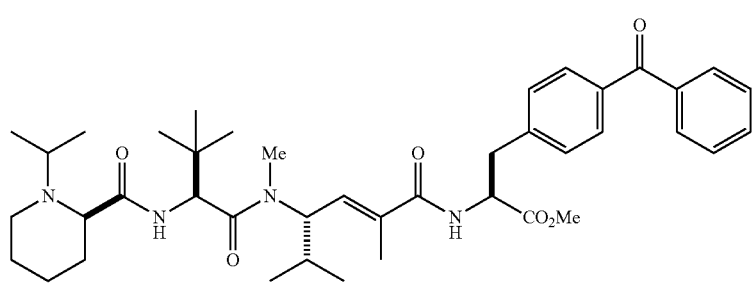 [SMILES: COC(=O)[C@H](Cc1ccc(C(=O)c2ccccc2)cc1)NC(=O)/C(C)=C/[C@H](C(C)C)N(C)C(=O)[C@@H](NC(=O)[C@H]1CCCCN1C(C)C)C(C)(C)C] |

| Compound | Structure |
|---|---|
| | 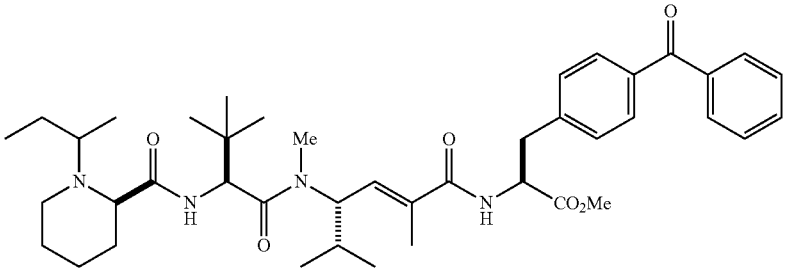 [SMILES: CCC(C)N1CCCC[C@@H]1C(=O)N[C@H](C(=O)N(C)[C@H](/C=C(\C)C(=O)N[C@@H](Cc1ccc(C(=O)c2ccccc2)cc1)C(=O)OC)C(C)C)C(C)(C)C] |
| | 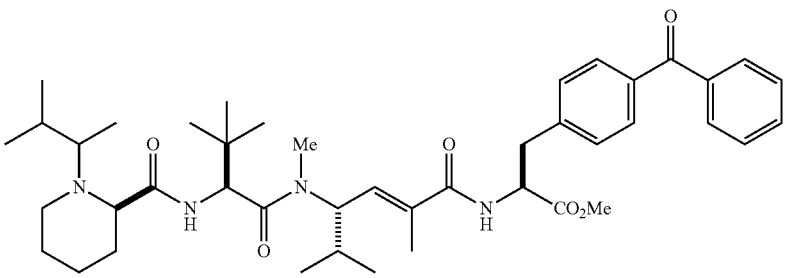 [SMILES: COC(=O)[C@H](Cc1ccc(C(=O)c2ccccc2)cc1)NC(=O)/C(C)=C/[C@H](C(C)C)N(C)C(=O)[C@@H](NC(=O)[C@H]1CCCCN1C(C)C(C)C)C(C)(C)C] |
| | 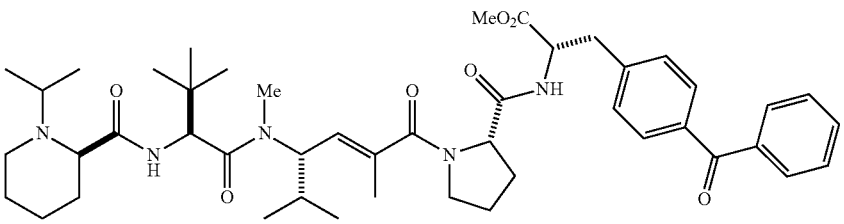 [SMILES: COC(=O)[C@H](Cc1ccc(C(=O)c2ccccc2)cc1)NC(=O)[C@@H]1CCCN1C(=O)/C(C)=C/[C@H](C(C)C)N(C)C(=O)[C@@H](NC(=O)[C@H]1CCCCN1C(C)C)C(C)(C)C] |
| | 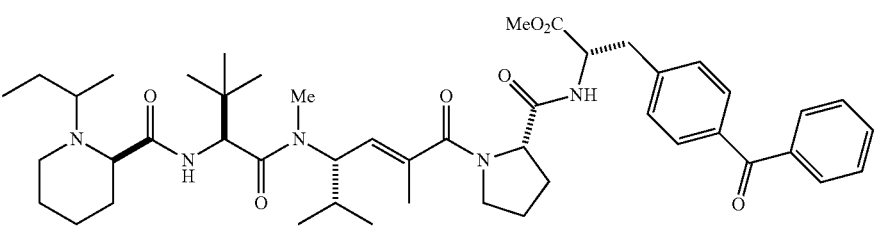 [SMILES: CCC(C)N1CCCC[C@@H]1C(=O)N[C@H](C(=O)N(C)[C@H](/C=C(\C)C(=O)N1CCC[C@H]1C(=O)N[C@@H](Cc1ccc(C(=O)c2ccccc2)cc1)C(=O)OC)C(C)C)C(C)(C)C] |
| | 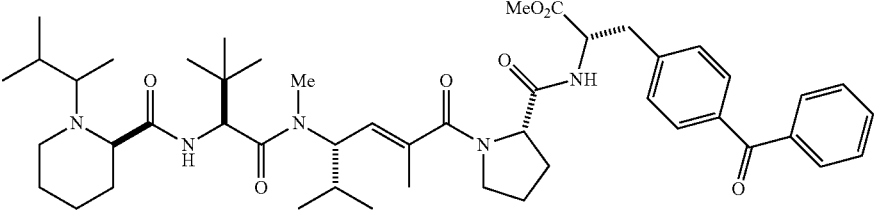 |

General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography (TLC), by proton nuclear magnetic resonance or by high-pressure liquid chromatography (HPLC), of a suitably worked up sample of the reaction mixture.

Listed below are abbreviations used for some common organic reagents referred to herein:

BOC or BOC$_2$O: Di-tert-Butyl dicarbonate
CMC: 1-Cyclohexyl-3-(2-morpholinoethyl)carbodiimide metho-p-toluenesulfonate
DCM: Dichloromethane
DEPC: Diethylphosphoryl cyanide (Diethyl cyanophosphonate)
DIBAL: Diisobutylaluminum hydride
DIEA: Diisopropylethylamine
DMF: N,N-Dimethylformamide
DMSO: Dimethylsulfoxide
Ether: Diethyl ether
HBTU: O-(1-H-benzotriazol-1-yl)-N,N,N,N-tetramethyluronium hexafluorophosphate
HOAt: 1-Hydroxy-7-azabenzotriazole
LAH: Lithium aluminum hydride
MSA: Methane sulfonic acid
NMM: N-Methyl Morpholine
TBME: Tert-butyl methyl ether
TFA: Trichloroacetic acid
THF: Tetrahydrofuran
TMEDA: Tetramethylethylenediamine General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (eg. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium thiosulphate in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself bad acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, then filtered. The crude products were then isolated by removal of solvent(s) by rotary evaporation under reduced, pressure, at an appropriate temperature (generally less than 45° C.).

On occasions where triphenylphosphine oxide was a major byproduct of the reaction, the reaction mixture was added directly to a large volume of well-stirred hexane. The resultant precipitate of triphenylphosphine oxide was removed by filtration, and the filtrate processed in the usual manner.

General Purification Procedures:

Chromatographic purification refers either to flash column chromatography on silica, using a single solvent or mixed solvent as eluent, or HPLC on a C18 column. Suitably purified desired product containing elutes were combined and concentrated under reduced pressure at an appropriate temperature (generally less than 45° C.) to constant mass. Final compounds were prepared for biological testing by either a) dissolved in 50% aqueous acetonitrile, filtered and transferred to vials, then freeze-dried under high vacuum; or b) dissolved in methanol, filtered and transferred to vials, then concentrated to dryness using a Centrifugal vacuum evaporator.

Example 1

Preparation of Amine Esters 18, Amine Acids 20 and Amine Amides 23

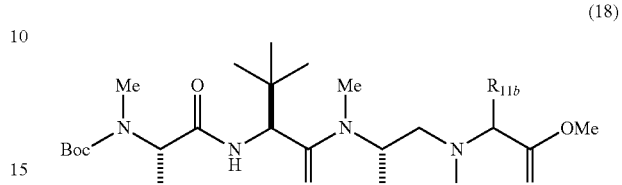

(18)

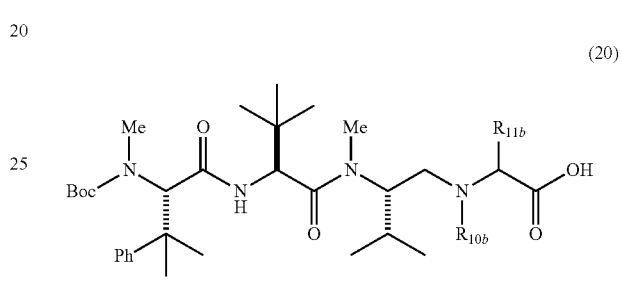

(20)

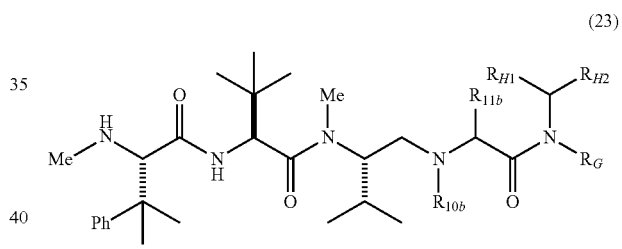

(23)

Preparation of Compound 13

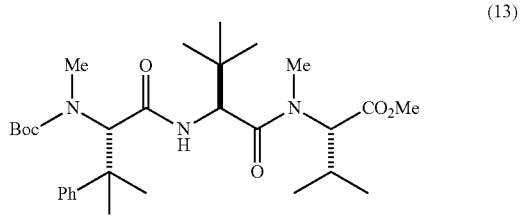 [SMILES: COC(=O)[C@H](C(C)C)N(C)C(=O)[C@@H](NC(=O)[C@@H](N(C)C(=O)OC(C)(C)C)C(C)(C)c1ccccc1)C(C)(C)C]

(13)

To a solution of Compound 12 (205 mg) in DMF (3.8 ml), at room temperature, was added (S)—N-Boc-neo-phenylalanine (6) (140 mg), NMM (0.30 ml), HOAt (0.1.24 g), and CMC (1.16 g). The reaction mixture was shaken at room temperature for 24 hr. Aqueous workup followed by chromatographic purification gave Compound 13 (153 mg, 61%).

Preparation of Compound 14

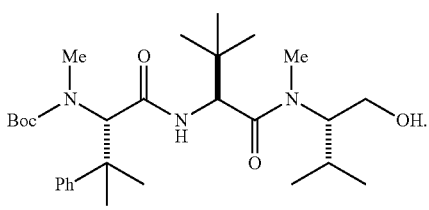
(14)

To a solution, of compound 13 (153 mg) in methanol (20 ml), at 0° C., was added sodium borohydride (3.18 g) portionwise with shaking over a 3 day period, The reaction mixture temperature was maintained between 0°-5° C. On occasion where the reaction mixture turned into a solidified mass, THF was added to aid agitation. The reaction mixture was allowed to warm to room temperature then re-cooled to 0° C. and worked up in the usual manner to give compound 14 (140 mg, 96%).

Preparation of Compound 15

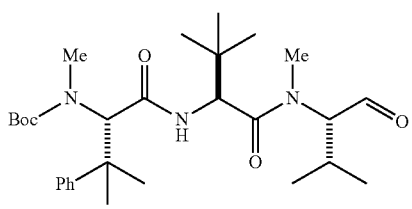
(15)

To a solution of compound 14 (50 mg) in THF (3 ml), at room temperature, was added Dess Martin periodinane (204 mg) in one portion. The resultant suspension was stirred vigorously for 4.5 hr. An aqueous work up gave crude compound 15 (50 mg) which was used immediately in the next stage without purification.

General Procedure for the Preparation of Amine Esters 18

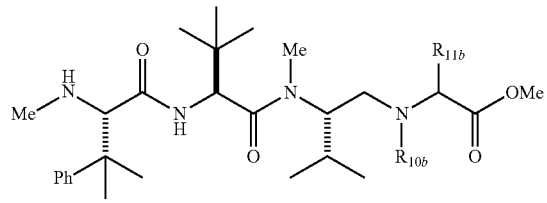
(18)

To a solution of compound 15 (1 equivalent) in a suitable volume of 1,2-dichlorethane, at room temperature, was added 4A molecular sieves (crushed and dried) (equal mass to that of the amine hydrochloride). A suitably chosen amine hydrochloride (16) (10 equivalents) was added with vigorous stirring followed by sodium triacetoxyborohydride (1-5 equivalents). The reaction mixture was stirred at an appropriate temperature (20°-50° C. until compound 15 was consumed to a satisfactory degree. Aqueous work up followed by chromatographic purification gave the corresponding N-Boc Amine Ester 17. Deprotection of the N-Boc moiety under suitable conditions would give the corresponding N-terminal free amine 18.

General Procedure for the Preparation of Amine Acids 20

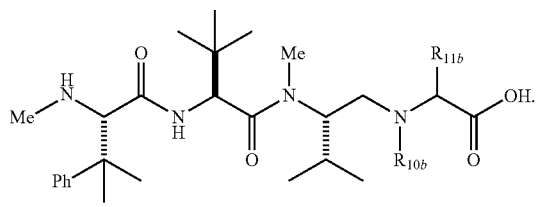
(20)

To a solution of the N-Boc Amine Ester 17 in a suitable mixture of THF and methanol, was added 1M lithium hydroxide solution (10-50 equivalents). When the N-Boc Amine Ester 17 was hydrolyzed to a satisfactory degree, the reaction mixture was given an aqueous work up. The N-Boc Amine Acid 19 was purified chromatographically. Deprotection of the N-Boc moiety under suitable conditions would give the corresponding N-terminal free amine 20.

General procedure for the Preparation of Amine Amides 23

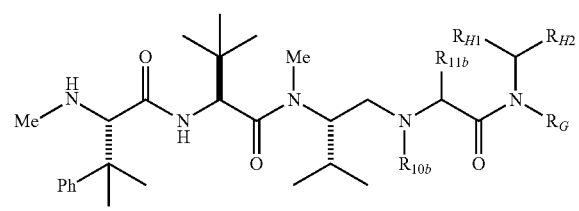
(23)

To a solution of the N-Boc Amine Acid 19 in DMF, at room temperature, was added NMM (20 equivalents). A suitably chosen amine hydrochloride (21) (20 equivalents) was added followed by DEPC (20 equivalents). When the N-Boc Amine Acid 19 was consumed to a satisfactory degree the N-Boc Amine Amide 22 was isolated either by direct chromatographic purification of the reaction mixture, or by an aqueous work up followed by chromatographic purification. Deprotection of the N-Boc moiety under suitable conditions would give the corresponding N-terminal free amine 23.

Example 2

Preparation of N-Acetyl Amime Amides 27

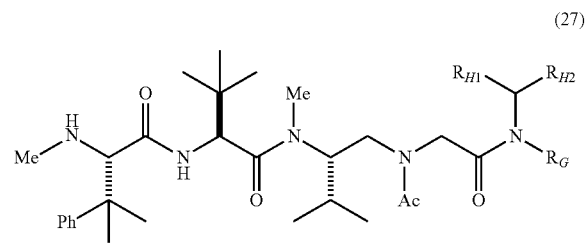
(27)

Preparation of Compound 24

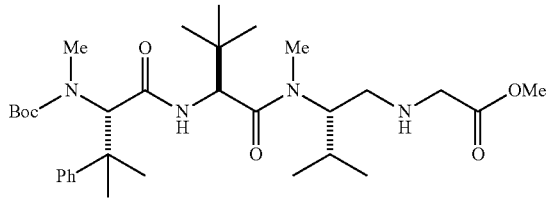
(24)

To a solution of aldehyde 13 (50 mg) in 1,2-dichloroethane (2 ml), at room temperature, was added 4A molecular sieves (crushed and dried) (50 mg). Glycine methyl ester hydrochloride (120 mg) was added with vigorous stirring followed by sodium triacetoxyborohydride (205 mg). The reaction mixture was stirred at 40° C.) for two hours. Aqueous work up followed by chromatographic purification gave compound 24 (31 mg, 46%).

Preparation of Compound 25

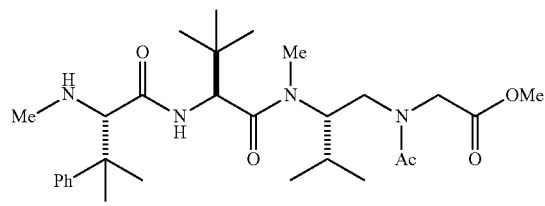
(25)

To a solution of compound 24 (5.5 mg) in DMF (0.4 ml), at room temperature, was added pyridine (0.006 ml) followed by acetic anhydride (0.004 ml). The reaction mixture was shaken for three hours at room temperature then concentrated in vacuo to dryness. The residue was dissolved in saturated HCl in methanol (1 ml) and stood at room temperature for 15 minutes. The reaction mixture was concentrated in vacuo to give compound 25 (4 mg, 90%).

Preparation of Compound 26

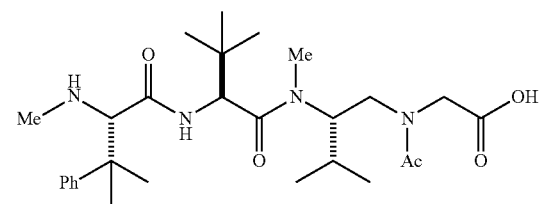
(26)

To a solution of compound 25 (3.35 mg) in methanol (0.2 ml), was added 1 M lithium hydroxide solution (0.118 mL). The reaction mixture was stirred at room temperature for 5 hr.

Chromatographic purification followed by treatment with methanolic HCl gave the hydrochloride salt of compound 26 (1.95 mg, 61%).

General Procedure for the Preparation of N-Acetyl Amine Amides 27

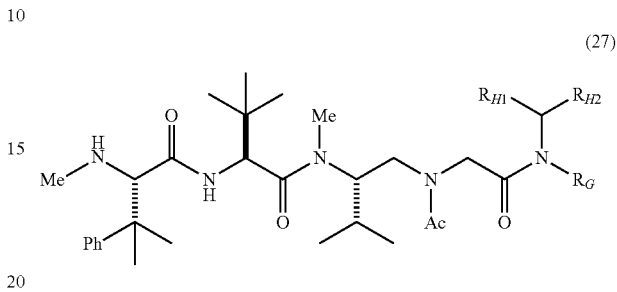
(27)

To a solution of compound 26 (1 equivalent) in DMF, at room temperature, was added NMM (20 equivalents). A suitably chosen amine hydrochloride (21) (20 equivalents) was added followed by DEPC (20 equivalents). When compound 26 was consumed to a satisfactory degree the N-Acetyl Amine Amide (27) was isolated by direct chromatographic purification of the reaction mixture Example 3

Preparation of Compound 33

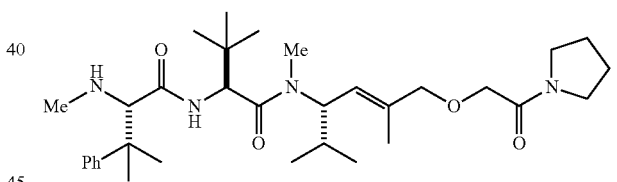
(33)

Preparation of Compound 28

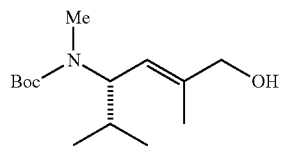
(28)

To a solution of compound 3b (1.94 g) in dry DCM (20 mL), at 0° C. under an inert atmosphere, was added a 1 M solution of DIBAL (32 mL) dropwise. The reaction mixture was stirred at 0° C. for 2.5 hr then methanol (4.4 mL) was added dropwise followed by a saturated solution of ammonium chloride (8.8 mL). DCM (200 mL) was added and the reaction mixture stirred vigorously at room temperature for 30 min. Filtration followed by concentrated in vacuo gave crude compound 28 (1.08 g, 65%)

Preparation of Compound 29

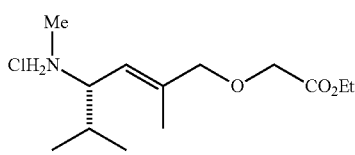
(29)

To a solution of compound 28 (207 mg) in THF (5 ml), at 0° C. under an inert atmosphere, was added sodium hydride (60% dispersion in mineral oil; 160 mg) portionwise. The reaction mixture was stirred at 0° C. for 45 min then treated with ethyl bromoacetate (0.47 mL). The reaction mixture was allowed to warm to room temperature. An aqueous work up followed by chromatographic purification gave an intermediate Boo compound (185 mg, 67%). The intermediate Boc compound (139 mg) was dissolved in ethanol (2 mL) and treated with saturated HCl in ethanol (2 mL). The reaction mixture was stood at room temperature for 10 min then concentrated in vacuo to dryness to give compound 29 (114 mg).

Preparation of Compound 30

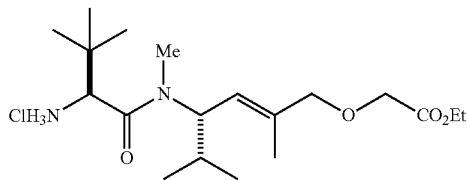
(30)

To a solution of compound 29 (114 mg) in DMF (1.8 mL), at room temperature, was added (S)—N-Boc-tert-leucine (4) (283 mg), NMM (0.135 mL), HOAt (56 mg), and CMC (518 mg). The reaction mixture was shaken at room temperature for 16 hr. Aqueous workup followed by chromatographic purification gave an intermediate Boc compound (42 mg, 22%). The intermediate Boc compound (42 mg) was dissolved in saturated HCl in ethanol (5 mL) and stood at room temperature for 10 min. Concentration in vacuo gave compound 30 (37 mg).

Preparation of Compound 31

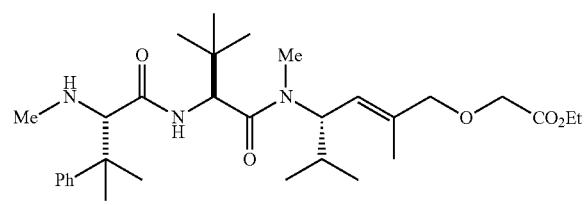
(31)

To a solution of compound 30 (24 mg) in DMF (0.26 mL), at room temperature, was added (S)—N-Boc-neo-phenylalanine (6) (38 mg), NMM (0.014 mL), HOAt (8.3 mg), and CMC (52 mg). The reaction mixture was shaken at room temperature for 16 hr. Aqueous workup followed by cinematographic purification gave an intermediate Boc compound (38 mg, 64%). The intermediate Boc compound (38 mg) was dissolved in saturated HCl in ethanol (5 mL) and stood at room temperature for 10 min. Concentration in vacuo gave compound 31 as its HCl salt.

Preparation of Compound 32

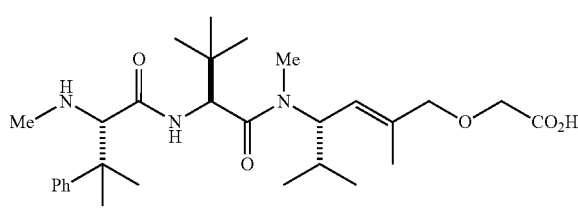
(32)

A solution of compound 31 (4 mg) in ethanol (2 mL) was treated with 1M lithium hydroxide (0.5 ml). The reaction mixture was stirred at room temperature for 1.5 hr. Aqueous work up followed by chromatographic purification gave compound 32 (2.9 mg, 76%).

Preparation of Compound 33

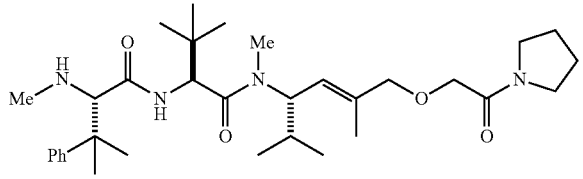
(33)

To a solution of compound 32 (1.9 mg) in DMF (70 µl), at room temperature, was added NMM (3.8 µl), pyrrolidine (2.8 µl), and DEPC (5.2 µl). The reaction mixture was stirred at room temperature for 16 hr. The reaction mixture was purified chromatographically to give compound 33 (1.2 mg, 58%).

Example 4

Preparation of Amine Esters 42, Amine Acids 43 and Amine Amides 45

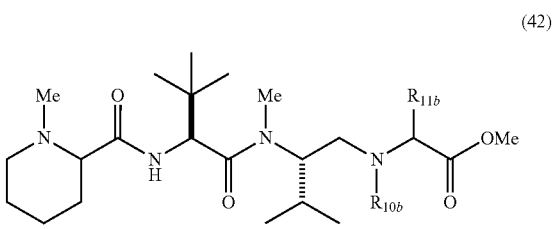
(42)

381

-continued (43)

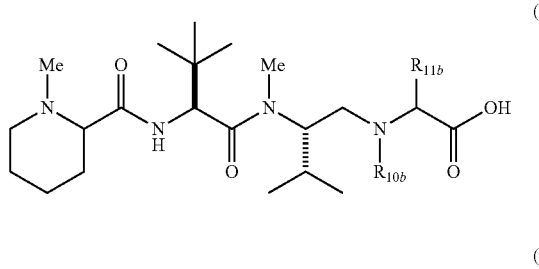

(45)

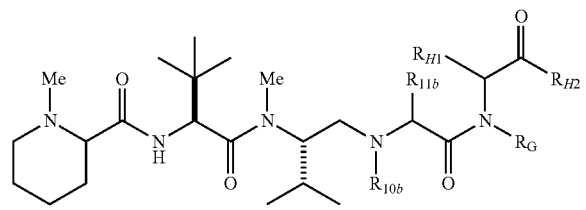

Preparation of Compound 39

(39)

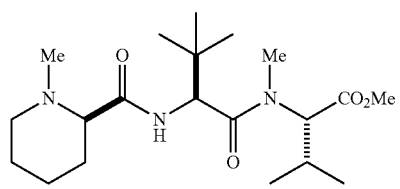

To a solution of compound 1.2 (1.25 g) in DMF (21 mL), at room, temperature, was added (R)—N-methylpipecoline hydrochloride (38) (0.38 g), NMM (1.4 mL), HOAt (0.575 g), and CMC (5.37 g). The reaction mixture was shaken at room temperature for 24 hr. Aqueous workup gave compound 39 (0.511 g, 63%).

Preparation of Compound 40

(40)

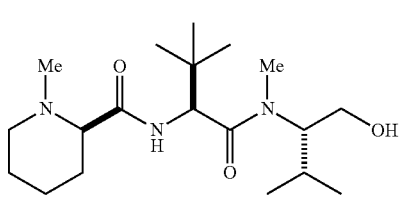

To a solution of compound 39 (0.8 g) in methanol (8 mL), at 0° C., was added sodium borohydride (7.9 g) portionwise over a 3 day period. The reaction mixture temperature was maintained between 0°-5° C. On occasion where the reaction mixture turned into a solidified mass, THF was added to aid storing. The reaction mixture was allowed to warm to room temperature then re-cooled to 0° C. and quenched with saturated sodium bicarbonate solution. Aqueous workup gave compound 40.

382

Preparation of Compound 41

(41)

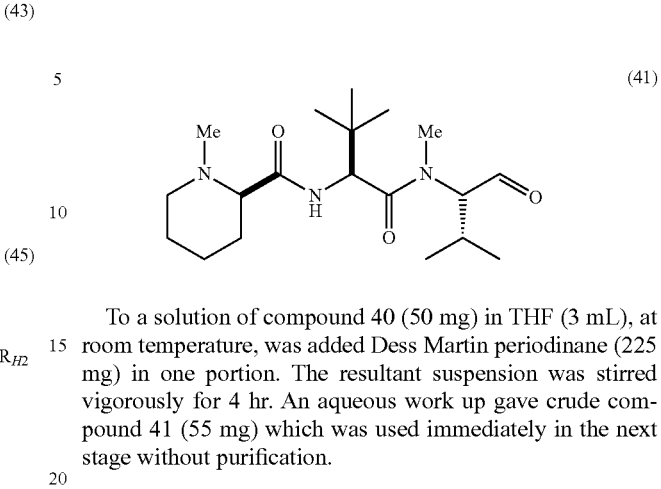

To a solution of compound 40 (50 mg) in THF (3 mL), at room temperature, was added Dess Martin periodinane (225 mg) in one portion. The resultant suspension was stirred vigorously for 4 hr. An aqueous work up gave crude compound 41 (55 mg) which was used immediately in the next stage without purification.

General Procedure for the Preparation of N-Terminal N-Heterocyclic Amine Esters 42

(42)

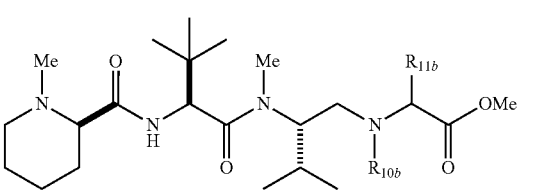

To a solution of compound 41 (300 mg) in 1,2-dichloroethane (10 mL), at room temperature, was added 4A molecular sieves (crushed and dried) (1.5 g). The amino acid ester hydrochloride (16) (10 equivalents) was added and the reaction mixture stirred, vigorously for ~10 min. Sodium triacetoxyborohydride (290 mg) was added in one portion and the reaction mixture stirred vigorously at room temperature. When compound 41 was consumed to a satisfactory degree, the reaction mixture was given an aqueous work up. The terminal N-heterocyclic Amine Esters 42 was purified chromatographically, except in eases where it was deemed unnecessary.

General Procedure for the Preparation of N-Terminal N-Heterocyclic Amine Acids 43

(43)

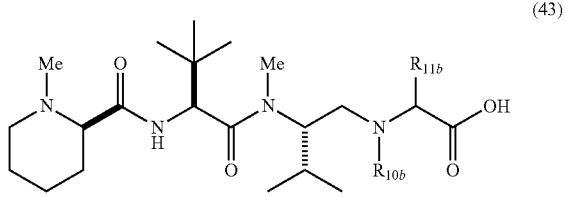

To a solution of the N-terminal N-heterocyclic Amine Esters (42) in a suitable mixture of THF and methanol, was added 1 M lithium hydroxide solution (10-50 equivalents). When the N-terminal N-heterocyclic Amine Esters 42 was hydrolyzed to a satisfactory degree, the reaction mixture was given an aqueous work up. The N-terminal N-heterocyclic Amine acid 43 was purified chromatographically, except in cases where it was deemed unnecessary.

General Procedure for the Preparation of N-Terminal N-Heterocyclic Amine Amides 45

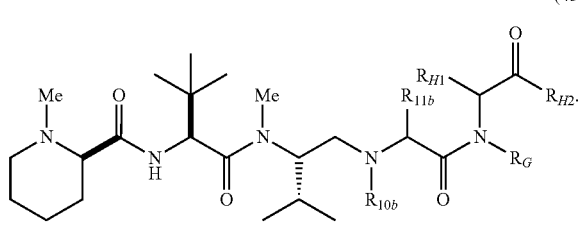
(45)

To a solution of the N-terminal N-heterocyclic Amine acid 43 in DMF, at room temperature, was added NMM (20 equivalents). A suitably chosen amine hydrochloride (44) (20 equivalents) was added followed by DEPC (20 equivalents). When the N-terminal N-heterocyclic Amine acid 43 was consumed to a satisfactory degree the N-terminal N-heterocyclic Amine Amide 45 was isolated either by direct chromatographic purification of the reaction mixture, or by an aqueous work up followed by chromatographic purification.

Example 5

Preparation of Compounds 51 and 52

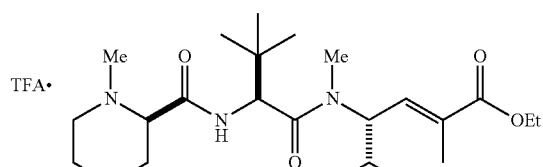
(51)

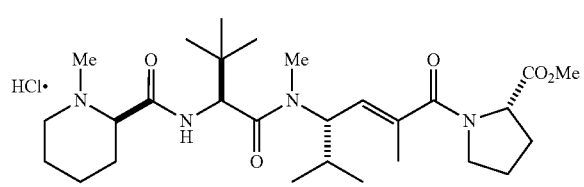
(52)

Step 1: Preparation of Compound 49

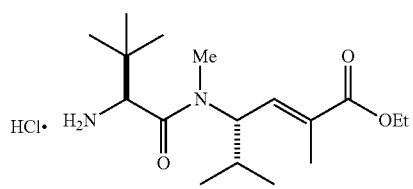
(49)

Preparation of Compound 47

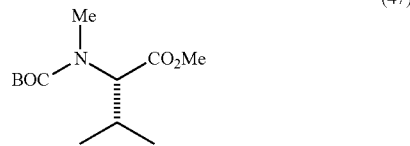
(47)

Procedure a.

Compound 46 (1.0405 g, 4.4984 mmol) was dissolved in DMF (8.0 mL). $K_2CO_3$ (0.6258 g, 4.5279 mmol) was added. Methyl iodide (0.6 mL, 9.6379 mmol) was added. The milky suspension was stirred at room temp under nitrogen for 3 days. Standard aqueous workup yielded ester 47 as a colorless oil (1.0590 g, 96%).

Preparation of Compound 2

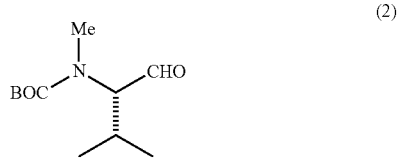
(2)

Compound 47 (0.9447 g, 3.8509 mmol) was dissolved in toluene (15 mL), and the solution was cooled to −78° C. under nitrogen. DIBAL (6.0 mL, 6.00 mmol, 1.0 M in hexanes) was added via syringe over 5 min. The solution was stirred for 1 h, and was quenched with MeOH (1.0 mL) at −78° C. The bath was removed, and 5.0 mL of saturated potassium sodium tartrate solution was added. The mixture was stirred for ca. 1 h, and was filtered through Celite. The filtrate was washed with $H_2O$ and brine, and dried over $Na_2SO_4$, filtered, and evaporated to give compound 2 (0.8413 g, 101%) sufficiently pure for the next step.

Preparation of Compound 3b

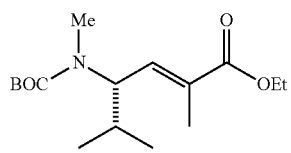
(3b)

Compound 2 (0.8413 g, 3.8509 mmol) was dissolved in $CH_2Cl_2$ (5.0 mL) and (carbethoxyethylidene)triphenylphosphorane (1.8212 g, 5.0254 mmol) was added. The solution was stirred at room temp under nitrogen overnight. The solution was evaporated, and the residue was diluted with EtOAc (70 mL) and washed with $H_2O$ (2×25 mL) and brine (25 mL), and dried over $Na_2SO_4$, filtered, and evaporated to give an oil.

Purification by Flash Chromatography on SiO₂ (FC) gave pure compound 3b (0.7863 g, 68%).

Preparation of Compound 48

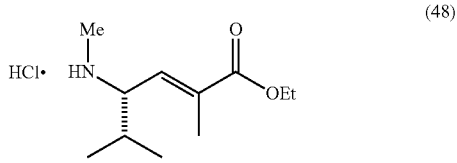

(48)

Compound 3b (0.7863 g, 2.6262 mmol) was dissolved in CH₂Cl₂ (1.0 mL) and triethylsilane (0.460 mL, 2,880 mmol) was added. Trifluoroacetic acid (TFA) (2.5 mL) was added at room temp. After 30 min (complete reaction as judged by HPLC), the solution was evaporated to give a solid (1.1307 g). This solid was dissolved in CH₃CN (ca. 10 mL) and 5.5 N HCl (2.4 mL, 13.2 mmol) was added. Evaporation gave the HCl salt, compound 48 (0.618 g, 100%).

Preparation of Compound 5b

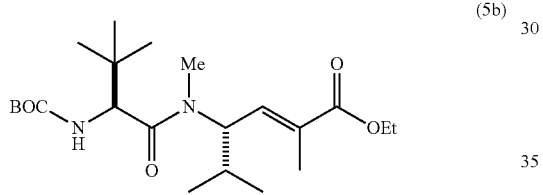

(5b)

Compound 48 (0.390 g, 1.6543 mmol), L-N—BOC-t-butylglycine (1.0106 g, 4.3694 mmol), CMC (1.9704 g, 4.6518 mmol), HOAt (0.5905 g, 4.3384 mmol), and NMM (0.490 mL, 4.4567 mmol) were combined, and DMF (4.0 mL) was added. The solution was stirred at room temp under nitrogen for 25 h. The solution was diluted with EtOAc (70 mL) and was washed with H₂O (2×25 mL), aq. pH 7.2 phosphate buffer (25 mL), H₂O (25 mL), and brine (25 mL), and dried, over MgSO₄, filtered, and evaporated to give a solid which was purified by FC to give compound 5b (0.4239 g, 62%), Preparation of Compound 49

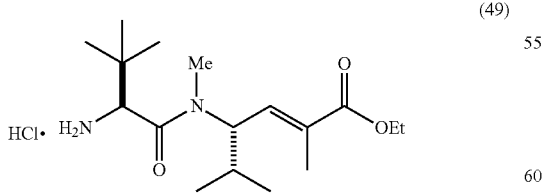

(49)

Compound 5b (0.1159 g, 0.2809 mmol) was dissolved in CH₂Cl₂ (3.0 mL) and triethylsilane (0.050 mL, 0.3130 mmol) was added. Trifluoroacetic acid (TFA) (2.5 mL) was added at room temp. After 30 min (complete reaction as judged by HPLC), the solution was evaporated to give a solid. This solid was dissolved in CH₃CN (ca. 5 mL) and 5.5 N HCl was added (0.3 mL, 1.65 mmol). Evaporation gave the HCl salt, compound 49 (0.0662 g, 100%), Step 2: Preparation of Compound 51

Preparation of Compound 50

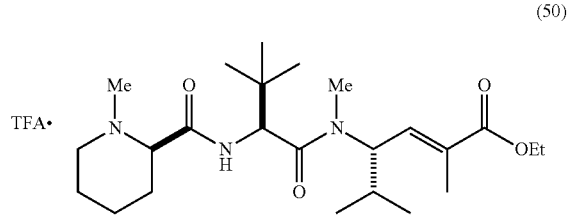

(50)

Compound 49 (0.0774 g, 0.2219 mmol), (R)—N-methylpipecolic (0.0705 g, 0.3925 mmol), CMC (0.1752 g, 0.4136 mmol), HOAt (0.0344 g, 0.2527 mmol), and NMM (0.063 mL, 0.5730 mmol) were combined, and DMF (2.0 mL) was added. The solution was stirred at room temp under nitrogen for 20 h. The solution was purified directly by RP HPLC to give compound 50 (0.0989 g, 81%).

Preparation of Compound 51

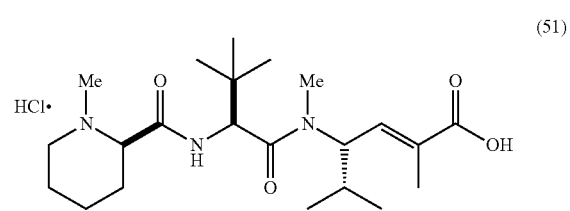

(51)

Compound 50 (0.0989 g, 0.2086 mmol) was dissolved in 1:1 H₂O/MeOH (14 mL) at room temp. LiOH (0.0537 g, 2.2422 mmol) was added. The suspension was stirred at room temp. 19 h. The solution was acidified with 5.5 N HCl (0.50 mL), and purified by RP HPLC to give the TFA salt of 11 (0.0978 g, 90%). This was dissolved m CH₃CN (ca. 5 mL) and treated with 5.5 N HCl (ca. 1 mL, 5.5 mmol) and evaporated to give the HCl salt of compound 51 (0.0867 g, 72%).

Step 2: Preparation of Compound 52

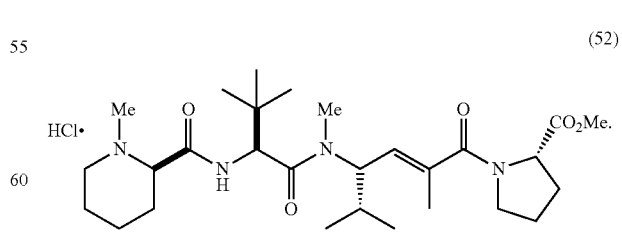

(52)

Compound 51 (0.0062 g, 0.0139 mmol), L-proline methyl ester hydrochloride (0.0263 g, 0.1588 mmol) were dissolved in DMF (3.0 mL) at room temp, under nitrogen. DEPC (0.017 mL, 0.1120 mmol) was added via syringe. NMM (0.025 mL, 0.2274 mmol) was added via syringe. The solution was stirred overnight, quenched with H₂O (1.0 mL), and purified by RP HPLC to give the TFA salt of compound 52. This was dissolved in CH₃CN (ca. 3 mL) and treated with 5.5 N HCl (0.10 mL, 0.55 mmol) and evaporated to give the HCl salt of compound 52 (0.0078 g, 100%).

Example 6

Preparation of Compound 62a

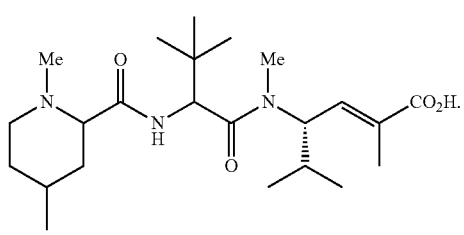
(62a)

Preparation of compound 54

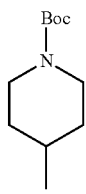
(54)

To a solution of 4-methylpiperidine (53) (600 µL, 5.0 mmol) in MeOH (20 mL) was added Et₃N (770 µL, 5.5 mmol) followed by Boc₂O (1.2 g, 5.5 mmol) at 0° C. After 15 minutes, the reaction mixture was warmed to room temperature and allowed to stir overnight. The reaction solution was then diluted with H₂O and extracted several times with ether. The ether extracts were combined, dried over Mg₂SO₄, filtered, and concentrated to provide compound 54 (926.5 mg) quantitatively as a colorless oil.

Preparation of Compound 55

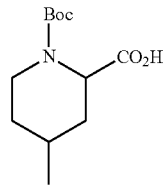
(55)

A solution of compound 54 (926.5 mg, 5.0 mmol) in Et₂O (10.5 mL) was cooled to −78° C. and treated with TMEDA (755 µL, 5.0 mmol) followed by slow addition of a 1.3 M cyclohexane solution of sec-butyllithium (4.6 mL, 6.0 mmol) over a 30 minute period. The reaction solution was then warmed to −20° C. and maintained at that temperature for 30 minutes, after which the solution was re-cooled to −78° C. and purged with gaseous carbon dioxide for 15 minutes. The reaction solution was then slowly warmed to 0° C. and poured into a biphasic mixture of 1 N HCl (100 mL) and EtOAc (50 mL). The reaction solution was then extracted several times with EtOAc. The EtOAc extracts were combined, dried over Mg₂SO₄, filtered, and concentrated to provide compound 55 (1.07 g) in 89% yield as a colorless oil (a mixture of two cis enantiomers).

Preparation of Compound 59a

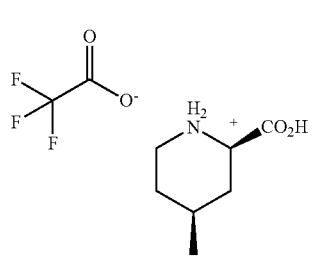
(59a)

To a solution of compound 55 (292 mg, 1.2 mmol) in CH₂Cl₂ (2.4 mL) at 0° C. was added TEA (2.4 mL). After 15 minutes, the reaction solution was warmed to r.t. and stirred for 3 hours. The reaction mature was then concentrated in vacuo to provide compound 59a (309 mg) quantitatively as a light yellow oil.

Preparation of Compound 59b

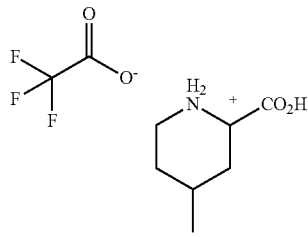
(59b)

Step 1: Preparation of Compound 56

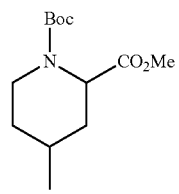
(56)

To a solution of compound 55 (780 mg, 3.2 mmol) in DMF (6.4 mL) was added K₂CO₃ (663 mg, 4.8 mmol) followed by MeI (300 µL, 4.5 mmol). The reaction solution was allowed to stir overnight The reaction mixture was then diluted with H₂O and extracted several times with ether. The ether extracts were combined, dried over Mg₂SO₄, filtered, and concentrated in vacuo. Purification of the residue by silica gel chromatography (4% EtOAc in hexanes) yielded 535 mg (65%) of compound 56 as a colorless oil.

Step 2: Preparation of Compound 57

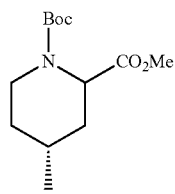
(57)

To a solution of compound 56 (463 mg, 1.8 mmol) is MeOH (2.6 mL) was added a 25 wt % solution of NaOMe in MeOH (100 µL). The solution was allowed to stir overnight. The reaction mixture was then diluted with H₂O and extracted several times with ether. The ether extracts were combined, dried over Mg₂SO₄, filtered, and concentrated in vacuo. Purification of the residue by silica gel chromatography (4% EtOAc in hexanes) yielded 363.6 mg (79%) of racemic compound 57 as a colorless oil.

Step 3: Preparation of Compound 58

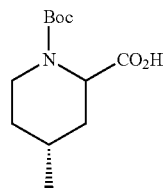
(58)

To a solution of compound 57 (360 mg, 1.4 mmol) In a 2:1 mixture of H₂O (2.75 mL) and EtOH (5.50 mL) was added KOH pellets (786 mg, 14 mmol) and the reaction solution was stirred at room temperature until complete by TLC. The reaction mixture was then diluted with H₂O and extracted several times with ether. The ether extracts were combined, dried over Mg₂SO₄, filtered, and concentrated to provide compound 58 (341 mg) quantitatively as a white solid.

Step 4: Preparation of Compound 59b

To a solution of compound 58 (292 mg, 1.2 mmol) in CH₂Cl₂ (2.4 mL) at 0° C. was added TFA (2.4 mL). After 15 minutes, the reaction solution was warmed to r.t. and stirred for 3 hours. The reaction mixture was then concentrated in vacuo to provide compound 59b (309 mg) quantitatively as a light yellow oil.

Step 4: Preparation of Compound 59b

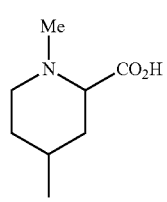
(60a and 60b)

To a solution of compound 59a (or 59b) (283 mg, 1.1 mmol) in MeOH (5 mL) was added Pd(OH)₂ (75 mg) followed by a 37 wt % solution of formaldehyde in H₂O (300 µL). Gaseous H₂ (balloon pressure) was charged in and the reaction mixture was allowed to stir under an H₂ atmosphere overnight. The reaction solution was then filtered through a bed of celite, and concentrated to provide compound 60a (or 60b) (173 mg) quantitatively as a white solid.

Preparation of Compounds 61a and 61b

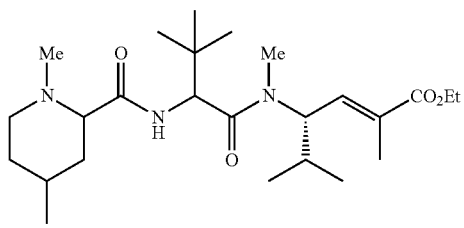
(61a and 61b)

To a solution of compound 60a and 60b (11.0 mg, 0.07 mmol) in CH₂Cl₂ (350 µL) was added HBTU (40 mg, 0.11 mmol) and DIEA (37 µL, 0.21 mmol). After 5 minutes, amine 49 (22.0 mg, 0.11 mmol) was added. The reaction mixture was stirred for 30 minutes, filtered, and concentrated. Purification of the residue by silica gel chromatography (2% EtOH in CH₂Cl₂) yielded 15.1 mg (96%) of each diastereomer 61a and 61b as colorless oils.

Preparation of Compound 62a

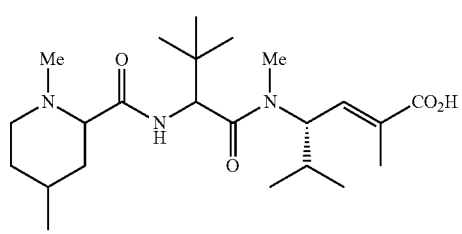
(62a)

To a solution of diastereomer 61a (9.0 mg, 0.02 mmol) in a 2:1 mixture of H₂O (80 µL) and EtOH (160 µL) was added LiOH.H₂O (840 mg, 0.20 mmols). The reaction solution was allowed to stir overnight. The reaction mixture was then acidified with 1 N HCl until the pH=6.00. The solution was then extracted several times with CH₂Cl₂. The CH₂Cl₂ extracts were combined, dried over Mg₂SO₄, filtered, and concentrated to provide compound 62a (8.4 mg) quantitatively as a white solid.

Example 7

Preparation of Compound 67b

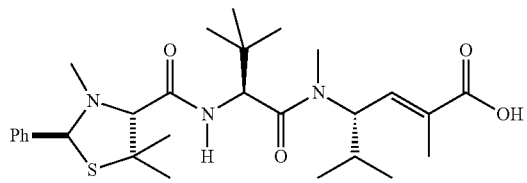
(67b)

Preparation of Compound 64

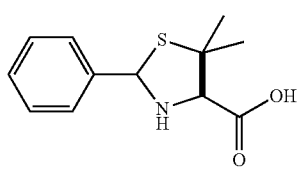
(64)

To a suspension of L-penicillamine (63) (300 mg, 2.0 mmol) in methanol (10 mL) was added benzaldehyde (233 mg, 2.2 mmol) followed by sodium bicarbonate (336 mg, 4.0 mmol). The mixture was heated to reflux with stirring for 16 h. After cooling to r.t., it was acidified to pH 5 with 1 N HCl and extracted with ethyl acetate three times. The organic phase was concentrated to give a yellow solid as the crude product 64 (469 mg, 99%)

Preparation of Compound 65

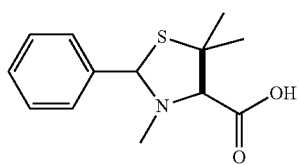
(65)

To a solution of crude 64 (47 mg, 0.2 mmol) in THF (1 mL) was added aq. 37% formaldehyde solution (49 µl, 0.6 mmol) followed by NaBH$_4$ (38 mg, 0.6 mmol). The mixture was stirred at r.t. for 24 h. After acidifying to pH 5 and extracting with ethyl acetate, the organic phase was dried and concentrated to give crude product 65 (67 mg, >100%).

Preparation of Compounds 66a and 66b

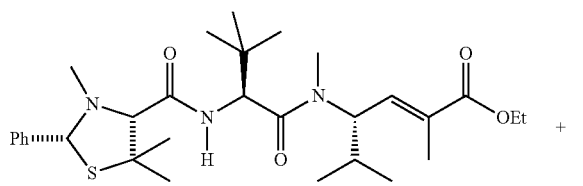
(66a)

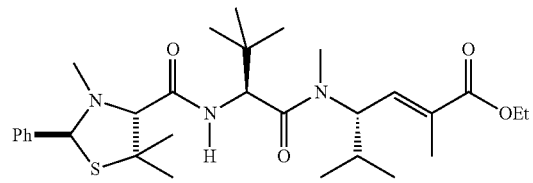
(66b)

To a mixture of 65 (29 mg, 0.115 mmol), amine HCl salt 49 (15 mg, 0.043 mmol), CMC (55 mg, 0.129 mmol), and HOAt (3 mg, 0.022 mmol) was added DMF (0.5 mL) followed by NMM (6 ml, 0.055 mmol). The mixture was stirred at r.t. for 24 h. The reaction was quenched by adding water (0.5 mL) and methanol (0.5 mL). The products 66a (32%), and 66b (75%) were obtained after separation by RP HPLC (0-100% B in 30 min. A: 5% MeCN+0.15% TFA in H$_2$O; B: 0.15% TFA in MeCN) and lyophilization.

Preparation of Compounds 67b

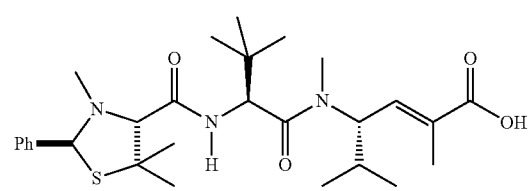
(67b)

To a solution of 66b (4 mg, 0.0073 mmol) in methanol (0.5 mL) was added aq. LiOH (1 M, 0.5 mL). The mixture was stirred for 16 h and acidified with 1 N HCl. Product 67b (2.79 mg, 74%) was obtained after RP HPLC purification and lyophilization.

Example 8

Preparation of Compound 74

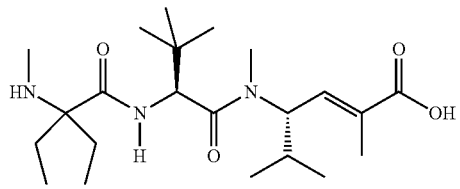
(74)

Preparation of Compound 69

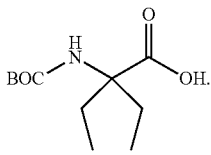
(69)

To a solution of diethylglycine (68) (131 mg, 1.0 mmol) in 1 N NaOH (1.5 mL) was added a solution of di-t-butyl-dicarbonate (436 mg, 2.0 mmol) in dioxane (1.0 mL). The mixture was stirred for 16 h. It was acidified to pH 3 with 1 N HCl and extracted with ethyl acetate three times. The organic phases were combined, dried, and concentrated to yield crude product 69 (135 mg, 58%).

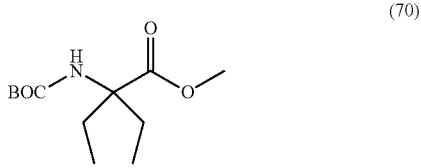 [SMILES: CCC(CC)(NC(=O)OC(C)(C)C)C(=O)OC]
(70)

To a solution of crude 69 (135 mg, 0.58 mmol) in MeOH (0.5 mL) and THF (0.5 mL) was added trimethylsilyldiaz-omethane (2 M in hexanes, 2.0 mmol). The solution was stirred at r.t. for 1 h. Evaporation gave crude product 70 (0.58 mmol).

Preparation of Compound 71

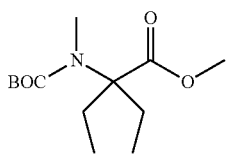
(71)

To a mixture of sodium hydride (160 mg 60%, 4 mmol) in DMF (1 mL) was added a solution of compound 70 (0.58 mmol) in DMF (1 mL) followed by methyl iodide (188 µl, 3 mmol). The mixture was stirred at room temperature for 24 h. Water was added to quench the reaction. The product 71 (118 mg, 78% 2 steps) was extracted with ethyl acetate and purified by flash column chromatography (silica, ethyl acetate/hexanes).

Preparation of Compound 72

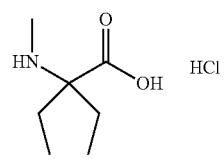
(72)

A solution of compound 71 (118 mg, 0.46 mmol) in conc. HCl (1 mL) was stirred at room temp. for 24 h. Product 72 was obtained after evaporation of volatiles.

Preparation of Compound 73

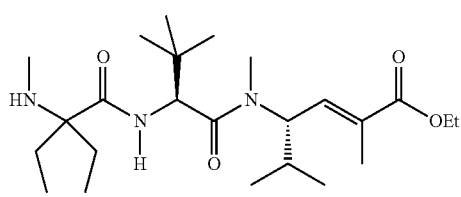
(73)

To a mixture of compound 72 (30 mg, 0.166 mmol), amine 49 HCl salt (39 mg, 0.166 mmol), CMC (141 mg, 0.332 mmol), and HOAt (14 mg, 0.103 mmol) was added DMF (1.5 mL) followed by NMM (6 ml, 0.128 mmol). The mixture was stirred at room temp. for 24 h. The reaction was quenched by adding water (0.5 mL) and methanol (0.5 mL). Product 73 (27 mg, 34%) was obtained after separation by RP HPLC (0-100% B is 30 min. A: 5% MeCN+0.15% TFA in $H_2O$; B: 0.15% TFA in MeCN) and lyophilization.

Preparation of Compound 74

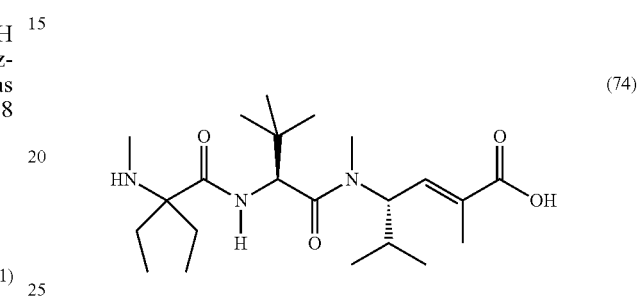
(74)

To a solution of compound 73 (18 mg) in methanol (0.5 mL) was added aq. LiOH (1 M, 0.5 mL). The mixture was stirred for 16 h and then acidified by 1 N HCl. Product 74 (12.3 mg, 73%) was obtained after RP HPLC purification and lyophilization.

Example 9

Preparation of Compound 78

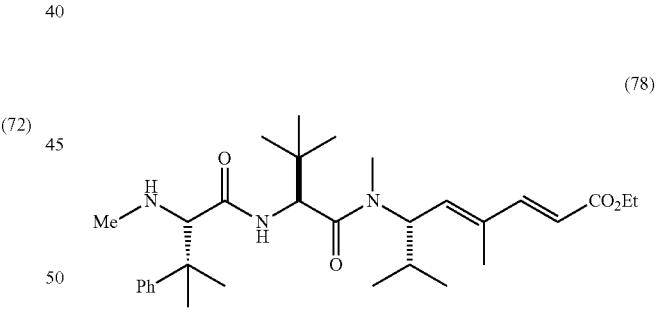
(78)

Preparation of Compound 76

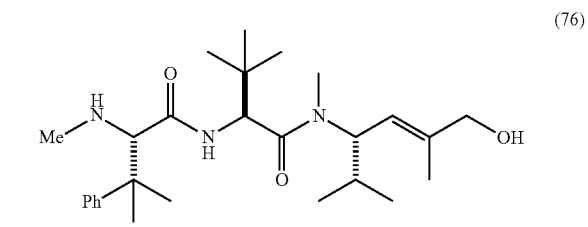 [SMILES: CN[C@H](C(=O)N[C@H](C(=O)N(C)[C@H](/C=C(\C)CO)C(C)C)C(C)(C)C)C(C)(C)c1ccccc1]
(76)

To a solution of compound 75 (123 mg) in dry DCM (1 mL), at 0° C. under an inert atmosphere, was added a 1 M solution of DIBAL (1.6 mL) dropwise. The reaction mixture was stared at 0° C. for 2 hr then allowed to warm to 10° C. then re-cooled to 0° C. Methanol (0.22 mL) was added dropwise followed by a saturated solution of ammonium chloride (0.44 mL). DCM (20 mL) was added and the reaction mixture stirred vigorously at room temperature for 30 min. Filtration followed by concentrated in vacuo gave compound 76 (73 mg, 65%).

Preparation of Compound 77

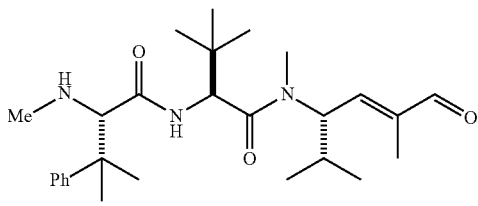
(77)

To a solution of compound 76 (3 mg) in acetonitrile (0.6 mL) was added Dess Martin periodinane (3.1 mg). The reaction mixture was stirred at room temperature for 1 hr then diluted with diethyl ether (2 mL). The resultant suspension was filtered through a 0.25 μm PTFE syringe filter and concentrated in vacuo to give crude compound 77 (4 mg).

Preparation of Compound 78

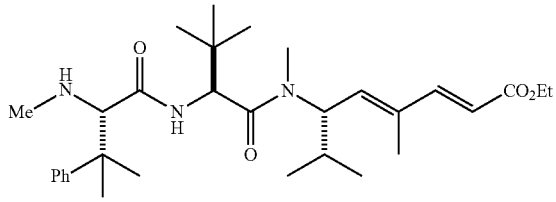
(78)

To a solution of compound 77 (3 mg) in DCM (0.5 mL), at room temperature, was added ethyl carbethoxymethylidene triphenylphosphorane (21 mg). The reaction mixture was stirred at room temperature for 16 hr then concentrated in vacuo to dryness. Chromatographic purification gave compound 78 (1.48 mg, 44%).

Example 10

Preparation of Compound 81

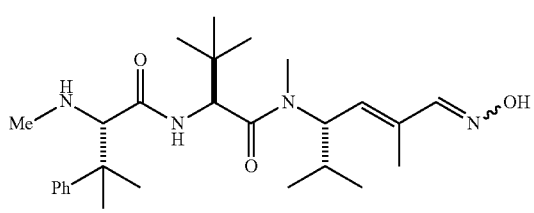
(81)

Preparation of Compound 79

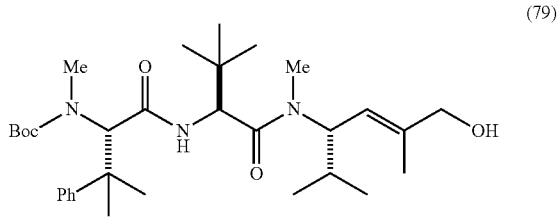 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)CO]
(79)

To a solution of compound 7b (10 mg) in dry DCM (0.5 ml), at 0° C. under an inert atmosphere, was added a 1M solution of DIBAL (0.035 mL) dropwise. The reaction mixture was stirred at 0° C. for 1.5 hr then methanol (0.012 mL) was added dropwise followed by a saturated solution of ammonium chloride (0.024 ml). DCM (5 mL) was added and the reaction mixture stirred vigorously at room temperature for 20 min. Filtration followed by concentrated in vacuo gave crude compound 79 (9 mg, 95%).

Preparation of Compound 80

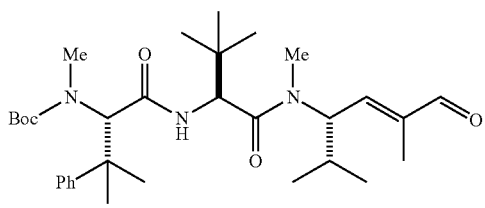
(80)

To a solution of compound 79 (5 mg) in THF (0.5 mL) was added sodium bicarbonate (3.6 mg) and Dess Martin periodinane (7.2 mg). The reaction mixture was stirred at room temperature for 3 hr then concentrated in vacuo to give crude compound 80.

Preparation of Compound 81

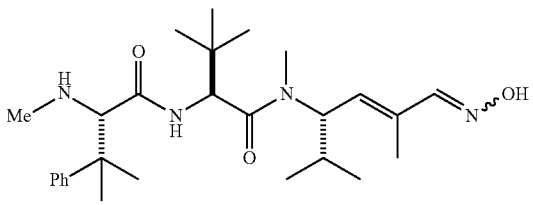
(81)

To a solution of compound 80 (4.8 mg) in ethanol (0.5 mL), at room temperature, was added hydroxylamine hydrochloride (4 mg) and sodium acetate (6 mg). The reaction mixture was stirred at 40° C. for 1.5 hr then concentrated to dryness. The residue was dissolved in DCM (0.2 mL) and treated with TFA (0.2 ml) and stood at room temperature for 10 min. Concentration in vacuo to dryness followed by chromatographic purification gave compound 81 (2.04 mg).

Example 11

Preparation of Compound 87

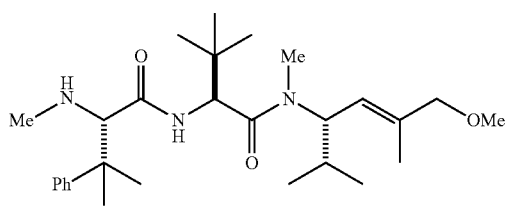
(87)

Preparation of Compound 84

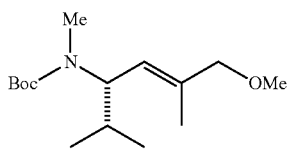
(84)

To a solution of compound 28 (335 mg) in THF (1.0 mL), at 0° C. under an inert atmosphere, was added sodium hydride (65% dispersion in mineral oil; 144 mg) portionwise. The reaction mixture was stirred at 0° C. for 30 min then treated with methyl iodide (0.405 mL). The reaction mixture was allowed to warm to room temperature and stirred at room temperature for 3 hr. An aqueous work up followed by chromatographic purification gave compound 84 (254 mg, 72%).

Preparation of Compound 85

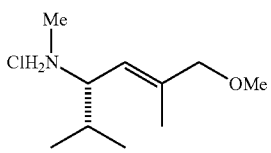
(85)

Compound 84 (189 mg) was treated with saturated HCl in methanol (5 mL). The reaction mixture was stood at room temperature for 2 hr then concentrated in vacuo to dryness to give compound 85 (145 mg).

Preparation of Compound 86

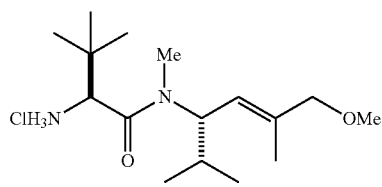
(86)

To a solution of compound 85 (145 mg) in DMF (3 mL), at room temperature, was added (S)—N-Boc-tert-leucine (483 mg), NMM (0.230 mL), HOAt (95 mg), and CMC (884 mg). The reaction mixture was shaken at room temperature for 16 hr. Aqueous workup followed by chromatographic purification gave an intermediate Boc compound (249 mg, 93%). The intermediate Boc compound (60 mg) was dissolved in methanol (1 mL) and treated with saturated HCl in methanol (3 mL) and stood at room temperature for 30 min. Concentration in vacuo gave compound 86 (49 mg).

Preparation of Compound 87

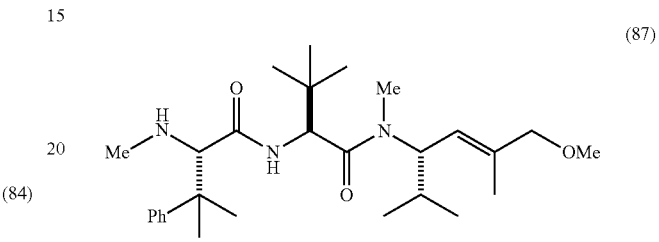
(87)

To a solution of compound 86 (49 mg) in DMF (0.44 mL), at room temperature, was added (S)—N-Boc-neo-phenylalanine (94 mg), NMM (34 µl), HOAt (21 mg), and CMC (130 mg). The reaction mixture was shaken at room temperature for 16 hr. Aqueous workup followed by chromatographic purification gave an intermediate Boc compound (41 mg, 47%). The intermediate Boc compound (5.5 mg) was dissolved in DCM (1 mL) and treated with TFA (1 mL). The reaction mixture was stood at room temperature for 30 min then concentrated in vacuo to dryness. The residue was dissolved in saturated HCl in methanol (1 mL) and stood at room temperature and then concentrated in vacuo to give compound 87 (4.39 mg, 89%).

Example 12

Preparation of Compound 91

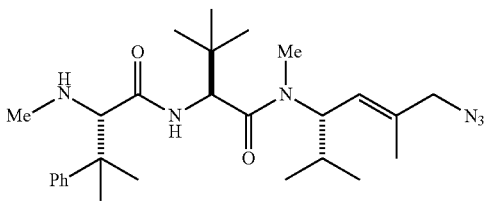
(91)

Preparation of Compound 88

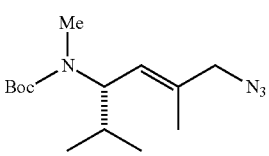
(88)

To a solution of compound 28 (344 mg) in 0.5 M Hunnig's base in DCM (8 mL), at 0° C. under an inert atmosphere, was added methane sulphonyl chloride (0.207 mL) dropwise. The reaction mixture was stirred at 0° C. for 1.5 hr then subjected to an aqueous work up followed by chromatographic purification to give an intermediate mesylate (444 mg). The intermediate mesylate was dissolved in DMSO (2 mL) and treated with sodium azide (258 mg). The reaction mixture was heated at 40° C. for 6 hr. An aqueous work up gave compound 88 (306 mg, 82%).

Preparation of Compound 89

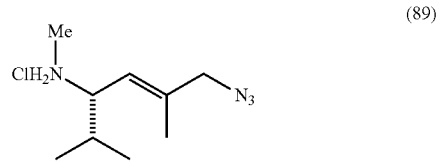
(89)

Compound 88 (140 mg) was dissolved in DCM (1 mL) and treated with TFA (1 mL). The reaction mixture was stood at room temperature for 30 min then concentrated in vacuo to dryness, The residue was dissolved in saturated HCl in methanol (1 mL) and stood at room temperature and then concentrated in vacuo to give compound 89 (109 mg).

Preparation of compound 90

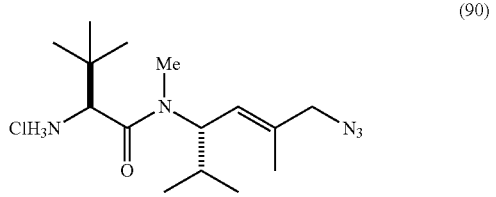
(90)

To a solution of compound 89 (109 mg) in DMF (2 mL), at room temperature, was added (S)—N-Boc-tert-leucine (347 mg), NMM (0.165 mL), HOAt (68 mg), and CMC (635 mg). The reaction mixture was stirred at room temperature for 16 hr. Aqueous workup followed by chromatographic purification gave an intermediate Boc compound (173 mg, 87%). The intermediate Boc compound (51 mg) was dissolved in methanol (1 mL) and treated with saturated HCl in methanol (3 mL) and stood at room temperature for 30 min. Concentration in vacuo gave compound 90 (43 mg).

Preparation of Compound 91

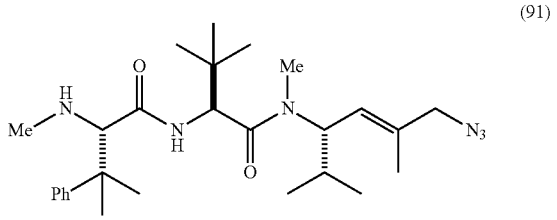 [SMILES: CN[C@H](C(=O)N[C@H](C(=O)N(C)[C@H](/C=C(\C)CN=[N+]=[N-])C(C)C)C(C)(C)C)C(C)(C)c1ccccc1]
(91)

To a solution of compound 90 (42 mg) in DMF (0.37 mL), at room temperature, was added (S)—N-Boc-neo-phenylalanine (79 mg), NMM (28 µl), HOAt (17 mg), and CMC (108 mg). The reaction mixture was shaken at room temperature for 16 hr. Aqueous workup followed by chromatographic purification gave an intermediate Boc compound (88 mg).

The intermediate Boc compound (88 mg) was dissolved in saturated HCl in methanol (5 mL) and stood at room temperature for 30 min and then concentrated in vacuo to give compound 91 (70 mg, 89%).

Example 13

General Procedure for the Preparation of C-Terminal Acid Compounds

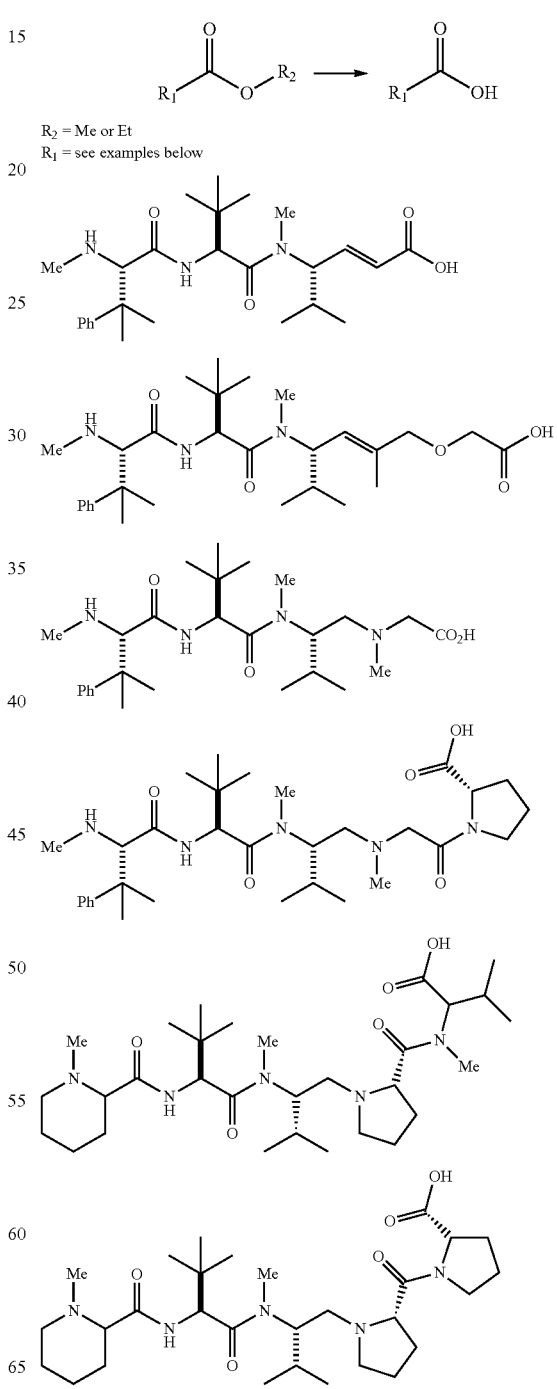

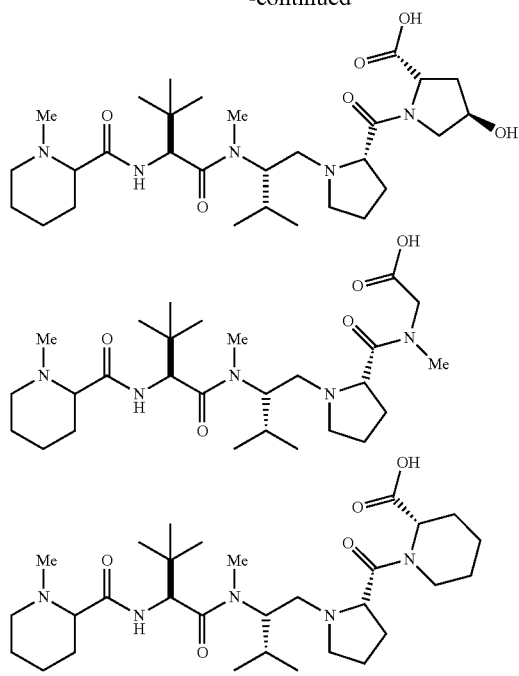

To a solution of the corresponding methyl or ethyl ester (e.g., compound 7b) in a suitable mixture of methanol and tetrahydrofuran, at room temperature, was added aqueous 1 M lithium hydroxide (10-50 equivalents). The reaction mixture was stirred or shaken or stood at room temperature until the starting ester had been satisfactorily hydrolyzed. The usual workup followed by chromatographic purification gave the desired C-terminal acid compound (e.g., compound 82).

Example 14

Preparation of Compound ER-807974

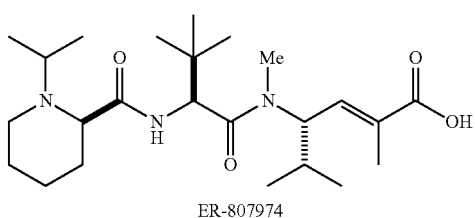 [SMILES: C/C(=C\[C@H](C(C)C)N(C)C(=O)[C@@H](NC(=O)[C@H]1CCCCN1C(C)C)C(C)(C)C)C(=O)O]

ER-807974

Preparation of Compound ER-807641

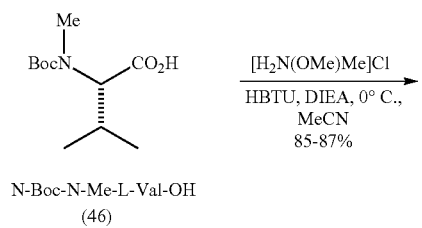

N-Boc-N-Me-L-Val-OH
(46)

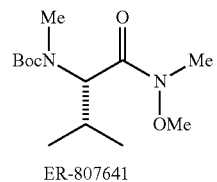

ER-807641

To a stirred solution of M-Boc-N-Me-L-Valine (200 g, 0.86 mols), N,O-demethylhdroxylamine (92.8 g, 0.95 mols, 1.1 eq) and DIEA (316.3 mL, 1.82 mol, 2.1 eq) in CH$_3$CN (2 L) at 0° C. was added HBTU (360.7 g, 0.95 mols, 1.1 eq) in portions. The solution was stirred at 0° C. for additional 15 min and then for 1 h at 25° C. Reaction was monitored by TLC (Hept/EtOAc 1:1) and deemed completed when no 46 was observed. The solution was concentrated by rota-vap and then diluted in TBME (1 L). The organic solution was washed with HCl (1N, 500 mL), water (250 mL), NaHCO$_3$ (sat. 250 mL) and brine (250 mL). The organic solution was dried over MgSO$_4$ (~120 g). The solution was filtered through a silica gel bed (~200 g) and concentrated. Crude amide ER-807641 was used without any further purification.

Preparation of Compound ER-808993

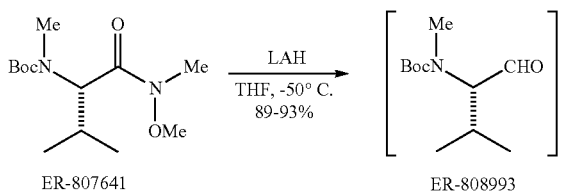

To a stirred solution of amide ER-807641 (207 g, 755 mmol, 1 eq.) in dry THF (2070 mL) at −78° C. was added a solution of LiAlH$_4$ (1.0M/THF, 754 mL, 755 mmol, 1.0 eq.). The solution was stirred at −78° C. for 1 h. Reaction was quenched at −78° C. by addition of reaction solution to a suspension of Na$_2$SO$_4$.10H$_2$O (243 g) in TBME (1.5 L). The slurry was allowed to warm up to ~15° C. and was then filtered through a Celite pad. The filtrate was concentrated, and the crude aldehyde ER-80S993 was obtained as a clear oil and used without further purification.: 157.9 g (97%).

Preparation of compound ER-808995-01

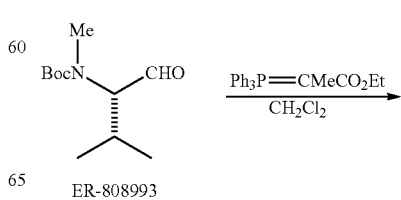

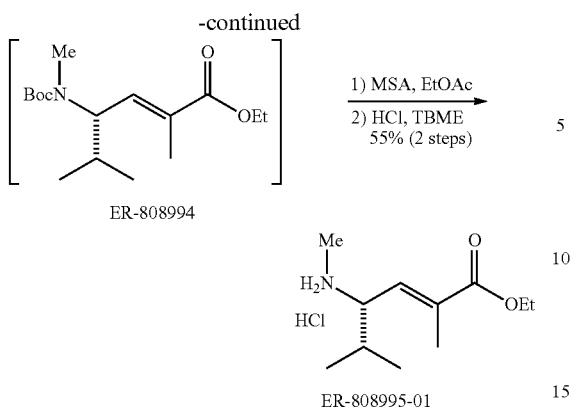

ER-808994

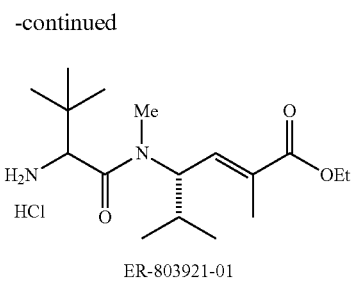

ER-803921-01

ER-808995-01

Part A:

To a stirred solution of aldehyde ER-808993 (138 g, 641 mmol, 1 eq.) in dry THF (1.4 L) at 25° C. was added Ph₃P═CMeCO₂Et (256 g, 705.1 mmol, 1.1 eq.). The solution was stirred at r.t for 18 h. Reaction was not completed after that time. The solution was heated to reflux for 5 h, after which TLC showed no aldehyde remaining, The solution was cooled to room temp and heptane (1.5 L) was added. Precipitation of by-product Ph₃P═O was observed. The mixture was filtered through a silica gel (200 g) plug. The filtrate was concentrated to a minimum volume (~50 mL), and the residue was dissolved in EtOAc (800 mL).

Part B:

To a stirred solution of crude ER-80S994 in EtOAc (800 mL) was added MSA (80 mL). The mixture was stirred at r.t. for 45 min. (until complete by TLC). The amino-ester MSA salt was extracted from organic solution with water (2×300 mL). The aqueous layer was neutralized to pH 7-8 with sat. NaHCO₃ (300 mL). The resultant solution was extracted with EtOAc (2×400 mL), washed with brine (300 mL), dried over MgSO₄, and filtered. The EtOAc solution of the free amino-ester was bubbled with HQ (gas), and the HCl salt of ER-808995 precipitated and was collected by filtration under N₂.

Preparation of Compound ER-803921-01

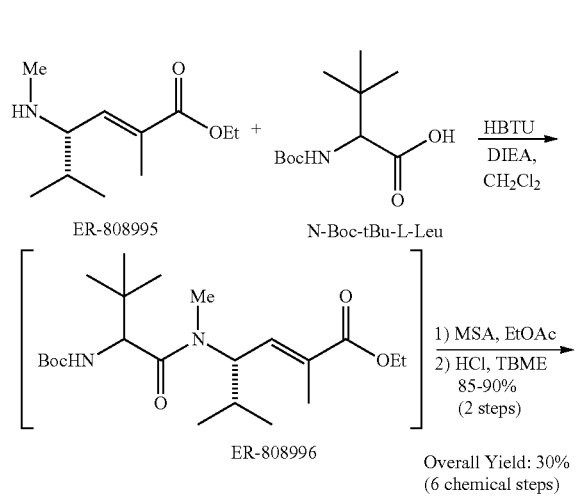

To a stirred solution of ER-808995 (61.2 g, 259.6 mmol, 1 eq.), N-Boc-tBu-Gly-OH (90.1 g, 389.4 mmol, 1.5 eq) and DIEA (158 mL, 906.6 mmol, 3.5 eq) in dry DCM (612 mL) at 25° C. was added HBTU (147.7 g, 380.4 mmol 1.5 eq.). The solution was stirred at room temp for 4 h. After concentration, the solid residue was suspended in TBME (250 mL). The mixture was filtered through a silica gel bed (~120 g), and the filtrate was washed with a solution of aq. HCl (1N, 200 mL), water (200 mL) and NaHCO₃ (sat, 200 mL). The organic layer was dried over MgSO₄, filtered and concentrated. The N-Boc-amino-ester ER-808996 was isolated as an oil. This intermediate was re-dissolved in EtOAc (120 mL) and MSA (75 mL) was added. The solution was stirred at room temp for 1 h, at which time the reaction was deemed complete by TLC. The amine-ester MSA salt was extracted with water (2×250 mL), followed by neutralization with a solution NaOH (ca. 50%, 300 mL) to pH~8-9. The free amine was extracted with TBME (2×30 mL). The combined organic solution was washed with water (200 mL) and brine (200 mL). After drying over MgSO₄ and filtration, HCl (g) was bubbled to obtain the hydrochloride salt of ER-803921 as a white solid collected by filtration at ca. 5° C.

Preparation of Compound ER-808998

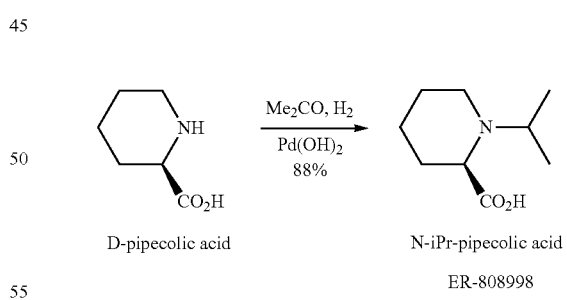

D-pipecolic acid     N-iPr-pipecolic acid

ER-808998

A stirred suspension of D-pipecolic acid (100.0 g, 0.77 mol, 1 eq.) and Pd(OH)₂ (20% wt. Pd, 10 g) in a mixture MeOH/acetone (2:1 v/v, 1.5 L) was submitted to hydrogenation (H₂60 psi) for 24 h. Reaction was monitored by TLC (ethanol) and deemed complete when no D-pipecolic acid was observed. The mixture was filtered through a Celite (~50 g) bed. The clear filtrate was concentrated to ca. 100 mL and TBME (50 mL) was added. ER-808998 was filtered as a white crystalline solid in 88% yield.

Preparation of Compound ER-807961

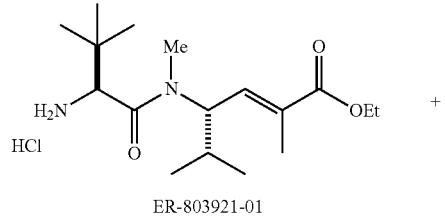

ER-803921-01

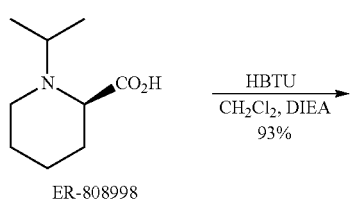

ER-808998

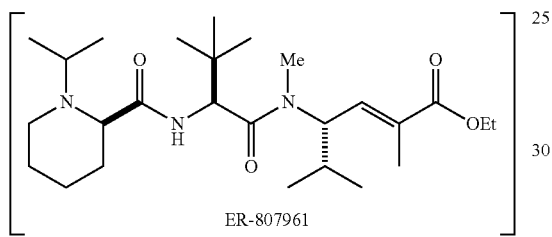

ER-807961

To a stirred solution of dipeptide ER-803921 (5.0 g, 16.8 mmol, 1 eq.), N-iPr-pipecolic acid ER-808998 (3.7 g, 21.8 mmols, 1.3 eq.) and HBTU (8.3 g, 21.8 mmols, 1.3 eq.) in 50 mL DCM was added DIEA (7.3 mL, 41.9 mmols, 2.5 eq.) dropwise at 25° C. The mixture was stirred for 18 h (overnight) at which time reaction was deemed complete by TLC (heptane/EtOAc 1:1). The mixture was concentrated under vacuum and TBME (50 mL) was added. The residual "thick" oil was separated from the ethereal solution by filtration through a Celite pad. The filtrate was washed wife aq HCl (1M, 3×25 mL). The combined aqueous phases were neutralized with NH₄OH to pH 8-9 in the presence of EtOAc (25 mL). The aqueous layer was separated and back-extracted with TBME (25 mL). The combined organic phase was washed with brine and dried over MgSO₄, filtered, arid concentrated to give tripeptide-amino-ester ER-807961 in 93% yield.

Preparation of Compound ER-807974

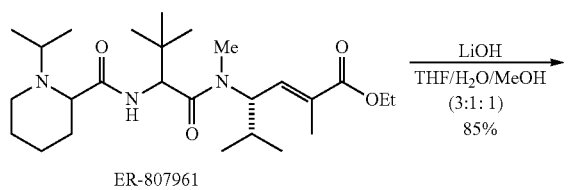

ER-807961

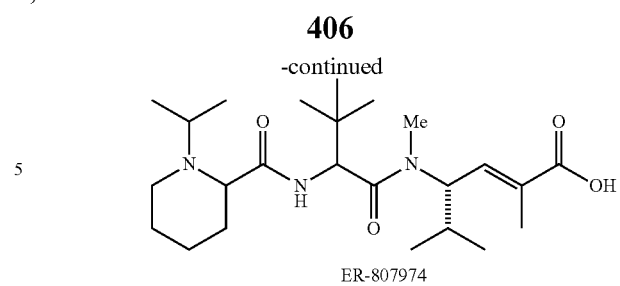

ER-807974

To a stirred solution of ester ER-807961 (5.0 g, 16.8 mmol) in 5:1 THF/H₂O (50 mL) was added LiOH (3.50 g, 83.8 mmol), and the mixture was stirred at room temperature for 20 h. The reaction was monitored by TLC (ethanol) and deemed complete when no ER-807961 was observed. The suspension was acidified with H₂SO₄ (~0.50 mL) to ph 7. The mixture was extracted with EtOAc (3×25 ml). The combined organic solution was washed with brine (20 mL), dried over MgSO₄, filtered, and concentrated. The residue was triturated with TBME: 1.8 g (83%) of thick oil free-base ER-807974 was obtained.

Example 15

Preparation of Compound ER-808367

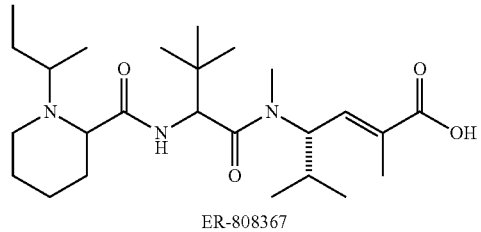 [SMILES: CCC(C)N1CCCCC1C(=O)NC(C(=O)N(C)[C@H](/C=C(\C)C(=O)O)C(C)C)C(C)(C)C]

ER-808367

Preparation of Compound 2Z

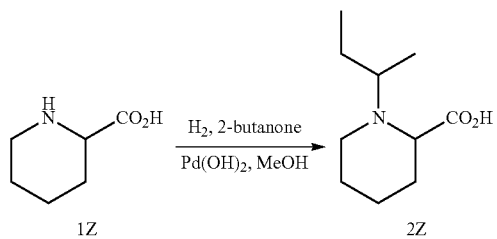

1Z    2Z

To a suspension of D-pipecolic acid 1Z (750 mg, 5.81 mmol) in MeOH (23.2 mL) and 2-butanone (11.6 mL) was added Pd(OH)₂ (175 mg). Gaseous H₂ (balloon pressure) was charged in and the reaction mixture was allowed to stir under an H₂ atmosphere overnight. The reaction solution was then filtered through a bed of celite, and concentrated to give a crude white solid. The crude product was subjected to flash chromatography (SiO₂) eluting with 100% EtOH. This provided compound 2Z (721 mg, white solid) as a mixture of diastereomers in 67% yield.

Preparation of Compounds 3Z and 4Z

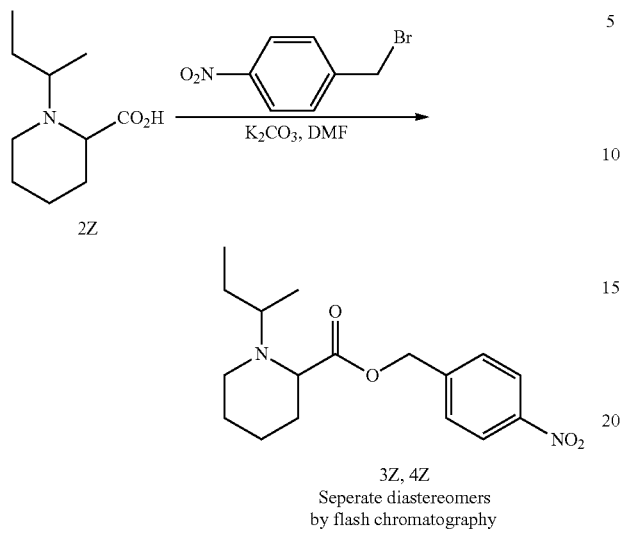

3Z, 4Z
Seperate diastereomers
by flash chromatography

To a solution of 2Z (650 mg, 3.51 mmol) in DMF (8.8 mL) was added $K_2CO_3$ (728 mg 5.27 mmol) and p-nitrobenzyl-bromide (1.1 g, 5.27 mmol). The reaction mixture was allowed to stir overnight. The reaction solution was diluted with water and extracted several times with diethyl ether. The ether extracts were combined, washed with water and brine. The solution was dried over $MgSO_4$, filtered, and concentrated in vacuo. The crude mixture of diasteomers was then separated by flash chromatography eluting with 8% EtOAc in hexanes to give each diastereomer as a pate yellow oil. Compound 3Z (360 mg) was obtained in 32% yield with an $R_f$=0.590 ($SiO_2$) using 30% EtOAc in hexanes. Compound 4Z (652 mg) was obtained in 58% yield with an $R_f$=0.482 ($SiO_2$) using 30% EtOAc in hexanes.

Preparation of Compound ER-809439

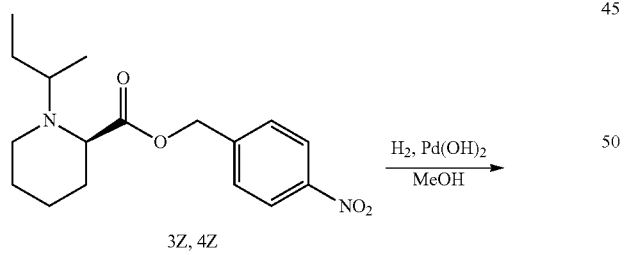

To a solution of compound 3Z (320 mg, 1.0 mmol) in MeOH (10 mL) was added $Pd(OH)_2$ (50 mg). Gaseous $H_2$ (balloon pressure) was charged in and the reaction mixture was allowed to stir under an $H_2$ atmosphere for 3 hours. The reaction solution was then filtered, through a bed of celite, and concentrated to provide compound ER-809439 (185 mg) as a white solid, quantitatively. Compound ER-809439, $R_f$= ($SiO_2$, 0.292, 100% EtOH).

Preparation of Compound ER-809447

A procedure similar to that used for the preparation of compound ER-809439 was used. Compound ER-809447, $R_f$=($SiO_2$, 0.292, 100% EtOH).

Preparation of Compound ER-808357

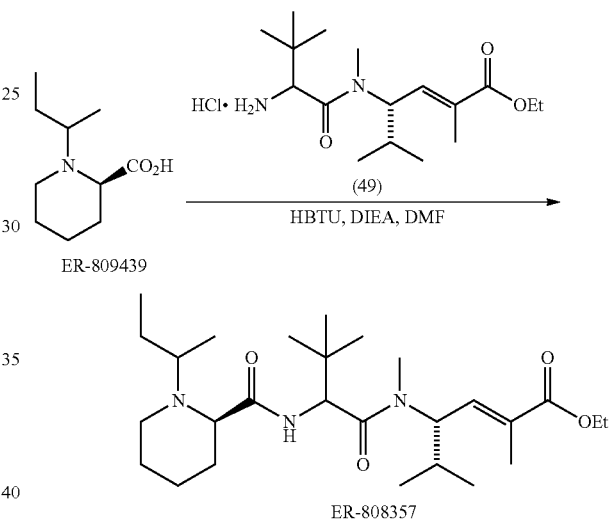

Compound 49 (9.6 mg, 0.031 mmol), N-sec-butylpipecolic ER-809439 (5.2 mg, 0.028 mmol), HBTU (12.9 mg, 0.034 mmol), were combined. DMF (0.28 mL) was added, followed by DIEA (14.9 mL, 0,084 mmol). The solution was stirred at room temperature under nitrogen for 20 h. The solution was purified directly by RP HPLC to give the TFA salt of compound ER-808357 (13.6 mg, 82%).

Preparation of Compound ER-808367

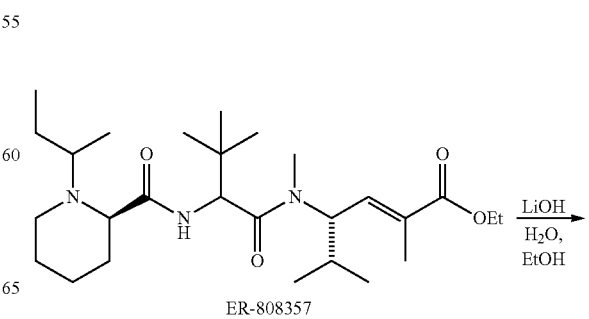

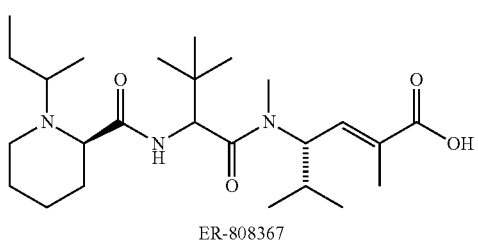

ER-808367

The TFA salt of compound ER-088357 (10.4 mg, 0.018 mmol) was dissolved in 1:2 H₂O/EtOH (0.072 mL/0.144 mL) at room temperature. LiOH (7.5 g, 0.18 mmol) was added. The suspension was stirred at room temperature for 19 hours. The solution was purified directly by RP HPLC to give the TFA salt of compound ER-808367 (10.1 mg, quantitative).

Example 16

Preparation of Compound ER-808368

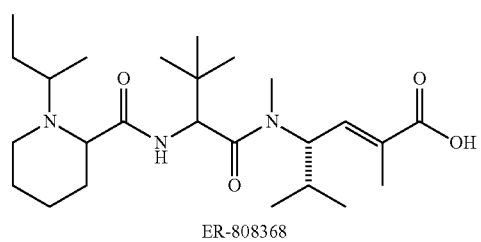 [SMILES: CCC(C)N1CCCCC1C(=O)NC(C(=O)N(C)[C@H](/C=C(\C)C(=O)O)C(C)C)C(C)(C)C]

ER-808368

Preparation of Compound ER-808358

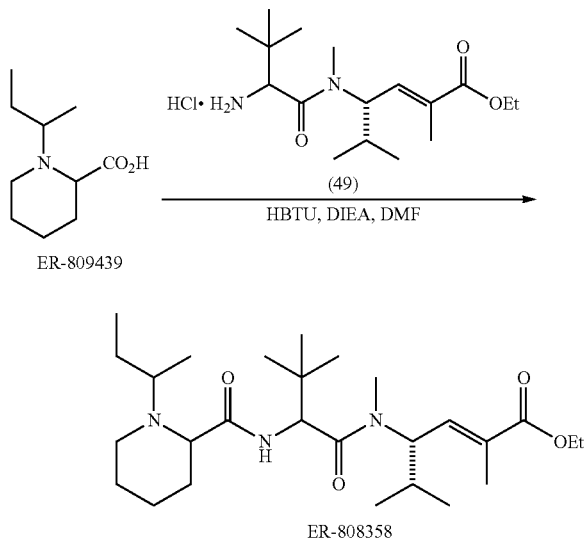

A procedure similar to that used for the preparation of compound ER-808357 was used.

Preparation of Compound ER-808368

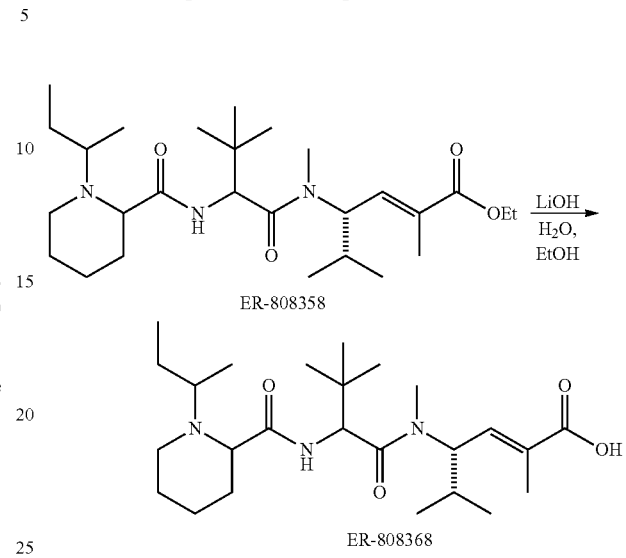

A procedure similar to that used for the preparation of compound ER-808367 was used.

Example 17

Preparation of Compound ER-808662

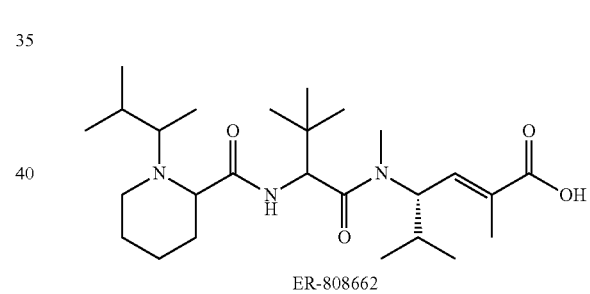

Preparation of Compound 5Z

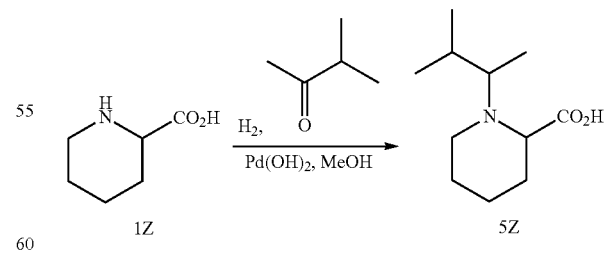

To a suspension of D-pipecolic acid 1Z (1.00 g, 7.74 mmol) in MeOH (31 mL) and 3-methyl-2-butanone (15.5 mL) was added Et₃N (1.1 mL) and Pd(OH)₂ (250 mg). Gaseous H₂ (balloon pressure) was charged in and the reaction mixture was allowed to stir under an H₂ atmosphere overnight. The reaction solution was then filtered through a bed of celite, and concentrated to give a crude white solid The crude product was subjected to flash chromatography (SiO$_2$) eluting with 100% EtOH. This provided compound 5Z (377.9 mg, white solid) as a single diastereomer in 24.5% yield. R$_f$=(SiO$_2$, 0.280, 100% EtOH).

Preparation of Compound ER-808656

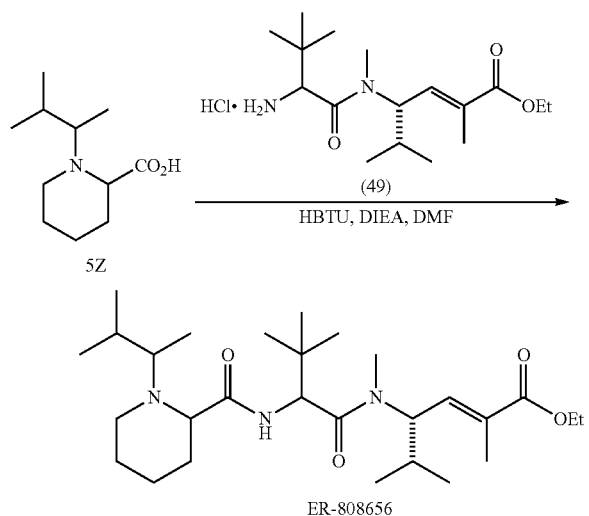

A procedure similar to that used for the preparation of compound, ER-808357 was used.

Preparation of Compound ER-808662

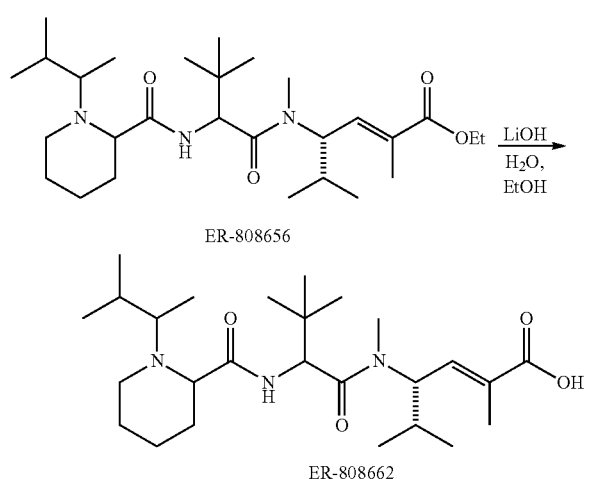

A procedure similar to feat used for the preparation of compound ER-803367 was used.

Compounds ER-809638 through ER-809650 were made according to the procedures for ER-808368 or ER-808662 with the one change: N—BOC-L-Valine was used in place of N—BOC—N-Methyl-L-Valine (46). Compounds ER-808998, ER-809439 and 5Z were used as required.

Example 18

Preparation of Compound ER-808824

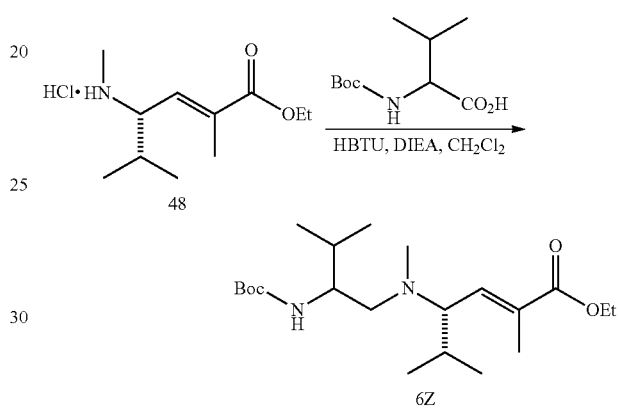

Preparation of Compound 6Z

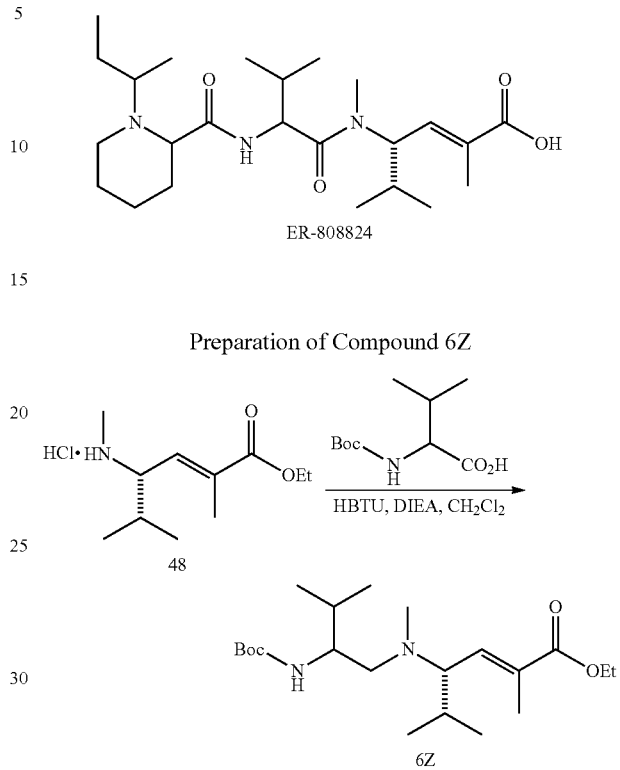

Compound 48 (325.5 mg, 1.38 mmol), L-N—BOC-valine (300.0 mg, 1.33 mmol). HBTU (628.3 mg, 1.66 mmol), were combined. CH$_2$Cl$_2$ (7 mL) was added, followed by DIEA (0.72 mL, 4.14 mmol). The solution was stirred at room temperature under nitrogen for 1 hour. The solution was concentrated in vacuo, and the crude was purified by flash chromatography (SiO$_2$) elating with 4% EtOAc in hexanes. This provided compound 6Z (476.8 mg) as a colorless oil in 86.7% yield.

Preparation of Compound 7Z

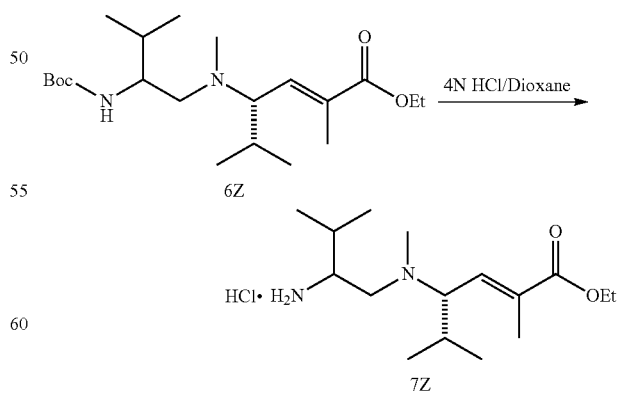

Compound 6Z (450 mg, 1.13 mmol) was dissolved directly in 4N HCl/dioxane (2.8 mL). The reaction was stirred for overnight and then concentrated in vacuo to give compound 72 (374.8 mg) as a white solid, quantitatively.

Preparation of Compound ER-808815

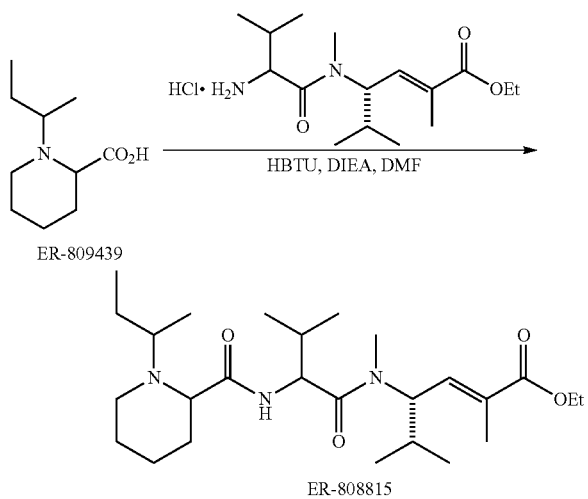

ER-809439

ER-808815

A procedure similar to that used for the preparation of compound ER-808357 was used.

Preparation of Compound ER-808824

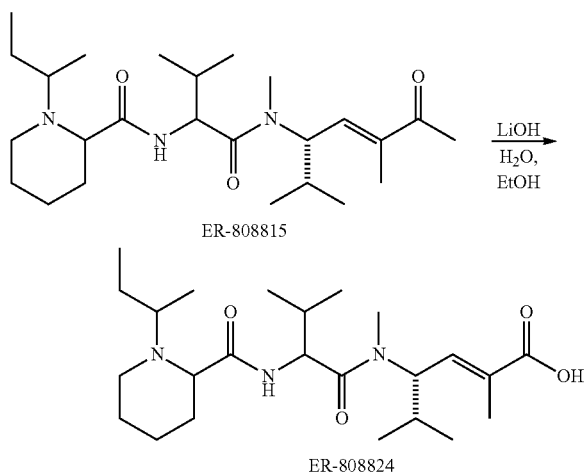

ER-808815

ER-808824

A procedure similar to that used for the preparation of compound ER-808367 was used.

Example 19

Biological Assays

In certain embodiments, compounds of the invention were tested for in vitro and in vivo activity. Screening methods included standard in vitro cell growth inhibition assays using a panel of human cancer cell lines, a U937 (ATCC accession number CRL 1593) mitotic block reversibility assay, mouse serum stability assay, MDR assay, and cytotoxicity assay. In certain other embodiments, compounds of the invention were evaluated in tumor xenograft in vivo growth inhibition assays.

In vitro potency was determined in the MDA-MB-435 cell growth inhibition assay, and active compounds ($IC_{50}$<20 nM) were evaluated in the reversibility, MDR, and mouse serum stability assays. In addition, the active compounds were tested in the IMR-90 cytotoxicity assay and in additional cell growth inhibition assays in a panel of human cancer cell lines, both solid and non-solid tumors.

Cell Growth Inhibition Assay:

Cultured human cancer cells (including breast, prostate, colon, lung, leukemia, lymphoma and other) were plated in 96-well plates and grown in the continuous presence of test compounds for 72 or 96 hours. The human cell lines used in this cell growth inhibition assay, include, but are not limited to, the following solid tumor cell lines and non-solid tumor cell lines: DLD-1 colon cancer cells (ATCC accession number CCL-221), DU 145 prostate cancer cells (ATCC accession number HTB-81), H460 non small cell lung cancer, HCT-15 colon cancer cells (ATCC accession number CCL-225), HEL erythroleukemia cells, HL-60 promyelocytic leukemia cells (ATCC accession number CCL-240), K562 leukemia (ATCC accession number CCL-243), LOX melanoma, MDA-MB-435 breast cancer cells, U937 lymphoma cells (ATCC accession number CRL 1593), PANC-1 pancreatic cancer (ATCC accession number CRL-1469), HCC-2998 colon cancer (NCI-Frederick Cancer DCTD Tumor/Cell Line Repository), HCT 116 colon cancer (ATCC accession number CCL-247), HT-29 colon cancer (ATCC accession number HTB-38), LoVo colon cancer (ATCC accession number CCL-229), SW-480 colon cancer (ATCC accession number CCL-228), SW-620 colon cancer (ATCC accession number CCL-227) and COLO-205 colon cancer (ATCC accession number CCL-222). For monolayer cultures, growth was assessed using modifications (Amin et al, Cancer Res., 47: 6040-6045, 1987) of a methylene blue-based microculture assay (Finlay et al, Anal. Biochem., 139: 272-277, 1984). Absorbances at 620 and 405 nm were measured on a Titertek Multiscan MCC/340 plate reader and absorbances at 405 nm were subtracted from absorbances at 620 nm. For suspension cultures, growth was assessed using a 3-(4,5-dimethylthiazol-2-yl)-2,5-diphenyl tetrazolium bromide-based assay (Mosmann et al, J. Immunol. Methods, 65: 55-63, 1983) modified as follows. After 4 days of incubation with test compounds, sterile-filtered 3-(4,5-dimethylthiazol-2-yl)-2,5-diphenyl tetrazolium bromide was added to each well (final concentration, 0.5 mg/ml), and plates were incubated at 37° C. for 4 h. Acid-isopropanol (0.1 N HCl in isopropanol, 150 mL) was then added to each well, and the resultant formazan crystals were dis-solved by gentle mixing. Absorbances at 540 nm were measured on a Titertek Multiscan MCC/340 plate reader.

Mitotic Block Reversibility Assay was Performed as Described (See, U.S. Pat. No. 6,214,865 B1, by B. Littelfield et al, Apr. 10, 2001; which is incorporated herein be reference in its entirety).

Briefly, U937 (ATCC accession number CRP 1593) were exposed to various concentration of compounds for 12 hours. The compounds were washed away and the cells were allowed to recover for an additional 10 hours. The cells were collected by centrifugation and fixed overnight in 70% ethanol. The cells were washed in PBS, incubated with RNase A and stained with propidium iodide. Single channel flow cytometry was performed on a Becton Dickinson FACScan; the collection and analysis of data were performed using Becton Dickinson CELLQuest software. Doublet events were eliminated from analyses by proper gating on FL2-W/FL2-A primary plots before histogram analysis of DNA content (measured as FL2-A).

Determination of Activity In Vitro Utilizing the MDR Assay.

This is a modification of the standard cell growth inhibition assays described above. Two cultured human cancer cell lines were used: human uterine sarcoma MDR negative MES-SA cells (ATCC accession number CRL-1976) and human uterine sarcoma MDR-positive MES-SA/Dx5 cells (ATCC accession number CRL-1977). Cells were plated in a 96-well microtiter plates at a density of 7500 cells/well. The cells were incubated in the presence or absence of test compounds for 96 hours. Cell growth was assessed using modifications (Amin et al, Cancer Res., 47: 6040-6045, 1987) of a methylene blue-based microculture assay (Finlay et al, Anal. Biochem., 139: 272-277, 1984), Absorbances at 620 and 405 nm were measured on a Titertek Multiscan MCC/340 plate reader and absorbances at 405 nm were subtracted from absorbances at 620 nm. The ratio of the concentrations of the compounds inhibiting the growth of cells by 50% was calculated and used to estimate the sensitivity of the compounds to MDR (multi-drug-resistance, or P-glycoprotein-mediated drug efflux). In some cases, a different pair of cell lines was used: MDR-negative murine leukemia cells P388/S, and MDR-positive murine leukemia cells P388/VMDRC.04. Cells were plated in a 96-well microtiter plates at a density of 4000 cells/well. The cells were incubated in the presence or absence of test compounds for 72 hours. Cell growth was assessed using a 3-(4,5-dimethylthiazol-2-yl)-2,5-diphenyl tetrazolium bromide-based assay (Mosmann et al, J. Immunol. Methods, 65: 55-63,1983) modified as follows. After 3 days of incubation with test compounds, sterile-filtered 3-(4,5-dimethylthiazol-2-yl)-2,5-diphenyl tetrazolium bromide was added to each well (final concentration, 0.5 mg/ml), and plates were incubated at 37° C. for 4 h. Acid-isopropanol (0.1 N HCl in isopropanol, 150 mL) was then added to each well, and the resultant formazan crystals were dis-solved by gentle mixing. Absorbances at 540 nm were measured on a Titertek Multiscan MCC/340 plate reader.

Stability to esterase degradation was determined in the mouse serum stability assays. The enzymatic activity of mouse serum can result in inactivation of compounds in vivo despite their promising in vitro activity. A modification of the standard cell growth inhibition assays described above was used to determine stability of the test compounds to esterase degradation. Human breast carcinoma cell line MDA-MB-435 or human prostate carcinoma cell line DU 145 were used. The cells were plated in a 96-well microliter plates at a density of 7500 cells/well. Prior to adding the test compounds to cells in the cell growth inhibition assay, the test compounds were incubated in 100% mouse serum or normal growth medium for 6 hours at 37° C. After that, the test compounds were added to the 96-well microliter plates containing the cells. The cells were incubated in the presence or absence of test compounds for 96 hours. Cell growth was assessed using modifications (Amin et al, Cancer Res., 47: 6040-6045, 1987) of a methylene blue-based microculture assay (Finlay et al, Anal. Biochem., 139: 272-277,1984). Absorbances at 620 and 405 nm were measured on a Titertek Multiscan MCC/340. Ability of test compounds to inhibit cell growth after compounds exposure to mouse serum esterases was assessed.

Cytotoxicity Assay.

To determine toxicity of compounds against normal, non-dividing cells, quiescent IMR-90 normal human fibroblasts (ATCC accession number CCL-186) were used. IMR-90 cells were plated in a 96-well microliter plate format and grown to confluency (for 72 hours). After the 72-hour growth, the cells were washed and the medium was replaced from normal medium containing 10% fetal bovine serum to medium containing low concentration of serum (0.1%). Cells were made quiescent by incubation in 0.1% serum-containing growth medium for additional 72 hours. Cells were incubated with the test compounds for 24 hours. Cellular ATP levels were measured using a ViaLight HS kit (LumiTech Ltd). A cytotoxic compound carbonyl cyanide was used in all assays as a positive control for cytotoxicity.

Determination of Antitumor Activity In Vivo in Mice.

In vivo tumor xenograft studies were performed in immunocompromised (nude) mice. Mice (female Ncr athymic) were implanted subcutaneously with human tumor xenografts (including breast MDA-MB-435, colon COLO-205, HCT-15, HCT-116, HCC-2998, HT-29, SW-620, DLD-1, LoVo, melanoma LOX, lung H522, pancreatic PANC-1). After the xenografts reached an average size of 75-200 mm³ or 400-600 mm³, the animals were weighed and randomly divided into groups of 8-10 on the first day of compound administration. Test compounds were administered intravenously or intraperitoneally. Tumor and body weight measurements were done twice weekly.

In certain other embodiments, compounds of formula (I) are defined as follows:

$X_1$ and $X_2$ are each independently $CHR_AR_B$, $SO_2$ or $C=O$; wherein $R_A$ and $R_B$ are each independently hydrogen or substituted or unsubstituted, linear or branched cyclic or acyclic, or saturated or unsaturated lower alkyl;

$R_1$ and $R_2$ are each independently hydrogen, or a linear or branched, cyclic or acyclic, or saturated or unsaturated lower alkyl, lower heteroalkyl or acyl moiety, or an aryl or heteroaryl moiety; wherein the alkyl, heteroalkyl, and moieties may be substituted or unsubstituted; or

What is claimed is:
1. A compound having the structure

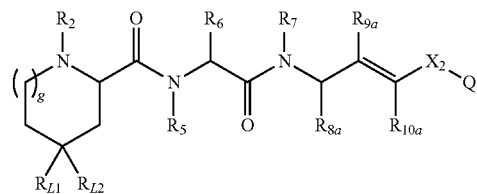

or a pharmaceutically acceptable salt, ester or salt of an ester thereof;
wherein g is 0, 1, 2 or 3;
$X_2$ is $C(=O)$, $CR_AR_B$, or $—SO_2—$; wherein each occurrence of $R_A$ and $R_B$ is independently hydrogen, or an aliphatic, alicyclic, heteroaliphatic, heteroalicyclic, aryl or heteroaryl moiety;
$R_2$ is hydrogen, $—(C=O)R_C$ or an aliphatic, alicyclic, heteroaliphatic, heteroalicyclic, aryl or heteroaryl moiety; wherein each occurrence of $R_C$ is independently hydrogen, OH, $OR_D$, or an aliphatic, alicyclic, heteroaliphatic, heteroalicyclic, aryl or heteroaryl moiety; wherein $R_D$ is an aliphatic, alicyclic, heteroaliphatic, heteroalicyclic, aryl or heteroaryl moiety;
$R_5$, $R_6$ and $R_7$ are each independently hydrogen, $—(C=O)R_E$ or an aliphatic, alicyclic, heteroaliphatic, heteroalicyclic, aryl or heteroaryl moiety, wherein each occurrence of $R_E$ is independently hydrogen, OH, $OR_F$, or an aliphatic, alicyclic, heteroaliphatic, heteroalicyclic, aryl or heteroaryl moiety, or wherein any two $R_5$, $R_6$ and $R_7$ groups, taken together, form an alicyclic, heteroalicyclic, alicyclic(aryl), heteroalicyclic(aryl), alicyclic(heteroaryl) or heteroalicyclic(heteroaryl) moiety, or an aryl or heteroaryl moiety; wherein $R_F$ is an aliphatic, alicyclic, heteroaliphatic, heteroalicyclic, aryl or heteroaryl moiety; $R_{8a}$, $R_{9a}$ and $R_{10a}$ are each independently hydrogen, or an aliphatic, alicyclic, heteroaliphatic, heteroalicyclic, aryl or heteroaryl moiety;

$R_{L1}$ and $R_{L2}$ are each independently hydrogen or an aliphatic, alicyclic, heteroaliphatic, heteroalicyclic, aryl or heteroaryl moiety; and Q is $NR^{Q'}R^{Q''}$; wherein $R^{Q'}$ and $R^{Q''}$, taken together with the nitrogen atom to which they are attached, form a heteroalicyclic moiety.

2. The compound of claim 1 having the structure

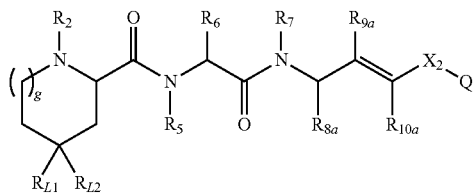

or a pharmaceutically acceptable salt, ester or salt of an ester thereof;

wherein g is 0, 1, 2 or 3;

$X_2$ is $CR_AR_B$, $C(=O)$, or $-SO_2-$; wherein each occurrence of $R_A$ and $R_B$ is independently hydrogen, or an aliphatic, alicyclic, heteroaliphatic, heteroalicyclic, aryl or heteroaryl moiety;

$R_2$ is hydrogen, substituted or unsubstituted, linear or branched, cyclic or acyclic, saturated or unsaturated $C_{1-6}$ alkyl, substituted or unsubstituted heteroalkyl, -alkyl (aryl), or acyl group, wherein the acyl group is a nitrogen protecting group;

$R_5$ and $R_{9a}$ are each hydrogen, and $R_6$, $R_7$, $R_{8a}$ and $R_{10a}$ are each independently alkyl, whereby the alkyl moiety may be substituted or unsubstituted, linear or branched, cyclic or acyclic;

$R_{L1}$ and $R_{L2}$ are each independently hydrogen or an aliphatic, alicyclic, heteroaliphatic, heteroalicyclic, aryl or heteroaryl moiety.

3. The compound of claim 1, wherein $X_2$ is C=O and $R_2$ is hydrogen, or linear or branched, cyclic or acyclic, $C_{1-6}$ alkyl or benzyl.

4. The compound of claim 1 wherein $R_2$ is hydrogen, or $C_{1-6}$ alkyl; $R_6$ is tert-butyl, $R_7$ and $R_{10a}$ are each methyl and $R_{8a}$ is iso-propyl; $R_{L1}$ and $R_{L2}$ are each independently hydrogen, $C_{1-6}$ alkyl, heteroalkyl, aryl or heteroaryl.

5. The compound of claim 1 wherein Q is selected from the group consisting of:

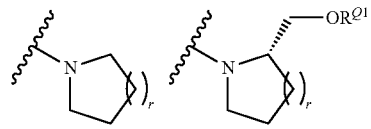

-continued

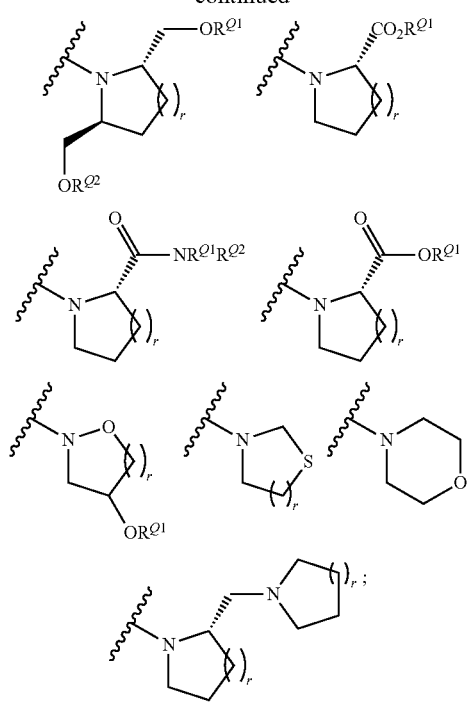

wherein each occurrence of r is 0, 1 or 2;

wherein each occurrence of $R^{Q1}$ and $R^{Q2}$ is independently hydrogen, or a substituted or unsubstituted, linear or branched, cyclic or acyclic alkyl or heteroalkyl moiety, or a substituted or unsubstituted aryl or heteroaryl moiety; or $R^{Q1}$ and $R^{Q2}$, taken together with the nitrogen atom to which they are attached, form a substituted or unsubstituted heterocyclic moiety;

or a pharmaceutically acceptable salt, ester or salt of ester thereof.

6. The compound of claim 5 wherein Q is:

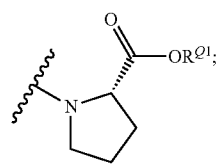

or a pharmaceutically acceptable salt, ester or salt of ester thereof.

7. The compound of claim 5 wherein Q is:

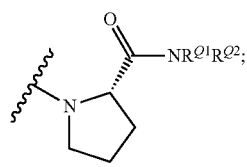

or a pharmaceutically acceptable salt, ester or salt of ester thereof.

8. The compound of claim 5 wherein Q is:

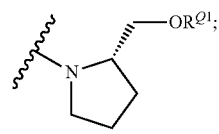

or a pharmaceutically acceptable salt, ester or salt of ester thereof.

9. The compound of any one of claims 5-8, wherein each occurrence of $R^{Q1}$ and $R^{Q2}$ is independently hydrogen, or a substituted or unsubstituted, linear or branched, cyclic or acyclic, alkyl or heteroalkyl moiety.

10. The compound of claim 5 having the structure:

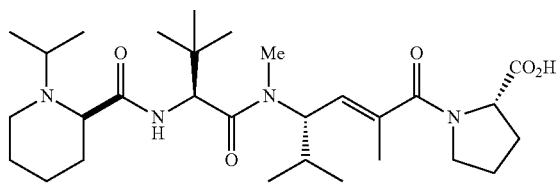 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)O]

or a pharmaceutically acceptable salt, ester or salt of an ester thereof.

11. The compound of claim 10, wherein the compound is a pharmaceutically acceptable ester or salt of ester of:

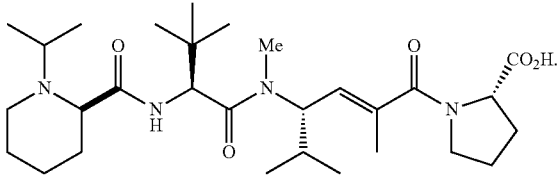 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)O]

12. The compound of claim 10, wherein the compound is:

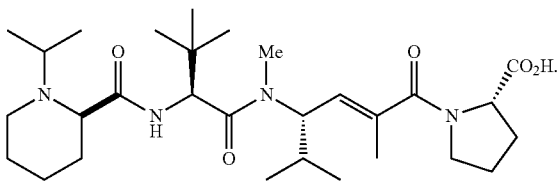 [SMILES: C/C(=C\[C@H](C(C)C)N(C)C(=O)[C@@H](NC(=O)[C@H]1CCCCN1C(C)C)C(C)(C)C)C(=O)N1CCC[C@H]1C(=O)O]

13. The compound of claim 1 having a structure selected from:

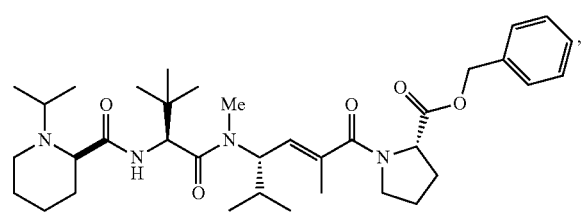

-continued

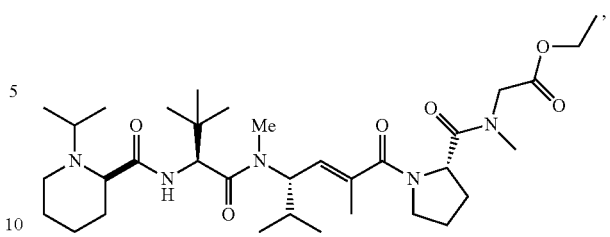

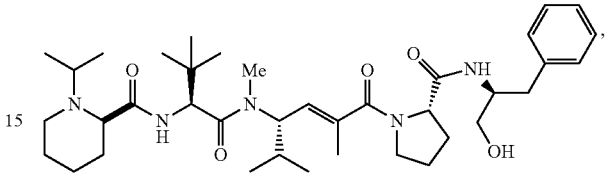

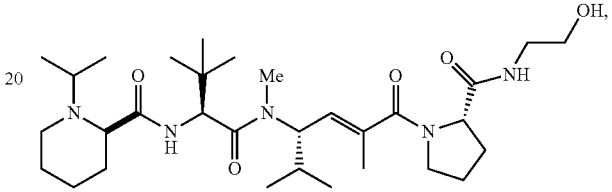

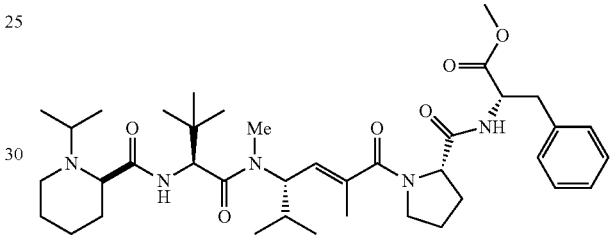

or a pharmaceutically acceptable salt, ester or salt of an ester thereof.

14. A pharmaceutical composition comprising a compound of claim 1, a pharmaceutically acceptable carrier or diluent, and optionally further comprising an additional therapeutic agent.

15. The pharmaceutical composition of claim 14 wherein the compound is present in an amount effective to inhibit cancer cell growth in vitro.

16. The pharmaceutical composition of claim 14 wherein the compound is present in an amount effective to cause tumor regression in vivo.

17. A method for treating cancer comprising: administering to a subject in need thereof a therapeutically acceptable amount of the pharmaceutical composition of claim 14.

18. A method for treating cancer comprising: administering to a subject in need thereof a therapeutically acceptable amount of a compound of any one of claims 1 and 10.

19. The method of claim 18 further comprising the administration of a pharmaceutically acceptable carrier or diluent, and optionally an additional therapeutic agent.

20. The method of claim 18, wherein the cancer is prostate, breast, colon, bladder, cervical, skin, testicular, kidney, ovarian, stomach, brain, liver, pancreatic or esophageal cancer or lymphoma, leukemia, or multiple myeloma.

* * * * *